US012433946B2

(12) United States Patent
Irvine et al.

(10) Patent No.: US 12,433,946 B2
(45) Date of Patent: *Oct. 7, 2025

(54) # IMMUNOMODULATORY FUSION PROTEIN-METAL HYDROXIDE COMPLEXES AND METHODS THEREOF

(71) Applicant: Massachusetts Institute of Technology, Cambridge, MA (US)

(72) Inventors: Darrell J. Irvine, Arlington, MA (US); Karl Dane Wittrup, Boston, MA (US); Tyson Moyer, Boston, MA (US); Yash Agarwal, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 282 days.

This patent is subject to a terminal disclaimer.

(21) Appl. No.: 18/172,905

(22) Filed: Feb. 22, 2023

(65) Prior Publication Data

US 2023/0302128 A1 Sep. 28, 2023

Related U.S. Application Data

(63) Continuation of application No. 16/857,999, filed on Apr. 24, 2020, now Pat. No. 11,642,409.

(60) Provisional application No. 62/867,162, filed on Jun. 26, 2019.

(51) Int. Cl.

| | |
|---|---|
| ***A61K 39/395*** | (2006.01) |
| ***A61K 33/08*** | (2006.01) |
| ***A61K 38/19*** | (2006.01) |
| ***A61K 38/20*** | (2006.01) |
| ***A61P 35/00*** | (2006.01) |
| ***C07K 14/52*** | (2006.01) |
| ***C07K 14/525*** | (2006.01) |
| ***C07K 14/54*** | (2006.01) |
| ***C07K 16/28*** | (2006.01) |

(52) U.S. Cl.

CPC .......... *A61K 39/3955* (2013.01); *A61K 33/08* (2013.01); *A61K 38/191* (2013.01); *A61K 38/195* (2013.01); *A61K 38/20* (2013.01); *A61P 35/00* (2018.01); *C07K 14/521* (2013.01); *C07K 14/525* (2013.01); *C07K 14/54* (2013.01); *C07K 16/2809* (2013.01); *C07K 2319/30* (2013.01)

(58) Field of Classification Search

CPC .................................................. A61K 39/3955

See application file for complete search history.

(56) References Cited

U.S. PATENT DOCUMENTS

| | | | |
|---|---|---|---|
| 5,086,881 | A | 2/1992 | Gagnon et al. |
| 2012/0177681 | A1 | 7/2012 | Singh et al. |
| 2019/0358312 | A1 | 11/2019 | Irvine et al. |

FOREIGN PATENT DOCUMENTS

| | | |
|---|---|---|
| WO | 2004/097000 | 11/2004 |
| WO | 2017/181128 | 10/2017 |
| WO | 2019126371 | 6/2019 |
| WO | 2020/263399 | 12/2020 |

OTHER PUBLICATIONS

International Preliminary Report on Patentability, PCT/US2018/066576, dated Jun. 23, 2020, 8 pages.

Cerofolini, L. et al., "Structural characterization of a protein adsorbed on aluminum hydroxide adjuvant in vaccine formulation," NPJ Vaccines, vol. 4(1):5 pages (2019).

International Search Report and Written Opinion, PCT/US2020/029852, dated Aug. 7, 2020, 19 pages.

International Search Report and Written Opinion, PCT/US2018/066576, dated Mar. 29, 2019, 17 pages.

Yer, S. et al., "Effect of the degree of phosphate substitution in aluminum hydroxide adjuvant on the adsorption of phosphorylated proteins," Pharmaceutical Development and Technology. vol. 8(1):81-86 (2003).

Morefield, G.L. et al., "Effect of phosphorylation of ovalbumin on adsorption by aluminum-containing adjuvants and elution upon exposure to interstitial fluid," Vaccine, vol. 23 (12):1502-1506 (2005).

Moyer, T. et al., "Engineered immunogen binding to alum adjuvant enhances humoral immunity," Nature Medicine, vol. 26(3):430-440 (2020).

Weissburg R. et al., "Characterization of the MN gp120 HIV-1 vaccine: antigen binding to alum," Pharmaceutical Rese, vol. 12 (10) 8 pages (1995).

Aznar, M. Angela, et al. "Intratumoral delivery of immunotherapy-act locally, think globally," The Journal of Immunology, vol. 198(1): 31-39 (2017).

Bordoli, M et al., "A Secreted Tyrosine Kinase Acts in the Extracellular Environment," Cell, vol. 158 (Issue 5): 1033-1044 (2014).

Buchbinder, Elizabeth I., et al. "Therapy with high-dose Interleukin-2 (HD IL-2) in metastatic melanoma and renal cell carcinoma following PD1 or POL 1 inhibition," Journal for Immunotherapy of Cancer, vol. 7(49): 7 pages (2019).

(Continued)

*Primary Examiner* — Prema M Mertz

(74) *Attorney, Agent, or Firm* — MCDONNELL BOEHNEN HULBERT & BERGHOFF LLP

(57) ABSTRACT

The present disclosure provides immunomodulatory fusion proteins-metal hydroxide complexes comprising an immunomodulatory domain adsorbed to a metal hydroxide via ligand exchange. The disclosure also features compositions and methods of using the same, for example, to treat cancer.

24 Claims, 33 Drawing Sheets

Specification includes a Sequence Listing.

(56) References Cited

OTHER PUBLICATIONS

Castro, Flavia, et al. “Interferon-gamma at the crossroads of tumor immune surveillance or evasion.” Frontiers in Immunology 9: 847 (2018).
Flarend, Richard E., et al. “In vivo absorption of aluminium-containing vaccine adjuvants using 26AI.” Vaccine 15.12-13 (1997): 1314-1318.
Hodi, F. Stephen, et al. “Improved survival with ipilimumab in patients with metastatic melanoma.” New England Journal of Medicine 363:8: 711-723 (2010).
HogenEsch, H. et al. “Optimizing the utilization of aluminum adjuvants in vaccines: you might just get what you want.” NPJ Vaccines, vol. 3(Article 51) 11 pages (2018).
Ishikawa, H. et al., “Four-jointed is a Golgi kinase that phosphorylates a subset of cadherin domains,” Science, vol. 621(5887):401-404 (2008).
Jacobson, Lee S., et al. “Cathepsin-mediated necrosis controls the adaptive immune response by Th2 (T helper type 2)-associated adjuvants.” Journal of Biological Chemistry 288.11 (2013): 7 481-7 491.
Jully, Vanessa, et al. “Mechanisms of antigen adsorption onto an aluminum-hydroxide adjuvant evaluated by high throughput screening” Journal of Pharmaceutical Sciences, vol. 105.6:1829-1836 (2016).
Milling, Lauren, et al., “Delivering safer immunotherapies for cancer.” Advanced drug delivery reviews, 114: 79-101 (2017).
Moynihan, Kelly D., Opel, Cary F. et al. “Eradication of large established tumors in mice by combination Immunotherapy that engages innate and adaptive immune responses.” Nature medicine 22.12 (2016): 1402.
Ribas, Antoni, and Jedd D. Wolchok. “Cancer immunotherapy using checkpoint blockade,” Science, vol. 359(6382) 1350-1355 (2018).
Riley, Rachel S., et al., “Delivery technologies for cancer immunotherapy.” Nature Reviews Drug Discovery, vol. 181:175-196 (2019).
Tagliabracci, Vincent S., et al. “A single kinase generates the majority of the secreted phosphoproteome,” Cell, vol. 161(7):1619-1632 (2015).
Tagliabracci, Vincent S., et al. “Secreted kinase phosphorylates extracellular proteins that regulate biomineralization.” Science 336. 6085 (2012): 1150-1153.
Zheng, Y. et al., “Structural changes of protein antigens due to adsorption onto and release from aluminium hydroxide using FTIR-ATR,” Spectroscopy, vol. 21: 211-226 (2007).
Zghu, E. et al., “Synergistic Innate and Adaptive Immune Response to Combination Immunotherapy with Anti-Tumor antigen Antibodies and Extended Serum Half-Life IL-2,” Cancer Cell, vol. 27(4) : 489-501 (2015).
U.S. Appl. No. 16/226,376, filed Dec. 19, 2018 (Darrell J. Irvine).

Alum + MSA-IL2-ABP10K

Free MSA-IL2-ABP10K

Protein

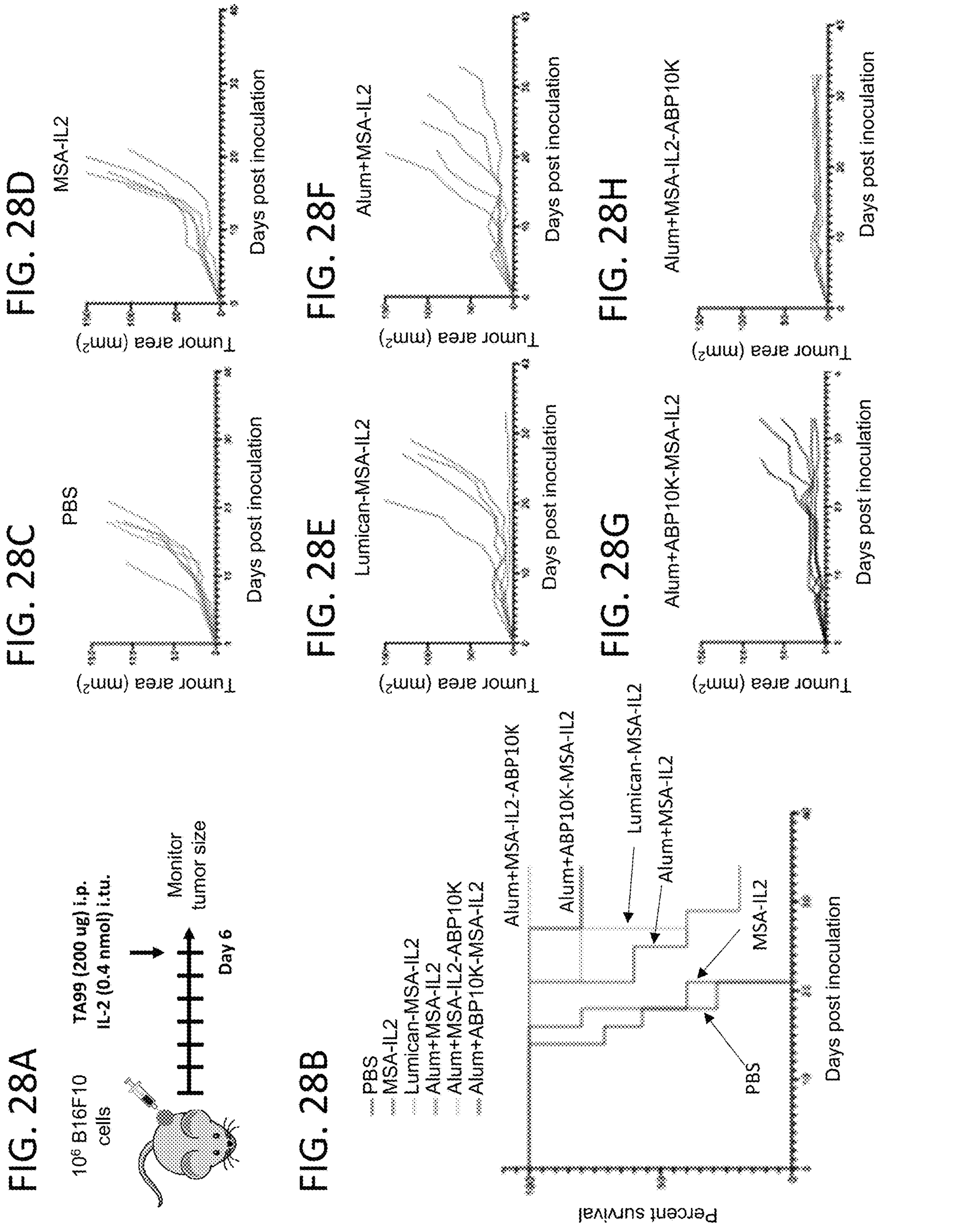
FIG. 28A
$10^6$ B16F10 cells
TA99 (200 ug) i.p.
IL-2 (0.4 nmol) i.tu.
Monitor tumor size
Day 6
FIG. 28B
PBS
MSA-IL2
Lumican-MSA-IL2
Alum+MSA-IL2
Alum+MSA-IL2-ABP10K
Alum+ABP10K-MSA-IL2
Percent survival
Days post inoculation
FIG. 28C
PBS
Tumor area ($mm^2$)
Days post inoculation
FIG. 28D
MSA-IL2
Tumor area ($mm^2$)
Days post inoculation
FIG. 28E
Lumican-MSA-IL2
Tumor area ($mm^2$)
Days post inoculation
FIG. 28F
Alum+MSA-IL2
Tumor area ($mm^2$)
Days post inoculation
FIG. 28G
Alum+ABP10K-MSA-IL2
Tumor area ($mm^2$)
Days post inoculation
FIG. 28H
Alum+MSA-IL2-ABP10K
Tumor area ($mm^2$)
Days post inoculation

IMMUNOMODULATORY FUSION PROTEIN-METAL HYDROXIDE COMPLEXES AND METHODS THEREOF

CROSS-REFERENCE TO RELATED APPLICATIONS

This application is a continuation of U.S. application Ser. No. 16/857,999, filed Apr. 24, 2020, which claims priority to U.S. Provisional Application Ser. No. 62/867,162, filed on Jun. 26, 2019. The entire contents of the above-referenced applications are incorporated herein by reference.

GOVERNMENT FUNDING

This invention was made with Government support under Grant No. R01 CA174795 awarded by the National Institutes of Health (NIH). The Government has certain rights in the invention.

REFERENCE TO SEQUENCE LISTING

The instant application contains a Sequence Listing which has been submitted electronically in ASCII format and is hereby incorporated by reference in its entirety. Said ASCII copy, created Feb. 16, 2023, is named “21-0840-US-CON.xml” and is 402963 bytes in size.

BACKGROUND

Immune checkpoint blockade therapy can significantly extend progression-free survival in patients afflicted with non-small cell lung cancer, metastatic melanoma and more (Hodi et al (2010) 363:711-723; Ribas et al (2018) *Science* 359:1350-1355). However, these treatment regiments typically only show improvements in a subset of patients. While combinations of these therapies with immunomodulatory cytokines like IL-2 have shown promise in mice (Moynihan, Kelly D., et al *Nature medicine* 22:1402 (2016)), translating these from preclinical models to clinical studies has been difficult due to dose-limiting toxicities of the potent cytokines (Milling, et al *Advanced drug delivery reviews* 114:79-101 (2017)). Hence, there is significant interest in limiting toxicity while maintaining efficacy. Alternate routes of administration along with novel mechanisms of in vivo retention may be key to boosting anti-tumor immune responses in all treated individuals while preventing any toxic side-effects (Aznar et al. *The Journal Immunology* 198:31-39 (2017)). Some in vivo retention strategies proposed involve fusing payloads to other high half-life proteins and conjugating proteins to degradable biomaterials like hydrogels (Zhu, et al. *Cancer cell* 27:489-501 (2015); Chao, et al. *Nature Biomedical Engineering* 2:611 (2018)). Even these, however, can only extend persistence of proteins for a short-term and can rely on multiple doses of therapy for efficacy.

Accordingly, there remains a need for novel immunotherapy approaches.

SUMMARY OF THE DISCLOSURE

The present disclosure is based, at least in part, on a surprising discovery that an immunomodulatory domain (e.g., a cytokine, anti-immune receptor antibody, anti-tumor associated-antigen antibody, etc.) engineered to conjugate with aluminum hydroxide (alum) has increased anti-tumor efficacy when delivered by intratumoral injection relative to an unconjugated immunomodulatory domain. Alum provides a particulate scaffold that is known to persist at sites of injection in preclinical models for many weeks. Without being bound by theory, alum provides a particulate scaffold for retaining an immunomodulatory domain at the site of intratumoral injection, thereby increasing persistence of the immunotherapy within the tumor microenvironment, while limiting systemic exposure of the immunotherapy to below levels that result in undesirable toxicity. It is well understood that phosphorylated protein antigens show stronger adsorption to alum via ligand exchange. This discovery has led to the development of phosphonated small molecule adjuvants such as phosphonated TLR agonists that can be localized at the site of vaccination by adsorption to alum. However, the use of adsorption to alum for localization of immunomodulatory polypeptides for the treatment of cancer has not been demonstrated. Accordingly, provided herein are immunomodulatory fusion proteins comprising hydroxyl replacement groups (e.g., phosphate groups) for adsorption via ligand exchange with a metal hydroxide (e.g., alum), for the purpose of improving tumor retention and anti-tumor efficacy of an immunomodulatory domain for use in a cancer immunotherapy.

In some aspects, the disclosure provides methods to improve efficacy of an immunomodulatory domain, wherein the immunomodulatory domain is modified to provide tight binding to a metal hydroxide (e.g., alum) via one or more phosphoserine residues. In some aspects, the disclosure provides methods and compositions comprising immunomodulatory domains modified with a peptide comprising phosphorylated residues, wherein the phosphorylated peptide undergoes ligand exchange reactions with the surface of alum to anchor the immunomodulatory domain to the metal hydroxide (e.g., alum). As a result of such linkage, it was discovered that the modified immunomodulatory domain has increased binding to alum in vitro compared to an unmodified immunomodulatory domain that adsorbs non-specifically to alum. Furthermore, it was discovered that the modified immunomodulatory domain when adsorbed to alum by ligand exchange persisted in tumors for over 29 days, whereas in the absence of alum, the immunomodulatory domain cleared from the tumors within 3 days. Additionally, it was found that improved retention corresponded to improved anti-tumor efficacy, wherein a modified immunomodulatory domain adsorbed to alum by ligand exchange promoted increased survival and tumor clearance in tumor-bearing animals compared to an unmodified immunomodulatory domain or an immunomodulatory domain adsorbed to alum by non-specific interactions. Thus, strong binding to a metal hydroxide (e.g., alum) mediated by ligand exchange promotes improved tumor retention and anti-tumor efficacy of an immunomodulatory therapy.

Accordingly, in some aspects, the present disclosure provides an immunomodulatory fusion protein-metal hydroxide complex comprising: (a) an immunomodulatory fusion protein comprising an immunomodulatory domain, a metal hydroxide-binding peptide comprising at least one target motif of a secretory pathway kinase that is modified with a phosphate group, and optionally, a stabilizing domain, and (b) a metal hydroxide (e.g., alum), wherein the immunomodulatory fusion protein is adsorbed via ligand exchange to the metal hydroxide via the one or more phosphate groups of the metal hydroxide-binding peptide, thereby forming an immunomodulatory fusion protein-metal hydroxide complex.

In some aspects, the present disclosure provides immunomodulatory fusion protein-metal hydroxide complexes and uses thereof. In some aspects, the present disclosure provides an immunomodulatory fusion protein-metal hydroxide complex comprising:

(a) an immunomodulatory fusion protein comprising
  (i) an immunomodulatory domain,
  (ii) a metal hydroxide-binding peptide comprising at least one kinase target motif of a secretory pathway kinase that comprises at least one phosphorylated amino acid, and
  (iii) optionally, a stabilizing domain; and
(b) a metal hydroxide wherein the immunomodulatory fusion protein is adsorbed via ligand exchange to the metal hydroxide via the at least one phosphorylated amino acid of the metal hydroxide-binding peptide, thereby forming an immunomodulatory fusion protein-metal hydroxide complex.

In some aspects, the immunomodulatory fusion protein comprises a metal hydroxide-binding peptide comprising at least one kinase target motif, wherein the kinase target motif comprises an amino acid sequence that is phosphorylated by a kinase selected from a group consisting of: Fam20C, protein kinase A, cAMP-dependent protein kinase, cyclin-dependent kinase, extracellular-regulated kinase-2, casein kinase 1, casein kinase 2, glycogen synthase kinase-3, calmodulin-dependent protein kinase-2, Abelson murine leukemia virus tyrosine kinase, rous sarcoma virus tyrosine kinase, insulin receptor tyrosine kinase, protein kinase B, protein kinase D, proviral integration site kinase 1-3, AMP-activated protein kinase, mitogen-activated protein kinase, or NimA-related kinase.

In some aspects, the immunomodulatory fusion protein comprises a metal hydroxide-binding peptide comprising at least one kinase target motif, wherein the at least one kinase target motif comprises an amino acid sequence that is phosphorylated by Fam20C. In some aspects, the at least one kinase target motif of the metal hydroxide-binding peptide comprises a phosphoserine, phosphotyrosine or phosphothreonine. In some aspects, the at least one kinase target motif of the metal hydroxide-binding peptide comprises an amino acid sequence selected from a group consisting of: S-X-E, S-X-pS, or S-X-Q-X-X-D-E (SEQ ID NO: 206), wherein X is any amino acid. In some aspects, the at least one kinase target motif of the metal hydroxide-binding peptide comprises an amino acid sequence S-X-E, wherein X is any amino acid and wherein serine is phosphorylated. In some aspects, X is selected from E, S, V, H, Q and G. In some aspects X is E.

In other aspects, the present disclose provides an immunomodulatory fusion protein-metal hydroxide complex comprising:

(a) an immunomodulatory fusion protein comprising
  (i) an immunomodulatory domain,
  (ii) a metal hydroxide-binding peptide comprising at least one kinase target motif of the secretory pathway kinase Fam20C that comprises the amino acid sequence S-X-E, and
  (iii) optionally, a stabilizing domain; and
(b) a metal hydroxide, wherein the at least one kinase target motif of the metal hydroxide-binding peptide comprises a phosphoserine, and wherein the immunomodulatory fusion protein is adsorbed via ligand exchange to the metal hydroxide via the at least one phosphoserine of the metal hydroxide-binding peptide, thereby forming an immunomodulatory fusion protein-metal hydroxide complex.

In some aspects, the immunomodulatory fusion protein-metal hydroxide complex comprises a metal hydroxide-binding peptide which is operably linked, optionally via a linker, to either the N-terminus or C-terminus of the immunomodulatory domain.

In some aspects, the immunomodulatory fusion protein-metal hydroxide complex comprises an immunomodulatory domain, a stabilizing domain, and a metal hydroxide-binding peptide, wherein the stabilizing domain is operably linked, optionally via an amino acid linker, to either the N-terminus or C-terminus of the immunomodulatory domain, and wherein the metal-hydroxide binding peptide is operably linked, optionally via a linker, to the terminus of either the immunomodulatory domain or the stabilizing domain.

In some aspects, the immunomodulatory fusion protein-metal hydroxide complex comprises an immunomodulatory domain, a stabilizing domain, and a metal hydroxide-binding peptide, wherein the metal hydroxide-binding peptide is operably linked, optionally via an amino acid linker, to either the N-terminus or C-terminus of the immunomodulatory domain, and wherein the stabilizing domain is operably linked, optionally via a linker, to the terminus of either the metal hydroxide-binding peptide or the immunomodulatory domain.

In any of the foregoing or related aspects, the metal-hydroxide binding peptide comprises about 3-6, about 6-15, about 10-25, or about 10-50 amino acids.

In any of the foregoing or related aspects, the metal-hydroxide binding peptide comprises 1, 2, 3, 4, 5, 6, 7, 8, 9, 10, 11, 12, 13, 14, 15 or more kinase target motifs comprising a phosphorylated amino acid.

In any of the foregoing or related aspects, wherein the kinase target motif(s) comprises a phosphorylated amino acid that is phosphoserine.

In any of the foregoing or related aspects, the metal-hydroxide binding peptide comprises two or more kinase target motifs of a secretory pathway kinase, wherein the two or more kinase target motifs comprise an amino acid sequence that is the same or different, optionally wherein the two or more kinase target motifs are separated by a peptide linker.

In any of the foregoing or related aspects, the at least one kinase target motif comprises an amino acid sequence S-X-E, wherein X is any amino acid, and wherein serine is phosphorylated. In some aspects, X is selected from E, S, V, H, Q and G. In some aspects, X is E.

In any of the foregoing or related aspects, the metal hydroxide-binding peptide comprises at least one, two, or three kinase target motifs, optionally wherein the kinase target motifs are sequential. In any of the foregoing or related aspects, the metal-hydroxide-binding peptide comprises an amino acid sequence selected from: SEQ ID NO: 117, SEQ ID NO: 119, SEQ ID NO: 121, SEQ ID NO: 123, and SEQ ID NO: 125.

In any of the foregoing or related aspects, the metal hydroxide-binding peptide comprises the amino acid sequence XXSXEXX (SEQ ID NO: 127) or XXSEEXX (SEQ ID NO: 128), wherein X is any amino acid.

In any of the foregoing or related aspects, the metal hydroxide-binding peptide comprises the amino acid sequence $Xaa_1$-$Xaa_2$-S-$Xaa_3$-E-$Xaa_4$-$Xaa_5$ (SEQ ID NO: 127), wherein $Xaa_1$ is F, M or G; $Xaa_2$ is Q, E or G; $Xaa_3$ is E, S, V, H, Q and G; $Xaa_4$ is Q, S or G; and $Xaa_5$ is Q, N, or G. In some aspects, $Xaa_3$ is E. In some aspects, $Xaa_3$ is E; $Xaa_1$ is F; and $Xaa_2$ is Q. In some aspects, $Xaa_3$ is E; $Xaa_1$ is M; and $Xaa_2$ is E. In some aspects, $Xaa_3$ is E; $Xaa_1$ is G; and $Xaa_2$ is G. In some aspects, $Xaa_3$ is E; $Xaa_4$ is Q; and $Xaa_5$ is Q. In some aspects, $Xaa_3$ is E; $Xaa_4$ is E; and $Xaa_5$ is S. In some aspects, $Xaa_3$ is E; $Xaa_4$ is G; and $Xaa_5$ is G.

In any of the foregoing or related aspects, the metal hydroxide-binding peptide comprises an amino acid sequence FQSEEQQ (SEQ ID NO: 129), MESEESN (SEQ ID NO: 130), or GGSEEGG (SEQ ID NO: 131).

In any of the foregoing or related aspects, the metal hydroxide-binding peptide comprises the amino acid sequence $Xaa_1$-$Xaa_2$-S-$Xaa_3$-E-$Xaa_4$-$Xaa_5$-[L]-S-$Xaa_3$-E-$Xaa_6$-$Xaa_7$ (SEQ ID NO: 133), wherein $Xaa_1$ is F, M or G; $Xaa_2$ is Q, E or G; $Xaa_3$ is E, S, V, H, Q and G; $Xaa_4$ is Q, S or G; $Xaa_5$ is Q, N, or G; $Xaa_5$ is G and $Xaa_5$ is G, and wherein L is a peptide linker, optionally a G/S linker, optionally GGGS (SEQ ID NO: 132).

In any of the foregoing or related aspects, the metal hydroxide-binding peptide comprises a sequence of linked amino acids comprising the formula [A]x, wherein A is an amino acid sequence selected from a group consisting of: SEQ ID NO: 127, SEQ ID NO: 128, SEQ ID NO: 129, SEQ ID NO: 130, or SEQ ID NO: 131 wherein x is an integer whose value indicates the number of linked amino acid sequences indicated by A, and wherein x=1–4.

In any of the foregoing or related aspects, the metal hydroxide-binding peptide comprises a sequence of linked amino acids comprising the formula [A]-[B], wherein A and B are amino acid sequences that are the same or different selected from a group consisting of: SEQ ID NO: 127, SEQ ID NO: 128, SEQ ID NO: 129, SEQ ID NO: 130, or SEQ ID NO: 131.

In any of the foregoing or related aspects, the metal hydroxide-binding peptide comprises a sequence of linked amino acids comprising the formula $([A]\text{-}[B])_x$, wherein A and B are amino acid sequences that are the same or different selected from a group consisting of: SEQ ID NO: 127, SEQ ID NO: 128, SEQ ID NO: 129, SEQ ID NO: 130, or SEQ ID NO: 131, wherein x is an integer whose value indicates the number of linked amino acid sequences indicated by [A]-[B], and wherein x=1–4.

In any of the foregoing or related aspects, the metal hydroxide-binding peptide comprises a sequence of linked amino acids comprising the formula [A]-[L]-[A], wherein A is an amino acid sequence selected from a group consisting of: SEQ ID NO: 127, SEQ ID NO: 128, SEQ ID NO: 129, SEQ ID NO: 130, or SEQ ID NO: 131, wherein L is a peptide linker, optionally a G/S linker, optionally GGGS (SEQ ID NO: 132).

In any of the foregoing or related aspects, the metal hydroxide-binding peptide comprises a sequence of linked amino acids comprising the formula ([A]-[L]-[A]), wherein A is an amino acid sequence selected from a group consisting of: SEQ ID NO: 127, SEQ ID NO: 128, SEQ ID NO: 129, SEQ ID NO: 130, or SEQ ID NO: 131 wherein x is an integer whose value indicates the number of linked amino acid sequences indicated by [A]-[L]-[A], wherein x=1–4, and wherein L is a peptide linker, optionally a G/S linker, optionally GGGS (SEQ ID NO: 132).

In any of the foregoing or related aspects, the metal hydroxide-binding peptide comprises a sequence of linked amino acids comprising the formula [A]-[L]-[B], wherein A and B are amino acid sequences that are the same or different selected from a group consisting of: SEQ ID NO: 127, SEQ ID NO: 128, SEQ ID NO: 129, SEQ ID NO: 130, or SEQ ID NO: 131, and wherein L is a peptide linker, optionally a G/S linker, optionally GGGS (SEQ ID NO: 132).

In any of the foregoing or related aspects, the metal hydroxide-binding peptide comprises a sequence of linked amino acids comprising the formula ([A]-[L]-[B]), wherein A and B are amino acid sequences that are the same or different selected from a group consisting of: SEQ ID NO: 127, SEQ ID NO: 128, SEQ ID NO: 129, SEQ ID NO: 130, or SEQ ID NO: 131, wherein x is an integer whose value indicates the number of linked amino acid sequences indicated by [A]-[L]-[B], wherein x=1–4, and wherein L is a peptide linker, optionally a G/S linker, optionally GGGS (SEQ ID NO: 132).

In any of the foregoing or related aspects, the metal hydroxide-binding peptide comprises an amino acid sequence selected from a group consisting of: SEQ ID NO: 91, SEQ ID NO: 93, SEQ ID NO: 95, SEQ ID NO: 97, SEQ ID NO: 99, and SEQ ID NO: 101.

In any of the foregoing or related aspects, the metal hydroxide-binding peptide comprises a sequence of linked amino acids comprising the formula $[C]_x$ wherein C is an amino acid sequence selected from a group consisting of: SEQ ID NO: 91, SEQ ID NO: 93, SEQ ID NO: 95, SEQ ID NO: 97, SEQ ID NO: 99, and SEQ ID NO: 101, and wherein x is an integer whose value indicates the number of linked amino acid sequences indicated by C, wherein x=1–4.

In any of the foregoing or related aspects, the metal hydroxide-binding peptide comprises a sequence of linked amino acids comprising the formula $[C]_x\text{-}[D]_y$, wherein C and D are amino acid sequences that are the same or different, and wherein C and D are selected from a group consisting of: SEQ ID NO: 91, SEQ ID NO: 93, SEQ ID NO: 95, SEQ ID NO: 97, SEQ ID NO: 99, and SEQ ID NO: 101, wherein x is an integer whose value indicates the number of linked amino acid sequences indicated by C, wherein y is an integer whose value indicates the number of linked amino acid sequences indicated by D, wherein x=1–4, wherein y=1-4, and wherein x and y are the same or different.

In any of the foregoing or related aspects, the metal hydroxide-binding peptide comprises an amino acid sequence selected from a group consisting of: SEQ ID NO: 103, SEQ ID NO: 105, SEQ ID NO: 107, SEQ ID NO: 115. In some aspects, the metal hydroxide-binding peptide comprises the amino acid sequence of SEQ ID NO: 103. In some aspects, the metal hydroxide-binding peptide comprises the amino acid sequence of SEQ ID NO: 105. In some aspects, the metal hydroxide-binding peptide comprises the amino acid sequence of SEQ ID NO: 107. In some aspects, the metal hydroxide-binding peptide comprises the amino acid sequence of SEQ ID NO: 115.

In any of the foregoing or related aspects, the metal hydroxide-binding peptide comprises about 1-5, 1-10, 1-15, 1-20 phosphoserine residues, and wherein the immunomodulatory fusion protein is adsorbed via ligand exchange of the phosphoserine residues to the metal hydroxide.

In other aspects, the present disclosure provides an immunomodulatory fusion protein-metal hydroxide complex comprising:

(a) an immunomodulatory fusion protein comprising
  (i) an immunomodulatory domain, optionally linked to a stabilizing domain;
  (ii) a terminal metal hydroxide-binding peptide comprising one or more hydroxyl replacement groups that is coupled, optionally via a linker, by a protein-reactive moiety; and
(b) a metal hydroxide, wherein the immunomodulatory fusion protein is adsorbed via ligand exchange to the metal hydroxide via the at least one hydroxyl replacement groups of the metal hydroxide-binding peptide, thereby forming an immunomodulatory fusion protein-metal hydroxide complex.

In some aspects, the disclosure provides an immunomodulatory fusion protein-metal hydroxide complex, wherein the protein-reactive moiety comprises a sulfhydryl-reactive moiety, optionally wherein the sulfhydryl-reactive moiety is maleimide.

In some aspects, the disclosure provides an immunomodulatory fusion protein-metal hydroxide complex, wherein the protein-reactive moiety comprises a sortase recognition motif.

In any of the foregoing or related aspects, the metal hydroxide-binding peptide comprises 3, 4, 5, 6, 7, 8, 9, 10, 11, 12, 13, 14, 15, 16, 17, 18, 19, 20 or more hydroxyl-replacement groups. In some aspects, the hydroxyl-replacement group is selected from the group consisting of a fluoride group, a citrate group, a phosphate group, a carbonate group, and a sulfate group, optionally wherein the hydroxyl-replacement group is a phosphate group. In some aspects, the hydroxyl-replacement group comprises at least one phosphorylated amino acid residue, optionally wherein the phosphorylated amino acid residue is selected from phosphoserine, phosphotyrosine, and phosphothreonine. In some aspects, the phosphorylated amino acid residue is phosphoserine.

In any of the foregoing or related aspects, the metal hydroxide is selected from aluminum hydroxide, aluminum phosphate, calcium hydroxide, calcium phosphate, iron hydroxide, magnesium hydroxide, barium hydroxide, calcium hydroxide, zinc hydroxide, and zirconium hydroxide. In some aspects, the metal hydroxide is aluminum hydroxide (alum).

In other aspects, the disclosure provides an immunomodulatory fusion protein comprising:

(a) an immunomodulatory domain, (b) a metal hydroxide-binding peptide comprising at least one kinase target motif of the secretory pathway kinase Fam20C that comprises the amino acid sequence S-X-E, (c) optionally, a stabilizing domain; and wherein the at least one kinase target motif of the metal hydroxide-binding peptide comprise a serine that is modified with a phosphate group, and wherein the immunomodulatory fusion protein undergoes ligand exchange with alum via the at least one phosphoserine of the metal hydroxide-binding peptide, thereby coupling the immunomodulatory fusion protein to alum to form an immunomodulatory fusion protein-metal hydroxide complex.

In other aspects, the disclosure provides an immunomodulatory fusion protein comprising:

(a) an immunomodulatory domain, optionally linked to a stabilizing domain; and (b) a metal hydroxide-binding peptide comprising one or more phosphorylated amino acids that is coupled, optionally via a linker, by a protein-reactive moiety, wherein the immunomodulatory fusion protein undergoes ligand exchange with alum via the at least one hydroxyl replacement groups of the metal hydroxide-binding peptide, thereby coupling the immunomodulatory fusion protein to alum to form an immunomodulatory fusion protein-metal hydroxide complex.

In some aspects, the metal hydroxide-binding peptide is coupled to the N-terminus or C-terminus of the immunomodulatory domain by a protein-reactive moiety.

In some aspects, the disclosure provides an immunomodulatory fusion protein comprising an immunomodulatory domain, a stabilizing domain, and a metal hydroxide-binding peptide, wherein the stabilizing domain is operably linked, optionally via an amino acid linker, to either the N-terminus or C-terminus of the immunomodulatory domain, and wherein the metal-hydroxide binding peptide is coupled to the terminus of the immunomodulatory domain or the stabilizing domain by a protein-reactive moiety.

In other aspects, the disclosure provides a method for increasing phosphorylation of an immunomodulatory fusion protein, the method comprising contacting a cell with:

(a) a nucleotide sequence encoding an immunomodulatory fusion protein comprising:
  - an immunomodulatory domain,
  - a metal hydroxide-binding peptide comprising one or more kinase target motif,
  - optionally, a stabilizing domain; and (b) a nucleotide sequence encoding a kinase comprising:
  - an ER targeting leader sequence operably linked to
  - a kinase domain operably linked to
  - an anchor peptide wherein the kinase is localized to the secretory pathway and wherein the one or more kinase target motifs of the metal hydroxide-binding peptide are phosphorylated by the kinase in the secretory pathway, thereby increasing phosphorylation of the immunomodulatory fusion protein.

In some aspects of the foregoing method, the kinase comprises an ER targeting leader sequence that directs the kinase to the secretory pathway, optionally wherein the kinase comprises a kinase domain selected from a group consisting of: protein kinase A, cAMP-dependent protein kinase, cyclin-dependent kinase, extracellular-regulated kinase-2, casein kinase 1, casein kinase 2, glycogen synthase kinase-3, calmodulin-dependent protein kinase-2, Abelson murine leukemia virus tyrosine kinase, rous sarcoma virus tyrosine kinase, insulin receptor tyrosine kinase, protein kinase B, protein kinase D, proviral integration site kinase 1-3, AMP-activated protein kinase, mitogen-activated protein kinase, or NimA-related kinase.

In some aspects of the foregoing method, the kinase comprises Fam20C, wherein Fam20C comprises the amino acid sequence as set forth by SEQ ID NO: 135.

In some aspects of the foregoing method, the kinase comprises an anchor peptide that inhibits secretion of the kinase, optionally wherein the anchor peptide comprises the amino acid sequence KDEL (SEQ ID NO: 233) or HDEL (SEQ ID NO: 234).

In some aspects of the foregoing method, the cell is contacted with an expression vector comprising a nucleic acid encoding the immunomodulatory fusion protein.

In some aspects of the foregoing method, the cell is contacted with an expression vector comprising a nucleic acid encoding the kinase.

In some aspects of the foregoing method, the cell is contacted with an expression vector comprising a nucleic acid encoding the kinase and a nucleic acid encoding the immunomodulatory fusion protein.

In other aspects the disclosure provides a method for increasing phosphorylation of an immunomodulatory fusion protein comprising an immunomodulatory domain, a metal hydroxide-binding peptide comprising one or more kinase target motifs of the secretory pathway kinase Fam20C, and optionally a stabilizing domain, the method comprising contacting a cell with an expression vector comprising nucleic acid encoding the immunomodulatory fusion protein and an expression vector comprising nucleic acid encoding the secretory pathway kinase Fam20C operably linked to an anchor peptide, wherein the secretory pathway kinase Fam20C is localized to the secretory pathway by the anchor peptide, and wherein the one or more kinase target motifs are phosphorylated by Fam20C in the secretory pathway, thereby increasing phosphorylation of the immunomodulatory fusion protein.

In some aspects, the method comprises maintaining the cell under conditions permitting expression of the immunomodulatory fusion protein. In some aspects, the method further comprises isolating the immunomodulatory fusion protein.

Other aspects of the disclosure feature immunomodulatory fusion proteins produced by the methods of the present disclosure, wherein the immunomodulatory fusion protein comprises at least one phosphorylated amino acid, wherein the immunomodulatory fusion protein is adsorbed via ligand exchange with alum via the at least one phosphorylated amino acid, thereby coupling the immunomodulatory fusion protein to alum to form an immunomodulatory fusion protein-metal hydroxide complex.

In any of the foregoing or related aspects, the immunomodulatory domain comprises a polypeptide that activates, enhances or promotes a response by an immune cell.

In any of the foregoing or related aspects, the immunomodulatory domain comprises a polypeptide that inhibits, reduces or suppresses a response by an immune cell.

In any of the foregoing or related aspects, the immune cell is a lymphoid cell selected from an innate lymphoid cell, a T cell, a B cell, an NK cell, and a combination thereof.

In any of the foregoing or related aspects, the immune cell is a myeloid cell selected from a monocyte, a neutrophil, a granulocyte, a mast cell, a macrophage, a dendritic cell, and a combination thereof.

In any of the foregoing or related aspects, the response by the immune cell comprises cytokine production, antibody production, production of antigen-specific immune cells, increased effector function and/or cytotoxicity, and a combination thereof.

In any of the foregoing or related aspects, the immunomodulatory domain comprises one or more selected from a cytokine, a chemokine, an activating ligand/receptor, an inhibitory ligand/receptor, or a combination thereof.

In any of the foregoing or related aspects, the immunomodulatory domain comprises one or more cytokines. In some aspects, the cytokine is a human gamma common chain receptor interleukin selected from IL-2, IL-4, IL-7, IL-9, IL-13, IL-15, IL-15/IL-15RA, IL-21, and a combination thereof. In some aspects, the cytokine is IL-2. In some aspects, the cytokine is IL-15/IL15RA. In some aspects, the cytokine is a human IL-12 family member selected from IL-12 (p35), IL-12 (p40), IL-12(p35)/IL-12(p40), IL-23, IL-27, IL-35, and a combination thereof. In some aspects, the cytokine is a single chain fusion of IL-12(p35)/IL-12 (p40). In some aspects, the cytokine is a human IL-1 family member selected from IL-1, IL-18, IL-33, and a combination thereof. In some aspects, the cytokine is IL-18. In some aspects, the cytokine is selected from TNFα, INFα, IFN-γ, GM-CSF, FLT3L, G-CSF, M-CSF, and a combination thereof.

In any of the foregoing or related aspects, the immunomodulatory domain comprises one or more chemokines. In some aspects, the chemokine is selected from LIF, MIP-2, MIP-1α, MIP-1β, CXCL1, CXCL9, CXCL10, MCP-1, Eotaxin, RANTES, LIX and a combination thereof. In some aspects, the chemokine is selected from CCL3, CCL4, CCL5, Eotaxin and a combination thereof.

In any of the foregoing or related aspects, the immunomodulatory domain comprises one or more activating ligands/receptors. In some aspects, the activating ligand/receptor is selected from a TNF superfamily, a CD28 receptor superfamily, a B7 ligand family, and a T cell receptor. In some aspects, the activating ligand/receptor is a TNF superfamily ligand selected from TNF-alpha, CD40L, 4-1BBL, OX40, and a combination thereof. In some aspects, the activating ligand/receptor is a TNF superfamily receptor and the immunomodulatory domain comprises an antibody or antigen binding fragment thereof selected from an anti-TNFR1 antibody, an anti-TNFR2 antibody, an anti-CD40 antibody, an anti-4-1BB antibody and an anti-OX40 antibody. In some aspects, the activating ligand/receptor is a CD28 superfamily member or a B7 family member selected from ICOS ligand, CD80, and CD86, and a combination thereof. In some aspects, the activating ligand/receptor is a CD28 superfamily member and the immunomodulatory domain comprises an antibody or antigen binding fragment thereof selected from an anti-ICOS antibody and an anti-CD28 antibody. In some aspects, the activating ligand/receptor is a T cell receptor and the immunomodulatory domain comprises an antibody or antigen binding fragment thereof selected from an anti-CD3γ antibody, an anti-CD3δ antibody, an anti-CD3ξ antibody, and an anti-CD3ε antibody.

In any of the foregoing or related aspects, the immunomodulatory domain comprises one or more inhibitory ligands/receptors. In some aspects, the inhibitory ligand/receptor is selected from a CD28 receptor superfamily, a TNF superfamily, and a checkpoint inhibitor. In some aspects, the inhibitory ligand/receptor is a CD28 superfamily member and the immunomodulatory domain comprises an antibody or antigen binding fragment thereof selected from an anti-PD-1 antibody, an anti-PD-L1 antibody, an anti-PD-L2 antibody, an anti-CTLA4 antibody. In some aspects, the inhibitory ligand/receptor is a TNF superfamily member and the immunomodulatory domain comprises an antibody or antigen binding fragment selected from an anti-TIGIT antibody and an anti-BTLA antibody. In some aspects, the inhibitory ligand/receptor is a TNF superfamily member and the immunomodulatory domain comprises an antibody or antigen binding fragment that is an anti-TIGIT antibody. In some aspects, the inhibitory ligand/receptor is a checkpoint inhibitor and the immunomodulatory domain comprises an antibody or antigen binding fragment selected from an anti-VISTA antibody, an anti-TIM-3 antibody, an anti-LAG-3 antibody, an anti-CD47 antibody, and an anti-SIRPα antibody.

In any of the foregoing or related aspects, the stabilizing domain comprises human serum albumin or fragment thereof.

In any of the foregoing or related aspects, the stabilizing domain comprises an Fc domain or a mutant Fc domain with reduced FcR interaction.

In any of the foregoing or related aspects, the immunomodulatory fusion protein-metal hydroxide complex is of sufficient mass to reduce size dependent diffusion from the site of injection upon administration in vivo.

In other aspects, the present disclosure provides a pharmaceutical composition comprising an immunomodulatory fusion protein-metal hydroxide complex of the disclosure, and a pharmaceutically acceptable carrier. In other aspects, the present disclosure provides a pharmaceutical composition comprising an immunomodulatory fusion protein of the disclosure, and a pharmaceutically acceptable carrier.

In other aspects, the present disclosure provides a nucleic acid comprising a nucleotide sequence encoding an immunomodulatory fusion protein of the disclosure. In other aspects, the present disclosure provides an expression vector comprising a nucleic acid of the disclosure. In other aspects, the present disclosure provides a cell transformed with an expression vector of the disclosure.

In other aspects, the disclosure provides a method for producing an immunomodulatory fusion protein, the method comprising maintaining a cell under conditions permitting expression of the immunomodulatory fusion protein. In some aspects, the method further comprises obtaining the immunomodulatory fusion protein and adsorbing the immunomodulatory fusion protein to a metal hydroxide, thereby forming an immunomodulatory fusion protein-metal hydroxide complex.

In other aspects, the present disclosure provides a method for activating, enhancing or promoting a response by an immune cell in a subject, comprising administering to a subject in need thereof, an effective amount of an immunomodulatory fusion protein-metal hydroxide complex of the disclosure or a pharmaceutical composition of the disclosure. In other aspects, the present disclosure provides a method for activating, enhancing or promoting a response by an immune cell in a subject, comprising administering to a subject in need thereof, an effective amount of an immunomodulatory fusion of the disclosure or a pharmaceutical composition thereof.

In other aspects, the present disclosure provides a method for inhibiting, reducing or suppressing a response by an immune cell in a subject, comprising administering to a subject in need thereof, an effective amount of immunomodulatory fusion protein-metal hydroxide complex of the disclosure, or a pharmaceutical composition of the disclosure. In other aspects, the present disclosure provides a method for inhibiting, reducing or suppressing a response by an immune cell in a subject, comprising administering to a subject in need thereof, an effective amount of immunomodulatory fusion protein of the disclosure, or a pharmaceutical composition thereof. In some aspects, the immune cell is a lymphoid cell selected from an innate lymphoid cell, a T cell, a B cell, an NK cell, and a combination thereof. In some aspects, the immune cell is a myeloid cell selected from a monocyte, a neutrophil, a granulocyte, a mast cell, a macrophage, a dendritic cell, and a combination thereof. In some aspects, the response by an immune cell comprises cytokine production, antibody production, production of antigen-specific immune cells, increased effector function and/or cytotoxicity, and a combination thereof. In some aspects, the response by the immune cell occurs in a tumor microenvironment.

In other aspects, the disclosure provides a method for reducing or inhibiting tumor growth, comprising administering to a subject in need thereof, an effective amount an immunomodulatory fusion protein-metal hydroxide complex of the disclosure or a pharmaceutical composition of the disclosure. In other aspects, the disclosure provides a method for reducing or inhibiting tumor growth, comprising administering to a subject in need thereof, an effective amount an immunomodulatory fusion protein of the disclosure or a pharmaceutical composition thereof.

In other aspects, the disclosure provides a method for treating cancer in a subject, comprising administering to a subject in need thereof, an effective amount of an immunomodulatory fusion protein-metal hydroxide complex of the disclosure or a pharmaceutical composition of the disclosure. In some aspects, an anti-tumor immune response is induced in the subject after administration of an immunomodulatory fusion protein-metal hydroxide complex or the pharmaceutical composition. In some aspects, the immunomodulatory fusion protein-metal hydroxide complex or pharmaceutical composition is administered intratumorally.

In other aspects, the disclosure provides a method for treating cancer in a subject, comprising administering to a subject in need thereof, an effective amount of an immunomodulatory fusion protein of the disclosure or a pharmaceutical composition thereof. In some aspects, an anti-tumor immune response is induced in the subject after administration of an immunomodulatory fusion protein or the pharmaceutical composition. In some aspects, the immunomodulatory fusion protein or pharmaceutical composition is administered intratumorally.

In other aspects, the disclosure provides a kit comprising a container comprising an immunomodulatory fusion protein-metal hydroxide complex of the disclosure, and an optional pharmaceutically acceptable carrier, or a pharmaceutical composition of the disclosure, and a package insert comprising instructions for administration of the fusion protein or pharmaceutical composition, for treating or delaying progression of cancer or reducing or inhibiting tumor growth in a subject in need thereof.

In other aspects, the disclosure provides a kit comprising a container comprising an immunomodulatory fusion protein of the disclosure, and an optional pharmaceutically acceptable carrier, or a pharmaceutical composition of the disclosure, and a package insert comprising instructions for administration of the fusion protein or pharmaceutical composition, for treating or delaying progression of cancer or reducing or inhibiting tumor growth in a subject in need thereof.

In other aspects, the disclosure provides a kit comprising a container comprising an immunomodulatory fusion protein-metal hydroxide complex of the disclosure, and an optional pharmaceutically acceptable carrier, or a pharmaceutical composition of the disclosure, and a package insert comprising instructions for administration of the antibody or pharmaceutical composition alone or in combination with another agent, for treating or delaying progression of cancer or reducing or inhibiting tumor growth in a subject in need thereof.

In other aspects, the disclosure provides a kit comprising a container comprising an immunomodulatory fusion protein of the disclosure, and an optional pharmaceutically acceptable carrier, or a pharmaceutical composition of the disclosure, and a package insert comprising instructions for administration of the antibody or pharmaceutical composition alone or in combination with another agent, for treating or delaying progression of cancer or reducing or inhibiting tumor growth in a subject in need thereof.

Other aspects of the disclosure provide the use of an immunomodulatory fusion protein-metal hydroxide complex of the disclosure, and an optional pharmaceutically acceptable carrier, or a pharmaceutical composition of the disclosure, for the manufacture of a medicament for treating or delaying progression of cancer or reducing or inhibiting tumor growth in a subject in need thereof.

In some aspects, the disclosure provide the use of an immunomodulatory fusion protein of the disclosure, and an optional pharmaceutically acceptable carrier, or a pharmaceutical composition of the disclosure, for the manufacture of a medicament for treating or delaying progression of cancer or reducing or inhibiting tumor growth in a subject in need thereof.

In yet other aspects, the disclosure provides an immunomodulatory fusion protein-metal hydroxide complex of the disclosure, and an optional pharmaceutically acceptable carrier, or a pharmaceutical composition of the disclosure, in the manufacture of a medicament for treating or delaying progression of cancer or reducing or inhibiting tumor growth in a subject in need thereof.

In other aspects, the disclosure provides an immunomodulatory fusion protein of the disclosure, and an optional pharmaceutically acceptable carrier, or a pharmaceutical composition of the disclosure, in the manufacture of a medicament for treating or delaying progression of cancer or reducing or inhibiting tumor growth in a subject in need thereof.

Other aspects provide an immunomodulatory fusion protein-metal hydroxide complex of the disclosure, and an optional pharmaceutically acceptable carrier, or a pharmaceutical composition of the disclosure, for use as a medicament. In some aspects, the disclosure provides an immunomodulatory fusion of the disclosure, and an optional pharmaceutically acceptable carrier, or a pharmaceutical composition of the disclosure, for use as a medicament.

In other aspects, the disclosure provides a method for reducing or inhibiting tumor growth or treating cancer in a subject, the method comprising administering to a subject in need thereof, an effective amount an immunomodulatory fusion protein-metal hydroxide complex of the disclosure, or the pharmaceutical composition of the disclosure, and an effective amount of a second composition comprising a tumor antigen-targeting antibody, or antigen-binding fragment thereof, thereby reducing or inhibiting tumor growth or treating cancer in the subject. In other aspects, the disclosure provides a method for reducing or inhibiting tumor growth or treating cancer in a subject, the method comprising administering to a subject in need thereof, an effective amount an immunomodulatory fusion protein of the disclosure, or the pharmaceutical composition of the disclosure, and an effective amount of a second composition comprising a tumor antigen-targeting antibody, or antigen-binding fragment thereof, thereby reducing or inhibiting tumor growth or treating cancer in the subject.

In any of the foregoing or related aspects, the tumor antigen is a tumor-associated antigen (TAA), a tumor-specific antigen (TSA), or a tumor neoantigen. In some aspects, the tumor antigen-targeting antibody specifically binds human HER-2/neu, EGFR, VEGFR, CD20, CD33, or CD38.

In other aspects, the disclosure provides a method for reducing or inhibiting tumor growth or treating cancer in a subject, the method comprising administering to a subject in need thereof, an effective amount an immunomodulatory fusion protein-metal hydroxide complex of any one of the disclosure, or the pharmaceutical composition of the disclosure, and an effective amount of a second composition comprising a cancer vaccine, thereby reducing or inhibiting tumor growth or treating cancer in the subject. In other aspects, the disclosure provides a method for reducing or inhibiting tumor growth or treating cancer in a subject, the method comprising administering to a subject in need thereof, an effective amount an immunomodulatory fusion protein of any one of the disclosure, or the pharmaceutical composition of the disclosure, and an effective amount of a second composition comprising a cancer vaccine, thereby reducing or inhibiting tumor growth or treating cancer in the subject.

In any of the foregoing or related aspects, the cancer vaccine is a population of cells immunized in vitro with a tumor antigen and administered to the subject. In some aspects, the cancer vaccine is a peptide comprising one or more tumor-associated antigens. In some aspects, the cancer vaccine is an amphiphilic peptide conjugate comprising a tumor-associated antigen, a lipid, and optionally a linker, wherein the amphiphilic peptide conjugate binds albumin under physiological conditions. In some aspects, the cancer vaccine further comprises an adjuvant.

Yet other aspects of the disclosure provide a method for reducing or inhibiting tumor growth or treating cancer in a subject, the method comprising administering to a subject in need thereof, an effective amount an immunomodulatory fusion protein-metal hydroxide complex of the disclosure, or the pharmaceutical composition of the disclosure, and an effective amount of a second composition comprising an immune checkpoint inhibitor, thereby reducing or inhibiting tumor growth or treating cancer in the subject. In some aspects, the disclosure provides a method for reducing or inhibiting tumor growth or treating cancer in a subject, the method comprising administering to a subject in need thereof, an effective amount an immunomodulatory fusion protein of the disclosure, or the pharmaceutical composition of the disclosure, and an effective amount of a second composition comprising an immune checkpoint inhibitor, thereby reducing or inhibiting tumor growth or treating cancer in the subject.

In any of the foregoing or related aspects, the immune checkpoint inhibitor comprises an antibody or antigen binding fragment thereof which binds PD-1, PD-L1, CTLA-4, LAG3, or TIM3.

Other aspects of the disclosure provide a method for reducing or inhibiting tumor growth or treating cancer in a subject, the method comprising administering to a subject in need thereof, an effective amount an immunomodulatory fusion protein-metal hydroxide complex of the disclosure, or the pharmaceutical composition of the disclosure, and an effective amount of a second composition comprising an adoptive cell therapy, thereby reducing or inhibiting tumor growth or treating cancer in the subject. In some aspects, the disclosure provides a method for reducing or inhibiting tumor growth or treating cancer in a subject, the method comprising administering to a subject in need thereof, an effective amount an immunomodulatory fusion protein of the disclosure, or the pharmaceutical composition of the disclosure, and an effective amount of a second composition comprising an adoptive cell therapy, thereby reducing or inhibiting tumor growth or treating cancer in the subject.

In any of the foregoing or related aspects, the adoptive cell therapy comprises an immune effector cell comprising a chimeric antigen receptor (CAR) molecule which binds to a tumor antigen. In some aspects, the CAR molecule comprises an antigen binding domain, a transmembrane domain, and an intracellular domain comprising a costimulatory domain and/or a primary signaling domain. In some aspects, the antigen binding domain binds to the tumor antigen associated with the disease. In some aspects, the tumor antigen is selected from CD19, EGFR, Her2/neu, CD30 and BCMA. In some aspects, the immune effector cell is a T cell, such as a CD8+ T cell. In some aspects, the immune effector cell is a natural killer (NK) cell.

In any of the foregoing or related aspects, the immunomodulatory fusion protein-metal hydroxide complex or the pharmaceutical composition are administered intratumorally. In some aspects, the immunomodulatory fusion protein-metal hydroxide complex or the pharmaceutical composition and the second composition are administered concurrently or sequentially.

In any of the foregoing or related aspects, the immunomodulatory fusion protein or the pharmaceutical composition are administered intratumorally. In some aspects, the immunomodulatory fusion protein or the pharmaceutical composition and the second composition are administered concurrently or sequentially.

In any of the foregoing or related aspects, the methods described herein comprise administering more than one immunomodulatory fusion protein-metal hydroxide complex, immunomodulatory fusion protein or pharmaceutical composition, wherein the immunomodulatory domains are different. In some aspects, the immunomodulatory domains are different cytokines. In some aspects, the more than one immunomodulatory fusion protein-metal hydroxide complex, immunomodulatory fusion protein or pharmaceutical composition are formulated together. In some aspects, the more than one immunomodulatory fusion protein-metal hydroxide complex, immunomodulatory fusion protein or pharmaceutical composition are formulated separately. In some aspects, the more than one immunomodulatory fusion protein-metal hydroxide complex, immunomodulatory fusion protein or pharmaceutical composition are administered concurrently or sequentially.

BRIEF DESCRIPTION OF THE DRAWINGS

FIG. 4A provides MW comparison for IFNg-IFNg-ABP10 (SEQ ID NO: 162; K and IK), IFNg-IFNg-MSA-ABP10 (SEQ ID NO: 160; K and IK), MSA-IL2-ABP10 (SEQ ID NO: 146; K and IK), and MSA-IL2 (SEQ ID NO: 204; K and IK). FIG. 4B provides MW comparison for MSA-IL2-ABP10 (K and IK), lysozyme, and lysozyme-ABP10 (SEQ ID NO: 156).

FIG. 5A provides quantification for MSA-IL2 alone or fused to ABP3 (SEQ ID NO: 91), ABP4 (SEQ ID NO: 93), ABP 5 (SEQ ID NO: 95), ABP6 (SEQ ID NO: 97), ABP7 (SEQ ID NO: 99), ABP8 (SEQ ID NO: 101), ABP10 (SEQ ID NO: 103), or ABP11 (SEQ ID NO: 105); FIG. 5B provides quantification for MSA-IL2 alone or fused to ABP8 (MSA-IL2-ABP8; SEQ ID NO: 150); and FIG. 5C provides quantification for MSA-IL2 alone, MSA-IL2-ABP10 or MSA-IL2 fused to ABP17 (MSA-IL2-ABP17; SEQ ID NO: 152).

ABP10K and scIL12-MSA-ABP10K, either as free protein or complexed with alum, as measured by in vitro activation of IL12 signaling in HEK-Blue IL12 reporter cells. Shown is a comparison to scIL12-MSA as positive control and MSA as negative control.

FIG. 28A provides a schematic showing a treatment schedule for mice inoculated with B16F10 melanoma flank tumors and treated with a single dose of a tumor-targeting antibody (TA99) administered by intraperitoneal (i.p.) injection and an MSA-IL2 fusion protein administered by intratumoral (i.tu.) injection. FIG. 28B provides a line graph showing mouse survival following treatment according to FIG. 28A with TA99 alone or in combination with free MSA-IL2, MSA-IL2 fused to a collagen-binding domain (lumican), MSA-IL2 adsorbed to alum, MSA-IL2-ABP10K adsorbed to alum, or ABP10K-MSA-IL2 adsorbed to alum. FIGS. 28C-28H provide line graphs showing tumor area measured at regular intervals following treatment according to FIG. 28A with TA99 alone (FIG. 28C) or in combination with MSA-IL2 (FIG. 28D), lumican-MSA-IL2 (FIG. 28E), MSA-IL2 adsorbed to alum (FIG. 28F), MSA-IL2-ABP10K adsorbed to alum (FIG. 28G), or ABP10K-MSA-IL2 adsorbed to alum (FIG. 28H).

Figures 29A, 29B, 29C:
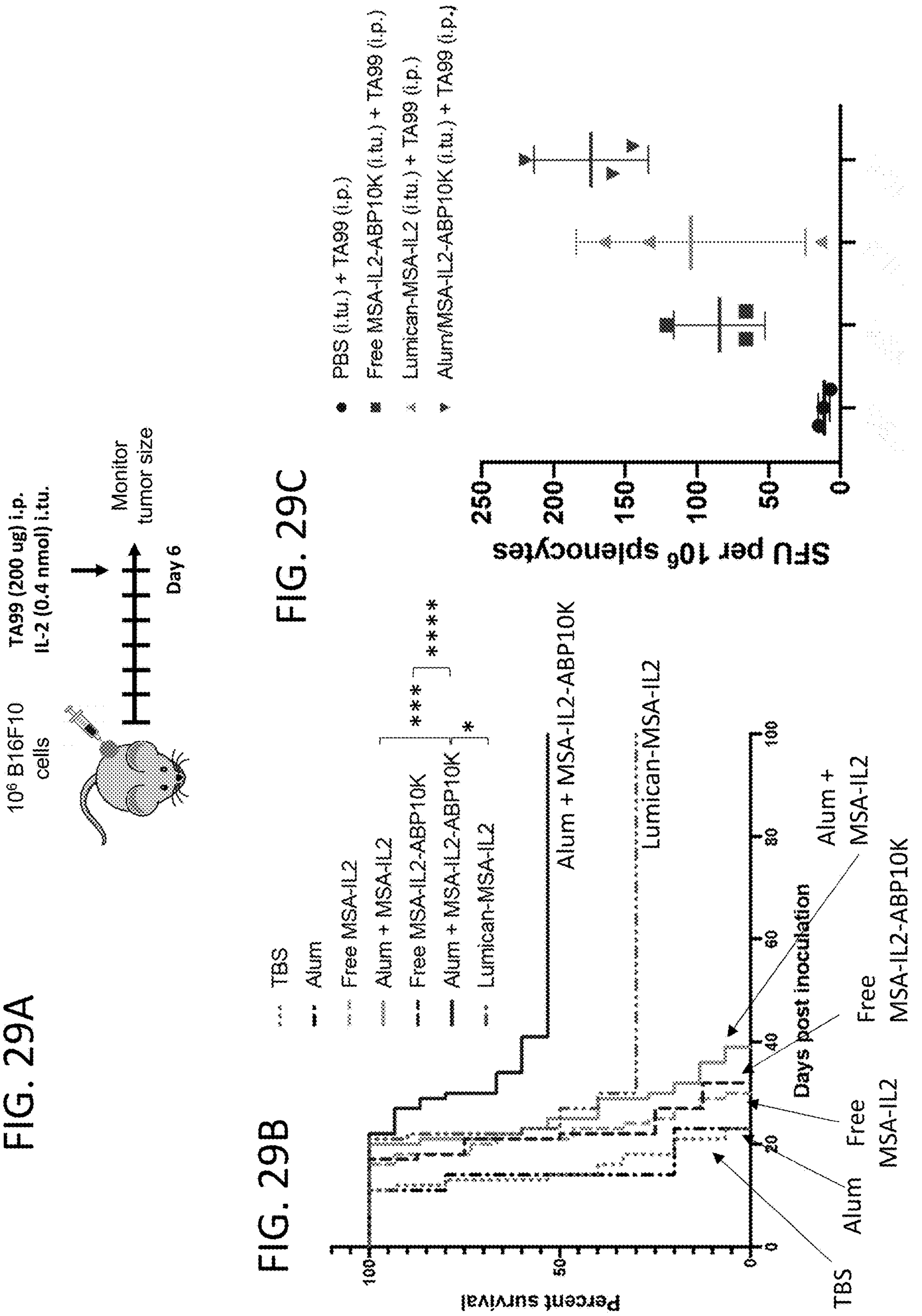
Figure 29D:
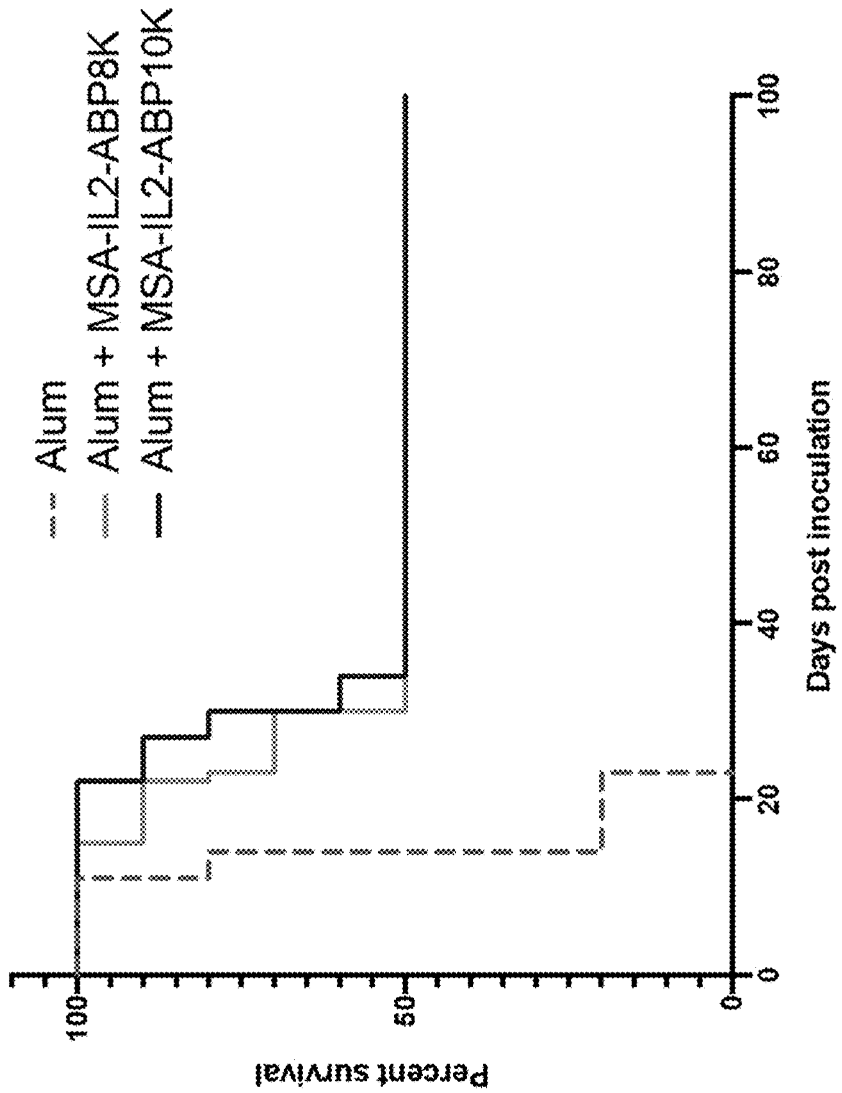

FIG. 29A provides a schematic showing a treatment schedule for mice inoculated with B16F10 flank tumors and treated with a single dose of TA99 administered by i.p. injection and MSA-IL2 fusion protein by i.tu. injection. FIG. 29B provides a graph showing mouse survival following treatment according to FIG. 29A with TA99 alone or in combination with free MSA-IL2, MSA-IL2 with alum, free MSA-IL2-ABP10K, MSA-IL2-ABP10K complexed with alum, Lumican-MSA-IL2, or alum alone. *=p<0.05, *=p<0.001, =p<0.0001 FIG. 29C provides a graph quantifying the number of B16F10-reactive spot forming units (SFU) per 1 million splenocytes as measured by an IFNγ ELISPOT. The splenocytes were isolated on day 12 post tumor inoculation from mice treated according to FIG. 29A. FIG. 29D provides a graph showing mouse survival following treatment according to the schedule shown in FIG. 29**A, with TA99 in combination with MSA-IL2-ABP10K complexed with alum, MSA-IL2-ABP8K complexed with alum, or alum alone.

Figure 30A:
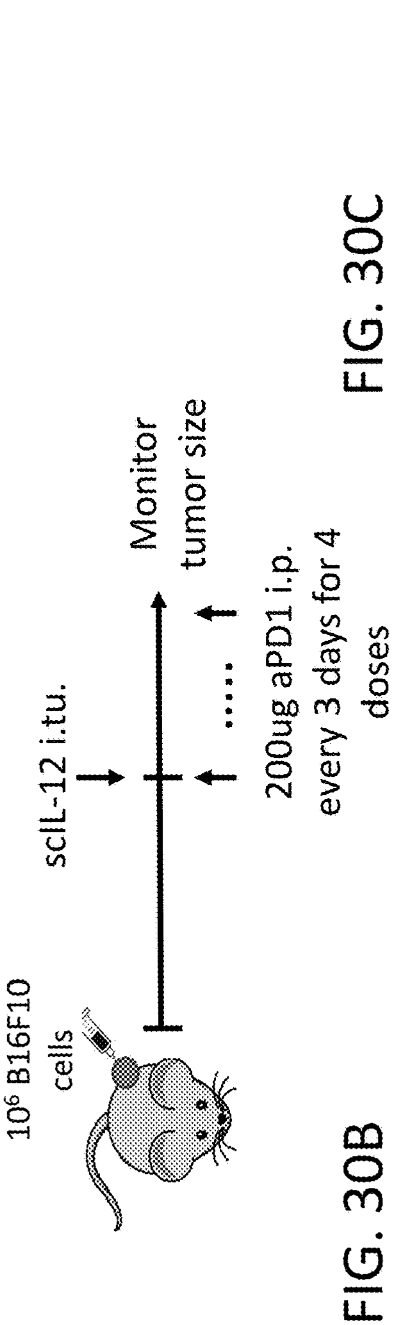
Figure 30B:
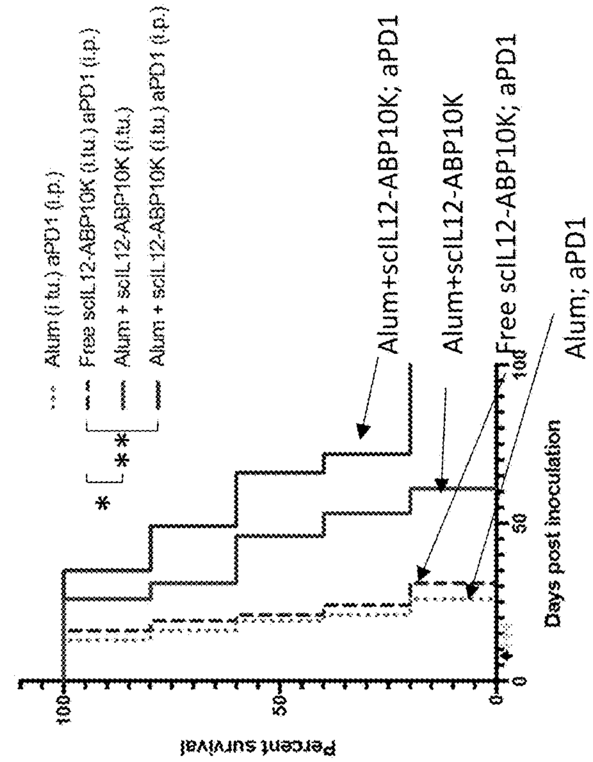
Figure 30C:
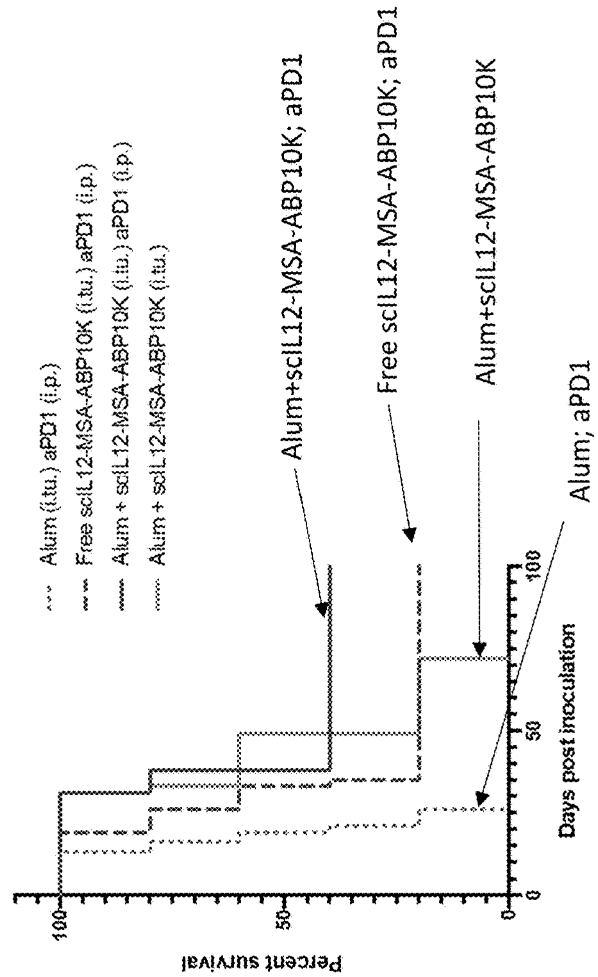

FIG. 30A provides a schematic showing a treatment schedule for mice inoculated with B16F10 flank tumors and treated with anti-PD-1 antibody administered by ip injection and single-dose IL12 fusion protein administered by i.tu. injection. The IL12 fusion protein was either scIL12 directly fused to ABP10 (scIL12-ABP10) or scIL12-MSA fused to ABP10 (scIL12-MSA-ABP10). The mice received IL12 fusion protein complexed with alum alone, IL12 fusion protein complexed with alum and anti-PD-1 antibody, or free IL12 fusion protein and anti-PD-1 antibody. Control mice received alum by i.tu injection and anti-PD-1 antibody by ip injection. FIGS. 30B-30C provide graphs showing mouse survival following administration according to FIG. 30A, either with scIL12-ABP10 fusion protein (FIG. 30B) or scIL12-MSA-ABP10 fusion protein (FIG. 30C). *=p<0.05, **=p<0.01

Figure 31A:
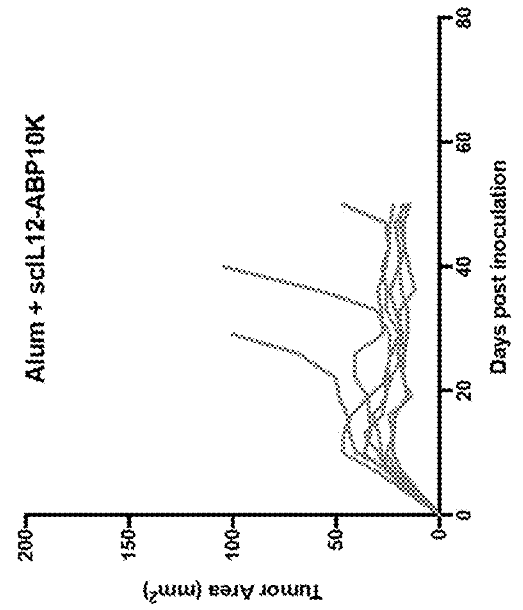
Figure 31B:
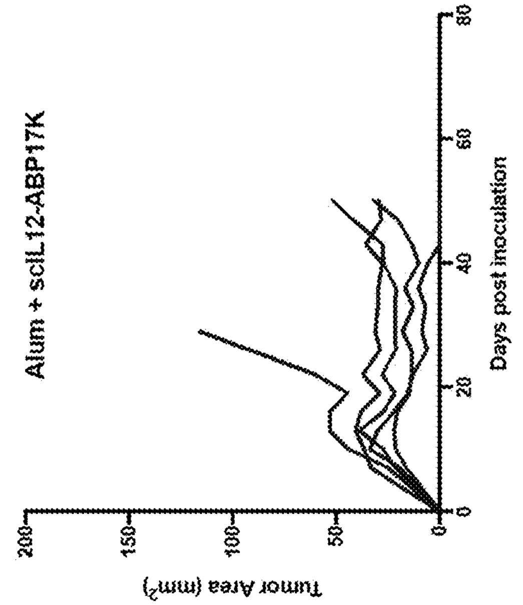

FIGS. 31A-31D provides graphs showing tumor area over time following tumor inoculation in B16F10-tumor bearing mice administered anti-PD-1 antibody and IL12 fusion proteins according to the treatment schedule depicted in FIG. 30A. The IL12 fusion proteins were either scIL12 fused to ABP10 (scIL12-ABP10) and complexed with alum (FIG. 31A) or scIL12 fused to ABP17 (scIL12-ABP17) and complexed with alum (FIG. 31B). Treatment with scIL12-ABP10 without alum (FIG. 31C) and alum alone (FIG. 31D) were used as control groups.

Figure 32A:
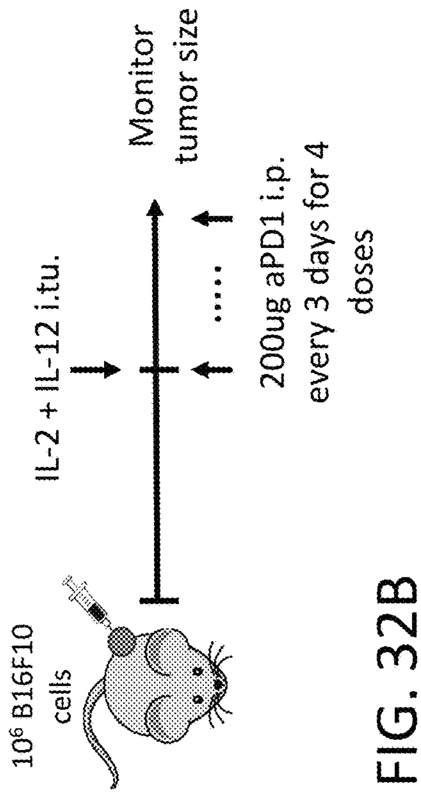
Figure 32B:
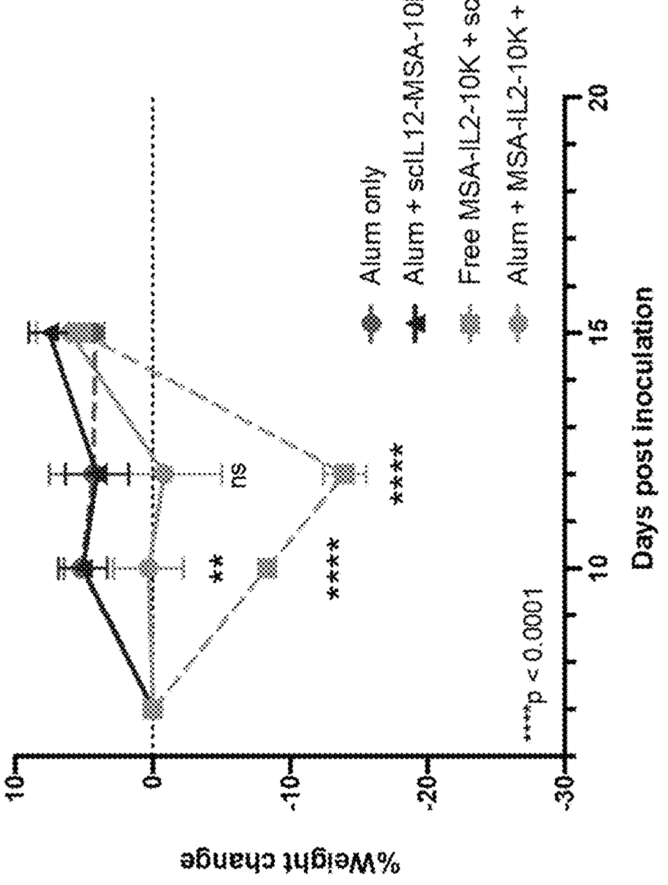
Figure 32C:
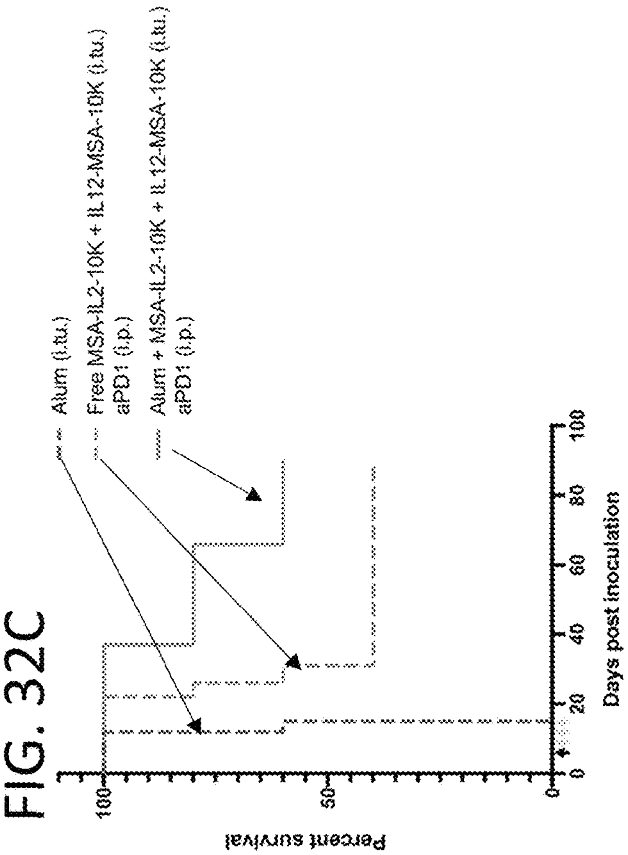

FIG. 32A provides a schematic showing a treatment schedule for mice inoculated with B16F10 flank tumors and treated with anti-PD-1 antibody administered by ip injection and single-dose IL12 and/or IL2 fusion proteins administered by i.tu injection. The mice were administered anti-PD-1 antibody in combination with (i) free MSA-IL2-ABP10K and free scIL12-MSA-ABP10K, (ii) MSA-IL2-ABP10K and scIL12-MSA-ABP10K each complexed to alum, or (iii) scIL12-MSA-ABP10K complexed to alum. Control mice received an i.tu injection of alum. FIGS. 32B-32C provide graphs showing % body weight change over time normalized to body weight prior to treatment (FIG. 32B) and survival of mice (FIG. 32C) following treatment according to FIG. 32A.  p<0.01; **p<0.0001.

DETAILED DESCRIPTION OF THE DISCLOSURE

Immunomodulatory Fusion Proteins and Metal Hydroxide Complexes

The present disclosure provides novel compositions and methods directed to enhancing an immune response against a tumor (e.g., a cancer-specific immune response) resulting from administration of an immunomodulatory fusion protein to a vertebrate. In accordance with the disclosure, the immune response is enhanced by administering an immunomodulatory fusion protein in a form whereby its presentation to the immune response potentiates a response. For example, promoting, increasing, or enhancing the duration wherein the immunomodulatory fusion protein is available in the tumor or in tumor draining lymph nodes, or promoting, increasing, or enhancing activation of immune cells (e.g., dendritic cells, cytotoxic T cells) against tumor cells. The present disclosure arises from discoveries that an immunomodulatory fusion protein adsorbed to a metal hydroxide (e.g., alum) by electrostatic and other secondary forces alone does not remain adsorbed to the metal hydroxide (e.g., alum) to a high degree. However, the antigen adsorbed to the metal hydroxide (e.g., alum) by ligand exchange remains tightly bound and following injection at a tumor site, remains at the site of injection for an extended period, resulting in a robust cancer-specific immune response. Thus, provided herein are methods and compositions for generating an immunomodulatory fusion protein for adsorption via ligand exchange to a metal hydroxide (e.g., alum) for use in generating a cancer-specific immune response following administration in vivo.

Accordingly, provided herein are methods for increasing phosphorylation of an immunomodulatory fusion protein to increase adsorption, or to decrease release from, a metal hydroxide (e.g., alum). In some embodiments, a method of the disclosure provides an immunomodulatory fusion protein comprising an immunomodulatory domain, a metal hydroxide-binding peptide, and optionally a stabilizing domain, wherein the metal hydroxide-binding peptide comprises one or more kinase target motifs of a secretory pathway kinase. When expressed in a host cell comprising the secretory pathway kinase, the one or more kinase target motifs are phosphorylated, providing an immunomodulatory fusion protein modified during recombinant expression with phosphate groups. The resulting immunomodulatory fusion protein is further contacted with a metal hydroxide (e.g., alum), wherein the phosphorylated kinase target motifs of the metal hydroxide-binding peptide allow adsorption via ligand exchange to the metal hydroxide (e.g., alum), thereby forming an immunomodulatory fusion protein-metal hydroxide complex. Such a method is useful, for example, by enabling an easier mode of manufacturing using methods of recombinant protein expression and purification known to one skilled in the art.

In other embodiments, a method of the disclosure provides a polypeptide comprising an immunomodulatory domain, optionally linked to a stabilizing domain, that is further crosslinked to a metal hydroxide-binding peptide comprising one or more hydroxyl replacement groups (e.g., phosphorylated amino acid residues) via a polypeptide-reactive moiety. Thus, the method enables modification of a polypeptide comprising an immunomodulatory domain following recombinant expression of the polypeptide. The resulting immunomodulatory fusion protein is further contacted with a metal hydroxide (e.g., alum), wherein the one or more hydroxyl replacement groups (e.g., phosphorylated amino acid residues) of the metal hydroxide-binding peptide enable adsorption via ligand exchange to a metal hydroxide (e.g., alum), thereby forming an immunomodulatory fusion protein-metal hydroxide complex. Such a method is useful to the skilled artisan. For example, by enabling the covalent attachment of a metal hydroxide-binding peptide comprising non-natural amino acid residues that confer higher affinity binding to a metal hydroxide (e.g., alum).

Metal Hydroxides

In some embodiments, the disclosure provides an immunomodulatory fusion protein-metal hydroxide complex, wherein an immunomodulatory fusion protein is absorbed to a metal hydroxide. Adsorption to a metal hydroxide occurs by a ligand exchange mechanism, and the substitution results in the formation of an inner-sphere surface complex, including the immunomodulatory fusion protein and the metal hydroxide, whereby the immunomodulatory fusion protein is strongly adsorbed to the adjuvant particle. As used herein, the term "ligand exchange" is defined as a substitution, or exchange, of a surface hydroxyl by another ligand, in this case an antigen comprising a hydroxyl-replacement group. Methods for measuring adsorption via ligand exchange are known to those of skill in the art. For example, adsorption can be measured by ellipsometry (ELM), surface plasmon resonance (SPR), optical waveguide lightmode spectroscopy (OWLS), attenuated total internal reflectance-infrared spectroscopy (ATR-IR), circular dichroism spectroscopy (CD), total internal reflectance-infrared spectroscopy (TIRF), and other high resolution microscopy techniques. In some embodiments, these methods show the spatial arrangement between the domains of the immunomodulatory fusion protein.

As used herein, the term "metal hydroxide" is used to refer to a substance that includes at least one hydroxyl group bound to a metal, that is capable of adsorbing an immunomodulatory fusion protein having a hydroxyl-replacement moiety, and that is capable of aiding the immunomodulatory fusion protein in eliciting a cancer-specific immune response when delivered to a vertebrate. In some embodiments, the metal hydroxide is selected to be one that is biocompatible for humans and non-humans. A preferred metal hydroxide adjuvant for use in accordance with the present invention is an aluminum-containing metal hydroxide. The term "aluminum-containing metal hydroxide" is defined as a substance that includes at least one hydroxyl group bound to aluminum. Examples of aluminum-containing metal hydroxide are aluminum hydroxide and aluminum phosphate.

A person skilled in the relevant field will appreciate that the term "aluminum hydroxide" is used in this field to identify a crystalline aluminum oxyhydroxide compound. Aluminum hydroxide has only hydroxyl groups at the surface, covalently bonded to aluminum. The term "aluminum phosphate" is used in this field to identify amorphous aluminum hydroxyphosphate. Aluminum phosphate has phosphate groups and hydroxyl groups at the surface, covalently bonded to aluminum.

The principles of the present invention are similarly applicable to metal hydroxide other than aluminum-containing metal hydroxides. As further alternative, non-limiting examples of metal hydroxides, the present invention contemplates that iron hydroxide or calcium phosphate are suitable for use in accordance with the invention.

The present invention also contemplates the use of modified metal hydroxides, such as, for example, modified aluminum-containing metal hydroxides, in immunogenic formulations for delivering modified, hydroxyl-replacing immunomodulatory fusion proteins. As used herein, the term "modified metal hydroxide" is used to refer to a metal hydroxide in which a fraction of the surface hydroxyl groups have been replaced or modified such that the number of surface hydroxyl groups available for ligand exchange is reduced. One exemplary manner of modifying a metal hydroxide adjuvant in accordance with the invention is by contacting the metal hydroxide with a phosphate-containing solution for a period of time sufficient to cause phosphate substitution of surface hydroxyl groups to occur (also referred to herein as phosphorylating some of the surface hydroxyl groups). For example, when aluminum hydroxide is exposed to phosphate, the phosphate can displace a surface hydroxyl and form an inner-sphere surface complex (covalent bond) with surface aluminum, thereby modifying the surface structure of the aluminum hydroxide adjuvant. Surface hydroxyl groups of aluminum phosphate adjuvant can be phosphorylated in a similar manner.

A metal hydroxide (e.g., alum) can be modified as described in order to alter the density of hydroxyl groups on the surface of metal hydroxide particles that are available for ligand exchange. Alternatively or in addition, modification of a metal hydroxide (e.g., alum) in this manner may be desirable for other reasons. For example, the disclosure contemplates that a modification in the density of hydroxyl groups on the surface of metal hydroxide (e.g., alum) particles will accordingly modify the degree of adsorption or coupling of an immunogenic composition.

Non-limiting examples of hydroxyl-replacement groups include, fluoride groups, citrate groups, phosphate groups, sulfate groups and carbonate groups. Aluminum hydroxide has a high affinity for phosphate, which can replace surface hydroxyls in a ligand exchange reaction. In some embodiments, a metal hydroxide-binding comprises one or more hydroxyl-replacement groups comprising a phosphate group. Aluminum has even higher affinity for fluorine. In some embodiments, a metal hydroxide-binding comprises one or more hydroxyl-replacement groups comprising a fluorine group.

In some embodiments, an immunomodulatory fusion protein adsorbed via ligand exchange to a metal hydroxide is of sufficient mass to prevent size-dependent diffusion from the site of injection in a tissue (e.g., a tumor). Methods for measuring diffusion from the tissue are known to those of skill in the art. For example, diffusion can be measured by in vivo imaging, or via microscopy of tissue sections over time. Exemplary methods are described in at least Schmidt & Wittrup, Mol Canc Ther. 2009' and Wittrup et al., Methods in Enzymol 2012, each of which is herein incorporated by reference in their entirety.

Kinase Target Motifs

In some embodiments, the present disclosure provides an immunomodulatory fusion protein comprising a metal hydroxide-binding peptide comprising at least one kinase target motif. Protein kinases catalyze the transfer of the γ-phosphate from ATP to a specific amino acid in a protein. A kinase target motif comprises an amino acid that is phosphorylated by a kinase (e.g., a kinase phopshoacceptor). In eukaryotes, the amino acids that are generally phosphorylated by a kinase are serine (Ser), threonine (Thr), and tyrosine (Tyr) residues. Additionally, many kinases comprise structural elements that confer specificity such that the kinase phosphorylates a phosphoacceptor amino acid of a particular kinase target motif. A kinase target motif refers to the amino acid sequence immediately N-terminal and C-terminal to the phosphoacceptor amino acid residue that is necessary for kinase recognition and phosphorylation. The kinase target motifs recognized by cellular kinases varies widely. Methods of identifying a kinase target motif of a given kinase are known in the art. For example, a mutational analysis of a known kinase substrate is used to determine a kinase target motif as described by Kemp, et al, (1975) PNAS 72:3448-3452, Daile, et al., (1975) *Nature* 257:416-418, and Pearson, et al (1991) *Methods Enzymol.* 200:62-81. In another example, a peptide library screen is used to determine a kinase target motif, wherein a kinase of interest is added with ATP to a soluble mixture of $10^9$ peptides with only a single phosphorylatable residue as described by Songyang, et al (1994) *Curr Biol* 4:973-982. The kinase reaction is allowed to occur for a short period of time before the phosphorylated peptides are separated from non-phosphorylated peptides and the mixture is sequenced. Identification of preferred amino acids at each position is obtained by comparing the abundance of amino acids at each position in the phosphorylated fraction compared to the starting mixture. In another example, biotinylated dual-oriented peptide libraries comprising a Ser and/or Thr residue in a first fixed position and a second fixed amino acid as described by Hutti, et al (2004) *Nature Methods* 1:27-29. The peptide mixture is incubated with the kinase in a 96-well plate format, then transferred to avidin-coated membrane for analysis of phosphorylation by autoradiography. Using such methods, the kinase target motifs of certain cellular kinases have been identified, such as those listed in Table 1 and further described by the references listed or by Pinna, et al (1996) *Biochim Biophys Acta* 1314:191-225.

TABLE 1 kinase target motifs of cellular kinases

| Kinase | Kinase target motif | Reference |
|---|---|---|
| Protein kinase A (PKA) | R-R-X-S/T-Φ | Songyang, et al (1994) Curr Biol 4:973-982 |
| cAMP-dependent protein kinase | R-R/K-X-S-Φ | Kemp, et al. J Biol Chem, 252:4888 |
| Cyclin-dependent kinase (CDK) | S/T-P-X-K/R | Songyang, et al (1994) Curr Biol 4:973-982 |
| Extracellular-regulated kinase-2 (ERK2) | P-X-S/T-P | Songyang, et al (1996) Mol Cell Biol 16:6486-6493 |
| Casein kinase-1 (CK1) | pS-X-X-S/T D/E-D/E-D/E-X-X-S/T-Φ-pS/pT-X-X-S/T-Φ | Flotow, et al (1990) J. Biol Chem. 265:14264-14269; Marin et al (2003) PNAS 100:10193-10200 |
| Casein kinase-2 (CK2) | S/T-D/E-X-D/E | Meggio, et al (2003) FASEB J 17:349-368 |
| Glycogen synthase kinase-3 (GSK3) | S-X-X-X-pS | Fiol, et al (1990) J. Biol Chem. 265:6061-6065 |
| Calmodulin-dependent protein kinase-2 (CaMK2) | R-X-X-S/T | Songyang, et al (1996) Mol Cell Biol 16:6486-6493 |
| Abelson murine leukaemia virus tyrosine kinase (ABL) | I/V/L-Y-X-X-P/F | Till, et al (1999) J Biol Chem 274:4995-5003 |
| Epidermal growth factor receptor (EGFR) | E-E-E-Y-F (SEQ ID NO: 207) | Songyang, et al (1995) Nature 373:536-539 |
| Rous sarcoma virus tyrosine kinase (Src) | E-E-I-Y-E/G-X-F (SEQ ID NO: 208) | Songyang, et al (1995) Nature 373:536-539 |
| Insulin receptor tyrosine kinase (IRK) | Y-M-M-M (SEQ ID NO: 209) | Songyang, et al (1995) Nature 373:536-539 |

TABLE 1-continued kinase target motifs of cellular kinases

| Kinase | Kinase target motif | Reference |
|---|---|---|
| Protein kinase B (PKB/AKT) | R-X-R-X-X-S/T | Obata, et al (2000) J. Biol Chem 275:36108-36115; Alessi, et al (1996) FEBS Lett399:333-338d |
| Protein kinase D (PKD) | L/I-X-R-X-X-S/T | Hutti, et al (2004) Nature Methods 1:27-29 |
| Proviral integration site kinases 1-3 (PIM 1-3) | R-X-R-X-X-S/T | Hutti, et al (2004) Nature Methods 1:27-29, Friedmann, et al (1992) Arch. Biochem. Biophys. 298:54-601 |
| AMP-activated protein kinase (AMPK) | Φ-X-R-X-X-S-X-X-X-I/L | Dale, et al (1995) FEBS Lett, 361:191-195; Gwinn, et al (2008) Mol Cell 30:214-226 |
| Mitogen-activated protein kinase | P/Φ-X-S/T-P | Gonzalez et al (1991) JBC 266:22159-22163 |
| NimA-related kinase | Φ-X-X-S/T | Songyang,et al (1996) Mol Cell Biol 16:6486-6493 |

Phosphoacceptor amino acid underlined
Φ = hydrophobic amino acid
X = any amino acid
pS or pT = priming phosphoserine or phosphothreonine In some embodiments, the disclosure provides immunomodulatory fusion proteins comprising a metal hydroxide-binding peptide comprising one or more kinase target motifs of a secretory pathway kinase. The secretory pathway refers to the endoplasmic reticulum (ER), Gogh apparatus, and the vesicles that travel in between them as well as the cell membrane and lysosomal storage compartments. The secretory pathway provides the pathway whereby a cell secretes proteins into the extracellular environment. Numerous proteins are synthesized and sorted into the secretory pathway by entering the ER. This occurs during translation when a ribosome synthesizing the protein is bound to the rough ER and the protein being synthesized crosses the ER membrane cotranslationally. Entry into the secretory pathway is directed by an ER-targeting leader sequence. An ER-targeting leader sequence comprising a stretch of hydrophobic amino acids is generally present at the N-terminus of a protein, and directs translocation of the protein into the ER lumen.

Proteins sorted into the secretory pathway that are soluble are localized in the ER lumen and are subsequently sorted to the lumen of other organelles or secreted from the cell. Proteins destined to be secreted are incorporated into small transport vesicles and move to the cis-Gogli reticulum. The proteins are either recycled back to the ER or move by cisternal migration to the trans-Golgi. From the trans face of the Golgi, secretory proteins are sorted into transport vesicles for secretion or to secretory vesicles for storage within the cell.

It is known in the art that an intracellular protein that localizes to the cytosol or nucleus can be modified with an ER-targeting leader sequence to direct the protein to the secretory pathway. Accordingly, in some embodiments, a kinase that localizes to the cytosol or nucleus, such as those listed in Table 1, is modified with an ER-targeting leader sequence to direct the kinase to the secretory pathway, thereby generating a “secretory pathway kinase”. Moreover, it is known in the art that polypeptides comprising a C-terminal anchor peptide (e.g., KDEL (SEQ ID NO: 233), e.g., HDEL (SEQ ID NO: 234)) have increased retention in the secretory pathway. In some embodiments, a kinase is further modified with an anchor peptide to promote or increase retention in the secretory pathway and/or decreased secretion.

In some embodiments, an immunomodulatory fusion protein comprising an immunomodulatory domain, a metal hydroxide-binding peptide, and optionally a stabilizing domain described herein is made in transfected host cells using recombinant DNA techniques, wherein the metal hydroxide-binding peptide comprises one or more kinase target motifs of a cellular kinase listed in Table 1. In some embodiments, a cell is transfected with a recombinant DNA molecule encoding the immunomodulatory fusion protein and a recombinant DNA molecule encoding a kinase that comprises an ER-targeting leader sequence, a kinase domain derived from a kinase in Table 1, and an anchor peptide, wherein the kinase is localized to the secretory pathway by the ER-targeting leader sequence and the anchor peptide, and wherein the one or more kinase target motifs of the metal hydroxide-binding peptide are phosphorylated by the kinase in the secretory pathway, thereby increasing phosphorylation of the immunomodulatory fusion protein.

Most kinases are localized to the nucleus or cytosol of the cell. However, some kinases are present in the secretory pathway and function to phosphorylate proteins destined for secretion. Naturally-occurring secretory pathway kinases have been identified and described (Ishikawa, et al (2008) *Science* 321:401-404; Tagliabracci et al, (2012) *Science* 336:1150-1153; Tagliabracci, et al (2015) *Cell* 161:1619-1632; Tagliabracci et al (2013) *Trends Biochem Sci* 38:121-130). As described, the secretory pathway kinases comprise an N-terminal ER-targeting leader sequence for directing the kinase to the secretory pathway and a C-terminal kinase domain. Additionally, the secretory pathway kinases lack a predicted transmembrane helix, allowing the kinase domain to orient in the ER and/or Golgi lumen in close proximity to proteins in the secretory pathway. Naturally-occurring human secretory pathway kinases include, but are not limited to, four jointed box kinase 1, Fam20A, Fam20B, Fam20C (also referred to as Golgi casein kinase), Fam198A, Fam198B, Fam69A, Fam69B, Fam69C, and vertebrate lonesome kinase (VLK).

In some embodiments, the disclosure provides immunomodulatory fusion proteins comprising a metal hydroxide-binding peptide comprising two or more kinase target motifs of the secretory pathway kinase Fam20C. Fam20C is a human kinase that has been identified for phosphorylation of more than 100 secreted phosphoproteins, which comprises a substantial portion of the extracellular phosphoproteome (Tagliabracci, et al (2015) *Cell* 161:1619-1632). Fam20C phosphorylates casein and is often referred to as Golgi enriched fraction casein kinase. Additionally, Fam20C phosphorylates serine and has been shown to phosphorylate kinase targets motif comprising the amino acid sequence Ser-X-Glu (e.g., S-X-E), Ser-X-pSer (e.g., S-X-pS), and Ser-X-Gln-X-X-Asp-Glu-Glu (S-X-Q-X-X-D-E-E)(SEQ ID NO: 210) wherein X is any amino acid, and pS is phosphorylated serine (Mercier, et al (1981) *Biochimie,* 63:1-17; Mercier et al (1971) *Eur J. Biochem.* 23:41-51; Lasa-Benito (1996) *FEBS Lett.* 382:149; Brunati, et al (2000) 3:765, Tagliabracci, et al (2015) *Cell* 161:1619-1632; Tagliabracci, et al (2012) Science 336:1150-1153). For example, a peptide substrate derived from β-casein comprising the amino acid sequence KKIEKFQSEEQQQ (β28-40, SEQ ID NO: 99) comprises an S-X-E kinase target motif, wherein the serine is phosphorylated by Fam20C.

In some embodiments, the disclosure provides an immunomodulatory fusion protein comprising a metal hydroxide-binding peptide comprising one or more kinase target motifs of the secretory pathway kinase Fam20C, wherein the kinase target motif comprises an amino acid sequence S-X-E, wherein X is any amino acid, and wherein serine is modified with a phosphate. In some embodiments, the one or more kinase target motifs of the secretory pathway kinase Fam20C, comprises an amino acid sequence S-X-E, wherein X is E, S, V, or G, and wherein serine is modified with a phosphate. In some embodiments, the one or more kinase target motifs of the secretory pathway kinase Fam20C, comprises an amino acid sequence S-E-E.

In some embodiments, the disclosure provides an immunomodulatory fusion protein comprising a metal hydroxide-binding peptide comprising one or more kinase target motifs of the secretory pathway kinase Fam20C, wherein the kinase target motif comprises an amino acid sequence S-X-S, wherein X is any amino acid, and wherein one or both serine residues are modified with a phosphate.

In some embodiments, the metal hydroxide-binding peptide comprises at least one, two, or three kinase target motifs. In some embodiments, the kinase target motifs are sequential.

Metal-Hydroxide Binding Peptide

In some embodiments, the disclosure provides an immunomodulatory fusion protein comprising a metal hydroxide-binding peptide. In some embodiments, the metal hydroxide-binding peptide comprises at least one phosphorylated amino acid. In some embodiments, the metal hydroxide-binding peptide comprises at least two phosphorylated amino acids. In some embodiments, the metal hydroxide-binding peptide comprises at least three phosphorylated amino acids. In some embodiments, the metal hydroxide-binding peptide comprises at least four phosphorylated amino acids. In some embodiments, the metal hydroxide-binding peptide comprises at least five phosphorylated amino acids. In some embodiments, the metal hydroxide-binding peptide comprises at least six phosphorylated amino acids. In some embodiments, the metal hydroxide-binding peptide comprises at least seven phosphorylated amino acids. In some embodiments, the metal hydroxide-binding peptide comprises at least eight phosphorylated amino acids. In some embodiments, the metal hydroxide-binding peptide comprises at least nine phosphorylated amino acids. In some embodiments, the metal hydroxide-binding peptide comprises at least ten phosphorylated amino acids. In some embodiments, the metal hydroxide-binding peptide comprises at least eleven phosphorylated amino acids. In some embodiments, the metal hydroxide-binding peptide comprises at least twelve phosphorylated amino acids. In some embodiments, the metal hydroxide-binding peptide comprises at least thirteen phosphorylated amino acids. In some embodiments, the metal hydroxide-binding peptide comprises at least fourteen phosphorylated amino acids. In some embodiments, the metal hydroxide-binding peptide comprises at least fifteen phosphorylated amino acids.

In some embodiments, a metal hydroxide-binding peptide comprises a phosphorylated amino acid that is selected from a group consisting of: phosphorserine, phoshotyrosine, or phosphothreonine. In some embodiments, a metal hydroxide-binding peptide comprises at least one phosphoserine.

In some embodiments, a metal hydroxide-binding peptide comprises phosphoserine residues. In some embodiments, a metal hydroxide-binding peptide comprises 1-15 consecutive phosphoserine residues.

In some embodiments, a metal hydroxide-binding peptide is about 6-15, about 10-25, about 10-50, about 10-100 amino acids in length. In some embodiments, a metal hydroxide-binding peptide is about 10 amino acids in length. In some embodiments, a metal hydroxide-binding peptide is about 15 amino acids in length. In some embodiments, a metal hydroxide-binding peptide is about 20 amino acids in length. In some embodiments, a metal hydroxide-binding peptide is about 25 amino acids in length. In some embodiments, a metal hydroxide-binding peptide is about 30 amino acids in length. In some embodiments, a metal hydroxide-binding peptide is about 35 amino acids in length. In some embodiments, a metal hydroxide-binding peptide is about 40 amino acids in length. In some embodiments, a metal hydroxide-binding peptide is about 45 amino acids in length. In some embodiments, a metal hydroxide-binding peptide is about 50 amino acids in length. In some embodiments, a metal hydroxide-binding peptide is about 55 amino acids in length. In some embodiments, a metal hydroxide-binding peptide is about 60 amino acids in length. In some embodiments, a metal hydroxide-binding peptide is about 65 amino acids in length. In some embodiments, a metal hydroxide-binding peptide is about 70 amino acids in length. In some embodiments, a metal hydroxide-binding peptide is about 75 amino acids in length. In some embodiments, a metal hydroxide-binding peptide is about 80 amino acids in length. In some embodiments, a metal hydroxide-binding peptide is about 85 amino acids in length. In some embodiments, a metal hydroxide-binding peptide is about 90 amino acids in length. In some embodiments, a metal hydroxide-binding peptide is about 95 amino acids in length. In some embodiments, a metal hydroxide-binding peptide is about 100 amino acids in length.

In some embodiments, a metal hydroxide-binding peptide of the disclosure comprises one or more target motifs of a secretory pathway kinase. In some embodiments, a metal hydroxide-binding peptide comprises one kinase target motif of a secretory pathway kinase. In some embodiments, a metal hydroxide-binding peptide comprises two kinase target motifs of a secretory pathway kinase. In some embodiments, a metal hydroxide-binding peptide comprises three kinase target motifs of a secretory pathway kinase. In some embodiments, a metal hydroxide-binding peptide comprises four kinase target motifs of a secretory pathway kinase. In some embodiments, a metal hydroxide-binding peptide comprises five kinase target motifs of a secretory pathway kinase. In some embodiments, a metal hydroxide-binding peptide comprises six kinase target motifs of a secretory pathway kinase. In some embodiments, a metal hydroxide-binding peptide comprises seven kinase target motifs of a secretory pathway kinase. In some embodiments, a metal hydroxide-binding peptide comprises eight kinase target motifs of a secretory pathway kinase. In some embodiments, a metal hydroxide-binding peptide comprises nine kinase target motifs of a secretory pathway kinase. In some embodiments, a metal hydroxide-binding peptide comprises ten kinase target motifs of a secretory pathway kinase. In some embodiments, a metal hydroxide-binding peptide comprises eleven kinase target motifs of a secretory pathway kinase. In some embodiments, a metal hydroxide-binding peptide comprises twelve kinase target motifs of a secretory pathway kinase.

In some embodiments, a metal hydroxide-binding peptide of the disclosure comprises two or more kinase target motifs of a secretory pathway kinase, wherein the amino acid sequence of the two or more kinase target motifs is the same. In some embodiments, a metal hydroxide-binding peptide of the disclosure comprises two or more kinase target motifs of a secretory pathway kinase, wherein the amino acid sequence of the two or more kinase target motifs is different.

In some embodiments, a metal hydroxide-binding peptide of the disclosure comprises two or more kinase target motifs of a secretory pathway kinase that are sequential without an intervening amino acid linker. In some embodiments, the metal hydroxide-binding peptide comprises two kinase target motifs of a secretory pathway kinase that are sequential without an intervening amino acid linker. In some embodiments, the metal hydroxide-binding peptide comprises three kinase target motifs of a secretory pathway kinase that are sequential without an intervening amino acid linker. In some embodiments, the metal hydroxide-binding peptide comprises four kinase target motifs of a secretory pathway kinase that are sequential without an intervening amino acid linker. In some embodiments, the metal hydroxide-binding peptide comprises five kinase target motifs of a secretory pathway kinase that are sequential without an intervening amino acid linker. In some embodiments, the metal hydroxide-binding peptide comprises six kinase target motifs of a secretory pathway kinase that are sequential without an intervening amino acid linker. In some embodiments, the metal hydroxide-binding peptide comprises seven kinase target motifs of a secretory pathway kinase that are sequential without an intervening amino acid linker. In some embodiments, the metal hydroxide-binding peptide comprises eight kinase target motifs of a secretory pathway kinase that are sequential without an intervening amino acid linker.

In some embodiments, a metal hydroxide-binding peptide of the disclosure comprises two or more kinase target motifs of a secretory pathway kinase with an intervening amino acid linker, wherein the amino acid linker comprises about 1-5, about 1-10, about 1-15, about 1-20, about 1-25, about 1-30, about 1-35, about 1-40, about 1-45, about 1-50 amino acids. In some embodiments, the metal hydroxide-binding peptide comprises two or more kinase target motifs of a secretory pathway kinase with an intervening amino acid linker, wherein the amino acid linker comprises about 15, about 14, about 13, about 12, about 11, about 10, about 9, about 8, about 7, about 6, about 5, about 4, about 3, about 2, or about 1 amino acids. In some embodiments, a linker comprises a gly-ser polypeptide linker.

In some embodiments, a metal hydroxide-binding peptide comprises an amino acid sequence $([A]-[L])_x$, wherein A comprises the amino acid sequence of a kinase target motif of a secretory pathway kinase disclosed herein, wherein L comprises the amino acid sequence of an amino acid linker, and wherein x=1-15.

In some embodiments, a metal hydroxide-binding peptide of the disclosure comprises one or more kinase target motifs of a secretory pathway kinase, wherein the first kinase target motif (e.g., N-terminal kinase target motif) is positioned at the N-terminus of the metal hydroxide-binding peptide. In some embodiments, the metal hydroxide-binding peptide comprises one or more kinase target motifs of a secretory pathway kinase, wherein the first kinase target motif (e.g., N-terminal kinase target motif) is separated from the N-terminus by about 1-5, about 1-10, about 5-10, about 5-15, about 10-15, about 10-20, about 10-30, about 10-40, about 10-50 amino acids. In some embodiments, the metal hydroxide-binding peptide comprises one or more kinase target motifs of a secretory pathway kinase, wherein the first kinase target motif (e.g., N-terminal kinase target motif) is separated from the N-terminus by about 15, about 14, about 13, about 12, about 11, about 10, about 9, about 8, about 7, about 6, about 5, about 4, about 3, about 2, about 1 amino acids. In some embodiments, the metal hydroxide-binding peptide comprises one or more kinase target motifs of a secretory pathway kinase, wherein the first kinase target motif (e.g., N-terminal kinase target motif) is separated from the N-terminus by one amino acid. In some embodiments, the metal hydroxide-binding peptide comprises one or more kinase target motifs of a secretory pathway kinase, wherein the first kinase target motif (e.g., N-terminal kinase target motif) is separated from the N-terminus by two amino acids. In some embodiments, the metal hydroxide-binding peptide comprises one or more kinase target motifs of a secretory pathway kinase, wherein the first kinase target motif (e.g., N-terminal kinase target motif) is separated from the N-terminus by three amino acids. In some embodiments, the metal hydroxide-binding peptide comprises one or more kinase target motifs of a secretory pathway kinase, wherein the first kinase target motif (e.g., N-terminal kinase target motif) is separated from the N-terminus by four amino acids. In some embodiments, the metal hydroxide-binding peptide comprises one or more kinase target motifs of a secretory pathway kinase, wherein the first kinase target motif (e.g., N-terminal kinase target motif) is separated from the N-terminus by five amino acids.

In some embodiments, a metal hydroxide-binding peptide of the disclosure comprises one kinase target motif of a secretory pathway kinase, wherein the kinase target motif is positioned at or near (e.g., separated by 20, 19, 18, 17, 16, 15, 14, 13, 12, 11, 10, 9, 8, 7, 6, 5, 4, 3, 2, 1 amino acids) the C-terminus of the metal hydroxide-binding peptide. In some embodiments, the metal hydroxide-binding peptide comprises two kinase target motifs of a secretory pathway kinase, wherein the second kinase target motif (e.g., C-terminal kinase target motif) is positioned at or near (e.g., separated by 20, 19, 18, 17, 16, 15, 14, 13, 12, 11, 10, 9, 8, 7, 6, 5, 4, 3, 2, 1 amino acids) the C-terminus of the metal hydroxide-binding peptide. In some embodiments, the metal hydroxide-binding peptide comprises three kinase target motifs of a secretory pathway kinase, wherein the third kinase target motif (e.g., C-terminal kinase target motif) is positioned at or near (e.g., separated by 20, 19, 18, 17, 16, 15, 14, 13, 12, 11, 10, 9, 8, 7, 6, 5, 4, 3, 2, 1 amino acids) the C-terminus of the metal hydroxide-binding peptide. In some embodiments, the metal hydroxide-binding peptide comprises four kinase target motifs of a secretory pathway kinase, wherein the fourth kinase target motif (e.g., C-terminal kinase target motif) is positioned at or near (e.g., separated by 20, 19, 18, 17, 16, 15, 14, 13, 12, 11, 10, 9, 8, 7, 6, 5, 4, 3, 2, 1 amino acids) the C-terminus of the metal hydroxide-binding peptide. In some embodiments, the metal hydroxide-binding peptide comprises five kinase target motifs of a secretory pathway kinase, wherein the fifth kinase target motif (e.g., C-terminal kinase target motif) is positioned at or near (e.g., separated by 20, 19, 18, 17, 16, 15, 14, 13, 12, 11, 10, 9, 8, 7, 6, 5, 4, 3, 2, 1 amino acids) the C-terminus of the metal hydroxide-binding peptide. In some embodiments, the metal hydroxide-binding peptide comprises six kinase target motifs of a secretory pathway kinase, wherein the sixth kinase target motif (e.g., C-terminal kinase target motif) is positioned at or near (e.g., separated by 20, 19, 18, 17, 16, 15, 14, 13, 12, 11, 10, 9, 8, 7, 6, 5, 4, 3, 2, 1 amino acids) the C-terminus of the metal hydroxide-binding peptide.

Exemplary Metal-Hydroxide Binding Peptides

In some embodiments, the disclosure provides an immunomodulatory fusion protein comprising a metal hydroxide-binding peptide comprising one or more kinase target motifs of the secretory pathway kinase Fam20C, wherein the one or more kinase target motifs comprises an amino acid sequence S-X-E, wherein X is any amino acid, and wherein serine is modified with a phosphate. In some embodiments, the metal hydroxide-binding peptide comprises two kinase target motifs comprising an amino acid sequence S-X-E, wherein X is any amino acid sequence, wherein serine is modified with a phosphate, and wherein the kinase target motifs are the same or different. In some embodiments, the metal hydroxide-binding peptide comprises three kinase target motifs comprising an amino acid sequence S-X-E, wherein X is any amino acid sequence, wherein serine is modified with a phosphate, and wherein the kinase target motifs are the same or different. In some embodiments, the metal hydroxide-binding peptide comprises four kinase target motifs comprising an amino acid sequence S-X-E, wherein X is any amino acid sequence, wherein serine is modified with a phosphate, and wherein the kinase target motifs are the same or different. In some embodiments, the metal hydroxide-binding peptide comprises five kinase target motifs comprising an amino acid sequence S-X-E, wherein X is any amino acid sequence, wherein serine is modified with a phosphate, and wherein the kinase target motifs are the same or different. In some embodiments, the metal hydroxide-binding peptide comprises six kinase target motifs comprising an amino acid sequence S-X-E, wherein X is any amino acid sequence, wherein serine is modified with a phosphate, and wherein the kinase target motifs are the same or different. In some embodiments, the metal hydroxide-binding peptide comprises seven kinase target motifs comprising an amino acid sequence S-X-E, wherein X is any amino acid sequence, wherein serine is modified with a phosphate, and wherein the kinase target motifs are the same or different. In some embodiments, the metal hydroxide-binding peptide comprises eight kinase target motifs comprising an amino acid sequence S-X-E, wherein X is any amino acid sequence, wherein serine is modified with a phosphate, and wherein the kinase target motifs are the same or different. In some embodiments, the metal hydroxide-binding peptide comprises nine kinase target motifs comprising an amino acid sequence S-X-E, wherein X is any amino acid sequence, wherein serine is modified with a phosphate, and wherein the kinase target motifs are the same or different. In some embodiments, the metal hydroxide-binding peptide comprises ten kinase target motifs comprising an amino acid sequence S-X-E, wherein X is any amino acid sequence, wherein serine is modified with a phosphate, and wherein the kinase target motifs are the same or different. In some embodiments, the metal hydroxide-binding peptide comprises eleven kinase target motifs comprising an amino acid sequence S-X-E, wherein X is any amino acid sequence, wherein serine is modified with a phosphate, and wherein the kinase target motifs are the same or different. In some embodiments, the metal hydroxide-binding peptide comprises twelve kinase target motifs comprising an amino acid sequence S-X-E, wherein X is any amino acid sequence, wherein serine is modified with a phosphate, and wherein the kinase target motifs are the same or different.

In some embodiments, a metal hydroxide-binding peptide of the disclosure comprises at least one kinase target motif comprising an amino acid sequence S-X-E, wherein X is any amino acid, and wherein serine is modified with a phosphate. In some embodiments, a metal hydroxide-binding peptide of the disclosure comprises at least one kinase target motif comprising an amino acid sequence S-X-E, wherein X is selected from a group consisting of: E, S, V, H, and Q, and wherein at least one serine is modified with a phosphate. In some embodiments, a metal hydroxide-binding peptide of the disclosure comprises at least one kinase target motif comprising an amino acid sequence S-X-E, wherein X is E, and wherein serine is modified with a phosphate.

In some embodiments, a metal hydroxide-binding peptide of the disclosure comprises at least one kinase target motif comprising an amino acid sequence S-X-E, wherein the metal hydroxide-binding peptide comprises an amino acid sequence selected from a group consisting of: XXSXEXX (SEQ ID NO: 127) or XXSEEXX (SEQ ID NO: 128), wherein X is any amino acid, and wherein at least one serine is modified with a phosphate.

In some embodiments, a metal hydroxide-binding peptide of the disclosure comprises at least one kinase target motif comprising an amino acid sequence S-X-E, wherein the metal hydroxide-binding peptide comprises an amino acid sequence $Xaa_1$-$Xaa_2$-S-$Xaa_3$-E-$Xaa_4$-$Xaa_5$ (SEQ ID NO: 127), wherein $Xaa_1$ is F, M or G; $Xaa_2$ is Q, E or G; $Xaa_3$ is E, S, V, H, Q and G; $Xaa_4$ is Q, S or G; and $Xaa_5$ is Q, N, or G, and wherein at least one serine is modified with a phosphate. In some embodiments, $Xaa_3$ is E. In some embodiments, $Xaa_1$ is F; and $Xaa_2$ is Q. In some embodiments, $Xaa_1$ is M; and $Xaa_2$ is E. In some embodiments, $Xaa_1$ is G; and $Xaa_2$ is G. In some embodiments, $Xaa_4$ is Q; $Xaa_5$ is Q. In some embodiments, $Xaa_4$ is E; $Xaa_5$ is S. In some embodiments, $Xaa_4$ is G; $Xaa_5$ is G.

In some embodiments, a metal hydroxide-binding peptide of the disclosure comprises at least one kinase target motif comprising an amino acid sequence S-X-E, wherein the metal hydroxide-binding peptide comprises an amino acid sequence selected from a group consisting of: SEQ ID NO: 127, SEQ ID NO: 128, SEQ ID NO: 129; SEQ ID NO: 130, or SEQ ID NO: 131, wherein X is any amino acid, and wherein at least one serine is phosphorylated.

In some embodiments, a metal hydroxide-binding peptide of the disclosure comprises at least one kinase target motif comprising an amino acid sequence S-E-E, wherein the metal hydroxide-binding peptide comprises an amino acid sequence selected from a group consisting of: SEQ ID NO: 129; SEQ ID NO: 130, or SEQ ID NO: 131, wherein at least one serine is phosphorylated.

In some embodiments, a metal hydroxide-binding peptide of the disclosure comprises at least one kinase target motif comprising an amino acid sequence S-X-E, wherein the metal hydroxide-binding peptide comprises an amino acid sequence $Xaa_1$-$Xaa_2$-S-$Xaa_3$-E-$Xaa_4$-$Xaa_5$-[L]-S-$Xaa_3$-E-$Xaa_6$-$Xaa_7$ (SEQ ID NO: 133), wherein $Xaa_1$ is F, M or G; $Xaa_2$ is Q, E or G; $Xaa_3$ is E, S, V, H, Q and G; $Xaa_4$ is Q, S or G; $Xaa_5$ is Q, N, or G; $Xaa_5$ is G and $Xaa_6$ is G, and wherein L is a peptide linker, optionally a gly-ser polypeptide linker, optionally GGGS (SEQ ID NO: 132).

TABLE 2

Exemplary sequences for constructing a metal-hydroxide binding peptide

| Name | Amino acid sequence | SEQ ID NO |
|---|---|---|
| ABP22 | XX**SXE**XX | 127 |
| ABP23 | XX**SEE**XX | 128 |
| ABP24 | FQ**SEE**QQ | 129 |
| ABP25 | ME**SEE**SN | 130 |
| ABP26 | GG**SEE**GG | 131 |
| L (linker) | GGGS | 132 |
| ABP27 | XXSXEXXLSXEXX | 133 |

Shown in bold is the Fam20C kinase target motif S-X-E
Shown in bold underline is a serine residue modified with a phosphate
X is any amino acid In some embodiments, a metal hydroxide-binding peptide of the disclosure comprises at least one kinase target motifs comprising an amino acid sequence S-X-E, wherein the metal hydroxide-binding peptide comprises a sequence of linked amino acids comprising the formula $[A]_x$, wherein A is an amino acid sequence selected from a group consisting of: SEQ ID NO: 127, SEQ ID NO: 128, SEQ ID NO: 129, SEQ ID NO: 130, or SEQ ID NO: 131, wherein x is an integer whose value indicates the number of linked amino acid sequences indicated by A, and wherein x=1-15.

In some embodiments, a metal hydroxide-binding peptide of the disclosure comprises at least one kinase target motifs comprising an amino acid sequence S-X-E, wherein the metal hydroxide-binding peptide comprises a sequence of linked amino acids comprising the formula [A]-[B], wherein A and B are amino acid sequences that are the same or different selected from a group consisting of: SEQ ID NO: 127, SEQ ID NO: 128, SEQ ID NO: 129, SEQ ID NO: 130, or SEQ ID NO: 131.

In some embodiments, a metal hydroxide-binding peptide of the disclosure comprises at least one kinase target motifs comprising an amino acid sequence S-X-E, wherein the metal hydroxide-binding peptide comprises a sequence of linked amino acids comprising the formula $[A]-[B]_x$, wherein A and B are amino acid sequences that are the same or different selected from a group consisting of: SEQ ID NO: 127, SEQ ID NO: 128, SEQ ID NO: 129, SEQ ID NO: 130, or SEQ ID NO: 131, wherein x is an integer whose value indicates the number of linked amino acid sequences indicated by [A]-[B], and wherein x=1-8.

In some embodiments, a metal hydroxide-binding peptide of the disclosure comprises at least one kinase target motifs comprising an amino acid sequence S-X-E, wherein the metal hydroxide-binding peptide comprises a sequence of linked amino acids comprising the formula [A]-[L]-[A], wherein A is an amino acid sequence selected from a group consisting of: SEQ ID NO: 127, SEQ ID NO: 128, SEQ ID NO: 129, SEQ ID NO: 130, or SEQ ID NO: 131, and wherein L comprises an amino acid linker such as those described herein. In some embodiments, a linker comprises a gly-ser polypeptide linker. In some embodiments, L comprises the amino acid sequence GGGS (SEQ ID NO: 132).

In some embodiments, a metal hydroxide-binding peptide of the disclosure comprises at least one kinase target motifs comprising an amino acid sequence S-X-E, wherein the metal hydroxide-binding peptide comprises a sequence of linked amino acids comprising the formula $[A]-[L]-[A]_x$, wherein A is an amino acid sequence selected from a group consisting of: SEQ ID NO: 127, SEQ ID NO: 128, SEQ ID NO: 129, SEQ ID NO: 130, or SEQ ID NO: 131 wherein x is an integer whose value indicates the number of linked amino acid sequences indicated by [A]-[L]-[A], wherein x=1-4, and wherein L comprises an amino acid linker such as those described herein. In some embodiments, a linker comprises a gly-ser polypeptide linker. In some embodiments, L comprises the amino acid sequence GGGS (SEQ ID NO: 132).

In some embodiments, a metal hydroxide-binding peptide of the disclosure comprises at least one kinase target motifs comprising an amino acid sequence S-X-E, wherein the metal hydroxide-binding peptide comprises a sequence of linked amino acids comprising the formula [A]-[L]-[B], wherein A and B are amino acid sequences that are the same or different selected from a group consisting of: SEQ ID NO: 127, SEQ ID NO: 128, SEQ ID NO: 129, SEQ ID NO: 130, or SEQ ID NO: 131, and wherein L comprises an amino acid linker such as those described herein. In some embodiments, a linker comprises a gly-ser polypeptide linker. In some embodiments, L comprises the amino acid sequence GGGS (SEQ ID NO: 132).

In some embodiments, a metal hydroxide-binding peptide of the disclosure comprises at least one kinase target motifs comprising an amino acid sequence S-X-E, wherein the metal hydroxide-binding peptide comprises a sequence of linked amino acids comprising the formula $([A]-[L]-[B])_x$, wherein A and B are amino acid sequences that are the same or different selected from a group consisting of: SEQ ID NO: 127, SEQ ID NO: 128, SEQ ID NO: 129, SEQ ID NO: 130, or SEQ ID NO: 131, wherein x is an integer whose value indicates the number of linked amino acid sequences indicated by [A]-[L]-[B], wherein x=1-4, and wherein L comprises an amino acid linker such as those described herein. In some embodiments, a linker comprises a gly-ser polypeptide linker. In some embodiments, L comprises the amino acid sequence GGGS (SEQ ID NO: 132).

In some embodiments, a metal hydroxide-binding peptide of the disclosure comprises at least one kinase target motifs comprising an amino acid sequence S-X-E, wherein the metal hydroxide-binding peptide comprises an amino acid sequence selected from a group consisting of: SEQ ID NO: 91, SEQ ID NO: 93, SEQ ID NO: 95, SEQ ID NO: 97, SEQ ID NO: 99, and SEQ ID NO: 101 as shown in Table 3.

TABLE 3

Exemplary metal-hydroxide binding peptides comprising S-X-E motifs

| Name | Amino acid sequence | SEQ ID NO |
|---|---|---|
| ABP28 | XXSEEXXGGGSGGSEEGG | 134 |
| ABP3 | FQSEEQQGGGSGGSEEGG | 91 |
| ABP4 | MESEESNGGGSGGSEE | 93 |
| ABP5 | FRISHELDSASSEV | 95 |
| ABP6 | ASSQESGEEAGSQEN | 97 |
| ABP7 | KKIEKFQSEEQQQ | 99 |
| ABP8 | TVSSETDSISSEESVEHI | 101 |

Shown in bold is the Fam20C kinase target motif S-X-E, wherein X is any amino acid
Shown in underline is a serine residue modified with a phosphate In some embodiments, a metal hydroxide-binding peptide of the disclosure comprises one or more kinase target motifs comprising an amino acid sequence S-X-E, wherein the metal hydroxide-binding peptide comprises a sequence of linked amino acids comprising the formula $[C]_x$ wherein C is an amino acid sequence selected from a group consisting of: SEQ ID NO: 91, SEQ ID NO: 93, SEQ ID NO: 95, SEQ ID NO: 97, SEQ ID NO: 99, and SEQ ID NO: 101, and wherein x is an integer whose value indicates the number of linked amino acid sequences indicated by C, wherein x=1–4.

In some embodiments, a metal hydroxide-binding peptide comprising the formula $[C]_x$, wherein C is an amino acid sequence set forth by SEQ ID NO: 91, and wherein x=2, comprises an amino acid sequence set forth by SEQ ID NO: 115.

In some embodiments, a metal hydroxide-binding peptide comprising the formula $[A]_x$, wherein A comprises an amino acid sequence set forth by SEQ ID NO: 8 and wherein x=2, comprises an amino acid sequence set forth by SEQ ID NO: 107.

In some embodiments, a metal hydroxide-binding peptide of the disclosure comprises one or more kinase target motifs comprising an amino acid sequence S-X-E, wherein the metal hydroxide-binding peptide comprises a sequence of linked amino acids comprising the formula $[C]_x$-$[D]_y$, wherein C and D are amino acid sequences that are the same or different, and wherein C and D are selected from a group consisting of: SEQ ID NO: 91, SEQ ID NO: 93, SEQ ID NO: 95, SEQ ID NO: 97, SEQ ID NO: 99, and SEQ ID NO: 101, wherein x is an integer whose value indicates the number of linked amino acid sequences indicated by C, wherein y is an integer whose value indicates the number of linked amino acid sequences indicated by D, wherein x=1–4, wherein y=1-4, and wherein x and y are the same or different.

In some embodiments, a metal hydroxide-binding peptide comprising the formula $[C]_x$-$[D]_y$, wherein C is an amino acid sequence set forth by SEQ ID NO: 91, wherein D is an amino acid sequence set forth by SEQ ID NO: 93, wherein x=1, and wherein y=1, comprises an amino acid sequence set forth by SEQ ID NO: 103.

TABLE 4 exemplary metal hydroxide-binding peptides comprising four or more S-X-E motifs

| Name | Amino acid sequence | SEQ ID NO |
|---|---|---|
| ABP10 | FQSEEQQGGGSGGSEEGGME SEESNGGGSGGSEEGG | 103 |
| ABP11 | MESEESNGGGSGGSEEGGME SEESNGGGSGGSEEGG | 105 |
| ABP12 | TVSSETDSISSEESVEHITV SSETDSISSEESVEHI | 107 |
| ABP16 | FQSEEQQGGGSGGSEEGGFQ SEEQQGGGSGGSEEGG | 115 |

Shown in bold is the Fam20C kinase target motif S-X-E, wherein X is any amino acid
Shown in underline is a serine residue modified with a phosphate

Polypeptide-Reactive Moieties

In some embodiments, a polypeptide comprising at least one immunomodulatory domain, and optionally a stabilizing domain, is modified with a polypeptide-reactive moiety linked to a metal hydroxide-binding peptide, thereby forming an immunomodulatory fusion protein.

In some embodiments provided by the disclosure, the polypeptide-reactive moiety comprises a reactive or functional group selected from the group consisting of an amine-reactive group, a carboxyl-to-amine reactive group, a sulfhydryl-reactive group, an aldehyde- or carbonyl-reactive group, a hydroxyl reactive group, an azide-reactive group, and a photo-reactive group.

In some embodiments, the polypeptide-reactive moiety comprises an amine-reactive group. Non-limiting examples of amine-reactive groups include isothiocyanate, isocyanate, sulfonyl chloride, aldehydes, carbodiimide, acyl azide, anhydride, fluorobenzene, carbonate, N-hydroxysuccinimide ester (NHS ester), imidoester, epoxide, and fluorophenyl ester. In some embodiments, the polypeptide-reactive moiety comprises an amine-reactive group selected from the group consisting of N-hydroxysuccinimide ester (NHS ester), sulfo-NHS ester, imidoester, pentafluorophenyl ester, and hydroxymethyl phosphine.

In some embodiments, the polypeptide-reactive moiety comprises a carboxyl-to-amine reactive group comprising a carbodiimide In some embodiment, the carbodiimide is EDC. In other embodiments, the carbodiimide is DCC.

In some embodiments, the polypeptide-reactive moiety comprises a sulfhydryl-reactive group. Non-limiting examples of sulfhydryl-reactive groups include maleimide, haloacetyl (bromo- or iodo-), pyridyldisulfide, thiosulfonate, and vinylsulfone. In some embodiments, the polypeptide-reactive moiety comprises a sulfhydryl-reactive group comprising maleimide.

In some embodiments, the polypeptide-reactive moiety comprises an aldehyde- or carbonyl-reactive group. Examples of aldehyde- or carbonyl-reactive groups include, but are not limited to, hydrazide and alkoxyamine.

In some embodiments, the polypeptide-reactive moiety comprises a hydroxyl-reactive group. A non-limiting example of hydroxyl-reactive group is isocyanate.

In some embodiments, the polypeptide-reactive moiety comprises an azide-reactive group. A non-limiting example of an azide-reactive group is phosphine.

In some embodiments, the polypeptide-reactive moiety comprises a photo-reactive group. Examples of photo-reactive groups include, but are not limited to, phenyl azide, ortho-hydroxyphenyl azide, meta-hydroxyphenyl azide, tetrafluorophenyl azide, ortho-nitrophenyl azide, meta-nitrophenyl azide, diazirine, azido-methylcoumarin, and psoralen.

In some embodiments, the polypeptide-reactive moiety targets and reacts with a reactive or functional group selected from: a primary amine group (—NH2), a carboxyl group (—COOH), a sulfhydryl group (—SH), a carbonyl group (—CHO), an azide group (—N3).

In some embodiments provided by the disclosure, the polypeptide-reactive moiety may react with one or more reactive or functional groups comprising polypeptides of interest under conditions wherein the polypeptide is maintained in a folded state (e.g., physiological conditions). In some embodiments, the polypeptide-reactive moiety reacts with one or more reactive or functional groups of an antigen, such as a sidechain group of Lys, Cys, Ser, Thr, Tyr, His or Arg amino acid residues of the antigen. The polypeptide-reactive moiety may be amino-reactive, thiol-reactive, hydroxyl-reactive, imidazolyl-reactive or guanidinyl-reactive. Further exemplary reactive or functional groups suitable for the polypeptide-reactive moiety and methods of using the same are described in Hermanson "Bioconjugate Techniques" 3rd Edition, Academic Press, 2013, herein incorporated by reference in its entirety.

In some embodiments, the polypeptide-reactive moiety comprises a sortase recognition motif, wherein the moiety reacts with a terminal amino acid residues (e.g., glycine and/or alanine residues) of an immunomodulatory fusion protein upon catalytic action of sortase. Methods for use of sortase to mediate crosslinking between N-terminal or C-terminal amino acid residues (e.g., glycine and/or alanine residues) of a protein and a sortase recognition motif are known in the art and further described by Theile, et al (2013) *Nat Protoc* 8:1800-1807 and Guimaraes, et al (2013) *Nat. Protoc.* 8:1787-1799, and references listed therein. Briefly, a peptide (e.g., a metal hydroxide-binding peptide) comprising a sortase recognition motif, such as a LPXTG (SEQ ID NO: 211) or LPXTA (SEQ ID NO: 212) amino acid sequence wherein X is any amino acid, is added to a polypeptide of interest modified with a terminal amino acid sequence comprising glycine and/or alanine residues (e.g., an immunomodulatory fusion protein comprising an immunomodulatory domain, and optionally a stabilizing domain, and further comprising a terminal stretch of glycine and/or alanine residues) along with sortase, such as Sortase A derived from *Staphylococcus aureas*. Sortase cleaves between the threonine and glycine or alanine residues of the sortase recognition motif, forming a thioester intermediate with the peptide (e.g., a metal hydroxide-binding peptide). Nucleophilic attach by the terminally modified polypeptide of interest (e.g., an immunomodulatory fusion protein comprising an immunomodulatory domain, and optionally a stabilizing domain) results in the formation of a covalent bond between the peptide (e.g., a metal hydroxide-binding peptide) and the terminus of the polypeptide of interest.

Additionally, in some embodiments, a polypeptide of interest (e.g., an immunomodulatory fusion protein comprising an immunomodulatory domain, and optionally a stabilizing domain) comprises a sortase recognition motif that reacts via a sortase-mediated reaction to an amino acid linker comprising glycine and/or alanine residues attached to the metal hydroxide binding peptide. In some embodiments, a polypeptide of interest comprises a terminal sortase recognition motif (e.g., an N-terminal or a C-terminal) that reacts via a sortase-mediated reaction to an amino acid linker comprising glycine and/or alanine residues attached to the metal hydroxide binding peptide. In some embodiments, a polypeptide of interest comprises an internal loop comprising a sortase recognition motif that reacts via a sortase-mediated reaction to an amino acid linker comprising glycine and/or alanine residues attached to the metal hydroxide binding peptide.

Linkers

In some embodiments, a polypeptide comprising at least one immunomodulatory domain, and optionally a stabilizing domain, is modified with a polypeptide-reactive moiety linked to a metal hydroxide-binding peptide, thereby forming an immunomodulatory fusion protein. In some embodiments, a metal hydroxide-binding peptide is coupled to a polypeptide-reactive moiety with a linker.

In some embodiments, an immunomodulatory fusion protein comprises an immunomodulatory domain and a metal hydroxide-binding peptide, wherein the metal hydroxide-binding peptide is operably linked, optionally via a linker, by a polypeptide-reactive moiety to the terminus (e.g., N-terminus or C-terminus) of the immunomodulatory domain, thereby forming an immunomodulatory fusion protein.

In some embodiments, an immunomodulatory fusion protein comprises an immunomodulatory domain, a stabilizing domain, and a metal hydroxide-binding peptide, wherein the stabilizing domain is operably linked, optionally via a linker, to either the N-terminus or C-terminus of the immunomodulatory domain, and wherein the metal hydroxide-binding peptide is operably linked, optionally via a linker, by a polypeptide-reactive moiety to the terminus (e.g., N-terminus or C-terminus) of either the immunomodulatory domain or the stabilizing domain, thereby forming an immunomodulatory fusion protein.

In some embodiments, the metal hydroxide-binding peptide, optionally comprising a polypeptide-reactive moiety and/or a linker, provides at least one hydroxyl replacement groups (e.g., phosphate groups) that are effective to substitute for hydroxyl groups of a metal hydroxide (e.g., alum), thereby promoting, increasing, or enhancing adsorption to the metal hydroxide via ligand exchange.

For example, in some embodiments, a metal hydroxide-binding peptide comprising 1-15 consecutive phosphoserine residues is attached to a short poly(ethylene glycol) linker and an N-terminal maleimide functional group. In some embodiments, the maleimide functional group at the N-terminus of the metal hydroxide-binding peptide is covalently linked via a thioether linkage to a thiol group on a polypeptide comprising at least one immunomodulatory domain, and optionally a stabilizing domain, thereby forming an immunomodulatory fusion protein. In some embodiments, the immunomodulatory fusion protein is adsorbed to a metal hydroxide via the 1-15 consecutive phosphoserine residues of the metal hydroxide-binding peptide.

As a further example, in some embodiments, a metal hydroxide-binding peptide comprising 1-15 consecutive phosphoserine residues is attached via a short amino acid linker to an N-terminal sortase recognition tag. In some embodiments, the sortase recognition tag at the N-terminus of the metal hydroxide-binding peptide is cleaved by a sortase-mediated reaction to form an amide bond with a terminal glycine on a polypeptide comprising at least one immunomodulatory domain, and optionally a stabilizing domain, thereby forming an immunomodulatory fusion protein.

In some embodiments, the linker is a polypeptide linker, an ethylene glycol linker, or an oligonucleotide linker.

In yet another embodiment, the linker comprising a metal hydroxide-binding peptide are conjugated to an immunomodulatory fusion protein via azide functional groups and coupled to a DBCO-modified immunomodulatory fusion protein. Preferably, a linker compatible with the instant invention will be relatively non-immunogenic and not inhibit any non-covalent association among monomer subunits of a binding protein (e.g. an antibody). Exemplary linker domains are disclosed in U.S. Pat. No. 6,660,843, which is incorporated by reference herein.

In some embodiments, the linker may be a non-cleavable linker or a cleavable linker. A non-cleavable linker may include an amide bond or phosphate bond, and the cleavable linker may include a disulfide bond, acid-cleavable linkage, ester bond, anhydride bond, biodegradable bond, or enzyme-cleavable linkage.

Polypeptide Linkers

In some embodiments, a polypeptide linker is used to covalently link a polypeptide-reactive moiety comprising a sulfhydryl-reactive moiety to a metal hydroxide-binding peptide that comprises one or more hydroxyl-replacement groups, wherein the hydroxyl-replacement group comprises a phosphate group.

In some embodiments, the polypeptide linker is synthetic. As used herein, the term "synthetic" with respect to a polypeptide linker includes peptides (or polypeptides) which comprise an amino acid sequence (which may or may not be naturally occurring) that is linked in a linear sequence of amino acids to a reactive moiety. For example, the polypeptide linker may comprise non-naturally occurring polypeptides which are modified forms of naturally occurring polypeptides (e.g., comprising a mutation such as an addition, substitution or deletion) or which comprise a first amino acid sequence (which may or may not be naturally occurring).

In some embodiments, a polypeptide linker comprises or consists of a Gly-Ser linker. As used herein, the term "Gly-Ser linker" refers to a peptide that consists of glycine and serine residues. An exemplary Gly-Ser linker comprises an amino acid sequence of the formula $(Gly_4Ser)_n$(SEQ ID NO: 213), wherein n is a positive integer (e.g., 1, 2, 3, 4, or 5). In certain embodiments the Gly-Ser linker is $(Gly_4Ser)_1$ (SEQ ID NO: 214). In certain embodiments the Gly-Ser linker is $(Gly_4Ser)_2$ (SEQ ID NO: 215). In certain embodiments the Gly-Ser linker is $(Gly_4Ser)_3$ (SEQ ID NO: 216). In certain embodiments the Gly-Ser linker is $(Gly_4Ser)_4$ (SEQ ID NO: 217). In certain embodiments the Gly-Ser linker is $(Gly_4Ser)_5$ (SEQ ID NO: 218). In certain embodiments, the gly-ser linker may be inserted between two other sequences of the polypeptide linker (e.g., any of the polypeptide linker sequences described herein). In other embodiments, a Gly-Ser linker is attached at one or both ends of another sequence of the polypeptide linker (e.g., any of the polypeptide linker sequences described herein). In yet other embodiments, two or more Gly-Ser linker are incorporated in series in a polypeptide linker.

Other linkers that are suitable for use to prepare a metal hydroxide binding peptide linked to a polypeptide-reactive moiety described herein are known in the art, for example, the serine-rich linkers disclosed in U.S. Pat. No. 5,525,491, the helix forming peptide linkers (e.g., A(EAAAK)nA (n=2-5) (SEQ ID NO: 219)) disclosed in Arai et al., *Protein Eng* 2001; 14:529-32, and the stable linkers disclosed in Chen et al., *Mol Pharm* 2011; 8:457-65, i.e., the dipeptide linker LE, a thrombin-sensitive disulfide cyclopeptide linker, and the alpha-helix forming linker $LEA(EAAAK)_4ALEA(EAAAK)_4ALE$ (SEQ ID NO: 220).

Other exemplary linkers include GS linkers (i.e., (GS)n (SEQ ID NO: 221)), GGSG linkers (SEQ ID NO: 222) (i.e., (GGSG)n (SEQ ID NO: 223)), GSAT linkers (SEQ ID NO: 224), SEG linkers, and GGS linkers (i.e., (GGSGGS)n (SEQ ID NO: 225)), wherein n is a positive integer (e.g., 1, 2, 3, 4, or 5). Other suitable linkers for use in the to prepare a metal hydroxide binding peptide linked to a polypeptide-reactive moiety can be found using publicly available databases, such as the Linker Database (ibi.vu.nl/programs/linkerdbwww). The Linker Database is a database of inter-domain linkers in multi-functional enzymes which serve as potential linkers in novel fusion proteins (see, e.g., George et al., *Protein Engineering* 2002; 15:871-9).

It will be understood that variant forms of these exemplary polypeptide linkers can be created by introducing one or more nucleotide substitutions, additions or deletions into the nucleotide sequence encoding a polypeptide linker such that one or more amino acid substitutions, additions or deletions are introduced into the polypeptide linker. Mutations may be introduced by standard techniques, such as site-directed mutagenesis and PCR-mediated mutagenesis.

Polypeptide linkers of the invention are at least one amino acid in length and can be of varying lengths. In one embodiment, a polypeptide linker of the invention is from about 1 to about 50 amino acids in length. As used in this context, the term "about" indicates +/− two amino acid residues. Since linker length must be a positive integer, the length of from about 1 to about 50 amino acids in length, means a length of from 1 to 48-52 amino acids in length. In another embodiment, a polypeptide linker of the invention is from about 1-5 amino acids in length. In another embodiment, a polypeptide linker of the invention is from about 5-10 amino acids in length. In another embodiment, a polypeptide linker of the invention is from about 10-20 amino acids in length. In another embodiment, a polypeptide linker of the invention is from about 15 to about 50 amino acids in length.

In another embodiment, a polypeptide linker of the invention is from about 20 to about 45 amino acids in length. In another embodiment, a polypeptide linker of the invention is from about 15 to about 25 amino acids in length. In another embodiment, a polypeptide linker of the invention is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or 61 or more amino acids in length.

Polypeptide linkers can be introduced into polypeptide sequences using techniques known in the art. Modifications can be confirmed by DNA sequence analysis. Plasmid DNA can be used to transfect host cells for stable production of the polypeptides produced.

Ethylene Glycol Linkers

In some embodiments, the linker is one or more ethylene glycol (EG) units, more preferably 2 or more EG units (i.e., polyethylene glycol (PEG)). In some embodiments, a linker comprises or consists of a polyethylene glycol (PEG) linker. Polyethylene glycol or PEG refers to a chemical compound composed of repeating ethylene glycol units. An exemplary "PEG linker" comprises a compound of the formula: H—(O—CH2-CH2)n-OH, wherein n is a positive integer (e.g., 1, 10, 20, 50, 100, 200, 300, 400, 500, 600). In some embodiments, the PEG linker is PEG1000. In some embodiments, the PEG linker is PEG2000. In some embodiments, the PEG linker is PEG3000.

In some embodiments, a metal hydroxide binding peptide linked to a polypeptide-reactive moiety provided by the disclosure may comprise any polyethylene glycol (PEG) linker to join any protein reactive moiety to any metal hydroxide binding peptide comprising one or more hydroxyl-replacement groups described herein. For example, in some embodiments, a polyethylene glycol (PEG) linker can be used to covalently link an protein reactive moiety comprising a sulfhydryl-reactive moiety to an metal hydroxide binding peptide comprising one or more hydroxyl-replacement groups, wherein the hydroxyl-replacement group comprises a phosphate group.

In some embodiments, the precise number of ethylene glycol (EG) units comprising the metal hydroxide binding peptide linked to a polypeptide-reactive moiety may range between about 1 and about 100, between about 20 and about 80, between about 30 and about 70, or between about 40 and about 60 EG units. In some embodiments, the ethylene glycol linker has between about 45 and 55 EG, units. For example, in one embodiment, the ethylene glycol linker has 45 EG units. For example, in one embodiment, the ethylene glycol linker has 48 EG units.

Oligonucleotide Linkers

In some embodiments, the linker is an oligonucleotide. The linker can be have any sequence, for example, the sequence of the oligonucleotide can be a random sequence, or a sequence specifically chosen for its molecular or biochemical properties. In some embodiments, the linker includes one or more series of consecutive adenine (A), cytosine (C), guanine (G), thymine (T), uracil (U), or analog thereof. In some embodiments, the linker consists of a series of consecutive adenine (A), cytosine (C), guanine (G), thymine (T), uracil (U), or analog thereof.

In one embodiment, the linker is one or more guanines, for example between 1-10 guanines. In some embodiments, the linker in an ABP conjugate can include 0, 1, or 2 guanines. In some embodiments, the oligonucleotide comprises phosphorothioate intersubunit linkages Immunomodulatory Domain The immunomodulatory fusion proteins disclosed herein comprise at least one immunomodulatory domain. In some embodiments, the immunomodulatory fusion protein comprises one, two, three, four, or five immunomodulatory domains. In some embodiments, when more than one immunomodulatory domain is present in the fusion protein, the immunomodulatory domains are the same. In some embodiments, when more than one immunomodulatory domain is present in the fusion protein, the immunomodulatory domains are different.

In some embodiments, an immunomodulatory fusion protein comprises at least one immunomodulatory domain and a metal hydroxide-binding peptide comprising one or more phosphorylated amino acids, wherein the metal hydroxide-binding peptide is operably linked, optionally via a linker, to either the N-terminus or C-terminus of the immunomodulatory domain, thereby forming an immunomodulatory fusion protein.

In some embodiments, an immunomodulatory fusion protein comprises an immunomodulatory domain, a stabilizing domain, and a metal hydroxide-binding peptide, wherein the stabilizing domain is operably linked, optionally via a linker, to either the N-terminus or C-terminus of the immunomodulatory domain, and wherein the metal-hydroxide binding peptide is operably linked, optionally via a linker, to the terminus of either the immunomodulatory domain or the stabilizing domain, thereby forming an immunomodulatory fusion protein.

In some embodiments, an immunomodulatory fusion protein comprises an immunomodulatory domain, a stabilizing domain, and a metal hydroxide-binding peptide, wherein the metal hydroxide-binding peptide is operably linked, optionally via a linker, to either the N-terminus or C-terminus of the immunomodulatory domain, and wherein the stabilizing domain is operably linked, optionally via an amino acid linker, to the terminus of either the metal hydroxide-binding peptide or the immunomodulatory domain, thereby forming an immunomodulatory fusion protein.

In some embodiments, an immunomodulatory fusion protein comprises at least one immunomodulatory domain and a metal hydroxide-binding peptide, wherein the metal hydroxide-binding peptide is operably linked, optionally via a linker, by a polypeptide-reactive moiety to the terminus (e.g., N-terminus or C-terminus) of the at least one immunomodulatory domain, thereby forming an immunomodulatory fusion protein.

In some embodiments, an immunomodulatory fusion protein comprises at least one immunomodulatory domain, a stabilizing domain, and a metal hydroxide-binding peptide, wherein the stabilizing domain is operably linked, optionally via a linker, to either the N-terminus or C-terminus of the at least one immunomodulatory domain, and wherein the metal hydroxide-binding peptide is operably linked, optionally via a linker, by a polypeptide-reactive moiety to the remaining terminus (e.g., N-terminus or C-terminus) the at least one immunomodulatory domain or to the terminus of the stabilizing domain, thereby forming an immunomodulatory fusion protein.

In some embodiments, the immunomodulatory domain activates the activity of a cell of the immune system. For example, in some embodiments the immunomodulatory domain is an immune response stimulatory, such as, but not limited to, a cytokine, such as an interleukin, a chemokine, a member of the TNF family, an agonistic antibody, an immune checkpoint blocker, or a combination thereof. In some embodiments, the immunomodulatory domain enhances an immune response. In some embodiments, enhancement of an immune response includes stimulation of T cells, stimulation of B cells, stimulation of dendritic cell responses, or a combination thereof. In some embodiments, enhancement of an immune response results in cytokine production, antibody production, antigen-specific immune cell (e.g., CD8+ T cells or CD4+ T cells) production, stimulation of Type I interferon responses, or combinations thereof.

In some embodiments, the immunomodulatory domain comprises a polypeptide that activates, enhances or promotes a response by an immune cell. In some embodiments, the immunomodulatory domain comprises a polypeptide that inhibits, reduces or suppresses a response by an immune cell. In some embodiments, the immune cell is a lymphoid cell, including but not limited to T cells, B cells, NK cells and innate lymphoid cells. In some embodiments, the immune cell is a myeloid cell, including but not limited to monocytes, neutrophils, macrophages, dendritic cells, mast cells and granulocytes.

In some embodiments, the response of the immune cell is cytokine production, antibody production, production of antigen-specific immune cells, or a combination thereof.

Interleukins

In some embodiments, the immunomodulatory domain suitable for use in the immunomodulatory fusion proteins of the present disclosure, is an interleukin (IL). Interleukins are secreted proteins that bind to their specific receptors and play a role in the communication among leukocytes. Interleukins suitable for use as an immunomodulatory domain of the immunomodulatory fusion proteins include, but are not limited to: IL-2, IL-12, IL-15, IL-15 superagonist (IL-15SA), IL-21, IL-6, IL-5, IL-8, IL-7, IL-17, IL-23, IL-18, IL-1, IL-4, IL-3, IL-10, IL-13, and IL-9. In some embodiments, the interleukin suitable for use as an immunomodulatory domain comprises an amino acid sequence selected from SEQ ID NOs: 1-5 and 9-24. In some embodiments, the immunomodulatory domain is an IL-2 polypeptide. In some embodiments, the immunomodulatory domain is an IL-12 polypeptide. In some embodiments, the immunomodulatory domain is an IL-15 polypeptide. In some embodiments, the immunomodulatory domain is an IL-15 SA polypeptide.

In some embodiments, the immunomodulatory domain is an interleukin polypeptide that binds to a common gamma chain receptor. Interleukins that bind the common gamma chain receptor include, but are not limited to, IL-2, IL-4, IL-7, IL-9, IL-13, IL-15, IL-15/IL-15Rα and IL-21.

In some embodiments, the immunomodulatory domain is a polypeptide belonging to the IL-12 family. The IL-12 family comprises heterodimeric ligands comprised of an a subunit with helical structure (e.g., IL-12p35, IL-23p19, IL-27p28) and a β subunit (e.g., IL-12p40, IL-23p40 (which is identical to IL-12p40), EBI3). Exemplary members include IL-12, IL-23, IL-27 and IL-35.

In some embodiments, the immunomodulatory domain is a polypeptide belonging to the IL-1 superfamily. The Interleukin-1 (IL-1) family consists of 11 structurally related family members (IL-1α, IL-1-β, IL-1Ra, IL-18, IL-33 and IL-1F5 to IL-1 F10), that are among the most potent immune system signaling molecules, acting through a group of closely related receptors. All IL-1 receptors have a similar mode of activation: upon binding of ligand to the primary receptor subunit (i.e. IL-1R1 for IL-1α and β, IL-18R for IL-18 and ST2 for IL-33), a second receptor subunit is recruited (i.e. IL-1RAP for IL-1α and β, IL-18RAP for IL-18 and IL-1RAP for IL-33) and signaling is initiated via juxtaposition of the receptor subunits' cytoplasmic Toll/IL-1 receptor (TIR) domains. The dimerized TIR domains provide a docking platform for the MYD88 adaptor protein, which via recruitment of other intermediates leads to activation of the pro-inflammatory nuclear factor-κB (NF-κB) and mitogen-activated protein kinase (MAPK) pathways. The IL-1 family members are primarily produced by innate immune cells and act on a variety of cell types during the immune response. Accordingly, in some embodiments the immunomodulatory domain is an IL-18 polypeptide.

Interleukin-2 (IL-2)

In some embodiments, the immunomodulatory fusion protein comprises a member of the IL-2 family. In some embodiments, the member of the IL-2 family is IL-2. Interleukin-2 (IL-2) is a cytokine that induces proliferation of antigen-activated T cells and stimulates natural killer (NK) cells. The biological activity of IL-2 is mediated through a multi-subunit IL-2 receptor complex (IL-2R) of three polypeptide subunits that span the cell membrane: p55 (IL-2Rα, the alpha subunit, also known as CD25 in humans), p75 (IL-2Rβ, the beta subunit, also known as CD 122 in humans) and p64 (IL-2Rγ, the gamma subunit, also known as CD 132 in humans). T cell response to IL-2 depends on a variety of factors, including: (1) the concentration of IL-2; (2) the number of IL-2R molecules on the cell surface; and (3) the number of IL-2R occupied by IL-2 (i.e., the affinity of the binding interaction between IL-2 and IL-2R (Smith, "Cell Growth Signal Transduction is Quantal" In Receptor Activation by Antigens, Cytokines, Hormones, and Growth Factors 766:263-271, 1995)). The IL-2:IL-2R complex is internalized upon ligand binding and the different components undergo differential sorting. IL-2Rα is recycled to the cell surface, while IL-2 associated with the IL-2:IL-2RPγ complex is routed to the lysosome and degraded. When administered as an intravenous (i.v.) bolus, IL-2 has a rapid systemic clearance (an initial clearance phase with a half-life of 12.9 minutes followed by a slower clearance phase with a half-life of 85 minutes) (Konrad et al., Cancer Res. 50:2009-2017, 1990).

Outcomes of systemic IL-2 administration in cancer patients are far from ideal. While 15 to 20 percent of patients respond objectively to high-dose IL-2, the great majority do not, and many suffer severe, life-threatening side effects, including nausea, confusion, hypotension, and septic shock. The severe toxicity associated with high-dose IL-2 treatment is largely attributable to the activity of natural killer (NK) cells. NK cells express the intermediate-affinity receptor, IL-2RP$\gamma_c$, and thus are stimulated at nanomolar concentrations of IL-2, which do in fact result in patient sera during high-dose IL-2 therapy. Attempts to reduce serum concentration, and hence selectively stimulate IL-2RaP$\gamma_c$-bearing cells, by reducing dose and adjusting dosing regimen have been attempted, and while less toxic, such treatments were also less efficacious. Given the toxicity issues associated with high dose IL-2 cancer therapy, numerous groups have attempted to improve anti-cancer efficacy of IL-2 by simultaneously administering therapeutic antibodies. Yet, such efforts have been largely unsuccessful, yielding no additional or limited clinical benefit compared to IL-2 therapy alone. Accordingly, novel IL-2 therapies are needed to more effectively combat various cancers.

In some embodiments, the IL-2 is a human recombinant IL-2 such as Proleukin® (aldesleukin). Proleukin® is a human recombinant interleukin-2 product produced in *E. coli*. Proleukin® differs from the native interleukin-2 in the following ways: a) it is not glycosylated; b) it has no N-terminal alanine; and c) it has serine substituted for cysteine at amino acid positions 125. Proleukin® exists as biologically active, non-covalently bound microaggregates with an average size of 27 recombinant interleukin-2 molecules. Proleukin® (aldesleukin) is administered by intravenous infusion. In some embodiments, IL-2 is wild-type IL-2 (e.g., human IL-2 in its precursor form or mature IL-2. In some embodiments, IL-2 comprises the amino acid sequence set forth in SEQ ID NO: 1.

In certain embodiments, IL-2 is mutated such that it has an altered affinity (e.g., a higher affinity) for the IL-2R alpha receptor compared with unmodified IL-2. Site-directed mutagenesis can be used to isolate IL-2 mutants that exhibit high affinity binding to CD25, i.e., IL-2Rα, as compared to wild-type IL-2. Increasing the affinity of IL-2 for IL-2Rα at the cell surface will increase receptor occupancy within a limited range of IL-2 concentration, as well as raise the local concentration of IL-2 at the cell surface.

In some embodiments, the disclosure features IL-2 mutants, which may be, but are not necessarily, substantially purified and which can function as high affinity CD25 binders. IL-2 is a T cell growth factor that induces proliferation of antigen-activated T cells and stimulation of NK cells. Exemplary IL-2 mutants which are high affinity binders include those described in WO2013/177187A2 (herein incorporated by reference in its entirety). Further exemplary IL-2 mutants with increased affinity for CD25 are disclosed in U.S. Pat. No. 7,569,215, the contents of which are incorporated herein by reference.

In some embodiments, the disclosure features IL-2 mutants with reduced binding affinity to CD25 relative to wild-type IL-2. In some embodiments, the IL-2 mutant does not bind to CD25.

In some embodiments, IL-2 mutants comprise an amino acid sequence that is at least 80% identical to SEQ ID NO: 1 that bind CD25. For example, some embodiments an IL-2 mutant has at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) that increases the affinity for the alpha subunit of the IL-2 receptor relative to wild-type IL-2. It should be understood that mutations identified in mouse IL-2 may be made at corresponding residues in full length human IL-2 (nucleic acid sequence (accession: NM000586); amino acid sequence (accession: P60568)) or human IL-2 without the signal peptide. Accordingly, in some embodiments, the IL-2 is human IL-2. In other embodiments, the IL-2 is a mutant human IL-2.

In some embodiments, IL-2 mutants are at least or about 50%, at least or about 65%, at least or about 70%, at least or about 80%, at least or about 85%, at least or about 87%, at least or about 90%, at least or about 95%, at least or about 97%, at least or about 98%, or at least or about 99% identical in amino acid sequence to wild-type IL-2 (in its precursor form or, preferably, the mature form). The mutation can consist of a change in the number or content of amino acid residues. For example, the IL-2 mutants can have a greater or a lesser number of amino acid residues than wild-type IL-2. Alternatively, or in addition, IL-2 mutants can contain a substitution of one or more amino acid residues that are present in the wild-type IL-2.

By way of illustration, a polypeptide that includes an amino acid sequence that is at least 95% identical to a reference amino acid sequence of SEQ ID NO: 1 is a polypeptide that includes a sequence that is identical to the reference sequence except for the inclusion of up to five alterations of the reference amino acid of SEQ ID NO: 1. For example, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino (N—) or carboxy (C—) terminal positions of the reference amino acid sequence or anywhere between those terminal positions, interspersed either individually among residues in the reference sequence or in one or more contiguous groups within the reference sequence.

The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine. These mutations can be at amino acid residues that contact IL-2Rα.

Interleukin-12 (IL-12)

In some embodiments, the immunomodulatory fusion protein comprises an IL-12 polypeptide. Interleukin-12 (IL-12) is a pro-inflammatory cytokine that plays an important role in innate and adaptive immunity. Gately, M K et al., *Annu Rev Immunol.* 16: 495-521 (1998). IL-12 functions primarily as a 70 kDa heterodimeric protein consisting of two disulfide-linked p35 and p40 subunits. The precursor form of the IL-12 p40 subunit (NM_002187; P29460; also referred to as IL-12B, natural killer cell stimulatory factor 2, cytotoxic lymphocyte maturation factor 2) is 328 amino acids in length, while its mature form is 306 amino acids long. The precursor form of the IL-12 p35 subunit (NM_000882; P29459; also referred to as IL-12A, natural killer cell stimulatory factor 1, cytotoxic lymphocyte maturation factor 1) is 219 amino acids in length and the mature form is 197 amino acids long. Id. The genes for the IL-12 p35 and p40 subunits reside on different chromosomes and are regulated independently of each other. Gately, M K et al., *Annu Rev Immunol.* 16: 495-521 (1998). Many different immune cells (e.g., dendritic cells, macrophages, monocytes, neutrophils, and B cells) produce IL-12 upon antigenic stimuli. The active IL-12 heterodimer is formed following protein synthesis. Id.

Due to its ability to activate both NK cells and cytotoxic T cells, IL-12 protein has been studied as a promising anti-cancer therapeutic since 1994. See Nastala, C. L. et al., *J Immunol* 153: 1697-1706 (1994). But despite high expectations, early clinical studies did not yield satisfactory results. Lasek W. et al., *Cancer Immunol Immunother* 63: 419-435, 424 (2014). Repeated administration of IL-12, in most patients, led to adaptive response and a progressive decline of IL-12-induced interferon gamma (IFNγ) levels in blood. Id. Moreover, while it was recognized that IL-12-induced anti-cancer activity is largely mediated by the secondary secretion of IFNγ, the concomitant induction of IFNγ along with other cytokines (e.g., TNF-α) or chemokines (IP-10 or MIG) by IL-12 caused severe toxicity. Id.

In addition to the negative feedback and toxicity, the marginal efficacy of the IL-12 therapy in clinical settings may be caused by the strong immunosuppressive environment in humans. Id. To minimize IFNγ toxicity and improve IL-12 efficacy, scientists tried different approaches, such as different dose and time protocols for IL-12 therapy. See Sacco, S. et al., *Blood* 90: 4473-4479 (1997); Leonard, J. P. et al., *Blood* 90: 2541-2548 (1997); Coughlin, C. M. et al., *Cancer Res.* 57: 2460-2467 (1997); Asselin-Paturel, C. et al., *Cancer* 91: 113-122 (2001); and Saudemont, A. et al., *Leukemia* 16: 1637-1644 (2002). Nonetheless, these approaches have not significantly impacted patient survival. Kang, W. K., et al., *Human Gene Therapy* 12: 671-684 (2001).

Membrane-anchored versions of IL-12 have been studied as a means of reducing toxicity associated with systemic administration, using retroviral and adenoviral vectors for expression in tumor cells. See Pan, W-Y. et al., *Mol. Ther.* 20(5): 927-937 (2012). But, the use of viral vectors presents a potential health risk, since the underlying viruses can act as oncogenes and the viral vectors can be immunogenic.

Accordingly, in some embodiments, the immunomodulatory fusion proteins disclosed herein comprise an IL-12 polypeptide. In some embodiments, the IL-12 polypeptide comprises IL-12A (e.g., SEQ ID NO: 3). In some embodiments, the IL-12 polypeptide comprises IL-12B (e.g., SEQ ID NO: 2). In some embodiments, the IL-12 polypeptide comprises both IL-12A and IL-12B.

In some embodiments, IL-12B is located N-terminal to IL-12A in the IL-12 polypeptide. In some embodiments, IL-12A is located N-terminal to IL-12B in the IL-12 polypeptide. The phrase "located N-terminal to" indicates location in a polypeptide with respect to other sequences in the polypeptide in relation to the N-terminus of the polypeptide. For example, IL-12B that is "N-terminal to" IL-12A means that IL-12B is located closer to the N-terminus of the IL-12 polypeptide than IL-12A.

In some embodiments, the IL-12 polypeptide comprises a single polypeptide chain comprising IL-12B and IL-12A, which are fused directly to one another or are linked to one another by a linker (referred to herein as an "subunit linker"). Non-limiting examples of linkers are disclosed elsewhere herein.

In some embodiments, the IL-12 polypeptide of the disclosure comprises IL-12A and/or IL-12B that is a variant, that is a functional fragment, or that contains a substitution, an insertion and/or an addition, a deletion, and/or a covalent modification with respect to a wild-type IL-12A or IL-12B sequence. In some embodiments, amino acid residues located at the carboxy, amino terminal, or internal regions of the IL-12 polypeptide are deleted, thereby providing for fragments.

In some embodiments, the IL-12 polypeptide comprises a substitutional variant of an IL-12A and/or IL-12B amino acid sequence, which can comprise one, two, three or more than three substitutions. In some embodiments, the substitutional variant can comprise one or more conservative amino acids substitutions. In other embodiments, the variant is an insertional variant. In other embodiments, the variant is a deletional variant.

As recognized by those skilled in the art, IL-12 protein fragments, functional protein domains, variants, and homologous proteins (orthologs) are also considered to be within the scope of the IL-12 polypeptides of the disclosure. Nonlimiting examples of IL-12 polypeptides suitable for use in the immunomodulatory fusion proteins disclosed herein are set forth in SEQ ID NOs: 2-3.

In some embodiments, the immunomodulatory fusion protein comprises an IL-12 polypeptide comprising the amino acid sequence set forth in SEQ ID NO: 2. In some embodiments, the immunomodulatory fusion protein comprises an IL-12 polypeptide comprising the amino acid sequence set forth in SEQ ID NO: 3. In some embodiments, the immunomodulatory fusion protein comprises an IL-12 polypeptide comprising the amino acid sequences set forth in SEQ ID NOs: 2 and 3.

Interleukin-15 (IL-15)

In some embodiments, the immunomodulatory fusion protein comprises an IL-15 polypeptide. IL-15 is a member of the 4α-helix bundle family of cytokines and plays an important role in the development of an effective immune response. Waldmann, T. A., Cancer Immunol. Res. 3: 219-227 (2015). IL-15 is essential for the proper development of NK cells and long-term maintenance of memory CD8+ T cells. The IL-15 gene encodes a 162 amino acid preprotein having a signal peptide of 48 amino acids, with the mature protein being 114 amino acids in length. Bamford, R. N., et al., Proc. Natl. Acad. Sci. USA 93: 2897-2902 (1996). See also, e.g., GenBank Accession Numbers NM_000585 for the *Homo sapiens* IL15 transcript variant 3 mRNA sequence and NP_000576 for the corresponding IL15 isoform 1 preproprotein.

IL-15 shares certain structural similarity to interleukin-2 (IL-2). Like IL-2, IL-15 signals through the IL-2 receptor beta chain (CD122) and the common gamma chain (CD132). But, unlike IL-2, IL-15 cannot effectively bind CD122 and CD132 on its own. IL-15 must first bind to the IL-15 alpha receptor subunit (IL-15Rα). The IL-15Rα gene encodes a 267 amino acid preprotein having a signal peptide of 30 amino acids, with the mature protein being 237 amino acids in length. See, e.g., GenBank Accession Numbers NM_002189 for the *Homo sapiens* IL-15Rα transcript variant 1 mRNA and NP_002180 for the *Homo sapiens* IL-15Rα isoform 1 precursor amino acid sequence.

Human IL-15Rα is predominantly a transmembrane protein that binds to IL-15 on the surface of cells such as activated dendritic cells and monocytes. Waldmann, T. A., Cancer Immunol. Res. 3: 219-227 (2015). The membrane bound complex of IL-15/IL-15Rα then presents IL-15 in trans to CD122 and CD132 subunits. Accordingly, IL-15α is an essential component of IL-15 activity.

To overcome the short half-life of systemically injected IL-15, pre-complexation of IL-15 with soluble recombinant IL-15Rα, resulting in IL-15 superagonist (IL-15SA) has been shown to enhance the systemic potency of IL-15 by ~50 fold, and also raises the half-life of the cytokine in serum following systemic injection to ~20 hrs. (Stoklasek et al., J Immunol 177(9): 6072, 2006; Dubois et al., J Immunol 180(4): 2099, 2008; Rubinstein et. al. Proc Natl Acad Sci USA 103(24): 9166, 2006.)

Accordingly, in some embodiments, the immunomodulatory domain of the immunomodulatory fusion protein is an IL-15 polypeptide. In some embodiments, the IL-15 polypeptide comprises the amino acid sequence set forth in SEQ ID NO: 5. In some embodiments, the IL-15 polypeptide comprises the amino acid sequence set forth in SEQ ID NO: 4. In some embodiments, the IL-15 polypeptide is an IL-15 superagonist, comprising IL-15 and IL-15α. In some embodiments, the IL-15 superagonist comprises the amino acid sequences set forth in SEQ ID NOs: 4 and 5.

Interferons

In some embodiments, the immunomodulatory domain suitable for use in the immunomodulatory fusion proteins of the present disclosure, is an interferon (IFN). Interferons comprise a family of secretory proteins induced in response to specific extracellular stimuli through stimulation of toll-like receptors (TLRs). In some embodiments, interferons heighten anti-viral defenses of the immune system (e.g., antigen presentation). Through high-affinity cell surface receptors, IFNs stimulate genes using signaling molecules. Interferons suitable for use as an immunomodulatory domain of the immunomodulatory fusion proteins include, but are not limited to: IFN-gamma and IFN-alpha.

In some embodiments, the immunomodulatory fusion protein comprises an IFN-gamma polypeptide. IFN-gamma is produced by a variety of immune cells, such as activated T cells and NK cells. IFN-gamma interacts with a specific receptor at the cell surface and activates signal transduction pathways that produce immunomodulatory effects. Accordingly, in some embodiments, the immunomodulatory domain is an IFN-gamma polypeptide. In some embodiments, the IFN-gamma polypeptide comprises the amino acid sequence set forth in SEQ ID NO: 7.

In some embodiments, the immunomodulatory fusion protein comprises an IFN-alpha polypeptide. IFN-alpha is produced by B lymphocytes, null lymphocytes and macrophages, and activates NK cells, along with having antiviral and antitumor activities. Accordingly, in some embodiments, the immunomodulatory domain is an IFN-alpha polypeptide. In some embodiments, the IFN-alpha polypeptide comprises the amino acid sequence set forth in SEQ ID NO: 8.

Immune Cell Differentiation Stimulating Factors

In some embodiments, the immunomodulatory domain suitable for use in the immunomodulatory fusion proteins of the present disclosure, is an immune cell differentiation stimulating factor. In some embodiments, immune cell differentiation stimulating factors activate intracellular signaling pathways that drive hematopoietic progenitor cell differentiation, development and proliferation into specific subtypes of immune cells Immune cell differentiation stimulating factors suitable for use in the immunomodulatory fusion proteins disclosed herein include, but are not limited to: GM-CSF (granulocyte-macrophage colony-stimulating factor), G-CSF (granulocyte colony-stimulating factor) and FLT3L (FMS-like tyrosine kinase 3 ligand).

In some embodiments, the immunomodulatory domain is a GM-CSF polypeptide. GM-CSF is a monomeric glycoprotein secreted by macrophages, T cells, mast cells, NK cells, endothelial cells and fibroblasts. In addition to having a function of growth stimulation and differentiation on hematopoietic precursor cells, GM-CSF has a variety of effects on immune cells expressing the GM-CSF receptor. In some embodiments, the GM-CSF polypeptide comprises the amino acid sequence set forth in SEQ ID NO: 27.

In some embodiments, the immunomodulatory domain is a FLT3L polypeptide. FLT3 is a receptor tyrosine kinase (RTK) which is expressed by immature hematopoietic precursor cells. FLT3L is a transmembrane protein or soluble protein and is expressed by a large number of cells, including hematopoietic cells and stroma cells in the bone marrow. In combination with other growth factors, FLT3L stimulates proliferation and development of various cells types, including myeloid and lymphoid precursor cells, dendritic cells and NK cells. In some embodiments, the FLT3L polypeptide comprises the amino acid sequence set forth in SEQ ID NO: 28.

In some embodiments, the immunomodulatory domain is an G-CSF polypeptide. In some embodiments, G-CSF regulates proliferation, differentiation and functional activation of neutrophilic granulocytes. In some embodiments, the G-CSF polypeptide comprises the amino acid sequence set forth in SEQ ID NO: 29.

Chemokines

In some embodiments, the immunomodulatory domain suitable for use in the immunomodulatory fusion proteins of the present disclosure, is a chemokine. In some embodiments, chemokines are proteins that induce directed chemotaxis of a responsive cell (e.g., leukocytes). In general, chemokines are grouped into four subfamilies: CXC, CC, (X)C, and CX3C. In the CXC chemokines, one amino acid separates the first two cysteines ("the CXC motif"). ELR+ CXC chemokines are ligands for CXCR1 and/or CXCR2 chemokine receptors, which are G-protein coupled seven transmembrane domain-type receptors that specifically bind ELR+ CXC chemokines. The seven human ELR+ CXC chemokines are human Gro-alpha (also known as CXCL1), human Gro-beta (also known as CXCL2), human Gro-gamma (also known as CXCL3), human ENA-78 (also known as CXCL5), human GCP-2 (also known as CXCL6), human NAP-2 (also known as CXCL7), and human IL-8 (also known as CXCL8). All ELR+ CXC chemokines bind the CXCR2 receptor; moreover, some ELR+ CXC chemokines bind both CXCR1 and CXCR2 receptors (i.e., CXCL6 and CXCL8), all of which contributes to redundancy in the activation pathways. The five murine ELR+ CXC chemokines are keratinocyte chemoattractant (KC) (also known as CXCL1), Macrophage Inflammatory Protein-2 (MIP-2) (also known as CXCL2), dendritic cell inflammatory protein-1 (DCIP-1) (also known as CXCL3), lipopolysaccharide-induced CXC chemokine (LIX) (also known as CXCL5), and neutrophil activating peptide-2 (NAP-2) (also known as CXCL7).

Chemokines suitable for use in the immunomodulatory fusion protein disclosed herein include, but are not limited to: LIF, M-CSF, MIP-2, MIP-1beta, KP (CXLC1), MIG (CXCL9), IP-10 (CXCL10), MCP-1, eotaxin, RANTES, LIX and MIP-1-1alpha.

Amino acids encoding exemplary chemokines suitable for use as an immunomodulatory domain for the immunomodulatory fusion protein disclosed herein, are set forth below:

| Chemokine | Amino acid sequence (SEQ ID NO) |
|---|---|
| LIF | 30 |
| M-CSF | 31 |
| MIP-2 | 32 |
| MIP-1beta | 33 |
| KP (CXCL1) | 34 |
| MIG (CXCL9) | 35 |
| IP-10 (CXCL10) | 36 |
| MCP-1 | 37 |
| Eotaxin | 38 |
| RANTES | 39 |
| LIX | 40 |
| MIP-1alpha | 41 |

Tumor Necrosis Factor (TNF) Superfamily

In some embodiments, the immunomodulatory domain suitable for use in the immunomodulatory fusion proteins of the present disclosure, is an extracellular domain of a member of the tumor necrosis factor (TNF) superfamily. The tumor necrosis factor super family of ligands and receptors are a series of structurally homologous cell surface proteins that signal via forming trimeric clusters of ligand-receptor complexes. Ligation of activating TNF superfamily receptors can lead to a wide range of pro-immune responses, including proliferation, enhanced effector function, and production of chemokines and cytokines. Some ligands, such as Fas, can lead to the induction of apoptosis and are expressed on the surface of immune cells. Additionally, other ligands function as inhibitory receptors which weaken the immune response. In some embodiments, the extracellular domain is derived from: TNF-alpha, LIGHT, LT-alpha, LT-beta, BTLA, CD160, CD40L, FasL, CD30L, 4-1BBL, CD27L, OX40L, TWEAK, APRIL, BAFF, RANKL, TRAIL, EDA1, EDA2 or GITRL. The extracellular domain is capable of binding the selected TNF superfamily member's receptor, thereby inducing or stimulating an immune response.

The following table shows the receptor corresponding to the derived extracellular domain:

| Ligand | Receptor | Amino acid sequence of ligand extracellular domain (SEQ ID NO) |
|---|---|---|
| TNF-alpha | TNFR1, TNFR2 | 49 |
| LIGHT | HEVM, LT-betaR | 50 |
| LT-alpha | TNFR1, TNFR2, HEVM | 51 |
| LT-beta | LT-BetaR | 52 |
| CD160 | HVEM | 54 |
| CD40L | CD40 | 55 |
| FasL | Fas | 56 |
| CD30L | CD30 | 57 |
| 4-1BBL | 4-1BB | 58 |
| CD27L | CD27 | 59 |
| OX40L | OX40 | 60 |
| TWEAK | Fn14 | 61 |
| APRIL | BCMA, TACI | 62 |
| BAFF | BCMA, TACI, BAFFR | 63 |
| RANKL | RANK, OPG | 64 |
| TRAIL | OPG, TRAIL R1 (DR4), TRAIL R2 (DR5), DcR1, DcR2 | 65 |
| EDA1 | EDAR | 66 |
| EDA2 | XEDAR | 67 |
| GITRL | GITR | 68 |

CD28 Family

In some embodiments, the immunomodulatory domain suitable for use in the immunomodulatory fusion proteins of the present disclosure, is an extracellular domain of a member of the CD28 family. The CD28 family is a family of inhibitory (PD1, CTLA-4) and activating (CD28, ICOS) receptors that bind to members of the B7 family of ligands. CD28 is a co-stimulatory receptor that provides the second signal required to activate naive T cells (along with ligation of the TCR) and has two natural ligands, CD80 and CD86. CD28 signaling can serve to increase proliferation, effector function, and anti-apoptotic signaling CD28 signaling has recently been shown to be required in effective PD1/PDL1 blockade. ICOS (Inducible T cell Costimulator) is a closely related surface receptor that is expressed on activated T cells and displays similar functions as CD28.

Accordingly, in some embodiments, the immunomodulatory domain is an extracellular domain of CD80 (B7-1). In some embodiments, the immunomodulatory domain comprises the amino acid sequence set forth in SEQ ID NO: 69.

Accordingly, in some embodiments, the immunomodulatory domain is an extracellular domain of CD86 (B7-2), capable of binding CD28. In some embodiments, the immunomodulatory domain comprises the amino acid sequence set forth in SEQ ID NO: 70.

Accordingly, in some embodiments, the immunomodulatory domain is an extracellular domain of ICOSLG. In some embodiments, the immunomodulatory domain comprises the amino acid sequence set forth in SEQ ID NO: 71.

Agonistic Antibodies

In some embodiments, the immunomodulatory domain suitable for use in the immunomodulatory fusion proteins of the present disclosure, is an agonistic antibody, or antigen binding fragment thereof. Agonistic antibodies activate their target of interest, in contrast to antagonistic antibodies which block the function of their target. In some embodiments, the agonistic antibodies, or antigen binding fragments thereof, bind to immune activating receptors. In some embodiments, immune activating receptors include, but are not limited to: tumor necrosis factor (TNF) receptors, CD28 family members, T-cell receptors (TCRs), Killer cell Ig-Like receptors (KIRs), Leukocyte Ig-Like receptors (LIRs), CD94/NKG2 receptors, Fc receptors, signaling lymphocytic activation molecules (SLAMs), and activating Siglec receptors.

Tumor Necrosis Factor (TNF) Superfamily

In some embodiments, the immunomodulatory domain suitable for use in the immunomodulatory fusion proteins of the present disclosure, is an agonistic antibody, or antigen binding fragment thereof, that binds to a tumor necrosis factor (TNF) superfamily member receptor. The TNF superfamily is described supra. For example, in some embodiments, the immunomodulatory domain is an agonistic antibody, or antigen binding fragment, that binds to TNFR1, thereby activating the receptor.

The following table provides a list of TNF superfamily member receptors that agonistic antibodies, or antigen binding fragments thereof, can be generated to target, suitable for use in the immunomodulatory fusion protein described herein:

-continued

| Ligand | Receptor | Receptor Uniprot KB |
|---|---|---|
| TNF-alpha | TNFR1 | P19438 |
| | TNFR2 | P20333 |
| LIGHT | HEVM | Q92956 |
| | LT-betaR | Q06643 |
| LT-alpha | TNFR1 | P19438 |
| | TNFR2 | P20333 |
| | HEVM | Q92956 |
| LT-beta | LT-BetaR | Q06643 |
| CD160 | HVEM | Q92956 |
| CD40L | CD40 | P25942 |
| FasL | Fas | P25445 |
| CD30L | CD30 | P28908 |
| 4-1BBL | 4-1BB | Q07011 |
| CD27L | CD27 | P26842 |
| OX40L | OX40 | P43489 |
| TWEAK | Fn14 | Q9NP84 |
| APRIL | BCMA | Q02223 |
| | TACI | O14836 |
| BAFF | BCMA | Q02223 |
| | TACI | O14836 |
| | BAFFR | Q96RJ3 |
| RANKL | RANK | Q9Y6Q6 |
| | OPG | O00300 |
| TRAIL | OPG | O00300 |
| | TRAIL R1 (DR4) | O00220 |
| | TRAIL R2 (DR5) | O14763 |
| | DcR1 | O14798 |
| | DcR2 | Q9UBN6 |
| EDA1 | EDAR | Q9UNE0 |
| EDA2 | XEDAR | Q9HAV5 |
| GITRL | GITR | Q9Y5U5 |

In some embodiments, the immunomodulatory domain is an anti-4-1BB agonist antibody. In some embodiments, the immunomodulatory domain is an anti-OX40 agonist antibody. In some embodiments, the immunomodulatory domain is a CD40 agonist antibody.

CD28 Receptor Superfamily

In some embodiments, the immunomodulatory domain suitable for use in the immunomodulatory fusion proteins of the present disclosure, is an agonistic antibody, or antigen binding fragment thereof, that binds to a CD28 superfamily receptor. The CD28 superfamily is described supra. For example, in some embodiments, the immunomodulatory domain is an agonistic antibody, or antigen binding fragment, that binds to CD28, thereby activating the receptor.

The following table provides a list of CD28 superfamily member receptors that agonistic antibodies, or antigen binding fragments thereof, can be generated to target, suitable for use in the immunomodulatory fusion protein described herein:

| Ligand | Receptor | Receptor Uniprot KB |
|---|---|---|
| CD80 (B7-1) | CD28 | P10747 |
| CD86 (B7-2) | CD28 | P10747 |
| ICOSLG | ICOS | Q9Y6W8 |

T Cell Receptor (TCR) Complex

In some embodiments, the immunomodulatory domain suitable for use in the immunomodulatory fusion proteins of the present disclosure, is an agonistic antibody, or antigen binding fragment thereof, that binds to a T-cell Receptor (TCR) complex. The T-cell Receptor (TCR) is the cell surface receptor responsible for imparting antigen specificity to T-cells. Each TCR is specific for a particular peptide presented either by MHC Class I (for CD8+ T cells) or MHC Class II (for CD4+ T cells). For naive T cells, ligation of the TCR provides the first of two signals required to activate the T cell. TCR ligation of CD8+ T cells leads to death of the cell displaying the cognate pMHC (and potentially bystander cells) via release of soluble factors, such as perforin and granzyme B, as well as upregulation of apoptosis inducing ligands, such as Fas ligand. For CD4+ helper T cells, ligation of the TCR with its cognate pMHC results in the release of cytokines, Accordingly, in some embodiments, the immunomodulatory domain is an agonistic antibody, or antigen binding fragment thereof, that binds to a TCR. For example, in some embodiments, the immunomodulatory domain is an agonistic antibody, or antigen binding fragment, that binds to CD3γ, thereby activating the receptor.

The following table provides a list of members of TCR complexes that agonistic antibodies, or antigen binding fragments thereof, can be generated to target, suitable for use in the immunomodulatory fusion protein described herein:

| TCR Binder | TCR Complex Member | Member Uniprot KB |
|---|---|---|
| pMHC | CD3γ | P09693 |
| pMHC | CD3δ | P04234 |
| pMHC | CD3ζ | P20963 |
| pMHC | CD3ε | P07766 |

Killer Cell Ig-Like Receptor (KIR)

In some embodiments, the immunomodulatory domain suitable for use in the immunomodulatory fusion proteins of the present disclosure, is an agonistic antibody, or antigen binding fragment thereof, that binds to a Killer Cell Ig-Like Receptor (KIR). The killer cell immunoglobulin like receptor (KIR) is a family of receptors expressed mainly on NK cells and on some subsets of T cells. These receptors are primarily responsible through recognition of self (and therefore inhibitory function), by binding to MHC class I (HLA-A, HLA-B, and HLA-C) molecules. These receptors can be either activating or inhibitory, depending on the length of the cytoplasmic tail. Inhibitory receptors have a longer tail and contain an ITIM domain. Activating KIRs have a shorter cytoplasmic domain and associate with DAP12 to mediate signaling.

Activating KIRs are provided in the table below, in which agonistic antibodies, or antigen binding fragments thereof, can be generated to target, suitable for use in the immunomodulatory fusion protein described herein:

| Ligand | Receptor | Receptor Uniprot KB |
|---|---|---|
| HLA molecules | KIR 2DS1 | Q14954 |
| HLA molecules | KIR 2DS2 | P43631 |
| HLA molecules | KIR 2DS3 | Q14952 |
| HLA molecules | KIR 2DS4 | P43632 |
| HLA molecules | KIR 2DS5 | Q14953 |
| HLA molecules | KIR 3DS1 | Q14943 |

Leukocyte Ig-Like Receptor (LIR)

In some embodiments, the immunomodulatory domain suitable for use in the immunomodulatory fusion proteins of the present disclosure, is an agonistic antibody, or antigen binding fragment thereof, that binds to a leukocyte Ig-Like receptor (LIR). LIR receptors are a class of immune receptors expressed primarily on innate immune cells. Their primary ligand is MHC Class I molecules and they largely exhibit inhibitory functions, although some have activating functions. LIRA2, for example, acts as an innate sensor of immunoglobulin fragments that have been cleaved by microbial proteases.

In some embodiments, the immunomodulatory domain is an agonistic antibody, or antigen binding fragment thereof, that binds to LIRA2. In some embodiments, antibodies capable of binding to LIRA2 can be generated based on Uniprot ID Q8N149.

CD94/NKG2 Receptor Family

In some embodiments, the immunomodulatory domain suitable for use in the immunomodulatory fusion proteins of the present disclosure, is an agonistic antibody, or antigen binding fragment thereof, that binds to a CD94/NKG2 receptor. CD94/NKG2 are heterodimer C-type lectin receptors that are expressed on the surface of NK cells and some subsets of CD8 T cells. They bind to HLA-E molecules (non-classical MHC Class I molecules) and can transmit both inhibitory and activating signals to NK Cells. Inhibitory receptors contain ITIM domains in their cytoplasmic tails, while activating receptors associate with DAP12 and DAP10 which contain ITAM domains.

Activating CD94/NKG2 receptors are provided in the table below, in which agonistic antibodies, or antigen binding fragments thereof, can be generated to target, suitable for use in the immunomodulatory fusion protein described herein.

In some embodiments, the immunomodulatory domain suitable for use in the immunomodulatory fusion proteins of the present disclosure is an extracellular domain of a CD94/NKG2 ligand. The following table shows the receptor corresponding to the derived extracellular domain.

| Ligand | Receptor | Receptor Uniprot KB | Amino acid sequence of ligand extracellular domain (SEQ ID NO) |
|---|---|---|---|
| MICA | CD94 | Q13241 | 72 |
| | NKG2D | P26718 | |
| MICB | CD94 | Q13241 | 73 |
| | NKG2D | P26718 | |
| ULBP1 | CD94 | Q13241 | 74 |
| | NKG2D | P26718 | |
| ULBP2 | CD94 | Q13241 | 75 |
| | NKG2D | P26718 | |
| ULBP3 | CD94 | Q13241 | 76 |
| | NKG2D | P26718 | |
| ULBP4 | CD94 | Q13241 | 77 |
| | NKG2D | P26718 | |
| ULBP5, | CD94 | Q13241 | 78 |
| isoform 1 | NKG2D | P26718 | |
| ULBP5, | CD94 | Q13241 | 79 |
| isoform 2 | NKG2D | P26718 | |
| ULBP6 | NKG2D | P26718 | 80 |
| | NKG2C | P26717 | |
| | NKG2E | Q07444 | |
| | NKG2H | O43908 | |
| | CD94 | Q13241 | |

Fc Receptors

In some embodiments, the immunomodulatory domain suitable for use in the immunomodulatory fusion proteins of the present disclosure, is an agonistic antibody, or antigen binding fragment thereof, that binds to an Fc receptor. Fc receptors are immune cell receptors expressed primarily on innate immune cells which bind to the constant region of antibodies and elicit a wide range of functions. Fc receptors are almost exclusively activating (except for FcγRIIB, which transmits inhibitory signals). Fc receptor ligation can lead to ADCC, phagocytosis, degranulation, and the transmission of activating signals which increase effector function.

The following table provides a list of Fc receptors that agonistic antibodies, or antigen binding fragments thereof, can be generated to target, suitable for use in the immunomodulatory fusion protein described herein:

| Ligand | Receptor | Receptor Uniprot KB |
|---|---|---|
| IgG | FcγRI | P12314 |
| IgG | FcγRIIC | P31995 |
| IgG | FcγRIIIA | P12318 |
| IgG | FcγRIIIB | P31994 |
| IgE | FcεRI | P30273 |
| IgE | FcεRII | P06734 |
| IgA | FcαR | P24071 |
| IgA/IgM | FcμR | Q8WWV6 |

Signaling Lymphocytic Activation Molecules (SLAM)

In some embodiments, the immunomodulatory domain suitable for use in the immunomodulatory fusion proteins of the present disclosure, is an agonistic antibody, or antigen binding fragment thereof, that binds to a signaling lymphocytic activation molecule (SLAM) receptor. SLAM receptors are a series of molecules that function both as receptors and ligands. SLAM molecules interact with one another on adjacent cells to send either activating or inhibitory signals. SLAM molecules contain Immunoreceptor Tyrosine based Swith motifs in their cytoplasmic tails, allowing them to associate with both activating and inhibitory signaling molecules intracellularly.

The following table provides a list of SLAM receptors that agonistic antibodies, or antigen binding fragments thereof, can be generated to target, suitable for use in the immunomodulatory fusion protein described herein.

In some embodiments, the immunomodulatory domain suitable for use in the immunomodulatory fusion proteins of the present disclosure is an extracellular domain of a SLAM ligand. The following table shows the receptor corresponding to the derived extracellular domain.

| Ligand | Receptor | Receptor Uniprot KB | Amino acid sequence of ligand extracellular domain (SEQ ID NO) |
|---|---|---|---|
| SLAMF1 | SLAMF1 | Q13291 | 81 |
| SLAMF2 | SLAMF2 | P09326 | 82 |
| SLAMF3 | SLAMF3 | Q9HBG7 | 83 |
| SLAMF4 | SLAMF4 | Q9BZW8 | 84 |
| SLAMF5 | SLAMF5 | Q9UIB8 | 85 |
| SLAMF6 | SLAMF6 | Q96DU3 | 86 |
| SLAMF7 | SLAMF7 | Q9NQ25 | 87 |

Siglec Family Receptors

In some embodiments, the immunomodulatory domain suitable for use in the immunomodulatory fusion proteins of the present disclosure, is an agonistic antibody, or antigen binding fragment thereof, that binds to a Siglec family receptor. Siglecs are a family of surface receptors found mainly on immune cells that are part of the lectin family (sugar binding proteins). These receptors bind to sialic acid containing ligands. These receptors function mainly as inhibitory receptors on a wide range of immune cell types, although some (siglec 14, 15, and 16) contain an ITAM activating domain.

Activating Siglec receptors are provided in the table below, in which agonistic antibodies, or antigen binding fragments thereof, can be generated to target, suitable for use in the immunomodulatory fusion protein described herein:

| Receptor | Receptor Uniprot KB |
|---|---|
| Siglec 14 | Q08ET2 |
| Siglec 15 | Q6ZMC9 |
| Siglec 16 | A6NMB1 |

Antagonistic Antibodies

In some embodiments, the immunomodulatory domain suitable for use in the immunomodulatory fusion proteins of the present disclosure, is an antagonistic antibody, or antigen binding fragment thereof. Antagonistic antibodies block the function of their target. In some embodiments, the antagonistic antibodies, or antigen binding fragments thereof, bind to immune inhibitory receptors, thereby allowing for the induction of an immune response. In some embodiments, the antagonistic antibodies, or antigen binding fragments thereof, bind to immune inhibitory ligands, thereby allowing for the induction of an immune response. In some embodiments, immune inhibitor receptors and ligands include, but are not limited to: CD28 receptors, tumor necrosis factor (TNF) superfamily receptors, Siglec receptors, CD94/NKG2 receptors, Leukocyte Ig-Like receptors (LIRs), Killer Cell Ig-Like receptors (KIRs), Fc receptors, adenosine pathway molecules, other checkpoint inhibitors, and LAIR1.

CD28 Molecules

In some embodiments, the immunomodulatory domain suitable for use in the immunomodulatory fusion proteins of the present disclosure, is an antagonistic antibody, or antigen binding fragment thereof, that binds a CD28 molecule. As described supra, the CD28 family includes both activating and inhibitory molecules. Accordingly, in some embodiments, antagonizing the inhibitory molecules results in an induction or stimulation of immune responses.

The following table provides a list of CD28 molecules that antagonistic antibodies, or antigen binding fragments thereof, can be generated to target, suitable for use in the immunomodulatory fusion protein described herein.

| Molecule | Molecule Uniprot KB |
|---|---|
| PD1 | Q15116 |
| PDL1 | Q9NZQ7 |
| PDL2 | Q9BQ51 |
| CTLA-4 | P16410 |
| B7-H4 | Q7Z7D3 |
| B7-H3 | Q5ZPR3 |

In some embodiments, the immunomodulatory domain is an antagonistic antibody, or antigen binding fragment thereof, that binds PD-1. In some embodiments, the immunomodulatory domain is an antagonistic antibody, or antigen binding fragment thereof, that binds PD-L1. In some embodiments, the immunomodulatory domain is an antagonistic antibody, or antigen binding fragment thereof, that binds CTLA-4.

TNF Superfamily Molecules

In some embodiments, the immunomodulatory domain suitable for use in the immunomodulatory fusion proteins of the present disclosure, is an antagonistic antibody, or antigen binding fragment thereof, that binds a TNF superfamily member. As described supra, the TNF superfamily includes both activating and inhibitory molecules. Accordingly, in some embodiments, antagonizing the inhibitory molecules results in an induction or stimulation of immune responses.

The following table provides a list of TNF superfamily molecules that antagonistic antibodies, or antigen binding fragments thereof, can be generated to target, suitable for use in the immunomodulatory fusion protein described herein.

| Molecule | Molecule Uniprot KB |
|---|---|
| TIGIT | Q495A1 |
| BTLA | Q7Z6A9 |

Siglec Receptors

In some embodiments, the immunomodulatory domain suitable for use in the immunomodulatory fusion proteins of the present disclosure, is an antagonistic antibody, or antigen binding fragment thereof, that binds a Siglec receptor. As described supra, the Siglec family includes both activating and inhibitory molecules. Accordingly, in some embodiments, antagonizing the inhibitory molecules results in an induction or stimulation of immune responses.

The following table provides a list of Siglec receptors that antagonistic antibodies, or antigen binding fragments thereof, can be generated to target, suitable for use in the immunomodulatory fusion protein described herein.

| Receptor | Receptor Uniprot KB |
|---|---|
| Siglec 1 (siualoadhesion) | Q9BZZ2 |
| Siglec 2 (CD22) | P20273 |
| Siglec 3 (CD33) | P20138 |
| Siglec 4a (MAG) | P20916 |
| Siglec 5 | O15389 |
| Siglec 6 | O43699 |
| Siglec 7 | Q9Y286 |
| Siglec 8 | Q9NYZ4 |
| Siglec 9 | Q9Y336 |
| Siglec 10 | Q96LC7 |
| Siglec 11 | Q96RL6 |
| Siglec 12 | Q96PQ1 |

CD94/NKG2 Receptors

In some embodiments, the immunomodulatory domain suitable for use in the immunomodulatory fusion proteins of the present disclosure, is an antagonistic antibody, or antigen binding fragment thereof, that binds a CD94/NKG2 receptors. As described supra, the CD94/NKG2 family includes both activating and inhibitory molecules. Accordingly, in some embodiments, antagonizing the inhibitory molecules results in an induction or stimulation of immune responses.

Accordingly, in some embodiments, the immunomodulatory domain is an antagonistic antibody, or antigen binding fragment thereof, that binds CD94/NKG2A. In some embodiments, such antibodies are generated based on UniProt ID P26715.

In some embodiments, the immunomodulatory domain is an antagonistic antibody, or antigen binding fragment thereof, that binds CD94/NKG2B. In some embodiments, such antibodies are generated based on UniProt ID Q13241.

Leukocyte Ig-Like Receptors (LIRs)

In some embodiments, the immunomodulatory domain suitable for use in the immunomodulatory fusion proteins of the present disclosure, is an antagonistic antibody, or antigen binding fragment thereof, that binds a Leukocyte Ig-Like Receptors (LIR). As described supra, the LIR family includes both activating and inhibitory molecules. Accordingly, in some embodiments, antagonizing the inhibitory molecules results in an induction or stimulation of immune responses.

The following table provides a list of LIRs that antagonistic antibodies, or antigen binding fragments thereof, can be generated to target, suitable for use in the immunomodulatory fusion protein described herein.

| Receptor | Receptor Uniprot KB |
|---|---|
| LIRB1 | Q8NHL6 |
| LIRB2 | Q8N423 |
| LIRB3 | O75022 |
| LIRB4 | Q8NHJ6 |

Killer Cell Ig-Like Receptors (KIRs)

In some embodiments, the immunomodulatory domain suitable for use in the immunomodulatory fusion proteins of the present disclosure, is an antagonistic antibody, or antigen binding fragment thereof, that binds a Killer Cell Ig-Like Receptor (KIR). As described supra, the KIR family includes both activating and inhibitory molecules. Accordingly, in some embodiments, antagonizing the inhibitory molecules results in an induction or stimulation of immune responses.

The following table provides a list of KIRs that antagonistic antibodies, or antigen binding fragments thereof, can be generated to target, suitable for use in the immunomodulatory fusion protein described herein.

| Receptor | Receptor Uniprot KB |
|---|---|
| KIR 2DL1 | P43626 |
| KIR 2DL2 | P43627 |
| KIR 2DL3 | P43628 |
| KIR 2DL4 | Q99706 |
| KIR 2DL5A | Q8N109 |
| KIR 2DL5B | Q8NHK3 |
| KIR 3DL1 | P43629 |
| KIR 3DL2 | P43630 |
| KIR 3DL3 | Q8N743 |

Fc Receptors

In some embodiments, the immunomodulatory domain suitable for use in the immunomodulatory fusion proteins of the present disclosure, is an antagonistic antibody, or antigen binding fragment thereof, that binds an Fc receptor. As described supra, the family of Fc receptors includes both activating and inhibitory molecules. Accordingly, in some embodiments, antagonizing the inhibitory molecules results in an induction or stimulation of immune responses.

In some embodiments, the inhibitor Fc receptor is FcγRIIB. In some embodiments, the immunomodulatory domain is an antagonistic antibody, or antigen binding fragment thereof, that binds FcγRIIB. In some embodiments, such antibodies are generated based on UniProt ID P31994.

Adenosine Pathway Molecules

In some embodiments, the immunomodulatory domain suitable for use in the immunomodulatory fusion proteins of the present disclosure, is an antagonistic antibody, or antigen binding fragment thereof, that binds a member of the adenosine pathway. For example, CD39 and CD73 are enzymes expressed on the surface of cells which catalyze the transfectation of ATP into adenosine. Extracellular ATP is a danger molecule which elicits an immune response, while adenosine is immunosuppressive. These molecules contribute to a locally immunosuppressive environment by generating adenosine.

Accordingly, in some embodiments, the immunomodulatory domain is an antagonistic antibody, or antigen binding fragment thereof, that binds CD39. In some embodiments, such antibodies are generated based on UniProt ID P49961.

In some embodiments, the immunomodulatory domain is an antagonistic antibody, or antigen binding fragment thereof, that binds CD73. In some embodiments, such antibodies are generated based on UniProt ID P21589.

Other Checkpoint Inhibitors

In some embodiments, the immunomodulatory domain suitable for use in the immunomodulatory fusion proteins of the present disclosure, is an antagonistic antibody, or antigen binding fragment thereof, that binds an immune checkpoint inhibitor. In some embodiments, by antagonizing such immune checkpoint inhibitors, an immune response is induced or stimulated.

The following table provides a list of immune checkpoint inhibitors that antagonistic antibodies, or antigen binding fragments thereof, can be generated to target, suitable for use in the immunomodulatory fusion protein described herein.

| Molecule | Molecule Uniprot KB |
|---|---|
| VISTA | Q9H7M9 |
| TIM-3 | Q8TDQ0 |
| LAG-3 | P18627 |
| CD47 | Q08722 |
| SIRPα | P78324 |

Stabilizing Domain

In some embodiments, an immunomodulatory fusion protein comprises one or more immunomodulatory domains and a stabilizing domain. In some embodiments, a stabilizing domain comprises a polypeptide that promotes or increases the expression of the immunomodulatory fusion protein. In some embodiments, a stabilizing domain promotes or increases expression of an immunomodulatory fusion protein by promoting or maintaining folding of an immunomodulatory fusion protein following expression. In some embodiments, a stabilizing domain promotes or increases expression of an immunomodulatory fusion protein by preventing or decreasing aggregation of an immunomodulatory fusion protein following expression. In some embodiments, a stabilizing domain promotes or increases expression of an immunomodulatory fusion protein by preventing or decreasing degradation of an immunomodulatory fusion protein following expression.

In some embodiments, host cells transfected with recombinant nucleic acid encoding an immunomodulatory fusion protein comprising a stabilizing domain have increased expression relative to transfection with recombinant nucleic acid encoding an immunomodulatory fusion protein lacking a stabilizing domain. In some embodiments, expression is increased by about 10%, about 20%, about 30%, about 40%, about 50%, about 60%, about 70%, about 80%, about 90%, or about 100%. In some embodiments, expression is increased by about 2-fold, about 3-fold, about 4-fold, about 5-fold, about 6-fold, about 7-fold, about 8-fold, about 9-fold, or about 10-fold.

In some embodiments, a stabilizing domain comprises a polypeptide that promotes or increases the stability of an immunomodulatory fusion protein following expression and isolation. Methods of measuring protein stability are known in the art and include differential scanning calorimetry, circular dichroism spectroscopy, thermal shift analysis, mass spectrometry, or an activity-based assay.

A stabilizing domain useful to the disclosure is a non-immunogenic protein domain that does not induce an immune response in a patient being treated. Exemplary stabilizing domains are further described below.

Serum Albumin

In some embodiments, an immunomodulatory fusion protein comprises a stabilizing domain that is a serum albumin, or fragments thereof. Methods of fusing serum albumin to proteins are disclosed in, e.g., US2010/0144599, US2007/0048282, and US2011/0020345, which are herein incorporated by reference in their entirety. In some embodiments, the stabilizing domain is human serum albumin (HSA), or variants or fragments thereof, such as those disclosed in U.S. Pat. No. 5,876,969, WO 2011/124718, WO 2013/075066, and WO 2011/0514789.

Suitable albumins for use in the immunomodulatory fusion proteins can be from human, primate, rodent, bovine, equine, donkey, rabbit, goat, sheep, dog, chicken, or pig. In some embodiments, the albumin is a serum albumin, for example, a human serum albumin (SEQ ID NO: 88), primate serum albumin (e.g., chimpanzee serum albumin, gorilla serum albumin), rodent serum albumin (e.g., hamster serum albumin, guinea pig serum albumin, mouse albumin and rat serum albumin), bovine serum albumin, equine serum albumin, donkey serum albumin, rabbit serum albumin, goat serum albumin, sheep serum albumin, dog serum albumin, chicken serum albumin and pig serum albumin.

In some embodiments, the albumin, or a variant or fragment thereof, has a sequence identity to the sequence of wild-type HSA as set forth in SEQ ID NO: 88 of at least 50%, such as at least 60%, at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In some embodiments, the number of alterations, e.g., substitutions, insertions, or deletions, in an albumin variants is 1-20, e.g., 1-10 and 1-5, such as 1, 2, 3, 4, 5, 6, 7, 8, 9 or 10 alterations compared to the corresponding wild-type albumin (e.g., HSA).

In some embodiments, fragments of albumin, or fragments of variants thereof, are suitable for use in the immunomodulatory fusion proteins. Exemplary albumin fragments are disclosed in WO 2011/124718. In some embodiments, a fragment of albumin (e.g., a fragment of HSA) is at least 20 amino acids in length, such as at least 40 amino acids, at least 60 amino acids, at least 80 amino acids, at least 100 amino acids, at least 150 amino acids, at least 200 amino acids, at least 300 amino acids, at least 400 amino acids, or at least 500 amino acids in length.

In some embodiments, an albumin fragment may comprise at least one whole sub-domain of albumin. Domains of HSA have been expressed as recombinant proteins (Dockal et al., *JBC* 1999; 274:9303-10), where domain I was defined as consisting of amino acids 1-197, domain II was defined as consisting of amino acids 189-385, and domain III was defined as consisting of amino acids 381-585 of HSA (SEQ ID NO: 88). Partial overlap of the domains occurs given the extended α-helix structure (h10-h1) which exists between domains I and II, and between domains II and III (Peters, 1996, op. cit, Table 2-4). HSA also comprises six sub-domains (sub-domains IA, IB, NA, NB, INA and NIB). Sub-domain IA comprises amino acids 6-105, sub-domain IB comprises amino acids 120-177, sub-domain NA comprises amino acids 200-291, sub-domain NB comprises amino acids 316-369, sub-domain INA comprises amino acids 392-491 and sub-domain NIB comprises amino acids 512-583 of SEQ ID NO: 88.

In some embodiments, a fragment comprises a whole or part of one or more domains or sub-domains as defined above, or any combination of those domains and/or sub-domains. In some embodiments, an albumin fragment comprises at least 50, 60, 70, 75, 80, 85, 90, 95, 96, 97, 98, or 99% of an albumin or of a domain of an albumin, or a variant or fragment thereof.

Fc Domains

In some embodiments, the stabilizing domain suitable for use in the immunomodulatory fusion protein described herein is an Fc domain. In some embodiments, the Fc domain is a component of the agonist or antagonist antibodies described supra, and therefore a separate Fc domain is not needed.

In certain embodiments, the Fc domain comprises the amino acid sequence set forth in SEQ ID NO: 90. In some embodiments, the Fc domain does not contain a variable region that binds to antigen. In some embodiments, the Fc domain contains a variable region that binds to antigen. Fc domains suitable for the immunomodulatory fusion proteins disclosed herein may be obtained from a number of different sources. In certain embodiments, an Fc domain is derived from a human immunoglobulin. In certain embodiments, the Fc domain is from a human IgG1 constant region. The Fc domain of human IgG1 is set forth in SEQ ID NO: 90. It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the Fc domain or portion thereof may be derived from any immunoglobulin class, including IgM, IgG, IgD, IgA, and IgE, and any immunoglobulin isotype, including IgG1, IgG2, IgG3, and IgG4.

In some embodiments, the immunomodulatory fusion protein comprises a mutant Fc domain. In some embodiments, the immunomodulatory fusion protein comprises a mutant, IgG1 Fc domain. In some embodiments, a mutant Fc domain comprises one or more mutations in the hinge, CH2, and/or CH3 domains. In some aspects, a mutant Fc domain includes a D265A mutation.

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g. hinge, CH2, and/or CH3 sequences, or portions thereof) can be derived from these sequences using art recognized techniques. The genetic material obtained using any of the foregoing methods may then be altered or synthesized to obtain polypeptides suitable for use in the methods disclosed herein. It will further be appreciated that the scope of this disclosure encompasses alleles, variants and mutations of constant region DNA sequences.

Fc domain sequences can be cloned, e.g., using the polymerase chain reaction and primers which are selected to amplify the domain of interest. To clone an Fc domain sequence from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7: 1509); rapid amplification of cDNA ends (Ruberti, F. et al. 1994. J. Immunol. Methods 173:33); antibody leader sequences (Larrick et al. Biochem Biophys Res Commun 1989; 160: 1250). The cloning of antibody sequences is further described in Newman et al., U.S. Pat. No. 5,658,570, filed Jan. 25, 1995, which is herein incorporated by reference.

In some embodiments, the immunomodulatory fusion protein disclosed comprises one or more Fc domains (e.g., 2, 3, 4, 5, 6, 7, 8, 9, 10, or more Fc domains). In certain embodiments, the Fc domains may be of different types. In certain embodiments, at least one Fc domain present in the immunomodulatory fusion protein comprises a hinge domain or portion thereof. In certain embodiments, the immunomodulatory fusion protein comprises at least one Fc domain which comprises at least one CH2 domain or portion thereof. In certain embodiments, the immunomodulatory fusion protein comprises at least one Fc domain which comprises at least one CH3 domain or portion thereof. In certain embodiments, the immunomodulatory fusion protein comprises at least one Fc domain which comprises at least one CH4 domain or portion thereof. In certain embodiments, the immunomodulatory fusion protein comprises at least one Fc domain which comprises at least one hinge domain or portion thereof and at least one CH2 domain or portion thereof (e.g., in the hinge-CH2 orientation). In certain embodiments, the immunomodulatory fusion protein comprises at least one Fc domain which comprises at least one CH2 domain or portion thereof and at least one CH3 domain or portion thereof (e.g., in the CH2-CH3 orientation). In certain embodiments, the immunomodulatory fusion protein comprises at least one Fc domain comprising at least one hinge domain or portion thereof, at least one CH2 domain or portion thereof, and least one CH3 domain or portion thereof, for example in the orientation hinge-CH2-CH3, hinge-CH3-CH2, or CH2-CH3-hinge.

In certain embodiments, immunomodulatory fusion protein comprises at least one complete Fc region derived from one or more immunoglobulin heavy chains (e.g., an Fc domain including hinge, CH2, and CH3 domains, although these need not be derived from the same antibody). In certain embodiments, immunomodulatory fusion protein comprises at least two complete Fc domains derived from one or more immunoglobulin heavy chains. In certain embodiments, the complete Fc domain is derived from a human IgG immunoglobulin heavy chain (e.g., human IgG1).

In certain embodiments, the immunomodulatory fusion protein comprises at least one Fc domain comprising a complete CH3 domain. In certain embodiments, the immunomodulatory fusion protein comprises at least one Fc domain comprising a complete CH2 domain. In certain embodiments, the immunomodulatory fusion protein comprises at least one Fc domain comprising at least a CH3 domain, and at least one of a hinge region, and a CH2 domain. In certain embodiments, the immunomodulatory fusion protein comprises at least one Fc domain comprising a hinge and a CH3 domain. In certain embodiments, the immunomodulatory fusion protein comprises at least one Fc domain comprising a hinge, a CH2, and a CH3 domain. In certain embodiments, the Fc domain is derived from a human IgG immunoglobulin heavy chain (e.g., human IgG1).

The constant region domains or portions thereof making up an Fc domain of the immunomodulatory fusion protein may be derived from different immunoglobulin molecules. For example, a polypeptide suitable for use in the immunomodulatory fusion proteins disclosed herein may comprise a CH2 domain or portion thereof derived from an IgG1 molecule and a CH3 region or portion thereof derived from an IgG3 molecule. In some embodiments, the immunomodulatory fusion protein comprises an Fc domain comprising a hinge domain derived, in part, from an IgG1 molecule and, in part, from an IgG3 molecule. As set forth herein, it will be understood by one of ordinary skill in the art that an Fc domain may be altered such that it varies in amino acid sequence from a naturally occurring antibody molecule.

In certain embodiments, the immunomodulatory fusion protein lacks one or more constant region domains of a complete Fc region, i.e., they are partially or entirely deleted. In certain embodiments, the immunomodulatory fusion protein lacks an entire CH2 domain. In certain embodiments, the immunomodulatory fusion protein comprises CH2 domain-deleted Fc regions derived from a vector (e.g., from IDEC Pharmaceuticals, San Diego) encoding an IgG1 human constant region domain (see, e.g., WO02/060955A2 and WO02/096948A2). This exemplary vector is engineered to delete the CH2 domain and provide a synthetic vector expressing a domain-deleted IgG1 constant region. It will be noted that these exemplary constructs are preferably engineered to fuse a binding CH3 domain directly to a hinge region of the respective Fc domain.

In other constructs it may be desirable to provide a peptide spacer between one or more constituent Fc domains. For example, a peptide spacer may be placed between a hinge region and a CH2 domain and/or between a CH2 and a CH3 domain. For example, compatible constructs could be expressed wherein the CH2 domain has been deleted and the remaining CH3 domain (synthetic or unsynthetic) is joined to the hinge region with a 1-20, 1-10, or 1-5 amino acid peptide spacer. Such a peptide spacer may be added, for instance, to ensure that the regulatory elements of the constant region domain remain free and accessible or that the hinge region remains flexible. Preferably, any stabilizing domain peptide compatible used in the instant disclosure will be relatively non-immunogenic and not prevent proper folding of the Fc.

In certain embodiments, an Fc domain employed in the immunomodulatory fusion protein is altered or modified, e.g., by amino acid mutation (e.g., addition, deletion, or substitution). As used herein, the term "Fc domain variant" refers to an Fc domain having at least one amino acid modification, such as an amino acid substitution, as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region.

In certain embodiments, the Fc variant comprises a substitution at an amino acid position located in a hinge domain or portion thereof. In certain embodiments, the Fc variant comprises a substitution at an amino acid position located in a CH2 domain or portion thereof. In certain embodiments, the Fc variant comprises a substitution at an amino acid position located in a CH3 domain or portion thereof. In certain embodiments, the Fc variant comprises a substitution at an amino acid position located in a CH4 domain or portion thereof.

In certain embodiments, the immunomodulatory fusion protein comprises an Fc variant comprising more than one amino acid substitution. The immunomodulatory fusion protein may comprise, for example, 2, 3, 4, 5, 6, 7, 8, 9, 10 or more amino acid substitutions in the Fc domain. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, or 25 amino acid positions or more.

In some embodiments, an Fc domain includes changes in the region between amino acids 234-238, including the sequence LLGGP at the beginning of the CH2 domain. In some embodiments, an Fc variant alters Fc mediated effector function, particularly ADCC, and/or decrease binding avidity for Fc receptors. In some aspects, sequence changes closer to the CH2-CH3 junction, at positions such as K322 or P331 can eliminate complement mediated cytotoxicity and/or alter avidity for FcR binding. In some embodiments, an Fc domain incorporates changes at residues P238 and P331, e.g., changing the wild type prolines at these positions to serine. In some embodiments, alterations in the hinge region at one or more of the three hinge cysteines, to encode CCC, SCC, SSC, SCS, or SSS at these residues can also affect FcR binding and molecular homogeneity, e.g., by elimination of unpaired cysteines that may destabilize the folded protein.

Other amino acid mutations in the Fc domain are contemplated to reduce binding to the Fc gamma receptor and Fc gamma receptor subtypes. For example, mutations at positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 322, 324, 327, 329, 330, 331, 333, 334, 335, 337, 338, 340, 356, 360, 373, 376, 378, 379, 382, 388, 389, 398, 414, 416, 419, 430, 434, 435, 437, 438 or 439 of the Fc region can alter binding as described in U.S. Pat. No. 6,737,056, issued May 18, 2004, incorporated herein by reference in its entirety. This patent reported that changing Pro331 in IgG3 to Ser resulted in six fold lower affinity as compared to unmutated IgG3, indicating the involvement of Pro331 in Fc gamma RI binding. In addition, amino acid modifications at positions 234, 235, 236, and 237, 297, 318, 320 and 322 are disclosed as potentially altering receptor binding affinity in U.S. Pat. No. 5,624,821, issued Apr. 29, 1997 and incorporated herein by reference in its entirety.

Further mutations contemplated for use include, e.g., those described in U.S. Pat. App. Pub. No. 2006/0235208, published Oct. 19, 2006 and incorporated herein by reference in its entirety. Additionally, mutations described in U.S. Pat. App. Pub. No. 2006/0235208, incorporated herein by reference in its entirety, are contemplated for use. The mutant L234A/L235A is described, e.g., in U.S. Pat. App. Pub. No. 2003/0108548, published Jun. 12, 2003 and incorporated herein by reference in its entirety. In embodiments, the described modifications are included either individually or in combination. In certain embodiments, the mutation is D265A in human IgG1.

In certain embodiments, the immunomodulatory fusion protein comprises an Fc variant comprising an amino acid substitution which alters the antigen-dependent effector functions of the polypeptide, in particular ADCC or complement activation, e.g., as compared to a wild type Fc region. Such immunomodulatory fusion protein exhibit decreased binding to FcR gamma when compared to wild-type polypeptides and, therefore, mediate reduced effector function. Fc variants with decreased FcR gamma binding affinity are expected to reduce effector function, and such molecules are also useful, for example, for treatment of conditions in which target cell destruction is undesirable, e.g., where normal cells may express target molecules, or where chronic administration of the polypeptide might result in unwanted immune system activation.

In certain embodiments, the immunomodulatory fusion protein exhibits altered binding to an activating FcγR (e.g. Fcγl, Fcγlla, or FcγRIIIa). In certain embodiments, the immunomodulatory fusion protein exhibits altered binding affinity to an inhibitory FcγR (e.g. FcγRIIb). Exemplary amino acid substitutions which altered FcR or complement binding activity are disclosed in International PCT Publication No. WO05/063815 which is incorporated by reference herein.

In some embodiments, the immunomodulatory fusion protein comprises an amino acid substitution which alters the glycosylation of the fusion protein. For example, in some embodiments, the Fc domain comprises a mutation leading to reduced glycosylation (e.g., N- or O-linked glycosylation) or comprises an altered glycoform of the wild-type Fc domain (e.g., a low fucose or fucose-free glycan). In certain embodiments, the immunomodulatory fusion protein has an amino acid substitution near or within a glycosylation motif, for example, an N-linked glycosylation motif that contains the amino acid sequence NXT or NXS. Exemplary amino acid substitutions which reduce or alter glycosylation are disclosed in WO05/018572 and US2007/0111281, the contents of which are incorporated by reference herein. In certain embodiments, the immunomodulatory fusion protein comprises at least one Fc domain having engineered cysteine residue or analog thereof which is located at the solvent-exposed surface. In certain embodiments, the immunomodulatory fusion protein comprise an Fc domain comprising at least one engineered free cysteine residue or analog thereof that is substantially free of disulfide bonding with a second cysteine residue. Any of the above engineered cysteine residues or analogs thereof may subsequently be conjugated to a functional domain using art-recognized techniques (e.g., conjugated with a thiol-reactive heterobifunctional stabilizing domain).

In certain embodiments, the immunomodulatory fusion protein comprises a genetically fused Fc domain having two or more of its constituent Fc domains independently selected from the Fc domains described herein. In certain embodiments, the Fc domains are the same. In certain embodiments, at least two of the Fc domains are different. For example, the Fc domains comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In certain embodiments, the Fc domains differ in sequence at one or more amino acid positions. For example, at least two of the Fc domains may differ at about 5 amino acid positions (e.g., 1, 2, 3, 4, or 5 amino acid positions), about 10 positions, about 15 positions, about 20 positions, about 30 positions, about 40 positions, or about 50 positions).

Exemplary Immunomodulatory Fusion Proteins

In some embodiments, an immunomodulatory fusion protein comprises an immunomodulatory domain and a metal hydroxide-binding peptide comprising at least one kinase motif of the secretory pathway kinase Fam20C modified with a phosphate group, wherein the metal hydroxide-binding peptide is operably linked, optionally via a linker, to either the N-terminus or C-terminus of the immunomodulatory domain, thereby forming an immunomodulatory fusion protein.

In some embodiments, an immunomodulatory fusion protein comprises an immunomodulatory domain, a stabilizing domain, and a metal hydroxide-binding peptide comprising at least one kinase motif of the secretory pathway kinase Fam20C modified with a phosphate group, wherein the stabilizing domain is operably linked, optionally via a linker, to either the N-terminus or C-terminus of the immunomodulatory domain, and wherein the metal-hydroxide binding peptide is operably linked, optionally via an amino acid linker, to the terminus of either the immunomodulatory domain or the stabilizing domain, thereby forming an immunomodulatory fusion protein.

In some embodiments, an immunomodulatory fusion protein comprises an immunomodulatory domain, a stabilizing domain, and a metal hydroxide-binding peptide comprising at least one kinase motif of the secretory pathway kinase Fam20C modified with a phosphate group, wherein the metal hydroxide-binding peptide is operably linked, optionally via a linker, to either the N-terminus or C-terminus of the immunomodulatory domain, and wherein the stabilizing domain is operably linked, optionally via an amino acid linker, to the terminus of either the metal hydroxide-binding peptide or the immunomodulatory domain, thereby forming an immunomodulatory fusion protein.

IL-2 Fusion Proteins

In some embodiments, the immunomodulatory fusion protein comprises IL-2, serum albumin and a metal hydroxide-binding peptide comprising at least one kinase motif of the secretory pathway kinase Fam20C modified with a phosphate group. In some embodiments, IL-2 is operably linked to serum albumin. In some embodiments, the metal hydroxide-binding peptide is operably linked to IL-2 or to serum albumin.

In some embodiments, the immunomodulatory fusion protein comprises human IL-2 operably linked to the N-terminus of human serum albumin, and further comprises the metal hydroxide-binding peptide operably linked to the C-terminus of human serum albumin or the N-terminus of human IL-2. In some embodiments, the immunomodulatory fusion protein comprises human IL-2 operably linked to the C-terminus of human serum albumin, and further comprises the metal hydroxide-binding peptide operably linked to the N-terminus of human serum albumin or the C-terminus of human IL-2.

In some embodiments, the immunomodulatory fusion protein comprises human IL-2 operably linked to human serum albumin sequence set forth in SEQ ID NO: 88. In some embodiments, the immunomodulatory fusion protein further comprises the metal hydroxide-binding peptide comprising four kinase motif of the secretory pathway kinase Fam20C set forth by SEQ ID NO: 103, wherein the metal hydroxide-binding peptide is operably linked to IL-2 or to serum albumin.

IL-12 Fusion Proteins

In some embodiments, the immunomodulatory fusion protein comprises IL-12, serum albumin and a metal hydroxide-binding peptide comprising at least one kinase motif of the secretory pathway kinase Fam20C modified with a phosphate group. In some embodiments, IL-12 is operably linked to serum albumin. In some embodiments, the metal hydroxide-binding peptide is operably linked to IL-12 or to serum albumin.

In some embodiments, the immunomodulatory fusion protein comprises human IL-12 operably linked to the N-terminus of human serum albumin, and further comprises the metal hydroxide-binding peptide operably linked to the C-terminus of human serum albumin or the N-terminus of human IL-12. In some embodiments, the immunomodulatory fusion protein comprises human IL-12 operably linked to the C-terminus of human serum albumin, and further comprises the metal hydroxide-binding peptide operably linked to the N-terminus of human serum albumin or the C-terminus of human IL-12.

In some embodiments, the immunomodulatory fusion protein comprises human IL-12 operably linked to human serum albumin sequence set forth in SEQ ID NO: 88. In some embodiments, the immunomodulatory fusion protein further comprises the metal hydroxide-binding peptide comprising four kinase motif of the secretory pathway kinase Fam20C set forth by SEQ ID NO: 103, wherein the metal hydroxide-binding peptide is operably linked to IL-12 or to serum albumin.

IFNg Fusion Proteins

In some embodiments, the immunomodulatory fusion protein comprises at least one IFNg, serum albumin and a metal hydroxide-binding peptide comprising at least one kinase motif of the secretory pathway kinase Fam20C modified with a phosphate group. In some embodiments, IFNg is operably linked to serum albumin. In some embodiments, the metal hydroxide-binding peptide is operably linked to IFNg or to serum albumin.

In some embodiments, the immunomodulatory fusion protein comprises two operably linked human IFNg polypeptides operably linked to the N-terminus of human serum albumin, and further comprises the metal hydroxide-binding peptide operably linked to the C-terminus of human serum albumin or the N-terminus of human IFNg. In some embodiments, the immunomodulatory fusion protein comprises comprises two operably linked human IFNg polypeptides operably linked to the C-terminus of human serum albumin, and further comprises the metal hydroxide-binding peptide operably linked to the N-terminus of human serum albumin or the C-terminus of human IFNg.

In some embodiments, the immunomodulatory fusion protein comprises two operably linked human IFNg polypeptides, and further comprises the metal hydroxide-binding peptide operably linked to the C-terminus or N-terminus of the two IFNg polypeptides.

In some embodiments, the immunomodulatory fusion protein comprises two operably linked human IFNg polypeptides operably linked to human serum albumin sequence set forth in SEQ ID NO: 88. In some embodiments, the immunomodulatory fusion protein further comprises the metal hydroxide-binding peptide comprising four kinase motif of the secretory pathway kinase Fam20C set forth by SEQ ID NO: 103, wherein the metal hydroxide-binding peptide is operably linked to IFNg or to serum albumin.

In some embodiments, the immunomodulatory fusion protein comprises two operably linked human IFNg polypeptides operably linked to the metal hydroxide-binding peptide comprising four kinase motif of the secretory pathway kinase Fam20C set forth by SEQ ID NO: 103, wherein the metal hydroxide-binding peptide is operably linked to IFNg or to serum albumin.

Antibody Fusion Proteins

In some embodiments, the immunomodulatory fusion protein comprises an anti-4-1-BB antibody and a metal hydroxide-binding peptide comprising at least one kinase motif of the secretory pathway kinase Fam20C modified with a phosphate group, wherein the anti-4-1-BB antibody is operably linked to the metal hydroxide-binding peptide. In some embodiments, the anti-4-1-BB antibody is operably linked to the N-terminus of the metal hydroxide-binding peptide. In some embodiments, anti-4-1-BB antibody is operably linked to the C-terminus of the metal hydroxide-binding peptide.

In some embodiments, the immunomodulatory fusion protein comprises an anti-OX40 antibody and a metal hydroxide-binding peptide comprising at least one kinase motif of the secretory pathway kinase Fam20C modified with a phosphate group, wherein the anti-OX40 antibody is operably linked to the metal hydroxide-binding peptide. In some embodiments, the anti-OX40 antibody is operably linked to the N-terminus of the metal hydroxide-binding peptide. In some embodiments, anti-OPX40 antibody is operably linked to the C-terminus of the metal hydroxide-binding peptide.

Methods of Making an Immunomodulatory Fusion Protein-Metal Hydroxide Complex

In some aspects, the polypeptides described herein (e.g., kinases, cytokines, antibodies, stabilizing domains, metal hydroxide-binding peptides) are made in transfected host cells using recombinant DNA techniques. To do so, a recombinant DNA molecule coding for the polypeptide is prepared. Methods of preparing such DNA molecules are well known in the art. For instance, sequences coding for the polypeptides could be excised from DNA using suitable restriction enzymes. Alternatively, the DNA molecule could be synthesized using chemical synthesis techniques, such as the phosphoramidate method. Also, a combination of these techniques could be used.

The methods of making polypeptides also include a vector capable of expressing the peptides in an appropriate host. The vector comprises the DNA molecule that codes for the peptides operatively linked to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be suitable for use in the methods disclosed herein. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

The nucleic acid molecules described above can be contained within a vector that is capable of directing their expression in, for example, a cell that has been transduced with the vector. Accordingly, in addition to polypeptide mutants, expression vectors containing a nucleic acid molecule encoding a mutant and cells transfected with these vectors are among the certain embodiments.

Vectors suitable for use include T7-based vectors for use in bacteria (see, for example, Rosenberg et al., Gene 56: 125, 1987), the pMSXND expression vector for use in mammalian cells (Lee and Nathans, J. Biol. Chem. 263:3521, 1988), and baculovirus-derived vectors (for example the expression vector pBacPAKS from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neon) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that are suitable for use include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes a polypeptide mutant are also suitable for use. A cell is a transfected cell, i.e., a cell into which a nucleic acid molecule, for example a nucleic acid molecule encoding a mutant polypeptide, has been introduced by means of recombinant DNA techniques. The progeny of such a cell are also considered suitable for use in the methods disclosed herein.

The precise components of the expression system are not critical. For example, a polypeptide mutant can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., as therapeutic agents, as described herein.

In some embodiments, an immunomodulatory fusion protein comprising an immunomodulatory domain, a metal hydroxide-binding peptide comprising one or more kinase target motifs, and optionally a stabilizing domain described herein is made in transfected host cells using recombinant DNA techniques. To do so, a recombinant DNA molecule encoding the polypeptide is prepared. The method further comprises a vector capable of expressing a recombinant DNA molecule encoding the polypeptide. The resulting vector comprising the recombinant DNA molecule is used to transfect an appropriate host cell. A method provided by the disclosure for increasing phosphorylation of the immunomodulatory fusion protein comprises transfecting a cell with a recombinant DNA molecule encoding the immunomodulatory fusion protein and a recombinant DNA molecule encoding a kinase comprising an ER-targeting leader sequence, a kinase domain, and an anchor peptide, wherein the kinase is localized to the secretory pathway by the ER-targeting leader sequence and the anchor peptide, and wherein the one or more kinase target motifs of the metal hydroxide-binding peptide are phosphorylated by the kinase in the secretory pathway, thereby increasing phosphorylation of the immunomodulatory fusion protein. In some embodiments, the kinase is a naturally-occurring kinase comprising an ER-targeting leader sequence that localizes the kinase to the secretory pathway. In some embodiments, the naturally-occurring kinase is modified with a terminal (e.g., C-terminal) anchor peptide to increase, promote, or improve localization to the secretory pathway and/or to decrease or prevent secretion. In some embodiments, a kinase of the disclosure comprises any kinase domain modified with an ER-targeting leader sequence and an anchor peptide to increase, promote, or improve localization to the secretory pathway and/or to decrease or prevent secretion.

In some embodiments, the recombinant DNA molecule encoding the immunomodulatory fusion protein and the recombinant DNA molecule encoding a kinase comprising an ER-targeting leader sequence, a kinase domain, and an anchor peptide used to transfect a cell are the same or different.

Accordingly, in some embodiments, an immunomodulatory fusion protein prepared according to such a method of the disclosure comprises an immunomodulatory domain, a metal hydroxide-binding peptide comprising at least one kinase target motif of a secretory pathway kinase that comprises a phosphorylated amino acid, and optionally a stabilizing domain. In some embodiments, the immunomodulatory fusion protein undergoes ligand exchange with a metal hydroxide (e.g., alum) via the at least one phosphorylated amino acid of the metal hydroxide-binding peptide, thereby coupling the immunomodulatory fusion protein to the metal hydroxide (e.g., alum) to form an immunomodulatory fusion protein-metal hydroxide complex.

In some embodiments, an immunomodulatory fusion protein comprising an immunomodulatory domain, and optionally a stabilizing domain, is made in transfected host cells using recombinant DNA techniques, and further coupled with a metal hydroxide-binding peptide comprising at least one hydroxyl replacement groups, a polypeptide-reactive moiety, and optionally a linker, thereby preparing an immunomodulatory fusion protein comprising an immunomodulatory domain, a metal hydroxide-binding peptide, and optionally a stabilizing domain that undergoes ligand exchange with a metal hydroxide (e.g., alum) via the at least one hydroxyl replacement groups to form an immunomodulatory fusion protein-metal hydroxide complex.

In some embodiments, an immunomodulatory fusion protein comprising an immunomodulatory domain, and optionally a stabilizing domain, are modified to include one or more amino acids (e.g. cysteine) not present in the native form for the purpose of creating or increasing the ability of the immunomodulatory fusion protein to react with an polypeptide-reactive moiety.

In some embodiments, a metal hydroxide-binding peptide of the disclosure comprising at least one hydroxyl replacement groups (e.g., a phosphorylated amino acid) that is operably linked to a polypeptide-reactive moiety, optionally via a linker, reacts with an immunomodulatory fusion protein comprising an immunomodulatory domain, and optionally a stabilizing domain, wherein the polypeptide-reactive moiety crosslinks the metal hydroxide-binding peptide, optionally comprising a linker, to the immunomodulatory fusion protein.

One non-limiting manner of achieving this modification that is known in the art, which is particularly well suited for modifying polypeptides, is by inclusion of an amino acid into the immunomodulatory fusion protein that provides a reactive moiety (e.g. cysteine, —SH) and by further contacting the modified immunomodulatory fusion protein comprising a reactive moiety with a polypeptide-reactive moiety operably linked, optionally via a linker, to a metal hydroxide-binding peptide. Another non-limiting manner of achieving this modification that is known in the art, is by inclusion of a short sequence of terminal amino acids (e.g., sequence of glycine or alanine amino acids) into the immunomodulatory fusion protein that allows a reaction catalyzed by recombinant sortase with a metal hydroxide-binding peptide comprising a polypeptide-reactive moiety that is a sortase recognition motif, thereby forming a covalent linkage between the immunomodulatory fusion protein and the metal hydroxide-binding peptide.

In some embodiments, the disclosure contemplates that an immunomodulatory fusion protein that includes one or more hydroxyl-replacement moieties in its native form can be modified in accordance with the invention to increase the rate of ligand exchange adsorption or to increase the strength of adsorption of the immunomodulatory fusion protein to a metal hydroxide.

Pharmaceutical Compositions and Modes of Administration

In certain embodiments, the disclosure provides for a pharmaceutical composition comprising an immunomodulatory fusion protein-metal hydroxide complex with a pharmaceutically acceptable diluent, carrier, solubilizer, emulsifier, preservative and/or adjuvant. In certain embodiments, the disclosure provides for a pharmaceutical composition comprising an immunomodulatory fusion protein with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In certain embodiments, the formulation material(s) are for s.c. and/or I.V. administration. In certain embodiments, the formulation material(s) are for local administration, e.g., intratumoral administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the immunomodulatory fusion protein-metal hydroxide complex.

In some embodiments, the formulations comprising an immunomodulatory fusion protein-metal hydroxide complex or an immunomodulatory fusion protein described herein are 4° C. to 37° C. when administered to a subject.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an immunomodulatory fusion protein-metal hydroxide complex or an immunomodulatory fusion protein is prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an immunomodulatory fusion protein-metal hydroxide complex or an immunomodulatory fusion protein is formulated as a lyophilizate using appropriate excipients such as sucrose.

In certain embodiments, the pharmaceutical composition is selected for parenteral delivery. In certain embodiments, the compositions are selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition is in the form of a pyrogen-free, parenterally acceptable aqueous solution comprising an immunomodulatory fusion protein-metal hydroxide complex or an immunomodulatory fusion protein, in a pharmaceutically acceptable vehicle. In certain embodiments, a vehicle for parenteral injection is sterile distilled water in which the immunomodulatory fusion protein-metal hydroxide complex or an immunomodulatory fusion protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition is formulated for inhalation. In certain embodiments, an immunomodulatory fusion protein-metal hydroxide complex or an immunomodulatory fusion protein is formulated as a dry powder for inhalation. In certain embodiments, an inhalation solution comprising an immunomodulatory fusion protein-metal hydroxide complex or an immunomodulatory fusion protein is formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations are administered orally. In certain embodiments, an immunomodulatory fusion protein-metal hydroxide complex or an immunomodulatory fusion protein administered in this fashion is formulated with or without those carriers customarily used in the compounding of solid dosage forms such as tablets and capsules. In certain embodiments, a capsule is designed to release the active portion of the formulation at the point in the gastrointestinal tract when bioavailability is maximized and pre-systemic degradation is minimized In certain embodiments, at least one additional agent is included to facilitate absorption of the immunomodulatory fusion protein-metal hydroxide complex or an immunomodulatory fusion protein. In certain embodiments, diluents, flavorings, low melting point waxes, vegetable oils, lubricants, suspending agents, tablet disintegrating agents, and binders can also be employed.

In certain embodiments, a pharmaceutical composition comprises an effective quantity of immunomodulatory fusion protein-metal hydroxide complex or an immunomodulatory fusion protein in a mixture with non-toxic excipients which are suitable for the manufacture of tablets. In certain embodiments, by dissolving the tablets in sterile water, or another appropriate vehicle, solutions are prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an immunomodulatory fusion protein-metal hydroxide complex or an immunomodulatory fusion protein, in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this is accomplished by filtration through sterile filtration membranes. In certain embodiments, where the composition is lyophilized, sterilization using this method is conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising immunomodulatory fusion protein-metal hydroxide complex or an immunomodulatory fusion protein to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which the immunomodulatory fusion protein-metal hydroxide complex or an immunomodulatory fusion protein is being used, the route of administration, and the size (body weight, body surface or organ size) and/or condition (the age and general health) of the patient. In certain embodiments, the clinician can titer the dosage and modify the route of administration to obtain the optimal therapeutic effect.

In certain embodiments, the frequency of dosing will take into account the pharmacokinetic parameters of the immunomodulatory fusion protein-metal hydroxide complex or an immunomodulatory fusion protein in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intraocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising an immunomodulatory fusion protein-metal hydroxide complex or an immunomodulatory fusion protein in an ex vivo manner. In such instances, cells, tissues and/or organs that have been removed from the patient are exposed to a pharmaceutical composition comprising the immunomodulatory fusion protein-metal hydroxide complex or an immunomodulatory fusion protein after which the cells, tissues and/or organs are subsequently implanted back into the patient.

In certain embodiments, an immunomodulatory fusion protein-metal hydroxide complex or an immunomodulatory fusion protein is delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Methods of Treatment

The immunomodulatory fusion protein-metal hydroxide complexes, immunomodulatory fusion proteins and/or nucleic acids expressing the immunomodulatory fusion proteins described herein, or compositions thereof described herein, are useful for treating a disorder associated with abnormal apoptosis or a differentiative process (e.g., cellular proliferative disorders (e.g., hyperproliferative disorders) or cellular differentiative disorders, such as cancer). Non-limiting examples of cancers that are amenable to treatment with the methods of the present disclosure are described below.

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. Accordingly, the compositions used herein, comprising, e.g., immunomodulatory fusion protein-metal hydroxide complex, can be administered to a patient who has cancer.

As used herein, the terms "cancer" (or "cancerous"), "hyperproliferative," and "neoplastic" refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The immunomodulatory fusion protein-metal hydroxide complexes, immunomodulatory fusion proteins or compositions thereof can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macro globulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

It will be appreciated by those skilled in the art that amounts of an immunomodulatory fusion protein-metal hydroxide complex, immunomodulatory fusion protein or a composition thereof sufficient to reduce tumor growth and size, or a therapeutically effective amount, will vary not only on the particular compounds or compositions selected, but also with the route of administration, the nature of the condition being treated, and the age and condition of the patient, and will ultimately be at the discretion of the patient's physician or pharmacist. The length of time during which the compounds used in the instant method will be given varies on an individual basis.

It will be appreciated by those skilled in the art that the B16 melanoma model used herein is a generalized model for solid tumors. That is, efficacy of treatments in this model is also predictive of efficacy of the treatments in other non-melanoma solid tumors. For example, as described in Baird et al. (J Immunology 2013; 190:469-78; Epub Dec. 7, 2012), efficacy of cps, a parasite strain that induces an adaptive immune response, in mediating anti-tumor immunity against B16F10 tumors was found to be generalizable to other solid tumors, including models of lung carcinoma and ovarian cancer. In another example, results from a line of research into VEGF targeting lymphocytes also shows that results in B16F10 tumors were generalizable to the other tumor types studied (Chinnasamy et al., *JCI* 2010; 120:3953-68; Chinnasamy et al., *Clin Cancer Res* 2012; 18:1672-83). In yet another example, immunotherapy involving LAG-3 and PD-1 led to reduced tumor burden, with generalizable results in a fibrosarcoma and colon adenocarcinoma cell lines (Woo et al., *Cancer Res* 2012; 72:917-27).

In certain embodiments, the immunomodulatory fusion protein-metal hydroxide complexes, immunomodulatory fusion proteins, or compositions thereof disclosed herein are used to treat cancer. In certain embodiments, the immunomodulatory fusion protein-metal hydroxide complexes, immunomodulatory fusion proteins, or compositions thereof disclosed herein are used to treat melanoma, leukemia, lung cancer, breast cancer, prostate cancer, ovarian cancer, colon cancer, and brain cancer.

In certain embodiments, the immunomodulatory fusion protein-metal hydroxide complexes, immunomodulatory fusion proteins, or compositions thereof disclosed herein inhibit the growth and/or proliferation of tumor cells. In certain embodiments, the immunomodulatory fusion protein-metal hydroxide complexes immunomodulatory fusion proteins, or compositions thereof disclosed herein reduce tumor size. In certain embodiments, the immunomodulatory fusion protein-metal hydroxide complexes immunomodulatory fusion proteins, or compositions thereof disclosed herein inhibit metastases of a primary tumor.

It will be appreciated by those skilled in the art that reference herein to treatment extends to prophylaxis as well as the treatment of the noted cancers and symptoms.

Combination Therapy

In some embodiments, the immunomodulatory fusion protein-metal hydroxide complexes or immunomodulatory fusion proteins disclosed herein are used in combination with other therapies. For example, in some embodiments the immunomodulatory fusion protein-metal hydroxide complexes or immunomodulatory fusion proteins are used in combination with another immunotherapy. Exemplary immunotherapies include, but are not limited to, chimeric antigen receptor (CAR) T cell therapy, tumor-associated antigen targeting antibodies, immune checkpoint inhibitors, and cancer vaccines. In some embodiments, an immunomodulatory fusion protein-metal hydroxide complex or immunomodulatory fusion protein is used in combination with another immunomodulatory fusion protein-metal hydroxide complex or immunomodulatory fusion protein having a different immunomodulatory domain.

Chimeric Antigen Receptor (CAR) Effector Cells

In some aspects, the disclosure provides immunomodulatory fusion protein-metal hydroxide complexes or immunomodulatory fusion proteins to be used or performed in conjunction with chimeric antigen receptor (CAR) effector cell therapy (e.g., CAR T cells).

Chimeric antigen receptors (CARs) are genetically-engineered, artificial transmembrane receptors, which confer an arbitrary specificity for a ligand onto an immune effector cell (e.g. a T cell, natural killer cell or other immune cell) and which results in activation of the effector cell upon recognition and binding to the ligand. Typically these receptors are used to impart the antigen specificity of a monoclonal antibody onto a T cell.

In some embodiments, CARs contain three domains: 1) an ectodomain typically comprising a signal peptide, a ligand or antigen recognition region (e.g. scFv), and a flexible spacer; 2) a transmembrane (TM) domain; 3) an endodomain (alternatively known as an "activation domain") typically comprising one or more intracellular signaling domains. The ectodomain of the CAR resides outside of the cell and is exposed to the extracellular space, whereby it is accessible for interaction with its cognate ligand. The TM domain allows the CAR to be anchored into the cell membrane of the effector cell. The third endodomain (also known as the "activation domain") aids in effector cell activation upon binding of the CAR to its specific ligand. In some embodiments, effector cell activation comprises induction of cytokine and chemokine production, as well as activation of the cytolytic activity of the cells. In some embodiments, the CARs redirect cytotoxicity toward tumor cells.

In some embodiments, CARs comprise a ligand- or antigen-specific recognition domain that binds to a specific target ligand or antigen (also referred to as a binding domain) In some embodiments, the binding domain is a single-chain antibody variable fragment (scFv), a tethered ligand or the extracellular domain of a co-receptor, fused to a transmembrane domain, which is linked, in turn, to a signaling domain. In some embodiments, the signaling domain is derived from CD3ζ or FcRγ. In some embodiments, the CAR comprises one or more co-stimulatory domains derived from a protein such as CD28, CD137 (also known as 4-1BB), CD134 (also known as OX40) and CD278 (also known as ICOS).

Engagement of the antigen binding domain of the CAR with its target antigen on the surface of a target cell results in clustering of the CAR and delivers an activation stimulus to the CAR-containing cell. In some embodiments, the main characteristic of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific co-receptors. Although scFv-based CARs engineered to contain a signaling domain from CD3 or FcRγ have been shown to deliver a potent signal for T cell activation and effector function, they are not sufficient to elicit signals that promote T cell survival and expansion in the absence of a concomitant co-stimulatory signal. A new generation of CARs containing a binding domain, a hinge, a transmembrane and the signaling domain derived from CD3 or FcRγ together with one or more co-stimulatory signaling domains (e.g., intracellular co-stimulatory domains derived from CD28, CD137, CD134 and CD278) has been shown to more effectively direct antitumor activity as well as increased cytokine secretion, lytic activity, survival and proliferation in CAR expressing T cells in vitro, in animal models and cancer patients (Milone et al., Molecular Therapy, 2009; 17: 1453-1464; Zhong et al., Molecular Therapy, 2010; 18: 413-420; Carpenito et al., PNAS, 2009; 106:3360-3365).

In some embodiments, chimeric antigen receptor-expressing effector cells (e.g. CAR-T cells) are cells that are derived from a patient with a disease or condition and genetically modified in vitro to express at least one CAR with an arbitrary specificity to a ligand. The cells perform at least one effector function (e.g. induction of cytokines) that is stimulated or induced by the specific binding of the ligand to the CAR and that is useful for treatment of the same patient's disease or condition. The effector cells may be T cells (e.g. cytotoxic T cells or helper T cells). One skilled in the art would understand that other cell types (e.g. a natural killer cell or a stem cell) may express CARs and that a chimeric antigen receptor effector cell may comprise an effector cell other than a T cell. In some embodiments, the effector cell is a T cell (e.g. a cytotoxic T cell) that exerts its effector function (e.g. a cytotoxic T cell response) on a target cell when brought in contact or in proximity to the target or target cell (e.g. a cancer cell) (see e.g., Chang and Chen (2017) Trends Mol Med 23(5):430-450).

Prolonged exposure of T cells to their cognate antigen can result in exhaustion of effector functions, enabling the persistence of infected or transformed cells. Recently developed strategies to stimulate or rejuvenate host effector function using agents that induce an immune checkpoint blockade have resulted in success towards the treatment of several cancers. Emerging evidence suggests that T cell exhaustion may also represent a significant impediment in sustaining long-lived antitumor activity by chimeric antigen receptor-expressing T cells (CAR-T cells. In some embodiments, the differentiation status of the patient-harvested T cells prior to CAR transduction and the conditioning regimen a patient undergoes before reintroducing the CAR-T cells (e.g., addition or exclusion of alkylating agents, fludarabine, total-body irradiation) can profoundly affect the persistence and cytotoxic potential of CAR-T cells. In vitro culture conditions that stimulate (via anti-CD3/CD28 or stimulator cells) and expand (via cytokines, such as IL-2) T cell populations can also alter the differentiation status and effector function of CAR-T cells (Ghoneim et al., (2016) Trends in Molecular Medicine 22(12):1000-1011).

In some embodiments, in particular for the treatment of ALL and/or NHL, suitable CARs target CD19 or CD20. Non-limiting examples include CARs comprising a structure: (i) an anti-CD19 scFv, a CD8 H/TM domain, an 4-1BB CS domain and a CD3ζTCR signaling domain; (ii) an anti-CD19 scFv, a CD28 hinge and transmembrane domain, a CD28 co-stimulatory domain and a CD3ζ TCR signaling domain; and (iii) an anti-CD20 scFv, an IgG hinge and transmembrane domain, a CD28/4-1BB co-stimulatory domain and a CD3ζ TCR signaling domain. In some embodiments, a CAR effector cell suitable for combination with the combinations and methods disclosed herein targets CD19 or CD20, including but not limited to Kymriah™ (tisagenlecleucel; Novartis; formerly CTL019) and Yescarta™ (axicabtagene ciloleucel; Kite Pharma).

Re-Targeted CAR T Cells

In some embodiments, the CAR-T therapy suitable for use in combination with the immunomodulatory fusion protein-metal hydroxide complex is a re-targeted CAR-T cell. In some embodiments, effector cells (e.g., T cells) modified to express a CAR which binds to a universal immune receptor, a tag, a switch or an Fc region on an immunoglobulin are suitable for the methods described herein.

In some embodiments, effector cells (e.g., T cells) are modified to express a universal immune receptor or UnivIR. One type of UnivIR is a biotin-binding immune receptor (BBIR) (see e.g., US Patent Publication US20140234348 A1 incorporated herein by reference in its entirety). Other examples of methods and compositions relating to universal chimeric receptors and/or effector cells expressing universal chimeric receptors are described in International Patent Applications WO2016123122A1, WO2017143094A1, WO2013074916A1, US Patent Application US20160348073A1, all of which are incorporated herein by reference in their entirety.

In some embodiments, effector cells (e.g., T cells) are modified to express a universal, modular, anti-tag chimeric antigen receptor (UniCAR). This system allows for retargeting of UniCAR engrafted immune cells against multiple antigens (see e.g., US Patent Publication US20170240612 A1 incorporated herein by reference in its entirety; Cartellieri et al., (2016) Blood Cancer Journal 6, e458 incorporated herein by reference in its entirety).

In some embodiments, effector cells (e.g., T cells) are modified to express a switchable chimeric antigen receptor and chimeric antigen receptor effector cell (CAR-EC) switches. In this system, the CAR-EC switches have a first region that is bound by a chimeric antigen receptor on the CAR-EC and a second region that binds a cell surface molecule on target cell, thereby stimulating an immune response from the CAR-EC that is cytotoxic to the bound target cell. In some embodiments, the CAR-EC is a T cell, wherein the CAR-EC switch may act as an "on-switch" for CAR-EC activity. Activity may be "turned off" by reducing or ceasing administration of the switch. These CAR-EC switches may be used with CAR-ECs disclosed herein, as well as existing CAR T-cells, for the treatment of a disease or condition, such as cancer, wherein the target cell is a malignant cell. Such treatment may be referred to herein as switchable immunotherapy (U.S. Pat. No. 9,624,276 B2 incorporated herein by reference in its entirety).

In some embodiments, effector cells (e.g., T cells) are modified to express a receptor that binds the Fc portion of human immunoglobulins (e.g., CD16V-BB-ζ) (Kudo et al., (2014) Cancer Res 74(1):93-103 incorporated herein by reference in its entirety).

In some embodiments, effector cells (e.g., T cells) are modified to express a universal immune receptor (e.g., switchable CAR, sCAR) that binds a peptide neo-epitope (PNE). In some embodiments, the peptide neo-epitope (PNE), has been incorporated at defined different locations within an antibody targeting an antigen (antibody switch). Therefore, sCAR-T-cell specificity is redirected only against PNE, not occurring in the human proteome, thus allowing an orthogonal interaction between the sCAR-T-cell and the antibody switch. In this way, sCAR-T cells are strictly dependent on the presence of the antibody switch to become fully activated, thus excluding CAR T-cell off-target recognition of endogenous tissues or antigens in the absence of the antibody switch (Arcangeli et al., (2016) Transl Cancer Res 5(Suppl 2):S174-S177 incorporated herein by reference in its entirety). Other examples of switchable CARs is provided by US Patent Application US20160272718A1 incorporated herein by reference in its entirety.

As used herein, the term "tag" encompasses a universal immune receptor, a tag, a switch, or an Fc region of an immunoglobulin as described supra. In some embodiments, an effector cell is modified to express a CAR comprising a tag binding domain. In some embodiments, the CAR binds fluorescein isothiocyanate (FITC), streptavidin, biotin, dinitrophenol, peridinin chlorophyll protein complex, green fluorescent protein, phycoerythrin (PE), horse radish peroxidase, palmitoylation, nitrosylation, alkalanine phosphatase, glucose oxidase, or maltose binding protein.

Anti-TAG Chimeric Antigen Receptors (AT-CAR)

In some embodiments, the CAR-T therapy suitable for use in combination with the immunomodulatory fusion protein-metal hydroxide complex or immunomodulatory fusion protein is an anti-tag CAR T cell. There are several limitations to the generalized clinical application of CAR T cells. For example, as there is no single tumor antigen universally expressed by all cancer types, each scFv in a CAR needs to be engineered with specificity for the desired tumor antigen. In addition, tumor antigens targeted by a CAR may be down-regulated or mutated in response to treatment resulting in tumor evasion.

As an alternative, universal, anti-tag chimeric antigen receptors (AT-CAR) and CAR-T cells have been developed. For example, human T cells have been engineered to express an anti-fluorescein isothiocyanate (FITC) CAR (referred to anti-FITC-CAR). This platform takes advantage of the high affinity interaction between the anti-FITC scFv (on the cell's surface) and FITC as well as the ability conjugate FITC molecules (or other tags) to any anti-cancer-based monoclonal antibody such as cetuximab (anti-EGFR), retuximab (anti-CD20) and herceptin (anti-Her2).

Accordingly, in some embodiments, effector cells (e.g., T cells) are modified to express a universal anti-tag chimeric antigen receptor (AT-CAR), as described at least in WO 2012082841 and US20160129109A1, incorporated herein by reference in its entirety. In such AT-CAR systems, T cells recognize and bind tagged proteins, such as antibodies. For example, in some embodiments an AT-CAR T cell recognizes tag-labeled antibodies, such as FITC-labeled antibodies. In some embodiments, an anti-tumor antigen antibody is conjugated to a tag (e.g., FITC), and administered prior to, concurrently, or after AT-CAR therapy. Anti-tumor antigen antibodies are known to those of skill in the art.

As indicated, the binding specificity of the tag-binding domain depends on the identity of the tag that is conjugated to the protein that is used to bind target cells. For example, in some aspects of the disclosure, the tag is FITC, the tag-binding domain is an anti-FITC scFv. Alternatively, in some aspects of the disclosure, the tag is biotin or PE (phycoerythrin) and the tag-binding domain is an anti-biotin scFv or an anti-PE scFv.

In some embodiments, the protein of each formulation of tagged proteins is the same or different and the protein is an antibody or an antigen-binding fragment thereof. In some aspects, the antibody or antigen-binding fragment thereof is cetuximab (anti-EGFR), nimotuzumab (anti-EGFR), panitumumab (anti-EGFR), retuximab (anti-CD20), omalizumab (anti-CD20), tositumomab (anti-CD20), trastuzumab (anti-Her2), gemtuzumab (anti-CD33), alemtuzumab (anti-CD52), and bevacuzimab (anti-VEGF).

Thus, in some embodiments, the tagged proteins include FITC-conjugated antibodies, biotin-conjugated antibodies, PE-conjugated antibodies, histidine-conjugated antibodies and streptavidin-conjugated antibodies, where the antibody binds to a TAA or a TSA expressed by the target cells. For example, the tagged proteins include, but are not limited to, FITC-conjugated cetuximab, FITC-conjugated retuximab, FITC-conjugated herceptin, biotin-conjugated cetuximab, biotin-conjugated retuximab, biotin-conjugated herceptin, PE-conjugated cetuximab, PE-conjugated retuximab, PE-conjugated herceptin, histidine-conjugated cetuximab, histidine-conjugated retuximab, histidine-conjugated herceptin, streptavidin-conjugated cetuximab, streptavidin-conjugated retuximab, and streptavidin-conjugated herceptin.

In some embodiments, the AT-CAR of each population of AT-CAR-expressing T cells is the same or different and the AT-CAR comprises a tag-binding domain, a transmembrane domain, and an activation domain. In some embodiments, the tag-binding domain is an antibody or an antigen-binding fragment thereof. In some aspects, the tag-binding domain specifically binds FITC, biotin, PE, histidine or streptavidin. In some embodiments the tag-binding domain is antigen-binding fragment and the antigen-binding fragment is a single chain variable fragment (scFv), such as a scFv that specifically binds FITC, biotin, PE, histidine or streptavidin. In some embodiments the transmembrane domain is the hinge and transmembrane regions of the human CD8a chain. In some embodiments, the activation domain comprises one or more of the cytoplasmic region of CD28, the cytoplasmic region of CD137 (41BB), OX40, HVEM, CD3ζ and FcRε.

In some embodiments, the tag of each formulation of tagged proteins is the same or different and the tag is selected from the group consisting of fluorescein isothiocyanate (FITC), streptavidin, biotin, histidine, dinitrophenol, peridinin chlorophyll protein complex, green fluorescent protein, phycoerythrin (PE), horse radish peroxidase, palmitoylation, nitrosylation, alkalanine phosphatase, glucose oxidase, and maltose binding protein.

The tag may be conjugated to the proteins using techniques such as chemical coupling and chemical cross-linkers. Alternatively, polynucleotide vectors can be prepared that encode the tagged proteins as fusion proteins. Cell lines can then be engineered to express the tagged proteins, and the tagged proteins can be isolated from culture media, purified and used in the methods disclosed herein.

In some embodiments, tagged proteins are administered to a subject prior to, or concurrent with, or after administration of the AT-CAR-expressing T cells. In some embodiments, the disclosure provide a method of treating cancer in a subject, comprising: (a) administering a formulation of tagged proteins to a subject in need of treatment, wherein the tagged proteins bind a cancer cell in the subject, and (b) administering a therapeutically-effective population of anti-tag chimeric antigen receptor (AT-CAR)-expressing T cells to the subject, wherein the AT-CAR-expressing T cells bind the tagged proteins and induce cancer cell death, thereby treating cancer in a subject.

Tandem CAR (TanCAR) Effector Cells

In some embodiments, the CAR-T therapy suitable for use in combination with the immunomodulatory fusion protein-metal hydroxide complex or immunomodulatory fusion protein is a tandem CAR effector cell. It has been observed that using a CAR approach for cancer treatment, tumor heterogeneity and immunoediting can cause escape from CAR treatment (Grupp et al., New Eng. J. Med (2013) 368:1509-1518). As an alternative approach, bispecific CARs, known as tandem CARs or TanCARs, have been developed in an attempt to target multiple cancer specific markers simultaneously. In a TanCAR, the extracellular domain comprises two antigen binding specificities in tandem, joined by a linker. The two binding specificities (scFvs) are thus both linked to a single transmembrane portion: one scFv being juxtaposed to the membrane and the other being in a distal position. As an exemplary TanCAR, Grada et al. (Mol Ther Nucleic Acids (2013) 2, e105) describes a TanCAR which includes a CD19-specific scFv, followed by a Gly-Ser linker and a HER2-specific scFv. The HER2-scFv was in the juxta-membrane position, and the CD19-scFv in the distal position. The TanCAR was shown to induce distinct T cell reactivity against each of the two tumor restricted antigens.

Accordingly, some aspects of the disclosure relate to a tandem chimeric antigen receptor that mediates bispecific activation and targeting of T cells. Although the present disclosure refers to bispecificity for the CAR, in some aspects the CARs are able to target three, four, or more tumor antigens. Targeting multiple antigens using CAR T cells may enhance T cell activation and/or offset tumor escape by antigen loss. TanCARs may also target multiple expressed antigens, target various tumors using the same cellular product with a broad specificity, and/or provide a better toxicity profile with a less intensely signaling CAR achieving the same results due to multiple specificity.

In some embodiments, the disclosure provides a TanCAR that includes two targeting domains. In some embodiments, the disclosure provides a multispecific TanCAR that includes three or more targeting domains. In another embodiment, the disclosure provides a first CAR and second CAR at the cell surface, each CAR comprising an antigen-binding domain, wherein the antigen-binding domain of the first CAR binds to a first tumor antigen (e.g., CD19, CD20, CD22, HER2) and the antigen-binding domain of the second CAR binds to another (different) tumor antigen. TanCARs are described in US20160303230A land US20170340705A1, incorporated herein by reference.

In some embodiments, the TanCAR of the disclosure targets two or more tumor antigens. Exemplary tumor antigens include one or more of CD19, CD20, CD22, k light chain, CD30, CD33, CD123, CD38, ROR1, ErbB2, ErbB3/4, EGFR vIII, carcinoembryonic antigen, EGP2, EGP40, mesothelin, TAG72, PSMA, NKG2D ligands, B7-H6, IL-13 receptor α 2, MUC1, MUC16, CA9, GD2, GD3, HMW-MAA, CD171, Lewis Y, G250/CALX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, and/or TEM8.

In some embodiments, the disclosure provides a bispecific TanCAR that targets CD19 and another tumor antigen. In some embodiments, the disclosure provides a bispecific TanCAR that targets CD22 and another tumor antigen. In some embodiments, the disclosure provides a bispecific TanCAR that targets HER2 and another tumor antigen. In some embodiments, the disclosure provides a bispecific TanCAR that targets IL13R-alpha2 and another tumor antigen. In some embodiments, the disclosure provides a bispecific TanCAR that targets VEGF-A and another tumor antigen. In some embodiments, the disclosure provides a bispecific TanCAR that targets Tem8 and another tumor antigen. In some embodiments, the disclosure provides a bispecific TanCAR that targets FAP and another tumor antigen. In some embodiments, the disclosure provides a bispecific TanCAR that targets EphA2 and another tumor antigen. In some embodiments, the disclosure provides a bispecific TanCAR that targets one or more, two or more, three or more, or four or more of the following tumor antigens: CD19, CD22, HER2, IL13R-alpha2, VEGF-A, Tem8, FAP, or EphA2, and any combination thereof. In some embodiments, the disclosure provides a bispecific TanCAR that targets HER2 and IL13R-alpha2. In some embodiments, the disclosure provides a bispecific TanCAR that targets CD19 and CD22.

Methods for Generating Chimeric Antigen Receptors and CAR Effector Cells

In some embodiments, a subject's effectors cells (e.g., T cells) are genetically modified with a chimeric antigen receptor (Sadelain et al., *Cancer Discov.* 3:388-398, 2013). For example, an effector cell (e.g., T cell) is provided and a recombinant nucleic acid encoding a chimeric antigen receptor is introduced into the patient-derived effector cell (e.g., T cell) to generate a CAR cell. In some embodiments, effector cells (e.g., T cells) not derived from the subject are genetically modified with a chimeric antigen receptor. For example, in some embodiments, effector cells (e.g., T cells) are allogeneic cells that have been engineered to be used as an "off the shelf" adoptive cell therapy, such as Universal Chimeric Antigen Receptor T cells (UCARTs), as developed by Cellectis. UCARTs are allogeneic CAR T cells that have been engineered to be used for treating the largest number of patients with a particular cancer type. Non-limiting examples of UCARTs under development by Cellectis include those that target the following tumor antigens: CD19, CD123, CD22, CS1 and A variety of different methods known in the art can be used to introduce any of the nucleic acids or expression vectors disclosed herein into an effector cell (e.g., T cell). Non-limiting examples of methods for introducing nucleic acid into a an effector cell (e.g., T cell) include: lipofection, transfection (e.g., calcium phosphate transfection, transfection using highly branched organic compounds, transfection using cationic polymers, dendrimer-based transfection, optical transfection, particle-based transfection (e.g., nanoparticle transfection), or transfection using liposomes (e.g., cationic liposomes)), microinjection, electroporation, cell squeezing, sonoporation, protoplast fusion, impalefection, hydrodynamic delivery, gene gun, magnetofection, viral transfection, and nucleofection. Furthermore, the CRISPR/Cas9 genome editing technology known in the art can be used to introduce CAR nucleic acids into effector cells (e.g., T cells) and/or to introduce other genetic modifications (e.g., as described below) into effector cells (e.g., T cells) to enhance CAR cell activity (for use of CRISPR/Cas9 technology in connection with CART cells, see e.g., U.S. Pat. Nos. 9,890,393; 9,855,297; US 2017/0175128; US 2016/0184362; US 2016/0272999; WO 2015/161276; WO 2014/191128; CN 106755088; CN 106591363; CN 106480097; CN 106399375; CN 104894068).

Provided herein are methods that can be used to generate any of the cells or compositions described herein where each cell can express a CAR (e.g., any of the CARs described herein).

Chimeric antigen receptors (CARs) include an antigen-binding domain, a transmembrane domain, and an cytoplasmic signaling domain that includes a cytoplasmic sequence of CD3ζ sequence sufficient to stimulate a T cell when the antigen-binding domain binds to the antigen, and optionally, a cytoplasmic sequence of one or more (e.g., two, three, or four) co-stimulatory proteins (e.g., a cytoplasmic sequence of one or more of B7-H3, BTLA, CD2, CD7, CD27, CD28, CD30, CD40, CD40L, CD80, CD160, CD244, ICOS, LAG3, LFA-1, LIGHT, NKG2C, 4-1BB, OX40, PD-1, PD-L1, TIM3, and a ligand that specifically binds to CD83) that provides for co-stimulation of the T cell when the antigen-binding domain binds to the antigen. In some embodiments, a CAR can further include a linker. Non-limiting aspects and features of CARs are described below. Additional aspects of CARs and CAR cells, including exemplary antigen-binding domains, linkers, transmembrane domains, and cytoplasmic signaling domains, are described in, e.g., Kakarla et al., *Cancer J.* 20:151-155, 2014; Srivastava et al., *Trends Immunol.* 36:494-502, 2015; Nishio et al., *Oncoimmunology* 4(2): e988098, 2015; Ghorashian et al., *Br. J. Haematol.* 169:463-478, 2015; Levine, *Cancer Gene Ther.* 22:79-84, 2015; Jensen et al., *Curr. Opin. Immunol.* 33:9-15, 2015; Singh et al., *Cancer Gene Ther.* 22:95-100, 2015; Li et al., *Zhongguo Shi Yan Xue Ye Xue Za Zhi* 22:1753-1756, 2014; Gill et al., *Immunol. Rev.* 263:68-89, 2015; Magee et al., *Discov. Med.* 18:265-271, 2014; Gargett et al., *Front. Pharmacol.* 5:235, 2014; Yuan et al., *Zhongguo Shi Yan Xue Ye Xue Za Zhi* 22:1137-1141, 2014; Pedgram et al., *Cancer J.* 20:127-133, 2014; Eshhar et al., *Cancer J.* 20:123-126, 2014; Ramos et al., *Cancer J.* 20:112-118, 2014; Maus et al., *Blood* 123:2625-2635, 2014; Jena et al., *Curr. Hematol. Malig. Rep.* 9:50-56, 2014; Maher et al., *Curr. Gene Ther.* 14:35-43, 2014; Riches et al., *Discov. Med.* 16:295-302, 2013; Cheadle et al., *Immunol. Rev.* 257:83-90, 2014; Davila et al., *Int. J. Hematol.* 99:361-371, 2014; Xu et al., *Cancer Lett.* 343:172-178, 2014; Kochenderfer et al., *Nat. Rev. Clin. Oncol.* 10:267-276, 2013; Hosing et al., *Curr. Hematol. Malig. Rep.* 8:60-70, 2013; Hombach et al., *Curr. Mol. Med.* 13:1079-1088, 2013; Xu et al., *Leuk. Lymphoma* 54:255-260, 2013; Gilham et al., *Trends Mol. Med.* 18:377-384, 2012; Lipowska-Bhalla et al., *Cancer Immunol. Immunother.* 61:953-962, 2012; Chmielewski et al., *Cancer Immunol. Immunother.* 61:1269-1277, 2013; Jena et al., *Blood* 116:1035-1044, 2010; Dotti et al, *Immunology Reviews* 257(1): 107-126, 2013; Dai et al., *Journal of the National Cancer Institute* 108(7): djv439, 2016; Wang and Riviere, *Molecular Therapy-Oncolytics* 3: 16015, 2016; U.S. Patent Application Publication Nos. 2018/0057609; 2018/0037625; 2017/0362295; 2017/0137783; 2016/0152723, 2016/0206656, 2016/0199412, 2016/0208018, 2015/0232880, 2015/0225480; 2015/0224143; 2015/0224142; 2015/0190428; 2015/0196599; 2015/0152181; 2015/0140023; 2015/0118202; 2015/0110760; 2015/0099299; 2015/0093822; 2015/0093401; 2015/0051266; 2015/0050729; 2015/0024482; 2015/0023937; 2015/0017141; 2015/0017136; 2015/0017120; 2014/0370045; 2014/0370017; 2014/0369977; 2014/0349402; 2014/0328812; 2014/0322275; 2014/0322216; 2014/0322212; 2014/0322183; 2014/0314795; 2014/0308259; 2014/0301993; 2014/0296492; 2014/0294784; 2014/0286973; 2014/0274909; 2014/0274801; 2014/0271635; 2014/0271582; 2014/0271581; 2014/0271579; 2014/0255363; 2014/0242701; 2014/0242049; 2014/0227272; 2014/0219975; 2014/0170114; 2014/0134720; 2014/0134142; 2014/0120622; 2014/0120136; 2014/0106449; 2014/0106449; 2014/0099340; 2014/0086828; 2014/0065629; 2014/0050708; 2014/0024809; 2013/0344039; 2013/0323214; 2013/0315884; 2013/0309258; 2013/0288368; 2013/0287752; 2013/0287748; 2013/0280221; 2013/0280220; 2013/0266551; 2013/0216528; 2013/0202622; 2013/0071414; 2012/0321667; 2012/0302466; 2012/0301448; 2012/0301447; 2012/0060230; 2011/0213288; 2011/0158957; 2011/0104128; 2011/0038836; 2007/0036773; and 2004/0043401. Additional aspects of CARs and CAR cells, including exemplary antigen-binding domains, linkers, transmembrane domains, and cytoplasmic signaling domains, are described in WO 2016/168595; WO 12/079000; 2015/0141347; 2015/0031624; 2015/0030597; 2014/0378389; 2014/0219978; 2014/0206620; 2014/0037628; 2013/0274203; 2013/0225668; 2013/0116167; 2012/0230962; 2012/0213783; 2012/0093842; 2012/0071420; 2012/0015888; 2011/0268754; 2010/0297093; 2010/0158881; 2010/0034834; 2010/0015113; 2009/0304657; 2004/0043401; 2014/0322253; 2015/0118208; 2015/0038684; 2014/0024601; 2012/0148552; 2011/0223129; 2009/0257994; 2008/0160607; 2008/0003683; 2013/0121960; 2011/0052554; and 2010/0178276.

Antigen Binding Domains

Antigen binding domains included in the chimeric antigen receptor (CAR) can specifically bind to an antigen (e.g., a tumor associated antigen (TAA) or an antigen that is not expressed on a non-cancerous cell) or a universal receptor (e.g., a tag). Non-limiting examples of an antigen binding domain include: a monoclonal antibody (e.g., IgG1, IgG2, IgG3, IgG4, IgM, IgE, and IgD) (e.g., a fully human or a chimeric (e.g., a humanized) antibody), an antigen binding fragment of an antibody (e.g., Fab, Fab', or F(ab')2 fragments) (e.g., a fragment of a fully human or a chimeric (e.g., humanized) antibody), a diabody, a triabody, a tetrabody, a minibody, a scFv, scFv-Fc, $(scFv)_2$, scFab, bis-scFv, hc-IgG, a BiTE, a single domain antibody (e.g., a V-NAR domain or a VhH domain), IgNAR, and a multispecific (e.g., bispecific antibody) antibody. Methods of making these antigen-binding domains are known in the art.

In some embodiments, an antigen binding domain includes at least one (e.g., one, two, three, four, five, or six) CDR (e.g., any of the three CDRs from an immunoglobulin light chain variable domain or any of the three CDRs from an immunoglobulin heavy chain variable domain) of an antibody that is capable of specifically binding to the target antigen, such as immunoglobulin molecules (e.g., light or heavy chain immunoglobulin molecules) and immunologically-active (antigen-binding) fragments of immunoglobulin molecules.

In some embodiments, an antigen binding domain is a single-chain antibody (e.g., a V-NAR domain or a $V_H$H domain, or any of the single-chain antibodies as described herein). In some embodiments, an antigen binding domain is a whole antibody molecule (e.g., a human, humanized, or chimeric antibody) or a multimeric antibody (e.g., a bispecific antibody).

In some embodiments, antigen-binding domains include antibody fragments and multispecific (e.g., bi-specific) antibodies or antibody fragments. Examples of antibodies and antigen-binding fragments thereof include, but are not limited to: single-chain Fvs (sdFvs), Fab fragments, Fab' fragments, F(ab')2, disulfide-linked Fvs (sdFvs), Fvs, and fragments containing either a VL or a VH domain.

Additional antigen binding domains provided herein are polyclonal, monoclonal, multispecific (multimeric, e.g., bispecific), human antibodies, chimeric antibodies (e.g., human-mouse chimera), single-chain antibodies, intracellularly-made antibodies (i.e., intrabodies), and antigen-binding fragments thereof. The antibodies or antigen-binding fragments thereof can be of any type (e.g., IgG, IgE, IgM, IgD, IgA, and IgY), class (e.g., $IgG_1$, $IgG_2$, $IgG_3$, $IgG_4$, $IgA_1$, and $IgA_2$), or subclass. In some embodiments, the antigen binding domain is an $IgG_1$ antibody or antigen-binding fragment thereof. In some examples, the antigen binding domain is an $IgG_4$ antibody or antigen-binding fragment thereof. In some embodiments, the antigen binding domain is an immunoglobulin comprising a heavy and light chain.

Additional examples of antigen binding domains are antigen-binding fragments of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4), an antigen-binding fragment of an IgA (e.g., an antigen-binding fragment of $IgA_1$ or $IgA_2$) (e.g., an antigen-binding fragment of a human or humanized IgA, e.g., a human or humanized $IgA_1$ or $IgA_2$), an antigen-binding fragment of an IgD (e.g., an antigen-binding fragment of a human or humanized IgD), an antigen-binding fragment of an IgE (e.g., an antigen-binding fragment of a human or humanized IgE), or an antigen-binding fragment of an IgM (e.g., an antigen-binding fragment of a human or humanized IgM).

In some embodiments, an antigen binding domain can bind to a particular antigen (e.g., a tumor-associated antigen) with an affinity ($K_D$) about or less than $1\times10^{-7}$ M (e.g., about or less than $1\times10^{-8}$ M, about or less than $5\times10^{-9}$ M, about or less than $2\times10^{-9}$M, or about or less than $1\times10^{-9}$ M), e.g., in saline or in phosphate buffered saline.

In some embodiments, CAR effector cells (e.g., CAR T cells) comprise a CAR molecule that binds to a tumor antigen (e.g., comprises a tumor antigen binding domain). In some embodiments, the CAR molecule comprises an antigen binding domain that recognizes a tumor antigen of a solid tumor (e.g., breast cancer, colon cancer, etc.). In some embodiments, the CAR molecule is a tandem CAR molecule as described supra, which comprises at least two antigen binding domains. In some embodiments, the CAR molecule comprises an antigen binding domain that recognizes a tumor antigen of a hematologic malignancy (e.g., leukemia, acute lymphocytic leukemia, acute myelocytic leukemia, acute promyelocytic leukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera, Hodgkin's disease, non-Hodgkin's disease, multiple myeloma, etc.).

In some embodiments, the tumor antigen is a tumor-specific antigen (TSA). A TSA is unique to tumor cells and does not occur on other cells in the body. In some embodiments, the tumor antigen is a tumor-associated antigen (TAA). A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. In some embodiments, a TAA is expressed on normal cells during fetal development when the immune system is immature and unable to respond or is normally present at extremely low levels on normal cells but which are expressed at much higher levels on tumor cells.

In certain embodiments, the tumor-associated antigen is determined by sequencing a patient's tumor cells and identifying mutated proteins only found in the tumor. These antigens are referred to as "neoantigens." Once a neoantigen has been identified, therapeutic antibodies can be produced against it and used in the methods described herein.

In some embodiments, the tumor antigen is an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen. In certain embodiments, the tumor antigen is a lymphoma antigen (e.g., non-Hodgkin's lymphoma or Hodgkin's lymphoma), a B-cell lymphoma cancer antigen, a leukemia antigen, a myeloma (e.g., multiple myeloma or plasma cell myeloma) antigen, an acute lymphoblastic leukemia antigen, a chronic myeloid leukemia antigen, or an acute myelogenous leukemia antigen.

Tumor antigens, (e.g. tumor-associated antigens (TAAs) and tumor-specific antigens (TSAs)) that may be targeted by CAR effector cells (e.g., CAR T cells), include, but are not limited to, 1GH-IGK, 43-9F, 5T4, 791Tgp72, acyclophilin C-associated protein, alpha-fetoprotein (AFP), α-actinin-4, A3, antigen specific for A33 antibody, ART-4, B7, Ba 733, BAGE, BCR-ABL, beta-catenin, beta-HCG, BrE3-antigen, BCA225, BTAA, CA125, CA 15-3\CA 27.29\BCAA, CA195, CA242, CA-50, CAM43, CAMEL, CAP-1, carbonic anhydrase IX, c-Met, CA19-9, CA72-4, CAM 17.1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD68, CD70, CD70L, CD74, CD79a, CD79b, CD80, CD83, CD95, CD126, CD132, CD133, CD138, CD147, CD154, CDC27, CDK4, CDK4m, CDKN2A, CO-029, CTLA4, CXCR4, CXCR7, CXCL12, HIF-1a, colon-specific antigen-p (CSAp), CEA (CEACAM5), CEACAM6, c-Met, DAM, E2A-PRL, EGFR, EGFRvIII, EGP-1 (TROP-2), EGP-2, ELF2-M, Ep-CAM, fibroblast growth factor (FGF), FGF-5, Flt-1, Flt-3, folate receptor, G250 antigen, Ga733VEpCAM, GAGE, gp100, GRO-β, H4-RET, HLA-DR, HM1.24, human chorionic gonadotropin (HCG) and its subunits, HER2/neu, HMGB-1, hypoxia inducible factor (HIF-1), HSP70-2M, HST-2, HTgp-175, Ia, IGF-1R, IFN-γ, IFN-α, IFN-β, IFN-λ, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), KC4-antigen, KSA, KS-1-antigen, KS1-4, LAGE-1a, Le-Y, LDR/FUT, M344, MA-50, macrophage migration inhibitory factor (MIF), MAGE, MAGE-1, MAGE-3, MAGE-4, MAGE-5, MAGE-6, MART-1, MART-2, TRAG-3, mCRP, MCP-1, MIP-1A, MIP-1B, MIF, MG7-Ag, MOV18, MUC1, MUC2, MUC3, MUC4, MUC5ac, MUC13, MUC16, MUM-1/2, MUM-3, MYL-RAR, NB/70K, Nm23H1, NuMA, NCA66, NCA95, NCA90, NY-ESO-1, p15, p16, p185erbB2, p180erbB3, PAM4 antigen, pancreatic cancer mucin, PD1 receptor (PD-1), PD-1 receptor ligand 1 (PD-L1), PD-1 receptor ligand 2 (PD-L2), PI5, placental growth factor, p53, PLAGL2, Pme117 prostatic acid phosphatase, PSA, PRAME, PSMA, P1GF, ILGF, ILGF-1R, IL-6, IL-25, RCAS1, RS5, RAGE, RANTES, Ras, T101, SAGE, 5100, survivin, survivin-2B, SDDCAG16, TA-90\Mac2 binding protein, TAAL6, TAC, TAG-72, TLP, tenascin, TRAIL receptors, TRP-1, TRP-2, TSP-180, TNF-α, Tn antigen, Thomson-Friedenreich antigens, tumor necrosis antigens, tyrosinase, VEGFR, ED-B fibronectin, WT-1, 17-1A-antigen, complement factors C3, C3a, C3b, C5a, C5, an angiogenesis marker, bc1-2, bc1-6, and K-ras, an oncogene marker and an oncogene product (see, e.g., Sensi et al., Clin Cancer Res 2006, 12:5023-32; Parmiani et al., J Immunol 2007, 178:1975-79; Novellino et al. Cancer Immunol Immunother 2005, 54:187-207).

In some embodiments, the tumor antigen is a viral antigen derived from a virus associated with a human chronic disease or cancer (such as cervical cancer). For example, in some embodiments, the viral antigen is derived from Epstein-Barr virus (EBV), HPV antigens E6 and/or E7, hepatitis C virus (HCV), hepatitis B virus (HBV), or cytomegalovirus (CMV).

Exemplary cancers or tumors and specific tumor antigens associated with such tumors (but not exclusively), include acute lymphoblastic leukemia (etv6, aml1, cyclophilin b), B cell lymphoma (Ig-idiotype), glioma (E-cadherin, α-catenin, β-catenin, γ-catenin, p120ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-CO17-1A/GA733, APC), choriocarcinoma (CEA), epithelial cell cancer (cyclophilin b), gastric cancer (HER2/neu, c-erbB-2, ga733 glycoprotein), hepatocellular cancer (α-fetoprotein), Hodgkins lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus, testicular cancer (NY-ESO-1), and T cell leukemia (HTLV-1 epitopes), and viral products or proteins.

In some embodiments, the immune effector cell comprising a CAR molecule (e.g., CAR T cell) useful in the methods disclosed herein expresses a CAR comprising a mesothelin binding domain (i e, the CAR T cell specifically recognizes mesothelin). Mesothelin is a tumor antigen that is overexpressed in a variety of cancers including ovarian, lung and pancreatic cancers.

In some embodiments, the immune effector cell comprising a CAR molecule (e.g., CAR T cell) useful in the methods disclosed herein expresses a CAR comprising a CD19 binding domain. In some embodiments, the immune effector cell comprising a CAR molecule (e.g., CAR T cell) useful in the methods disclosed herein expresses a CAR comprising a HER2 binding domain. In some embodiments, the immune effector cell comprising a CAR molecule (e.g., CAR T cell) useful in the methods disclosed herein expresses a CAR comprising an EGFR binding domain.

In some embodiments, the CAR effector cell expressing a CAR comprising a CD19 targeting or binding domain is Kymriah™ (tisagenlecleucel; Novartis; see WO 2016109410, herein incorporated by reference in its entirety) or Yescarta™ (axicabtagene ciloleucel; Kite; see US 20160346326, herein incorporated by reference in its entirety).

Linker

Provided herein are CARs that can optionally include a linker (1) between the antigen binding domain and the transmembrane domain, and/or (2) between the transmembrane domain and the cytoplasmic signaling domain. In some embodiments, the linker can be a polypeptide linker. For example, the linker can have a length of between about 1 amino acid and about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, about 8 amino acids, about 6 amino acids, about 4 amino acids, or about 2 amino acids; about 2 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, about 8 amino acids, about 6 amino acids, or about 4 amino acids; about 4 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, about 8 amino acids, or about 6 amino acids; about 6 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, or about 8 amino acids; about 8 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, or about 10 amino acids; about 10 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, or about 12 amino acids; about 12 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, or about 14 amino acids; about 14 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, or about 16 amino acids; about 16 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, or about 18 amino acids; about 18 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, or about 20 amino acids; about 20 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, or about 25 amino acids; about 25 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, or about 30 amino acids; about 30 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, or about 35 amino acids; about 35 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, or about 40 amino acids; about 40 amino acids to about 500 amino acids, about 400 amino acids, about 300 amino acids, about 200 amino acids, about 100 amino acids, about 90 amino acids, about 80 amino acids, about 70 amino acids, about 60 amino acids, or about 50 amino acids; about 50 amino acids to about 500 amino acids, about 400 amino acids, about 300 amino acids, about 200 amino acids, about 100 amino acids, about 90 amino acids, about 80 amino acids, about 70 amino acids, or about 60 amino acids; about 60 amino acids to about 500 amino acids, about 400 amino acids, about 300 amino acids, about 200 amino acids, about 150 amino acids, about 100 amino acids, about 90 amino acids, about 80 amino acids, or about 70 amino acids; about 70 amino acids to about 500 amino acids, about 400 amino acids, about 300 amino acids, about 200 amino acids, about 100 amino acids, about 90 amino acids, or about 80 amino acids; about 80 amino acids to about 500 amino acids, about 400 amino acids, about 300 amino acids, about 200 amino acids, about 100 amino acids, or about 90 amino acids; about 90 amino acids to about 500 amino acids, about 400 amino acids, about 300 amino acids, about 200 amino acids, or about 100 amino acids; about 100 amino acids to about 500 amino acids, about 400 amino acids, about 300 amino acids, or about 200 amino acids; about 200 amino acids to about 500 amino acids, about 400 amino acids, or about 300 amino acids; about 300 amino acids to about 500 amino acids or about 400 amino acids; or about 400 amino acids to about 500 amino acids.

Additional examples and aspects of linkers are described in the references cited herein, and are thus incorporated in their entirety herein.

Transmembrane Domains

In some embodiments, the CARs described herein also include a transmembrane domain. In some embodiments, the transmembrane domain is naturally associated with a sequence in the cytoplasmic domain. In some embodiments, the transmembrane domain can be modified by one or more (e.g., two, three, four, five, six, seven, eight, nine, or ten) amino acid substitutions to avoid the binding of the domain to other transmembrane domains (e.g., the transmembrane domains of the same or different surface membrane proteins) to minimize interactions with other members of the receptor complex.

In some embodiments, the transmembrane domain may be derived from a natural source. In some embodiments, the transmembrane domain may be derived from any membrane-bound or transmembrane protein. Non-limiting examples of transmembrane domains that may be used herein may be derived from (e.g., comprise at least the transmembrane sequence or a part of the transmembrane sequence of) the alpha, beta, or zeta chain of the T-cell receptor, CD28, CD3 epsilon, CD33, CD37, CD64, CD80, CD45, CD4, CD5, CD8, CD9, CD16, CD22, CD86, CD134, CD137 or CD154.

In some embodiments, the transmembrane domain may be synthetic. For example, in some embodiments where the transmembrane domain is from a synthetic source, the transmembrane domain may include (e.g., predominantly include) hydrophobic residues (e.g., leucine and valine). In some embodiments, the synthetic transmembrane domain will include at least one (e.g., at least two, at least three, at least four, at least five, or at least six) triplet of phenylalanine, tryptophan, and valine at the end of a synthetic transmembrane domain. In some embodiments, the transmembrane domain of a CAR can include a CD8 hinge domain.

Additional specific examples of transmembrane domains are described in the references cited herein.

Cytoplasmic Domains

Also provided herein are CAR molecules that comprise, e.g., a cytoplasmic signaling domain that includes a cytoplasmic sequence of CD3ζ sufficient to stimulate a T cell when the antigen binding domain binds to the antigen, and optionally, a cytoplasmic sequence of one or more of co-stimulatory proteins (e.g., a cytoplasmic sequence of one or more of CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, B7-H3, a ligand that specifically binds to CD83, and any of the ITAM sequences described herein or known in the art) that provides for co-stimulation of the T cell. The stimulation of a CAR immune effector cell can result in the activation of one or more anti-cancer activities of the CAR immune effector cell. For example, in some embodiments, stimulation of a CAR immune effector cell can result in an increase in the cytolytic activity or helper activity of the CAR immune effector cell, including the secretion of cytokines. In some embodiments, the entire intracellular signaling domain of a co-stimulatory protein is included in the cytoplasmic signaling domain. In some embodiments, the cytoplasmic signaling domain includes a truncated portion of an intracellular signaling domain of a co-stimulatory protein (e.g., a truncated portion of the intracellular signaling domain that transduces an effector function signal in the CAR immune effector cell). Non-limiting examples of intracellular signaling domains that can be included in a cytoplasmic signaling domain include the cytoplasmic sequences of the T cell receptor (TCR) and co-receptors that act in concert to initiate signal transduction following antigen receptor engagement, as well as any variant of these sequences including at least one (e.g., one, two, three, four, five, six, seven, eight, nine, or ten) substitution and have the same or about the same functional capability.

In some embodiments, a cytoplasmic signaling domain can include two distinct classes of cytoplasmic signaling sequences: signaling sequences that initiate antigen-dependent activation through the TCR (primary cytoplasmic signaling sequences) (e.g., a CD3ζ cytoplasmic signaling sequence) and a cytoplasmic sequence of one or more of co-stimulatory proteins that act in an antigen-independent manner to provide a secondary or co-stimulatory signal (secondary cytoplasmic signaling sequences).

In some embodiments, the cytoplasmic domain of a CAR can be designed to include the CD3ζ signaling domain by itself or combined with any other desired cytoplasmic signaling sequence(s) useful in the context of a CAR. In some examples, the cytoplasmic domain of a CAR can include a CD3 chain portion and a costimulatory cytoplasmic signaling sequence. The costimulatory cytoplasmic signaling sequence refers to a portion of a CAR including a cytoplasmic signaling sequence of a costimulatory protein (e.g., CD27, CD28, 4-IBB (CD 137), OX40, CD30, CD40, PD-1, ICOS, lymphocyte function-associated antigen-1 (LFA-1), CD2, CD7, LIGHT, NKG2C, B7-H3, and a ligand that specifically binds with CD83).

In some embodiments, the cytoplasmic signaling sequences within the cytoplasmic signaling domain of a CAR are positioned in a random order. In some embodiments, the cytoplasmic signaling sequences within the cytoplasmic signaling domain of a CAR are linked to each other in a specific order. In some embodiments, a linker (e.g., any of the linkers described herein) can be used to form a linkage between different cytoplasmic signaling sequences.

In some embodiments, the cytoplasmic signaling domain is designed to include the cytoplasmic signaling sequence of CD3 and the cytoplasmic signaling sequence of the costimulatory protein CD28. In some embodiments, the cytoplasmic signaling domain is designed to include the cytoplasmic signaling sequence of CD3ζ and the cytoplasmic signaling sequence of costimulatory protein 4-IBB. In some embodiments, the cytoplasmic signaling domain is designed to include the cytoplasmic signaling sequence of CD3ζ and the cytoplasmic signaling sequences of costimulatory proteins CD28 and 4-1BB. In some embodiments, the cytoplasmic signaling domain does not include the cytoplasmic signaling sequences of 4-1BB.

Additional Modification of CAR T Cells in another embodiment, the therapeutic efficacy of CAR effector cells (e.g., CAR T cells) is enhanced by disruption of a methylcytosine dioxygenase gene (e.g., Tet1, Tet2, Tet3), which leads to decreased total levels of 5-hydroxymethylcytosine in association with enhanced proliferation, regulation of effector cytokine production and degranulation, and thereby increases CAR effector cell (e.g., CART cell) proliferation and/or function, as described in PCT Publication WO 2017/049166. Thus, an effector cell (e.g., T cell) can be engineered to express a CAR and wherein expression and/or function of Tet1, Tet2 and/or Tet3 in said effector cell (e.g., cell) has been reduced or eliminated.

In another embodiment, the therapeutic efficacy of CAR effector cells (e.g., CAR T cells) is enhanced by using an effector cell (e.g., T cell) that constitutively expresses a CAR (referred to as a nonconditional CAR) and conditionally expresses another agent useful for treating cancer, as described in PCT Publication WO 2016/126608 and US Publication No. 2018/0044424. In such embodiments, the conditionally expressed agent is expressed upon activation of the effector cell (e.g., T cell), e.g., the binding of the nonconditional CAR to its target. In one embodiment, the conditionally expressed agent is a CAR (referred to herein as a conditional CAR). In another embodiment, the conditionally expressed agent inhibits a checkpoint inhibitor of the immune response. In another embodiment, the conditionally expressed agent improves or enhances the efficacy of a CAR, and can include a cytokine.

In another embodiment, the therapeutic efficacy of CAR T cells is enhanced by modifying the CAR T cell with a nucleic acid that is capable of altering (e.g., downmodulating) expression of an endogenous gene selected from the group consisting of TCR α chain, TCR β chain, beta-2 microglobulin, a HLA molecule, CTLA-4, PD1, and FAS, as described in PCT Publication WO 2016/069282 and US Publication No. 2017/0335331.

In another embodiment, the therapeutic efficacy of CART cells is enhanced by co-expressing in the T cells the CAR and one or more enhancers of T cell priming ("ETPs"), as described in PCI' Publication WO 2015/112626 and US Publication No. 2016/0340406. The addition of an ETP component to the CAR T cell confers enhanced "professional" antigen-presenting cell (APC) function. In an embodiment, the CAR and one or more ETPs are transiently co-expressed in the T cell. Thus, the engineered T cells are safe (given the transient nature of the CAR/ETP expression), and induce prolonged immunity via APC function.

In another embodiment, the therapeutic efficacy of CAR T cells is enhanced by co-expressing in the T cells a CAR and an inhibitory membrane protein (IMP) comprising a binding (or dimerization) domain, as described in PCT Publication WO 2016/055551 and US Publication No. 2017/0292118. The CAR and the IMP are made both reactive to a soluble compound, especially through a second binding domain comprised within the CAR, thereby allowing the co-localization, by dimerization or ligand recognition, of the inhibitory signaling domain borne by the IMP and of the signal transducing domain borne by the CAR, having the effect of turning down the CAR activation. The inhibitory signaling domain is preferably the programmed death-I (PD-1), which attenuates T-cell receptor (TCR)-mediated activation of IL-2 production and T-cell proliferation.

In another embodiment, the therapeutic efficacy of CAR T cells is enhanced using a system where controlled variations in the conformation of the extracellular portion of a CAR containing the antigen-binding domain is obtained upon addition of small molecules, as described in PCT Publication WO 2017/032777. This integrated system switches the interaction between the antigen and the antigen binding domain between on/off states. By being able to control the conformation of the extracellular portion of a CAR, downstream functions of the CAR T cell, such as cytotoxicity, can be directly modulated. Thus, a CAR can be characterized in that it comprises: a) at least one ectodomain which comprises: i) an extracellular antigen binding domain; and ii) a switch domain comprising at least a first multimerizing ligand-binding domain and a second multimerizing ligand binding domain which are capable of binding to a predetermined multivalent ligand to form a multimer comprising said two binding domains and the multivalent ligand to which they are capable of binding; b) at least one transmembrane domain; and c) at least one endodomain comprising a signal transducing domain and optionally a co-stimulatory domain; wherein the switch domain is located between the extracellular antigen binding domain and the transmembrane domain.

Tumor-Associated Antigen Targeting Antibodies

In some aspects, the disclosure provides immunomodulatory fusion protein-metal hydroxide complexes or immunomodulatory fusion proteins to be used or performed in conjunction with antibodies that target tumor antigens.

Therapeutic monoclonal antibodies have been conceived as a class of pharmaceutically active agents which should allow tumor selective treatment by targeting tumor selective antigens or epitopes.

Methods of producing antibodies, and antigen-binding fragments thereof, are well known in the art and are disclosed in, e.g., U.S. Pat. Nos. 7,247,301, 7,923,221, and U.S. Patent Application 2008/0138336, all of which are herein incorporated by reference in their entirety.

Therapeutic antibodies that can be used in the methods of the present disclosure include, but are not limited to, any of the art-recognized anti-cancer antibodies that are approved for use, in clinical trials, or in development for clinical use. In certain embodiments, more than one anti-cancer antibody can be included in the combination therapy of the present disclosure.

Non-limiting examples of anti-cancer antibodies include the following, without limitation: trastuzumab (HERCEPTIN™. by Genentech, South San Francisco, Calif.), which is used to treat HER-2/neu positive breast cancer or metastatic breast cancer; bevacizumab (AVASTIN™ by Genentech), which are used to treat colorectal cancer, metastatic colorectal cancer, breast cancer, metastatic breast cancer, non-small cell lung cancer, or renal cell carcinoma; rituximab (RITUXAN™ by Genentech), which is used to treat non-Hodgkin's lymphoma or chronic lymphocytic leukemia; pertuzumab (OMNITARG™ by Genentech), which is used to treat breast cancer, prostate cancer, non-small cell lung cancer, or ovarian cancer; cetuximab (ERBITUX™ by ImClone Systems Incorporated, New York, N.Y.), which can be used to treat colorectal cancer, metastatic colorectal cancer, lung cancer, head and neck cancer, colon cancer, breast cancer, prostate cancer, gastric cancer, ovarian cancer, brain cancer, pancreatic cancer, esophageal cancer, renal cell cancer, prostate cancer, cervical cancer, or bladder cancer; IMC-1C11 (ImClone Systems Incorporated), which is used to treat colorectal cancer, head and neck cancer, as well as other potential cancer targets; tositumomab and tositumomab and iodine I 131 (BEXXAR XM by Corixa Corporation, Seattle, Wash.), which is used to treat non-Hodgkin's lymphoma, which can be CD20 positive, follicular, non-Hodgkin's lymphoma, with and without transformation, whose disease is refractory to Rituximab and has relapsed following chemotherapy; $In^{111}$ ibirtumomab tiuxetan; $Y^{90}$ ibirtumomab tiuxetan; $In^{111}$ ibirtumomab tiuxetan and $Y^{90}$ ibirtumomab tiuxetan (ZEVALIN™ by Biogen Idee, Cambridge, Mass.), which is used to treat lymphoma or non-Hodgkin's lymphoma, which can include relapsed follicular lymphoma; relapsed or refractory, low grade or follicular non-Hodgkin's lymphoma; or transformed B-cell non-Hodgkin's lymphoma; EMD 7200 (EMD Pharmaceuticals, Durham, N.C.), which is used for treating non-small cell lung cancer or cervical cancer; SGN-30 (a genetically engineered monoclonal antibody targeted to CD30 antigen by Seattle Genetics, Bothell, Wash.), which is used for treating Hodgkin's lymphoma or non-Hodgkin's lymphoma; SGN-15 (a genetically engineered monoclonal antibody targeted to a Lewisy-related antigen that is conjugated to doxorubicin by Seattle Genetics), which is used for treating non-small cell lung cancer; SGN-33 (a humanized antibody targeted to CD33 antigen by Seattle Genetics), which is used for treating acute myeloid leukemia (AML) and myelodysplasia syndromes (MDS); SGN-40 (a humanized monoclonal antibody targeted to CD40 antigen by Seattle Genetics), which is used for treating multiple myeloma or non-Hodgkin's lymphoma; SGN-35 (a genetically engineered monoclonal antibody targeted to a CD30 antigen that is conjugated to auristatin E by Seattle Genetics), which is used for treating non-Hodgkin's lymphoma; SGN-70 (a humanized antibody targeted to CD70 antigen by Seattle Genetics), which is used for treating renal cancer and nasopharyngeal carcinoma; SGN-75 (a conjugate comprised of the SGN70 antibody and an Auristatin derivative by Seattle Genetics); and SGN-17/19 (a fusion protein containing antibody and enzyme conjugated to melphalan prodrug by Seattle Genetics), which is used for treating melanoma or metastatic melanoma.

It should be understood that the therapeutic antibodies to be used in the methods of the present disclosure are not limited to those described supra. For example, the following approved therapeutic antibodies can also be used in the methods of the disclosure: brentuximab vedotin (ADCETRIS™) for anaplastic large cell lymphoma and Hodgkin lymphoma, ipilimumab (MDX-101; YERVOY™) for melanoma, ofatumumab (ARZERRA™) for chronic lymphocytic leukemia, panitumumab (VECTIBIX™) for colorectal cancer, alemtuzumab (CAMPATH™) for chronic lymphocytic leukemia, ofatumumab (ARZERRA™) for chronic lymphocytic leukemia, gemtuzumab ozogamicin (MYLOTARG™) for acute myelogenous leukemia.

Antibodies suitable for use in the methods disclosed herein can also target molecules expressed by immune cells, such as, but not limited to, OX86 which targets OX40 and increases antigen-specific CD8+ T cells at tumor sites and enhances tumor rejection; BMS-663513 which targets CD137 and causes regression of established tumors, as well as the expansion and maintenance of CD8+ T cells, and daclizumab (ZENAPAX™) which targets CD25 and causes transient depletion of CD4+CD25+FOXP3+Tregs and enhances tumor regression and increases the number of effector T cells. A more detailed discussion of these antibodies can be found in, e.g., Weiner et al., Nature Rev. Immunol 2010; 10:317-27.

Other therapeutic antibodies can be identified that target tumor antigens (e.g., tumor antigens associated with different types of cancers, such as carcinomas, sarcomas, myelomas, leukemias, lymphomas, and combinations thereof). For example, the following tumor antigens can be targeted by therapeutic antibodies in the methods disclosed herein.

The tumor antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen. In certain embodiments, the tumor antigen is a lymphoma antigen (e.g., non-Hodgkin's lymphoma or Hodgkin's lymphoma), a B-cell lymphoma cancer antigen, a leukemia antigen, a myeloma (e.g., multiple myeloma or plasma cell myeloma) antigen, an acute lymphoblastic leukemia antigen, a chronic myeloid leukemia antigen, or an acute myelogenous leukemia antigen. It should be understood that the described tumor antigens are only exemplary and that any tumor antigen can be targeted for use in the methods disclosed herein.

In certain embodiments, the tumor antigen is a mucin-1 protein or peptide (MUC-1) that is found on most or all human adenocarcinomas: pancreas, colon, breast, ovarian, lung, prostate, head and neck, including multiple myelomas and some B cell lymphomas. Patients with inflammatory bowel disease, either Crohn's disease or ulcerative colitis, are at an increased risk for developing colorectal carcinoma. MUC-1 is a type I transmembrane glycoprotein. The major extracellular portion of MUC-1 has a large number of tandem repeats consisting of 20 amino acids which comprise immunogenic epitopes. In some cancers it is exposed in an unglycosylated form that is recognized by the immune system (Gendler et al., *J Biol Chem* 1990; 265:15286-15293).

In certain embodiments, the tumor antigen is a mutated B-Raf antigen, which is associated with melanoma and colon cancer. The vast majority of these mutations represent a single nucleotide change of T-A at nucleotide 1796 resulting in a valine to glutamic acid change at residue 599 within the activation segment of B-Raf. Raf proteins are also indirectly associated with cancer as effectors of activated Ras proteins, oncogenic forms of which are present in approximately one-third of all human cancers. Normal non-mutated B-Raf is involved in cell signaling, relaying signals from the cell membrane to the nucleus. The protein is usually only active when needed to relay signals. In contrast, mutant B-Raf has been reported to be constantly active, disrupting the signaling relay (Mercer and Pritchard, Biochim Biophys Acta (2003) 1653(1):25-40; Sharkey et al., Cancer Res. (2004) 64(5): 1595-1599).

In certain embodiments, the tumor antigen is a human epidermal growth factor receptor-2 (HER-2/neu) antigen. Cancers that have cells that overexpress HER-2/neu are referred to as HER-2/neu$^+$ cancers. Exemplary HER-2/neu$^+$ cancers include prostate cancer, lung cancer, breast cancer, ovarian cancer, pancreatic cancer, skin cancer, liver cancer (e.g., hepatocellular adenocarcinoma), intestinal cancer, and bladder cancer.

HER-2/neu has an extracellular binding domain (ECD) of approximately 645 aa, with 40% homology to epidermal growth factor receptor (EGFR), a highly hydrophobic transmembrane anchor domain (TMD), and a carboxyterminal intracellular domain (ICD) of approximately 580 aa with 80% homology to EGFR. The nucleotide sequence of HER-2/neu is available at GENBANK™. Accession Nos. AH002823 (human HER-2 gene, promoter region and exon 1); M16792 (human HER-2 gene, exon 4): M16791 (human HER-2 gene, exon 3); M16790 (human HER-2 gene, exon 2); and M16789 (human HER-2 gene, promoter region and exon 1). The amino acid sequence for the HER-2/neu protein is available at GENBANK™. Accession No. AAA58637. Based on these sequences, one skilled in the art could develop HER-2/neu antigens using known assays to find appropriate epitopes that generate an effective immune response. Exemplary HER-2/neu antigens include p369-377 (a HER-2/neu derived HLA-A2 peptide); dHER2 (Corixa Corporation); li-Key MHC class II epitope hybrid (Generex Biotechnology Corporation); peptide P4 (amino acids 378-398); peptide P7 (amino acids 610-623); mixture of peptides P6 (amino acids 544-560) and P7; mixture of peptides P4, P6 and P7; HER2 [$9_{754}$]; and the like.

In certain embodiments, the tumor antigen is an epidermal growth factor receptor (EGFR) antigen. The EGFR antigen can be an EGFR variant 1 antigen, an EGFR variant 2 antigen, an EGFR variant 3 antigen and/or an EGFR variant 4 antigen. Cancers with cells that overexpress EGFR are referred to as EGFR$^+$ cancers. Exemplary EGFR$^+$ cancers include lung cancer, head and neck cancer, colon cancer, colorectal cancer, breast cancer, prostate cancer, gastric cancer, ovarian cancer, brain cancer and bladder cancer.

In certain embodiments, the tumor antigen is a vascular endothelial growth factor receptor (VEGFR) antigen. VEGFR is considered to be a regulator of cancer-induced angiogenesis. Cancers with cells that overexpress VEGFR are called VEGFR$^+$ cancers. Exemplary VEGFR$^+$ cancers include breast cancer, lung cancer, small cell lung cancer, colon cancer, colorectal cancer, renal cancer, leukemia, and lymphocytic leukemia.

In certain embodiments, the tumor antigen is prostate-specific antigen (PSA) and/or prostate-specific membrane antigen (PSMA) that are prevalently expressed in androgen-independent prostate cancers.

In certain embodiments, the tumor antigen is Glycoprotein 100 (gp 100), a tumor-specific antigen associated with melanoma.

In certain embodiments, the tumor antigen is a carcinoembryonic (CEA) antigen. Cancers with cells that overexpress CEA are referred to as CEA$^+$ cancers. Exemplary CEA$^+$ cancers include colorectal cancer, gastric cancer and pancreatic cancer. Exemplary CEA antigens include CAP-1 (i.e., CEA aa 571-579), CAP1-6D, CAP-2 (i.e., CEA aa 555-579), CAP-3 (i.e., CEA aa 87-89), CAP-4 (CEA aa 1-11), CAP-5 (i.e., CEA aa 345-354), CAP-6 (i.e., CEA aa 19-28) and CAP-7.

In certain embodiments, the tumor antigen is carbohydrate antigen 10.9 (CA 19.9). CA 19.9 is an oligosaccharide related to the Lewis A blood group substance and is associated with colorectal cancers.

In certain embodiments, the tumor antigen is a melanoma cancer antigen. Melanoma cancer antigens are useful for treating melanoma. Exemplary melanoma cancer antigens include MART-1 (e.g., MART-1 26-35 peptide, MART-1 27-35 peptide); MART-1/Melan A; pMel17; pMel17/gp100; gp100 (e.g., gp 100 peptide 280-288, gp 100 peptide 154-162, gp 100 peptide 457-467); TRP-1; TRP-2; NY-ESO-1; p16; beta-catenin; mum-1; and the like.

In certain embodiments, the tumor antigen is a mutant or wild type ras peptide. The mutant ras peptide can be a mutant K-ras peptide, a mutant N-ras peptide and/or a mutant H-ras peptide. Mutations in the ras protein typically occur at positions 12 (e.g., arginine or valine substituted for glycine), 13 (e.g., asparagine for glycine), 61 (e.g., glutamine to leucine) and/or 59. Mutant ras peptides can be useful as lung cancer antigens, gastrointestinal cancer antigens, hepatoma antigens, myeloid cancer antigens (e.g., acute leukemia, myelodysplasia), skin cancer antigens (e.g., melanoma, basal cell, squamous cell), bladder cancer antigens, colon cancer antigens, colorectal cancer antigens, and renal cell cancer antigens.

In certain embodiments, the tumor antigen is a mutant and/or wildtype p53 peptide. The p53 peptide can be used as colon cancer antigens, lung cancer antigens, breast cancer antigens, hepatocellular carcinoma cancer antigens, lymphoma cancer antigens, prostate cancer antigens, thyroid cancer antigens, bladder cancer antigens, pancreatic cancer antigens and ovarian cancer antigens.

Further tumor antigens are well known in the art and include, for example, a glioma-associated antigen, carcinoembryonic antigen (CEA), β-human chorionic gonadotropin, alphafetoprotein (AFP), lectin-reactive AFP, thyroglobulm, RAGE-1, MN-CA IX, human telomerase reverse transcriptase, RU1, RU2 (AS), intestinal carboxy esterase, mut hsp70-2, M-CSF, prostase, prostate-specific antigen (PSA), PAP, NY-ESO-1, LAGE-1a, p53, tyrosinase, prostein, PSMA, ras, Her2/neu, TRP-1, TRP-2, TAG-72, KSA, CA-125, PSA, BRCI, BRC-II, bcr-abl, pax3-fkhr, ews-fli-1, survivin and telomerase, prostate-carcinoma tumor antigen-1 (PCTA-1), MAGE, GAGE, GP-100, MUC-1, MUC-2, ELF2M, neutrophil elastase, ephrinB2, CD22, insulin growth factor (IGF)-I, IGF-II, IGF-I receptor, and mesothelin, In certain embodiments, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The tumor antigen may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-1), Pmel 17, tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations such as BCR-ABL, E2A-PRL, H4-RET, 1GH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p 1 80erbB-3, c-met, nm-23H 1, PSA, TAG-72, CA 19-9, CA 72-4, CAM 17.1, NuMa, K-ras, beta-Catenin, CDK4, Mum-1, p 15, p 16, 43-9F, 5T4 $_{(}$791Tgp72 $_{\}}$ alpha-fetoprotem, beta-HCG, BCA225, BTAA, CA 125, CA 15-3\CA 27.29\BCAA, CA 195, CA 242, CA-50, CAM43, CD68\ I, CO-029, FGF-5, G250, Ga733VEpCAM, HTgp-175, M344, MA-50, MG7-Ag, MOV 18, NB/70K, NY-CO-1, RCAS 1, SDCCAG16, TA-90\Mac-2 binding protein, Acyclophilin C-associated protein, TAAL6, TAG72, TLP, and TPS.

In certain embodiments, the tumor-associated antigen is determined by sequencing a patient's tumor cells and identifying mutated proteins only found in the tumor. These antigens are referred to as "neoantigens." Once a neoantigen has been identified, therapeutic antibodies can be produced against it and used in the methods described herein.

The therapeutic antibody can be a fragment of an antibody; a complex comprising an antibody; or a conjugate comprising an antibody. The antibody can optionally be chimeric or humanized or fully human Immune Checkpoint Blockade In some aspects, the disclosure provides immunomodulatory fusion protein-metal hydroxide complexes or immunomodulatory fusion proteins to be used or performed in conjunction with immune checkpoint inhibitors or immune checkpoint blockers.

T cell activation and effector functions are balanced by co-stimulatory and inhibitory signals, referred to as "immune checkpoints." Inhibitory ligands and receptors that regulate T cell effector functions are overexpressed on tumor cells. Subsequently, agonists of co-stimulatory receptors or antagonists of inhibitory signals, result in the amplification of antigen-specific T cell responses. In contrast to therapeutic antibodies which target tumor cells directly, immune checkpoint blocker enhances endogenous anti-tumor activity. In certain embodiments, the immune checkpoint blocker suitable for use in the methods disclosed herein, is an antagonist of inhibitory signals, e.g., an antibody which targets, for example, PD-1, PD-L1, CTLA-4, LAG3, B7-H3, B7-H4, or TIM3. These ligands and receptors are reviewed in Pardoll, D., Nature. 12: 252-264, 2012.

In certain embodiments, the immune checkpoint blocker is an antibody or an antigen-binding portion thereof, that disrupts or inhibits signaling from an inhibitory immunoregulator. In certain embodiments, the immune checkpoint blocker is a small molecule that disrupts or inhibits signaling from an inhibitory immunoregulator.

In certain embodiments, the inhibitory immunoregulator (immune checkpoint blocker) is a component of the PD-1/PD-L1 signaling pathway. Accordingly, certain embodiments of the disclosure provide methods for immunotherapy of a subject afflicted with cancer, which methods comprise administering to the subject a therapeutically effective amount of an antibody or an antigen-binding portion thereof that disrupts the interaction between the PD-1 receptor and its ligand, PD-L1. Antibodies known in the art which bind to PD-1 and disrupt the interaction between the PD-1 and its ligand, PD-L1, and stimulates an anti-tumor immune response, are suitable for use in the methods disclosed herein. In certain embodiments, the antibody or antigen-binding portion thereof binds specifically to PD-1. For example, antibodies that target PD-1 and are in clinical trials include, e.g., nivolumab (BMS-936558, Bristol-Myers Squibb) and pembrolizumab (lambrolizumab, MK03475, Merck). Other suitable antibodies for use in the methods disclosed herein are anti-PD-1 antibodies disclosed in U.S. Pat. No. 8,008,449, herein incorporated by reference. In certain embodiments, the antibody or antigen-binding portion thereof binds specifically to PD-L1 and inhibits its interaction with PD-1, thereby increasing immune activity. Antibodies known in the art which bind to PD-L1 and disrupt the interaction between the PD-1 and PD-L1, and stimulates an anti-tumor immune response, are suitable for use in the methods disclosed herein. For example, antibodies that target PD-L1 and are in clinical trials, include BMS-936559 (Bristol-Myers Squibb) and MPDL3280A (Genetech). Other suitable antibodies that target PD-L1 are disclosed in U.S. Pat. No. 7,943,743. It will be understood by one of ordinary skill that any antibody which binds to PD-1 or PD-L1, disrupts the PD-1/PD-L1 interaction, and stimulates an anti-tumor immune response, is suitable for use in the methods disclosed herein.

In certain embodiments, the inhibitory immunoregulator is a component of the CTLA-4 signaling pathway. Accordingly, certain embodiments of the disclosure provide methods for immunotherapy of a subject afflicted with cancer, which methods comprise administering to the subject a therapeutically effective amount of an antibody or an antigen-binding portion thereof that targets CTLA-4 and disrupts its interaction with CD80 and CD86. Exemplary antibodies that target CTLA-4 include ipilimumab (MDX-010, MDX-101, Bristol-Myers Squibb), which is FDA approved, and tremelimumab (ticilimumab, CP-675, 206, Pfizer), currently undergoing human trials. Other suitable antibodies that target CTLA-4 are disclosed in WO 2012/120125, U.S. Pat. Nos. 6,984,720, 6,682,7368, and U.S. Patent Applications 2002/0039581, 2002/0086014, and 2005/0201994, herein incorporated by reference. It will be understood by one of ordinary skill that any antibody which binds to CTLA-4, disrupts its interaction with CD80 and CD86, and stimulates an anti-tumor immune response, is suitable for use in the methods disclosed herein.

In certain embodiments, the inhibitory immunoregulator is a component of the LAG3 (lymphocyte activation gene 3) signaling pathway. Accordingly, certain embodiments of the disclosure provide methods for immunotherapy of a subject afflicted with cancer, which methods comprise administering to the subject a therapeutically effective amount of an antibody or an antigen-binding portion thereof that targets LAG3 and disrupts its interaction with MHC class II molecules. An exemplary antibody that targets LAG3 is IMP321 (Immutep), currently undergoing human trials. Other suitable antibodies that target LAG3 are disclosed in U.S. Patent Application 2011/0150892, herein incorporated by reference. It will be understood by one of ordinary skill that any antibody which binds to LAG3, disrupts its interaction with MHC class II molecules, and stimulates an anti-tumor immune response, is suitable for use in the methods disclosed herein.

In certain embodiments, the inhibitory immunoregulator is a component of the B7 family signaling pathway. In certain embodiments, the B7 family members are B7-H3 and B7-H4. Accordingly, certain embodiments of the disclosure provide methods for immunotherapy of a subject afflicted with cancer, which methods comprise administering to the subject a therapeutically effective amount of an antibody or an antigen-binding portion thereof that targets B7-H3 or H4. The B7 family does not have any defined receptors but these ligands are upregulated on tumor cells or tumor-infiltrating cells. Preclinical mouse models have shown that blockade of these ligands can enhance anti-tumor immunity. An exemplary antibody that targets B7-H3 is MGA271 (Macrogenics), currently undergoing human trials. Other suitable antibodies that target LAG3 are disclosed in U.S. Patent Application 2013/0149236, herein incorporated by reference. It will be understood by one of ordinary skill that any antibody which binds to B7-H3 or H4, and stimulates an anti-tumor immune response, is suitable for use in the methods disclosed herein.

In certain embodiments, the inhibitory immunoregulator is a component of the TIM3 (T cell membrane protein 3) signaling pathway. Accordingly, certain embodiments of the disclosure provide methods for immunotherapy of a subject afflicted with cancer, which methods comprise administering to the subject a therapeutically effective amount of an antibody or an antigen-binding portion thereof that targets LAG3 and disrupts its interaction with galectin 9. Suitable antibodies that target TIM3 are disclosed in U.S. Patent Application 2013/0022623, herein incorporated by reference. It will be understood by one of ordinary skill that any antibody which binds to TIM3, disrupts its interaction with galectin 9, and stimulates an anti-tumor immune response, is suitable for use in the methods disclosed herein.

It should be understood that antibodies targeting immune checkpoints suitable for use in the methods disclosed herein are not limited to those described supra. Moreover, it will be understood by one of ordinary skill in the art that other immune checkpoint targets can also be targeted by antagonists or antibodies in the methods described herein, provided that the targeting results in the stimulation of an anti-tumor immune response as reflected in, e.g., an increase in T cell proliferation, enhanced T cell activation, and/or increased cytokine production (e.g., IFN-γ, IL-2).

Cancer Vaccine

In some aspects, the disclosure provides immunomodulatory fusion protein-metal hydroxide complexes or immunomodulatory fusion proteins to be used or performed in conjunction with a cancer vaccine. In certain embodiments, the cancer vaccine stimulates a specific immune response against a specific target, such as a tumor-associated antigen.

In certain embodiments, the cancer vaccine includes viral, bacterial or yeast vectors to deliver recombinant genes to antigen presenting cells (APCs).

In certain embodiments the cancer vaccine uses autologous or allogeneic tumor cells. In certain embodiments, these tumor cells may be modified for expression of MHC, costimulatory molecules, or cytokines.

In certain embodiments, the tumor-associated antigen is determined by sequencing a patient's tumor cells and identifying mutated proteins only found in the tumor. These antigens are referred to as "neoantigens." Once a neoantigen has been identified, it can be used as the antigen for a vaccine or for developing monoclonal antibodies specifically reactive with the neoantigen.

In certain embodiments, the vaccine includes irradiated tumor cells transduced with cytokines such as GM-CSF or loaded with adjuvant compounds, such as the GM-CSF-secreting tumor cell vaccine GVAX (*Immunological Reviews,* 222(1): 287-298, 2008). In certain embodiments the vaccine includes one or more tumor-associated antigens in the form of an immunogenic composition, optionally in combination with an adjuvant. For example, vaccination against HPV-16 oncoproteins resulted in positive clinical outcomes for vulvar intraepithelial neoplasia (*The New England Journal of Medicine,* 361(19), 1838-1847, 2012). Also, multipeptide immune response to cancer vaccine IMA901 after single-dose cyclophosphamide associates with longer patient survival (*Nature Medicine,* 18(8): 1254-61, 2012). Alternatively, a DNA-based approach can be used to immunize a patient with one or more tumor-associated antigens. Improved tumor immunity is observed using a DNA vaccine in combination with an anti-tyrosinase related protein-1 monoclonal antibody in murine melanoma (*Cancer Research,* 68(23), 9884-9891, 2008).

Other vaccine approaches utilize patient immune cells, such as dendritic cells which can be cultured with a tumor-associated antigen to produce antigen presenting cells that will stimulate the immune system and target the antigen of interest. A current FDA approved cancer treatment vaccine using this approach is Provenge® (Dendreon), approved for use in some men with metastatic prostate cancer. This vaccine stimulates an immune response to prostatic acid phosphatase (PAP), an antigen found on most prostate cancer cells. The vaccine is created by isolating a specific patient's immune cells and culturing dendritic cells with PAP to produce antigen presenting cells that will stimulate the immune system and target PAP. These and other cancer vaccines can be used in combination with other treatments as described herein.

Amphiphile Vaccines

In some embodiments, the cancer vaccine suitable for use with the immunomodulatory fusion protein-metal hydroxide complex described herein is an amphiphile vaccine, as described in US 2013/0295129, herein incorporated by reference. An amphiphile vaccine combines an albumin-binding lipid and a peptide antigen or molecular adjuvant to efficiently target the peptide or adjuvant to lymph nodes in vivo. Lipid conjugates bind to endogenous albumin, which targets them to lymphatics and draining lymph nodes where they accumulate due to the filtering of albumin by antigen presenting cells. When the lipid conjugate includes an antigenic peptide or molecular adjuvant, the conjugates induce or enhance a robust immune response.

Lymph node-targeting conjugates typically include three domains: a highly lipophilic, albumin-binding domain (e.g., an albumin-binding lipid), a cargo such as a molecular adjuvant or a peptide antigen, and a polar block linker, which promotes solubility of the conjugate and reduces the ability of the lipid to insert into cellular plasma membranes. Accordingly, in certain embodiments, the general structure of the conjugate is L-P-C, where "L" is an albumin-binding lipid, "P" is a polar block, and "C" is a cargo such as a molecular adjuvant or a polypeptide. In some embodiments, the cargo itself can also serve as the polar block domain, and a separate polar block domain is not required. Therefore, in certain embodiments the conjugate has only two domains: an albumin-binding lipid and a cargo.

The cargo of the conjugates suitable for use in the methods disclosed herein is typically a molecular adjuvant such as an immunostimulatory oligonucleotide, or a peptide antigen. However, the cargo can also be other oligonucleotides, peptides, Toll-like receptor agonists or other immunomodulatory compounds, dyes, MRI contrast agents, fluorophores or small molecule drugs that require efficient trafficking to the lymph nodes.

In certain embodiments, a lipid-oligonucleotide conjugates includes an immunostimulatory oligonucleotide which is conjugated directly to a lipid, or is linked to a linker which is conjugated to a lipid. Other embodiments are directed to lipid-peptide conjugates which include an antigenic peptide conjugated directly to a lipid, or is linked to a linker which is conjugated to a lipid.

Lipids

The lipid conjugates typically include a hydrophobic lipid. The lipid can be linear, branched, or cyclic. The lipid is preferably at least 17 to 18 carbons in length, but may be shorter if it shows good albumin binding and adequate targeting to the lymph nodes. Lymph node-targeting conjugates include lipid-oligonucleotide conjugates and lipid-peptide conjugates that can be trafficked from the site of delivery through the lymph to the lymph node. In certain embodiments, the activity relies, in-part, on the ability of the conjugate to associate with albumin in the blood of the subject. Therefore, lymph node-targeted conjugates typically include a lipid that can bind to albumin under physiological conditions. Lipids suitable for targeting the lymph node can be selected based on the ability of the lipid or a lipid conjugate including the lipid to bind to albumin. Suitable methods for testing the ability of the lipid or lipid conjugate to bind to albumin are known in the art.

For example, in certain embodiments, a plurality of lipid conjugates is allowed to spontaneously form micelles in aqueous solution. The micelles are incubated with albumin, or a solution including albumin such as Fetal Bovine Serum (FBS). Samples can be analyzed, for example, by ELISA, size exclusion chromatography or other methods to determine if binding has occurred. Lipid conjugates can be selected as lymph node-targeting conjugates if in the presence of albumin, or a solution including albumin such as Fetal Bovine Serum (FBS), the micelles dissociate and the lipid conjugates bind to albumin as discussed above.

Examples of preferred lipids for use in lymph node targeting lipid conjugates include, but are not limited to, fatty acids with aliphatic tails of 8-30 carbons including, but not limited to, linear unsaturated and saturated fatty acids, branched saturated and unsaturated fatty acids, and fatty acids derivatives, such as fatty acid esters, fatty acid amides, and fatty acid thioesters, diacyl lipids, cholesterol, cholesterol derivatives, and steroid acids such as bile acids, Lipid A or combinations thereof.

In certain embodiments, the lipid is a diacyl lipid or two-tailed lipid. In some embodiments, the tails in the diacyl lipid contain from about 8 to about 30 carbons and can be saturated, unsaturated, or combinations thereof. The tails can be coupled to the head group via ester bond linkages, amide bond linkages, thioester bond linkages, or combinations thereof. In a particular embodiment, the diacyl lipids are phosphate lipids, glycolipids, sphingolipids, or combinations thereof.

Preferably, lymph node-targeting conjugates include a lipid that is 8 or more carbon units in length. It is believed that increasing the number of lipid units can reduce insertion of the lipid into plasma membrane of cells, allowing the lipid conjugate to remain free to bind albumin and traffic to the lymph node.

For example, the lipid can be a diacyl lipid composed of two C18 hydrocarbon tails. In certain embodiments, the lipid for use in preparing lymph node targeting lipid conjugates is not a single chain hydrocarbon (e.g., C18), or cholesterol. Cholesterol conjugation has been explored to enhance the immunomodulation of molecular adjuvants such as CpG and immunogenicity of peptides, but cholesterol conjugates, which associate well with lipoproteins but poorly with albumin, show poor lymph node targeting and low immunogenicity in vaccines compared to optimal albumin-binding conjugates.

Molecular Adjuvants

In certain embodiments, lipid-oligonucleotide conjugates are used in the vaccine. The oligonucleotide conjugates typically contain an immunostimulatory oligonucleotide.

In certain embodiments, the immunostimulatory oligonucleotide can serve as a ligand for pattern recognition receptors (PRRs). Examples of PRRs include the Toll-like family of signaling molecules that play a role in the initiation of innate immune responses and also influence the later and more antigen specific adaptive immune responses. Therefore, the oligonucleotide can serve as a ligand for a Toll-like family signaling molecule, such as Toll-Like Receptor 9 (TLR9).

For example, unmethylated CpG sites can be detected by TLR9 on plasmacytoid dendritic cells and B cells in humans (Zaida, et al., *Infection and Immunity,* 76(5):2123-2129, (2008)). Therefore, the sequence of oligonucleotide can include one or more unmethylated cytosine-guanine (CG or CpG, used interchangeably) dinucleotide motifs. The ‘p’ refers to the phosphodiester backbone of DNA, as discussed in more detail below, some oligonucleotides including CG can have a modified backbone, for example a phosphorothioate (PS) backbone.

In certain embodiments, an immunostimulatory oligonucleotide can contain more than one CG dinucleotide, arranged either contiguously or separated by intervening nucleotide(s). The CpG motif(s) can be in the interior of the oligonucleotide sequence. Numerous nucleotide sequences stimulate TLR9 with variations in the number and location of CG dinucleotide(s), as well as the precise base sequences flanking the CG dimers.

Typically, CG ODNs are classified based on their sequence, secondary structures, and effect on human peripheral blood mononuclear cells (PBMCs). The five classes are Class A (Type D), Class B (Type K), Class C, Class P, and Class S (Vollmer, J & Krieg, A M, *Advanced drug delivery reviews* 61(3): 195-204 (2009), incorporated herein by reference). CG ODNs can stimulate the production of Type I interferons (e.g., IFNα) and induce the maturation of dendritic cells (DCs). Some classes of ODNs are also strong activators of natural killer (NK) cells through indirect cytokine signaling Some classes are strong stimulators of human B cell and monocyte maturation (Weiner, G L, PNAS USA 94(20): 10833-7 (1997); Dalpke, A H, Immunology 106(1): 102-12 (2002); Hartmann, G, J of Immun 164(3):1617-2 (2000), each of which is incorporated herein by reference).

According to some embodiments, a lipophilic-CpG oligonucleotide conjugate is used to enhance an immune response to a peptide antigen. The lipophilic-CpG oligonucleotide is represented by the following, wherein “L” is a lipophilic compound, such as diacyl lipid, “$G_n$” is a guanine repeat linker and “n” represents 1, 2, 3, 4, or 5.

(SEQ ID NO: 226)
5'-L-$G_n$TCCATGACGTTCCTGACGTT-3'

Other PRR Toll-like receptors include TLR3, and TLR7 which may recognize double-stranded RNA, single-stranded and short double-stranded RNAs, respectively, and retinoic acid-inducible gene I (RIG-I)-like receptors, namely RIG-I and melanoma differentiation-associated gene 5 (MDAS), which are best known as RNA-sensing receptors in the cytosol. Therefore, in certain embodiments, the oligonucleotide contains a functional ligand for TLR3, TLR7, or RIG-I-like receptors, or combinations thereof.

Examples of immunostimulatory oligonucleotides, and methods of making them are known in the art, see for example, Bodera, P. *Recent Pat Inflamm Allergy Drug Discov.* 5(1):87-93 (2011), incorporated herein by reference.

In certain embodiments, the oligonucleotide cargo includes two or more immunostimulatory sequences.

The oligonucleotide can be between 2-100 nucleotide bases in length, including for example, 5 nucleotide bases in length, 10 nucleotide bases in length, 15 nucleotide bases in length, 20 nucleotide bases in length, 25 nucleotide bases in length, 30 nucleotide bases in length, 35 nucleotide bases in length, 40 nucleotide bases in length, 45 nucleotide bases in length, 50 nucleotide bases in length, 60 nucleotide bases in length, 70 nucleotide bases in length, 80 nucleotide bases in length, 90 nucleotide bases in length, 95 nucleotide bases in length, 98 nucleotide bases in length, 100 nucleotide bases in length or more.

The 3' end or the 5' end of the oligonucleotides can be conjugated to the polar block or the lipid. In certain embodiments the 5' end of the oligonucleotide is linked to the polar block or the lipid.

The oligonucleotides can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds. In certain embodiments, the oligonucleotides are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein ‘modified nucleotide” or “chemically modified nucleotide” defines a nucleotide that has a chemical modification of one or more of the heterocyclic base, sugar moiety or phosphate moiety constituents. In certain embodiments, the charge of the modified nucleotide is reduced compared to DNA or RNA oligonucleotides of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In certain embodiments, the analogs have a substantially uncharged, phosphorus containing backbone.

Peptide Antigens

The peptide conjugates suitable for use in the methods disclosed herein typically include an antigenic protein or polypeptide, such as a tumor-associated antigen or portion thereof.

The peptide can be 2-100 amino acids, including for example, 5 amino acids, 10 amino acids, 15 amino acids, 20 amino acids, 25 amino acids, 30 amino acids, 35 amino acids, 40 amino acids, 45 amino acids, or 50 amino acids. In some embodiments, a peptide can be greater than 50 amino acids. In some embodiments, the peptide can be >100 amino acids.

A protein/peptide can be linear, branched or cyclic. The peptide can include D amino acids, L amino acids, or a combination thereof. The peptide or protein can be conjugated to the polar block or lipid at the N-terminus or the C-terminus of the peptide or protein.

The protein or polypeptide can be any protein or peptide that can induce or increase the ability of the immune system to develop antibodies and T-cell responses to the protein or peptide. A cancer antigen is an antigen that is typically expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. The cancer antigen can be, but is not limited to, TRP-1, TRP-2, MART-1/Melan-A, gp100, adenosine deaminase-binding protein (ADAbp), FAP, cyclophilin b, colorectal associated antigen (CRC)—0017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-1, GAGE-2, GAGE-3, GAGE-4, GAGE-5, GAGE-6, GAGE-7, GAGE-8, GAGE-9, BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pme1117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, 1mp-1, PIA, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, or c-erbB-2. Additional cancer antigens include the tumor antigens described herein.

Suitable antigens are known in the art and are available from commercial government and scientific sources. In certain embodiments, the antigens are whole inactivated or irradiated tumor cells. The antigens may be purified or partially purified polypeptides derived from tumors. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

In certain embodiments, antigens may be provided as single antigens or may be provided in combination. Antigens may also be provided as complex mixtures of polypeptides or nucleic acids.

Polar Block/Linker

For the conjugate to be trafficked efficiently to the lymph node, the conjugate should remain soluble. Therefore, a polar block linker can be included between the cargo and the lipid to increase solubility of the conjugate. The polar block reduces or prevents the ability of the lipid to insert into the plasma membrane of cells, such as cells in the tissue adjacent to the injection site. The polar block can also reduce or prevent the ability of cargo, such as synthetic oligonucleotides containing a PS backbone, from non-specifically associating with extracellular matrix proteins at the site of administration. The polar block increases the solubility of the conjugate without preventing its ability to bind to albumin. It is believed that this combination of characteristics allows the conjugate to bind to albumin present in the serum or interstitial fluid, and remain in circulation until the albumin is trafficked to, and retained in a lymph node.

The length and composition of the polar block can be adjusted based on the lipid and cargo selected. For example, for oligonucleotide conjugates, the oligonucleotide itself may be polar enough to insure solubility of the conjugate, for example, oligonucleotides that are 10, 15, 20 or more nucleotides in length. Therefore, in certain embodiments, no additional polar block linker is required. However, depending on the amino acid sequence, some lipidated peptides can be essentially insoluble. In these cases, it can be desirable to include a polar block that mimics the effect of a polar oligonucleotide.

A polar block can be used as part of any of lipid conjugates suitable for use in the methods disclosed herein, for example, lipid-oligonucleotide conjugates and lipid-peptide conjugates, which reduce cell membrane insertion/preferential portioning onto albumin. Suitable polar blocks include, but are not limited to, oligonucleotides such as those discussed above, a hydrophilic polymer including but not limited to poly(ethylene glycol) (MW: 500 Da to 20,000 Da), polyacrylamide (MW: 500 Da to 20,000 Da), polyacrylic acid; a string of hydrophilic amino acids such as serine, threonine, cysteine, tyrosine, asparagine, glutamine, aspartic acid, glutamic acid, lysine, arginine, histidine, or combinations thereof polysaccharides, including but not limited to, dextran (MW: 1,000 Da to 2,000,000 Da), or combinations thereof.

The hydrophobic lipid and the linker/cargo are covalently linked. The covalent bond may be a non-cleavable linkage or a cleavable linkage. The non-cleavable linkage can include an amide bond or phosphate bond, and the cleavable linkage can include a disulfide bond, acid-cleavable linkage, ester bond, anhydride bond, biodegradable bond, or enzyme-cleavable linkage.

Ethylene Glycol Linkers

In certain embodiments, the polar block is one or more ethylene glycol (EG) units, more preferably two or more EG units (i.e., polyethylene glycol (PEG)). For example, in certain embodiments, a peptide conjugate includes a protein or peptide (e.g., peptide antigen) and a hydrophobic lipid linked by a polyethylene glycol (PEG) molecule or a derivative or analog thereof.

In certain embodiments, protein conjugates suitable for use in the methods disclosed herein contain protein antigen linked to PEG which is in turn linked to a hydrophobic lipid, or lipid-Gn-ON conjugates, either covalently or via formation of protein-oligo conjugates that hybridize to oligo micelles. The precise number of EG units depends on the lipid and the cargo, however, typically, a polar block can have between about 1 and about 100, between about 20 and about 80, between about 30 and about 70, or between about 40 and about 60 EG units. In certain embodiments, the polar block has between about 45 and 55 EG, units. For example, in certain embodiments, the polar block has 48 EG units.

Oligonucleotide Linkers

As discussed above, in certain embodiments, the polar block is an oligonucleotide. The polar block linker can have any sequence, for example, the sequence of the oligonucleotide can be a random sequence, or a sequence specifically chosen for its molecular or biochemical properties (e.g., highly polar). In certain embodiments, the polar block linker includes one or more series of consecutive adenine (A), cytosine (C), guanine (G), thymine (T), uracil (U), or analog thereof. In certain embodiments, the polar block linker consists of a series of consecutive adenine (A), cytosine (C), guanine (G), thymine (T), uracil (U), or analog thereof.

In certain embodiments, the linker is one or more guanines, for example between 1-10 guanines. It has been discovered that altering the number of guanines between a cargo such as a CpG oligonucleotide, and a lipid tail controls micelle stability in the presence of serum proteins. Therefore, the number of guanines in the linker can be selected based on the desired affinity of the conjugate for serum proteins such as albumin. When the cargo is a CpG immunostimulatory oligonucleotide and the lipid tail is a diacyl lipid, the number of guanines affects the ability of micelles formed in aqueous solution to dissociate in the presence of serum: 20% of the non-stabilized micelles (lipo-$G_0T_{10}$-CG) (SEQ ID NO: 227) were intact, while the remaining 80% were disrupted and bonded with FBS components. In the presence of guanines, the percentage of intact micelles increased from 36% (lipo-$G_2T_8$-CG) (SEQ ID NO: 228) to 73% (lipo-$G_4T_6$-CG) (SEQ ID NO: 229), and finally reached 90% (lipo-$G_6T_4$-CG) (SEQ ID NO: 230). Increasing the number of guanines to eight (lipo-$G_8T_2$-CG) (SEQ ID NO: 231) and ten (lipo-$G_{10}T_0$-CG) (SEQ ID NO: 232) did not further enhance micelle stability.

Therefore, in certain embodiments, the linker in a lymph node-targeting conjugate suitable for use in the methods disclosed herein can include 0, 1, or 2 guanines. As discussed in more detail below, linkers that include 3 or more consecutive guanines can be used to form micelle-stabilizing conjugates with properties that are suitable for use in the methods disclosed herein.

Immunogenic Compositions

The conjugates suitable for use in the methods disclosed herein can be used in immunogenic compositions or as components in vaccines. Typically, immunogenic compositions disclosed herein include an adjuvant, an antigen, or a combination thereof. The combination of an adjuvant and an antigen can be referred to as a vaccine. When administered to a subject in combination, the adjuvant and antigen can be administered in separate pharmaceutical compositions, or they can be administered together in the same pharmaceutical composition. When administered in combination, the adjuvant can be a lipid conjugate, the antigen can be a lipid conjugate, or the adjuvant and the antigen can both be lipid conjugates.

An immunogenic composition suitable for use in the methods disclosed herein can include a lipid conjugate that is an antigen such as an antigenic polypeptide-lipid conjugate, administered alone, or in combination with an adjuvant. The adjuvant may be without limitation alum (e.g., aluminum hydroxide, aluminum phosphate); saponins purified from the bark of the *Q. saponaria* tree such as QS21 (a glycolipid that elutes in the 21st peak with HPLC fractionation; Antigenics, Inc., Worcester, Mass.); poly [di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic).

Adjuvants may be TLR ligands, such as those discussed above. Adjuvants that act through TLR3 include, without limitation, double-stranded RNA. Adjuvants that act through TLR4 include, without limitation, derivatives of lipopolysaccharides such as monophosphoryl lipid A (MPLA; Ribi ImmunoChem Research, Inc., Hamilton, Mont.) and muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland). Adjuvants that act through TLRS include, without limitation, flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

The adjuvant can also be oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor.

Other Immunomodulatory Fusion Proteins or Immunomodulatory Fusion Protein-Metal Hydroxide Complex In some aspects, the disclosure provides immunomodulatory fusion protein-metal hydroxide complexes or immunomodulatory fusion proteins to be used or performed in conjunction with other immunomodulatory fusion protein-metal hydroxide complexes or immunomodulatory fusion proteins. In some embodiments, where more than one immunomodulatory fusion protein-metal hydroxide complex or immunomodulatory fusion protein is used, the immunomodulatory domains are different.

In some embodiments, the immunomodulatory domains are different cytokines (e.g., IL-2 and IL-12). In some embodiments, the immunomodulatory domains are different chemokines. In some embodiments, the immunomodulatory domains are different activating ligands/receptors. In some embodiments, the immunomodulatory domains are different inhibitory ligands/receptors. In some embodiments, the immunomodulatory domains are a cytokine and a chemokine. In some embodiments, the immunomodulatory domains are a cytokine and an activating ligand/receptor. In some embodiments, the immunomodulatory domains are a cytokine and an inhibitory ligand/receptor. In some embodiments, the immunomodulatory domains are a chemokine and an activating ligand/receptor. In some embodiments, the immunomodulatory domains are a chemokine and an inhibitory ligand/receptor. In some embodiments, the immunomodulatory domains are an activating ligand/receptor and an inhibitory ligand/receptor.

In some embodiments, the more than one immunomodulatory fusion protein-metal hydroxide complex or immunomodulatory fusion protein are formulated together. In some embodiments, the more than one immunomodulatory fusion protein-metal hydroxide complex or immunomodulatory fusion protein are formulated separately and administered concurrently or sequentially.

Kits

In some aspects, the disclosure provides kits comprising at least one immunomodulatory fusion protein-metal hydroxide complex or immunomodulatory fusion protein described herein and instructions for use. In some embodiments, the kits comprise, in a suitable container, an immunomodulatory fusion protein-metal hydroxide complex or immunomodulatory fusion protein, one or more controls, and various buffers, reagents, enzymes and other standard ingredients well known in the art. In some embodiments, the kits further comprise instructions for use in combination with an immunotherapy.

In some embodiments, the container is at least one vial, well, test tube, flask, bottle, syringe, or other container means, into which an immunomodulatory fusion protein-metal hydroxide complex or immunomodulatory fusion protein may be placed, and in some instances, suitably aliquoted. When an additional component is provided, the kit can contain additional containers into which this compound may be placed. The kits can also include a means for containing an immunomodulatory fusion protein-metal hydroxide complex or immunomodulatory fusion protein, and any other reagent containers in close confinement for commercial sale. Such containers may include injection or blow-molded plastic containers into which the desired vials are retained. Containers and/or kits can include labeling with instructions for use and/or warnings.

In some embodiments, the disclosure provides a kit comprising a container comprising an immunomodulatory fusion protein-metal hydroxide complex or immunomodulatory fusion protein described herein, an optional pharmaceutically acceptable carrier, and a package insert comprising instructions for administration of the composition for treating or delaying progression of cancer in an individual receiving an immunotherapy (e.g., CAR-T cells, cancer vaccine, anti-tumor associated antigen antibody, and/or immune checkpoint blockade).

In some embodiments, the disclosure provides a kit comprising a medicament comprising an immunomodulatory fusion protein-metal hydroxide complex or immunomodulatory fusion protein described herein, an optional pharmaceutically acceptable carrier, and a package insert comprising instructions for administration of the medicament alone or in combination with an immunotherapy (e.g., CAR-T cells, cancer vaccine, anti-tumor associated antigen antibody, and/or immune checkpoint blockade), for treating or delaying progression of cancer in an individual receiving CAR-T cell therapy.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise. Further, unless otherwise required by context, singular terms shall include pluralities and plural terms shall include the singular.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, the term "adjuvant" refers to any substance that acts to augment and/or direct antigen-specific immune responses when used in combination with specific antigens. When combined with a vaccine antigen, adjuvant increases the immune response to the vaccine antigen as compared to the response induced by the vaccine antigen alone. Adjuvants help drive immunological mechanisms and shape the output immune response to vaccine antigens.

As used herein, the term "agonist" refers to any molecule (e.g., an antibody or antigen binding fragment thereof) that partially or fully promotes, increases, or activates a biological activity of a native polypeptide disclosed herein. Suitable agonist molecules specifically include agonist antibodies or antibody fragments, fragments or amino acid sequence variants of native polypeptides, peptides, antisense oligonucleotides, small organic molecules, etc. In some embodiments, activation in the presence of the agonist is observed in a dose-dependent manner In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% higher than the signal measured with a negative control under comparable conditions. Also disclosed herein, are methods of identifying agonists suitable for use in the methods of the disclosure. For example, these methods include, but are not limited to, binding assays such as enzyme-linked immuno-absorbent assay (ELISA), Forte Bio© systems, and radioimmunoassay (RIA). These assays determine the ability of an agonist to bind the polypeptide of interest (e.g., a receptor or ligand) and therefore indicate the ability of the agonist to promote, increase or activate the activity of the polypeptide. Efficacy of an agonist can also be determined using functional assays, such as the ability of an agonist to activate or promote the function of the polypeptide. For example, a functional assay may comprise contacting a polypeptide with a candidate agonist molecule and measuring a detectable change in one or more biological activities normally associated with the polypeptide. The potency of an agonist is usually defined by its $EC_{50}$ value (concentration required to activate 50% of the agonist response). The lower the $EC_{50}$ value the greater the potency of the agonist and the lower the concentration that is required to activate the maximum biological response.

The term "albumin" refers to a protein having the same, or very similar three dimensional structure as human albumin (SEQ ID NO: 88) and having a long serum half-life for use as a stabilizing domain. Exemplary albumin proteins include human serum albumin primate serum albumin (such as chimpanzee serum albumin), gorilla serum albumin or macaque serum albumin, rodent serum albumin (such as hamster serum albumin), guinea pig serum albumin, mouse serum albumin and rat serum albumin, bovine serum albumin (such as cow serum albumin), equine serum albumin (such as horse serum albumin or donkey serum albumin), rabbit serum albumin, goat serum albumin, sheep serum albumin, dog serum albumin, chicken serum albumin and pig serum albumin.

The term "ameliorating" refers to any therapeutically beneficial result in the treatment of a disease state, e.g., cancer, including prophylaxis, lessening in the severity or progression, remission, or cure thereof.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups {e.g., norleucine) or modified peptide backbones, but retain the same basic chemical structure as a naturally occurring amino acid Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

As used herein, the term "anchor peptide" refers to a terminal target peptide sequence operably linked to the terminus of a polypeptide that that prevents secretion of the polypeptide. For example, an anchor peptide comprising the amino acid sequence KDEL (SEQ ID NO: 233) prevents secretion of a polypeptide comprising the anchor peptide at its C-terminus. The KDEL (SEQ ID NO: 233) anchor peptide is a ligand for the KDEL (SEQ ID NO: 233) receptor that is a Golgi integral membrane protein that functions to retrieve polypeptides comprising the KDEL (SEQ ID NO: 233) amino acid sequence and mediating retrograde transport of the polypeptides to the ER (Capitani, et al (2009) *FEBS Lett.* 583:3863-3871). The amino acid sequence KDEL (SEQ ID NO: 233) is an anchor peptide that prevents polypeptide secretion in mammalian cells. The amino acid sequence HDEL (SEQ ID NO: 234) is an anchor peptide that prevents polypeptide secretion in yeast and plant cells. In some embodiments, an anchor peptide comprises the amino acid sequence KDEL (SEQ ID NO: 233) or HDEL (SEQ ID NO: 234). In some embodiments, an anchor peptide is operably linked to the C-terminus of a polypeptide for preventing secretion. In some embodiments, an anchor peptide is operably linked to the C-terminus of a kinase comprising an ER-targeting leader sequence and a kinase domain to prevent secretion of the kinase.

As used herein, the term "antagonist" refers to any molecule that partially or fully blocks, inhibits, or neutralizes a biological activity of a native polypeptide disclosed herein. Suitable antagonist molecules specifically include antagonist antibodies or antibody fragments, fragments or amino acid sequence variants of native polypeptides, peptides, antisense oligonucleotides, small organic molecules, etc. In some embodiments, inhibition in the presence of the antagonist is observed in a dose-dependent manner. In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the signal measured with a negative control under comparable conditions. Also disclosed herein, are methods of identifying antagonists suitable for use in the methods of the disclosure. For example, these methods include, but are not limited to, binding assays such as enzyme-linked immuno-absorbent assay (ELISA), Forte Bio© systems, and radioimmunoassay (RIA). These assays determine the ability of an antagonist to bind the polypeptide of interest (e.g., a receptor or ligand) and therefore indicate the ability of the antagonist to inhibit, neutralize or block the activity of the polypeptide. Efficacy of an antagonist can also be determined using functional assays, such as the ability of an antagonist to inhibit the function of the polypeptide or an agonist. For example, a functional assay may comprise contacting a polypeptide with a candidate antagonist molecule and measuring a detectable change in one or more biological activities normally associated with the polypeptide. The potency of an antagonist is usually defined by its $IC_{50}$ value (concentration required to inhibit 50% of the agonist response). The lower the $IC_{50}$ value the greater the potency of the antagonist and the lower the concentration that is required to inhibit the maximum biological response.

As used herein, the term "antibody" refers to a whole antibody comprising two light chain polypeptides and two heavy chain polypeptides. Whole antibodies include different antibody isotypes including IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

The term "antigen presenting cell" or "APC" is a cell that displays foreign antigen complexed with MHC on its surface. T cells recognize this complex using T cell receptor (TCR). Examples of APCs include, but are not limited to, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis.

The term "antigen presentation" refers to the process by which APCs capture antigens and enables their recognition by T cells, e.g., as a component of an MHC-I and/or MHC-II conjugate.

As used herein, the term "cancer-specific immune response" refers to the immune response induced by the presence of tumors, cancer cells, or cancer antigens. In certain embodiments, the response includes the proliferation of cancer antigen specific lymphocytes. In certain embodiments, the response includes expression and upregulation of antibodies and T-cell receptors and the formation and release of lymphokines, chemokines, and cytokines. Both innate and acquired immune systems interact to initiate antigenic responses against the tumors, cancer cells, or cancer antigens. In certain embodiments, the cancer-specific immune response is a T cell response.

As used herein, the term "antibody fragment," "antigen-binding fragment," or similar terms refer to a fragment of an antibody that retains the ability to bind to a target antigen(s) and promote, induce, and/or increase the activity of the target antigen. Such fragments include, e.g., a single chain antibody, a single chain Fv fragment (scFv), an Fd fragment, an Fab fragment, an Fab' fragment, or an $F(ab')_2$ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al. (2001) *J Immunol Methods* 248(1):47-66; Hudson and Kortt (1999) *J Immunol Methods* 231(1):177-189; Poljak (1994) *Structure* 2(12):1121-1123; Rondon and Marasco (1997) *Annual Review of Microbiology* 51:257-283, the disclosures of each of which are incorporated herein by reference in their entirety.

As used herein, the term "antibody fragment" also includes, e.g., single domain antibodies such as camelized single domain antibodies. See, e.g., Muyldermans et al. (2001) *Trends Biochem Sci* 26:230-235; Nuttall et al. (2000) *Curr Pharm Biotech* 1:253-263; Reichmann et al. (1999) *J Immunol Meth* 231:25-38; PCT application publication nos. WO 94/04678 and WO 94/25591; and U.S. Pat. No. 6,005,079, all of which are incorporated herein by reference in their entireties. In some embodiments, the disclosure provides single domain antibodies comprising two VH domains with modifications such that single domain antibodies are formed.

The "B7 family" refers to activating and inhibitory ligands. The B7 family encompasses at least activating ligands B7-1 and B7-2, and inhibitory ligands B7-H1, B7-H2, B7-H3 and B7-H4. B7-1 and B7-2 bind to CD28, B7-H1 (i.e., PD-L1) binds to PD-1, and B7-H2 binds to ICOS. B7-H3 and B7-H4 bind unknown receptors. Further, B7-H3 and B7-H4 have been shown to be upregulated on tumor cells and tumor infiltrating cells. The complete hB7-H3 and hB7-H4 sequence can be found under GenBank Accession Nos. Q5ZPR3 and AAZ17406 (SEQ ID NOs: 47 and 48) respectively.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The anti-CD137 antibodies and tumor antigen-targeting antibodies described herein can be used to treat patients who have, who are suspected of having, or who may be at high risk for developing any type of cancer, including renal carcinoma or melanoma. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

As used herein, the term "crosslinking" or "crosslinks" refers to the process of chemically joining or linking two or more molecules involving a reaction in which a covalent bond is formed.

As used herein, the term "chimeric antigen receptor (CAR)" refers to an artificial transmembrane protein receptor comprising (i) an extracellular domain capable of binding to at least one predetermined CAR ligand or antigen, or a predetermined CAR ligand and an antigen, (ii) an intracellular segment comprising one or more cytoplasmic domains derived from signal transducing proteins different from the polypeptide from which the extracellular domain is derived, and (iii) a transmembrane domain. The "chimeric antigen receptor (CAR)" is sometimes called a "chimeric receptor", a "T-body", or a "chimeric immune receptor (CIR)."

The phrase "CAR ligand" used interchangeably with "CAR antigen" means any natural or synthetic molecule (e.g., small molecule, protein, peptide, lipid, carbohydrate, nucleic acid) or part or fragment thereof that can specifically bind to a CAR (e.g., the extracellular domain of a CAR). In some embodiments, the CAR ligand is a tumor-associated antigen, or fragment thereof. In some embodiments, the CAR ligand is a tag.

The "intracellular signaling domain" means any oligopeptide or polypeptide domain known to function to transmit a signal causing activation or inhibition of a biological process in a cell, for example, activation of an immune cell such as a T cell or a NK cell. Examples include ILR chain, CD28 and/or CD3ζ.

As used herein, "cancer antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

As used herein, "cancer vaccine" refers to a treatment that induces the immune system to attack cells with one or more tumor associated antigens. The vaccine can treat existing cancer (e.g., therapeutic cancer vaccine) or prevent the development of cancer in certain individuals (e.g., prophylactic cancer vaccine). The vaccine creates memory cells that will recognize tumor cells with the antigen and therefore prevent tumor growth.

As used herein, the term "chemokine" refers to a member of the family of small cytokines, or signaling proteins, that induce directed chemotaxis. Chemokines are grouped into four subfamilies: CXC, CC, (X)C, and CX3C.

As used herein, "combination therapy" embraces administration of each agent or therapy in a sequential or simultaneous manner in a regimen that will provide beneficial effects of the combination, and co-administration of these agents or therapies in a substantially simultaneous manner, such as in a single capsule having a fixed ratio of these active agents or in multiple, separate capsules for each agent. Combination therapy also includes combinations where individual elements may be administered at different times and/or by different routes but which act in combination to provide a beneficial effect by co-action or pharmacokinetic and pharmacodynamics effect of each agent or tumor treatment approaches of the combination therapy.

A "co-stimulatory signal", as used herein, refers to a signal, which in combination with a primary signal, such as TCR/CD3 ligation, leads to T cell proliferation and/or upregulation or downregulation of key molecules "Cytotoxic T Lymphocyte Associated Antigen-4 (CTLA-4)" is a T cell surface molecule and is a member of the immunoglobulin superfamily. This protein downregulates the immune system by binding to CD80 and CD86. The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. P16410.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting molecule. In certain embodiments, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In certain embodiments, the antigens of the disclosure are encoded by a nucleotide sequence. Nucleotide sequences of the invention can be useful for a number of applications, including: cloning, gene therapy, protein expression and purification, mutation introduction, DNA vaccination of a host in need thereof, antibody generation for, e.g., passive immunization, PCR, primer and probe generation, and the like.

It will also be understood by one of ordinary skill in the art that the immunomodulatory domains, stabilizing domains, and kinases suitable for use in the methods disclosed herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The polypeptides suitable for use in the immunomodulatory fusion proteins disclosed herein may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In certain embodiments, a string of amino acids can be replaced with a structurally similar string that differs in order and/or composition of side chain family members. Alternatively, in certain embodiments, mutations may be introduced randomly along all or part of a coding sequence, such as by saturation mutagenesis, and the resultant mutants can be incorporated into binding polypeptides of the invention and screened for their ability to bind to the desired target.

As used herein, the term "contacting" means establishing a physical connection between two or more entities. For example, contacting a cell with an agent (e.g., a DNA, an RNA, a lipid nanoparticle composition, or other pharmaceutical composition of the disclosure) means that the cell and the agent are made to share a physical connection. Methods of contacting cells with external entities both in vivo, in vitro, and ex vivo are well known in the biological arts. In exemplary embodiments of the disclosure, the step of contacting a mammalian cell with a composition (e.g., a recombinant DNA, an isolated RNA, nanoparticle, or pharmaceutical composition of the disclosure) is performed in vivo. For example, contacting a lipid nanoparticle composition and a cell (for example, a mammalian cell) which may be disposed within an organism (e.g., a mammal) may be performed by any suitable administration route (e.g., parenteral administration to the organism, including intravenous, intramuscular, intradermal, and subcutaneous administration). For a cell present in vitro, a composition (e.g., a lipid nanoparticle or an isolated RNA) and a cell may be contacted, for example, by adding the composition to the culture medium of the cell and may involve or result in transfection. Moreover, more than one cell may be contacted by an agent.

As used herein, the term antigen "cross-presentation" refers to presentation of exogenous protein antigens to T cells via MHC class I and class II molecules on APCs.

As used herein, the term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system. As used herein, the term "epitope" or "antigenic determinant" refers to a determinant or site on an antigen to which an antigen-binding protein (e.g., an immunoglobulin, antibody, or antigen-binding fragment) specifically binds. The epitopes of protein antigens can be demarcated into "linear epitopes" and "conformational epitopes". As used herein, the term "linear epitope" refers to an epitope formed from a contiguous, linear sequence of linked amino acids. Linear epitopes of protein antigens are typically retained upon exposure to chemical denaturants (e.g., acids, bases, solvents, crosslinking reagents, chaotropic agents, disulfide bond reducing agents) or physical denaturants (e.g. thermal heat, radioactivity, or mechanical shear or stress). In some embodiments, an epitope is non-linear, also referred to as an interrupted epitope. As used herein, the term "conformational epitope" refers to an epitope formed from noncontiguous amino acids juxtaposed by tertiary folding of a polypeptide. Conformational epitopes are typically lost upon treatment with denaturants. A epitope typically includes at least 3, 4, 5, 6, 7, 8, 9, 10, 11, 12, 13, 14 or 15 amino acids in a unique spatial conformation. Generally, an antibody, or antigen-binding fragment thereof, specific for a particular target molecule will preferentially recognize and bind to a specific epitope on the target molecule within a complex mixture of proteins and/or macromolecules.

As used herein, the term "effector cell" or "effector immune cell" refers to a cell involved in an immune response, e.g., in the promotion of an immune effector response. In some embodiments, immune effector cells specifically recognize an antigen. Examples of immune effector cells include, but are not limited to, Natural Killer (NK) cells, B cells, monocytes, macrophages, T cells (e.g., cytotoxic T lymphocytes (CTLs). In some embodiments, the effector cell is a T cell. As used herein, the term "immune effector function" or "immune effector response" refers to a function or response of an immune effector cell that promotes an immune response to a target.

As used herein, the term "endoplasmic reticulum (ER)-targeting leader sequence" refers to a signal peptide, leader sequence, or signal sequence that targets a protein to the secretory pathway during or following ribosomal translation. An ER-targeting leader sequence is a short (e.g., 10-50 amino acids) amino acid sequence comprising a polar N-terminus, an internal stretch of hydrophobic amino acids. The ER-targeting leader sequence is cleaved from a polypeptide upon entry of the polypeptide into the ER lumen, and thus generally comprises a C-terminal cleavage motif. The particular amino acid sequence and length of a ER-targeting leader sequence can vary widely. Methods of predicting an ER-targeting leader sequence in a polypeptide sequence are known in the art, and are further described by Meinken, et. Al. (2012) *Computational Molecular Biology* 2:1-7.

As used herein, the term "Fc region" refers to the portion of a native immunoglobulin formed by the respective Fc domains (or Fc moieties) of its two heavy chains In some embodiments, the term "Fc domain" refers to a portion of a single immunoglobulin (Ig) heavy chain wherein the Fc domain does not comprise an Fv domain. In some embodiments, the term "Fc domain" refers to a portion of a single immunoglobulin (Ig) heavy chain also comprising an Fv domain. As such, an Fc domain can also be referred to as "Ig" or "IgG." In certain embodiments, an Fc domain begins in the hinge region just upstream of the papain cleavage site and ends at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In certain embodiments, an Fc domain comprises a complete Fc domain (i.e., a hinge domain, a CH2 domain, and a CH3 domain). In certain embodiments, an Fc domain comprises a hinge domain (or portion thereof) fused to a CH3 domain (or portion thereof). In certain embodiments, an Fc domain comprises a CH2 domain (or portion thereof) fused to a CH3 domain (or portion thereof). In certain embodiments, an Fc domain consists of a CH3 domain or portion thereof. In certain embodiments, an Fc domain consists of a hinge domain (or portion thereof) and a CH3 domain (or portion thereof). In certain embodiments, an Fc domain consists of a CH2 domain (or portion thereof) and a CH3 domain. In certain embodiments, an Fc domain consists of a hinge domain (or portion thereof) and a CH2 domain (or portion thereof). In certain embodiments, an Fc domain lacks at least a portion of a CH2 domain (e.g., all or part of a CH2 domain) An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. A human IgG1 constant region can be found at Uniprot P01857 and SEQ ID NO: 89. The Fc domain of human IgG1 can be found in SEQ ID NO: 90. The Fc domain encompasses native Fc and Fc variant molecules. As with Fc variants and native Fc's, the term Fc domain includes molecules in monomeric or multimeric form, whether digested from whole antibody or produced by other means. The assignment of amino acid residue numbers to an Fc domain is in accordance with the definitions of Kabat. See, e.g., Sequences of Proteins of Immunological Interest (Table of Contents, Introduction and Constant Region Sequences sections), 5th edition, Bethesda, MD: NIH vol. 1:647-723 (1991); Kabat et al., "Introduction" Sequences of Proteins of Immunological Interest, US Dept of Health and Human Services, NIH, 5th edition, Bethesda, MD vol. 1: xiii-xcvi (1991); Chothia & Lesk, J. Mol. Biol. 196:901-917 (1987); Chothia et al., Nature 342:878-883 (1989), each of which is herein incorporated by reference for all purposes.

As set forth herein, it will be understood by one of ordinary skill in the art that any Fc domain may be modified such that it varies in amino acid sequence from the native Fc domain of a naturally occurring immunoglobulin molecule. In certain embodiments, the Fc domain has reduced effector function (e.g., FcγR binding).

The Fc domains suitable for use in the immunomodulatory fusion proteins disclosed herein may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

As used herein, the term "gly-ser polypeptide linker" or "gly-ser linker" refers to a peptide that consists of glycine and serine residues. An exemplary gly-ser polypeptide linker comprises the amino acid sequence Ser($Gly_4$Ser)n (SEQ ID NO: 235). In certain embodiments, n=1. In certain embodiments, n=2. In certain embodiments, n=3, i.e., Ser($Gly_4Ser)_3$ (SEQ ID NO: 236). In certain embodiments, n=4, i.e., Ser($Gly_4Ser)_4$ (SEQ ID NO: 237). In certain embodiments, n=5. In certain embodiments, n=6. In certain embodiments, n=7. In certain embodiments, n=8. In certain embodiments, n=9. In certain embodiments, n=10. Another exemplary gly-ser polypeptide linker comprises the amino acid sequence ($Gly_4$Ser)n (SEQ ID NO: 238). In certain embodiments, n=1. In certain embodiments, n=2. In certain embodiments, n=3. In certain embodiments, n=4. In certain embodiments, n=5. In certain embodiments, n=6. Another exemplary gly-ser polypeptide linker comprises the amino acid sequence ($Gly_3$Ser)n (SEQ ID NO: 239). certain embodiments, n=1. In certain embodiments, n=2. In certain embodiments, n=3. In certain embodiments, n=4. In certain embodiments, n=5. In certain embodiments, n=6.

As used herein, the term "human antibody" includes antibodies having variable and constant regions (if present) of human germline immunoglobulin sequences. Human antibodies of the disclosure can include amino acid residues not encoded by human germline immunoglobulin sequences (e.g., mutations introduced by random or site-specific mutagenesis in vitro or by somatic mutation in vivo) (See, e.g., Lonberg et al., (1994) *Nature* 368(6474): 856-859); Lonberg, (1994) *Handbook of Experimental Pharmacology* 113: 49-101; Lonberg & Huszar, (1995) *Intern. Rev. Immunol.* 13:65-93, and Harding & Lonberg, (1995) *Ann. N.Y. Acad. Sci.* 764:536-546). However, the term "human antibody" does not include antibodies in which CDR sequences derived from the germline of another mammalian species, such as a mouse, have been grafted onto human framework sequences (i.e. humanized antibodies).

As used herein, the term a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, the term "hydroxyl-replacement moiety" or "hydroxyl-replacing moiety" refers to a chemical moiety or group that is effective to substitute for a surface hydroxyl group comprising a metal hydroxide.

As used herein, the term "immunomodulatory fusion protein" refers to a metal hydroxide-binding peptide operably linked via a linker to a polypeptide comprising one or more immunomodulatory domains, and optionally a stabilizing domain.

As used herein, the term "immunomodulatory fusion protein-metal hydroxide complex" is used to refer to an immunomodulatory fusion protein comprising a metal hydroxide-binding peptide, wherein the immunomodulatory fusion protein is adsorbed via ligand exchange to a metal hydroxide via the metal hydroxide-binding peptide, thereby forming a complex.

As used herein, the term "immunogenic composition" refers to a preparation which, when administered to a vertebrate, especially a mammal, will induce an immune response. In some embodiments, an immunogenic composition comprises an immunomodulatory fusion protein-metal hydroxide complex for inducing an endogenous anti-tumor immune response in a subject with cancer.

The terms "inducing an immune response" and "enhancing an immune response" are used interchangeably and refer to the stimulation of an immune response (i.e., either passive or adaptive) to a particular antigen. The term "induce" as used with respect to inducing CDC or ADCC refer to the stimulation of particular direct cell killing mechanisms.

As used herein, the term "inhibits growth" (e.g., referring to cells) is intended to include any measurable decrease in the growth of a cell, e.g., the inhibition of growth of a cell by at least about 10%, 20%, 30%, 40%, 50%, 60%, 70%, 80%, 90%, 99%, or 100%.

As used herein, "immune cell" is a cell of hematopoietic origin and that plays a role in the immune response. Immune cells include lymphocytes (e.g., B cells and T cells), natural killer cells, and myeloid cells (e.g., monocytes, macrophages, eosinophils, mast cells, basophils, and granulocytes).

As used herein, "immune checkpoint" refers to co-stimulatory and inhibitory signals that regulates immune cells \. In certain embodiments, the immune checkpoint is an inhibitory signal. In certain embodiments, the inhibitory signal is the interaction between PD-1 and PD-L1. In certain embodiments, the inhibitory signal is the interaction between CTLA-4 and CD80 or CD86 to displace CD28 binding. In certain embodiments the inhibitory signal is the interaction between LAG3 and MHC class II molecules. In certain embodiments, the inhibitory signal is the interaction between TIM3 and galectin 9.

As used herein, "immune checkpoint blocker" refers to a molecule that totally or partially reduces, inhibits, interferes with or modulates one or more checkpoint proteins. In certain embodiments, the immune checkpoint blocker prevents inhibitory signals associated with the immune checkpoint. In certain embodiments, the immune checkpoint blocker is an antibody, or fragment thereof that disrupts inhibitory signaling associated with the immune checkpoint. In certain embodiments, the immune checkpoint blocker is a small molecule that disrupts inhibitory signaling. In certain embodiments, the immune checkpoint blocker is an antibody, fragment thereof, or antibody mimic, that prevents the interaction between checkpoint blocker proteins, e.g., an antibody, or fragment thereof, that prevents the interaction between PD-1 and PD-L1. In certain embodiments, the immune checkpoint blocker is an antibody, or fragment thereof, that prevents the interaction between CTLA-4 and CD80 or CD86. In certain embodiments, the immune checkpoint blocker is an antibody, or fragment thereof, that prevents the interaction between LAG3 and its ligands, or TIM-3 and its ligands.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an vaccine).

The term "in vitro" refers to processes that occur in an artificial environment, e.g., in a test tube or reaction vessel, in cell culture, in a Petri dish, etc., rather than within an organism (e.g., animal, plant, or microbe). The term "in vivo" refers to processes that occur in a living organism.

The term "in vivo" refers to processes that occur in a living organism.

As used herein, "interleukin (IL)-2," refers to a pleiotropic cytokine that activates and induces proliferation of T cells and natural killer (NK) cells. IL-2 signals by binding its receptor, IL-2R, which is comprised of alpha, beta, and gamma subunits. IL-2 signaling stimulates proliferation of antigen-activated T cells.

As used herein, the term "isolated antibody" is intended to refer to an antibody which is substantially free of other antibodies having different antigenic specificities. An isolated antibody that specifically binds to an epitope may, however, have cross-reactivity to other proteins or antigens of interest from different species. However, the antibody continues to display specific binding to an antigen of interest in a specific binding assay as described herein. In addition, an isolated antibody is typically substantially free of other cellular material and/or chemicals.

As used herein, the term "isolated nucleic acid molecule" refers to nucleic acids encoding fusion proteins, polypeptides, antibodies or antibody portions disclosed herein, is intended to refer to a nucleic acid molecule in which the nucleotide sequences encoding the fusion protein, polypeptide, antibody or antibody portion are free of other nucleotide sequences, which other sequences may naturally flank the nucleic acid in human genomic DNA.

As used herein, "isotype" refers to the antibody class (e.g., IgM or IgG1) that is encoded by heavy chain constant region genes. In some embodiments, an antibody of the disclosure is of the IgG1 isotype. In some embodiments, an antibody of the disclosure is of the IgG2 isotype. In some embodiments, an antibody of the disclosure is of the IgG3 isotype. In some embodiments, an antibody of the disclosure is of the IgG4 isotype.

As used herein, the term "kinase target motif" is intended to refer to an amino acid sequence recognized as a substrate for phosphorylation by a kinase when found in a peptide and comprises both the phosphoacceptor amino acid residue (e.g., the amino acid residue that is phosphorylated, and the amino acids directly adjacent to the phosphoacceptor amino acid residue. In mammalian cells, the phosphoacceptor amino acid is generally a serine, tyrosine or threonine amino acid.

As used herein the term "KD" or "$K_D$" refers to the equilibrium dissociation constant of a binding reaction between e.g., a ligand and a receptor, an antigen and an antibody. The value of $K_D$ is a numeric representation of the ratio of the binding protein off-rate constant (kd) to the binding protein on-rate constant (ka). The value of $K_D$ is inversely related to the binding affinity of the binding protein to its binding partner. The smaller the $K_D$ value the greater the affinity of the binding protein for its binding partner. Affinity is the strength of binding of a single molecule to its ligand and is typically measured and reported by the equilibrium dissociation constant ($K_D$), which is used to evaluate and rank order strengths of bimolecular interactions.

As used herein, the term "kd" or "$k_d$" (alternatively "koff" or "$k_{off}$") is intended to refer to the off-rate constant for the dissociation of a binding protein from binding protein/partner complex. The value of kd is a numeric representation of the fraction of complexes that decay or dissociate per second, and is expressed in units $sec^{-1}$.

As used herein, the term "ka" or "$k_a$" (alternatively "kon" or "$k_{on}$") is intended to refer to the on-rate constant for the association of a binding protein with a binding partner. The value of ka is a numeric representation of the number of antibody/antigen complexes formed per second in a 1 molar (1M) solution of binding partners, and is expressed in units $M^{-1}\ sec^{-1}$.

As used herein, the terms "linked," "fused", or "fusion", are used interchangeably. These terms refer to the joining together of two more elements, groups, components, domains, or moieties by whatever means including chemical conjugation or recombinant means. Relatedly, as used herein, the term "linker" refers to a chemical group or domain that joins two or more elements, groups, components, domains, or moieties. Methods of chemical conjugation (e.g., using heterobifunctional crosslinking agents) are known in the art.

As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

As used herein, the term "metal hydroxide-binding peptide" refers to a peptide comprising a plurality of hydroxyl-replacement groups (e.g., phosphate groups), wherein each of the hydroxyl-replacement groups is effective to substitute for surface hydroxyl groups of a metal hydroxide, thereby binding to the metal hydroxide. In some embodiments, a metal hydroxide-binding peptide comprises a plurality of phosphorylated amino acid residues.

As used herein, the term "monoclonal antibody" refers to an antibody which displays a single binding specificity and affinity for a particular epitope. Accordingly, the term "human monoclonal antibody" refers to an antibody which displays a single binding specificity and which has variable and optional constant regions derived from human germline immunoglobulin sequences. In some embodiments, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "nanocrystal" refer to submicron crystalline particles less than 100 nm in dimension. In some embodiments, when nanocrystals form aggregates, the size of the aggregates may exceed 100 nm. In some embodiments, an immunomodulatory fusion protein-metal hydroxide complex comprises a metal hydroxide that comprises a nanocrystal. In some embodiments, an immunomodulatory fusion protein-metal hydroxide complex comprising a metal hydroxide nanocrystal is of sufficient mass to reduce size dependent diffusion from the site of injection upon administration in vivo.

As used herein, the term "nanoparticle" refers to submicron particles less 100 nm in dimension. In some embodiments, when nanoparticles form aggregates, the size of the aggregates may exceed 100 nm. In some embodiments, an immunomodulatory fusion protein-metal hydroxide complex comprises a metal hydroxide that comprises a nanoparticle. In some embodiments, an immunomodulatory fusion protein-metal hydroxide complex comprising a metal hydroxide nanoparticle is of sufficient mass to reduce size dependent diffusion from the site of injection upon administration in vivo.

As used herein, the term "aggregate" refers to an amorphous cluster, collection or assembly of molecules lacking ordered intermolecular interactions, as is determinable by electron microscopy. In some embodiments, an aggregate comprises a cluster, collection or assembly of polypeptides. In some embodiments, an aggregate comprises a cluster, collection or assembly of nanoparticles or nanocrystals of a metal salt, such as a metal hydroxide. In some embodiments, an immunomodulatory fusion protein-metal hydroxide complex comprises a metal hydroxide that comprises an aggregate. In some embodiments, an immunomodulatory fusion protein-metal hydroxide complex comprising a metal hydroxide aggregate is of sufficient mass to reduce size dependent diffusion from the site of injection upon administration in vivo.

As used herein, the term "neoantigen" refers to an antigen that has at least one alteration that makes it distinct from the corresponding wild-type, parental antigen, e.g., via mutation in a tumor cells or post-translational modification specific to a tumor cell. A neoantigen can include a polypeptide sequence or a nucleotide sequence. A mutation can include a frameshift or non-frameshift deletion, missense or nonsense substitution, splice site alteration, genomic rearrangement or gene fusion, or any genomic or expression alternative giving rise to a neoantigen open reading frame. A mutation can also include a splice variant. Post-translational modifications specific to a tumor cell can include aberrant phosphorylation. Post-translational modifications specific to a tumor cell can also include a proteasome-generated splice antigen. See Liepe et al., A large fraction of HLA class I ligands are proteasome-generated spliced peptides, Science, 2016 Oct. 21; 354 (6310): 354-358. In some embodiments, the neoantigen is a "tumor neoantigen", which is a neoantigen present in a subject's tumor cell or tissue but not in a subject's corresponding normal cell or tissue.

The term "mammal" or "subject" or "patient" as used herein includes both humans and non-humans and includes, but is not limited to, humans, non-human primates, canines, felines, murines, bovines, equines, and porcines.

As used herein, the term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the term "operably linked" refers to the linkage of a first element to a second element such that the first element and second element are placed in a functional relationship. For example, when a first reactive moiety or group is "operably linked" to a second reactive moiety or group, the function or reactivity of the first and second moieties are linked. For example, a nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame.

As used herein, the term "paratope", also "antigen-binding site" refers to a portion of an antibody, or antigen-binding fragment thereof, which recognizes and binds to an epitope on an antigen, comprising the set of complementarity determining regions (CDRs) located within variable heavy and light chains.

As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

As used herein, the term "patient" includes human and other mammalian subjects that receive either prophylactic or therapeutic treatment.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the term "polypeptide-reactive moiety" refers to a chemical moiety comprising a functional group that targets by reacting directly with an accessible functional group of a polypeptide, or functional group comprising a pendant (e.g. oligosaccharide) attached to the polypeptide, to produce a covalent linkage. The reaction can occur spontaneously or after activation through contact with a catalyst (e.g., an enzyme, a metal catalyst) or stimulus (e.g., light, heat). In some embodiments, a chemical moiety comprises a function group that reacts with an accessible side chain of a polypeptide, for example, a lysine or cysteine side-chain to form a covalent linkage. In some embodiments, a chemical moiety comprises a function group that reacts with the side-chain of a terminal (e.g., a C-terminal or N-terminal) or an internal amino acid residue of a polypeptide to form a covalent linkage. Exemplary polypeptide-reactive moieties that react with a polypeptide side chain to form a covalent linkage are described herein and include, but are not limited to, an N-hydroxysuccinimide ester, a maleimide, or a cycloalkyne. In some embodiments, a chemical moiety comprises a functional group that reacts with the amino acid backbone of a terminal (e.g., a C-terminal or N-terminal) amino acid residue. For example, polypeptide-reactive moieties comprising a sortase tag, such as those described herein, react via an enzymatic reaction with a terminal amino acid residue of a polypeptide to form a covalent linkage.

As used herein, the terms "polypeptide," "peptide", and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "preventing" when used in relation to a condition, refers to administration of a composition which reduces the frequency of, or delays the onset of, symptoms of a medical condition in a subject relative to a subject which does not receive the composition.

As used herein, the term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

As used herein, the term "recombinant host cell" (or simply "host cell") is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "secretory pathway kinase" refers to a kinase comprising an ER-targeting sequence that directs the kinase to the secretory pathway during or following translation. In some embodiments, a kinase is a naturally-occurring secretory pathway kinase comprising an ER-targeting sequence. In some embodiments, a kinase is modified to enter the secretory pathway by operably linking an ER-targeting sequence to the N-terminus of the kinase domain.

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

As used herein, the terms "specifically binds" and "selectively binds" refers to binding by an antibody to an epitope on a predetermined antigen.

The term "sufficient amount" or "amount sufficient to" means an amount sufficient to produce a desired effect, e.g., an amount sufficient to reduce the size of a tumor.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present disclosure, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

As used herein, "tumor antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, (xi) neoantigens and (xii) any other type of antigen or antigen-presenting cell or material that is associated with a cancer or a tumor.

As used herein, the term "tumor-associated antigen" or "TAA" refers an immunogenic molecule, such as a protein, that is generally expressed at a higher level in tumor cells than in non-tumor cells, in which it may not be expressed at all, or only at low levels. In some embodiments, tumor-associated structures which are recognized by the immune system of the tumor-harboring host are referred to as tumor-associated antigens. In some embodiments, a tumor-associated antigen is a universal tumor antigen if its broadly expressed by most tumors. In some embodiments, tumor-associated antigens are differentiation antigens, mutational antigens, overexpressed cellular antigens or viral antigens.

As used herein, the term "tumor specific antigen" or "TSA" refers to an immunogenic molecule, such as a protein, that is unique to a tumor cell. Tumor specific antigens are exclusively expressed in tumor cells.

The terms "treat," "treating," and "treatment," as used herein, refer to therapeutic or preventative measures described herein. The methods of "treatment" employ administration to a subject, in need of such treatment, a human antibody of the present disclosure, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "T cell" refers to a type of white blood cell that can be distinguished from other white blood cells by the presence of a T cell receptor on the cell surface. There are several subsets of T cells, including, but not limited to, T helper cells (a.k.a. $T_H$ cells or $CD4^+$ T cells) and subtypes, including $T_H1$, $T_H2$, $T_H3$, $T_H17$, $T_H9$, and $T_{FH}$ cells, cytotoxic T cells (a.k.a Tc cells, $CD8^+$ T cells, cytotoxic T lymphocytes, T-killer cells, killer T cells), memory T cells and subtypes, including central memory T cells ($T_{CM}$ cells), effector memory T cells ($T_{EM}$ and $T_{EMRA}$ cells), and resident memory T cells ($T_{RM}$ cells), regulatory T cells (a.k.a. $T_{reg}$ cells or suppressor T cells) and subtypes, including $CD4^+$ $FOXP3^+$ $T_{reg}$ cells, $CD4^+FOXP3^-$ $T_{reg}$ cells, Tr1 cells, Th3 cells, and $T_{reg}17$ cells, natural killer T cells (a.k.a. NKT cells), mucosal associated invariant T cells (MAITs), and gamma delta T cells (γδ T cells), including Vγ9/Vδ2 T cells. Any one or more of the aforementioned or unmentioned T cells may be the target cell type for a method as disclosed herein.

The term "T cell cytotoxicity" includes any immune response that is mediated by CD8+ T cell activation. Exemplary immune responses include cytokine production, CD8+ T cell proliferation, granzyme or perforin production, and clearance of an infectious agent.

A "therapeutic antibody" is an antibody, fragment of an antibody, or construct that is derived from an antibody, and can bind to a cell-surface antigen on a target cell to cause a therapeutic effect. Such antibodies can be chimeric, humanized or fully human antibodies. Methods are known in the art for producing such antibodies. Such antibodies include single chain Fc fragments of antibodies, minibodies and diabodies. Any of the therapeutic antibodies known in the art to be useful for cancer therapy can be used in the combination therapy suitable for use in the methods disclosed herein. Therapeutic antibodies may be monoclonal antibodies or polyclonal antibodies. In preferred embodiments, the therapeutic antibodies target cancer antigens.

The term "therapeutically effective amount" is an amount that is effective to ameliorate a symptom of a disease. A therapeutically effective amount can be a "prophylactically effective amount" as prophylaxis can be considered therapy.

As used herein, "vaccine" refers to a formulation which contains an immunogenic composition as described herein, combined with an adjuvant, which is in a form that is capable of being administered to a vertebrate and which induces a protective immune response sufficient to induce immunity to prevent and/or ameliorate an infection or disease and/or to reduce at least one symptom of an infection or disease and/or to enhance the efficacy of another dose of the synthetic nanoparticle. Typically, the vaccine comprises a conventional saline or buffered aqueous solution medium in which a composition as described herein is suspended or dissolved. In this form, a composition as described herein is used to prevent, ameliorate, or otherwise treat an infection or disease. Upon introduction into a host, the vaccine provokes an immune response including, but not limited to, the production of antibodies and/or cytokines and/or the activation of cytotoxic T cells, antigen presenting cells, helper T cells, dendritic cells and/or other cellular responses.

As used herein, "protective" immune response refers to cell mediated and/or humoral (antibody) mediated immune response that will prevent or ameliorate a disease or infection. Protective humoral immune response or humoral immunity often involve the induction of broadly neutralizing antibodies that recognize specific epitopes on an antigen. For elicitation of protective humoral immunity by vaccination, B cells must be activated and enter germinal centers, where they proliferate and mutate their antibody genes toward enhanced recognition of an antigen. A portion of these cells must then differentiate into either long-lived plasma cells that secrete antibody constitutively or memory B cells that participate in a recall response on re-exposure to the pathogen.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

EXAMPLES

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure. Below are examples of specific embodiments for carrying out the present invention. The examples are offered for illustrative purposes only, and are not intended to limit the scope of the present invention in any way.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structure and Molecular Properties (W. H. Freeman and Company, 1993); A. L. Lehninger, Biochemistry (Worth Publishers, Inc., current addition); Sambrook, et al., Molecular Cloning: A Laboratory Manual ($2^{nd}$ Edition, 1989); Methods in Enzymology (S. Colowick and N. Kaplan eds., Academic Press, Inc.); Remington's Pharmaceutical Sciences, $18^{th}$ Edition (Easton, Pennsylvania; Mack Publishing Company; 1990); Carey and Sundberg Advanced Organic Chemistry $3^{rd}$ Ed. (Plenum Press) Vols A and B (1992).

Example 1: Alum Binding Proteins Can be Recombinantly Expressed

Proteins with more phosphonates are known to adsorb to alum much stronger via ligand exchange (Morefield et al., 2005). Thus, peptides were identified that could be fused to the N-terminus or C-terminus of a protein of interest that would be phosphorylated during secretory expression in mammalian cells in order to allow strong binding to alum. The peptides that were identified comprise sequences that target the kinase, Fam20C, which was recently discovered to be the Golgi Casein Kinase (Tagliabracci et al., (2012) Science 336:1150-1153). Based on the known targeting motif of Fam20C (S-X-E) and known peptide substrates of Fam20C, a panel of alum binding peptides (ABP) were designed to target overexpressed Fam20C (Table 5).

Of these ABP sequences, ABP5 (SEQ ID NO: 95), ABP6 (SEQ ID NO: 97) and ABP7 (SEQ ID NO: 99) were peptide sequences with S-X-E motifs that were identified as substrates for Fam20C (Tagliabracci et al., (2015) *Cell* 161: 1619-1632). ABP7 (SEQ ID NO: 99) is a peptide derived from bovine β-casein. ABP8 (SEQ ID NO: 101) was designed by aligning the bovine and murine β-casein amino acid sequences, and identifying a sequence in murine β-casein in close proximity to bovine β-casein peptide identified by SEQ ID NO: 99 comprising S-X-E motifs. ABP3 (SEQ ID NO: 91) and ABP4 (SEQ ID NO: 93) were designed by analyzing the sequences of peptides identified as substrates for Fam20C according to Tagliabracci et al., (2015) *Cell* 161:1619-1632. The peptides were designed according to the formula XXSEEXXGGGSGGSEEGG (SEQ ID NO: 134), wherein XX are amino acids adjacent to the SEE motif that occurred frequently in the analyzed peptide substrates of Fam20C.

Additional ABPs were designed by combining short peptides comprising S-X-E motifs. ABP16 (SEQ ID NO: 115) comprises an amino acid sequence consisting of two sequential ABP3 (SEQ ID NO: 91) sequences. ABP12 (SEQ ID NO: 107) comprises an amino acid sequence consisting of two sequential ABP8 (SEQ ID NO: 101) sequences. ABP11 (SEQ ID NO: 105) comprises an amino acid sequence consisting of two sequential ABP4 (SEQ ID NO: 93) sequences. And ABP10 (SEQ ID NO: 103) comprises an amino acid sequence consisting of sequential ABP3 (SEQ ID NO: 91) and ABP4 (SEQ ID NO: 93) sequences.

Figure 1:
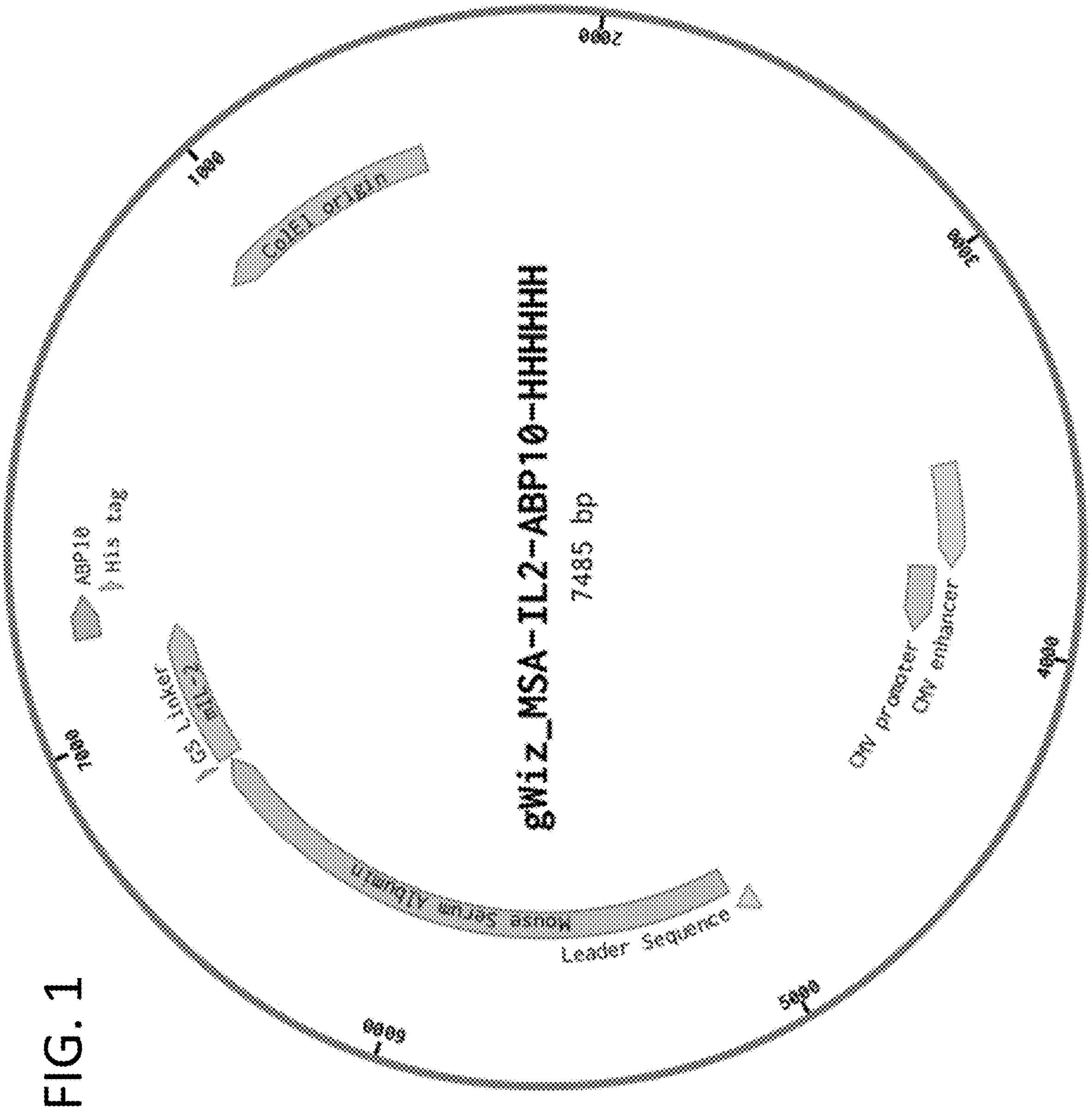
FIG. 1 provides a schematic showing a representative plasmid used to generate an alum binding protein. The plasmid shown was used to generate a fusion of mouse serum albumin (MSA) to interleukin-2 (IL2) and the Fam20C targeting motif ABP10 (MSA-IL2-ABP10; SEQ ID NO: 147) with an N-terminal secretory leader sequence and a C-terminal His tag.

The peptide, along with the protein of interest, a secretory leader sequence, and a C-terminal histidine tag, were cloned into a gWiz expression vector (Genlantis) using the In-fusion cloning system (Takara). A representative plasmid construct encoding a nucleotide sequence for mouse serum albumin (MSA) operably linked to mouse IL-2 (MSA-IL2) and a C-terminal ABP10 (MSA-IL2-ABP10; SEQ ID NO: 147) is shown in FIG. 1.

Proteins were co-expressed with wild-type (WT) Fam20C kinase or an inactive Fam20C kinase as a negative control. For co-expression with WT Fam20C kinase, cells were transfected with a gWiz vector encoding the sequence of WT Fam20C that was operably linked to a C-terminal KDEL sequence that was used to ensure Golgi localization (Fam20C-KDEL, SEQ ID NO: 136). For co-expression with inactive Fam20C kinase, cells were transfected with a gWiz vector encoding a Fam20C kinase with a D456A mutation that results in inactivation of kinase function (Fam20C (D456A)-KDEL; SEQ ID NO: 139) (e.g., see Tagliabracci et al., 2015).

Protein expression was performed by transiently transfecting HEK 293-F cells using the Freestyle 293 Expression system (Gibco). The cells were transfected with plasmid encoding the protein of interest operably linked to an ABP alone or in combination with plasmid encoding WT Fam20C kinase or inactive Fam20C kinase mutant. After 7 days, the cell culture supernatants were harvested and proteins were purified by Immobilized Metal Affinity Chromatography using NiNTA (Thermo Fisher). Further purification was performed by FPLC using a size exclusion chromatography column (Superdex 200 Increase 10/300 GL, GE Healthcare) in order to isolate monomeric protein. The concentration of purified protein was determined by measuring the absorbance at 280 nm on a NanoDrop 2000 spectrophotometer (Thermo Scientific).

TABLE 5

Amino acid sequence of alum binding peptides

| Name | Amino acid sequence | SEQ ID NO |
|---|---|---|
| ABP3 | FQ**SEE**QQGGGSGG**SEE**GG | 91 |
| ABP4 | ME**SEE**SNGGGSGG**SEE** | 93 |
| ABP5 | FRI**SHE**LDSA**SSE**V | 95 |
| ABP6 | AS**SQESGE**EAG**SQE**N | 97 |
| ABP7 | KKIEKFQ**SEE**QQQ | 99 |
| ABP8 | TV**SSE**TDSI**SSEESVE**HI | 101 |
| ABP10 | FQ**SEE**QQGGGSGG**SEE**GGME**SEE**SNGGGSGG**SEE**GG | 103 |
| ABP11 | ME**SEE**SNGGGSGG**SEE**GGME**SEE**SNGGGSGG**SEE**GG | 105 |
| ABP12 | TV**SSE**TDSI**SSEESVE**HITV**SSE**TDSI**SSEESVE**HI | 107 |
| ABP13 | FQAEEQQGGGSGGAEEGGMEAEESNGGGSGGAEEGG | 109 |
| ABP14 | MEAEESNGGGSGGAEEGGMEAEESNGGGSGGAEEGG | 111 |
| ABP15 | RRFQ**SEE**QQGGGSGG**SEE**GGRRME**SEE**SNGGGSGG**SEE**GG | 113 |
| ABP16 | FQ**SEE**QQGGGSGG**SEE**GGFQ**SEE**QQGGGSGG**SEE**GG | 115 |
| ABP17 | **SEESEESEESEE** | 117 |
| ABP18 | GGGSGG**SEE**GGGS | 119 |
| ABP19 | GGGSGG**SEESEE**GGGS | 121 |
| ABP20 | GGGSGG**SEESEESEE**GGGS | 123 |

Figure 2A:
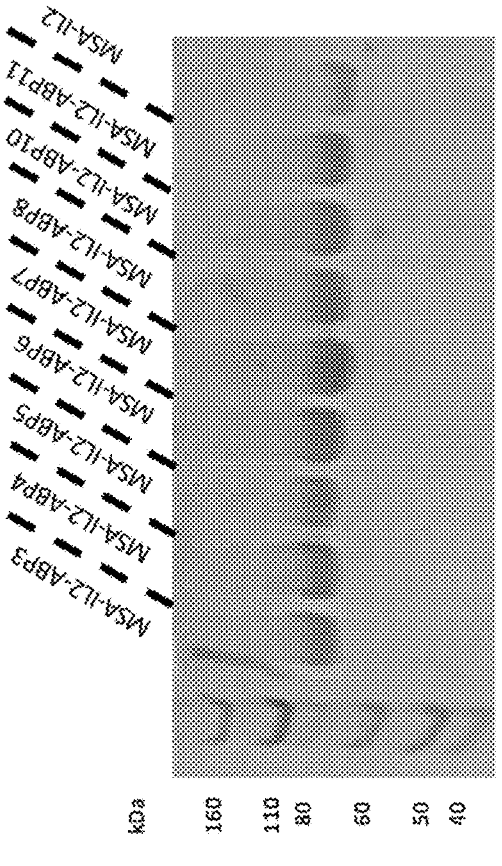
FIG. 2A provides an image of a denaturing SD S-PAGE gel showing the molecular weight of purified MSA-IL2 and MSA-IL2 protein variants with a C-terminal ABP, either ABP3 (SEQ ID NO: 91); ABP4 (SEQ ID NO: 93), ABP5 (SEQ ID NO: 95), ABP6 (SEQ ID NO: 97), ABP7 (SEQ ID NO: 99), ABP8 (SEQ ID NO: 101), ABP10 (SEQ ID NO: 103), or ABP11 (SEQ ID NO: 105).
Figure 2B:
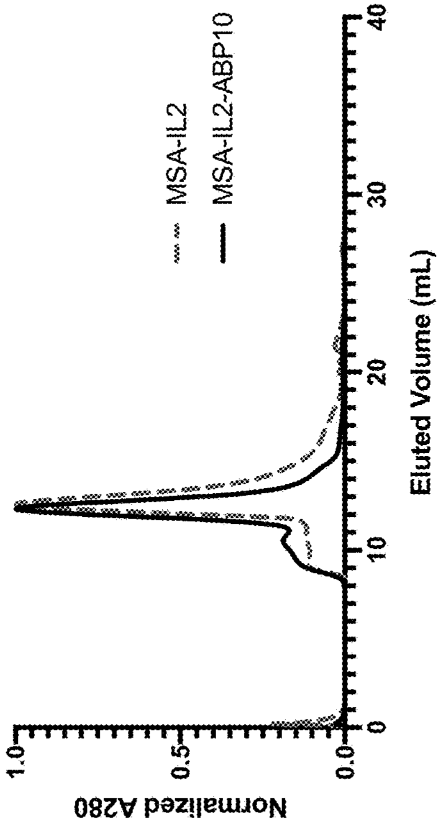
FIG. 2B provides a line graph showing the protein elution peaks measured by size exclusion fast protein liquid chromatography (FPLC) for purified MSA-IL2 and MSA-IL2 with a C-terminal ABP10 (MSA-IL2-ABP10; SEQ ID NO: 146).

Expression of MSA-IL2 fused to a C-terminal ABP was evaluated. IL2 is an inflammatory cytokine that is known to be a potent inducer of anti-tumor immune responses, while the fusion with MSA assists with the recombinant expression of IL2 while increasing its serum half-life (Zhu, et at *Cancer cell* 27.4 (2015): 489-501). MSA-IL2 fusion proteins linked to different C-terminal ABPs were expressed and the purified protein products were assessed by denaturing and reducing SDS-PAGE as shown in FIG. 2A. Proteins bands for MSA-IL2 proteins fused to an ABP were of the expected molecular weight (85-90 kDa). Additionally, the MSA-IL2-ABP fusion proteins were determined to be predominantly monomeric when purified by size exclusion FPLC. As shown in FIG. 2B, monomeric protein peaks for MSA-IL2 and MSA-IL2-ABP10 were identified in the 12-14 mL elution volume.

Figure 2C:
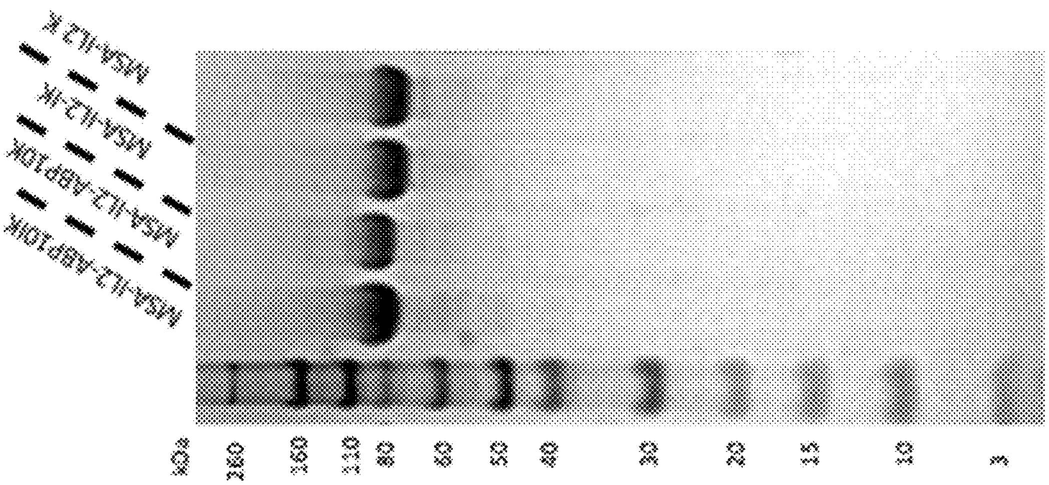
FIG. 2C provides an image of a denaturing SDS-PAGE gel showing the molecular weight of purified MSA-IL2 or MSA-IL2-ABP10 following co-transfection with wild-type Fam20C kinase (indicated by “K” annotation) or an inactive Fam20C kinase (indicated by “IK” annotation).

Having demonstrated that MSA-IL2 fused to a C-terminal ABP could be readily expressed and purified, it was determined if the protein could be produced when co-expressed in combination with kinase capable of phosphorylating the ABP. MSA-IL2 and MSA-IL2-ABP10 were selected for evaluation of co-expression. Plasmids encoding the proteins were co-transfected with plasmid encoding WT Fam20C kinase or plasmid encoding inactive Fam20C kinase. The MSA-IL2 fusion was purified as described above and evaluated for aggregation by size exclusion chromatography and expected molecular weight by SDS-PAGE. The fusion protein co-transfected with WT Fam20C kinase is annotated with the suffix K (i.e., MSA-IL2 K or MSA-IL2-ABP10K) and fusion protein co-transfected with inactive mutant Fam20C kinase is annotated with the suffix IK (i.e., MSA-IL2 IK or MSA-IL2-ABP10IK). As shown in FIG. 2C, the molecular weight of the purified MSA-IL2 proteins (K or IK) and the MSA-IL2-ABP10 proteins (K or IK) were of the expected values (around 85 kDa for MSA-IL2 and 91 kDa for MSA-IL2-ABP10) when co-expressed with Fam20C kinase, WT or inactive. Additionally, no Fam20C kinase (approximately 60 kDa) was detectable by SDS-PAGE, indicating the purification was sufficient for removal of the kinase. When analyzed by size exclusion chromatography, the proteins were predominantly monomeric (data not shown), and only the monomeric portion was collected for further analysis.

Figure 3A:
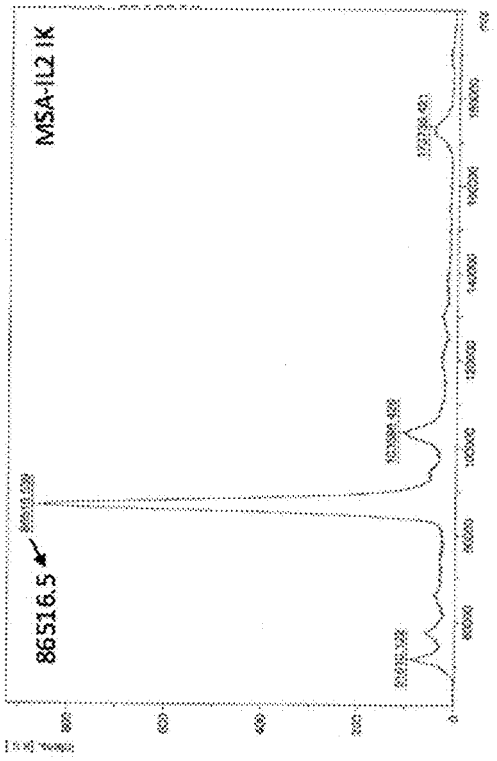
FIGS. 3A-3D provide line graphs showing measurement of protein molecular weight by MALDI-MS for purified MSA-IL2 or MSA-IL2-ABP10 following co-transfection with wild-type Fam20C kinase (FIG. 3C and FIG. 3D respectively) or an inactive Fam20C kinase (FIG. 3A and FIG. 3B respectively).
Figure 3B:
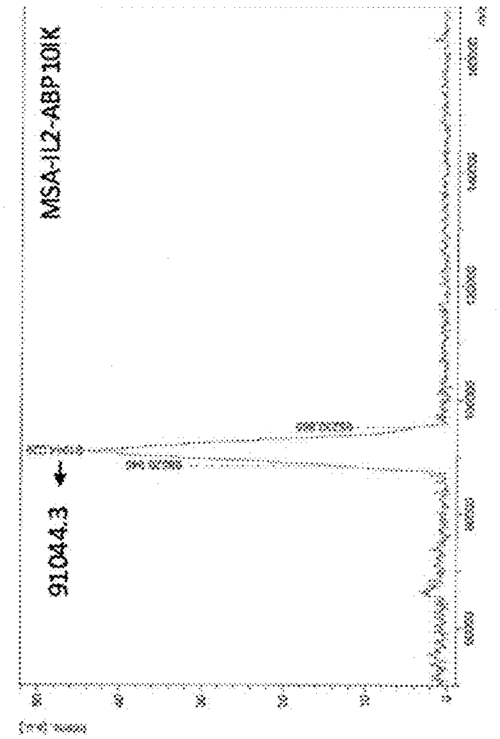
Figure 3C:
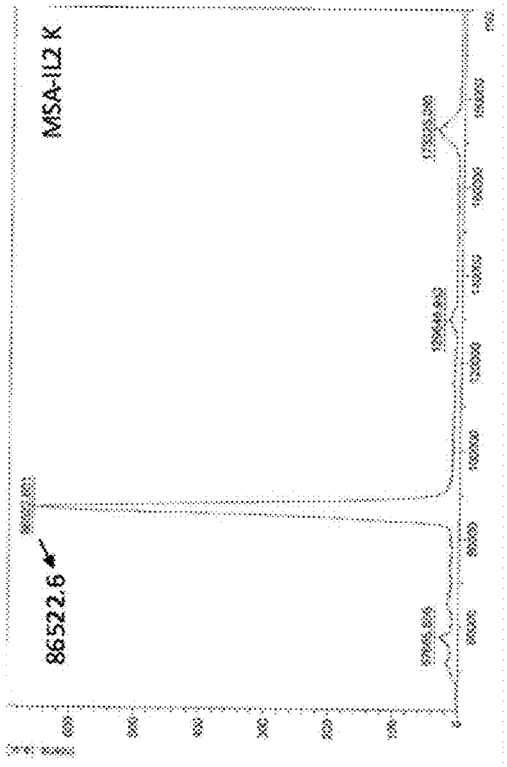
Figure 3D:
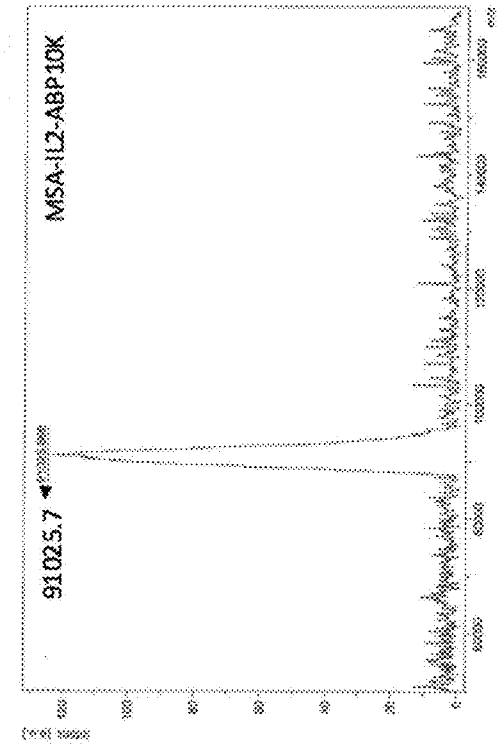

The molecular weight of the purified proteins was also confirmed by MALDI-MS as shown in FIGS. 3A-3D. The peaks detected by MALDI-MS were of the expected molecular weight for the MSA-IL2 proteins (FIG. 3A and FIG. 3C) and MSA-IL2-ABP10 proteins (FIG. 3B and FIG. 3D). However, the resolution of the analysis was deemed too low to detect mass differences due to phosphorylation of the ABP. Additional assays were performed as described in Example 2 to measure phosphorylation of the ABP following co-expression with Fam20C kinase.

Figure 4B:
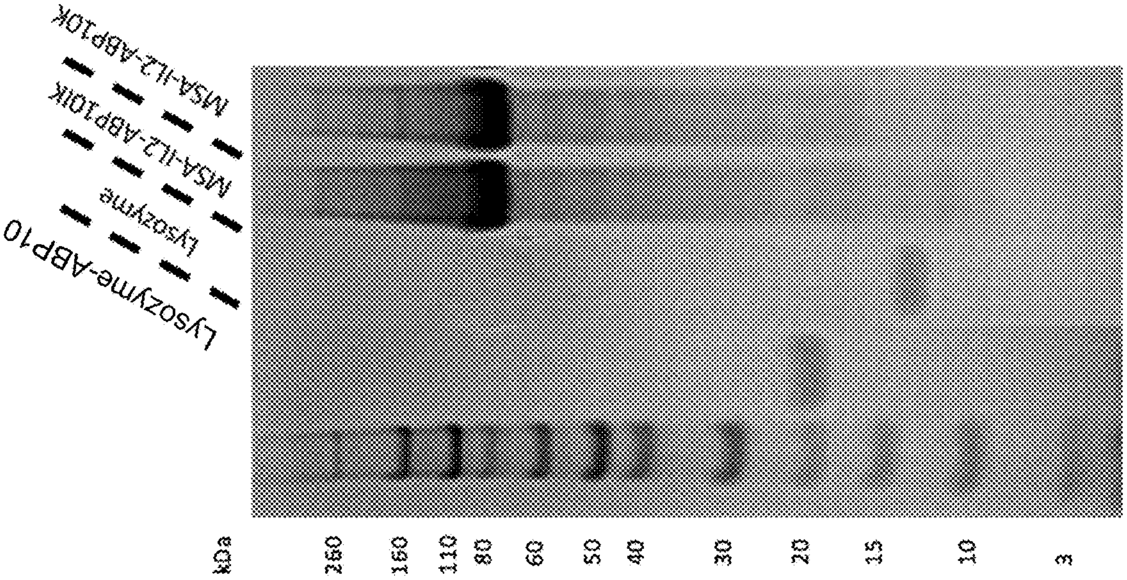
FIGS. 4A-4B provide images of denaturing SD S-PAGE gels showing molecular weight (MW) of purified proteins of interest fused to a C-terminal ABP and either expressed alone or co-expressed with wild-type Fam20C kinase (K) or inactive Fam20C kinase (IK).
Figure 4A:
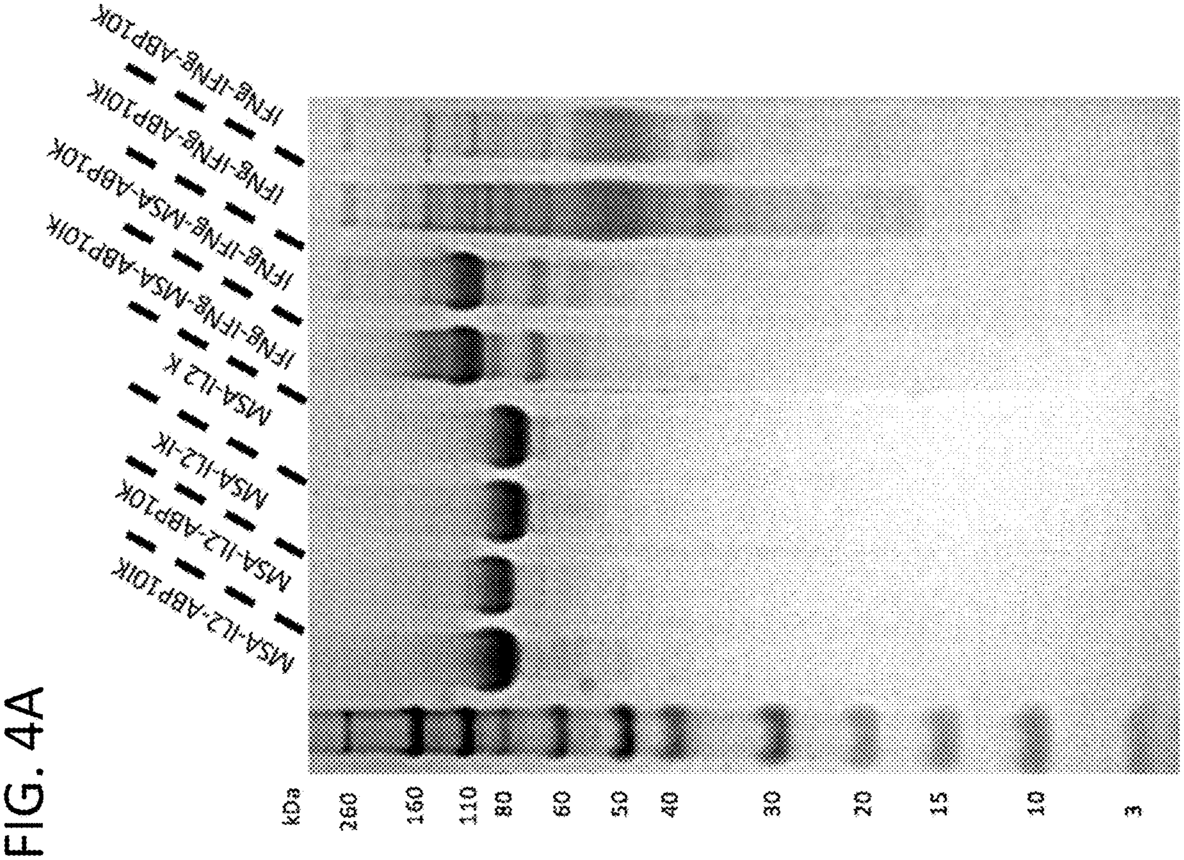

The strategy was evaluated for other proteins of interest, including IFNg-IFNg-MSA, IFNg-IFNg, and Lysozyme. Plasmids encoding the proteins included a C-terminal ABP10 (SEQ ID NO: 103) and the proteins were expressed alone or in combination with a plasmid encoding WT Fam20C kinase or a plasmid encoding mutant Fam20C kinase. Molecular weight of the purified protein products was assessed by SDS-PAGE. The purified proteins were found to have the expected molecular weights as shown in FIGS. 4A-4B. The additional bands present in samples of proteins comprising an IFNg were deemed to be due to contamination that can be removed by purification using size exclusion chromatography.

Exemplary protein fusions operably linked to ABPs are identified by sequence in the following table. Shown are fusion proteins linked to ABP10 (SEQ ID NO: 103), ABP8 (SEQ ID NO: 101), and ABP17 (SEQ ID NO: 117). However, the particular ABP is readily exchanged (e.g., with an alternative ABP such as those identified in Table 5). Additionally, the positioning of the ABP at either termini of the protein domain is also readily altered (e.g., positioning the ABP at the N-terminus or C-terminus of the protein). Listed in Table 6 are mouse proteins, however protein homologs from humans are readily swapped in to replace the mouse components (e.g., with human serum albumin or human cytokines). The peptide linker used to attach the ABP to the cytokine or MSA-cytokine fusion is typically a Gly-Ser linker (e.g., -GGGS-) (SEQ ID NO: 132). However, given that the Ser of the linker could potentially be phosphorylated by Fam20C kinase, fusions proteins to ABP17 as listed in Table 6 were prepared with a -GGGG- (SEQ ID NO: 240) linker for attachment of the ABP, thereby limiting potential phosphorylation of the linker.

TABLE 6

Exemplary fusion protein comprising ABPs

| Fusion Protein | SEQ ID NO (amino acid) | SEQ ID NO (DNA) |
|---|---|---|
| MSA-mIL2-ABP10<br>MSA-(GGGS)$_1$-IL2-(GGGS)$_1$-ABP10-(GGGS)$_1$-(H)$_6$ | 146 | 147 |
| MSA-mIL2-ABP8<br>MSA-(GGGS)$_1$-IL2-(GGGS)$_1$-ABP8-(GGGS)$_1$-(H)$_6$ | 150 | 151 |
| MSA-mIL2-ABP17<br>MSA-(GGGS)$_1$-IL2-(GGGG)$_1$-ABP17-(GGGG)$_1$-(H)$_6$ | 152 | 153 |
| ABP10-MSA-mIL2<br>ABP10-(GGGS)$_1$-MSA-(GGGS)$_1$-IL2-(H)$_6$ | 148 | 149 |
| mIFNg-mIFNg-MSA-ABP10<br>IFNg-(GGGS)$_4$-IFNg-(GSGGGS)$_1$-MSA-(GGGS)$_1$-ABP10-(GGGS)$_1$-(H)$_6$ | 160 | 161 |
| mIFNg-mIFNg-ABP10<br>IFNg-(GGGS)$_4$-IFNg-(GSGGGSGGGS)$_1$-ABP10-(GGGS)$_1$-(H)$_6$ | 162 | 163 |
| Lysozyme-ABP10<br>Lysozyme-(GGGS)$_1$-ABP10-(GGGS)$_1$-(H)$_6$ | 156 | 157 |
| mscIL12-MSA-ABP10<br>*IL12p40*-GGS(GGGS)$_3$-*IL12p35*-GS(GGGS)$_1$-MSA-(GGGS)$_1$-ABP10-(GGGS)$_1$-(H)$_6$ | 168 | 169 |
| mscIL12-ABP10<br>*IL12p40*-GGS(GGGS)$_3$-*IL12p35*-GS(GGGS)$_1$-ABP10-(GGGS)$_1$-(H)$_6$ | 172 | 173 |
| mscIL12-MSA-ABP17<br>*IL12p40*-GGS(GGGS)$_3$-*IL12p35*-GS(GGGS)$_1$-MSA-(GGGG)-ABP17-(GGGG)-(H)$_6$ | 170 | 171 |
| mscIL12-ABP17<br>*IL12p40*-GGS(GGGS)$_3$-*IL12p35*-(GGGG)-ABP 17-(GGGG)-(H)$_6$ | 174 | 175 |
| MSA-ABP10<br>MSA-(GGGS)$_1$-ABP10-(GGGS)$_1$-(H)$_6$ | 204 | 205 |

Example 2: Recombinantly Expressed Alum Binding Proteins are Phosphorylated

Figure 5C:
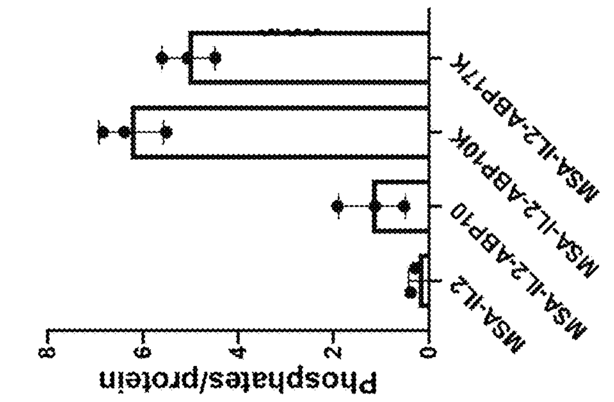
FIGS. 5A-5C provide bar graphs showing quantification of phosphate content using a malachite green assay for purified MSA-IL2 or MSA-IL2 variants fused to a C-terminal ABP expressed alone (No Fam20C) or co-expressed with wild-type Fam20C kinase (K).
Figure 5B:
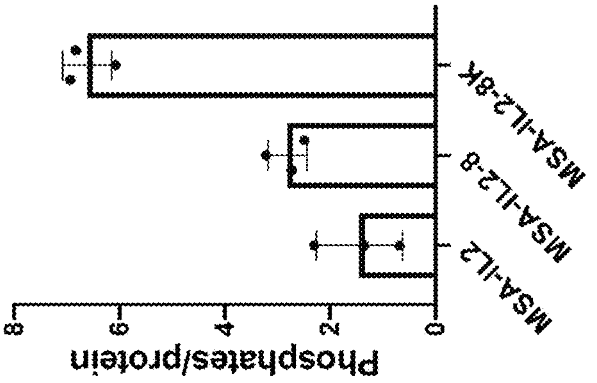
Figure 5A:
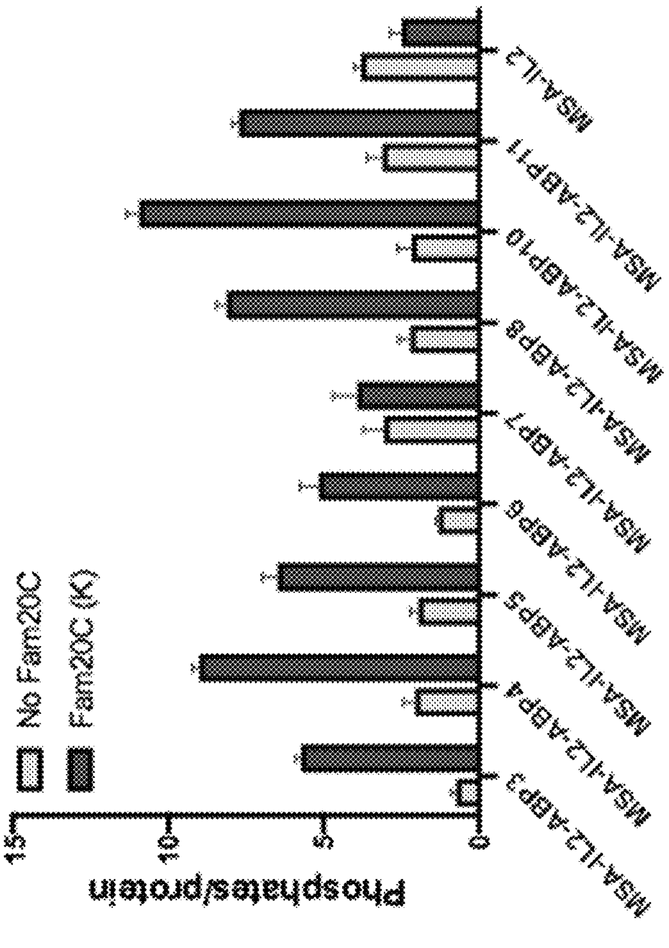

The extent of phosphorylation of proteins fused to certain ABPs identified in Table 5 was determined using a malachite green assay (Thermo Fisher). A malachite green assay can be used for a semi-quantitative measure of the phosphate content for each protein based on a standard curve derived with a known amount of a highly phosphorylated protein, Phosvitin. Quantification of phosphorylation was determined for MSA-IL2 proteins fused to different ABPs that were expressed either alone or in combination with a plasmid encoding Fam20C kinase. Some phosphorylation was detected for MSA-IL2 protein, but was the same if the protein was expressed alone or in combination with Fam20C kinase. For MSA-IL2 proteins linked to different C-terminal ABPs, the extent of phosphorylation was similar to that of MSA-IL2 when the proteins were expressed alone. However, phosphorylation was greatly increased when the proteins were co-expressed with Fam20C kinase as shown in FIGS. 5A-5C. In particular, MSA-IL2-ABP10, MSA-IL2-ABP8, and MSA-IL2-ABP17 expressed with WT Fam20C kinase demonstrated high and comparable levels of phosphorylation.

Figure 6A:
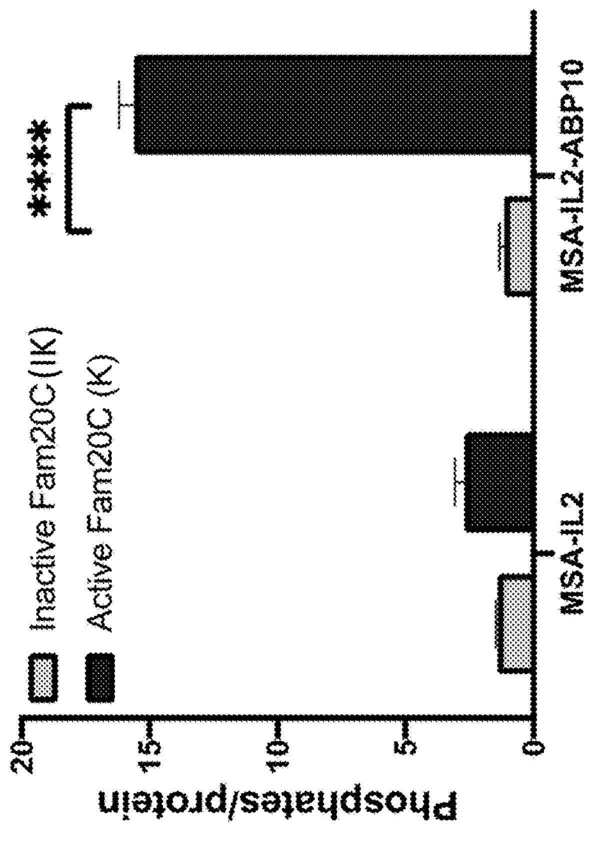
FIGS. 6A-6B provide bar graphs showing quantification of phosphate content using a malachite green assay for purified MSA-IL2 or MSA-IL2-ABP10 protein following co-expression with either wild-type Fam20C kinase (K) or inactive Fam20C kinase (IK). The figures represent data collected for proteins isolated from separate purification runs. ****$p<0.0001$.
Figure 6B:
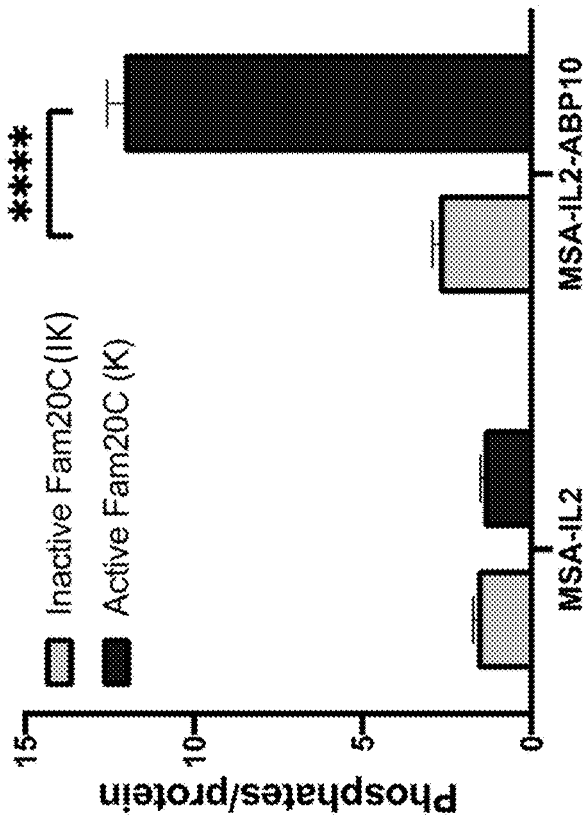

Notably, MSA-IL2 fused to ABP10 (MSA-IL2-ABP10) demonstrated the highest phosphorylation with an increase of phosphorylation of more than 6-fold when the protein was expressed with WT Fam20C kinase (MSA-IL2-APB10K) compared to when the protein was expressed with mutant Fam20C kinase (MSA-IL2-ABPIK). This result was consistent for proteins isolated from separate purification batches, as shown in FIGS. 6A-6B.

Figure 7:
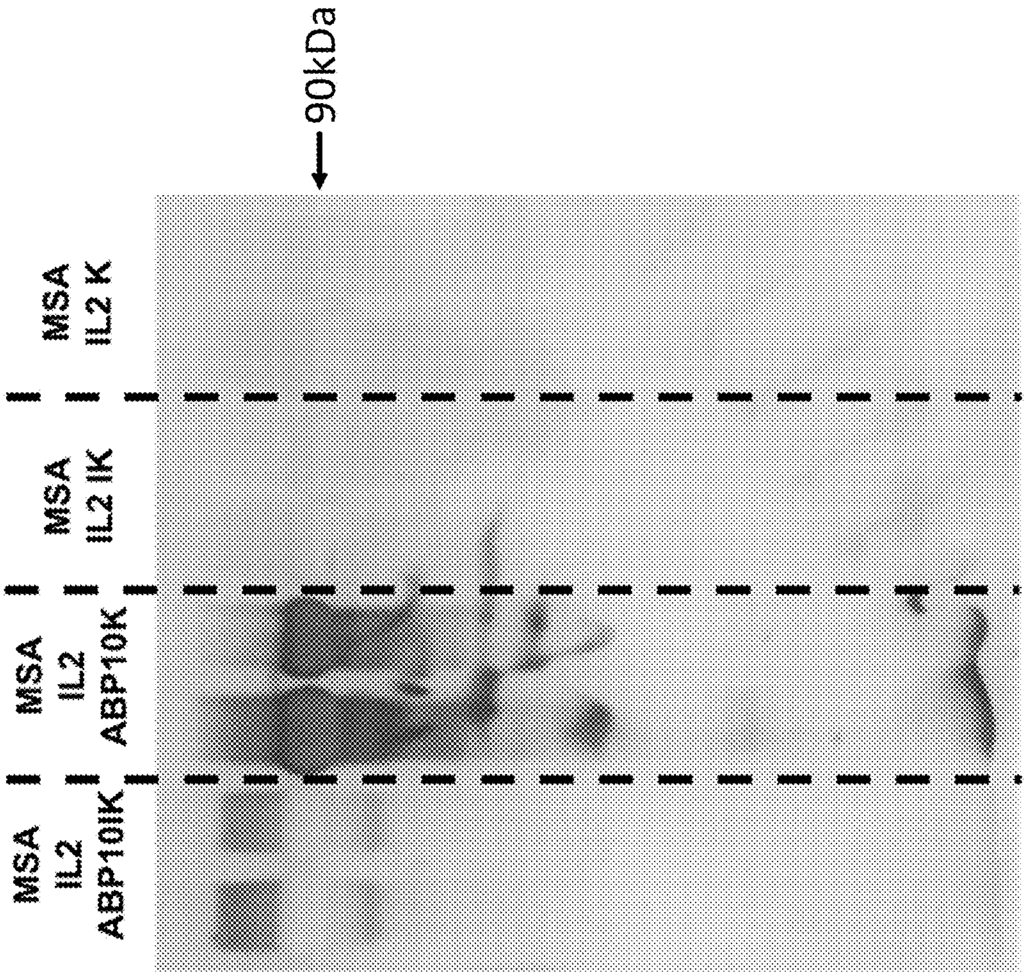
FIG. 7 provides an image of an immunoblot measuring serine phosphorylation of purified MSA-IL2 or MSA-IL2-ABP10 following co-expression with either wild-type Fam20C kinase (K) or inactive Fam20C kinase (IK).

The increased phosphorylation of MSA-IL2-ABP10K protein compared to MSA-IL2-ABP10IK, MSA-IL2-IK, or MSA-IL2-K was also confirmed using an anti-phosphoserine immunoblot. Samples of purified protein was separated on a NuPAGE gel and transferred onto a nitrocellulose membrane using the iBlot system (Thermo Fisher). The membrane was stained with a rabbit anti-phosphoserine antibody (Abeam, ab9332) and an anti-rabbit HRP antibody (Biolegend, 406401). The expected molecular weight of MSA-IL2 protein fusions is 90 kDa. At this molecular weight, only MSA-IL2-ABP10K was detected by the immunoblot, indicating strong phosphorylation of phosphoserine for MSA-IL2-ABP10K, but not for the other proteins tested (MSA-IL2-ABP10IK, MSA-IL2K, MSA-IL2IK) (FIG. 7).

Figure 8:
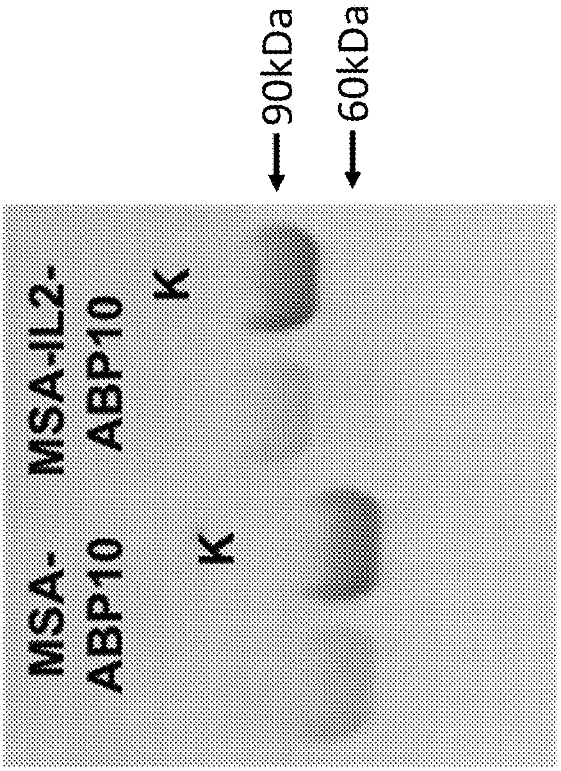
FIG. 8 provides an image of an immunoblot measuring serine phosphorylation of purified MSA-ABP10 (60 kDa) or MSA-IL2-ABP10 (90 kDa) following co-expression with wild-type Fam20C kinase (lane labeled “K”) as compared to expression without the kinase.

Phosphorylation of MSA fused to ABP10 (MSA-ABP10) was also evaluated by immunoblot as described above and compared to MSA-IL2-ABP10, with detection of the rabbit anti-phosphoserine antibody using an IRDye 680RD Donkey anti-rabbit IgG (LI-COR 926-68073). As shown in FIG. 8, a strong phosphorylation band was detected for MSA-ABP10 (MW 60 kDa) and MSA-IL2-ABP10 (90 kDa) only if the proteins were co-expressed with WT Fam20C kinase (denoted as "K" in FIG. 8), while a band was only weakly detected if the proteins were not co-expressed with the kinase.

Figure 9:
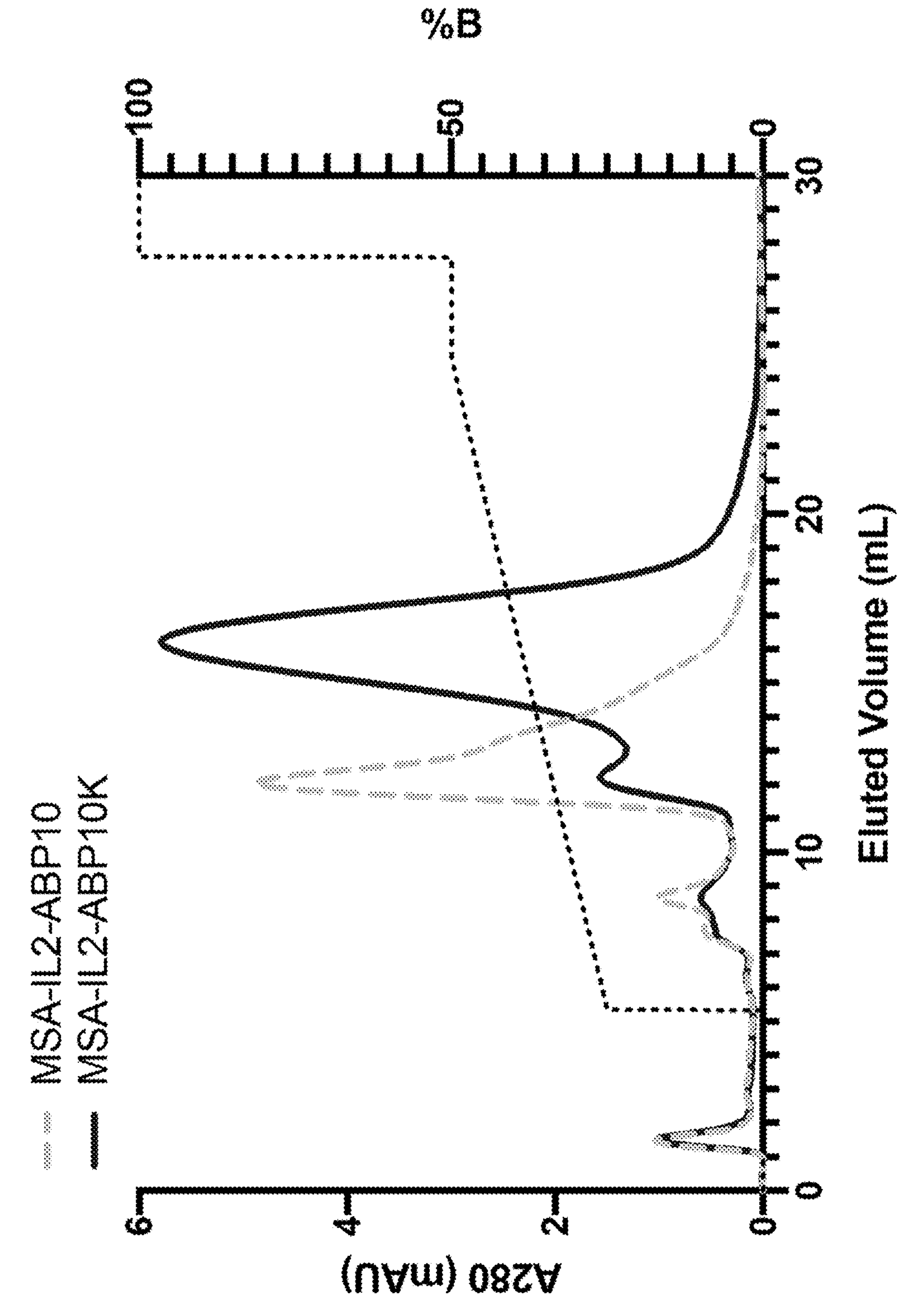
FIG. 9 provides a graph showing protein elution peaks measured by anionic exchange chromatography using FPLC for MSA-IL2-ABP10 co-expressed with Fam20C kinase (MSA-IL2-ABP10K) or expressed without the kinase (MSA-IL2-ABP10).

Phosphorylation was further measured using ion exchange chromatography (IEX). Specifically, samples of purified MSA-IL2-ABP10 expressed either in combination with wild-type Fam20C kinase (MSA-IL2-ABP10K) or without the kinase were analyzed by FPLC using a strong-anion exchange chromatography column (HiTrap Q HP column). The column was equilibrated with 20 mM Tris-HCl pH 8.5 buffer (Buffer A), and bound protein was eluted with increasing gradient of 20 mM Tris-HCL, 1M NaCl pH 8.5 buffer (Buffer B). Phosphorylated protein is expected to have longer column retention due to interaction between phosphate groups of the protein and cationic groups of the column Indeed, as shown in FIG. 9, MSA-IL2-ABP10K was found to elute in a later column fraction compared to MSA-IL2-ABP10, indicating a higher degree of phosphorylation.

Figure 10:
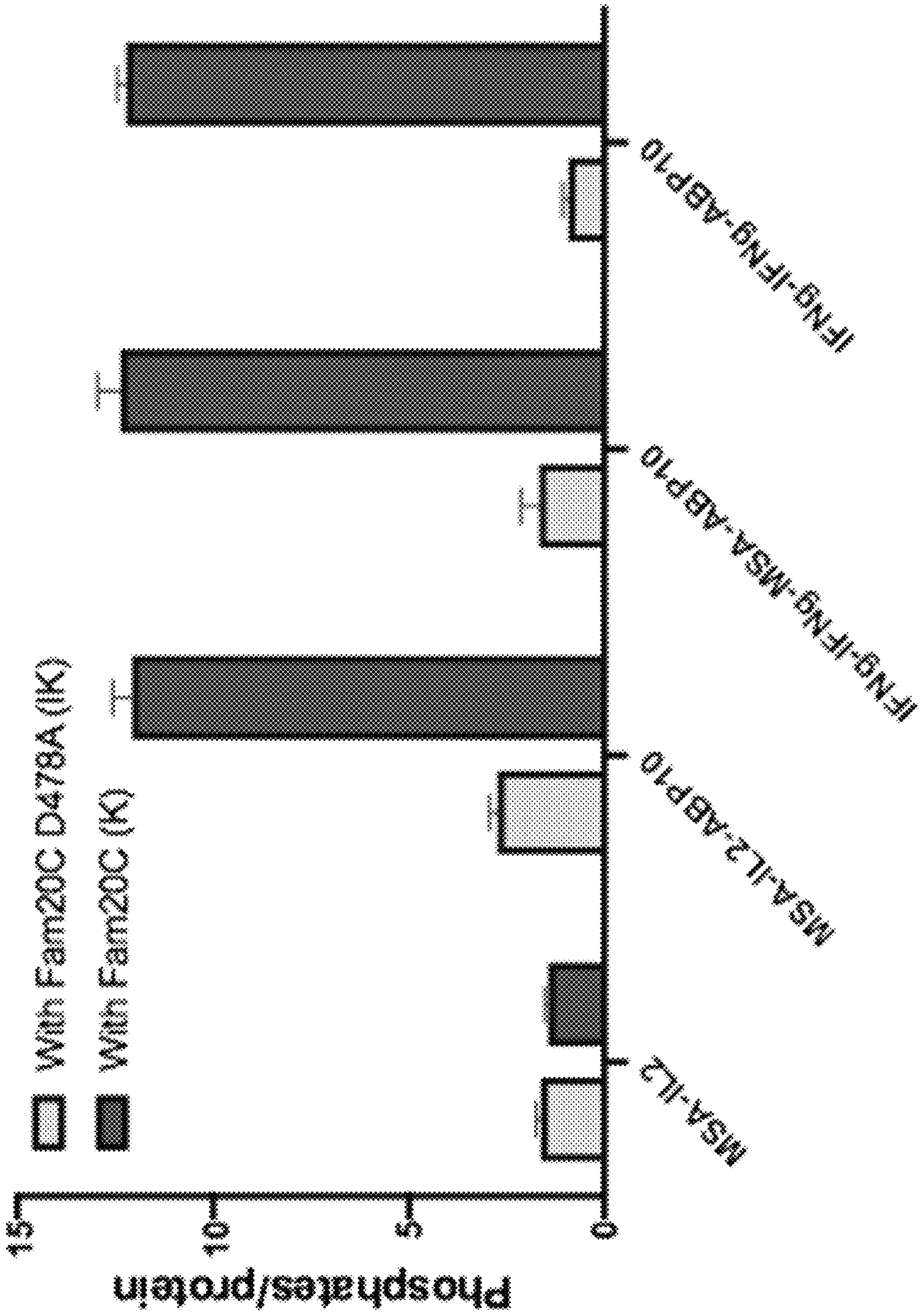
FIG. 10 provides a bar graph showing quantification of phosphate content measured by a malachite green assay for purified MSA-IL2 or IFNg-IFNg-MSA proteins alone or fused to a C-terminal ABP10 following co-expression with either wild-type Fam20C kinase (K) or inactive Fam20C kinase (IK).

Having identified MSA-IL2 fusions to ABP10 as having high phosphoserine content when co-expressed with Fam20C kinase, this strategy was evaluated for other proteins of interest. Namely, fusions of IFNg-IFNg-MSA or IFNg-IFNg to ABP10 (sequences identified in Table 6) were evaluated for phosphorylation by the malachite green assay as shown in FIG. 10. For each of the proteins fused to ABP10, the level of phosphorylation was significantly higher when the protein was co-expressed with WT Fam20C kinase (K) compared to the inactive Fam20C kinase (IK).

Figure 11A:
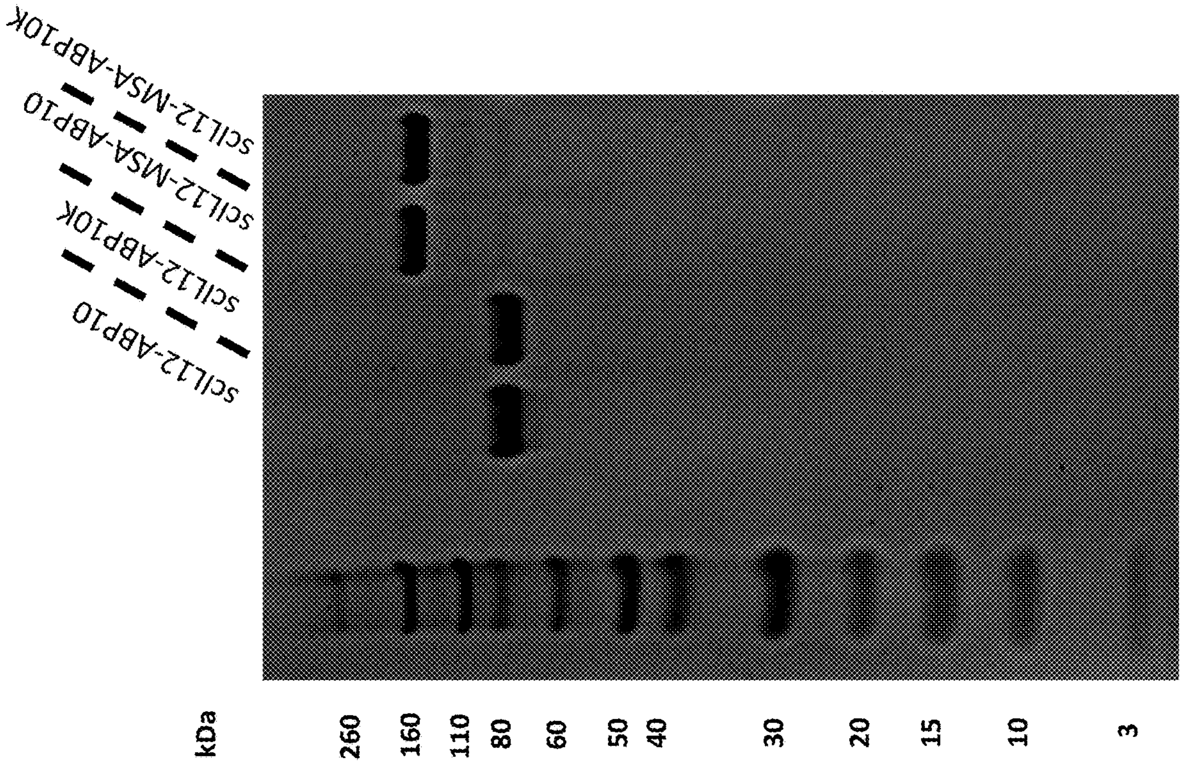
FIG. 11A provides an image of a denaturing SDS-PAGE gel showing molecular weight (MW) of purified scIL12-ABP10 or scIL12-MSA-ABP10 co-expressed with wild-type Fam20C kinase (K) or without the kinase.
Figure 11C:
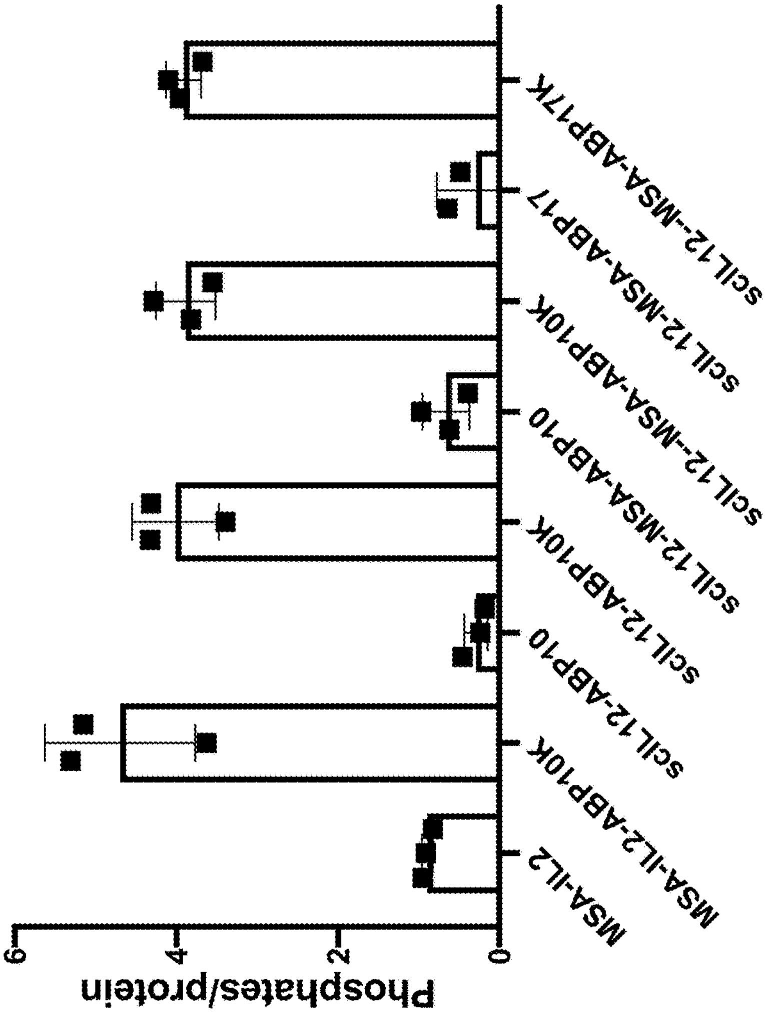
FIGS. 11B-11C provide bar graphs showing quantification of phosphate content measured by a malachite green assay for purified scIL12-ABP10 or scIL12-MSA-ABP10 co-expressed with wild-type Fam20C kinase (K) or without the kinase (FIG. 11B; **$p<0.0001$) or for purified scIL12-ABP10, scIL12-MSA-ABP10, scIL12-ABP17, and scIL12-MSA-ABP17 co-expressed with wild-type Fam20C kinase (K) or without the kinase (FIG. 11**C). Comparison is made to purified MSA-IL2 and MSA-IL2-ABP10K.
Figure 11B:
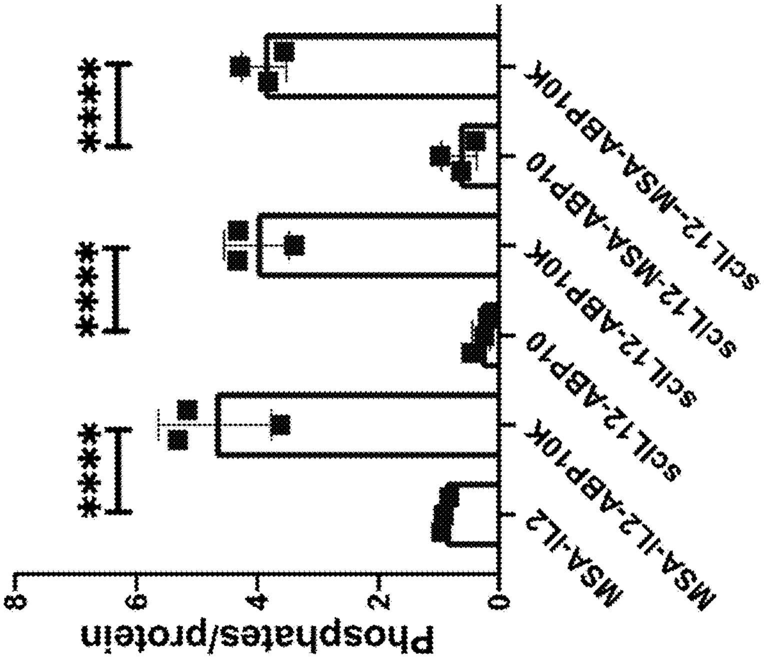

Additionally, the strategy was evaluated for IL12 fusion proteins. Specifically, fusions comprising single-chain IL12 linked to either ABP10 or ABP17 were evaluated. Murine IL-12 was expressed in a single chain format with a 15 amino acid Gly-Ser linker between the p40 and p35 subunits (scIL12). The scIL12 was either expressed as a fusion protein directly linked to ABP10 (scIL12-ABP10; SEQ ID NO: 172) or to ABP17 (scIL12-ABP17; SEQ ID NO: 174). Additionally, scIL12 was expressed as a fusion protein to MSA linked to either ABP10 (scIL12-MSA-ABP10; SEQ ID NO: 168) or to ABP17 (scIL12-MSA-ABP17; SEQ ID NO: 170). The fusion proteins scIL12-ABP10, scIL12-ABP17, scIL12-MSA-ABP10, and scIL12-MSA-ABP17 were co-expressed with wild-type Fam20C kinase or expressed without the kinase. The molecular weight of the purified proteins was determined as described above. The purified proteins were found to have the expected molecular weights as shown in FIG. 11A. Phosphorylation was measured via the malachite green assay described above. MSA-IL2 expressed without kinase and MSA-IL2-ABP10 expressed with wild-type Fam20C kinase (MSA-IL2-ABP10K) were used for comparison. As shown in FIGS. 11B-11C, co-expression with Fam20C kinase resulted in a substantial increase in the number of phosphate groups per protein for each of the fusion proteins evaluated, with scIL12-ABP10K, scIL12-MSA-ABP10K, and scIL12-MSA-ABP17K each having similar levels of phosphorylation to MSA-IL2-ABP10K. Thus, the strategy of using an ABP fusion with co-expression of Fam20C kinase can be generalized broadly to other proteins of interest to achieve high levels of phosphorylation.

Figure 12:
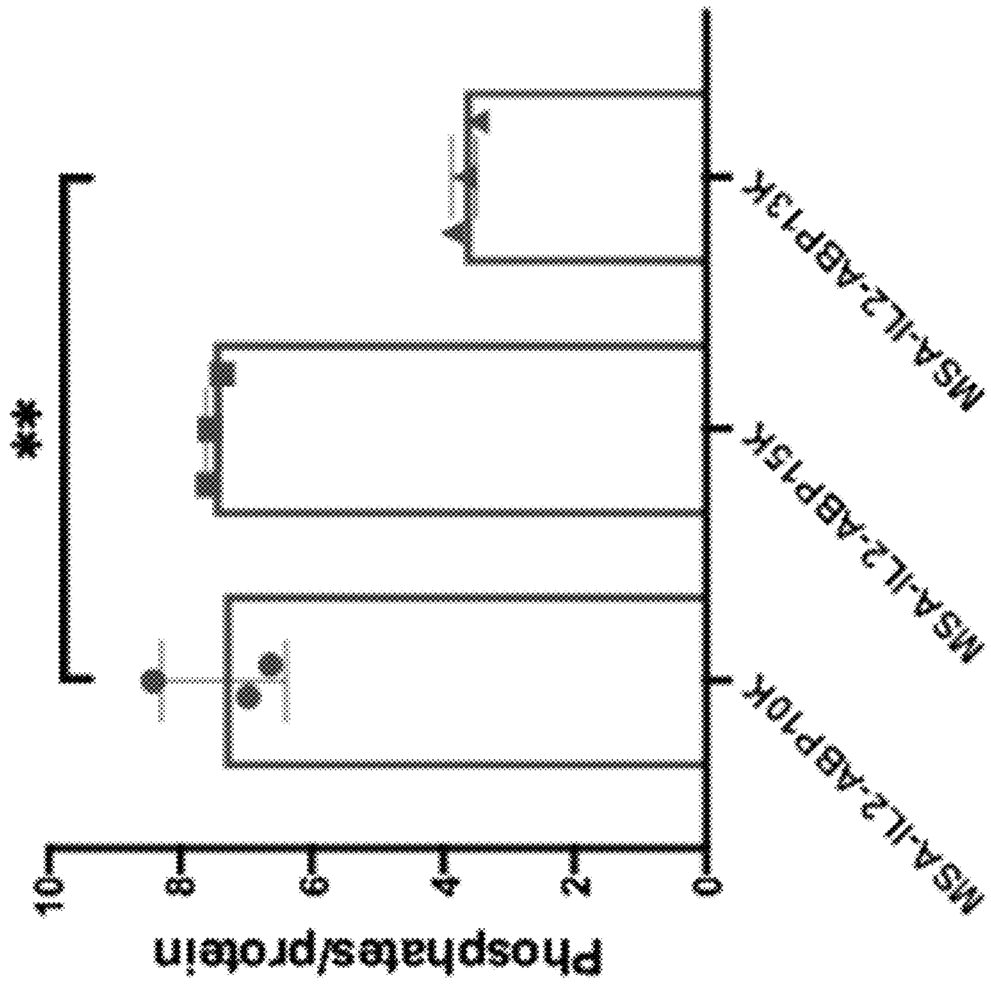
FIG. 12 provides a bar graph showing quantification of phosphate content measured by a malachite green assay for purified MSA-IL2 variants following co-expression with Fam20C kinase (K). The MSA-IL2 variants were fused to a C-terminal ABP with functional phosphorylation motifs (ABP10), a C-terminal ABP10 wherein the motifs were altered to prevent Fam20C phosphorylation (ABP13), or a C-terminal ABP10 comprising trypsin cleavage sites (ABP15). ** $p<0.01$.

Also evaluated were the serine residues of ABP10 that are phosphorylated when a fusion protein of ABP10 is co-expressed with WT Fam20C kinase. To do so, the four S-E-E motifs that are expected to be phosphorylated by WT Fam20C kinase were altered by substitution of serine with alanine (S→A), yielding the peptide ABP13 (SEQ ID NO: 109). MSA-IL2 fusions to ABP10 and ABP13 were evaluated for phosphorylation by a malachite green assay following co-expression with WT Fam20C kinase. As shown in FIG. 12, the substitution of serine residues resulted in a substantial decrease in phosphorylation. Additionally, a variant of ABP10 was prepared with tryptic cut sites to facilitate fragmentation for analysis by mass spectrometry (e.g., ABP15, SEQ ID NO: 113). MSA-IL2 fused to ABP15 yielded similar level of phosphorylation to ABP10 (FIG. 12). Subsequent digestion of MSA-IL2-ABP15-K and MSA-IL2-ABP15-IK proteins, followed by phosphopeptide enrichment using the high-select Fe-NTA phosphopeptide enrichment kit (Thermo Fisher) and analysis by HPLC-MS/MS revealed high phosphorylation activity on serines of the C-terminal ABP15 when co-expressed with WT Fam20C kinase (data not shown). Together, these data indicate phosphorylation by WT Fam20C kinase occurs at the S-E-E motifs of the ABP.

Example 3: Recombinantly Expressed Alum Binding Proteins Adsorb to Alum in Serum Proteins adsorbed to alum can be eluted off fairly quickly in the presence of serum or interstitial fluid (Weissburg, et al *Pharmaceutical research* 12.10 (1995): 14394446). However, proteins with greater phosphorylation tend to be retained on alum for much longer in serum conditions (Morefield, et al. *Vaccine* 23.12 (2005): 1502-1506) by relying on ligand exchange for adsorption. The retention of proteins engineered with an ABP when adsorbed to alum was evaluated in the presence of 10% serum. The release of protein was assessed in phosphate-free tris-buffered saline (TBS), which is not known to impact adsorption of proteins on alum (HogenEsch, et al, *npj Vaccines* 3:51 (2018)). As a comparison, release was also assessed in phosphate buffered saline (PBS), which is known to interfere with the adsorption of any protein to alum that relies solely on electrostatic interactions for adherence (Sully, et al. *Journal of pharmaceutical sciences* 105:1829-1836 (2016)). Thus, assessment of release in phosphate-free buffer or PBS was used to interrogate whether protein adsorption to alum was reliant on relatively weak electrostatic interactions or on stronger ligand exchange interactions.

For assessment of release, proteins were first labeled with an Alexa Fluor 647 succinymidyl (NHS) ester (Thermo Fisher, labeled with a molar ratio of 10:1 dye:protein) and purified by centrifugal filtration, yielding similar levels of labeling for all proteins. The proteins were mixed with alum (with mass ratio of 10:1 alum:protein unless otherwise stated; Alhydrogel, Invivogen) in TBS and rotated at room temperature for 30 minutes to allow for initial binding. The samples were then centrifuged at 10,000×g for 5 minutes to pellet alum and adsorbed protein, the supernatant containing unbound protein was collected, and the pelleted alum was resuspended in mouse serum (MS) or fetal bovine serum (FBS) at a final concentration of 10% (v/v) in either TBS or PBS. The suspension was then rotated at 37° C. At certain time points, the sample was centrifuged at 10,000×g for 5 minutes to pellet the alum and adsorbed protein, and supernatant containing unbound protein was collected. The alum pellet was re-suspended in fresh release buffer (10% serum in the respective buffer (TBS or PBS)). This was repeated for as many time points as required. For fluorescently-labeled protein, the quantity of unbound protein was determined by measuring the fluorescence of supernatant obtained from a sample of alum:protein and normalizing to the fluorescence of a sample of labelled protein prepared at the same initial protein concentration but without alum. For unlabeled protein, the primary readout was the concentration of the protein of interest determined using an ELISA-based measurement.

Figure 13B:
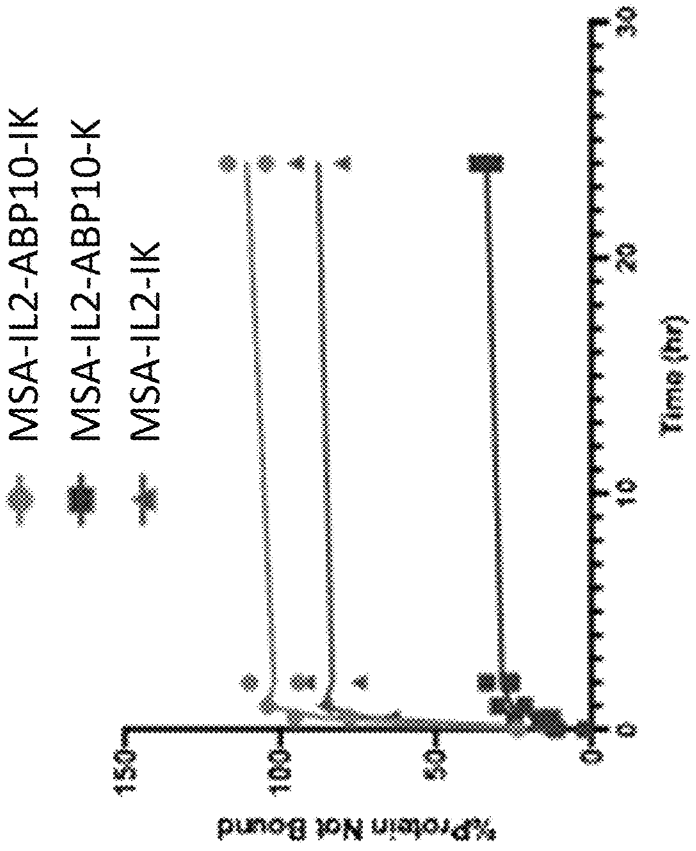
FIGS. 13A-13B provide line graphs showing quantification of unbound protein in the supernatant of a mixture of alum and protein measured by fluorescence spectroscopy over time. Adsorption to alum was measured for fluorescently-labeled MSA-IL2 or MSA-IL2-ABP10 that had been co-expressed with wild-type Fam20C kinase (K) or inactive Fam20C kinase (IK). Presence of unbound protein in the supernatant was measured for a protein:alum mixture following incubation with 10% mouse serum (MS) in phosphate-free buffer (FIG. 13A) or 10% MS in phosphate buffered saline (PBS) (FIG. 13B).
Figure 13A:
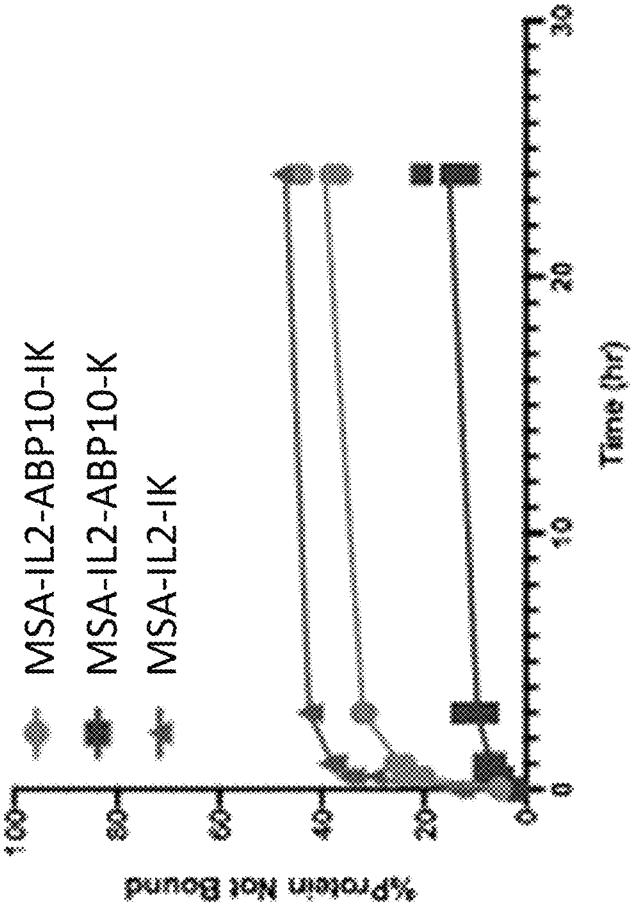

Using labeled protein and fluorescence quantification, the kinetics of release from alum of labeled MSA-IL2 or MSA-IL2-ABP10 that had been co-expressed with WT Fam20C kinase (K) or mutant Fam20C kinase (IK) was assessed. The proteins with low phosphate content (MSA-IL2-IK and MSA-IL2-ABP10-IK) were found to adsorb to alum, even with exposure to serum (FIG. 13A). However, if the release buffer was changed to PBS which is expected to disrupt electrostatic interactions, these proteins did not remain adsorbed to alum (FIG. 13B). In contrast, highly phosphorylated MSA-IL2-ABP10K was found to adsorb strongly to alum either in the presence of 10% MS in phosphate-free TBS (FIG. 13A) or in the presence of 10% MS in PBS (FIG. 13B). Thus, while proteins with low phosphate content (MSA-IL2-IK or MSA-IL2-APB10IK) rely on electrostatic attraction or weak, monomeric ligand exchange for adsorption, proteins with high phosphate content (MSA-IL2-ABP10K) adsorb by a much more robust multimeric ligand exchange mechanism.

Figure 14A:
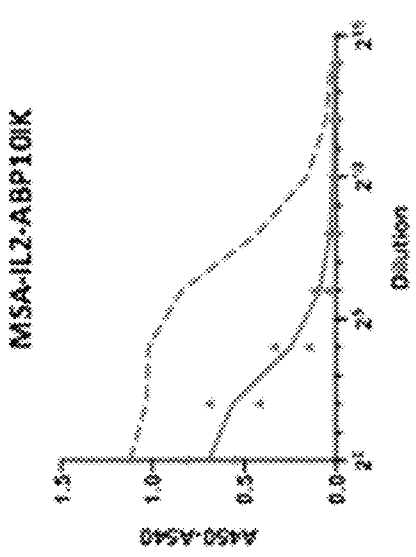
FIGS. 14A-14F provide line graphs showing quantification of unbound protein by sandwich ELISA in the supernatant of samples comprising a mixture of alum and protein (solid lines) or protein alone (dashed lines). Adsorption to alum was measured for the proteins indicated in FIGS. 13A-13B and incubated with 10% FBS in phosphate-free buffer (FIGS. 14A-C) or 10% FBS in PBS (FIG. 14D-F).
Figure 14B:
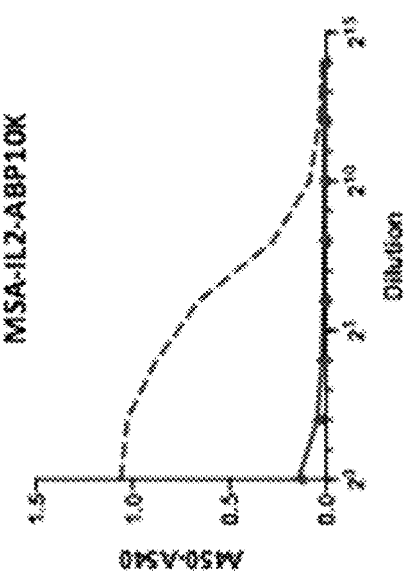
Figure 14C:
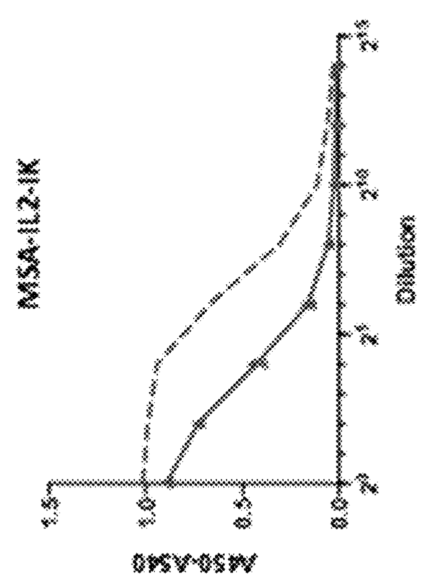
Figure 14D:
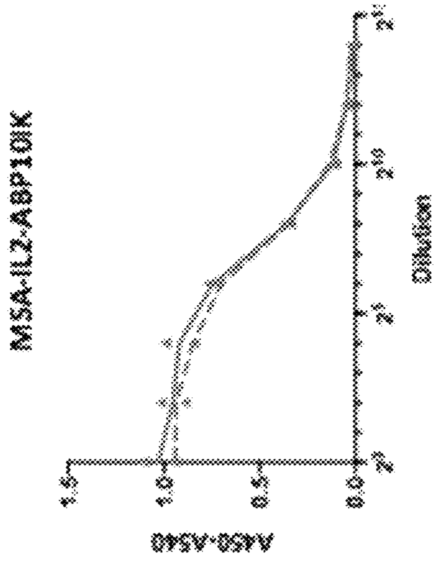
Figure 14E:
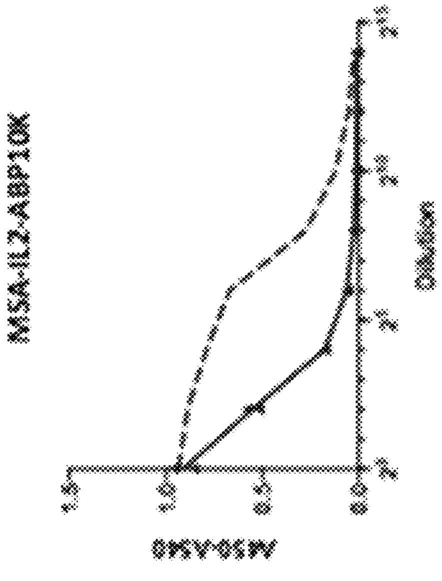
Figure 14F:
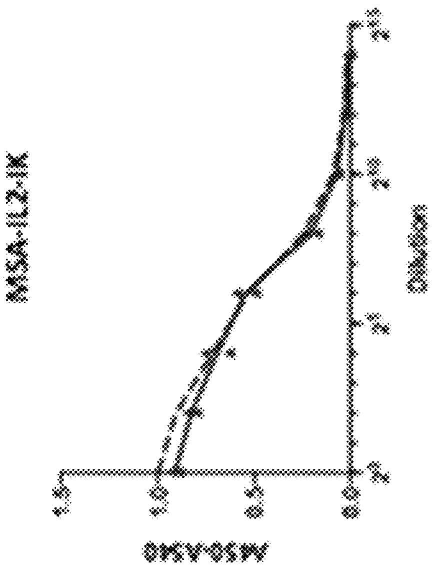

The release from alum was further evaluated for unlabeled proteins using an ELISA-based method for quantification of unbound protein. Protein and alum were mixed at room temperature for 30 minutes in TBS, followed by centrifugation and removal of supernatant, and resuspension in FBS at a final concentration of 10% (v/v) in either TBS or PBS as described above. Following incubation at 37° C. for 24 hours, alum and bound protein were sedimented by centrifugation and supernatant containing unbound protein was collected. Protein in the supernatant was quantified using a sandwich ELISA with an anti-MSA antibody (Abcam, ab19194) as the capture antibody and an anti-His HRP antibody (Biolegend, 652504) as the detection antibody. As shown in FIGS. 14A-14F, the quantity of protein in supernatant taken from the alum:protein mixture (solid lines) was compared to a sample of protein that was prepared at the same initial concentration but containing no alum (dashed lines). The release assay was performed in the presence of 10% FBS in phosphate-free buffer (FIGS. 14A-14C) or PBS (FIGS. 14D-14F). As shown in FIGS. 14A-14C, for highly phosphorylated MSA-IL2-ABP10K, less protein was measured in the supernatant compared to MSA-IL2-ABP10IK or MSA-IL2-IK that have low phosphate content, indicating stronger adsorption to alum. Moreover, adsorption to alum was eliminated for poorly phosphorylated MSA-IL2-ABP10IK or MSA-IL2-IK when the assay was performed in PBS, while MSA-IL2-ABP10K remained highly adsorbed (FIGS. 14D-14F).

Figure 15:
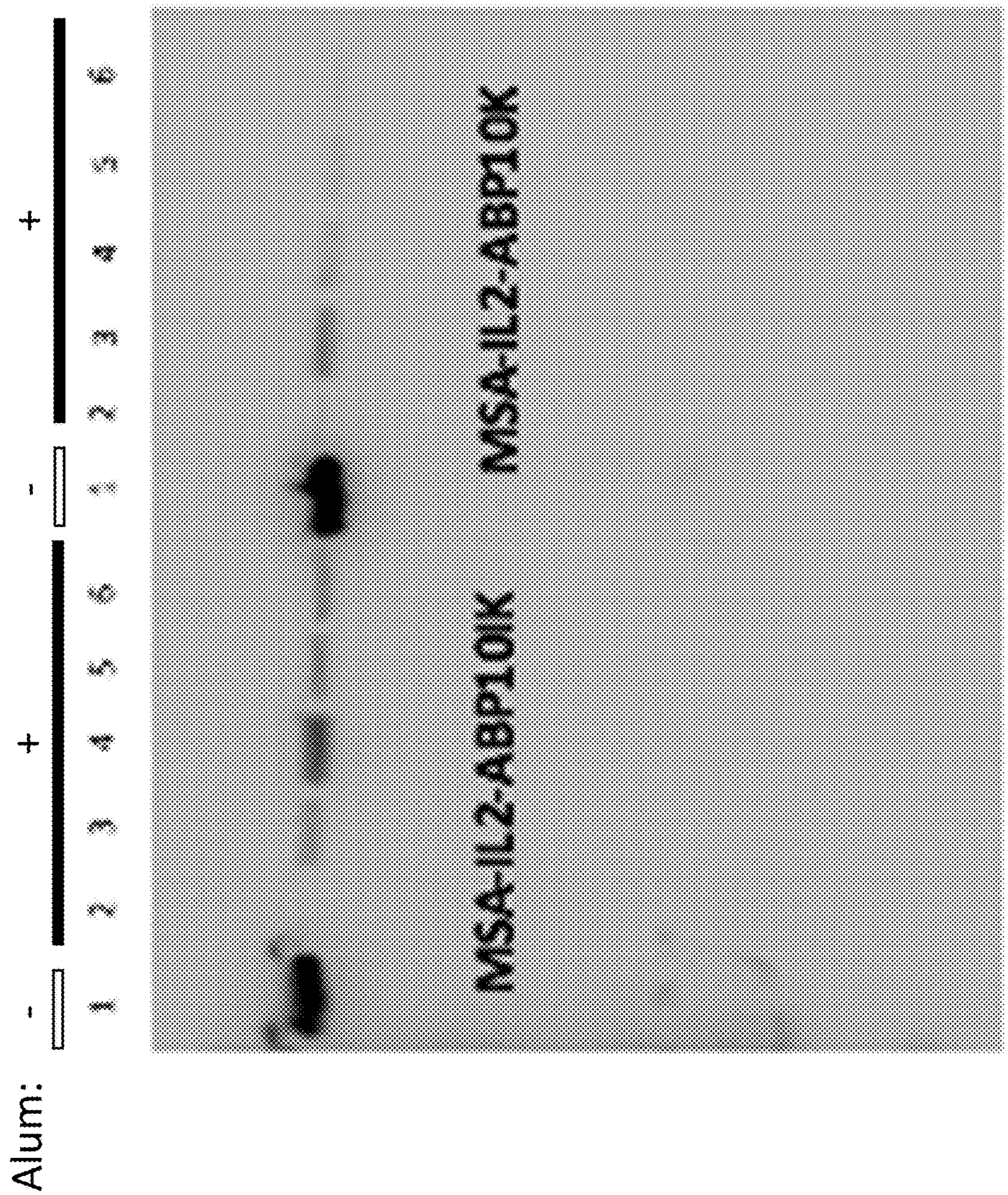
FIG. 15 provides an image of an immunoblot used to measure unbound protein in samples of protein alone (column 1) or in the supernatant of protein mixed with alum (columns 2-6). Adsorption to alum was measured for MSA-IL2-ABP10 co-expressed with wild-type Fam20C kinase (K) or inactive Fam20C kinase (IK). Presence of unbound protein in the supernatant was measured prior to the addition of mouse serum (column 2) or at specific time intervals following addition of mouse serum (column 3–6=0, 1, 2, or 24 h).

Release from alum of MSA-IL2-ABP10IK and MSA-IL2-ABP10K was also assessed by immunoblot. Release was performed using the assays described above. Supernatants were collected from a mixture of protein and alum following incubation at 37° C. in 10% MS in TBS. The supernatant was run by SDS-PAGE and transferred to a nitrocellulose membrane. Protein was quantified using an anti-His HRP antibody (Biolegend, 652504) that binds the His-tag of the recombinant fusion proteins. Also measured for comparison was protein prepared at the same initial concentration but containing no alum. As shown in FIG. 15, column 1 refers to supernatant collected from samples receiving no alum, while columns 2-6 are supernatants collected from samples combining protein and alum. Column 2 refers to supernatant collected prior to the addition of 10% mouse serum. Columns 3-6 refer to supernatant collected after the addition of 10% mouse serum, at 0 h, 1 h, 2 h, and 24 h respectively. Release of protein into the supernatant was only observed for mixtures of protein and alum following addition of mouse serum. However, the release of MSA-IL2-ABP10IK was much higher than for MSA-IL2-ABP10K, indicating stronger adsorption of the highly phosphorylated protein variant to alum.

Figure 16:
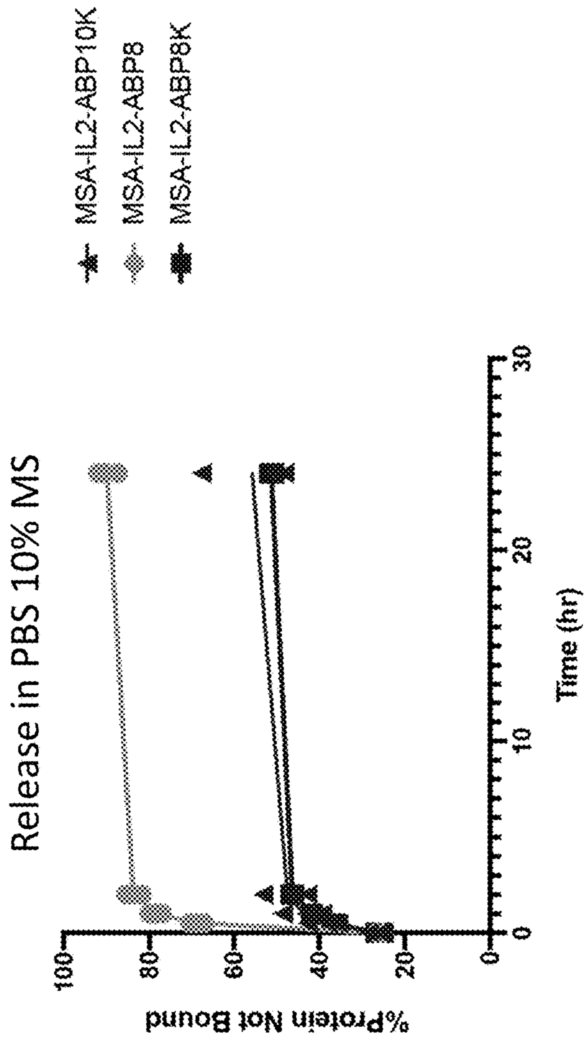
FIG. 16 provides a line graph showing quantification of unbound protein in the supernatant of a mixture of alum and protein measured by fluorescence spectroscopy over time following exposure to 10% MS in PBS. Adsorption to alum was measured for fluorescently-labeled fusion proteins, including MSA-IL2-ABP10 co-expressed with wild-type Fam20C kinase (MSA-IL2-ABP10K) and MSA-IL2-ABP8 either co-expressed with wild-type Fam20C kinase (MSA-IL2-ABP8K) or expressed alone.

The release properties of MSA-IL2 linked to phosphorylated ABP8 was investigated. Specifically, MSA-IL2 fused to a C-terminal ABP8 was expressed alone (MSA-IL2-ABP8) or co-expressed with WT Fam20C kinase (MSA-IL2-ABP8K) to generate a phosphorylated ABP. Alum binding was evaluated using the fluorescence-based assay described above, wherein the fusion proteins were fluorescently-labeled, pre-mixed with alum in serum-free/phosphate-free TBS (alum:protein ratio of 10:1) for 30 minutes at room temperature, then buffer-exchanged into 10% MS in PBS. Release of unbound fusion protein into supernatant was evaluated at distinct time points as described above. Comparison was made to release of MSA-IL2-ABP10K from alum. As shown in FIG. 16, while release of MSA-IL2-ABP8 was rapid following exposure to serum, both MSA-IL2-ABP8K and MSA-IL2-ABP10K demonstrated strong adsorption to alum.

Furthermore, the release properties of MSA-IL2 linked to phosphorylated ABP17 was evaluated under increasing levels of serum exposure. Briefly, alum binding for MSA-IL2-ABP17 expressed with WT Fam20C kinase (MSA-IL2-

Figure 17:
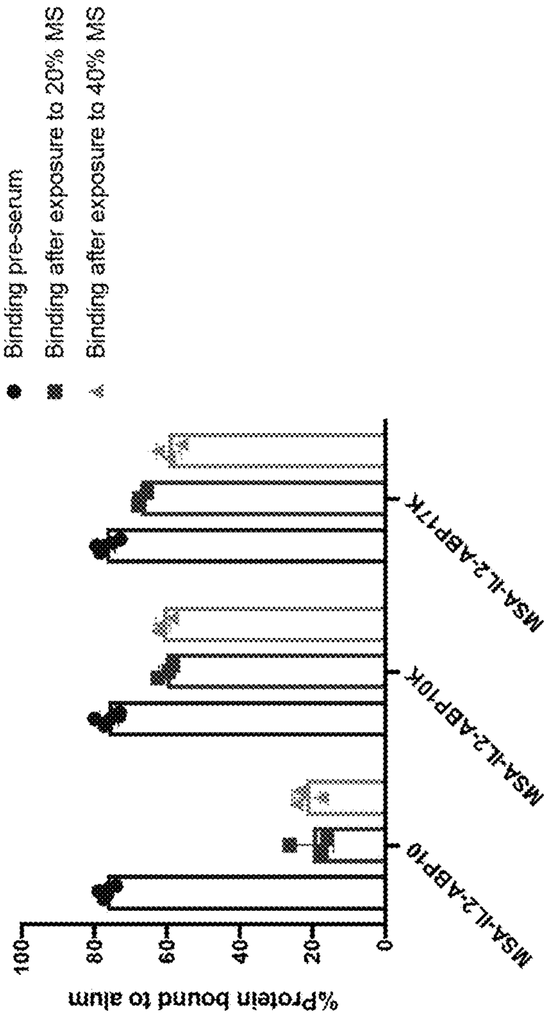
FIG. 17 provides a line graph showing quantification of alum-bound protein of a mixture of alum and protein measured by fluorescence spectroscopy either before or after 17 hours exposure to 20% MS or 40% MS in PBS. Adsorption to alum was measured for fluorescently-labeled MSA-IL2-ABP10 expressed alone or co-expressed with wild-type Fam20C kinase (MSA-IL2-ABP10K) and MSA-IL2-ABP17 co-expressed with wild-type Fam20C kinase (MSA-IL2-ABP17K).

ABP17K) was compared to MSA-IL2-ABP10 and MSA-IL2-ABP10K, using the fluorescent-based alum binding assay described above. Fluorescent proteins were pre-mixed with alum in TBS for 30 minutes at room temperature, then alum and adsorbed protein was exchanged into either 20% MS in PBS or 40% MS in PBS. At 17 hours following serum exposure, the quantity of unbound fusion protein present in supernatant was quantified by fluorescence measurement as described above and compared to the quantity of unbound protein in supernatant prior to serum exposure. As shown in FIG. 17, while the quantity of alum-bound protein decreased dramatically following serum exposure for MSA-IL2-ABP10, the majority of MSA-IL2-ABP10K or MSA-IL2-ABP17K remained bound to alum following serum exposure, even under high serum conditions.

Figure 18A:
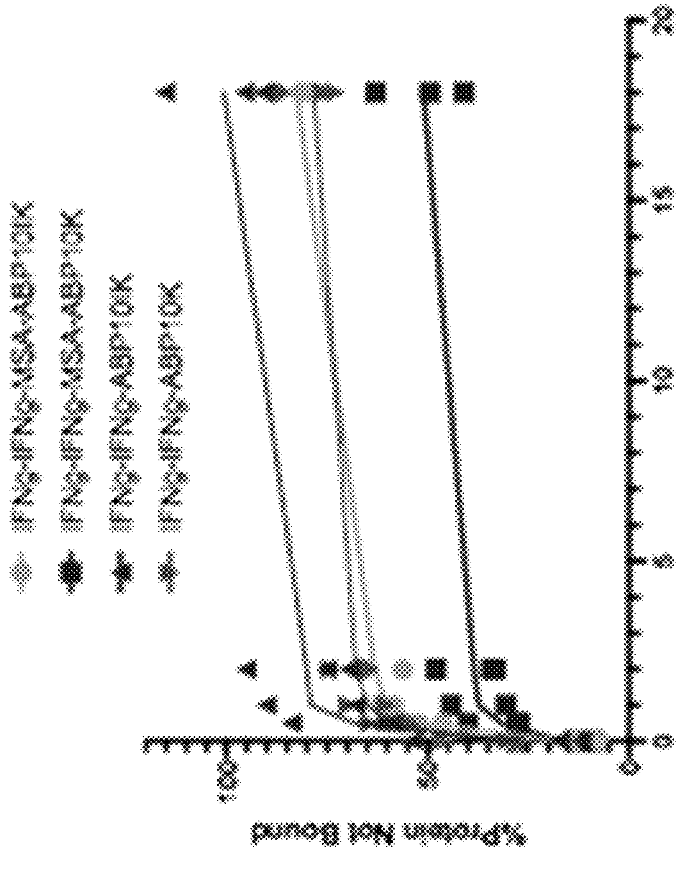
FIGS. 18A-18B provide line graphs showing quantification of unbound protein in the supernatant of a mixture of alum and protein measured by fluorescence spectroscopy over time. Adsorption to alum was measured for fluorescently-labeled IFNg-IFNg-ABP10 or IFNg-IFNg-MSA-ABP10 following co-expression with Fam20C kinase (K) or inactive Fam20C kinase (IK). Presence of unbound protein in the supernatant was measured for a protein:alum mixture incubated in 10% MS in phosphate-free TBS (FIG. 18A) or 10% MS in PBS (FIG. 18B).
Figure 18B:
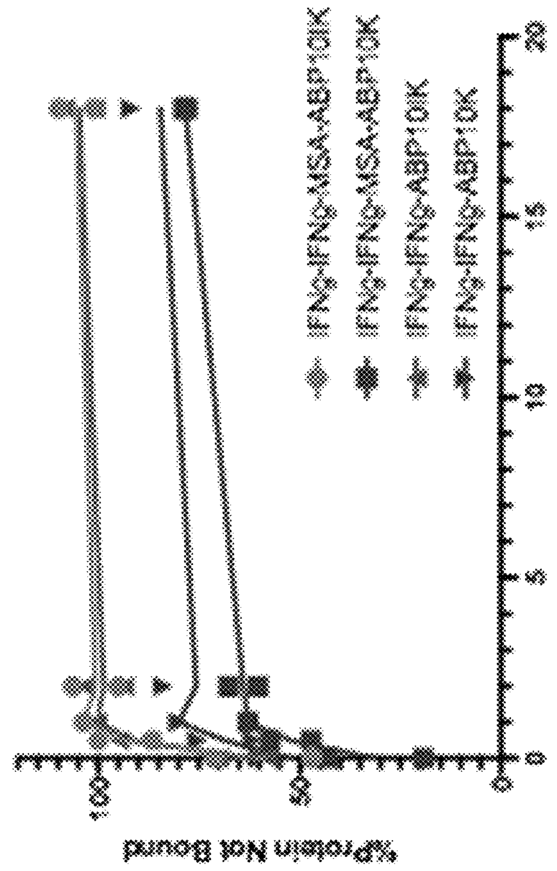

The release properties of other proteins of interest linked to an ABP and co-expressed with Fam20C kinase was evaluated. IFNg-IFNg-MSA and IFNg-IFNg were fused to a C-terminal ABP10 and co-expressed with either WT Fam20C kinase or mutant Fam20C kinase. Release was performed according to the assays described above. First, release was measured for labeled protein using a fluorescence-based assay, and measured in either phosphate-free buffer (FIG. 18A) or PBS (FIG. 18B) with 10% MS (v/v). The outcome was similar to that observed for MSA-IL2 fusions, wherein poorly phosphorylated protein (i.e., protein co-expressed with inactive Fam20C kinase) showed some adsorption to alum in phosphate-free buffer that was eliminated when the release was measured in PBS. However, highly phosphorylated protein (e.g., co-expressed with WT Fam20C kinase) retained adsorption to alum even in PBS (FIG. 18B).

Figure 19A:
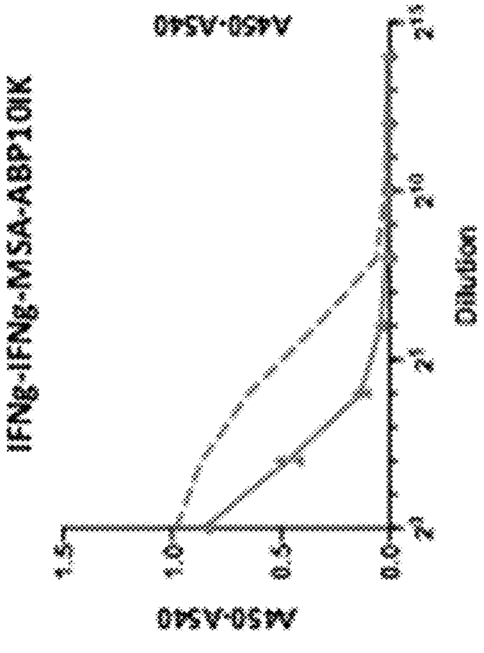
FIGS. 19A-19D provide line graphs showing quantification of unbound protein by sandwich ELISA in the supernatant of samples comprising a mixture of alum and protein (solid lines) or protein alone (dashed lines). Adsorption to alum was measured for the proteins indicated in FIGS. 18A-18B and incubated in 10% MS in phosphate-free TBS (FIGS. 19A-B) or 10% MS in PBS (FIG. 19C-D).
Figure 19B:
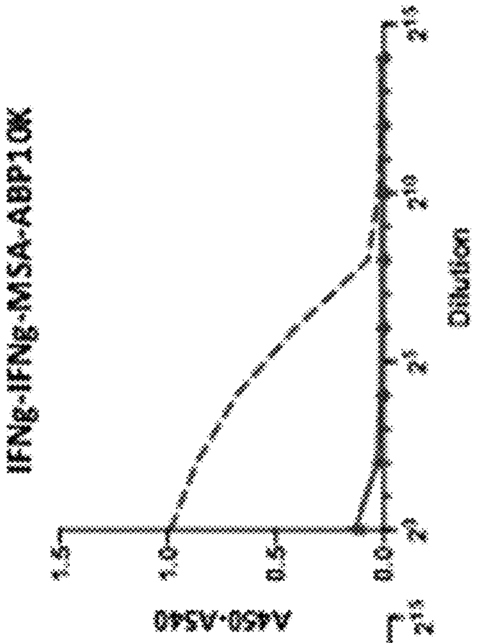
Figure 19C:
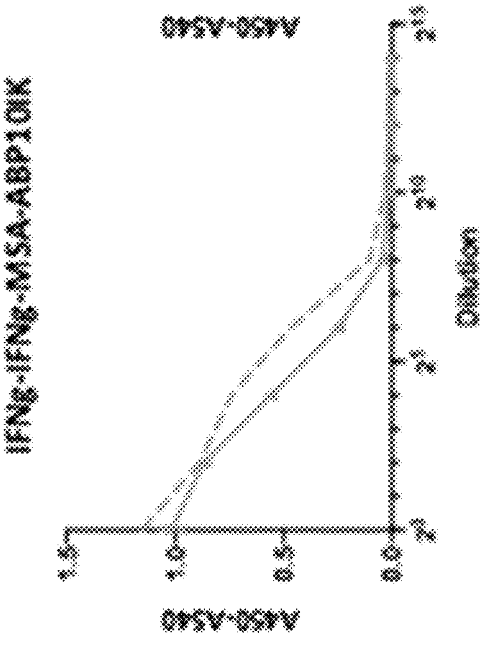
Figure 19D:
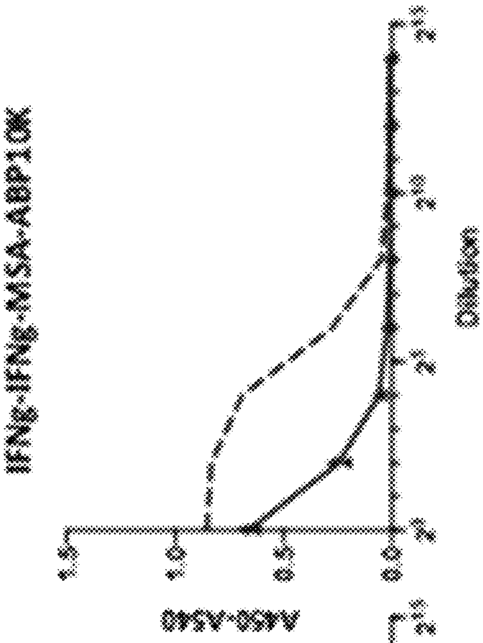

The same trend was observed when release from alum was measured for unlabeled protein using an ELISA-based assay. As shown in FIGS. 19A-19D, quantification of supernatant was compared for IFN-IFNg-MSA-ABP10K or IFNg-IFNg-MSA-ABP10IK mixed with alum (solid lines) or for protein at the same concentration with no alum (dashed lines). The release assay was performed in the presence of 10% FBS in phosphate-free buffer (FIGS. 19A-19B) or PBS (FIGS. 19C-19D) and supernatant was collected at 24 hours following addition of serum. As shown in FIGS. 19A-19B, for highly phosphorylated IFN-IFNg-MSA-ABP10K, stronger adsorption to alum was observed compared to IFN-IFNg-MSA-ABP10IK. Moreover, IFN-IFNg-MSA-ABP10IK did not adsorb to alum in PBS, while IFN-IFNg-MSA-ABP10K remained highly adsorbed (FIGS. 19C-19D).

Figure 20A:
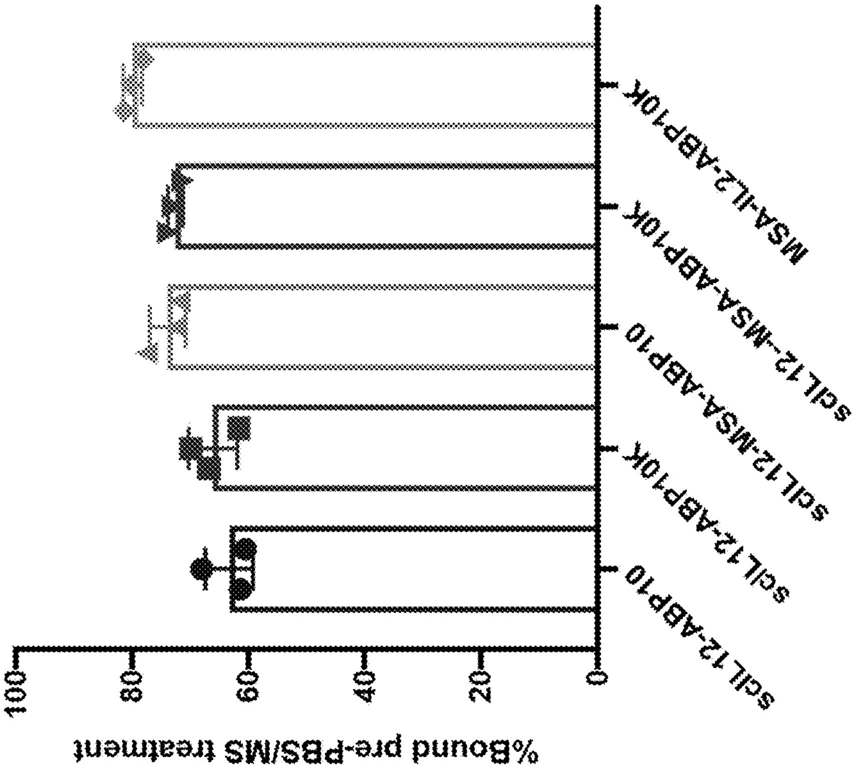
FIGS. 20A-20B provide bar graphs showing the percentage of protein bound to alum as measured by fluorescence spectroscopy either prior to treatment with serum (FIG. 20A) or following a 17 hour incubation in PBS containing 10% MS (FIG. 20B). Adsorption to alum was measured for purified fusion proteins scIL12-MSA-ABP10, scIL12-ABP10, and MSA-IL2-ABP10 that were expressed alone or co-expressed with wild-type Fam20C kinase (K).
Figure 20B:
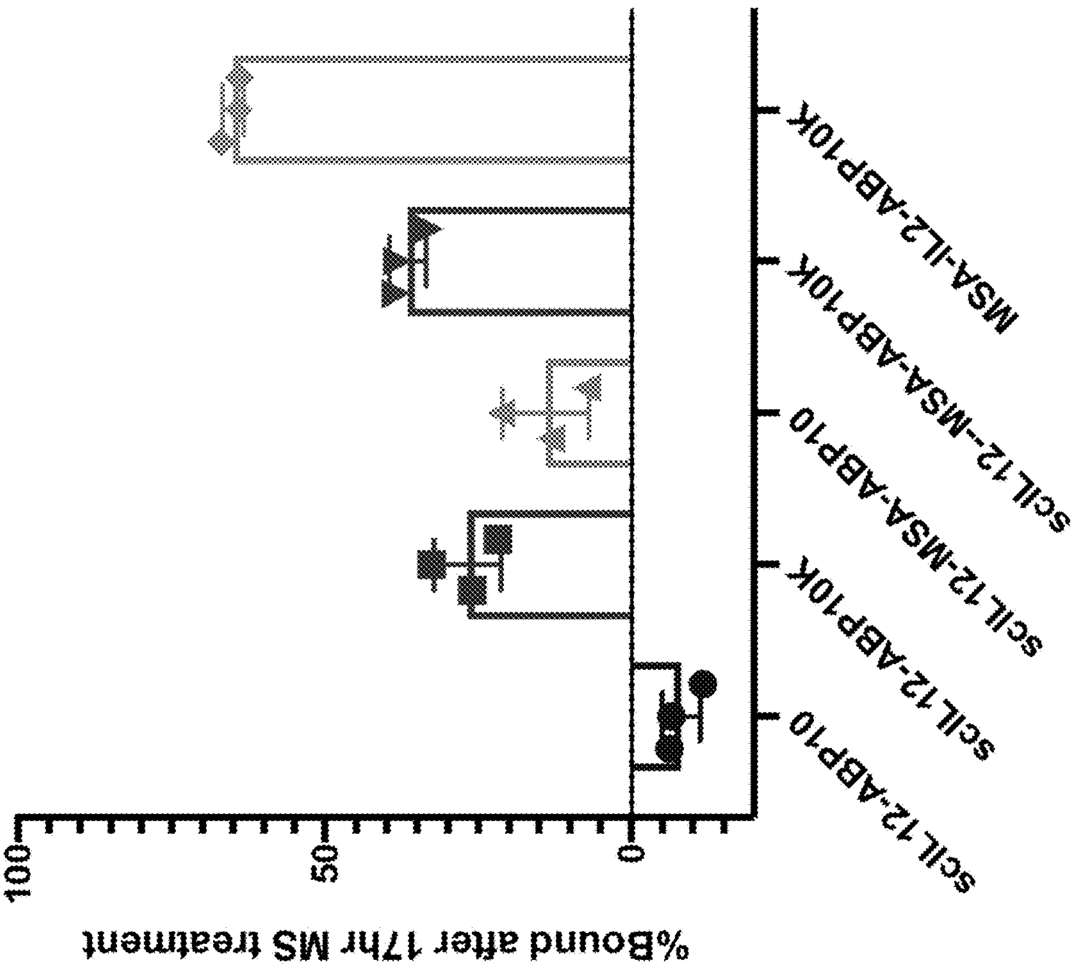

Release properties of IL12 fusions from alum was also evaluated using the fluorescence-based alum release assay described above. Specifically, release was measured for purified scIL12-ABP10 and scIL12-MSA-ABP10 fusion proteins expressed alone or co-expressed with wild-type Fam20C kinase. Comparison was made to release of MSA-IL2-ABP10K from alum. The fusion proteins were fluorescently labeled, pre-mixed with alum in TBS at room temperature for 30 minutes. Following centrifugation and removal of supernatant, alum and bound fusion protein was re-suspended in 10% MS in PBS, then incubated at 37° C. with rotation for 17 hours. Supernatant was collected, and unbound protein was determined by fluorescence readout. As shown in FIG. 20A, prior to addition of serum, adsorption to alum was comparable for each fusion protein tested. However, following the incubation in serum, substantially stronger adsorption was observed for fusion proteins co-expressed with Fam20C kinase compared to those expressed alone (FIG. 20B).

Together, these data indicate that fusion proteins having a phosphorylated ABP remain strongly adsorbed to alum, regardless of the immunomodulatory protein contained in the fusion.

Example 4: Alum Can be Used to Retain Proteins and Peptides in Tumors

Figure 21:
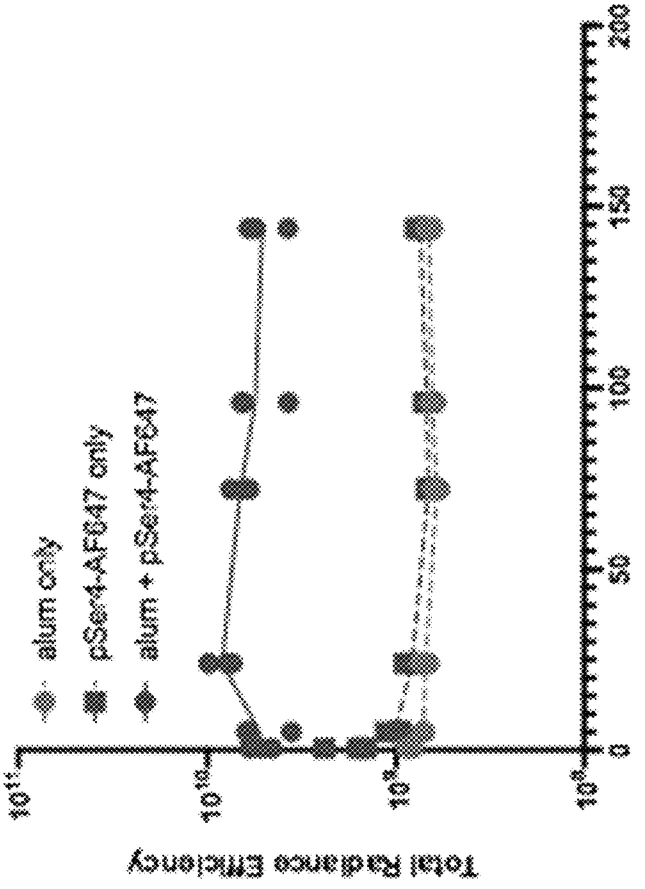
FIG. 21 provides a line graph showing fluorescence intensity measured by in vivo imaging system (IVIS) over time for mouse adenocarcinoma (MC38) flank tumors injected with alum only, fluorescent phosphoserine peptide (pSer4-AF647) only, or a complex of alum+pSer4-AF647 by intratumoral injection.

The persistence of alum following intratumoral injection was determined. To do so, alum was fluorescently labeled with a peptide comprising four phosphoserine amino acids that was covalently conjugated to Alexa Fluor 647 (pSer4-AF647). C57BL/6 mice were inoculated with one million murine adenocarcinoma (MC38) tumor cells by subcutaneous injection in the right flank. After six days, the tumors were injected intratumorally with 0.1 nmol of pSer4-AF647 prepared in saline with alum or without alum (n=3 animals per group). The fluorescence intensity of the tumor was assessed as a measure of alum retention using in vivo imaging by IVIS (PerkinElmer) at various time points following injection. The fluorescence of AF647 was measured using an excitation wavelength of 640 nm and an emission wavelength of 680 nm. The total radiance efficiency was calculated for each tumor and is shown in FIG. 21, where the solid line represents injection of alum+pSer4-AF647, and the dashed line represents free pSer4-AF647 alone. While free pSer4-AF647 peptide diffused rapidly from the tumor, peptide anchored to alum remained in the tumor at least six days following administration. This is consistent with the understanding in the literature that alum can persist in mice for many weeks (Flarend, et al. *Vaccine* 15.1314-1318 (1997)).

Figure 22:
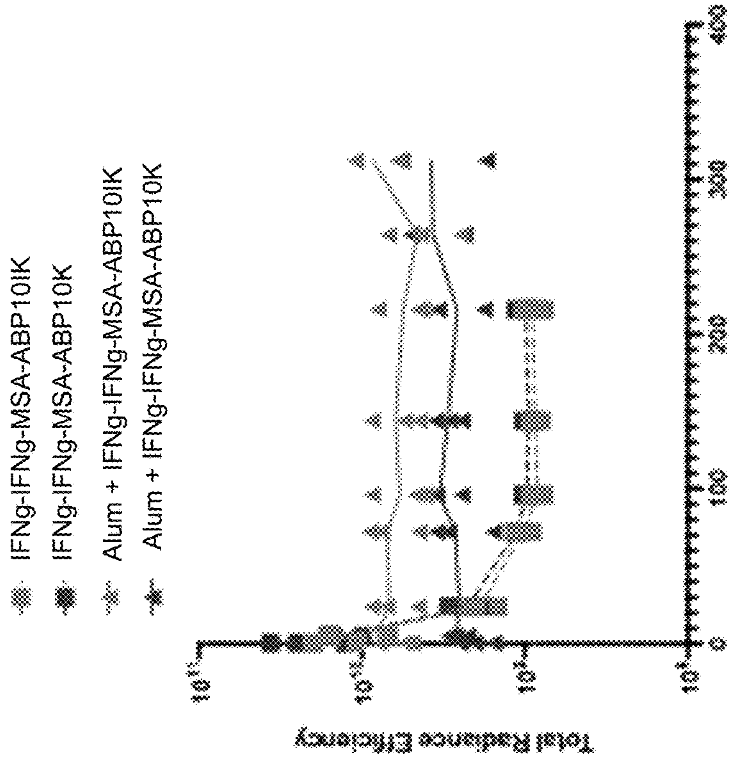
FIG. 22 provides a line graph showing fluorescence intensity measured by IVIS over time for mouse MC38 flank tumors injected with fluorescently-labeled IFNg-IFNg-MSA-ABP10 protein co-expressed with wild type Fam20C kinase (K) or inactive Fam20C kinase (IK) either alone (dashed lines) or complexed with alum (solid lines).

The intratumoral persistence of fusion proteins comprising a phosphorylated ABP when combined with alum was next assessed. To do so, C57BL/6 with flank MC38 tumors established as described above were injected with 5 μg of IFNg-IFNg-MSA-ABP10IK or IFNg-IFNg-MSA-APB10K labeled with AF647 (using an AF647 NHS ester, Thermo Fisher). The proteins were administered alone in saline or mixed with alum. Following administration, tumor fluorescence was assessed by imaging the mice using IVIS with an excitation and emission wavelength of 640 nm and 680 nm respectively (n=3 mice per group). The average total radiance efficiency was calculated and is shown in FIG. 22. While free protein is retained in the tumor for approximately one day post administration, protein anchored to alum remained in the tumor for more than 7 days and at least up to 13 days post administration (FIG. 22).

The in vivo tumor retention of IL2 fusions with a phosphorylated ABP was also assessed. B16F10-Trp2 knock-out tumors were established as described in Moynihan et al *NATURE MEDICINE* (2016) 22(12): 1402-1410, incorporated by reference herein. 9 μg (0.1 nmol) of MSA-IL2-ABP10K labeled with AF647 was administered by intratumoral injection in saline either as free protein or complexed with alum. Following administration, tumor fluorescence was measured using IVIS as described above. The total radiance efficiency was measured over time and normalized per mouse to the value immediately following injection. For comparison, an intratumoral injection of 13 μg (0.1 nmol) of Lumican-MSA-IL2 was administered. The protein is a fusion of MSA-IL2 to the C-terminus of the collagen-anchoring protein lumican. Fusions of immunomodulatory cytokines to lumican have been shown to improve tumor retention and anti-tumor effects following intratumoral administration, as described by Momin, et al *SCI. TRANSL.*

*MED* (2019) 11: eaaw2614 and US2020/0102370, both of which are incorporated by reference herein.

Figure 23:
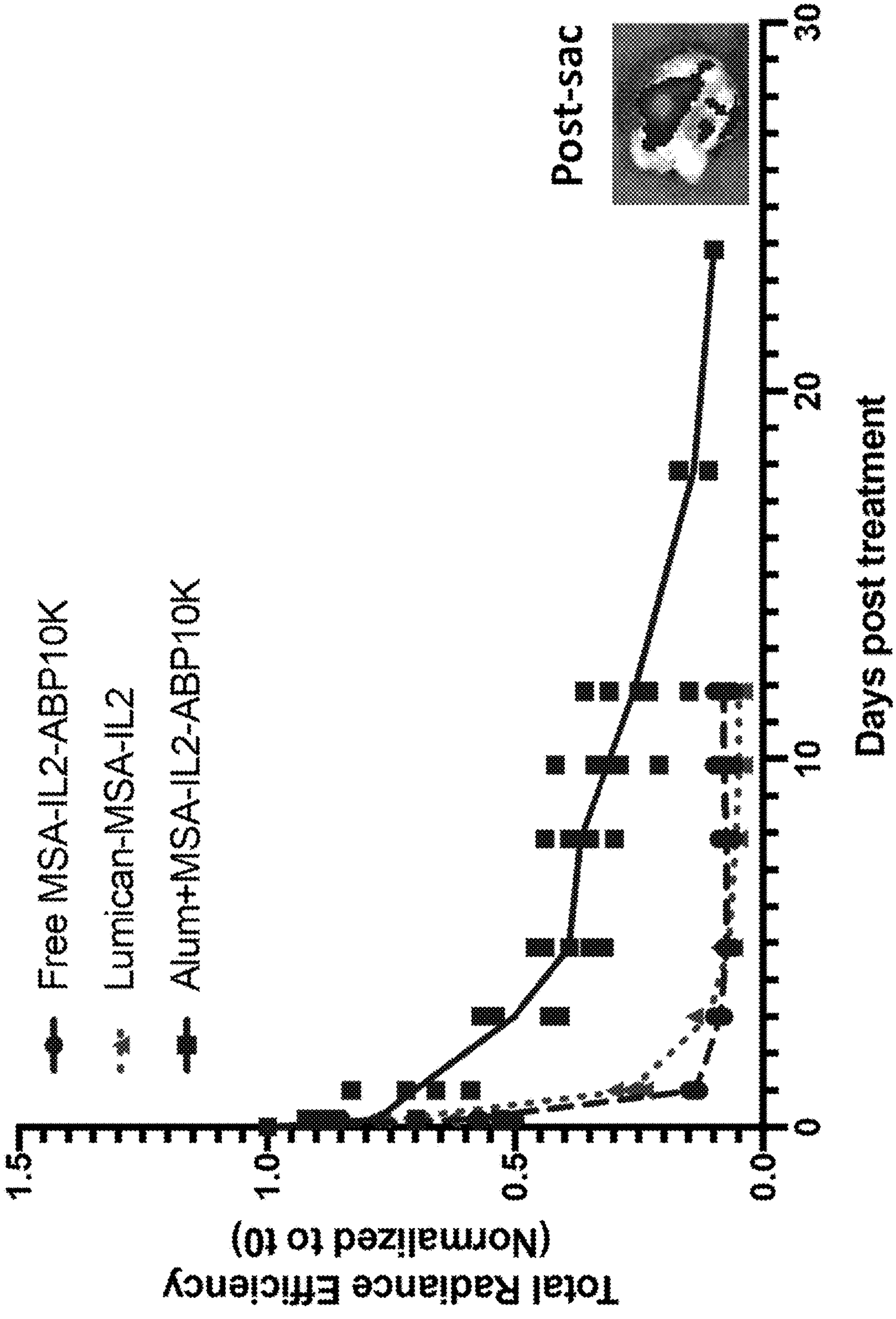
FIG. 23 provides a line graph showing fluorescence intensity measured by IVIS over time of mouse B16F10-Trp2 knock-out tumors injected with fluorescently-labeled MSA-IL2-ABP10K as free protein or complexed with alum or fluorescently-labeled Lumican-MSA-IL2 (MSA-IL2 fused to the C-terminus of the collagen-anchoring protein lumican). False color image of post-sacrifice ("post-sac") tumor injected with MSA-IL2-ABP10K complexed to alum as measured by IVIS shown by inset.

As shown in FIG. 23, MSA-IL2-ABP10K complexed with alum showed the longest duration of tumor retention. The fluorescent signal decayed to near-background levels by 24 days post-injection, however this may have been due to tissue occluding fluorescent signal from the injected intratumoral alum depot, as tumors excised from mice sacrificed at day 29 retained significant fluorescent protein signal (see "post-sac" IVIS image in FIG. 23).

Additionally, tumor retention of alum-bound fusion protein was evaluated by microscopy in mice bearing B16F10 melanoma tumors. Tumors were established by inoculating the right flank of C57BL6 mice with 1M B16F10 tumors cells in PBS by subcutaneous injection. The mice were administered 36 μg of AF647-labeled MSA-IL2-ABP10K by intratumoral injection at day 6 post tumor inoculation. The fusion protein was administered as free protein or complexed with alum, with n=3 per group. The alum was administered at a dose of 90 μg and was pre-labeled with fluorescent pSer4 using Alexa Flour 488 prior to complexation with fusion protein. The mice also received an intraperitoneal injection of the tumor-targeting antibody TA99 at a dose of 200 μg. Tumors were isolated from sacrificed mice at 1 hour following injection to evaluate initial distribution of fusion protein in the tumor, and at 5 days post-injection to evaluate retention of fusion protein following an extended period. Following isolation, the tumors were fixed in 4% paraformaldehyde, embedded in a 3% agarose gel, and sectioned into 100 μm sections using vibratome. The tumor sections were stained with Fluo-TA99 using Alexa Flour 568 as a marker of tumor cells. The sections were imaged by confocal microscopy using a Leica SP8 Laser Scanning Confocal Microscope.

Figure 24B:
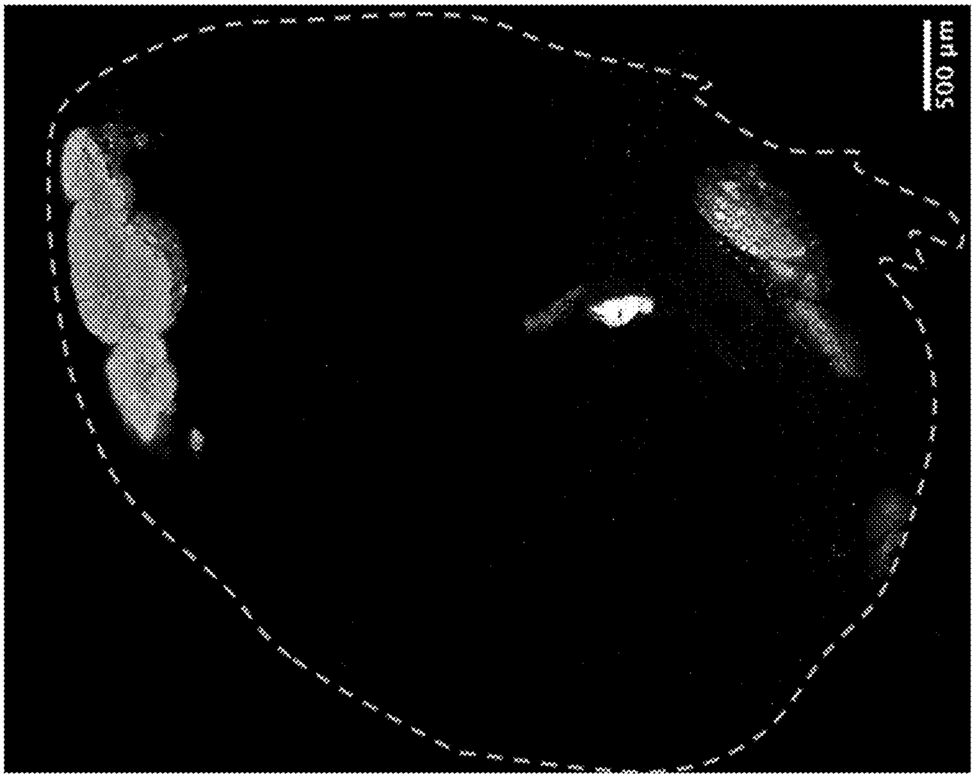
FIGS. 24A-24B provides confocal microscopy images of B16F10 tumors slices prepared from B16F10-tumor bearing mice administered an intratumoral injection of fluorescently-labeled MSA-IL2-ABP10K either free (FIG. 24A) or complexed with alum (FIG. 24B). Tumor isolation was performed at 5-days post injection. Provided are images showing the tumor boundary in outline and fluorescent MSA-IL2-ABP10K signal detected by confocal microscopy in white. Scale bar 500 μm.
Figure 24A:
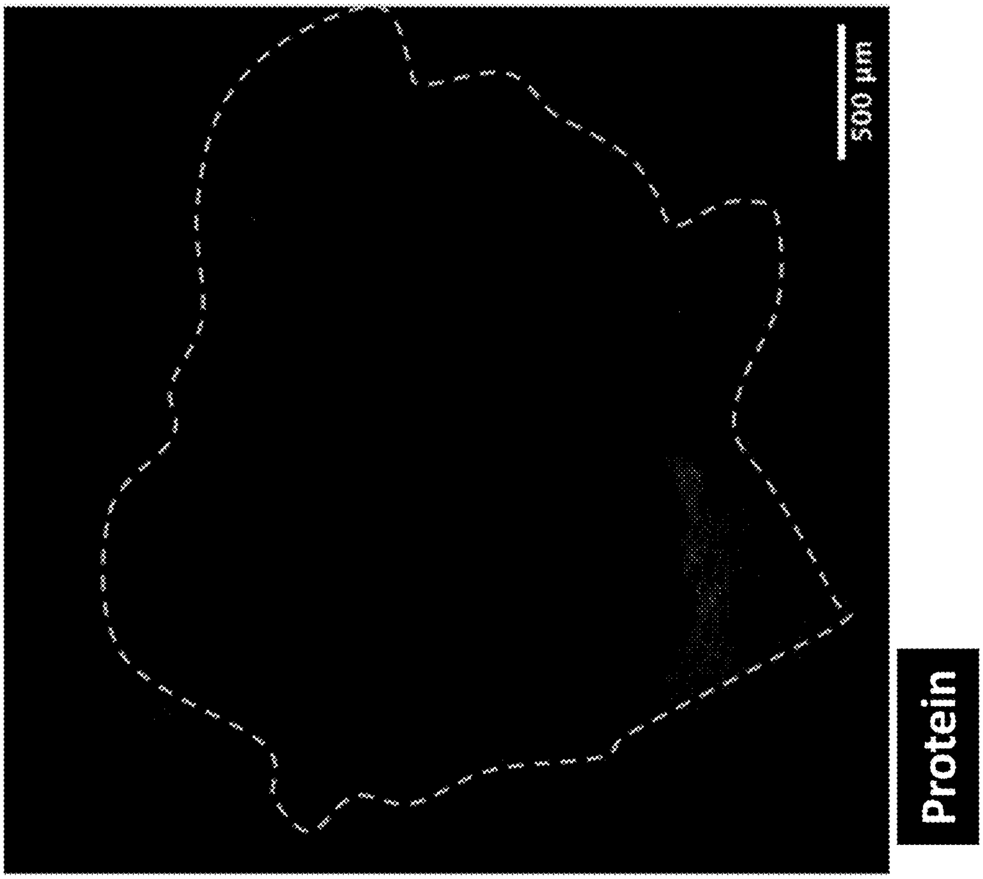
Figure 24C:
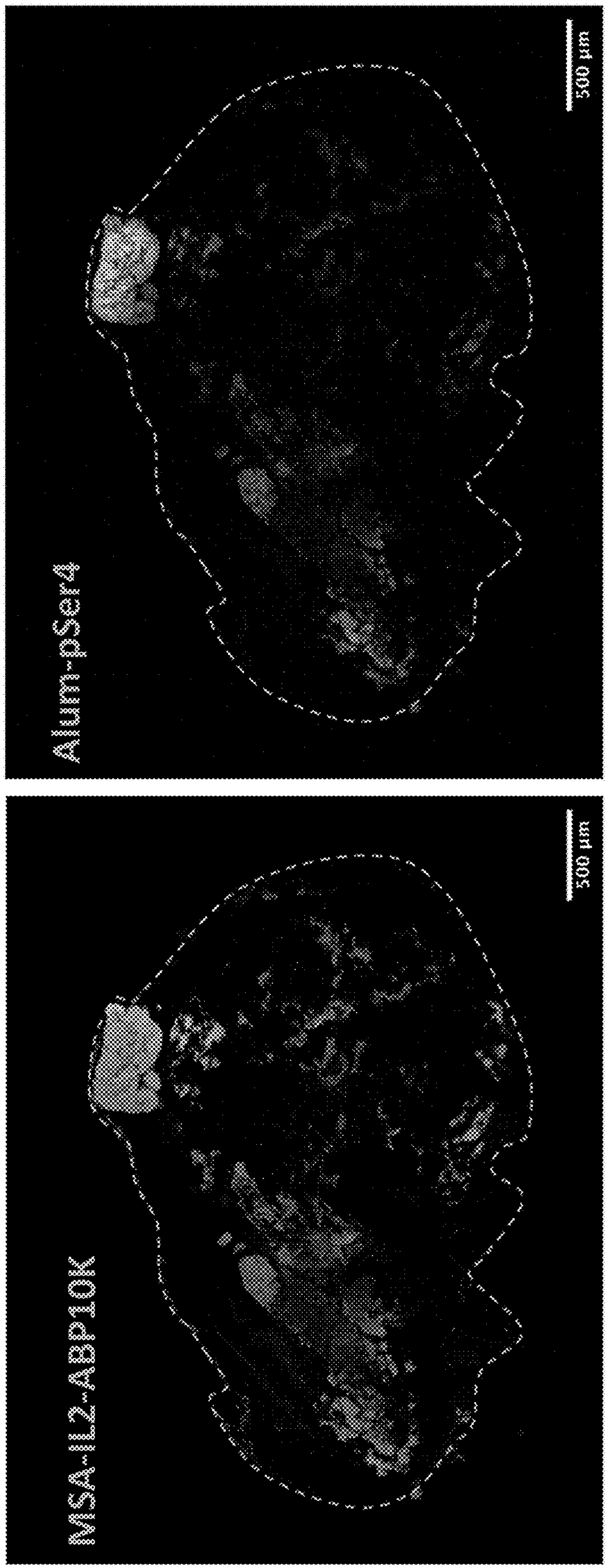
FIG. 24C provides confocal microscopy images of a B16F10 tumors slice prepared from a B16F10-tumor bearing mouse administered an intratumoral injection of fluorescently-labeled MSA-IL2-ABP10K complexed with fluorescent alum-pSer4. Tumor isolation was performed at 1 hour post injection. Provided are images of the tumor slice, with the tumor boundary shown in outline and the signal in gray depicting either fluorescent MSA-IL2-ABP10K (left panel) or fluorescent alum-pSer4 (right panel) as detected by confocal microscopy imaging. Scale bar 500 μm.

As shown in FIGS. 24A-24B, only tumors injected with MSA-IL2-ABP10K complexed with alum (FIG. 24B) had a detectable level of the fusion protein at 5 days post injection, while no protein signal above background was detected in tumors injected with free MSA-IL2-ABP10K (FIG. 24A). Additionally, tumors injected with the alum-MSA-IL2-ABP10K complex demonstrated distribution of fluorescent MSA-IL2-ABP10K and alum throughout the tumor at 1 hour post injection as shown in FIG. 24C. The figure provides a representative tumor image, with a panel (left) showing MSA-IL2-ABP10K fluorescent signal and a panel (right) showing alum-pSer4 fluorescent signal that was detected in the tumor slice. However, by 5 days post injection, the fusion protein was highly concentrated in peripheral regions of the tumor (FIG. 24B). The presence of these regions indicates that administration of the fusion protein with alum contributes to formation of fusion protein "depots", wherein the fusion protein-alum complex accumulates.

Figure 24D:
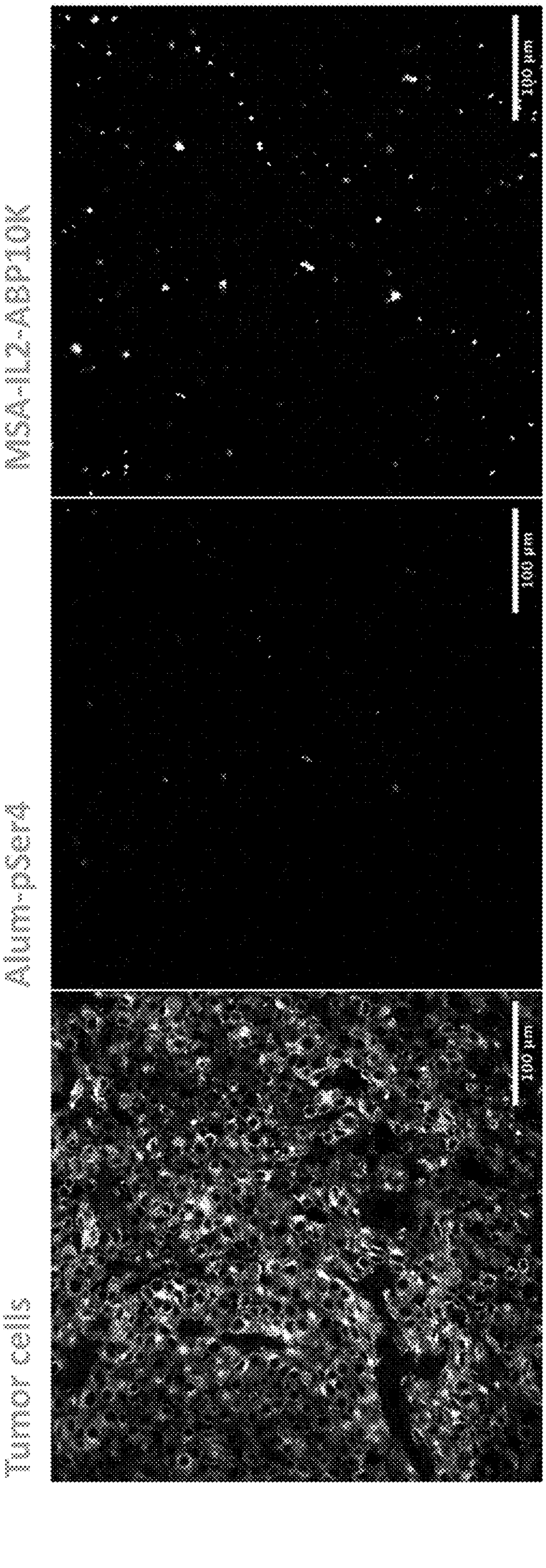
FIG. 24D provides a high resolution confocal microscopy image of a B16F10 tumor slice prepared from a B16F10-tumor bearing mouse administered an intratumoral injection of fluorescently-labeled MSA-IL2-ABP10K complexed with fluorescent alum-pSer4. Tumor isolation was performed at 5 days post injection. Provided are images of the tumor slice, with signal in gray depicting either tumor cells (left panel), fluorescent alum-pSer4 (middle panel), or fluorescent MSA-IL2-ABP10K (right panel) as detected by confocal microscopy imaging. Scale bar 100 μm.

Given the observed depot effect, it was further evaluated if the fusion protein was present in other regions of the tumor, where a lower fusion protein concentration might not be detected at the laser settings used to image regions with high fusion protein concentration. Specifically, the tumor sections were imaged using a high magnification objective (25×) and scanned for regions outside those with high fusion protein fluorescence intensity. A set of representative images is provided in FIG. 24D, with fluorescent signal due to TA99-labeled tumor cells shown in the left panel, fluorescent signal due to alum-pSer4 shown in the middle panel, and fluorescent signal due to MSA-IL2-ABP10K shown in the right panel. The images indicate fluorescent signal due to MSA-IL2-ABP10K was distributed throughout the tumor. Additionally, fluorescent signal due to alum was found to substantially overlap with MSA-IL2-ABP10K signal. Together, these data indicate that the fusion protein injected as a complex with alum both accumulates at a high concentration in peripheral regions of the tumor, but remains distributed throughout the tumor as a complex.

Example 5: IL2 and IL12 Fusion Proteins Bound to Alum Retain Functionality

Figure 25A:
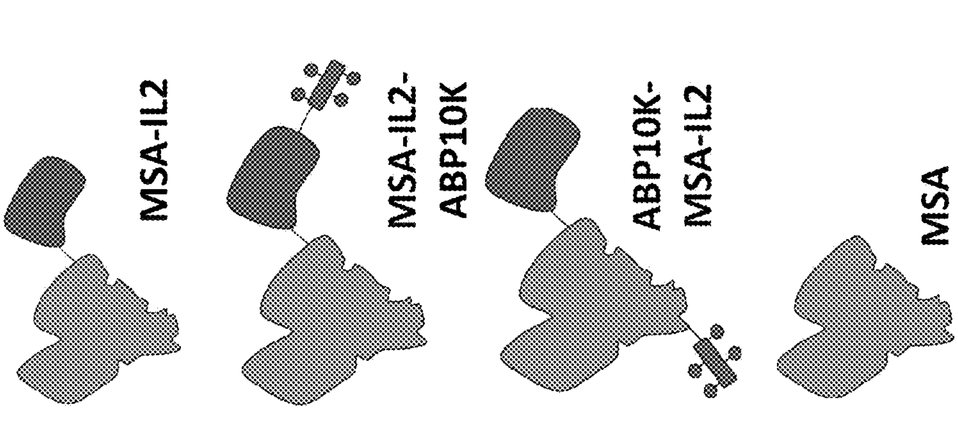
FIG. 25A provides a schematic showing the protein formats that were evaluated for alum binding, including MSA alone, MSA-IL2, or MSA-IL2 fused to a C-terminal or N-terminal ABP10 and co-expressed with wild-type Fam20C kinase (MSA-IL2-ABP10K and ABP10K-MSA-IL2 respectively).
Figure 25B:
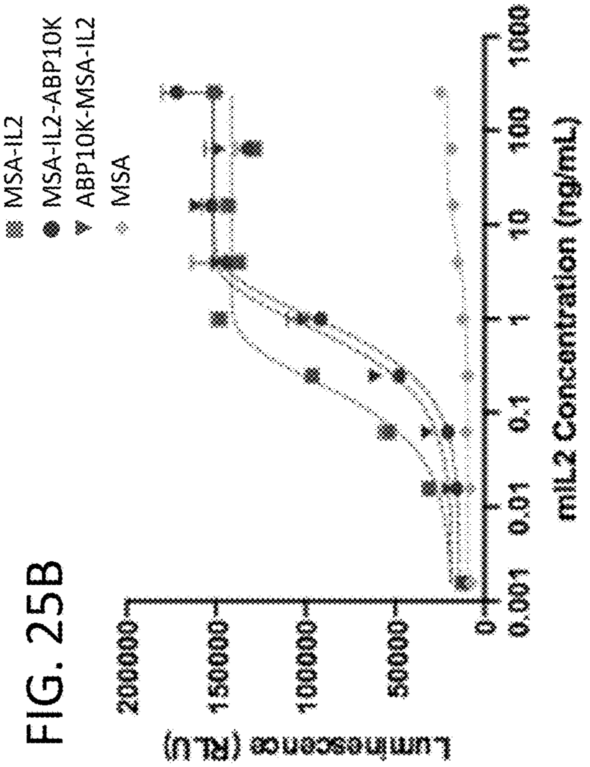
FIGS. 25B-25C provide line graphs showing proliferation of CTLL-2 cells as measured by a CellTiter Glo assay following treatment with different IL2 concentrations of the proteins depicted in FIG. 25A and administered to cells alone (FIG. 25B) or adsorbed to alum (FIG. 25C).
Figure 25C:
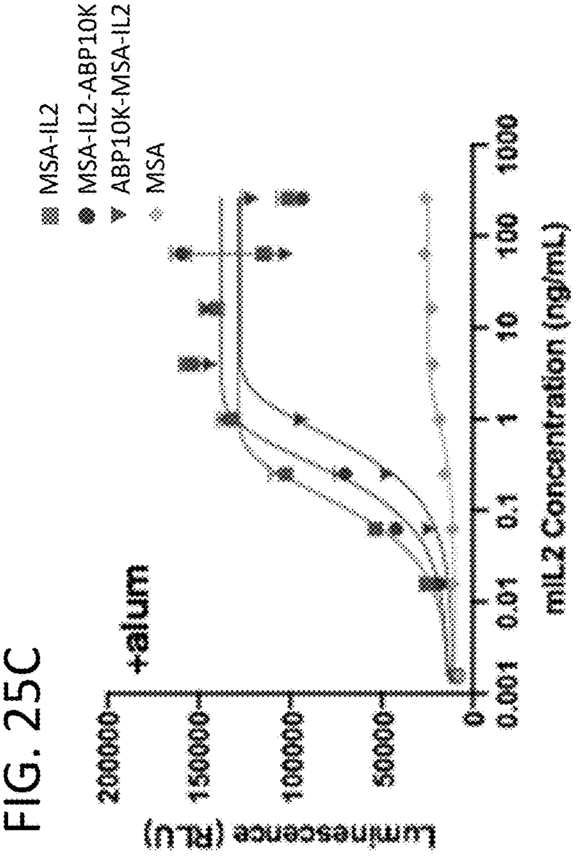

Potentially, adsorption to alum could render any payload unable to bind to its cognate receptor. Without being bound by theory, evidence in the literature indicates that secondary structures of proteins may only transiently change when adsorbed to alum, with proteins re-folding to their native state after release from alum (Zheng et al. 2007). To determine if fusion proteins comprising an ABP retain function when adsorbed to alum, various MSA-IL2 formats were assayed for inducing in vitro proliferation in CTLL-2 cells (ATCC). The MSA-IL2 formats evaluated include MSA, MSA-IL2, MSA-IL2 with a C-terminal phosphorylated ABP (MSA-IL2-ABP10K), and MSA-IL2 with an N-terminal phosphorylated ABP (ABP10K-MSA-IL2) as shown in FIG. 25A. Proliferation was measured by incubating 20,000 CTLL-2 cells with indicated concentrations of equivalent IL2 either as free protein (FIG. 25B) or as the protein adsorbed to alum (mass ratio of 10:1 alum:protein) (FIG. 25C). At 48 hours following incubation, cell viability was assayed using a CellTiter-Glo 2 assay (Promega). While MSA did not induce proliferation, each of the MSA-IL2 formats induced robust proliferation of CTLL-2 cells, regardless of whether the proteins were free or bound to alum. Moreover, the MSA-IL2 formats comprising a phosphorylated ABP were similarly effective compared to MSA-IL2 for inducing proliferation. Noted was some necrosis at high concentrations of protein and alum, potentially due to the particulate nature of alum (see e.g., Jacobson, et al. *Journal of Biological Chemistry* 288:7481-7491 (2013)).

Figure 26A:
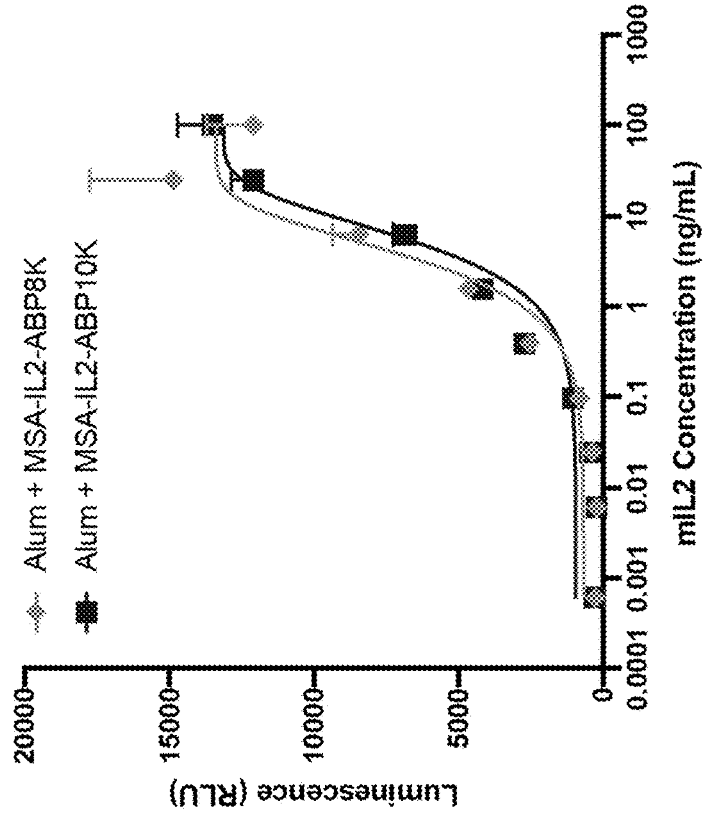
FIGS. 26A-26B provide line graphs showing proliferation of CTLL-2 cells as measured by a CellTiter Glo assay following treatment with alum-bound fusion proteins at different IL2 concentrations, including MSA-IL2-ABP10K or MSA-IL2-ABP8K (FIG. 26A) and MSA-IL2-ABP10K or MSA-IL-ABP17K (FIG. 26B).
Figure 26B:
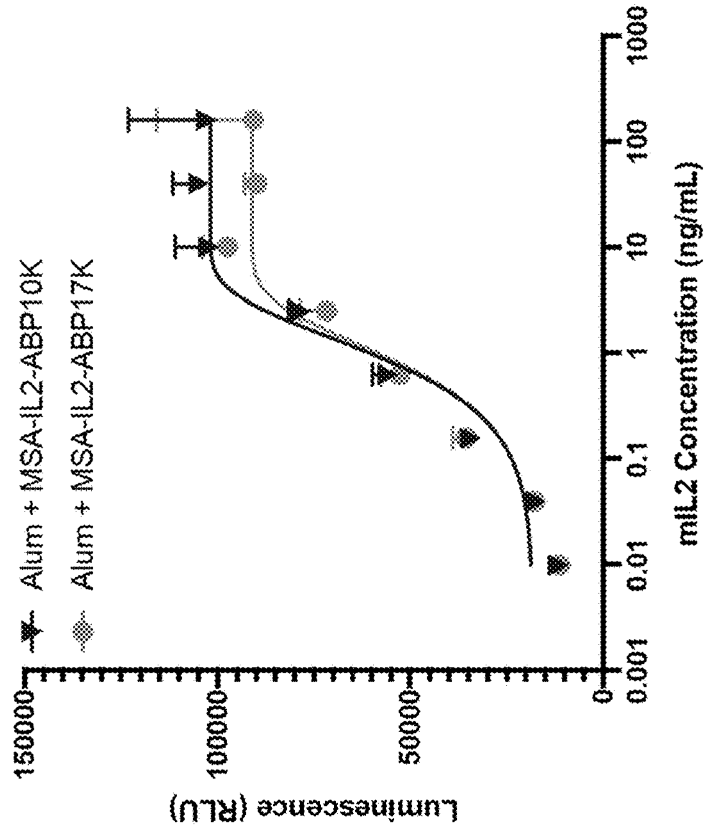

MSA-IL2 formats with a C-terminal phosphorylated ABP8 (MSA-IL2-ABP8K) or ABP17 (MSA-IL2-ABP17K) were also evaluated for functionality when adsorbed to alum using the CTLL-2 cell proliferation assay described above. Briefly, protein adsorbed to alum (mas ratio of 10:1 alum: protein) was incubated with 20,000 CTLL-2 cells at a range of IL-2 concentrations, and cell viability was assayed at 48 hours following incubation. Proliferation was evaluated using MSA-IL2-ABP10K adsorbed to alum as a positive control. As shown in FIGS. 26A-26B, both MSA-IL2-ABP8K and MSA-IL2-ABP17K induced high levels of cell proliferation that were comparable to those induced by MSA-IL2-ABP10K, indicating that IL2 fusions with alternate ABPs retain bioactivity following alum adsorption.

Figure 27A:
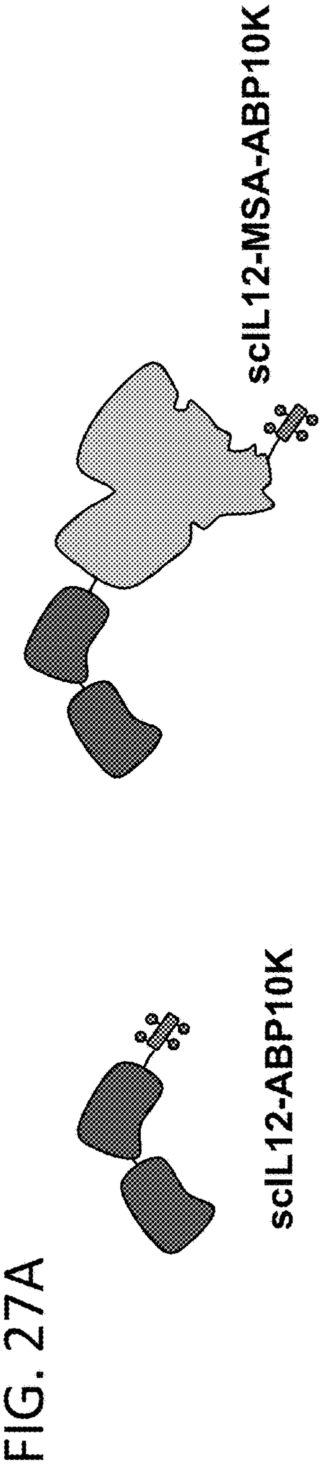
FIG. 27A provides schematics of scIL12 and scIL12-MSA fusion proteins to phosphorylated ABP10 (scIL12-ABP10K and scIL12-MSA-ABP10K respectively).
Figure 27B:
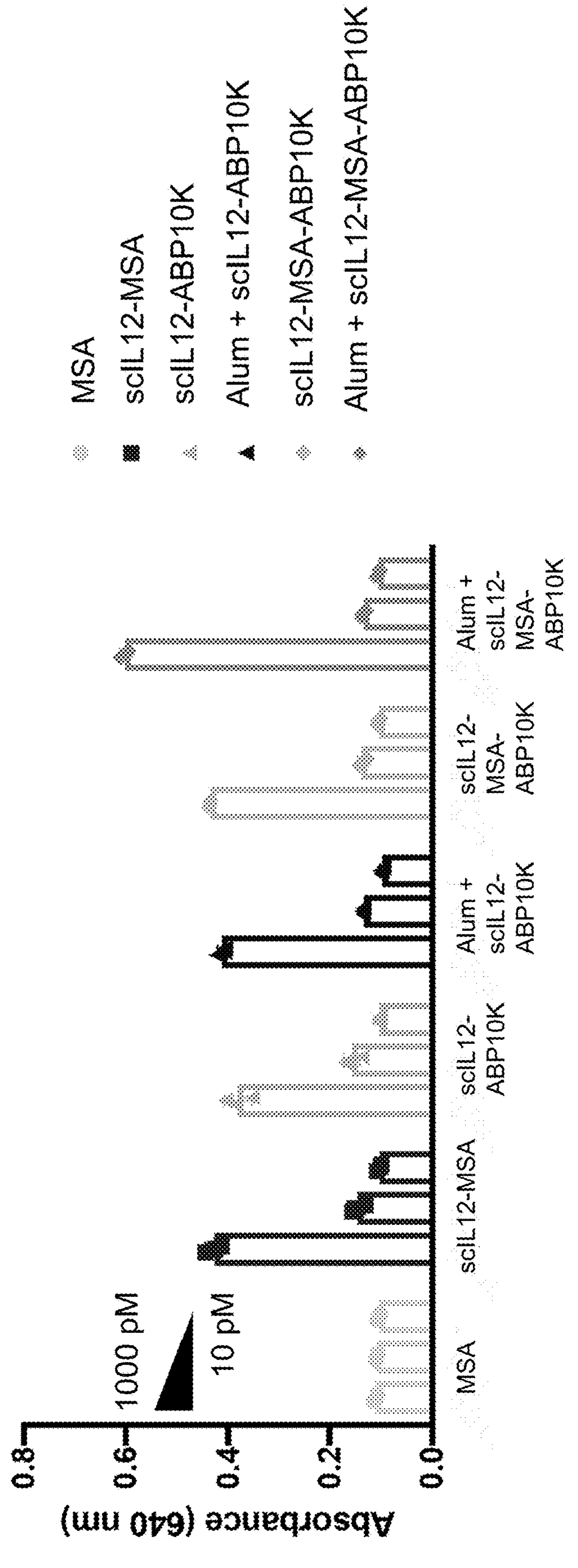
FIG. 27B provides a bar graph quantifying bioactivity of scIL12-

It was further evaluated whether IL12 fusion proteins retain functionality when bound to alum. The IL12 formats evaluated are shown in FIG. 27A. These included scIL12 and scIL12-MSA, both with a C-terminal phosphorylated ABP10 (scIL12-ABP10K and scIL12-MSA-ABP10K respectively). Cytokine functionality was assessed using HEK-Blue IL12 reporter cells (Invivogen) according to the manufacture's protocol. HEK-Blue IL12 cells express a STAT4-inducible SEAP (secreted embryonic alkaline phosphatase) reporter gene that enables detection of bioactive murine IL12 through activation of the STAT-4 pathway, Cells were treated with scIL12-ABP10K and scIL12-MSA-ABP10K either as free protein or complexed with alum at an IL12 concentration of 10 pM, 100 pM and 1000 pM. The fusion proteins were complexed with alum (mass ratio of 10:1 alum:protein) in TBS for 20 minutes prior to cell treatment. Cells were also treated with the equivalent concentrations of scIL12-MSA or MSA as positive and negative controls respectively. SEAP production was quantified using a QUANTI-Blue colorimetric assay. As shown in FIG. 27B, the phosphorylated IL12 fusion proteins either alone or complexed with alum induced levels of cell activation that were similar to those induced by scIL12-MSA, indicating the IL2 fusion protein are functional when linked to a phosphorylated ABP and further adsorbed to alum.

Example 6: IL2 Fusion Proteins Bound to Alum Treat B16F10 Tumors with Single Treatments The potency of immunomodulatory MSA-IL2 comprising a phosphorylated ABP and bound to alum was assessed for treatment of mouse tumors using the B16F10 melanoma tumor model. The treatment that was evaluated included MSA-IL2 in combination with TA99, an antibody that targets the B16F10 tumor antigen known as melanoma-associated antigen tyrosinase-related protein 1 (Trp1). Combinations of MSA-IL2 and TA99 (delivered IP, in the peritoneal cavity) have been reported to cure a subset of mice bearing B16F10 subcutaneous tumors (Moynihan, Kelly D., et al *Nature medicine* 22:1402 (2016); Zhu, et al. *Cancer cell* 27:489-501 (2015)). However, those treatments reportedly require multiple doses of systemic IL2, while still not curing all of the treated mice. Additionally, use of a collagen-anchoring domain (e.g., lumican) and administration of lumican-MSA-IL2 by intratumoral injection in combination with TA99 has been shown to cure a majority of mice bearing B16F10 tumors (see, e.g., Momin, et al SCI. TRANSL. MED (2019) 11: eaaw2614; US2020/0102370). However, the dosing regimen again relied on three doses of intratumoral lumican-MSA-IL2. Without being bound by theory, it was hypothesized that extending the IL2 residence time by strong adsorption to alum would promote a sufficiently robust anti-tumor immune response that would require only a single dose of MSA-IL2 and TA99 for an equivalent effect.

The efficacy of single dose therapy was evaluated for treatment of B16F10 tumors. The tumors were established by inoculating C57BL/6 mice with one million B16F10 tumor cells in the right flank by subcutaneous injection in PBS. The tumors were treated on day six with an intratumoral injection of MSA-IL2 at a dose of 0.4 nmol IL2 and an intraperitoneal (ip) injection of TA99 at a dose of 200 μg per mouse, with n=5 per treatment group. The treatment schedule is shown in FIG. 28A. Free MSA-IL2 was administered in various formats that included MSA-IL2 alone or MSA-IL2 fused to a collagen-binding lumican domain (Lumican-MSA-IL2). MSA-IL2 formats adsorbed to alum were also assessed, including MSA-IL2 or MSA-IL2 comprising a C-terminal or N-terminal phosphorylated ABP (MSA-IL2-ABP10K or ABP10K-MSA-IL2). For proteins prepared with alum, a mixture comprising 90 μg of alum and 0.4 nmol of protein that was rotated at room temperature for 20 minutes prior to administration was given per mouse Animals receiving no treatment were injected with saline only.

Survival of animals is shown in FIG. 28B and tumor growth curves are shown in FIGS. 28C-28H. Treatment with alum anchored MSA-IL2 (MSA-IL2-ABP10K or ABP10K-MSA-IL2) resulted in dramatically improved survival compared to free MSA-IL2 or collagen anchored Lumican-MSA-IL2. Together, these results demonstrate that adsorption to alum dramatically improves the anti-tumor immune response to MSA-IL2.

Additionally, long-term survival with the combination therapy (i.e, survival up to 100 days post tumor inoculation) was evaluated using larger cohort sizes (n=10-15). B16F10 tumors were established as described above, and mice were administered on day 6 post tumor inoculation according to the regimen depicted in FIG. 29A. Specifically, the mice were administered TA99 at a dose of 200 μg by ip injection. Mouse cohorts were further administered an intratumoral injection of Lumican-MSA-IL2, MSA-IL2-ABP10K as free protein or complexed with alum, MSA-IL2 as free protein or complexed with alum, or alum alone. IL-2 fusions were administered at a mass equivalent to 0.4 nmol IL2. For fusion proteins complexed to alum, the mixture was prepared with 90 μg alum. Survival of the mice following administration was monitored. As shown in FIG. 29B, long-term survival in mice receiving TA99 combined with phosphorylated MSA-IL2-ABP10K absorbed to alum was significantly higher than for mice receiving the combination with Lumican-MSA-IL2. No animals survived in the remaining treatment groups beyond 40 days post tumor inoculation.

The systemic anti-tumor T cell response induced by the combination therapy was evaluated using an IFNγ ELISPOT. Specifically, mice bearing B16F10 tumors were inoculated as described above. On day 6 post tumor inoculation, the mice were administered 200 μg TA99 by ip injection either alone or in combination with an intratumoral injection of free MSA-IL2-ABP10K, MSA-IL2-ABP10K complexed with alum, or Lumican-MSA-IL2. The fusion protein was administered at a dose of 0.4 nmol IL2. On day 12 post tumor inoculation, spleens were harvested and splenocytes were plated with irradiated B16F10 tumor cells. The number of IFNγ forming units (SFUs) in response to stimulation by B16F10 tumor cells was quantified by ELISPOT. As shown in FIG. 29C, the combination therapy with MSA-IL2-ABP10K complexed with alum provided the highest quantity of tumor-reactive IFNγ-producing T cells.

MSA-IL2 fusion proteins linked to ABP8 were also evaluated in the combination therapy. Briefly, B16F10 tumors were established as described above. On day 6 post tumor inoculation, the mice were administered an intratumoral injection of MSA-IL2-ABP8K complexed with alum or MSA-IL2-ABP10K complexed with alum. The fusion proteins were administered at a dose of 0.4 nmol IL2 and were complexed with 90 μg alum. Control mice received an intratumoral injection of 90 μg alum alone. Additionally, the mice received TA99 on day 6 post tumor inoculation at a dose of 200 μg by ip injection. Mouse survival was monitored. As shown in FIG. 29D, all mice receiving TA99+alum succumbed to tumor burden. In contrast, about 50% of mice administered TA99 in combination with MSA-IL2 fusions complexed to alum and having either a phosphorylated ABP8 or ABP10 were long-term survivors.

Together, these data indicate the intratumoral administration of alum-bound IL2 fusion protein in combination with TA99 tumor targeting antibody is highly effective for inducing a potent anti-tumor immune response and enabling cures in a substantial portion of mice.

Example 7: Synergistic Effects of IL12 Fusion Proteins and Immune Checkpoint Blockade in a Melanoma Tumor Model With the dramatic improvement in anti-tumor effects using IL2 fusion proteins adsorbed to alum as described above, the therapeutic effect of IL12 fusion proteins was evaluated to determine if the improvement with adsorption to alum could be generalized to other cytokine formats. IL-12 has been shown to induce powerful anti-tumor immune effects by inducing IFNγ production in T cells and NK cells (Green et al., (2017) J Biol Chem 292:13925-13933). However, IL12 has a narrow therapeutic window and systemic administration has been associated with severe toxicities in clinical trials (Lasek et al., (2014) Cancer Immunol Immunother 63(5):419-435). Additionally, safety concerns have limited the development of combinations to potentiate the anti-tumor effects of IL12 (e.g., combination with immune checkpoint blockade). Thus, there remains a need to localize the anti-tumor effects of IL12 to the tumor microenvironment without inducing a systemic inflammatory response. Adsorption of IL12 fusion protein to alum was investigated for this purpose.

Specifically, the efficacy of single-dose IL12 fusion protein combined with repeat dosing of anti-PD-1 antibody was evaluated in B16F10-tumor bearing mice according to the treatment schedule shown in FIG. 30A. Tumors were established as described in Example 6. Mice were administered 200 μg anti-PD-1 antibody (clone RMP1.14, BioXCell) by ip injection every 3 days beginning on day 6 for a total of four doses. The mice were further administered IL12 fusion protein, either scIL12-ABP10K or scIL12-MSA-ABP10K, as free protein or complexed with alum. The IL12 fusion protein was administered on day 6 post tumor inoculation by intratumoral injection at a dose of 2.5 μg (40 pmol) for scIL12-ABP10K and 5 μg (40 pmol) for scIL12-MSA-ABP10K, with 50 μg alum for fusion protein complexed with alum. One control group received an intratumoral injection of alum at a dose of 50 μg in combination with systemic anti-PD-1 antibody. The other control group received intratumoral IL12 fusion protein (scIL12-ABP10K or scIL12-MSA-ABP10K) complexed with alum and administered without anti-PD-1 antibody.

FIG. 30B provides survival outcomes for mice administered scIL12-ABP10K fusion protein and FIG. 30C provides survival outcomes for mice administered scIL12-MSA-ABP10K fusion protein. As shown by FIG. 30B, mice administered scIL12-ABP10K adsorbed to alum had improved survival compared to control mice (anti-PD-1 antibody+alum) or mice administered free scIL12-ABP10K with anti-PD-1 antibody. The combination of scIL12-ABP10K adsorbed to alum with anti-PD-1 antibody provided the highest level of long-term survival, with approximately 20% survival of mice in the treatment group when evaluated at day 100 post tumor inoculation. Similarly, as shown by FIG. 30C, highest level of long-term survival was observed for mice administered scIL12-MSA-ABP10K complexed with alum in combination with anti-PD-1 antibody, with approximately 40% survival of mice in the treatment group when evaluated at day 100 post tumor inoculation.

Figure 31C:
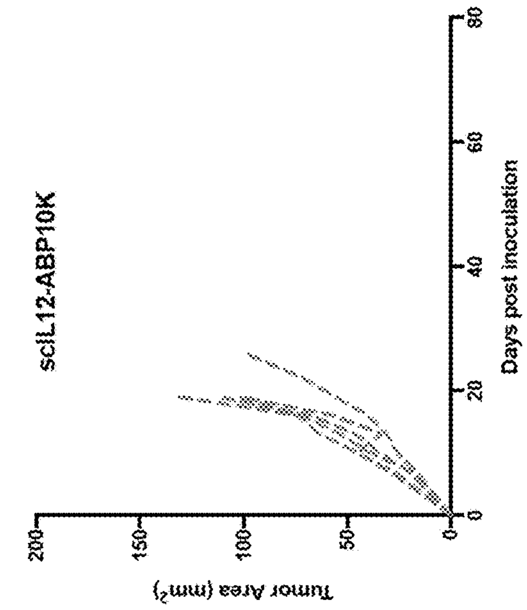
Figure 31D:
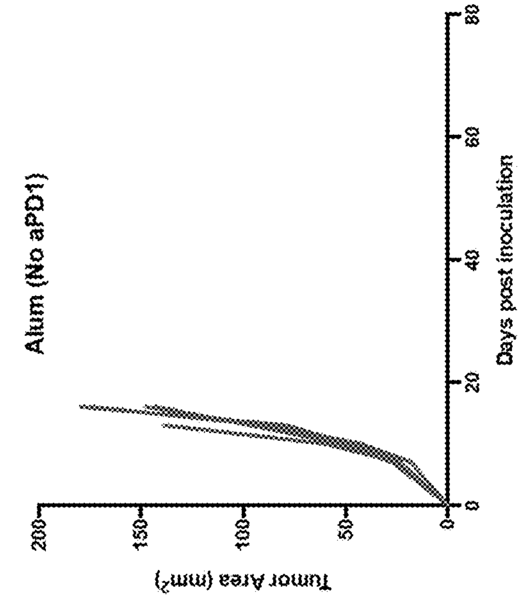

Furthermore, scIL2 fusion formats with ABP17 were evaluated according to the treatment schedule described above and shown in FIG. 30A. Briefly, on day 6 post tumor inoculation, B16F10 tumor bearing mice established were administered either scIL12-ABP10K (n=7) or scIL12-ABP17K (n=5) complexed to alum by intratumoral injection and anti-PD-1 therapy by ip injection. The scIL12 fusions were administered at a single dose of 40 pmol scIL12 (mass equivalent to 2.5 μg scIL12) and 50 μg alum. The anti-PD-1 was administered at a dose of 200 μg every 3 days for a total of 4 doses. Control groups were tumor bearing mice treated with (1) one dose of free scIL12-ABP10K (40 pmol) and 4 ip doses of anti-PD-1 (n=5), or (2) one 50 μg dose of alum with no anti-PD1 (n=5). Tumor size was measured using calipers and evaluated as tumor area (tumor length×width). While B16F10 tumors in control groups grew rapidly (comparable to those shown in FIG. 28C), tumors administered the combination therapy were effectively controlled in a majority of mice for both scIL12-ABP10K complexed with alum (FIG. 31A) and scIL12-ABP17K complexed with alum (FIG. 31B). Control groups are shown in FIGS. 31C-31D.

Together these data indicate that the use of alum to localize IL12 cytokine fusions to tumors is effective for improving survival following a single dose, both when the fusion is administered alone or in combination with immune checkpoint blockade.

Example 8: Synergistic Effects of IL2 and IL12 Fusion Proteins and Immune Checkpoint Blockade in a Melanoma Tumor Model IL-2 and IL-12 are known to engage complementary signaling pathways to stimulate NK cells and T cells (Wigginton & Wiltrout (2002) Expert Opin Biol Ther 2:513-524). Notably, the combination of IL-2 and IL-12 also significantly enhances the production of IFN-y by T cells and NK cells. Additionally, IL-2 upregulates the expression of a IL-12 receptor subunit beta 2 (Wang et al., (2000) Blood 95:3183) and IL-12 sustains surface expression the high-affinity IL-2 receptor CD25 (Starbeck-Miller et al., (2013) J Exp Med 211:105-120). By reciprocal positive feedback, IL-2 and IL-12 augment and prolong the effect of each other (Wigginton et al., (1996) J Natl Cancer Inst 88:38-43). However, despite promising efficacy, the toxicities associated with systemic administration of the cytokines has limited the clinical development of IL2/IL12 combination therapies (Gollob et al., (2003) J Clin Oncol 21:2564-2573; Cohen, J. (1995) *Science* 270:908; Toloza, et al (1996) *Cancer Gene Ther* 3:11; Brunda, et al (1993) *J Exp Med* 171:249; Nastala et al (1994) *J Immunol* 153:1697; Zou, et al (1995) *Int Immunol* 7:1135).

Accordingly, use of alum to localize IL2 and IL12 fusion proteins to tumors in combination with systemic immune checkpoint blockade was evaluated for synergistic therapeutic effect(s), without inducing toxicity. Specifically, combination therapy was evaluated in B16F10 tumor bearing mice according to the treatment schedule shown in FIG. 32A. Tumors were established as described in Example 6. Anti-PD-1 antibody was administered as described in Example 7, beginning on day 6 post tumor inoculation. On day 6, mice were administered MSA-IL2-ABP10K and/or scIL12-MSA-ABP10K either as soluble fusion proteins or adsorbed to alum. The fusion proteins were administered by intratumoral injection, with MSA-IL2-ABP10K administered at a dose of 20 μg and scIL12-MSA-ABP10K administered at a dose of 5 μg Complexed fusion proteins were administered with a dose of 50 μg alum. Control mice were administered alum alone via an intratumoral injection of 50 μg.

Toxicity of the combination therapy was evaluated by measuring animal body weight over time. As shown in FIG. 32B, mice that received the combination of free IL2 fusion protein and free IL12 fusion protein exhibited significant weight loss, with an average reduction in body weight of approximately 15% by day 12 post tumor inoculation relative to body weight prior to treatment. In contrast, mice that received IL12 fusion protein adsorbed to alum experienced no significant weight loss. Additionally, mice that received combination IL12 and IL2 fusion proteins adsorbed to alum experienced little to no weight loss. Additionally, as shown in FIG. 32C, the combination of IL2 and IL12 fusion proteins adsorbed to alum with anti-PD-1 antibody resulted in dramatically improved survival compared to control mice (administered alum only). Survival was similar if not improved compared to mice receiving free IL2 and IL12 fusion proteins with anti-PD-1 antibody.

These results demonstrate intratumoral administration of alum-bound IL2 and IL12 fusion proteins in combination with immune checkpoint blockade is effective for improving survival outcomes in the mouse B16F10 tumor model without inducing treatment-related toxicities. Thus, alum provides an effective therapeutic modality for localizing the cytokine combination to tumors and achieving a desirable balance of potent efficacy and low toxicity.

Summary Sequence Tables

TABLE 7 metal hydroxide binding peptides comprising a Fam20C kinase target motif

| Name | Type | Amino acid sequence | SEQ ID NO |
|---|---|---|---|
| ABP3 | Amino acid (aa) | FQSEEQQGGGSGGSEEGG | 91 |
| | DNA | TTCCAATCAGAAGAGCAACAGGGTGGGGGTTCCGGCGGTAG CGAGGAGGGTGGG | 92 |
| ABP4 | aa | MESEESNGGGSGGSEE | 93 |
| | DNA | ATGGAGAGTGAAGAATCAAATGGTGGGGGTTCCGGCGGTAG CGAGGAG | 94 |
| ABP5 | aa | FRISHELDSASSEV | 95 |
| | DNA | TTTAGAATTTCCCACGAGCTTGACAGTGCATCTTCTGAGGT G | 96 |
| ABP6 | aa | ASSQESGEEAGSQEN | 97 |
| | DNA | GCTTCTTCCCAGGAAAGCGGTGAAGAGGCTGGCAGTCAGGA GAAC | 98 |
| ABP7 | aa | KKIEKFQSEEQQQ | 99 |
| | DNA | AAGAAAATAGAAAAGTTTCAGTCCGAAGAGCAGCAACAA | 100 |
| ABP8 | aa | TVSSETDSISSEESVEHI | 101 |
| | DNA | ACTGTAAGCAGCGAAACAGACTCAATATCTTCAGAAGAAAG TGTCGAACACATT | 102 |
| ABP10 | aa | FQSEEQQGGGSGGSEEGGMESEESNGGGSGGS EEGG | 103 |
| | DNA | TTCCAATCAGAAGAGCAACAGGGTGGGGGTTCCGGCGGTAG CGAGGAGGGTGGGATGGAGAGTGAAGAATCAAATGGTGGGG GTTCCGGCGGTAGCGAGGAGGGTGGG | 104 |
| ABP11 | aa | MESEESNGGGSGGSEEGGMESEESNGGGSGGS EEGG | 105 |
| | DNA | ATGGAGAGTGAAGAATCAAATGGTGGGGGTTCCGGCGGTAG CGAGGAGGGTGGGATGGAGAGTGAAGAATCAAATGGTGGGG GTTCCGGCGGTAGCGAGGAG | 106 |
| ABP12 | aa | TVSSETDSISSEESVEHITVSSETDSISSEES VEHI | 107 |
| | DNA | ACTGTAAGCAGCGAAACAGACTCAATATCTTC AGAAGAAAGTGTCGAACACATTACTGTGAGCA GTGAAACTGACTCTATCTCCTCTGAGGAGTCT GTAGAACATATA | 108 |
| ABP13 | aa | FQAEEQQGGGSGGAEEGGMEAEESNGGGSGGA EEGG | 109 |
| | DNA | TTCCAAGCAGAAGAACAACAGGGTGGGGGTTCCGGCGGTGC GGAGGAGGGTGGGATGGAGGCAGAAGAATCAAATGGTGGGG GTTCCGGCGGTGCGGAGGAGGGTGGG | 110 |
| ABP14 | aa | MEAEESNGGGSGGAEEGGMEAEESNGGGSGGA EEGG | 111 |
| | DNA | ATGGAGGCAGAAGAATCAAATGGTGGGGGTTC CGGCGGTGCGGAGGAGGGTGGGATGGAGGCAG AAGAATCAAATGGTGGGGGTTCCGGCGGTGCG GAGGAG | 112 |
| ABP15 | aa | RRFQSEEQQGGGSGGSEEGGRRMESEESNGGG SGGSEEGG | 113 |
| | DNA | CGCCGGTTCCAATCAGAAGAGCAACAGGGTGGGGGTTCCGG CGGTAGCGAGGAGGGTGGGAGGAGAATGGAGAGTGAAGAAT CAAATGGTGGGGGTTCCGGCGGTAGCGAGGAGGGTGGG | 114 |

TABLE 7-continued metal hydroxide binding peptides comprising a Fam20C kinase target motif

| Name | Type | Amino acid sequence | SEQ ID NO |
|---|---|---|---|
| ABP16 | aa | FQSEEQQGGGSGGSEEGGFQSEEQQGGGSGGS EEGG | 115 |
| | DNA | TTCCAATCAGAAGAGCAACAGGGTGGGGGTTC CGGCGGTAGCGAGGAGGGTGGGTTTCAAAGCG AAGAACAACAGGGTGGGGGTTCCGGCGGTAGC GAGGAGGGTGGG | 116 |
| ABP17 | aa | SEESEESEESEE | 117 |
| | DNA | TCTGAAGAATCCGAGGAGAGTGAAGAGTCAGAGGAG | 118 |
| ABP18 | aa | GGGSGGSEEGGGS | 119 |
| | DNA | GGTGGGGGTTCCGGCGGTAGCGAGGAGGGTGG CGGTAGC | 120 |
| ABP19 | aa | GGGSGGSEESEEGGGS | 121 |
| | DNA | GGTGGGGGTTCCGGCGGTTCAGAAGAGAGCGAGGAGGGTGG CGGTAGC | 122 |
| ABP20 | aa | GGGSGGSEESEESEEGGGS | 123 |
| | DNA | GGTGGGGGTTCCGGCGGTAGCGAAGAATCAGAAGAGAGCGA GGAGGGGGGTGGTAGC | 124 |
| ABP21 | aa | GGGSGGSEESEESEESEEGGGS | 125 |
| | DNA | GGTGGGGGTTCCGGCGGTTCCGAGGAGAGCGAAGAATCAGA AGAGAGCGAGGAGGGGGGGTGGCAGC | 126 |
| ABP22 | aa | XXSXEXX | 127 |
| ABP23 | aa | XXSEEXX | 128 |
| ABP24 | aa | FQSEEQQ | 129 |
| ABP25 | aa | MESEESN | 130 |
| ABP26 | aa | GGSEEGG | 131 |
| L (linker) | aa | GGGS | 132 |
| ABP27 | aa | XXSXEXXLSXEXX | 133 |
| ABP28 | aa | XXSEEXXGGGSGGSEEGG | 134 |

X = any amino acid

TABLE 8

Fam20C kinase

| Name | Type | Amino acid sequence | SEQ ID NO |
|---|---|---|---|
| Fam20C | aa | MVFLVACALHIALDLLPRLERRGARPS GEPGCSCAQPAAEVAAPGWAQVRGRPG EPPAASSAAGDAGWPNKHTLRILQDFS SDPSSNLSSHSLEKLPPAAEPAERALR GRDPGALRPHDPAHRPLLRDPGPRRSE SPPGPGGDASLLARLFEHPLYRVAVPP LTEEDVLFNVNSDTRLSPKAAENPDWP HAGAEGAEFLSPGEAAVDSYPNWLKFH IGINRYELYSRHNPAIEALLHDLSSQR ITSVAMKSGGTQLKLIMTFQNYGQALF KPMKQTREQETPPDFFYFSDYERHNAE IAAFHLDRILDFRRVPPVAGRMVNMTK EIRDVTRDKKLWRTFFISPANNICFYG ECSYYCSTEHALCGKPDQIEGSLAAFL PDLSLAKRKTWRNPWRRSYHKRKKAEW EVDPDYCEEVKQTPPYDSSHRILDVMD MTIFDFLMGNMDRHHYETFEKFGNETF IIHLDNGRGFGKYSHDELSILVPLQQC | 135 |

TABLE 8-continued

Fam20C kinase

| Name | Type | Amino acid sequence | SEQ ID NO |
|---|---|---|---|
| | | CRIRKSTYLRLQLLAKEEYKLSLLMAE SLRGDQVAPVLYQPHLEALDRRLRVVL KAVRDCVERNGLHSVVDDDLDTEHRAA SAR | |
| Fam20C-KDEL | aa | MVFLVACALHIALDLLPRLERRGARPS GEPGCSCAQPAAEVAAPGWAQVRGRPG EPPAASSAAGDAGWPNKHTLRILQDFS SDPSSNLSSHSLEKLPPAAEPAERALR GRDPGALRPHDPAHRPLLRDPGPRRSE SPPGPGGDASLLARLFEHPLYRVAVPP LTEEDVLFNVNSDTRLSPKAAENPDWP HAGAEGAEFLSPGEAAVDSYPNWLKFH IGINRYELYSRHNPAIEALLHDLSSQR ITSVAMKSGGTQLKLIMTFQNYGQALF KPMKQTREQETPPDFFYFSDYERHNAE IAAFHLDRILDFRRVPPVAGRMVNMTK EIRDVTRDKKLWRTFFISPANNICFYG ECSYYCSTEHALCGKPDQIEGSLAAFL PDLSLAKRKTWRNPWRRSYHKRKKAEW EVDPDYCEEVKQTPPYDSSHRILDVMD | 136 |

TABLE 8-continued

Fam20C kinase

| Name | Type | Amino acid sequence | SEQ ID NO |
|---|---|---|---|
| | | MTIFDFLMGNMDRHHYETFEKFGNETF<br>IIHLDNGRGFGKYSHDELSILVPLQQC<br>CRIRKSTYLRLQLLAKEEYKLSLLMAE<br>SLRGDQVAPVLYQPHLEALDRRLRVVL<br>KAVRDCVERNGLHSVVDDDLDTEHRAA<br>SARGGGSKDEL | |
| Fam20C-KDEL | DNA | gacttcagctccgacccctcctccaac<br>ctctcgtcccactcgctggagaaactg<br>ccgcccgcggccgagccggccgagcgc<br>gccttgcgggggcgggatcccggcgcc<br>ctaagaccccacgaccccgcgcaccgg<br>ccgctgctgcgagaccccggcccgcgt<br>cggtccgagtcgcccccggccccggc<br>ggagacgcctccctcctggccaggctg<br>ttcgagcacccgctttaccgggtggcg<br>gttccgccgctcacggaggaggacgtc<br>ctgttcaatgtgaacagcgacaccagg<br>ctcagccccaaagcggcggagaacccg<br>gactggccgcatgcgggtgctgaaggt<br>gcagaattcctctcccccggggaggcg<br>gccgtggactcctatcccaactggctc<br>aagttccacattggtatcaaccggtac<br>gagctgtactccagacacaacccggcc<br>atcgaggccctgctgcacgacctcagc<br>tcccagaggatcaccagcgtggccatg<br>aagtcggggggcacgcagctgaagctc<br>atcatgaccttccagaattacgggcaa<br>gcgctgttcaaacccatgaaacaaacg<br>agggagcaggagacacccccctgacttt<br>ttttatttctctgactacgagaggcac<br>aatgcggagattgctgccttccacctg<br>gacaggatcctggacttccgccgggtc<br>cctcccgtggccggcaggatggtcaac<br>atgaccaaggagatccgggacgtcaca<br>cgggacaagaagctctggaggaccttc<br>ttcatctctccagccaacaacatctgc<br>ttctacggcgagtgttcctactactgc<br>tccacggagcacgccctgtgcgggaag<br>ccagaccagatcgagggctcgctggcg<br>gccttcctgcccgacctgtccctggcc<br>aagaggaagacctggcggaaccccttgg<br>cggcgttcctaccacaagcgcaagaag<br>gccgagtgggaggtggaccctgactac<br>tgcgaggaggtgaagcagacaccgccc<br>tacgacagcagccaccgcatcctggac<br>gtcatggacatgacgatcttcgacttc<br>ctcatgggaaacatggaccgtcaccac<br>tacgagacttttgagaagtttgggaat<br>gaaacgttcatcatccacttagacaat<br>ggaagagggtttgggaagtattcgcac<br>gacgagctctccatcctggtgccgcta<br>cagcagtgctgcaggatccggaagtcc<br>acctacctgcgtctgcagctcctggcc<br>aaggaggagtacaagctgagcctgctg<br>atggccgagtctctgcgggggggaccag<br>gtggcacccgtgctgtaccagccgcac<br>ctggaggccctggaccggcggctccgc<br>gtcgtgctaaaggccgtccgggactgc<br>gtggagaggaacgggctccacagcgtg<br>gtggatgacgacctggacactgagcac<br>agagccgcctcggcgaggGGAGGTGGA<br>TCAAAAGATGAACTG | 137 |
| Fam20C-(D456A) | aa | MVFLVACALHIALDLLPRLERRGARPS<br>GEPGCSCAQPAAEVAAPGWAQVRGRPG<br>EPPAASSAAGDAGWPNKHTLRILQDFS<br>SDPSSNLSSHSLEKLPPAAEPAERALR<br>GRDPGALRPHDPAHRPLLRDPGPRRSE<br>SPPGPGGDASLLARLFEHPLYRVAVPP<br>LTEEDVLFNVNSDTRLSPKAAENPDWP<br>HAGAEGAEFLSPGEAAVDSYPNWLKFH<br>IGINRYELYSRHNPAIEALLHDLSSQR<br>ITSVAMKSGGTQLKLIMTFQNYGQALF | 138 |

TABLE 8-continued

Fam20C kinase

| Name | Type | Amino acid sequence | SEQ ID NO |
|---|---|---|---|
| | | KPMKQTREQETPPDFFYFSDYERHNAE<br>IAAFHLDRILDFRRVPPVAGRMVNMTK<br>EIRDVTRDKKLWRTFFISPANNICFYG<br>ECSYYCSTEHALCGKPDQIEGSLAAFL<br>PDLSLAKRKTWRNPWRRSYHKRKKAEW<br>EVDPDYCEEVKQTPPYDSSHRILDVMD<br>MTIFDFLMGNMDRHHYETFEKFGNETF<br>IIHLANGRGFGKYSHDELSILVPLQQC<br>CRIRKSTYLRLQLLAKEEYKLSLLMAE<br>SLRGDQVAPVLYQPHLEALDRRLRVVL<br>KAVRDCVERNGLHSVVDDDLDTEHRAA<br>SAR | |
| Fam20C (D456A)-KDEL | aa | MVFLVACALHIALDLLPRLERRGARPS<br>GEPGCSCAQPAAEVAAPGWAQVRGRPG<br>EPPAASSAAGDAGWPNKHTLRILQDFS<br>SDPSSNLSSHSLEKLPPAAEPAERALR<br>GRDPGALRPHDPAHRPLLRDPGPRRSE<br>SPPGPGGDASLLARLFEHPLYRVAVPP<br>LTEEDVLFNVNSDTRLSPKAAENPDWP<br>HAGAEGAEFLSPGEAAVDSYPNWLKFH<br>IGINRYELYSRHNPAIEALLHDLSSQR<br>ITSVAMKSGGTQLKLIMTFQNYGQALF<br>KPMKQTREQETPPDFFYFSDYERHNAE<br>IAAFHLDRILDFRRVPPVAGRMVNMTK<br>EIRDVTRDKKLWRTFFISPANNICFYG<br>ECSYYCSTEHALCGKPDQIEGSLAAFL<br>PDLSLAKRKTWRNPWRRSYHKRKKAEW<br>EVDPDYCEEVKQTPPYDSSHRILDVMD<br>MTIFDFLMGNMDRHHYETFEKFGNETF<br>IIHLANGRGFGKYSHDELSILVPLQQC<br>CRIRKSTYLRLQLLAKEEYKLSLLMAE<br>SLRGDQVAPVLYQPHLEALDRRLRVVL<br>KAVRDCVERNGLHSVVDDDLDTEHRAA<br>SARGGGSKDEL | 139 |
| Fam20C (D456A)-KDEL | DNA | atggtgttcctggtggcctgcgcgctg<br>cacatcgccctggacctgctgcccagg<br>ctggagcgacgcggcgcgcggccctcg<br>ggggagcccggctgttcgtgcgcgcag<br>cccgccgccgaggtggccgcgcccggc<br>tgggcccaggttcggggccgccccggg<br>gagcccccggccgcctcctccgccgcc<br>ggcgacgcgggctggcccaacaagcac<br>acgctccgcatcctgcaggacttcagc<br>tccgacccctcctccaacctctcgtcc<br>cactcgctggagaaactgccgcccgcg<br>gccgagccggccgagcgcgccttgcgg<br>gggcgggatcccggcgccctaagaccc<br>cacgaccccgcgcaccggccgctgctg<br>cgagaccccggcccgcgtcggtccgag<br>tcgcccccggccccggcggagacgcc<br>tccctcctggccaggctgttcgagcac<br>ccgctttaccgggtggcggttccgccg<br>ctcacggaggaggacgtcctgttcaat<br>gtgaacagcgacaccaggctcagcccc<br>aaagcggcggagaacccggactggccg<br>catgcgggtgctgaaggtgcagaattc<br>ctctcccccggggaggcggccgtggac<br>tcctatcccaactggctcaagttccac<br>attggtatcaaccggtacgagctgtac<br>tccagacacaacccggccatcgaggcc<br>ctgctgcacgacctcagctcccagagg<br>atcaccagcgtggccatgaagtcgggg<br>ggcacgcagctgaagctcatcatgacc<br>ttccagaattacgggcaagcgctgttc<br>aaacccatgaaacaaacgagggagcag<br>gagacacccccctgactttttttatttc<br>tctgactacgagaggcacaatgcggag<br>attgctgccttccacctggacaggatc<br>ctggacttccgccgggtccctcccgtg<br>gccggcaggatggtcaacatgaccaag<br>gagatccgggacgtcacacgggacaag<br>aagctctggaggaccttcttcatctct | 140 |

TABLE 8-continued

| Fam20C kinase | | | |
|---|---|---|---|
| Name | Type | Amino acid sequence | SEQ ID NO |
| | | ccagccaacaacatctgcttctacggc gagtgttcctactactgctccacggag cacgccctgtgcgggaagccagaccag atcgagggctcgctggcggccttcctg cccgacctgtccctggccaagaggaag acctggcggaacccttggcggcgttcc taccacaagcgcaagaaggccgagtgg gaggtggaccctgactactgcgaggag gtgaagcagacaccgccctacgacagc agccaccgcatcctggacgtcatggac atgacgatcttcgacttcctcatggga aacatggaccgtcaccactacgagact tttgagaagtttgggaatgaaacgttc atcatccacttaGCTaatggaagaggg tttgggaagtattcgcacgacgagctc tccatcctggtgccgctacagcagtgc tgcaggatccggaagtccacctacctg cgtctgcagctcctggccaaggaggag tacaagctgagcctgctgatggccgag tctctgcgggggggaccaggtggcaccc gtgctgtaccagccgcacctggaggcc ctggaccggcggctccgcgtcgtgcta aaggccgtccgggactgcgtggagagg aacgggctccacagcgtggtggatgac gacctggacactgagcacagagccgcc tcggcgaggGGAGGTGGATCAAAAGAT GAACTG | |

TABLE 9

| Immunomodulatory domains | | |
|---|---|---|
| SEQ ID NO | Description | Sequence |
| 1 | IL-2 | APTSSSTKKTQLQLEHLLLDLQMILNGINNYKNPKLTRMLTFKFYMPKKATELKHL QCLEEELKPLEEVLNLAQSKNFHLRPRDLISNINVIVLELKGSETTFMCEYADETA TIVEFLNRWITFCQSIISTLT |
| 2 | Wild Type IL12B without signal (IL12B) Amino Acids | IWELKKDVYVVELDWYPDAPGEMVVLTCDTPEEDGITWTLDQSSEVLGSGKTLTIQ VKEFGDAGQYTCHKGGEVLSHSLLLLHKKEDGIWSTDILKDQKEPKNKTFLRCEAK NYSGRFTCWWLTTISTDLTFSVKSSRGSSDPQGVTCGAATLSAERVRGDNKEYEYS VECQEDSACPAAEESLPIEVMVDAVHKLKYENYTSSFFIRDIIKPDPPKNLQLKPL KNSRQVEVSWEYPDTWSTPHSYFSLTFCVQVQGKSKREKKDRVFTDKTSATVICRK NASISVRAQDRYYSSSWSEWASVPCS |
| 3 | Wild Type IL12A without signal peptide Amino acids | RNLPVATPDPGMFPCLHHSQNLLRAVSNMLQKARQTLEFYPCTSEEIDHEDITKDK TSTVEACLPLELTKNESCLNSRETSFITNGSCLASRKTSFMMALCLSSIYEDLKMY QVEFKTMNAKLLMDPKRQIFLDQNMLAVIDELMQALNENSETVPQKSSLEEPDFYK TKIKLCILLHAFRIRAVTIDRVMSYLNAS |
| 4 | IL-15Ra | ITCPPPMSVEHADIWVKSYSLYSRERYICNSGFKRKAGTSSLTECVLNKATNVAHW TTPSLKCIRDPALVHQRPAPPSTVTTAGVTPQPESLSPSGKEPAASSPSSNNTAAT TAAIVPGSQLMPSKSPSTGTTEISSHESSHGTPSQTTAKNWELTASASHQPPGVYP QGHSDTT |
| 5 | IL-15 | NWVNVISDLKKIEDLIQSMHIDATLYTESDVHPSCKVTAMKCFLLELQVISLESGD ASIHDTVENLIILANNSLSSNGNVTESGCKECEELEEKNIKEFLQSFVHIVQMFIN TS |
| 6 | TNF-alpha | VRSSSRTPSDKPVAHVVANPQAEGQLQWLNRRANALLANGVELRDNQLVVPSEGLY LIYSQVLFKGQGCPSTHVLLTHTISRIAVSYQTKVNLLSAIKSPCQRETPEGAEAK PWYEPIYLGGVFQLEKGDRLSAEINRPDYLDFAESGQVYFGIIAL |
| 7 | IFN-gamma | QDPYVKEAENLKKYFNAGHSDVADNGTLFLGILKNWKEESDRKIMQSQIVSFYFKL FKNFKDDQSIQKSVETIKEDMNVKFFNSNKKKRDDFEKLTNYSVTDLNVQRKAIHE LIQVMAELSPAAKTGKRKRSQMLFRG |
| 8 | IFN-alpha | CDLPQTHSLGSRRTLMLLAQMRKISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKE |
| 9 | IL-21 | QGQDRHMIRMRQLIDIVDQLKNYVNDLVPEFLPAPEDVETNCEWSAFSCFQKAQLK SANTGNNERIINVSIKKLKRKPPSTNAGRRQKHRLTCPSCDSYEKKPPKEFLERFK SLLQKMIHQHLSSRTHGSEDS |
| 10 | IL-6 | LAPRRCPAQEVARGVLTSLPGDSVTLTCPGVEPEDNATVHWVLRKPAAGSHPSRWA GMGRRLLLRSVQLHDSGNYSCYRAGRPAGTVHLLVDVPPEEPQLSCFRKSPLSNVV CEWGPRSTPSLTTKAVLLVRKFQNSPAEDFQEPCQYSQESQKFSCQLAVPEGDSSF YIVSMCVASSVGSKFSKTQTFQGCGILQPDPPANITVTAVARNPRWLSVTWQDPHS WNSSFYRLRFELRYRAERSKTFTTWMVKDLQHHCVIHDAWSGLRHVVQLRAQEEFG |

TABLE 9-continued

| Immunomodulatory domains | | |
|---|---|---|
| SEQ ID NO | Description | Sequence |
| | | QGEWSEWSPEAMGTPWTESRSPPAENEVSTPMQALTTNKDDDNILFRDSANATSLP VQDSSSVPLPTFLVAGGSLAFGTLLCIAIVLRFKKTWKLRALKEGKTSMHPPYSLG QLVPERPRPTPVLVPLISPPVSPSSLGSDNTSSHNRPDARDPRSPYDISNTDYFFP R |
| 11 | IL-5 | DLLPDEKISLLPPVNFTIKVTGLAQVLLQWKPNPDQEQRNVNLEYQVKINAPKEDD YETRITESKCVTILHKGFSASVRTILQNDHSLLASSWASAELHAPPGSPGTSIVNL TCTTNTTEDNYSRLRSYQVSLHCTWLVGTDAPEDTQYFLYYRYGSWTEECQEYSKD TLGRNIACWFPRTFILSKGRDWLAVLVNGSSKHSAIRPFDQLFALHAIDQINPPLN VTAEIEGTRLSIQWEKPVSAFPIHCFDYEVKIHNTRNGYLQIEKLMTNAFISIIDD LSKYDVQVRAAVSSMCREAGLWSEWSQPIYVGNDEHKPLREWFVIVIMATICFILL ILSLICKICHLWIKLEPPIPAPKSNIKDLFVTTNYEKAGSSETEIEVICYIEKPGV ETLEDSVF |
| 12 | IL-8 | AVLPRSAKELRCQCIKTYSKPFHPKFIKELRVIESGPHCANTEIIVKLSDGRELCL DPKENWVQRVVEKFLKRAENS |
| 13 | IL-7 | DCDIEGKDGKQYESVLMVSIDQLLDSMKEIGSNCLNNEFNFFKRHICDANKEGMFL FRAARKLRQFLKMNSTGDFDLHLLKVSEGTTILLNCTGQVKGRKPAALGEAQPTKS LEENKSLKEQKKLNDLCFLKRLLQEIKTCWNKILMGTKEH |
| 14 | IL-17A | GITIPRNPGCPNSEDKNFPRTVMVNLNIHNRNTNTNPKRSSDYYNRSTSPWNLHRN EDPERYPSVIWEAKCRHLGCINADGNVDYHMNSVPIQQEILVLRREPPHCPNSFRL EKILVSVGCTCVTPIVHHVA |
| 15 | IL-23alpha | RAVPGGSSPAWTQCQQLSQKLCTLAWSAHPLVGHMDLREEGDEETTNDVPHIQCGD GCDPQGLRDNSQFCLQRIHQGLIFYEKLLGSDIFTGEPSLLPDSPVGQLHASLLGL SQLLQPEGHHWETQQIPSLSPSQPWQRLLLRFKILRSLQAFVAVAARVFAHGAATL SP |
| 16 | IL-18 | YFGKLESKLSVIRNLNDQVLFIDQGNRPLFEDMTDSDCRDNAPRTIFIISMYKDSQ PRGMAVTISVKCEKISTLSCENKIISFKEMNPPDNIKDTKSDIIFFQRSVPGHDNK MQFESSSYEGYFLACEKERDLFKLILKKEDELGDRSIMFTVQNED |
| 17 | IL-1alpha | SAPFSFLSNVKYNFMRIIKYEFILNDALNQSIIRANDQYLTAAALHNLDEAVKFDM GAYKSSKDDAKITVILRISKTQLYVTAQDEDQPVLLKEMPEIPKTITGSETNLLFF WETHGTKNYFTSVAHPNLFIATKQDYWVCLAGGPPSITDFQILENQA |
| 18 | IL-1beta | APVRSLNCTLRDSQQKSLVMSGPYELKALHLQGQDMEQQVVESMSFVQGEESNDKI PVALGLKEKNLYLSCVLKDDKPTLQLESVDPKNYPKKKMEKRFVFNKIEINNKLEF ESAQFPNWYISTSQAENMPVFLGGTKGGQDITDFTMQFVSS |
| 19 | IL-4 | HKCDITLQEIIKTLNSLTEQKTLCTELTVTDIFAASKNTTEKETFCRAATVLRQFY SHHEKDTRCLGATAQQFHRHKQLIRFLKRLDRNLWGLAGLNSCPVKEANQSTLENF LERLKTIMREKYSKCSS |
| 20 | IL-3 | APMTQTTPLKTSWVNCSNMIDEIITHLKQPPLPLLDFNNLNGEDQDILMENNLRRP NLEAFNRAVKSLQNASAIESILKNLLPCLPLATAAPTRHPIHIKDGDWNEFRRKLT FYLKTLENAQAQQTTLSLAIF |
| 21 | IL-10 | SPGQGTQSENSCTHFPGNLPNMLRDLRDAFSRVKTFFQMKDQLDNLLLKESLLEDF KGYLGCQALSEMIQFYLEEVMPQAENQDPDIKAHVNSLGENLKTLRLRLRRCHRFL PCENKSKAVEQVKNAFNKLQEKGIYKAMSEFDIFINYIEAYMTMKIRN |
| 22 | IL-13 | PVPPSTALRELIEELVNITQNQKAPLCNGSMVWSINLTAGMYCAALESLINVSGCS AIEKTQRMLSGFCPHKVSAGQFSSLHVRDTKIEVAQFVKDLLLHLKKLFREGRFN |
| 23 | IL-17a | GITIPRNPGCPNSEDKNFPRTVMVNLNIHNRNTNTNPKRSSDYYNRSTSPWNLHRN EDPERYPSVIWEAKCRHLGCINADGNVDYHMNSVPIQQEILVLRREPPHCPNSFRL EKILVSVGCTCVTPIVHHVA |
| 24 | IL-9 | QGCPTLAGILDINFLINKMQEDPASKCHCSANVTSCLCLGIPSDNCTRPCFSERLS QMTNTTMQTRYPLIFSRVKKSVEVLKNNKCPYFSCEQPCNQTTAGNALTFLKSLLE IFQKEKMRGMRGKI |
| 25 | IFN-gamma | QDPYVKEAENLKKYFNAGHSDVADNGTLFLGILKNWKEESDRKIMQSQIVSFYFKL FKNEKDDQSIQKSVETIKEDMNVKFFNSNKKKRDDFEKLTNYSVTDLNVQRKAIHE LIQVMAELSPAAKTGKRKRSQMLFRG |

TABLE 9-continued

| Immunomodulatory domains | | |
|---|---|---|
| SEQ ID NO | Description | Sequence |
| 26 | IFN-alpha | CDLPQTHSLGSRRTLMLLAQMRKISLFSCLKDRHDFGFPQEEFGNQFQKAETIPVL HEMIQQIENLESTKDSSAAWDETLLDKEYTELYQQLNDLEACVIQGVGVTETPLMK EDSILAVRKYFQRITLYLKEKKYSPCAWEVVRAEIMRSFSLSTNLQESLRSKE |
| 27 | GM-CSF | APARSPSPSTQPWEHVNAIQEARRLLNLSRDTAAEMNETVEVISEMFDLQEPTCLQ TRLELYKQGLRGSLTKLKGPLTMMASHYKQHCPPTPETSCATQIITFESFKENLKD FLLVIPFDCWEPVQE |
| 28 | FLT3L | TQDCSFQHSPISSDFAVKIRELSDYLLQDYPVTVASNLQDEELCGGLWRLVLAQRW MERLKTVAGSKMQGLLERVNTEIHFVTKCAFQPPPSCLRFVQTNISRLLQETSEQL VALKPWITRQNFSRCLELQCQPDSSTLPPPWSPRPLEATAPTAPQPPLLLLLLLPV GLLLLAAAWCLHWQRTRRRTPRPGEQVPPVPSPQDLLLVEH |
| 29 | G-CSF | ATPLGPASSLPQSFLLKCLEQVRKIQGDGAALQEKLVSECATYKLCHPEELVLLGH SLGIPWAPLSSCPSQALQLAGCLSQLHSGLFLYQGLLQALEGISPELGPTLDTLQL DVADFATTIWQQMEELGMAPALQPTQGAMPAFASAFQRRAGGVLVASHLQSFLEVS YRVLRHLAQP |
| 30 | LIF | SPLPITPVNATCAIRHPCHNNLMNQIRSQLAQLNGSANALFILYYTAQGEPFPNNL DKLCGPNVTDFPPFHANGTEKAKLVELYRIVVYLGTSLGNITRDQKILNPSALSLH SKLNATADILRGLLSNVLCRLCSKYHVGHVDVTYGPDTSGKDVFQKKKLGCQLLGK YKQIIAVLAQAF |
| 31 | M-CSF | EEVSEYCSHMIGSGHLQSLQRLIDSQMETSCQITFEFVDQEQLKDPVCYLKKAFLL VQDIMEDTMRFRDNTPNAIAIVQLQELSLRLKSCFTKDYEEHDKACVRTFYETPLQ LLEKVKNVFNETKNLLDKDWNIFSKNCNNSFAECSSQDVVTKPDCNCLYPKAIPSS DPASVSPHQPLAPSMAPVAGLTWEDSEGTEGSSLLPGEQPLHTVDPGSAKQRPPRS TCQSFEPPETPVVKDSTIGGSPQPRPSVGAFNPGMEDILDSAMGTNWVPEEASGEA SEIPVPQGTELSPSRPGGGSMQTEPARPSNFLSASSPLPASAKGQQPADVTGTALP RVGPVRPTGQDWNHTPQKTDHPSALLRDPPEPGSPRISSLRPQGLSNPSTLSAQPQ LSRSHSSGSVLPLGELEGRRSTRDRRSPAEPEGGPASEGAARPLPRFNSVPLTDTG HERQSEGSFSPQLQESVFHLLVPSVILVLLAVGGLLFYRWRRRSHQEPQRADSPLE QPEGSPLTQDDRQVELPV |
| 32 | MIP-2 | APLATELRCQCLQTLQGIHLKNIQSVKVKSPGPHCAQTEVIATLKNGQKACLNPAS PMVKKIIEKMLKNGKSN |
| 33 | MIP-1beta | APMGSDPPTACCFSYTARKLPRNFVVDYYETSSLCSQPAVVFQTKRSKQVCADPSE SWVQEYVYDLELN |
| 34 | KP (aka CXCL1) | ASVATELRCQCLQTLQGIHPKNIQSVNVKSPGPHCAQTEVIATLKNGRKACLNPAS PIVKKIIEKMLNSDKSN |
| 35 | MIG (aka CXCL9) | TPVVRKGRCSCISTNQGTIHLQSLKDLKQFAPSPSCEKIEIIATLKNGVQTCLNPD SADVKELIKKWEKQVSQKKKQKNGKKHQKKKVLKVRKSQRSRQKKTT |
| 36 | IP-10 (CXCL10) | VPLSRTVRCTCISISNQPVNPRSLEKLEIIPASQFCPRVEIIATMKKKGEKRCLNP ESKAIKNLLKAVSKERSKRSP |
| 37 | MCP-1 | QPDAINAPVTCCYNFTNRKISVQRLASYRRITSSKCPKEAVIFKTIVAKEICADPK QKWVQDSMDHLDKQTQTPKT |
| 38 | Eotaxin | GPASVPTTCCFNLANRKIPLQRLESYRRITSGKCPQKAVIFKTKLAKDICADPKKK WVQDSMKYLDQKSPTPKP |
| 39 | RANTES | SPYSSDTTPCCFAYIARPLPRAHIKEYFYTSGKCSNPAVVFVTRKNRQVCANPEKK WVREYINSLEMS |
| 40 | LIX | AGPAAAVLRELRCVCLQTTQGVHPKMISNLQVFAIGPQCSKVEVVASLKNGKEICL DPEAPFLKKVIQKILDGGNKEN |
| 41 | MIP-1alpha | SLAADTPTACCFSYTSRQIPQNFIADYFETSSQCSKPGVIFLTKRSRQVCADPSEE WVQKYVSDLELSA |
| 42 | PD-1 | MQIPQAPWPVVWAVLQLGWRPGWFLDSPDPWNPPTFFPALLVVTEGDNATFTCSFS NTSESFVLNWYRMSPSNQTDKLAAFPEDRSQPGQDCRFRVTQLPNGRDFHMSVVRA RRNDSGTYLCGAISLAPKAQIKESLRAELRVTERRAEVPTAHPSPSPRPAGQFQTL VVGVVGGLLGSLVLLVWVLAVICSRAARGTIGARRTGQPLKEDPSAVPVFSVDYGE LDFQWREKTPEPPVPCVPEQTEYATIVFPSGMGTSSPARRGSADGPRSAQPLRPED GHCSWPL |
| 43 | PD-L-1 | MRIFAVFIFMTYWHLLNAFTVTVPKDLYVVEYGSNMTIECKFPVEKQLDLAALIVY WEMEDKNITQFVHGEEDLKVQHSSYRQRARLLKDQLSLGNAALQITDVKLQDAGVY RCMISYGGADYKRITVKVNAPYNKINQRILVVDPVTSEHELTCQAEGYPKAEVIWT SSDHQVLSGKTTTTNSKREEKLFNVTSTLRINTTTNEIFYCTFRRLDPEENHTAEL |

TABLE 9-continued

| Immunomodulatory domains | | |
|---|---|---|
| SEQ ID NO | Description | Sequence |
| | | VIPELPLAHPPNERTHLVILGAILLCLGVALTFIFRLRKGRMMDVKKCGIQDTNSK KQSDTHLEET |
| 44 | CTLA-4 | MACLGFQRHKAQLNLATRTWPCTLLFFLLFIPVFCKAMHVAQPAVVLASSRGIASF VCEYASPGKATEVRVTVLRQADSQVTEVCAATYMMGNELTFLDDSICTGTSSGNQV NLTIQGLRAMDTGLYICKVELMYPPPYYLGIGNGTQIYVIDPEPCPDSDFLLWILA AVSSGLFFYSFLLTAVSLSKMLKKRSPLTTGVYVKMPPTEPECEKQFQPYFIPIN |
| 45 | LAG3 | MWEAQFLGLLFLQPLWVAPVKPLQPGAEVPVVWAQEGAPAQLPCSPTIPLQDLSLL RRAGVTWQHQPDSGPPAAAPGHPLAPGPHPAAPSSWGPRPRRYTVLSVGPGGLRSG RLPLQPRVQLDERGRQRGDFSLWLRPARRADAGEYRAAVHLRDRALSCRLRLRLGQ ASMTASPPGSLRASDWVILNCSFSRPDRPASVHWFRNRGQGRVPVRESPHHHLAES FLFLPQVSPMDSGPWGCILTYRDGFNVSIMYNLTVLGLEPPTPLTVYAGAGSRVGL PCRLPAGVGTRSFLTAKWTPPGGGPDLLVTGDNGDFTLRLEDVSQAQAGTYTCHIH LQEQQLNATVTLAIITVTPKSFGSPGSLGKLLCEVTPVSGQERFVWSSLDTPSQRS FSGPWLEAQEAQLLSQPWQCQLYQGERLLGAAVYFTELSSPGAQRSGRAPGALPAG HLLLFLILGVLSLLLLVTGAFGFHLWRRQWRPRRFSALEQGIHPPQAQSKIEELEQ EPEPEPEPEPEPEPEPEPEQL |
| 46 | TIM3 | MFSHLPFDCVLLLLLLLLTRSSEVEYRAEVGQNAYLPCFYTPAAPGNLVPVCWGKG ACPVFECGNVVLRTDERDVNYWTSRYWLNGDFRKGDVSLTIENVTLADSGIYCCRI QIPGIMNDEKENLKLVIKPAKVTPAPTRQRDETAAFPRMLTTRGHGPAETQTLGSL PDINLTQISTLANELRDSRLANDLRDSGATIRGIYIGAGICAGLALALIFGALIFK WYSHSKEKIQNLSLISLANLPPSGLANAVAEGIRSEENIYTIEENVYEVEEPNEYY CYVSSRQQPSQPLGCRFAMP |
| 47 | B7-H3 | MLRRRGSPGMGVHVGAALGALWFCLTGALEVQVPEDPVVALVGTDATLCCSFSPEP GFSLQLNLIWQLTDTKQLVHSFAEGQDQGSAYANRTALFPDLLAQGNASLRLQRVR VADEGSFCFVSIRDFGSAAVSLQVAAPYSKPSMTLEPNKDLRPGDTVTITCSSYQG YPEAEVFWQDGQGVPLTGNVTTSQMANEQGLFDVHSILRVVLGANGTYSCLVRNPV LQQDAHSSVTITPQRSPTGAVEVQVPEDPVVALVGTDATLRCSFSPEPGFSLAQLN LIWQLTDTKQLVHSFTEGRDQGSAYANRTALFPDLLAQGNASLRLQRVRVADEGSF TCFVSIRDFGSAAVSLQVAAPYSKPSMTLEPNKDLRPGDTVTITCSSYRGYPEAEV FWQDGQGVPLTGNVTTSQMANEQGLFDVHSVLRVVLGANGTYSCLVRNPVLQQDAH GSVTITGQPMTFPPEALWVTVGLSVCLIALLVALAFVCWRKIKQSCEEENAGAEDQ DGEGEGSKTALQPLKHSDSKEDDGQEIA |
| 48 | B7-H4 | MASLGQILFWSIISIIIILAGAIALIIGEGISAFSMPEVNVDYNASSETLRCEAPR WFPQPTVVWASQVDQGANFSEVSNTSFELNSENVTMKVVSVLYNVTINNTYSCMIE NDIAKATGDIKVTESEIKRRSHLQLLNSKASLCVSSFFAISWALLPLSPYLMLK |
| 49 | TNF-alpha extracellular domain | GPQREEFPRDLSLISPLAQAVRSSSRTPSDKPVAHVVANPQAEGQLQWLNRRANAL LANGVELRDNQLVVPSEGLYLIYSQVLFKGQGCPSTHVLLTHTISRIAVSYQTKVN LLSAIKSPCQRETPEGAEAKPWYEPTYLGGVFQLEKGDRLSAEINRPDYLDFAESG QVYFGIIAL |
| 50 | LIGHT extracellular domain | LQLHWRLGEMVTRLPDGPAGSWEQLIQERRSHEVNPAAHLTGANSSLTGSGGPLLW ETQLGLAFLRGLSYHDGALVVTKAGYYYTYSKVQLGGVGCPLGLASTITHGLYKRT PRYPEELELLVSQQSPCGRATSSSRVWWDSSFLGGVVHLEAGEKVVVRVLDERLVR LRDGTRSYFGAFMV |
| 51 | LT-alpha extracellular domain | LPGVGLTPSAAQTARQHPKMHLAHSTLKPAAHLIGDPSKQNSLLWRANTDRAFLQD GFSLSNNSLLVPTSGIYFVYSQVVFSGKAYSPKATSSPLYLAHEVQLFSSQYPFHV PLLSSQKMVYPGLQEPWLHSMYHGAAFQLTQGDQLSTHTDGIPHLVLSPSTVFFGA FAL |
| 52 | LT-beta extracellular domain | QDQGGLVTETADPGAQAQQGLGFQKLPEEEPETDLSPGLPAAHLIGAPLKGQGLGW ETTKEQAFLTSGTQFSDAEGLALPQDGLYYLYCLVGYRGRAPPGGGDPQGRSVTLR SSLYRAGGAYGPGTPELLLEGAETVTPVLDPARRQGYGPLWYTSVGFGGLVQLRRG ERVYVNISHPDMVDFARGKTFFGAVMVG |
| 53 | BTLA extracellular domain | KESCDVQLYIKRQSEHSILAGDPFELECPVKYCANRPHVTWCKLNGTTCVKLEDRQ TSWKEEKNISFFILHFEPVLPNDNGSYRCSANFQSNLIESHSTTLYVTDVKSASER PSKDEMASRPWLLYR |
| 54 | CD160 extracellular domain | INITSSASQEGTRLNLICTVWHKKEEAEGFVVFLCKDRSGDCSPETSLKQLRLKRD PGIDGVGEISSQLMFTISQVTPLHSGTYQCCARSQKSGIRLQGHFFSILFTETGNY TVTGLKQRQHLEFSHNEGTLS |

TABLE 9-continued

| Immunomodulatory domains | | |
|---|---|---|
| SEQ ID NO | Description | Sequence |
| 55 | CD40L extracellular domain | MQKGDQNPQIAAHVISEASSKTTSVLQWAEKGYYTMSNNLVTLENGKQLTVKRQGL YYIYAQVTFCSNREASSQAPFIASLCLKSPGRFERILLRAANTHSSAKPCGQQSIH LGGVFELQPGASVFVNVTDPSQVSHGTGFTSFGLLKL |
| 56 | FasL extracellular domain | QIGHPSPPPEKKELRKVAHLTGKSNSRSMPLEWEDTYGIVLLSGVKYKKGGLVINE TGLYFVYSKVYFRGQSCNNLPLSHKVYMRNSKYPQDLVMMEGKMMSYCTTGQMWAR SSYLGAVFNLTSADHLYVNVSELSLVNFEESQTFFGLYKL |
| 57 | CD30L extracellular domain | FPQDRPFEDTCHGNPSHYYDKAVRRCCYRCPMGLFPTQQCPQRPTDCRKQCEPDYY LDEADRCTACVTCSRDDLVEKTPCAWNSSRVCECRPGMFCSTSAVNSCARCFEHSV CPAGMIVKFPGTAQKNTVCEPASPGVSPACASPENCKEPSSGTIPQAKPTPVSPAT SSASTMPVRGGTRLAQEAASKLTRAPDSPSSVGRPSSDPGLSPTQPCPEGSGDCRK QCEPDYYLDEAGRCTACVSCSRDDLVEKTPCAWNSSRTCECRPGMICATSATNSCA RCVPYPICAAETVTKPQDMAEKDTTFEAPPLGTQPDCNPTPENGEAPASTSPTQSL LVDSQASKTLPIPTSAPVALSSTGKPVLDAGPVLFWVILVLVVVVGSSAFLLCHRR ACRKRIRQKLHLCYPVQTSQPKLELVDSRPRRSSTQLRSGASVTEPVAEERGLMSQ PLMETCHSVGAAYLESLPLQDASPAGGPSSPRDLPEPRVSTEHTNNKIEKIYIMKA DTVIVGTVKAELPEGRGLAGPAEPELEEELEADHTPHYPEQETEPPLGSCSDVMLS VEEEGKEDPLPTAASGK |
| 58 | 4-1BBL extracellular domain | ACPWAVSGARASPGSAASPRLREGPELSPDDPAGLLDLRQGMFAQLVAQNVLLIDG PLSWYSDPGLAGVSLTGGLSYKEDTKELVVAKAGVYYVFFQLELRRVVAGEGSGSV SLALHLQPLRSAAGAAALALTVDLPPASSEARNSAFGFQGRLLHLSAGQRLGVHLH TEARARHAWQLTQGATVLGLFRVTPEIPAGLPSPRSE |
| 59 | CD27L extracellular domain | ATPAPKSCPERHYWAQGKLCCQMCEPGTFLVKDCDQHRKAAQCDPCIPGVSFSPDH HTRPHCESCRHCNSGLLVRNCTITANAECACRNGWQCRDKECTECDPLPNPSLTAR SSQALSPHPQPTHLPYVSEMLEARTAGHMQTLADFRQLPARTLSTHWPPQRSLCSS DFIR |
| 60 | OX40L extracellular domain | LHCVGDTYPSNDRCCHECRPGNGMVSRCSRSQNTVCRPCGPGFYNDVVSSKPCKPC TWCNLRSGSERKQLCTATQDTVCRCRAGTQPLDSYKPGVDCAPCPPGHFSPGDNQA CKPWTNCTLAGKHTLQPASNSSDAICEDRDPPATQPQETQGPPARPITVQPTEAWP RTSQGPSTRPVEVPGGRA |
| 61 | TWEAK extracellular domain | SAPKGRKTRARRAIAAHYEVHPRPGQDGAQAGVDGTVSGWEEARINSSSPLRYNRQ IGEFIVTRAGLYYLYCQVHFDEGKAVYLKLDLLVDGVLALRCLEEFSATAASSLGP QLRLCQVSGLLALRPGSSLRIRTLPWAHLKAAPFLTYFGLFQVH |
| 62 | APRIL extracellular domain | AVLTQKQKKQHSVLHLVPINATSKDDSDVTEVMWQPALRRGRGLQAQGYGVRIQDA GVYLLYSQVLFQDVTFTMGQVVSREGQGRQETLFRCIRSMPSHPDRAYNSCYSAGV FHLHQGDILSVIIPRARAKLNLSPHGTFLGFVKL |
| 63 | BAFF extracellular domain | AVQGPEETVTQDCLQLIADSETPTIQKGSYTFVPWLLSFKRGSALEEKENKILVKE TGYFFIYGQVLYTDKTYAMGHLIQRKKVHVFGDELSLVTLFRCIQNMPETLPNNSC YSAGIAKLEEGDELQLAIPRENAQISLDGDVTFFGALKLL |
| 64 | RANKL extracellular domain | YFRAQMDPNRISEDGTHCIYRILRLHENADFQDTTLESQDTKLIPDSCRRIKQAFQ GAVQKELQHIVGSQHIRAEKAMVDGSWLDLAKRSKLEAQPFAHLTINATDIPSGSH KVSLSSWYHDRGWAKISNMITSNGKLIVNQDGFYYLYANICFRHHETSGDLATEYL QLMVYVTKTSIKIPSSHTLMKGGSTKYWSGNSEFHFYSINVGGFFKLRSGEEISIE VSNPSLLDPDQDATYFGAFKVRDID |
| 65 | TRAIL extracellular domain | TNELKQMQDKYSKSGIACELKEDDSYWDPNDEESMNSPCWQVKWQLRQLVRKMILR TSEETISTVQEKQQNISPLVRERGPQRVAAHITGTRGRSNTLSSPNSKNEKALGRK INSWESSRSGHSFLSNLHLRNGELVIHEKGFYYTYSQTYFRFQEEIKENTKNDKQM VQYIYKYTSYPDPILLMKSARNSCWSKDAEYGLYSIYQGGIFELKENDRIFVSVTN EHLIDMDHEASFFGAFLVG |
| 66 | EDA1 extracellular domain | ELRSELRRERGAESRLGGSGTPGTSGTLSSLGGLDPDSPITSHLGQPSPKQQPLEP GEAALHSDSQDGHQMALLNFFFPDEKPYSEEESRRVRRNKRSKSNEGADGPVKNKK KGKKAGPPGPNGPPGPPGPPGPQGPPGIPGIPGIPGTTVMGPPGPPGPPGPQGPPG LQGPSGAADKAGTRENQPAVVHLQGQGSAIQVKNDLSGGVLNDWSRITMNPKVFKL HPRSGELEVLVDGTYFIYSQVEVYYINFTDFASYEVVVDEKPFLQCTRSIETGKTN YNTCYTAGVCLLKARQKIAVKMVHADISINMSKHTTFFGAIRLGEAPAS |
| 67 | EDA2 extracellular domain | ELRSELRRERGAESRLGGSGTPGTSGTLSSLGGLDPDSPITSHLGQPSPKQQPLEP GEAALHSDSQDGHQGHQ |

TABLE 9-continued

| Immunomodulatory domains | | |
|---|---|---|
| SEQ ID NO | Description | Sequence |
| 68 | GITRL extracellular domain | QLETAKEPCMAKFGPLPSKWQMASSEPPCVNKVSDWKLEILQNGLYLIYGQVAPNA NYNDVAPFEVRLYKNKDMIQTLTNKSKIQNVGGTYELHVGDTIDLIFNSEHQVLKN NTYWGIILLANPQFIS |
| 69 | CD80 (B7-1) extracellular domain | VIHVTKEVKEVATLSCGHNVSVEELAQTRIYWQKEKKMVLTMMSGDMNIWPEYKNR TIFDITNNLSIVILALRPSDEGTYECVVLKYEKDAFKREHLAEVTLSVKADFPTPS ISDFEIPTSNIRRIICSTSGGFPEPHLSWLENGEELNAINTTVSQDPETELYAVSS KLDFNMTTNHSFMCLIKYGHLRVNQTENWNTTKQEHFPDN |
| 70 | CD86 (B7-2) extracellular domain | APLKIQAYFNETADLPCQFANSQNQSLSELVVFWQDQENLVLNEVYLGKEKFDSVH SKYMGRTSFDSDSWTLRLHNLQIKDKGLYQCIIHHKKPTGMIRIHQMNSELSVLAN FSQPEIVPISNITENVYINLTCSSIHGYPEPKKMSVLLRTKNSTIEYDGVMQKSQD NVTELYDVSISLSVSFPDVTSNMTIFCILETDKTRLLSSPFSIELEDPQPPPDHIP |
| 71 | ICOSLG extracellular domain | DTQEKEVRAMVGSDVELSCACPEGSRFDLNDVYVYWQTSESKTVVTYHIPQNSSLE NVDSRYRNRALMSPAGMLRGDFSLRLFNVTPQDEQKFHCLVLSQSLGFQEVLSVEV TLHVAANFSVPVVSAPHSPSQDELTFTCTSINGYPRPNVYWINKTDNSLLDQALQN DTVELNMRGLYDVVSVLRIARTPSVNIGCCIENVLLQQNLTVGSQTGNDIGERDKI TENPVSTGEKNAAT |
| 72 | MICA extracellular domain | EPHSLRYNLTVLSWDGSVQSGFLTEVHLDGQPFLRCDRQKCRAKPQGQWAEDVLGN KTWDRETRDLTGNGKDLRMTLAHIKDQKEGLHSLQEIRVCEIHEDNSTRSSQHFYY DGELFLSQNLETKEWTMPQSSRAQTLAMNVRNFLKEDAMKTKTHYHAMHADCLQEL RRYLKSGVVLRRTVPPMVNVTRSEASEGNITVTCRASGFYPWNITLSWRQDGVSLS HDTQQWGDVLPDGNGTYQTWVATRICQGEEQRFTCYMEHSGNHSTHPVPSGKVLVL QSHW |
| 73 | MICH extracellular domain | AEPHSLRYNLMVLSQDESVQSGFLAEGHLDGQPFLRYDRQKRRAKPQGQWAEDVLG AKTWDTETEDLTENGQDLRRTLTHIKDQKGGLHSLQEIRVCEIHEDSSTRGSRHFY YDGELFLSQNLETQESTVPQSSRAQTLAMNVTNEWKEDAMKTKTHYRAMQADCLQK LQRYLKSGVAIRRTVPPMVNVTCSEVSEGNITVTCRASSFYPRNITLTWRQDGVSL SHNTQQWGDVLPDGNGTYQTWVATRIRQGEEQRFTCYMEHSGNHGTHPVPSGKVLV LQSQRTD |
| 74 | ULBP1 extracellular domain | GWVDTHCLCYDFIITPKSRPEPQWCEVQGLVDERPFLHYDCVNHKAKAFASLGKKV NVTKTWEEQTETLRDVVDFLKGQLLDIQVENLIPIEPLTLQARMSCEHEAHGHGRG SWQFLENGQKFLLFDSNNRKWTALHPGAKKMTEKWEKNRDVTMFFQKISLGDCKMW LEEFLMYWEQMLDPTKPPSLAPG |
| 75 | ULBP2 extracellular domain | GRADPHSLCYDITVIPKFRPGPRWCAVQGQVDEKTFLHYDCGNKTVTPVSPLGKKL NVTTAWKAQNPVLREVVDILTEQLRDIQLENYTPKEPLTLQARMSCEQKAEGHSSG SWQFSFDGQIFLLFDSEKRMWTTVHPGARKMKEKWENDKVVAMSFHYFSMGDCIGW LEDFLMGMDSTLEPSAGAPLAMS |
| 76 | ULBP3 extracellular domain | DAHSLWYNFTIIHLPRHGQQWCEVQSQVDQKNFLSYDCGSDKVLSMGHLEEQLYAT DAWGKQLEMLREVGQRLRLELADTELEDFTPSGPLTLQVRMSCECEADGYIRGSWQ FSFDGRKFLLFDSNNRKWTVVHAGARRMKEKWEKDSGLTTFFKMVSMRDCKSWLRD FLMHRKKRLEPTAPPTMAPG |
| 77 | ULBP4 extracellular domain | HSLCFNFTIKSLSRPGQPWCEAQVFLNKNLFLQYNSDNNMVKPLGLLGKKVYATST WGELTQTLGEVGRDLRMLLCDIKPQIKTSDPSTLQVEMFCQREAERCTGASWQFAT NGEKSLLFDAMNMTWTVINHEASKIKETWKKDRGLEKYFRKLSKGDCDHWLREFLG HWEAMPEPTVSPVNASDIHWSSSSLPD |
| 78 | ULBP5, isoform 1 extracellular domain | GLADPHSLCYDITVIPKFRPGPRWCAVQGQVDEKTFLHYDCGSKTVTPVSPLGKKL NVTTAWKAQNPVLREVVDILTEQLLDIQLENYIPKEPLTLQARMSCEQKAEGHGSG SWQLSFDGQIFLLFDSENRMWTTVHPGARKMKEKWENDKDMTMSFHYISMGDCTGW LEDFLMGMDSTLEPSAGAPPTMSSG |
| 79 | ULBP5, isoform 2 extracellular domain | GLADPHSLCYDITVIPKFRPGPRWCAVQGQVDEKTFLHYDCGSKTVTPVSPLGKKL NVTTAWKAQNPVLREVVDILTEQLLDIQLENYIPKEPLTLQARMSCEQKAEGHGSG SWQLSFDGQIFLLFDSENRMWTTVHPGARKMKEKWENDKDMTMSFHYISMGDCTGW LEDFLMGMDSTLEPSAGGTV |
| 80 | ULBP6 extracellular domain | RRDDPHSLCYDITVIPKFRPGPRWCAVQGQVDEKTFLHYDCGNKTVTPVSPLGKKL NVTMAWKAQNPVLREVVDILTEQLLDIQLENYTPKEPLTLQARMSCEQKAEGHSSG SWQFSIDGQTFLLFDSEKRMWTTVHPGARKMKEKWENDKDVAMSFHYISMGDCIGW LEDFLMGMDSTLEPSAGAPLAMSSG |

TABLE 9-continued

| Immunomodulatory domains | | |
|---|---|---|
| SEQ ID NO | Description | Sequence |
| 81 | SLAMF1 extracellular domain | ASYGTGGRMMNCPKILRQLGSKVLLPLTYERINKSMNKSIHIVVTMAKSLENSVEN KIVSLDPSEAGPPRYLGDRYKFYLENLTLGIRESRKEDEGWYLMTLEKNVSVQRFC LQLRLYEQVSTPEIKVLNKTQENGTCTLILGCTVEKGDHVAYSWSEKAGTHPLNPA NSSHLLSLTLGPQHADNIYICTVSNPISNNSQTFSPWPGCRTDPSETKP |
| 82 | SLAMF2 extracellular domain | QGHLVHMTVVSGSNVTLNISESLPENYKQLTWFYTFDQKIVEWDSRKSKYFESKFK GRVRLDPQSGALYISKVQKEDNSTYIMRVLKKTGNEQEWKIKLQVLDPVPKPVIKI EKIEDMDDNCYLKLSCVIPGESVNYTWYGDKRPFPKELQNSVLETTLMPHNYSRCY TCQVSNSVSSKNGTVCLSPPCTLARS |
| 83 | SLAMF3 extracellular domain | KDSAPTVVSGILGGSVTLPLNISVDTEIENVIWIGPKNALAFARPKENVTIMVKSY LGRLDITKWSYSLCISNLTLNDAGSYKAQINQRNFEVTTEEEFTLFVYEQLQEPQV TMKSVKVSENFSCNITLMCSVKGAEKSVLYSWTPREPHASESNGGSILTVSRTPCD PDLPYICTAQNPVSQRSSLPVHVGQFCTDPGASRGGTTGETVVGVLGEPVTLPLAL PACRDTEKVVWLENTSIISKEREEAATADPLIKSRDPYKNRVWVSSQDCSLKISQL KIEDAGPYHAYVCSEASSVTSMTHVTLLIYRRLRKPKITWSLRHSEDGICRISLTC SVEDGGNTVMYTWTPLQKEAVVSQGESHLNVSWRSSENHPNLTCTASNPVSRSSHQ FLSENICSGPERNTK |
| 84 | SLAMF4 extracellular domain | CQGSADHVVSISGVPLQLQPNSIQTKVDSIAWKKLLPSQNGFHHILKWENGSLPSN TSNDRFSFIVKNLSLLIKAAQQQDSGLYCLEVTSISGKVQTATFQVFVFESLLPDK VEKPRLQGQGKILDRGRCQVALSCLVSRDGNVSYAWYRGSKLIQTAGNLTYLDEEV DINGTHTYTCNVSNPVSWESHTLNLTQDCQNAHQEFRFWP |
| 85 | SLAMF5 extracellular domain | KDSEIFTVNGILGESVTFPVNIQEPRQVKIIAWTSKTSVAYVTPGDSETAPVVTVT HRNYYERIHALGPNYNLVISDLRMEDAGDYKADINTQADPYTTTKRYNLQIYRRLG KPKITQSLMASVNSTCNVTLTCSVEKEEKNVTYNWSPLGEEGNVLQIFQTPEDQEL TYTCTAQNPVSNNSDSISARQLCADIAMGFRTHHTG |
| 86 | SLAMF6 extracellular domain | QSSLTPLMVNGILGESVTLPLEFPAGEKVNFITWLFNETSLAFIVPHETKSPEIHV TNPKQGKRLNFTQSYSLQLSNLKMEDTGSYRAQISTKTSAKLSSYTLRILRQLRNI QVTNHSQLFQNMTCELHLTCSVEDADDNVSFRWEALGNTLSSQPNLTVSWDPRISS EQDYTCIAENAVSNLSFSVSAQKLCEDVKIQYTDTKM |
| 87 | SLAMF7 extracellular domain | SGPVKELVGSVGGAVTFPLKSKVKQVDSIVWTENTTPLVTIQPEGGTIIVTQNRNR ERVDFPDGGYSLKLSKLKKNDSGIYYVGIYSSSLQQPSTQEYVLHVYEHLSKPKVT MGLQSNKNGTCVTNLTCCMEHGEEDVIYTWKALGQAANESHNGSILPISWRWGESD MTFICVARNPVSRNFSSPILARKLCEGAADDPDSSM |
| 88 | Human serum albumin (HSA) | DAHKSEVAHRFKDLGEENFKALVLIAFAQYLQQCPFEDHVKLVNEVTEFAKTCVAD ESAENCDKSLHTLFGDKLCTVATLRETYGEMADCCAKQEPERNECFLQHKDDNPNL PRLVRPEVDVMCTAFHDNEETFLKKYLYEIARRHPYFYAPELLFFAKRYKAAFTEC CQAADKAACLLPKLDELRDEGKASSAKQGLKCASLQKFGERAFKAWAVARLSQRFP KAEFAEVSKLVTDLTKVHTECCHGDLLECADDRADLAKYICENQDSISSKLKECCE KPLLEKSHCIAEVENDEMPADLPSLAADFVGSKDVCKNYAEAKDVFLGMFLYEYAR RHPDYSVVLLLRLAKTYETTLEKCCAAADPHECYAKVFDEFKPLVEEPQNLIKQNC ELFEQLGEYKFQNALLVRYTKKVPQVSTPTLVEVSRNLGKVGSKCCKHPEAKRMPC AEDCLSVFLNQLCVLHEKTPVSDRVTKCCTESLVNGRPCFSALEVDETYVPKEFNA ETFTFHADICTLSEKERQIKKQTALVELVKHKPKATKEQLKAVMDDFAAFVEKCCK ADDKETCFAEEGKKLVAASQAALGL |
| 89 | Human IgG1 constant region (amino acid sequence) | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 90 | Human IgG1 Fc domain (amino acid sequence) | EPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKVSNKA LPAPIEKTISKAKGQPREPQVYTLPPSRDELTKNQVSLTCLVKGFYPSDIAVEWES NGQPENNYKTTPPVLDSDGSFFLYSKLTVDKSRWQQGNVFSCSVMHEALHNHYTQK SLSLSPGK |

TABLE 10

Exemplary immunomodulatory fusion proteins

| Name | Type | Amino acid sequence | SEQ ID NO |
|---|---|---|---|
| Mouse serum albumin (MSA) | aa | EAHKSEIAHRYNDLGEQHFKGLVLIAFSQYLQKCSYDEHAKLVQEVT<br>DFAKTCVADESAANCDKSLHTLFGDKLCAIPNLRENYGELADCCTKQ<br>EPERNECFLQHKDDNPSLPPFERPEAEAMCTSFKENPTTFMGHYLHE<br>VARRHPYFYAPELLYYAEQYNEILTQCCAEADKESCLTPKLDGVKEK<br>ALVSSVRQRMKCSSMQKFGERAFKAWAVARLSQTFPNADFAEITKLA<br>TDLTKVNKECCHGDLLECADDRAELAKYMCENQATISSKLQTCCDKP<br>LLKKAHCLSEVEHDTMPADLPAIAADFVEDQEVCKNYAEAKDVFLGT<br>FLYEYSRRHPDYSVSLLLRLAKKYEATLEKCCAEANPPACYGTVLAE<br>FQPLVEEPKNLVKTNCDLYEKLGEYGFQNAILVRYTQKAPQVSTPTL<br>VEAARNLGRVGTKCCTLPEDQRLPCVEDYLSAILNRVCLLHEKTPVS<br>EHVTKCCSGSLVERRPCFSALTVDETYVPKEFKAETFTFHSDICTLP<br>EKEKQIKKQTALAELVKHKPKATAEQLKTVMDDFAQFLDTCCKAADK<br>DTCFSTEGPNLVTRCKDALA | 141 |
| | DNA | GAAGCACACAAGAGTGAGATCGCCCATCGGTATAATGATTTGGGAGA<br>ACAACATTTCAAAGGCCTAGTCCTGATTGCCTTTTCCCAGTATCTCC<br>AGAAATGCTCATACGATGAGCATGCCAAATTAGTGCAGGAAGTAACA<br>GACTTTGCAAAGACGTGTGTTGCCGATGAGTCTGCCGCCAACTGTGA<br>CAAATCCCTTCACACTCTTTTTGGAGATAAGTTGTGTGCCATTCCAA<br>ACCTCCGTGAAAACTATGGTGAACTGGCTGACTGCTGTACAAAACAA<br>GAGCCCGAAAGAAACGAATGTTTCCTGCAACACAAAGATGACAACCC<br>CAGCCTGCCACCATTTGAAAGGCCAGAGGCTGAGGCCATGTGCACCT<br>CCTTTAAGGAAAACCCAACCACCTTTATGGGACACTATTTGCATGAA<br>GTTGCCAGAAGACATCCTTATTTCTATGCCCCAGAACTTCTTTACTA<br>TGCTGAGCAGTACAATGAGATTCTGACCCAGTGTTGTGCAGAGGCTG<br>ACAAGGAAAGCTGCCTGACCCCGAAGCTTGATGGTGTGAAGGAGAAA<br>GCATTGGTCTCATCTGTCCGTCAGAGAATGAAGTGCTCCAGTATGCA<br>GAAGTTTGGAGAGAGAGCTTTTAAAGCATGGGCAGTAGCTCGTCTGA<br>GCCAGACATTCCCCAATGCTGACTTTGCAGAAATCACCAAATTGGCA<br>ACAGACCTGACCAAAGTCAACAAGGAGTGCTGCCATGGTGACCTGCT<br>GGAATGCGCAGATGACAGGGCGGAACTTGCCAAGTACATGTGTGAAA<br>ACCAGGCGACTATCTCCAGCAAACTGCAGACTTGCTGCGATAAACCA<br>CTGTTGAAGAAAGCCCACTGTCTTAGTGAGGTGGAGCATGACACCAT<br>GCCTGCTGATCTGCCTGCCATTGCTGCTGATTTTGTTGAGGACCAGG<br>AAGTGTGCAAGAACTATGCTGAGGCCAAGGATGTCTTCCTGGGCACG<br>TTCTTGTATGAATATTCAAGAAGACACCCTGATTACTCTGTATCCCT<br>GTTGCTGAGACTTGCTAAGAAATATGAAGCCACTCTGGAAAAGTGCT<br>GCGCTGAAGCCAATCCTCCCGCATGCTACGGCACAGTGCTTGCTGAA<br>TTTCAGCCTCTTGTAGAAGAGCCTAAGAACTTGGTCAAAACCAACTG<br>TGATCTTTACGAGAAGCTTGGAGAATATGGATTCCAAAATGCCATTC<br>TAGTTCGCTACACCCAGAAAGCACCTCAGGTGTCAACCCCAACTCTC<br>GTGGAGGCTGCAAGAAACCTAGGAAGAGTGGGCACCAAGTGTTGTAC<br>ACTTCCTGAAGATCAGAGACTGCCTTGTGTGGAAGACTATCTGTCTG<br>CAATCCTGAACCGTGTGTGTCTGCTGCATGAGAAGACCCCAGTGAGT<br>GAGCATGTTACCAAGTGCTGTAGTGGATCCCTGGTGGAAAGGCGGCC<br>ATGCTTCTCTGCTCTGACAGTTGATGAAACATATGTCCCCAAAGAGT<br>TTAAAGCTGAGACCTTCACCTTCCACTCTGATATCTGCACACTTCCA<br>GAGAAGGAGAAGCAGATTAAGAAACAAACGGCTCTTGCTGAGCTGGT<br>GAAGCACAAGCCCAAGGCTACAGCGGAGCAACTGAAGACTGTCATGG<br>ATGACTTTGCACAGTTCCTGGATACATGTTGCAAGGCTGCTGACAAG<br>GACACCTGCTTCTCGACTGAGGGTCCAAACCTTGTCACTAGATGCAA<br>AGACGCCTTAGCC | 142 |
| Murine IL2 | aa | APTSSSTSSSTAEAQQQQQQQQQQQQHLEQLLMDLQELLSRMENYRN<br>LKLPRMLTFKFYLPKQATELKDLQCLEDELGPLRHVLDLTQSKSFQL<br>EDAENFISNIRVTVVKLKGSDNTFECQFDDESATVVDFLRRWIAFCQ<br>SIISTSPQ | 143 |
| | DNA | GCACCCACTTCAAGCTCCACTTCAAGCTCTACAGCGGAAGCACAGCA<br>GCAGCAGCAGCAGCAGCAGCAGCAGCAGCAGCACCTGGAGCAGCTGT<br>TGATGGACCTACAGGAGCTCCTGAGCAGGATGGAGAATTACAGGAAC<br>CTGAAACTCCCCAGGATGCTCACCTTCAAATTTTACTTGCCCAAGCA<br>GGCCACAGAATTGAAAGATCTTCAGTGCCTAGAAGATGAACTTGGAC<br>CTCTGCGGCATGTTCTGGATTTGACTCAAAGCAAAAGCTTTCAATTG<br>GAAGATGCTGAGAATTTCATCAGCAATATCAGAGTAACTGTTGTAAA<br>ACTAAAGGGCTCTGACAACACATTTGAGTGCCAATTCGATGATGAGT<br>CAGCAACTGTGGTGGACTTTCTGAGGAGATGGATAGCCTTCTGTCAA<br>AGCATCATCTCAACAAGCCCTCAA | 144 |
| His-tag | aa | HHHHHH | 145 |
| Murine MSA-IL2-ABP10 MSA **bold** IL2 | aa | **EAHKSEIAHRYNDLGEQHFKGLVLIAFSQYLQKCSYDEHAKLVQEVTDFAKT**<br>**CVADESAANCDKSLHTLFGDKLCAIPNLRENYGELADCCTKQEPERNECFLQ**<br>**HKDDNPSLPPFERPEAEAMCTSFKENPTTFMGHYLHEVARRHPYFYAPELLY**<br>**YAEQYNEILTQCCAEADKESCLTPKLDGVKEKALVSSVRQRMKCSSMQKFGE**<br>**RAFKAWAVARLSQTFPNADFAEITKLATDLTKVNKECCHGDLLECADDRAEL** | 146 |

TABLE 10-continued

Exemplary immunomodulatory fusion proteins

| Name | Type | Amino acid sequence | SEQ ID NO |
|---|---|---|---|
| *italics*<br>ABP10 ***bold***<br>***italics*** | | **AKYMCENQATISSKLQTCCDKPLLKKAHCLSEVEHDTMPADLPAIAADFVED**<br>**QEVCKNYAEAKDVFLGTFLYEYSRRHPDYSVSLLLRLAKKYEATLEKCCAEA**<br>**NPPACYGTVLAEFQPLVEEPKNLVKTNCDLYEKLGEYGFQNAILVRYTQKAP**<br>**QVSTPTLVEAARNLGRVGTKCCTLPEDQRLPCVEDYLSAILNRVCLLHEKTP**<br>**VSEHVTKCCSGSLVERRPCFSALTVDETYVPKEFKAETFTFHSDICTLPEKE**<br>**KQIKKQTALAELVKHKPKATAEQLKTVMDDFAQFLDTCCKAADKDTCFSTEG**<br>**PNLVTRCKDALA**GGGS*APTSSSTSSSTAEAQQQQQQQQQQQQHLEQLLMDLQ*<br>*ELLSRMENYRNLKLPRMLTFKFYLPKQATELKDLQCLEDELGPLRHVLDLTQ*<br>*SKSFQLEDAENFISNIRVTVVKLKGSDNTFECQFDDESATVVDFLRRWIAFC*<br>*QSIISTSPQGGGS****FQSEEQQGGGSGGSEEGGMESEESNGGGSGGSEE***GGGGG<br>SHHHHHH | |
| Murine<br>MSA-IL2-<br>ABP10<br>MSA **bold**<br>IL2<br>*italics*<br>ABP10 ***bold***<br>***italics*** | DNA | **GAAGCACACAAGAGTGAGATCGCCCATCGGTATAATGATTTGGGAGAACAAC**<br>**ATTTCAAAGGCCTAGTCCTGATTGCCTTTTCCCAGTATCTCCAGAAATGCTC**<br>**ATACGATGAGCATGCCAAATTAGTGCAGGAAGTAACAGACTTTGCAAAGACG**<br>**TGTGTTGCCGATGAGTCTGCCGCCAACTGTGACAAATCCCTTCACACTCTTT**<br>**TTGGAGATAAGTTGTGTGCCATTCCAAACCTCCGTGAAAACTATGGTGAACT**<br>**GGCTGACTGCTGTACAAAACAAGAGCCCGAAAGAAACGAATGTTTCCTGCAA**<br>**CACAAAGATGACAACCCCAGCCTGCCACCATTTGAAAGGCCAGAGGCTGAGG**<br>**CCATGTGCACCTCCTTTAAGGAAAACCCAACCACCTTTATGGGACACTATTT**<br>**GCATGAAGTTGCCAGAAGACATCCTTATTTCTATGCCCCAGAACTTCTTTAC**<br>**TATGCTGAGCAGTACAATGAGATTCTGACCCAGTGTTGTGCAGAGGCTGACA**<br>**AGGAAAGCTGCCTGACCCCGAAGCTTGATGGTGTGAAGGAGAAAGCATTGGT**<br>**CTCATCTGTCCGTCAGAGAATGAAGTGCTCCAGTATGCAGAAGTTTGGAGAG**<br>**AGAGCTTTTAAAGCATGGGCAGTAGCTCGTCTGAGCCAGACATTCCCCAATG**<br>**CTGACTTTGCAGAAATCACCAAATTGGCAACAGACCTGACCAAAGTCAACAA**<br>**GGAGTGCTGCCATGGTGACCTGCTGGAATGCGCAGATGACAGGGCGGAACTT**<br>**GCCAAGTACATGTGTGAAAACCAGGCGACTATCTCCAGCAAACTGCAGACTT**<br>**GCTGCGATAAACCACTGTTGAAGAAAGCCCACTGTCTTAGTGAGGTGGAGCA**<br>**TGACACCATGCCTGCTGATCTGCCTGCCATTGCTGCTGATTTTGTTGAGGAC**<br>**CAGGAAGTGTGCAAGAACTATGCTGAGGCCAAGGATGTCTTCCTGGGCACGT**<br>**TCTTGTATGAATATTCAAGAAGACACCCTGATTACTCTGTATCCCTGTTGCT**<br>**GAGACTTGCTAAGAAATATGAAGCCACTCTGGAAAAGTGCTGCGCTGAAGCC**<br>**AATCCTCCCGCATGCTACGGCACAGTGCTTGCTGAATTTCAGCCTCTTGTAG**<br>**AAGAGCCTAAGAACTTGGTCAAAACCAACTGTGATCTTTACGAGAAGCTTGG**<br>**AGAATATGGATTCCAAAATGCCATTCTAGTTCGCTACACCCAGAAAGCACCT**<br>**CAGGTGTCAACCCCAACTCTCGTGGAGGCTGCAAGAAACCTAGGAAGAGTGG**<br>**GCACCAAGTGTTGTACACTTCCTGAAGATCAGAGACTGCCTTGTGTGGAAGA**<br>**CTATCTGTCTGCAATCCTGAACCGTGTGTGTCTGCTGCATGAGAAGACCCCA**<br>**GTGAGTGAGCATGTTACCAAGTGCTGTAGTGGATCCCTGGTGGAAAGGCGGC**<br>**CATGCTTCTCTGCTCTGACAGTTGATGAAACATATGTCCCCAAAGAGTTTAA**<br>**AGCTGAGACCTTCACCTTCCACTCTGATATCTGCACACTTCCAGAGAAGGAG**<br>**AAGCAGATTAAGAAACAAACGGCTCTTGCTGAGCTGGTGAAGCACAAGCCCA**<br>**AGGCTACAGCGGAGCAACTGAAGACTGTCATGGATGACTTTGCACAGTTCCT**<br>**GGATACATGTTGCAAGGCTGCTGACAAGGACACCTGCTTCTCGACTGAGGGT**<br>**CCAAACCTTGTCACTAGATGCAAAGACGCCTTAGCCGGAGGGGGCTCCGCAC**<br>*CCACTTCAAGCTCCACTTCAAGCTCTACAGCGGAAGCACAGCAGCAGCAGCA*<br>*GCAGCAGCAGCAGCAGCAGCAGCACCTGGAGCAGCTGTTGATGGACCTACAG*<br>*GAGCTCCTGAGCAGGATGGAGAATTACAGGAACCTGAAACTCCCCAGGATGC*<br>*TCACCTTCAAATTTTACTTGCCCAAGCAGGCCACAGAATTGAAAGATCTTCA*<br>*GTGCCTAGAAGATGAACTTGGACCTCTGCGGCATGTTCTGGATTTGACTCAA*<br>*AGCAAAAGCTTTCAATTGGAAGATGCTGAGAATTTCATCAGCAATATCAGAG*<br>*TAACTGTTGTAAAACTAAAGGGCTCTGACAACACATTTGAGTGCCAATTCGA*<br>*TGATGAGTCAGCAACTGTGGTGGACTTTCTGAGGAGATGGATAGCCTTCTGT*<br>*CAAAGCATCATCTCAACAA*GCCCTCAAGGTGGAGGTAGT***TTCCAATCAGAAG***<br>***AGCAACAGGGTGGGGGTTCCGGAGGT AGCGAGGAGGGTGGGATGGAGAGTGA***<br>***AGAATCAAATGGTGGGGGTTCCGGCGGTAGCGAGGAGGGTGGG*** GGAGGTGGA<br>TCACACCATCACCACCATCAC | 147 |
| Murine<br>ABP10-MSA-<br>IL2<br>MSA **bold**<br>IL2<br>*italics*<br>ABP10 ***bold***<br>***italics*** | aa | ***FQSEEQQGGGSGGSEEGGMESEESNGGGSGGSEEGG*** GGGS**EAHKSEIAHRYN**<br>**DLGEQHFKGLVLIAFSQYLQKCSYDEHAKLVQEVTDFAKTCVADESAANCDK**<br>**SLHTLFGDKLCAIPNLRENYGELADCCTKQEPERNECFLQHKDDNPSLPPFE**<br>**RPEAEAMCTSFKENPTTFMGHYLHEVARRHPYFYAPELLYYAEQYNEILTQC**<br>**CAEADKESCLTPKLDGVKEKALVSSVRQRMKCSSMQKFGERAFKAWAVARLS**<br>**QTFPNADFAEITKLATDLTKVNKECCHGDLLECADDRAELAKYMCENQATIS**<br>**SKLQTCCDKPLLKKAHCLSEVEHDTMPADLPAIAADFVEDQEVCKNYAEAKD**<br>**VFLGTFLYEYSRRHPDYSVSLLLRLAKKYEATLEKCCAEANPPACYGTVLAE**<br>**FQPLVEEPKNLVKTNCDLYEKLGEYGFQNAILVRYTQKAPQVSTPTLVEAAR**<br>**NLGRVGTKCCTLPEDQRLPCVEDYLSAILNRVCLLHEKTPVSEHVTKCCSGS** | 148 |

TABLE 10-continued

| Exemplary immunomodulatory fusion proteins | | | |
|---|---|---|---|
| Name | Type | Amino acid sequence | SEQ ID NO |
| | | LVERRPCFSALTVDETYVPKEFKAETFTFHSDICTLPEKEKQIKKQTALAEL<br>VKHKPKATAEQLKTVMDDFAQFLDTCCKAADKDTCFSTEGPNLVTRCKDALA<br>GGGSAPTSSSTSSSTAEAQQQQQQQQQQQQHLEQLLMDLQELLSRMENYRNL<br>KLPRMLTFKFYLPKQATELKDLQCLEDELGPLRHVLDLTQSKSFQLEDAENF<br>ISNIRVTVVKLKGSDNTFECQFDDESATVVDFLRRWIAFCQSIISTSPQHHH<br>HHH | |
| Murine ABP10-MSA-IL2<br>MSA **bold**<br>IL2 *italics*<br>ABP10 ***bold italics*** | DNA | TTCCAATCAGAAGAGCAACAGGGTGGGGGTTCCGGCGGTAGCGAGGAGGGTG<br>GGATGGAGAGTGAAGAATCAAATGGTGGGGGTTCCGGCGGTAGCGAGGAGGG<br>TGGG GGAGGTGGATCAGAAGCACACAAGAGTGAGATCGCCCATCGGTATAAT<br>GATTTGGGAGAACAACATTTCAAAGGCCTAGTCCTGATTGCCTTTTCCCAGT<br>ATCTCCAGAAATGCTCATACGATGAGCATGCCAAATTAGTGCAGGAAGTAAC<br>AGACTTTGCAAAGACGTGTGTTGCCGATGAGTCTGCCGCCAACTGTGACAAA<br>TCCCTTCACACTCTTTTTGGAGATAAGTTGTGTGCCATTCCAAACCTCCGTG<br>AAAACTATGGTGAACTGGCTGACTGCTGTACAAAACAAGAGCCCGAAAGAAA<br>CGAATGTTTCCTGCAACACAAAGATGACAACCCCAGCCTGCCACCATTTGAA<br>AGGCCAGAGGCTGAGGCCATGTGCACCTCCTTTAAGGAAAACCCAACCACCT<br>TTATGGGACACTATTTGCATGAAGTTGCCAGAAGACATCCTTATTTCTATGC<br>CCCAGAACTTCTTTACTATGCTGAGCAGTACAATGAGATTCTGACCCAGTGT<br>TGTGCAGAGGCTGACAAGGAAAGCTGCCTGACCCCGAAGCTTGATGGTGTGA<br>AGGAGAAAGCATTGGTCTCATCTGTCCGTCAGAGAATGAAGTGCTCCAGTAT<br>GCAGAAGTTTGGAGAGAGAGCTTTTAAAGCATGGGCAGTAGCTCGTCTGAGC<br>CAGACATTCCCCAATGCTGACTTTGCAGAAATCACCAAATTGGCAACAGACC<br>TGACCAAAGTCAACAAGGAGTGCTGCCATGGTGACCTGCTGGAATGCGCAGA<br>TGACAGGGCGGAACTTGCCAAGTACATGTGTGAAAACCAGGCGACTATCTCC<br>AGCAAACTGCAGACTTGCTGCGATAAACCACTGTTGAAGAAAGCCCACTGTC<br>TTAGTGAGGTGGAGCATGACACCATGCCTGCTGATCTGCCTGCCATTGCTGC<br>TGATTTTGTTGAGGACCAGGAAGTGTGCAAGAACTATGCTGAGGCCAAGGAT<br>GTCTTCCTGGGCACGTTCTTGTATGAATATTCAAGAAGACACCCTGATTACT<br>CTGTATCCCTGTTGCTGAGACTTGCTAAGAAATATGAAGCCACTCTGGAAAA<br>GTGCTGCGCTGAAGCCAATCCTCCCGCATGCTACGGCACAGTGCTTGCTGAA<br>TTTCAGCCTCTTGTAGAAGAGCCTAAGAACTTGGTCAAAACCAACTGTGATC<br>TTTACGAGAAGCTTGGAGAATATGGATTCCAAAATGCCATTCTAGTTCGCTA<br>CACCCAGAAAGCACCTCAGGTGTCAACCCCAACTCTCGTGGAGGCTGCAAGA<br>AACCTAGGAAGAGTGGGCACCAAGTGTTGTACACTTCCTGAAGATCAGAGAC<br>TGCCTTGTGTGGAAGACTATCTGTCTGCAATCCTGAACCGTGTGTGTCTGCT<br>GCATGAGAAGACCCCAGTGAGTGAGCATGTTACCAAGTGCTGTAGTGGATCC<br>CTGGTGGAAAGGCGGCCATGCTTCTCTGCTCTGACAGTTGATGAAACATATG<br>TCCCCAAAGAGTTTAAAGCTGAGACCTTCACCTTCCACTCTGATATCTGCAC<br>ACTTCCAGAGAAGGAGAAGCAGATTAAGAAACAAACGGCTCTTGCTGAGCTG<br>GTGAAGCACAAGCCCAAGGCTACAGCGGAGCAACTGAAGACTGTCATGGATG<br>ACTTTGCACAGTTCCTGGATACATGTTGCAAGGCTGCTGACAAGGACACCTG<br>CTTCTCGACTGAGGGTCCAAACCTTGTCACTAGATGCAAAGACGCCTTAGCC<br>GGAGGGGGCTCCGCACCCACTTCAAGCTCCACTTCAAGCTCTACAGCGGAAG<br>CACAGCAGCAGCAGCAGCAGCAGCAGCAGCAGCAGCAGCACCTGGAGCAGCT<br>GTTGATGGACCTACAGGAGCTCCTGAGCAGGATGGAGAATTACAGGAACCTG<br>AAACTCCCCAGGATGCTCACCTTCAAATTTTACTTGCCCAAGCAGGCCACAG<br>AATTGAAAGATCTTCAGTGCCTAGAAGATGAACTTGGACCTCTGCGGCATGT<br>TCTGGATTTGACTCAAAGCAAAAGCTTTCAATTGGAAGATGCTGAGAATTTC<br>ATCAGCAATATCAGAGTAACTGTTGTAAAACTAAAGGGCTCTGACAACACAT<br>TTGAGTGCCAATTCGATGATGAGTCAGCAACTGTGGTGGACTTTCTGAGGAG<br>ATGGATAGCCTTCTGTCAAAGCATCATCTCAACAAGCCCTCAACACCATCAC<br>CACCATCAC | 149 |
| Murine MSA-IL2-ABP8<br>MSA **bold**<br>IL2 *italics*<br>ABP8 ***bold italics*** | aa | EAHKSEIAHRYNDLGEQHFKGLVLIAFSQYLQKCSYDEHAKLVQEVT<br>DFAKTCVADESAANCDKSLHTLFGDKLCAIPNLRENYGELADCCTKQ<br>EPERNECFLQHKDDNPSLPPFERPEAEAMCTSFKENPTTFMGHYLHE<br>VARRHPYFYAPELLYYAEQYNEILTQCCAEADKESCLTPKLDGVKEK<br>ALVSSVRQRMKCSSMQKFGERAFKAWAVARLSQTFPNADFAEITKLA<br>TDLTKVNKECCHGDLLECADDRAELAKYMCENQATISSKLQTCCDKP<br>LLKKAHCLSEVEHDTMPADLPAIAADFVEDQEVCKNYAEAKDVFLGT<br>FLYEYSRRHPDYSVSLLLRLAKKYEATLEKCCAEANPPACYGTVLAE<br>FQPLVEEPKNLVKTNCDLYEKLGEYGFQNAILVRYTQKAPQVSTPTL<br>VEAARNLGRVGTKCCTLPEDQRLPCVEDYLSAILNRVCLLHEKTPVS<br>EHVTKCCSGSLVERRPCFSALTVDETYVPKEFKAETFTFHSDICTLP<br>EKEKQIKKQTALAELVKHKPKATAEQLKTVMDDFAQFLDTCCKAADK<br>DTCFSTEGPNLVTRCKDALAGGGSAPTSSSTSSSTAEAQQQQQQQQ<br>QQQHLEQLLMDLQELLSRMENYRNLKLPRMLTFKFYLPKQATELKDL<br>QCLEDELGPLRHVLDLTQSKSFQLEDAENFISNIRVTVVKLKGSDNT<br>FECQFDDESATVVDFLRRWIAFCQSIISTSPQGGGSTVSSETDSISS<br>EESVEHI GGGSHHHHHH | 150 |
| Murine MSA-IL2- | DNA | GAAGCACACAAGAGTGAGATCGCCCATCGGTATAATGATTTGGGAGA<br>ACAACATTTCAAAGGCCTAGTCCTGATTGCCTTTTCCCAGTATCTCC | 151 |

TABLE 10-continued

Exemplary immunomodulatory fusion proteins

| Name | Type | Amino acid sequence | SEQ ID NO |
|---|---|---|---|
| ABP8<br>MSA **bold**<br>IL2<br>*italics*<br>ABP8 ***bold***<br>***italics*** | | **AGAAATGCTCATACGATGAGCATGCCAAATTAGTGCAGGAAGTAACA**<br>**GACTTTGCAAAGACGTGTGTTGCCGATGAGTCTGCCGCCAACTGTGA**<br>**CAAATCCCTTCACACTCTTTTTGGAGATAAGTTGTGTGCCATTCCAA**<br>**ACCTCCGTGAAAACTATGGTGAACTGGCTGACTGCTGTACAAAACAA**<br>**GAGCCCGAAAGAAACGAATGTTTCCTGCAACACAAAGATGACAACCC**<br>**CAGCCTGCCACCATTTGAAAGGCCAGAGGCTGAGGCCATGTGCACCT**<br>**CCTTTAAGGAAAACCCAACCACCTTTATGGGACACTATTTGCATGAA**<br>**GTTGCCAGAAGACATCCTTATTTCTATGCCCCAGAACTTCTTTACTA**<br>**TGCTGAGCAGTACAATGAGATTCTGACCCAGTGTTGTGCAGAGGCTG**<br>**ACAAGGAAAGCTGCCTGACCCCGAAGCTTGATGGTGTGAAGGAGAAA**<br>**GCATTGGTCTCATCTGTCCGTCAGAGAATGAAGTGCTCCAGTATGCA**<br>**GAAGTTTGGAGAGAGAGCTTTTAAAGCATGGGCAGTAGCTCGTCTGA**<br>**GCCAGACATTCCCCAATGCTGACTTTGCAGAAATCACCAAATTGGCA**<br>**ACAGACCTGACCAAAGTCAACAAGGAGTGCTGCCATGGTGACCTGCT**<br>**GGAATGCGCAGATGACAGGGCGGAACTTGCCAAGTACATGTGTGAAA**<br>**ACCAGGCGACTATCTCCAGCAAACTGCAGACTTGCTGCGATAAACCA**<br>**CTGTTGAAGAAAGCCCACTGTCTTAGTGAGGTGGAGCATGACACCAT**<br>**GCCTGCTGATCTGCCTGCCATTGCTGCTGATTTTGTTGAGGACCAGG**<br>**AAGTGTGCAAGAACTATGCTGAGGCCAAGGATGTCTTCCTGGGCACG**<br>**TTCTTGTATGAATATTCAAGAAGACACCCTGATTACTCTGTATCCCT**<br>**GTTGCTGAGACTTGCTAAGAAATATGAAGCCACTCTGGAAAAGTGCT**<br>**GCGCTGAAGCCAATCCTCCCGCATGCTACGGCACAGTGCTTGCTGAA**<br>**TTTCAGCCTCTTGTAGAAGAGCCTAAGAACTTGGTCAAAACCAACTG**<br>**TGATCTTTACGAGAAGCTTGGAGAATATGGATTCCAAAATGCCATTC**<br>**TAGTTCGCTACACCCAGAAAGCACCTCAGGTGTCAACCCCAACTCTC**<br>**GTGGAGGCTGCAAGAAACCTAGGAAGAGTGGGCACCAAGTGTTGTAC**<br>**ACTTCCTGAAGATCAGAGACTGCCTTGTGTGGAAGACTATCTGTCTG**<br>**CAATCCTGAACCGTGTGTGTCTGCTGCATGAGAAGACCCCAGTGAGT**<br>**GAGCATGTTACCAAGTGCTGTAGTGGATCCCTGGTGGAAAGGCGGCC**<br>**ATGCTTCTCTGCTCTGACAGTTGATGAAACATATGTCCCCAAAGAGT**<br>**TTAAAGCTGAGACCTTCACCTTCCACTCTGATATCTGCACACTTCCA**<br>**GAGAAGGAGAAGCAGATTAAGAAACAAACGGCTCTTGCTGAGCTGGT**<br>**GAAGCACAAGCCCAAGGCTACAGCGGAGCAACTGAAGACTGTCATGG**<br>**ATGACTTTGCACAGTTCCTGGATACATGTTGCAAGGCTGCTGACAAG**<br>**GACACCTGCTTCTCGACTGAGGGTCCAAACCTTGTCACTAGATGCAA**<br>**AGACGCCTTAGCC**ggaggggct*ccgcacccacttcaagctccactt*<br>*caagctctacagcggaagcacagcagcagcagcagcagcagcagcag*<br>*cagcagcagcacctggagcagctgttgatggacctacaggagctcct*<br>*gagcaggatggagaattacaggaacctgaaactccccaggatgctca*<br>*ccttcaaattttacttgcccaagcaggccacagaattgaaagatctt*<br>*cagtgcctagaagatgaacttggacctctgcggcatgttctggattt*<br>*gactcaaagcaaaagctttcaattggaagatgctgagaatttcatca*<br>*gcaatatcagagtaactgttgtaaaactaaagggctctgacaacaca*<br>*tttgagtgccaattcgatgatgagtcagcaactgtggtggactttct*<br>*gaggagatggatagccttctgtcaaagcatcatctcaacaagccctc*<br>*aa*GGTGGAGGTAGT***ACTGTAAGCAGCAAACAGACTCAATATCTTCA***<br>***GAAGAAAGTGTCGAACACATT*** GGAGGTGGATCACACCATCACCACCA<br>TCAC | |
| Murine<br>MSA-IL2-<br>ABP17<br>MSA **bold**<br>IL2<br>*italics*<br>ABP17 ***bold***<br>***italics*** | aa | **EAHKSEIAHRYNDLGEQHFKGLVLIAFSQYLQKCSYDEHAKLVQEVT**<br>**DFAKTCVADESAANCDKSLHTLFGDKLCAIPNLRENYGELADCCTKQ**<br>**EPERNECFLQHKDDNPSLPPFERPEAEAMCTSFKENPTTFMGHYLHE**<br>**VARRHPYFYAPELLYYAEQYNEILTQCCAEADKESCLTPKLDGVKEK**<br>**ALVSSVRQRMKCSSMQKFGERAFKAWAVARLSQTFPNADFAEITKLA**<br>**TDLTKVNKECCHGDLLECADDRAELAKYMCENQATISSKLQTCCDKP**<br>**LLKKAHCLSEVEHDTMPADLPAIAADFVEDQEVCKNYAEAKDVFLGT**<br>**FLYEYSRRHPDYSVSLLLRLAKKYEATLEKCCAEANPPACYGTVLAE**<br>**FQPLVEEPKNLVKTNCDLYEKLGEYGFQNAILVRYTQKAPQVSTPTL**<br>**VEAARNLGRVGTKCCTLPEDQRLPCVEDYLSAILNRVCLLHEKTPVS**<br>**EHVTKCCSGSLVERRPCFSALTVDETYVPKEFKAETFTFHSDICTLP**<br>**EKEKQIKKQTALAELVKHKPKATAEQLKTVMDDFAQFLDTCCKAADK**<br>**DTCFSTEGPNLVTRCKDALA**GGG*SAPTSSSTSSSTAEAQQQQQQQQ*<br>*QQQHLEQLLMDLQELLSRMENYRNLKLPRMLTFKFYLPKQATELKDL*<br>*QCLEDELGPLRHVLDLTQSKSFQLEDAENFISNIRVTVVKLKGSDNT*<br>*FECQFDDESATVVDFLRRWIAFCQSIISTSPQ*GGGGG***SEESEESEESE***<br>***E*** GGGGHHHHHH | 152 |
| Murine<br>MSA-IL2-<br>ABP17<br>MSA **bold**<br>IL2<br>*italics*<br>ABP17 ***bold*** | DNA | **gaagcacacaagagtgagatcgcccatcggtataatgatttgggaga**<br>**acaacatttcaaaggcctagtcctgattgccttttcccagtatctcc**<br>**agaaatgctcatacgatgagcatgccaaattagtgcaggaagtaaca**<br>**gactttgcaaagacgtgtgttgccgatgagtctgccgccaactgtga**<br>**caaatcccttcacactctttttggagataagttgtgtgccattccaa**<br>**acctccgtgaaaactatggtgaactggctgactgctgtacaaaacaa**<br>**gagcccgaaagaaacgaatgtttcctgcaacacaaagatgacaaccc** | 153 |

TABLE 10-continued

Exemplary immunomodulatory fusion proteins

| Name | Type | Amino acid sequence | SEQ ID NO |
|---|---|---|---|
| ***italics*** | | **cagcctgccaccatttgaaaggccagaggctgaggccatgtgcacct**<br>**cctttaaggaaaacccaaccacctttatgggacactatttgcatgaa**<br>**gttgccagaagacatccttatttctatgccccagaacttctttacta**<br>**tgctgagcagtacaatgagattctgacccagtgttgtgcagaggctg**<br>**acaaggaaagctgcctgaccccgaagcttgatggtgtgaaggagaaa**<br>**gcattggtctcatctgtccgtcagagaatgaagtgctccagtatgca**<br>**gaagtttggagagagagcttttaaagcatgggcagtagctcgtctga**<br>**gccagacattccccaatgctgactttgcagaaatcaccaaattggca**<br>**acagacctgaccaaagtcaacaaggagtgctgccatggtgacctgct**<br>**ggaatgcgcagatgacagggcggaacttgccaagtacatgtgtgaaa**<br>**accaggcgactatctccagcaaactgcagacttgctgcgataaacca**<br>**ctgttgaagaaagcccactgtcttagtgaggtggagcatgacaccat**<br>**gcctgctgatctgcctgccattgctgctgattttgttgaggaccagg**<br>**aagtgtgcaagaactatgctgaggccaaggatgtcttcctgggcacg**<br>**ttcttgtatgaatattcaagaagacaccctgattactctgtatccct**<br>**gttgctgagacttgctaagaaatatgaagccactctggaaaagtgct**<br>**gcgctgaagccaatcctcccgcatgctacggcacagtgcttgctgaa**<br>**tttcagcctcttgtagaagagcctaagaacttggtcaaaaccaactg**<br>**tgatctttacgagaagcttggagaatatggattccaaaatgccattc**<br>**tagttcgctacacccagaaagcacctcaggtgtcaaccccaactctc**<br>**gtggaggctgcaagaaacctaggaagagtgggcaccaagtgttgtac**<br>**acttcctgaagatcagagactgccttgtgtggaagactatctgtctg**<br>**caatcctgaaccgtgtgtgtctgctgcatgagaagaccccagtgagt**<br>**gagcatgttaccaagtgctgtagtggatccctggtggaaaggcggcc**<br>**atgcttctctgctctgacagttgatgaaacatatgtccccaaagagt**<br>**ttaaagctgagaccttcaccttccactctgatatctgcacacttcca**<br>**gagaaggagaagcagattaagaaacaaacggctcttgctgagctggt**<br>**gaagcacaagcccaaggctacagcggagcaactgaagactgtcatgg**<br>**atgactttgcacagttcctggatacatgttgcaaggctgctgacaag**<br>**gacacctgcttctcgactgagggtccaaaccttgtcactagatgcaa**<br>**agacgccttagcc**ggaggggggct*ccgcacccacttcaagctccactt*<br>*caagctctacagcggaagcacagcagcagcagcagcagcagcagcag*<br>*cagcagcagcacctggagcagctgttgatggacctacaggagctcct*<br>*gagcaggatggagaattacaggaacctgaaactccccaggatgctca*<br>*ccttcaaattttacttgcccaagcaggccacagaattgaaagatctt*<br>*cagtgcctagaagatgaacttggacctctgcggcatgttctggattt*<br>*gactcaaagcaaaagctttcaattggaagatgctgagaatttcatca*<br>*gcaatatcagagtaactgttgtaaaactaaagggctctgacaacaca*<br>*tttgagtgccaattcgatgatgagtcagcaactgtggtggactttct*<br>*gaggagatggatagccttctgtcaaagcatcatctcaacaagccctc*<br>*aa*GGGGGGGGAGGC***TCTGAAGAATCCGAGGAGAGTGAAGAGTCAGAG***<br>***GAG*** GGTGGCGGGGGGcaccatcaccaccatcac | |
| Lysozyme | aa | KVFGRCELAAAMKRHGLDNYRGYSLGNWVCAAKFESNFNTQATNRNT<br>DGSTDYGILQINSRWWCNDGRTPGSRNLCNIPCSALLSSDITASVNC<br>AKKIVSDGNGMNAWVAWRNRCKGTDVQAWIRGCRL | 154 |
| | DNA | AAAGTCTTTGGACGATGTGAGCTGGCAGCAGCTATGAAGCGTCACGG<br>ACTTGATAACTATCGGGGATACAGCCTGGGAAACTGGGTGTGTGCCG<br>CAAAATTCGAGAGTAACTTCAACACCCAGGCTACAAACCGTAACACC<br>GATGGGAGTACCGACTACGGAATCCTACAGATCAACAGCCGCTGGTG<br>GTGCAACGATGGCAGGACCCCAGGCTCCAGGAACCTGTGCAACATCC<br>CGTGCTCAGCCCTGCTGAGCTCAGACATAACAGCGAGCGTGAACTGC<br>GCGAAGAAGATCGTCAGCGATGGAAACGGCATGAACGCGTGGGTCGC<br>CTGGCGCAACCGCTGCAAGGGCACCGACGTCCAGGCGTGGATCAGAG<br>GCTGCCGGCTG | 155 |
| Lysozyme-<br>ABP10<br>Lysozyme<br>**bold**<br>ABP10 ***bold***<br>***italics*** | aa | **KVFGRCELAAAMKRHGLDNYRGYSLGNWVCAAKFESNFNTQATNRNTDGSTD**<br>**YGILQINSRWWCNDGRTPGSRNLCNIPCSALLSSDITASVNCAKKIVSDGNG**<br>**MNAWVAWRNRCKGTDVQAWIRGCRL**GGGS***FQSEEQQGGGSGGSEEGGMESEE***<br>***SNGGGSGGSEEGG*** GGGSHHHHHH | 156 |
| Lyzsozyme-<br>ABP10<br>Lysozyme<br>**bold**<br>ABP10 ***bold***<br>***italics*** | DNA | **AAAGTCTTTGGACGATGTGAGCTGGCAGCAGCTATGAAGCGTCACGGACTTG**<br>**ATAACTATCGGGGATACAGCCTGGGAAACTGGGTGTGTGCCGCAAAATTCGA**<br>**GAGTAACTTCAACACCCAGGCTACAAACCGTAACACCGATGGGAGTACCGAC**<br>**TACGGAATCCTACAGATCAACAGCCGCTGGTGGTGCAACGATGGCAGGACCC**<br>**CAGGCTCCAGGAACCTGTGCAACATCCCGTGCTCAGCCCTGCTGAGCTCAGA**<br>**CATAACAGCGAGCGTGAACTGCGCGAAGAAGATCGTCAGCGATGGAAACGGC**<br>**ATGAACGCGTGGGTCGCCTGGCGCAACCGCTGCAAGGGCACCGACGTCCAGG**<br>**CGTGGATCAGAGGCTGCCGGCTG**GGTGGAGGTAGT***TTCCAATCAGAAGAGCA***<br>***ACAGGGTGGGGGTTCCGGCGGTAGCGAGGAGGGTGGGATGGAGAGTGAAGAA***<br>***TCAAATGGTGGGGGTTCCGGCGGTAGCGAGGAGGGTGGG*** GGAGGTGGATCAC<br>ACCATCACCACCATCAC | 157 |

TABLE 10-continued

| Exemplary immunomodulatory fusion proteins | | | |
|---|---|---|---|
| Name | Type | Amino acid sequence | SEQ ID NO |
| Murine IFNg | aa | HGTVIESLESLNNYFNSSGIDVEEKSLFLDIWRNWQKDGDMKILQSQ<br>IISFYLRLFEVLKDNQAISNNISVIESHLITTFFSNSKAKKDAFMSI<br>AKFEVNNPQVQRQAFNELIRVVHQLLPESSLRKRKRSRC | 158 |
| | DNA | CACGGCACAGTCATTGAAAGCCTAGAAAGTCTGAATAACTATTTTAA<br>CTCAAGTGGCATAGATGTGGAAGAAAAGAGTCTCTTCTTGGATATCT<br>GGAGGAACTGGCAAAAGGATGGTGACATGAAAATCCTGCAGAGCCAG<br>ATTATCTCTTTCTACCTCAGACTCTTTGAAGTCTTGAAAGACAATCA<br>GGCCATCAGCAACAACATAAGCGTCATTGAATCACACCTGATTACTA<br>CCTTCTTCAGCAACAGCAAGGCGAAAAAGGATGCATTCATGAGTATT<br>GCCAAGTTTGAGGTCAACAACCCACAGGTCCAGCGCCAAGCATTCAA<br>TGAGCTCATCCGAGTGGTCCACCAGCTGTTGCCGGAATCCAGCCTCA<br>GGAAGCGGAAAAGGAGTCGCTGC | 159 |
| mIFNg-mIFNg-MSA-ABP10 mIFNg ***bold italics*** MSA **bold** ABP10 *italics* | aa | ***HGTVIESLESLNNYFNSSGIDVEEKSLFLDIWRNWQKDGDMKILQSQIISFY***<br>***LRLFEVLKDNQAISNNISVIESHLITTFFSNSKAKKDAFMSIAKFEVNNPQV***<br>***QRQAFNELIRVVHQLLPESSLRKRKRSRC*** GGGSGGGSGGGSGGGS***HGTVIES***<br>***LESLNNYFNSSGIDVEEKSLFLDIWRNWQKDGDMKILQSQIISFYLRLFEVL***<br>***KDNQAISNNISVIESHLITTFFSNSKAKKDAFMSIAKFEVNNPQVQRQAFNE***<br>***LIRVVHQLLPESSLRKRKRSRC*** GSGGGS**EAHKSEIAHRYNDLGEQHFKGLVL**<br>**IAFSQYLQKCSYDEHAKLVQEVTDFAKTCVADESAANCDKSLHTLFGDKLCA**<br>**IPNLRENYGELADCCTKQEPERNECFLQHKDDNPSLPPFERPEAEAMCTSFK**<br>**ENPTTFMGHYLHEVARRHPYFYAPELLYYAEQYNEILTQCCAEADKESCLTP**<br>**KLDGVKEKALVSSVRQRMKCSSMQKFGERAFKAWAVARLSQTFPNADFAEIT**<br>**KLATDLTKVNKECCHGDLLECADDRAELAKYMCENQATISSKLQTCCDKPLL**<br>**KKAHCLSEVEHDTMPADLPAIAADFVEDQEVCKNYAEAKDVFLGTFLYEYSR**<br>**RHPDYSVSLLLRLAKKYEATLEKCCAEANPPACYGTVLAEFQPLVEEPKNLV**<br>**KTNCDLYEKLGEYGFQNAILVRYTQKAPQVSTPTLVEAARNLGRVGTKCCTL**<br>**PEDQRLPCVEDYLSAILNRVCLLHEKTPVSEHVTKCCSGSLVERRPCFSALT**<br>**VDETYVPKEFKAETFTFHSDICTLPEKEKQIKKQTALAELVKHKPKATAEQL**<br>**KTVMDDFAQFLDTCCKAADKDTCFSTEGPNLVTRCKDALA**GGGS*FQSEEQQG*<br>*GGSGGSEEGGMESEESNGGGSGGSEEGG* GGGSHHHHHH | 160 |
| mIFNg-mIFNg-MSA-ABP10 mIFNg ***bold italics*** MSA **bold** ABP10 *italics* | DNA | ***CACGGCACAGTCATTGAAAGCCTAGAAAGTCTGAATAACTATTTTAACTCAA***<br>***GTGGCATAGATGTGGAAGAAAAGAGTCTCTTCTTGGATATCTGGAGGAACTG***<br>***GCAAAAGGATGGTGACATGAAAATCCTGCAGAGCCAGATTATCTCTTTCTAC***<br>***CTCAGACTCTTTGAAGTCTTGAAAGACAATCAGGCCATCAGCAACAACATAA***<br>***GCGTCATTGAATCACACCTGATTACTACCTTCTTCAGCAACAGCAAGGCGAA***<br>***AAAGGATGCATTCATGAGTATTGCCAAGTTTGAGGTCAACAACCCACAGGTC***<br>***CAGCGCCAAGCATTCAATGAGCTCATCCGAGTGGTCCACCAGCTGTTGCCGG***<br>***AATCCAGCCTCAGGAAGCGGAAAAGGAGTCGCTGC*** GGCGGAGGTTCTGGAGG<br>TGGCTCCGGTGGAGGTTCTGGAGGTGGCTCCC***ACGGCACAGTCATTGAAAGC***<br>***CTAGAAAGTCTGAATAACTATTTTAACTCAAGTGGCATAGATGTGGAAGAAA***<br>***AGAGTCTCTTCTTGGATATCTGGAGGAACTGGCAAAAGGATGGTGACATGAA***<br>***AATCCTGCAGAGAGCCAGATTATCTCTTTCTACCTCAGACTCTTTGAAGTCTTG***<br>***AAAGACAATCAGGCCATCAGCAACAACATAAGCGTCATTGAATCACACCTGA***<br>***TTACTACCTTCTTCAGCAACAGCAAGGCGAAAAAGGATGCATTCATGAGTAT***<br>***TGCCAAGTTTGAGGTCAACAACCCACAGGTCCAGCGCCAAGCATTCAATGAG***<br>***CTCATCCGAGTGGTCCACCAGCTGTTGCCGGAATCCAGCCTCAGGAAGCGGA***<br>***AAAGGAGTCGCTGC*** GGTTCCGGTGGCGGATCC**GAAGCACACAAGAGTGAGAT**<br>**CGCCCATCGGTATAATGATTTGGGAGAACAACATTTCAAAGGCCTAGTCCTG**<br>**ATTGCCTTTTCCCAGTATCTCCAGAAATGCTCATACGATGAGCATGCCAAAT**<br>**TAGTGCAGGAAGTAACAGACTTTGCAAAGACGTGTGTTGCCGATGAGTCTGC**<br>**CGCCAACTGTGACAAATCCCTTCACACTCTTTTTGGAGATAAGTTGTGTGCC**<br>**ATTCCAAACCTCCGTGAAAACTATGGTGAACTGGCTGACTGCTGTACAAAAC**<br>**AAGAGCCCGAAAGAAACGAATGTTTCCTGCAACACAAAGATGACAACCCCAG**<br>**CCTGCCACCATTTGAAAGGCCAGAGGCTGAGGCCATGTGCACCTCCTTTAAG**<br>**GAAAACCCAACCACCTTTATGGGACACTATTTGCATGAAGTTGCCAGAAGAC**<br>**ATCCTTATTTCTATGCCCCAGAACTTCTTTACTATGCTGAGCAGTACAATGA**<br>**GATTCTGACCCAGTGTTGTGCAGAGGCTGACAAGGAAAGCTGCCTGACCCCG**<br>**AAGCTTGATGGTGTGAAGGAGAAAGCATTGGTCTCATCTGTCCGTCAGAGAA**<br>**TGAAGTGCTCCAGTATGCAGAAGTTTGGAGAGAGAGCTTTTAAAGCATGGGC**<br>**AGTAGCTCGTCTGAGCCAGACATTCCCCAATGCTGACTTTGCAGAAATCACC**<br>**AAATTGGCAACAGACCTGACCAAAGTCAACAAGGAGTGCTGCCATGGTGACC**<br>**TGCTGGAATGCGCAGATGACAGGGCGGAACTTGCCAAGTACATGTGTGAAAA**<br>**CCAGGCGACTATCTCCAGCAAACTGCAGACTTGCTGCGATAAACCACTGTTG**<br>**AAGAAAGCCCACTGTCTTAGTGAGGTGGAGCATGACACCATGCCTGCTGATC**<br>**TGCCTGCCATTGCTGCTGATTTTGTTGAGGACCAGGAAGTGTGCAAGAACTA**<br>**TGCTGAGGCCAAGGATGTCTTCCTGGGCACGTTCTTGTATGAATATTCAAGA**<br>**AGACACCCTGATTACTCTGTATCCCTGTTGCTGAGACTTGCTAAGAAATATG**<br>**AAGCCACTCTGGAAAAGTGCTGCGCTGAAGCCAATCCTCCCGCATGCTACGG**<br>**CACAGTGCTTGCTGAATTTCAGCCTCTTGTAGAAGAGCCTAAGAACTTGGTC**<br>**AAAACCAACTGTGATCTTTACGAGAAGCTTGGAGAATATGGATTCCAAAATG**<br>**CCATTCTAGTTCGCTACACCCAGAAAGCACCTCAGGTGTCAACCCCAACTCT** | 161 |

TABLE 10-continued

Exemplary immunomodulatory fusion proteins

| Name | Type | Amino acid sequence | SEQ ID NO |
|---|---|---|---|
| | | **CGTGGAGGCTGCAAGAAACCTAGGAAGAGTGGGCACCAAGTGTTGTACACTT**<br>**CCTGAAGATCAGAGACTGCCTTGTGTGGAAGACTATCTGTCTGCAATCCTGA**<br>**ACCGTGTGTGTCTGCTGCATGAGAAGACCCCAGTGAGTGAGCATGTTACCAA**<br>**GTGCTGTAGTGGATCCCTGGTGGAAAGGCGGCCATGCTTCTCTGCTCTGACA**<br>**GTTGATGAAACATATGTCCCCAAAGAGTTTAAAGCTGAGACCTTCACCTTCC**<br>**ACTCTGATATCTGCACACTTCCAGAGAAGGAGAAGCAGATTAAGAAACAAAC**<br>**GGCTCTTGCTGAGCTGGTGAAGCACAAGCCCAAGGCTACAGCGGAGCAACTG**<br>**AAGACTGTCATGGATGACTTTGCACAGTTCCTGGATACATGTTGCAAGGCTG**<br>**CTGACAAGGACACCTGCTTCTCGACTGAGGGTCCAAACCTTGTCACTAGATG**<br>**CAAAGACGCCTTAGCC**GGTGGAGGTAGT***TTCCAATCAGAAGAGCAACAGGGT***<br>***GGGGGTTCCGGCGGTAGCGAGGAGGGTGGGATGGAGAGTGAAGAATCAAATG***<br>***GTGGGGGTTCCGGCGGTAGCGAGGAGGGTGGG*** GGAGGTGGATCACACCATCA<br>CCACCATCAC | |
| mIFNg-<br>mIFNg-<br>ABP10<br>mIFNg<br>*italics*<br>ABP10<br>**bold** | aa | *HGTVIESLESLNNYFNSSGIDVEEKSLFLDIWRNWQKDGDMKILQSQIISFY*<br>*LRLFEVLKDNQAISNNISVIESHLITTFFSNSKAKKDAFMSIAKFEVNNPQV*<br>*QRQAFNELIRVVHQLLPESSLRKRKRSRCGGGSGGGSGGGSGGGSHGTVIES*<br>*LESLNNYFNSSGIDVEEKSLFLDIWRNWQKDGDMKILQSQIISFYLRLFEVL*<br>*KDNQAISNNISVIESHLITTFFSNSKAKKDAFMSIAKFEVNNPQVQRQAFNE*<br>*LIRVVHQLLPESSLRKRKRSRC*GSGGGSGGGS**FQSEEQQGGGSGGSEEGGME**<br>**SEESNGGGSGGSEEGG**GGGSHHHHHH | 162 |
| mIFNg-<br>mIFNg-<br>ABP10<br>mIFNg<br>*italics*<br>ABP10 **bold** | DNA | *CACGGCACAGTCATTGAAAGCCTAGAAAGTCTGAATAACTATTTTAACTCAA*<br>*GTGGCATAGATGTGGAAGAAAAGAGTCTCTTCTTGGATATCTGGAGGAACTG*<br>*GCAAAAGGATGGTGACATGAAAATCCTGCAGAGCCAGATTATCTCTTTCTAC*<br>*CTCAGACTCTTTGAAGTCTTGAAAGACAATCAGGCCATCAGCAACAACATAA*<br>*GCGTCATTGAATCACACCTGATTACTACCTTCTTCAGCAACAGCAAGGCGAA*<br>*AAAGGATGCATTCATGAGTATTGCCAAGTTTGAGGTCAACAACCCACAGGTC*<br>*CAGCGCCAAGCATTCAATGAGCTCATCCGAGTGGTCCACCAGCTGTTGCCGG*<br>*AATCCAGCCTCAGGAAGCGGAAAAGGAGTCGCTGCGGCGGAGGTTCTGGAGG*<br>*TGGCTCCGGTGGAGGTTCTGGAGGTGGCTCCCACGGCACAGTCATTGAAAGC*<br>*CTAGAAAGTCTGAATAACTATTTTAACTCAAGTGGCATAGATGTGGAAGAAA*<br>*AGAGTCTCTTCTTGGATATCTGGAGGAACTGGCAAAAGGATGGTGACATGAA*<br>*AATCCTGCAGAGCCAGATTATCTCTTTCTACCTCAGACTCTTTGAAGTCTTG*<br>*AAAGACAATCAGGCCATCAGCAACAACATAAGCGTCATTGAATCACACCTGA*<br>*TTACTACCTTCTTCAGCAACAGCAAGGCGAAAAAGGATGCATTCATGAGTAT*<br>*TGCCAAGTTTGAGGTCAACAACCCACAGGTCCAGCGCCAAGCATTCAATGAG*<br>*CTCATCCGAGTGGTCCACCAGCTGTTGCCGGAATCCAGCCTCAGGAAGCGGA*<br>*AAAGGAGTCGCTGC*GGTTCCGGTGGCGGATCCGGTGGAGGTAGT**TTCCAATC**<br>**AGAAGAGCAACAGGGTGGGGGTTCCGGCGGTAGCGAGGAGGGTGGGATGGAG**<br>**AGTGAAGAATCAAATGGTGGGGGTTCCGGCGGTAGCGAGGAGGGTGGG**GGAG<br>GTGGATCACACCATCACCACCATCAC | 163 |
| Murine<br>IL12p40 | aa | MWELEKDVYVVEVDWTPDAPGETVNLTCDTPEEDDITWTSDQRHGVI<br>GSGKTLTITVKEFLDAGQYTCHKGGETLSHSHLLLHKKENGIWSTEI<br>LKNFKNKTFLKCEAPNYSGRFTCSWLVQRNMDLKFNIKSSSSSPDSR<br>AVTCGMASLSAEKVTLDQRDYEKYSVSCQEDVTCPTAEETLPIELAL<br>EARQQNKYENYSTSFFIRDIIKPDPPKNLQMKPLKNSQVEVSWEYPD<br>SWSTPHSYFSLKFFVRIQRKKEKMKETEEGCNQKGAFLVEKTSTEVQ<br>CKGGNVCVQAQDRYYNSSCSKWACVPCRVRS | 164 |
| | DNA | atgtgggagctggagaaagacgtttatgttgtagaggtggactggactcccg<br>atgcccctggagaaacagtgaacctcacctgtgacacgcctgaagaagatga<br>catcacctggacctcagaccagagacatggagtcataggctctggaaagacc<br>ctgaccatcactgtcaaagagtttctagatgctggccagtacacctgccaca<br>aaggaggcgagactctgagccactcacatctgctgctccacaagaaggaaaa<br>tggaatttggtccactgaaattttaaaaaatttcaaaaacaagactttcctg<br>aagtgtgaagcaccaaattactccggacggttcacgtgctcatggctggtgc<br>aaagaaacatggacttgaagttcaacatcaagagcagtagcagttcccctga<br>ctctcgggcagtgacatgtggaatggcgtctctgtctgcagagaaggtcaca<br>ctggaccaaagggactatgagaagtattcagtgtcctgccaggaggatgtca<br>cctgcccaactgccgaggagaccctgcccattgaactggcgttggaagcacg<br>gcagcagaataaatatgagaactacagcaccagcttcttcatcagggacatc<br>atcaaaccagacccgcccaagaacttgcagatgaagcctttgaagaactcac<br>aggtggaggtcagctgggagtaccctgactcctggagcactccccattccta<br>cttctccctcaagttctttgttcgaatccagcgcaagaaagaaaagatgaag<br>gagacagaggaggggtgtaaccagaaaggtgcgttcctcgtagagaagacat<br>ctaccgaagtccaatgcaaaggcgggaatgtctgcgtgcaagctcaggatcg<br>ctattacaattcctcatgcagcaagtgggcatgtgttccctgcagggtccga<br>tcc | 165 |

TABLE 10-continued

Exemplary immunomodulatory fusion proteins

| Name | Type | Amino acid sequence | SEQ ID NO |
|---|---|---|---|
| Murine IL12p35 | aa | RVIPVSGPARCLSQSRNLLKTTDDMVKTAREKLKHYSCTAEDIDHED<br>ITRDQTSTLKTCLPLELHKNESCLATRETSSTTRGSCLPPQKTSLMM<br>TLCLGSIYEDLKMYQTEFQAINAALQNHNHQQIILDKGMLVAIDELM<br>QSLNHNGETLRQKPPVGEADPYRVKMKLCILLHAFSTRVVTINRVMG<br>YLSSA | 166 |
| | DNA | agggtcattccagtctctggacctgccaggtgtcttagccagtcccgaaacc<br>tgctgaagaccacagatgacatggtgaagacggccagagaaaaactgaaaca<br>ttattcctgcactgctgaagacatcgatcatgaagacatcacacgggaccaa<br>accagcacattgaagacctgtttaccactggaactacacaagaacgagagtt<br>gcctggctactagagagacttcttccacaacaagagggagctgcctgccccc<br>acagaagacgtctttgatgatgaccctgtgccttggtagcatctatgaggac<br>ttgaagatgtaccagacagagttccaggccatcaacgcagcacttcagaatc<br>acaaccatcagcagatcattctagacaagggcatgctggtggccatcgatga<br>gctgatgcagtctctgaatcataatggcgagactctgcgccagaaacctcct<br>gtgggagaagcagacccttacagagtgaaaatgaagctctgcatcctgcttc<br>acgccttcagcacccgcgtcgtgaccatcaacagggtgatgggctatctgag<br>ctccgcc | 167 |
| Murine<br>scIL12-<br>MSA-ABP10<br>IL12p40<br>*italics*<br>IL12p35<br>underlined<br>MSA **bold**<br>ABP10 ***bold***<br>***italics*** | aa | *MWELEKDVVVWEVDWTPDAPGETVNLTCDTPEEDDITWTSDQRHGVIGSGKT*<br>*LTITVKEFLDAGQYTCHKGGETLSHSHLLLHKKENGIWSTEILKNFKNKTFL*<br>*KCEAPNYSGRFTCSWLVQRNMDLKFNIKSSSSSPDSRAVTCGMASLSAEKVT*<br>*LDQRDYEKYSVSCQEDVTCPTAEETLPIELALEARQQNKYENYSTSFFIRDI*<br>*IKPDPPKNLQMKPLKNSQVEVSWEYPDSWSTPHSYFSLKFFVRIQRKKEKMK*<br>*ETEEGCNQKGAFLVEKTSTEVQCKGGNVCVQAQDRYYNSSCSKWACVPCRVR*<br>*S*GGSGGGSGGGSGGGSRVIPVSGPARCLSQSRNLLKTTDDMVKTAREKLKHY<br>SCTAEDIDHEDITRDQTSTLKTCLPLELHKNESCLATRETSSTTRGSCLPPQ<br>KTSLMMTLCLGSIYEDLKMYQTEFQAINAALQNHNHQQIILDKGMLVAIDEL<br>MQSLNHNGETLRQKPPVGEADPYRVKMKLCILLHAFSTRVVTINRVMGYLSS<br>AGSGGGS**EAHKSEIAHRYNDLGEQHFKGLVLIAFSQYLQKCSYDEHAKLVQE**<br>**VTDFAKTCVADESAANCDKSLHTLFGDKLCAIPNLRENYGELADCCTKQEPE**<br>**RNECFLQHKDDNPSLPPFERPEAEAMCTSFKENPTTFMGHYLHEVARRHPYF**<br>**YAPELLYYAEQYNEILTQCCAEADKESCLTPKLDGVKEKALVSSVRQRMKCS**<br>**SMQKFGERAFKAWAVARLSQTFPNADFAEITKLATDLTKVNKECCHGDLLEC**<br>**ADDRAELAKYMCENQATISSKLQTCCDKPLLKKAHCLSEVEHDTMPADLPAI**<br>**AADFVEDQEVCKNYAEAKDVFLGTFLYEYSRRHPDYSVSLLLRLAKKYEATL**<br>**EKCCAEANPPACYGTVLAEFQPLVEEPKNLVKTNCDLYEKLGEYGFQNAILV**<br>**RYTQKAPQVSTPTLVEAARNLGRVGTKCCTLPEDQRLPCVEDYLSAILNRVC**<br>**LLHEKTPVSEHVTKCCSGSLVERRPCFSALTVDETYVPKEFKAETFTFHSDI**<br>**CTLPEKEKQIKKQTALAELVKHKPKATAEQLKTVMDDFAQFLDTCCKAADKD**<br>**TCFSTEGPNLVTRCKDALA**GGGS***FQSEEQQGGGSGGSEEGGMESEESNGGGS***<br>***GGSEEGG*** GGGSHHHHHH | 168 |
| Murine<br>scIL12-<br>MSA-ABP10<br>IL12p40<br>*italics*<br>IL12p35<br>underlined<br>MSA **bold**<br>ABP10 ***bold***<br>***italics*** | DNA | *atgtgggagctggagaaagacgtttatgttgtagaggtggactggactcccg*<br>*atgcccctggagaaacagtgaacctcacctgtgacacgcctgaagaagatga*<br>*catcacctggacctcagaccagagacatggagtcataggctctggaaagacc*<br>*ctgaccatcactgtcaaagagtttctagatgctggccagtacacctgccaca*<br>*aaggaggcgagactctgagccactcacatctgctgctccacaagaaggaaaa*<br>*tggaatttggtccactgaaattttaaaaaatttcaaaaacaagactttcctg*<br>*aagtgtgaagcaccaaattactccggacggttcacgtgctcatggctggtgc*<br>*aaagaaacatggacttgaagttcaacatcaagagcagtagcagttcccctga*<br>*ctctcgggcagtgacatgtggaatggcgtctctgtctgcagagaaggtcaca*<br>*ctggaccaaagggactatgagaagtattcagtgtcctgccaggaggatgtca*<br>*cctgcccaactgccgaggagaccctgcccattgaactggcgttggaagcacg*<br>*gcagcagaataaatatgagaactacagcaccagcttcttcatcagggacatc*<br>*atcaaaccagacccgcccaagaacttgcagatgaagcctttgaagaactcac*<br>*aggtggaggtcagctgggagtaccctgactcctggagcactccccattccta*<br>*cttctccctcaagttctttgttcgaatccagcgcaagaaagaaaagatgaag*<br>*gagacagaggaggggtgtaaccagaaaggtgcgttcctcgtagagaagacat*<br>*ctaccgaagtccaatgcaaaggcgggaatgtctgcgtgcaagctcaggatcg*<br>*ctattacaattcctcatgcagcaagtgggcatgtgttccctgcagggtccga*<br>*tcc*ggaggttccggtggtggatccggaggtggctccggcggcggatccaggg<br>tcattccagtctctggacctgccaggtgtcttagccagtcccgaaacctgct<br>gaagaccacagatgacatggtgaagacggccagagaaaaactgaaacattat<br>tcctgcactgctgaagacatcgatcatgaagacatcacacgggaccaaacca<br>gcacattgaagacctgtttaccactggaactacacaagaacgagagttgcct<br>ggctactagagagacttcttccacaacaagagggagctgcctgcccccacag<br>aagacgtctttgatgatgaccctgtgccttggtagcatctatgaggacttga<br>agatgtaccagacagagttccaggccatcaacgcagcacttcagaatcacaa<br>ccatcagcagatcattctagacaagggcatgctggtggccatcgatgagctg<br>atgcagtctctgaatcataatggcgagactctgcgccagaaacctcctgtgg<br>gagaagcagacccttacagagtgaaaatgaagctctgcatcctgcttcacgc<br>cttcagcacccgcgtcgtgaccatcaacagggtgatgggctatctgagctcc<br>gccggttccggtggcggatcc**gaagcacacaagagtgagatcgcccatcggt**<br>**ataatgatttgggagaacaacatttcaaaggcctagtcctgattgcctttttc** | 169 |

TABLE 10-continued

| Exemplary immunomodulatory fusion proteins | | | |
|---|---|---|---|
| Name | Type | Amino acid sequence | SEQ ID NO |
| | | **ccagtatctccagaaatgctcatacgatgagcatgccaaattagtgcaggaa**<br>**gtaacagactttgcaaagacgtgtgttgccgatgagtctgccgccaactgtg**<br>**acaaatcccttcacactctttttggagataagttgtgtgccattccaaacct**<br>**ccgtgaaaactatggtgaactggctgactgctgtacaaaacaagagcccgaa**<br>**agaaacgaatgtttcctgcaacacaaagatgacaaccccagcctgccaccat**<br>**ttgaaaggccagaggctgaggccatgtgcacctcctttaaggaaaacccaac**<br>**cacctttatgggacactatttgcatgaagttgccagaagacatccttatttc**<br>**tatgccccagaacttctttactatgctgagcagtacaatgagattctgaccc**<br>**agtgttgtgcagaggctgacaaggaaagctgcctgaccccgaagcttgatgg**<br>**tgtgaaggagaaagcattggtctcatctgtccgtcagagaatgaagtgctcc**<br>**agtatgcagaagtttggagagagagcttttaaagcatgggcagtagctcgtc**<br>**tgagccagacattccccaatgctgactttgcagaaatcaccaaattggcaac**<br>**agacctgaccaaagtcaacaaggagtgctgccatggtgacctgctggaatgc**<br>**gcagatgacagggcggaacttgccaagtacatgtgtgaaaaccaggcgacta**<br>**tctccagcaaactgcagacttgctgcgataaaccactgttgaagaaagccca**<br>**ctgtcttagtgaggtggagcatgacaccatgcctgctgatctgcctgccatt**<br>**gctgctgattttgttgaggaccaggaagtgtgcaagaactatgctgaggcca**<br>**aggatgtcttcctgggcacgttcttgtatgaatattcaagaagacaccctga**<br>**ttactctgtatccctgttgctgagacttgctaagaaatatgaagccactctg**<br>**gaaaagtgctgcgctgaagccaatcctcccgcatgctacggcacagtgcttg**<br>**ctgaatttcagcctcttgtagaagagcctaagaacttggtcaaaaccaactg**<br>**tgatctttacgagaagcttggagaatatggattccaaaatgccattctagtt**<br>**cgctacacccagaaagcacctcaggtgtcaaccccaactctcgtggaggctg**<br>**caagaaacctaggaagagtgggcaccaagtgttgtacacttcctgaagatca**<br>**gagactgccttgtgtggaagactatctgtctgcaatcctgaaccgtgtgtgt**<br>**ctgctgcatgagaagaccccagtgagtgagcatgttaccaagtgctgtagtg**<br>**gatccctggtggaaaggcggccatgcttctctgctctgacagttgatgaaac**<br>**atatgtccccaaagagtttaaagctgagaccttcaccttccactctgatatc**<br>**tgcacacttccagagaaggagaagcagattaagaaacaaacggctcttgctg**<br>**agctggtgaagcacaagcccaaggctacagcggagcaactgaagactgtcat**<br>**ggatgactttgcacagttcctggatacatgttgcaaggctgctgacaaggac**<br>**acctgcttctcgactgagggtccaaaccttgtcactagatgcaaagacgcct**<br>**tagcc**GGTGGAGGTAGT***TTCCAATCAGAAGAGCAACAGGGTGGGGGTTCCGG***<br>***CGGTAGCGAGGAGGGTGGGATGGAGAGTGAAGAATCAAATGGTGGGGGTTCC***<br>***GGCGGTAGCGAGGAGGGTGGG*** GGAGGTGGATCACACCATCACCACCATCAC | |
| Murine<br>scIL12-<br>MSA-ABP17<br>IL12p40<br>*italics*<br>IL12p35<br>underlined<br>MSA **bold**<br>ABP17 ***bold***<br>***italics*** | aa | *MWELEKDVYVVEVDWTPDAPGETVNLTCDTPEEDDITWTSDQRHGVIGSGKT*<br>*LTITVKEFLDAGQYTCHKGGETLSHSHLLLHKKENGIWSTEILKNFKNKTFL*<br>*KCEAPNYSGRFTCSWLVQRNMDLKFNIKSSSSSPDSRAVTCGMASLSAEKVT*<br>*LDQRDYEKYSVSCQEDVTCPTAEETLPIELALEARQQNKYENYSTSFFIRDI*<br>*IKPDPPKNLQMKPLKNSQVEVSWEYPDSWSTPHSYFSLKFFVRIQRKKEKMK*<br>*ETEEGCNQKGAFLVEKTSTEVQCKGGNVCVQAQDRYYNSSCSKWACVPCRVR*<br>*S*GGSGGGSGGGSGGGSRVIPVSGPARCLSQSRNLLKTTDDMVKTAREKLKHY<br>SCTAEDIDHEDITRDQTSTLKTCLPLELHKNESCLATRETSSTTRGSCLPPQ<br>KTSLMMTLCLGSIYEDLKMYQTEFQAINAALQNHNHQQIILDKGMLVAIDEL<br>MQSLNHNGETLRQKPPVGEADPYRVKMKLCILLHAFSTRVVTINRVMGYLSS<br>AGSGGGS**EAHKSEIAHRYNDLGEQHFKGLVLIAFSQYLQKCSYDEHAKLVQE**<br>**VTDFAKTCVADESAANCDKSLHTLFGDKLCAIPNLRENYGELADCCTKQEPE**<br>**RNECFLQHKDDNPSLPPFERPEAEAMCTSFKENPTTFMGHYLHEVARRHPYE**<br>**YAPELLYYAEQYNEILTQCCAEADKESCLTPKLDGVKEKALVSSVRQRMKCS**<br>**SMQKFGERAFKAWAVARLSQTFPNADFAEITKLATDLTKVNKECCHGDLLEC**<br>**ADDRAELAKYMCENQATISSKLQTCCDKPLLKKAHCLSEVEHDTMPADLPAI**<br>**AADFVEDQEVCKNYAEAKDVFLGTFLYEYSRRHPDYSVSLLLRLAKKYEATL**<br>**EKCCAEANPPACYGTVLAEFQPLVEEPKNLVKTNCDLYEKLGEYGFQNAILV**<br>**RYTQKAPQVSTPTLVEAARNLGRVGTKCCTLPEDQRLPCVEDYLSAILNRVC**<br>**LLHEKTPVSEHVTKCCSGSLVERRPCFSALTVDETYVPKEFKAETFTFHSDI**<br>**CTLPEKEKQIKKQTALAELVKHKPKATAEQLKTVMDDFAQFLDTCCKAADKD**<br>**TCFSTEGPNLVTRCKDALA**GGGG***SEESEESEESEE***GGGGHHHHHH | 170 |
| Murine<br>scIL12-<br>MSA-ABP17<br>IL12p40<br>*italics*<br>IL12p35<br>underlined<br>MSA **bold**<br>ABP17 ***bold***<br>***italics*** | DNA | *atgtgggagctggagaaagacgtttatgttgtagaggtggactggactcccg*<br>*atgcccctggagaaacagtgaacctcacctgtgacacgcctgaagaagatga*<br>*catcacctggacctcagaccagagacatggagtcataggctctggaaagacc*<br>*ctgaccatcactgtcaaagagtttctagatgctggccagtacacctgccaca*<br>*aaggaggcgagactctgagccactcacatctgctgctccacaagaaggaaaa*<br>*tggaatttggtccactgaaattttaaaaaatttcaaaaacaagactttcctg*<br>*aagtgtgaagcaccaaattactccggacggttcacgtgctcatggctggtgc*<br>*aaagaaacatggacttgaagttcaacatcaagagcagtagcagttcccctga*<br>*ctctcgggcagtgacatgtggaatggcgtctctgtctgcagagaaggtcaca*<br>*ctggaccaaagggactatgagaagtattcagtgtcctgccaggaggatgtca*<br>*cctgcccaactgccgaggagaccctgcccattgaactggcgttggaagcacg*<br>*gcagcagaataaatatgagaactacagcaccagcttcttcatcagggacatc*<br>*atcaaaccagacccgcccaagaacttgcagatgaagcctttgaagaactcac*<br>*aggtggaggtcagctgggagtaccctgactcctggagcactccccattccta*<br>*cttctccctcaagttctttgttcgaatccagcgcaagaaagaaaagatgaag* | 171 |

TABLE 10-continued

Exemplary immunomodulatory fusion proteins

| Name | Type | Amino acid sequence | SEQ ID NO |
|---|---|---|---|
| | | *gagacagaggaggggtgtaaccagaaaggtgcgttcctcgtagagaagacat*<br>*ctaccgaagtccaatgcaaaggcgggaatgtctgcgtgcaagctcaggatcg*<br>*ctattacaattcctcatgcagcaagtgggcatgtgttccctgcagggtccga*<br>*tcc*ggaggttccggtggtggatccggaggtggctccggcggcggatccaggg<br>tcattccagtctctggacctgccaggtgtcttagccagtcccgaaacctgct<br>gaagaccacagatgacatggtgaagacggccagagaaaaactgaaacattat<br>tcctgcactgctgaagacatcgatcatgaagacatcacacgggaccaaacca<br>gcacattgaagacctgtttaccactggaactacacaagaacgagagttgcct<br>ggctactagagagacttcttccacaacaagagggagctgcctgcccccacag<br>aagacgtctttgatgatgaccctgtgccttggtagcatctatgaggacttga<br>agatgtaccagacagagttccaggccatcaacgcagcacttcagaatcacaa<br>ccatcagcagatcattctagacaagggcatgctggtggccatcgatgagctg<br>atgcagtctctgaatcataatggcgagactctgcgccagaaacctcctgtgg<br>gagaagcagacccttacagagtgaaaatgaagctctgcatcctgcttcacgc<br>cttcagcacccgcgtcgtgaccatcaacagggtgatgggctatctgagctcc<br>gccggttccggtggcggatcc**gaagcacacaagagtgagatcgcccatcggt**<br>**ataatgatttgggagaacaacatttcaaaggcctagtcctgattgcctttc**<br>**ccagtatctccagaaatgctcatacgatgagcatgccaaattagtgcaggaa**<br>**gtaacagactttgcaaagacgtgtgttgccgatgagtctgccgccaactgtg**<br>**acaaatcccttcacactctttttggagataagttgtgtgccattccaaacct**<br>**ccgtgaaaactatggtgaactggctgactgctgtacaaaacaagagcccgaa**<br>**agaaacgaatgtttcctgcaacacaaagatgacaaccccagcctgccaccat**<br>**ttgaaaggccagaggctgaggccatgtgcacctcctttaaggaaaacccaac**<br>**cacctttatgggacactatttgcatgaagttgccagaagacatccttatttc**<br>**tatgccccagaacttctttactatgctgagcagtacaatgagattctgaccc**<br>**agtgttgtgcagaggctgacaaggaaagctgcctgaccccgaagcttgatgg**<br>**tgtgaaggagaaagcattggtctcatctgtccgtcagagaatgaagtgctcc**<br>**agtatgcagaagtttggagagagagcttttaaagcatgggcagtagctcgtc**<br>**tgagccagacattccccaatgctgactttgcagaaatcaccaaattggcaac**<br>**agacctgaccaaagtcaacaaggagtgctgccatggtgacctgctggaatgc**<br>**gcagatgacagggcggaacttgccaagtacatgtgtgaaaaccaggcgacta**<br>**tctccagcaaactgcagacttgctgcgataaaccactgttgaagaaagccca**<br>**ctgtcttagtgaggtggagcatgacaccatgcctgctgatctgcctgccatt**<br>**gctgctgattttgttgaggaccaggaagtgtgcaagaactatgctgaggcca**<br>**aggatgtcttcctgggcacgttcttgtatgaatattcaagaagacaccctga**<br>**ttactctgtatccctgttgctgagacttgctaagaaatatgaagccactctg**<br>**gaaaagtgctgcgctgaagccaatcctcccgcatgctacggcacagtgcttg**<br>**ctgaatttcagcctcttgtagaagagcctaagaacttggtcaaaaccaactg**<br>**tgatctttacgagaagcttggagaatatggattccaaaatgccattctagtt**<br>**cgctacacccagaaagcacctcaggtgtcaaccccaactctcgtggaggctg**<br>**caagaaacctaggaagagtgggcaccaagtgttgtacacttcctgaagatca**<br>**gagactgccttgtgtggaagactatctgtctgcaatcctgaaccgtgtgtgt**<br>**ctgctgcatgagaagaccccagtgagtgagcatgttaccaagtgctgtagtg**<br>**gatccctggtggaaaggcggccatgcttctctgctctgacagttgatgaaac**<br>**atatgtccccaaagagtttaaagctgagaccttcaccttccactctgatatc**<br>**tgcacacttccagagaaggagaagcagattaagaaacaaacggctcttgctg**<br>**agctggtgaagcacaagcccaaggctacagcggagcaactgaagactgtcat**<br>**ggatgactttgcacagttcctggatacatgttgcaaggctgctgacaaggac**<br>**acctgcttctcgactgagggtccaaaccttgtcactagatgcaaagacgcct**<br>**tagcc**GGGGGGGGAGGC***TCTGAAGAATCCGAGGAGAGTGAAGAGTCAGAGGA***<br>***G*** GGTGGCGGGGGGCACCATCACCACCATCAC | |
| Murine scIL12-ABP10 IL12p40 *italics* IL12p35 **bold** ABP10 ***bold italics*** | aa | *MWELEKDVYVVEVDWTPDAPGETVNLTCDTPEEDDITWTSDQRHGVIGSGKT*<br>*LTITVKEFLDAGQYTCHKGGETLSHSHLLLHKKENGIWSTEILKNFKNKTFL*<br>*KCEAPNYSGRFTCSWLVQRNMDLKFNIKSSSSSPDSRAVTCGMASLSAEKVT*<br>*LDQRDYEKYSVSCQEDVTCPTAEETLPIELALEARQQNKYENYSTSFFIRDI*<br>*IKPDPPKNLQMKPLKNSQVEVSWEYPDSWSTPHSYFSLKFFVRIQRKKEKMK*<br>*ETEEGCNQKGAFLVEKTSTEVQCKGGNVCVQAQDRYYNSSCSKWACVPCRVR*<br>*S*GGSGGGSGGGSGGGS**RVIPVSGPARCLSQSRNLLKTTDDMVKTAREKLKHY**<br>**SCTAEDIDHEDITRDQTSTLKTCLPLELHKNESCLATRETSSTTRGSCLPPQ**<br>**KTSLMMTLCLGSIYEDLKMYQTEFQAINAALQNHNHQQIILDKGMLVAIDEL**<br>**MQSLNHNGETLRQKPPVGEADPYRVKMKLCILLHAFSTRVVTINRVMGYLSS**<br>**A**GSGGGS***FQSEEQQGGGSGGSEEGGMESEESNGGGSGGSEEGG***GGGSHHHHH<br>H | 172 |
| Murine scIL12-ABP10 IL12p40 *italics* IL12p35 **bold** ABP10 ***bold italics*** | DNA | *atgtgggagctggagaaagacgtttatgttgtagaggtggactggactcccg*<br>*atgcccctggagaaacagtgaacctcacctgtgacacgcctgaagaagatga*<br>*catcacctggacctcagaccagagacatggagtcataggctctggaaagacc*<br>*ctgaccatcactgtcaaagagtttctagatgctggccagtacacctgccaca*<br>*aaggaggcgagactctgagccactcacatctgctgctccacaagaaggaaaa*<br>*tggaatttggtccactgaaattttaaaaaatttcaaaaacaagactttcctg*<br>*aagtgtgaagcaccaaattactccggacggttcacgtgctcatggctggtgc*<br>*aaagaaacatggacttgaagttcaacatcaagagcagtagcagttcccctga*<br>*ctctcgggcagtgacatgtggaatggcgtctctgtctgcagagaaggtcaca* | 173 |

TABLE 10-continued

Exemplary immunomodulatory fusion proteins

| Name | Type | Amino acid sequence | SEQ ID NO |
|---|---|---|---|
| | | *ctggaccaaagggactatgagaagtattcagtgtcctgccaggaggatgtca*<br>*cctgcccaactgccgaggagaccctgcccattgaactggcgttggaagcacg*<br>*gcagcagaataaatatgagaactacagcaccagcttcttcatcagggacatc*<br>*atcaaaccagacccgcccaagaacttgcagatgaagcctttgaagaactcac*<br>*aggtggaggtcagctgggagtaccctgactcctggagcactccccattccta*<br>*cttctccctcaagttctttgttcgaatccagcgcaagaaagaaaagatgaag*<br>*gagacagaggaggggtgtaaccagaaaggtgcgttcctcgtagagaagacat*<br>*ctaccgaagtccaatgcaaaggcgggaatgtctgcgtgcaagctcaggatcg*<br>*ctattacaattcctcatgcagcaagtgggcatgtgttccctgcagggtccga*<br>*tccggaggttccggtggtggatccggaggtggctccggcggcggatcc***aggg**<br>**tcattccagtctctggacctgccaggtgtcttagccagtcccgaaacctgct**<br>**gaagaccacagatgacatggtgaagacggccagagaaaaactgaaacattat**<br>**tcctgcactgctgaagacatcgatcatgaagacatcacacgggaccaaacca**<br>**gcacattgaagacctgtttaccactggaactacacaagaacgagagttgcct**<br>**ggctactagagagacttcttccacaacaagagggagctgcctgcccccacag**<br>**aagacgtctttgatgatgaccctgtgccttggtagcatctatgaggacttga**<br>**agatgtaccagacagagttccaggccatcaacgcagcacttcagaatcacaa**<br>**ccatcagcagatcattctagacaagggcatgctggtggccatcgatgagctg**<br>**atgcagtctctgaatcataatggcgagactctgcgccagaaacctcctgtgg**<br>**gagaagcagacccttacagagtgaaaatgaagctctgcatcctgcttcacgc**<br>**cttcagcacccgcgtcgtgaccatcaacagggtgatgggctatctgagctcc**<br>**gcc**ggttccGGTGGAGGTAGT***TTCCAATCAGAAGAGCAACAGGGTGGGGGTT***<br>***CCGGCGGTAGCGAGGAGGGTGGGATGGAGAGTGAAGAATCAAATGGTGGGGG***<br>***TTCCGGCGGTAGCGAGGAGGGTGGG*** GGAGGTGGATGAGAGGATGAGGAGGAT<br>CAC | |
| Murine scIL12-ABP17 IL12p40 *italics* IL12p35 **bold** ABP17 ***bold italics*** | aa | *MWELEKDVYVVEVDWTPDAPGETVNLTCDTPEEDDITWTSDQRHGVIGSGKT*<br>*LTITVKEFLDAGQYTCHKGGETLSHSHLLLHKKENGIWSTEILKNFKNKTFL*<br>*KCEAPNYSGRFTCSWLVQRNMDLKFNIKSSSSSPDSRAVTCGMASLSAEKVT*<br>*LDQRDYEKYSVSCQEDVTCPTAEETLPIELALEARQQNKYENYSTSFFIRDI*<br>*IKPDPPKNLQMKPLKNSQVEVSWEYPDSWSTPHSYFSLKFFVRIQRKKEKMK*<br>*ETEEGCNQKGAFLVEKTSTEVQCKGGNVCVQAQDRYYNSSCSKWACVPCRVR*<br>*S*GGSGGGSGGGSGGGS**RVIPVSGPARCLSQSRNLLKTTDDMVKTAREKLKHY**<br>**SCTAEDIDHEDITRDQTSTLKTCLPLELHKNESCLATRETSSTTRGSCLPPQ**<br>**KTSLMMTLCLGSIYEDLKMYQTEFQAINAALQNHNHQQIILDKGMLVAIDEL**<br>**MQSLNHNGETLRQKPPVGEADPYRVKMKLCILLHAFSTRVVTINRVMGYLSS**<br>**A**GGGG***SEESEESEESEE***GGGGHHHHHH | 174 |
| Murine scIL12-ABP17 IL12p40 *italics* IL12p35 **bold** ABP17 ***bold italics*** | DNA | *atgtgggagctggagaaagacgtttatgttgtagaggtggactggactcccg*<br>*atgcccctggagaaacagtgaacctcacctgtgacacgcctgaagaagatga*<br>*catcacctggacctcagaccagagacatggagtcataggctctggaaagacc*<br>*ctgaccatcactgtcaaagagtttctagatgctggccagtacacctgccaca*<br>*aaggaggcgagactctgagccactcacatctgctgctccacaagaaggaaaa*<br>*tggaatttggtccactgaaattttaaaaaatttcaaaaacaagactttcctg*<br>*aagtgtgaagcaccaaattactccggacggttcacgtgctcatggctggtgc*<br>*aaagaaacatggacttgaagttcaacatcaagagcagtagcagttcccctga*<br>*ctctcgggcagtgacatgtggaatggcgtctctgtctgcagagaaggtcaca*<br>*ctggaccaaagggactatgagaagtattcagtgtcctgccaggaggatgtca*<br>*cctgcccaactgccgaggagaccctgcccattgaactggcgttggaagcacg*<br>*gcagcagaataaatatgagaactacagcaccagcttcttcatcagggacatc*<br>*atcaaaccagacccgcccaagaacttgcagatgaagcctttgaagaactcac*<br>*aggtggaggtcagctgggagtaccctgactcctggagcactccccattccta*<br>*cttctccctcaagttctttgttcgaatccagcgcaagaaagaaaagatgaag*<br>*gagacagaggaggggtgtaaccagaaaggtgcgttcctcgtagagaagacat*<br>*ctaccgaagtccaatgcaaaggcgggaatgtctgcgtgcaagctcaggatcg*<br>*ctattacaattcctcatgcagcaagtgggcatgtgttccctgcagggtccga*<br>*tccggaggttccggtggtggatccggaggtggctccggcggcggatcc***aggg**<br>**tcattccagtctctggacctgccaggtgtcttagccagtcccgaaacctgct**<br>**gaagaccacagatgacatggtgaagacggccagagaaaaactgaaacattat**<br>**tcctgcactgctgaagacatcgatcatgaagacatcacacgggaccaaacca**<br>**gcacattgaagacctgtttaccactggaactacacaagaacgagagttgcct**<br>**ggctactagagagacttcttccacaacaagagggagctgcctgcccccacag**<br>**aagacgtctttgatgatgaccctgtgccttggtagcatctatgaggacttga**<br>**agatgtaccagacagagttccaggccatcaacgcagcacttcagaatcacaa**<br>**ccatcagcagatcattctagacaagggcatgctggtggccatcgatgagctg**<br>**atgcagtctctgaatcataatggcgagactctgcgccagaaacctcctgtgg**<br>**gagaagcagacccttacagagtgaaaatgaagctctgcatcctgcttcacgc**<br>**cttcagcacccgcgtcgtgaccatcaacagggtgatgggctatctgagctcc**<br>**gcc**GGGGGGGGAGGC***TCTGAAGAATCCGAGGAGAGTGAAGAGTCAGAGGAG***G<br>GTGGCGGGGGGCACCATCACCACCATCAC | 175 |
| 3/23 VL chain | aa | TVLTQSPALAVSPGERVTISCRASESVSTRMHWYQQRPGQPPKLLIYVASRL<br>ESGVPARFSGGGSGTDFTLTIDPVEANDTATYFCQQSWNDPWTFGGGTKLEL<br>K | 176 |

TABLE 10-continued

Exemplary immunomodulatory fusion proteins

| Name | Type | Amino acid sequence | SEQ ID NO |
|---|---|---|---|
| | DNA | actgtgctgacccagtctcctgctttggctgtgtctccaggagagagggtta<br>ccatctcctgtagggccagtgagagtgtcagtacacgtatgcactggtacca<br>acagagaccaggacagccacccaaactcctcatctacgttgcatcccgccta<br>gaatctggagtccctgccaggttcagtggcggtgggtctgggacagacttta<br>ccctcaccatagatcctgtggaggctaatgatactgcaacctatttctgtca<br>gcagagttggaatgatccgtggacgttcggtggaggcaccaagctggaattg<br>aaa | 177 |
| 3/23 LC<br>3/23 VL<br>chain **bold**<br>Murine<br>kappa<br>chain<br>*italics* | aa | **TVLTQSPALAVSPGERVTISCRASESVSTRMHWYQQRPGQPPKLLIYVASRL**<br>**ESGVPARFSGGGSGTDFTLTIDPVEANDTATYFCQQSWNDPWTFGGGTKLEL**<br>**K***RADAAPTVSIFPPSSEQLTSGGASVVCFLNNFYPKDINVKWKIDGSERQNG*<br>*VLNSWTDQDSKDSTYSMSSTLTLTKDEYERHNSYTCEATHKTSTSPIVKSFN*<br>*RNEC* | 178 |
| 3/23 LC<br>3/23 VL<br>chain **bold**<br>Murine<br>kappa<br>chain<br>italics | DNA | **actgtgctgacccagtctcctgctttggctgtgtctccaggagagagggtta**<br>**ccatctcctgtagggccagtgagagtgtcagtacacgtatgcactggtacca**<br>**acagagaccaggacagccacccaaactcctcatctacgttgcatcccgccta**<br>**gaatctggagtccctgccaggttcagtggcggtgggtctgggacagacttta**<br>**ccctcaccatagatcctgtggaggctaatgatactgcaacctatttctgtca**<br>**gcagagttggaatgatccgtggacgttcggtggaggcaccaagctggaattg**<br>**aaa***cgggctgatgctgcaccaactgtatccatcttcccaccatccagtgagc*<br>*agttaacatctggaggtgcctcagtcgtgtgcttcttgaacaacttctaccc*<br>*caaagacatcaatgtcaagtggaagattgatggcagtgaacgacaaaatggc*<br>*gtcctgaacagttggactgatcaggacagcaaagacagcacctacagcatga*<br>*gcagcaccctcacgttgaccaaggacgagtatgaacgacataacagctatac*<br>*ctgtgaggccactcacaagacatcaacttcacccattgtcaagagcttcaac*<br>*aggaatgagtgt* | 179 |
| 3/23 VH<br>chain | aa | VQLVESGGGLVQPGRSLKLSCAASGFTLSDYYMAWVRQAPKKGLEWVASINY<br>EGSSTYYGESVKGRFTISRDNAKSTLYLQMNSLRSEDTATYYCVRHDNYFDY<br>WGQGVLVTVSS | 180 |
| | DNA | gtgcagttggtggagtctgggggaggcttagtgcagcctggaaggtccctga<br>aactctcctgtgcagcctcaggattcactctcagtgactattacatggcctg<br>ggtccgccaggctccaaagaagggtctggagtgggtcgcatccattaattat<br>gagggtagtagcacttactatggagagtccgtgaagggccgattcactatct<br>ccagagataacgcaaaaagcaccctatacctgcaaatgaacagtctgaggtc<br>tgaggacacggccacttattattgtgtaagacatgataactactttgattat<br>tggggccaaggagtactagtcacagtctcctca | 181 |
| mIgG1 | aa | ATTKGPSVYPLAPGSAAQTNSMVTLGCLVKGYFPEPVTVTWNSGSLSSGVHT<br>FPAVLQSDLYTLSSSVTVPSSTWPSQTVTCNVAHPASSTKVDKKIVPRDCGC<br>KPCICTVPEVSSVFIFPPKPKDVLTITLTPKVTCVVVDISKDDPEVQFSWFV<br>DDVEVHTAQTKPREEQINSTFRSVSELPIMHQDWLNGKEFKCRVNSAAFPAP<br>IEKTISKTKGRPKAPQVYTIPPPKEQMAKDKVSLTCMITNFFPEDITVEWQW<br>NGQPAENYKNTQPIMDTDGSYFVYSKLNVQKSNWEAGNTFTCSVLHEGLHNH<br>HTEKSLSHSPGKG | 182 |
| | DNA | GCCACCACCAAGGGCCCATCTGTCTATCCACTGGCCCCTGGATCTGCTGCCC<br>AAACTAACTCCATGGTGACCCTGGGATGCCTGGTCAAGGGCTATTTCCCTGA<br>GCCAGTGACAGTGACCTGGAACTCTGGATCCCTGTCCAGCGGTGTGCACACC<br>TTCCCAGCTGTCCTGCAGTCTGACCTCTACACTCTGAGCAGCTCAGTGACTG<br>TCCCCTCCAGCACCTGGCCCAGCCAGACCGTCACCTGCAACGTTGCCCACCC<br>GGCCAGCAGCACCAAGGTGGACAAGAAAATTGTGCCCAGGGATTGTGGTTGT<br>AAGCCTTGCATATGTACAGTCCCAGAAGTATCATCTGTCTTCATCTTCCCCC<br>CAAAGCCCAAGGATGTGCTCACCATTACTCTGACTCCTAAGGTCACGTGTGT<br>TGTGGTAGACATCAGCAAGGATGATCCCGAGGTCCAGTTCAGCTGGTTTGTA<br>GATGATGTGGAGGTGCACACAGCTCAGACGAAACCCCGGGAGGAGCAGATCA<br>ACAGCACTTTCCGTTCAGTCAGTGAACTTCCCATCATGCACCAGGACTGGCT<br>CAATGGCAAGGAGTTCAAATGCAGGGTCAACAGTGCAGCTTTCCCTGCCCCC<br>ATCGAGAAAACCATCTCCAAAACCAAAGGCAGACCGAAGGCTCCACAGGTGT<br>ACACCATTCCACCTCCCAAGGAGCAGATGGCCAAGGATAAAGTCAGTCTGAC<br>CTGCATGATAACAAACTTCTTCCCTGAAGACATTACTGTGGAGTGGCAGTGG<br>AATGGGCAGCCAGCGGAGAACTACAAGAACACTCAGCCCATCATGGACACAG<br>ATGGCTCTTACTTCGTCTACAGCAAGCTCAATGTGCAGAAGAGCAACTGGGA<br>GGCAGGAAATACTTTCACCTGCTCTGTGTTACATGAGGGCCTGCACAACCAC<br>CATACTGAGAAGAGCCTCTCCCACTCTCCTGGTAAA | 183 |
| 3/23 HC-<br>ABP10<br>3/23 VH<br>chain **bold**<br>mIgG1<br>*italics* | aa | **VQLVESGGGLVQPGRSLKLSCAASGFTLSDYYMAWVRQAPKKGLEWVASINY**<br>**EGSSTYYGESVKGRFTISRDNAKSTLYLQMNSLRSEDTATYYCVRHDNYFDY**<br>**WGQGVLVTVSS***ATTKGPSVYPLAPGSAAQTNSMVTLGCLVKGYFPEPVTVTW*<br>*NSGSLSSGVHTFPAVLQSDLYTLSSSVTVPSSTWPSQTVTCNVAHPASSTKV*<br>*DKKIVPRDCGCKPCICTVPEVSSVFIFPPKPKDVLTITLTPKVTCVVVDISK*<br>*DDPEVQFSWFVDDVEVHTAQTKPREEQINSTFRSVSELPIMHQDWLNGKEFK* | 184 |

TABLE 10-continued

Exemplary immunomodulatory fusion proteins

| Name | Type | Amino acid sequence | SEQ ID NO |
|---|---|---|---|
| ABP10 ***bold italics*** | | CRVNSAAFPAPIEKTISKTKGRPKAPQVYTIPPPKEQMAKDKVSLTCMITNF<br>*FPEDITVEWQWNGQPAENYKNTQPIMDTDGSYFVYSKLNVQKSNWEAGNTFT*<br>*CSVLHEGLHNHHTEKSLSHSPGK*GGGSGGGSGGGSGGGS***FQSEEQQGGGSGG***<br>***SEEGGMESEESNGGGSGGSEEGG*** | |
| 3/23 HC-ABP10 3/23 VH chain **bold** mIgG1 *italics* ABP10 ***bold italics*** | DNA | **gtgcagttggtggagtctgggggaggcttagtgcagcctggaaggtccctga**<br>**aactctcctgtgcagcctcaggattcactctcagtgactattacatggcctg**<br>**ggtccgccaggctccaaagaagggtctggagtgggtcgcatccattaattat**<br>**gagggtagtagcacttactatggagagtccgtgaagggccgattcactatct**<br>**ccagagataacgcaaaaagcaccctatacctgcaaatgaacagtctgaggtc**<br>**tgaggacacggccacttattattgtgtaagacatgataactactttgattat**<br>**tggggccaaggagtactagtcacagtctcctca***GCCACCACCAAGGGCCCAT*<br>*CTGTCTATCCACTGGCCCCTGGATCTGCTGCCCAAACTAACTCCATGGTGAC*<br>*CCTGGGATGCCTGGTCAAGGGCTATTTCCCTGAGCCAGTGACAGTGACCTGG*<br>*AACTCTGGATCCCTGTCCAGCGGTGTGCACACCTTCCCAGCTGTCCTGCAGT*<br>*CTGACCTCTACACTCTGAGCAGCTCAGTGACTGTCCCCTCCAGCACCTGGCC*<br>*CAGCCAGACCGTCACCTGCAACGTTGCCCACCCGGCCAGCAGCACCAAGGTG*<br>*GACAAGAAAATTGTGCCCAGGGATTGTGGTTGTAAGCCTTGCATATGTACAG*<br>*TCCCAGAAGTATCATCTGTCTTCATCTTCCCCCCAAAGCCCAAGGATGTGCT*<br>*CACCATTACTCTGACTCCTAAGGTCACGTGTGTTGTGGTAGACATCAGCAAG*<br>*GATGATCCCGAGGTCCAGTTCAGCTGGTTTGTAGATGATGTGGAGGTGCACA*<br>*CAGCTCAGACGAAACCCCGGGAGGAGCAGATCAACAGCACTTTCCGTTCAGT*<br>*CAGTGAACTTCCCATCATGCACCAGGACTGGCTCAATGGCAAGGAGTTCAAA*<br>*TGCAGGGTCAACAGTGCAGCTTTCCCTGCCCCCATCGAGAAAACCATCTCCA*<br>*AAACCAAAGGCAGACCGAAGGCTCCACAGGTGTACACCATTCCACCTCCCAA*<br>*GGAGCAGATGGCCAAGGATAAAGTCAGTCTGACCTGCATGATAACAAACTTC*<br>*TTCCCTGAAGACATTACTGTGGAGTGGCAGTGGAATGGGCAGCCAGCGGAGA*<br>*ACTACAAGAACACTCAGCCCATCATGGACACAGATGGCTCTTACTTCGTCTA*<br>*CAGCAAGCTCAATGTGCAGAAGAGCAACTGGGAGGCAGGAAATACTTTCACC*<br>*TGCTCTGTGTTACATGAGGGCCTGCACAACCACCATACTGAGAAGAGCCTCT*<br>*CCCACTCTCCTGGT*AAAGGCGGAGGTTCTGGAGGTGGCTCCGGTGGAGGTTC<br>TGGAGGTGGCTCC***TTCCAATCAGAAGAGCAACAGGGTGGGGGTTCCGGCGGT***<br>***AGCGAGGAGGGTGGGATGGAGAGTGAAGAATCAAATGGTGGGGGTTCCGGCG***<br>***GTAGCGAGGAGGGTGGG*** GGAGGTGGATCA | 185 |
| LOB12.3 VL chain | aa | DIQMTQSPASLSASLEEIVTITCQASQDIGNWLAWYHQKPGKSPQLLIYGST<br>SLADGVPSRFSGSSSGSQYSLKISRLQVEDIGIYYCLQAYGAPWTFGGGTKL<br>ELK | 186 |
| | DNA | gatattcaaatgactcaatctccggcaagtctttccgcgtccctcgaagaaa<br>tcgtcacgataacgtgccaagcgagtcaggacatcggtaactggctggcttg<br>gtatcatcagaaacctggtaaatcaccacaactgcttatatacgggtctaca<br>agccttgcagatggagtgccaagtagattcagtggtagttccagcggatctc<br>aatattctttgaaaatatccagactccaggtagaggatattggaatttatta<br>ctgccttcaggcttacggtgcgccctggacttttgggggaggtacaaagctc<br>gaacttaaa | 187 |
| LOB12.3 LC LOB12.3 LC **bold** murine kappa chain *italics* | aa | **DIQMTQSPASLSASLEEIVTITCQASQDIGNWLAWYHQKPGKSPQLLIYGST**<br>**SLADGVPSRFSGSSSGSQYSLKISRLQVEDIGIYYCLQAYGAPWTFGGGTKL**<br>**ELK***RADAAPTVSIFPPSSEQLTSGGASVVCFLNNFYPKDINVKWKIDGSERQ*<br>*NGVLNSWTDQDSKDSTYSMSSTLTLTKDEYERHNSYTCEATHKTSTSPIVKS*<br>*FNRNEC* | 188 |
| LOB12.3 LC LOB12.3 LC **bold** murine kappa chain *italics* | DNA | **gatattcaaatgactcaatctccggcaagtctttccgcgtccctcgaagaaa**<br>**tcgtcacgataacgtgccaagcgagtcaggacatcggtaactggctggcttg**<br>**gtatcatcagaaacctggtaaatcaccacaactgcttatatacgggtctaca**<br>**agccttgcagatggagtgccaagtagattcagtggtagttccagcggatctc**<br>**aatattctttgaaaatatccagactccaggtagaggatattggaatttatta**<br>**ctgccttcaggcttacggtgcgccctggacttttgggggaggtacaaagctc**<br>**gaacttaaa***cgggctgatgctgcaccaactgtatccatcttcccaccatcca*<br>*gtgagcagttaacatctggaggtgcctcagtcgtgtgcttcttgaacaactt*<br>*ctaccccaaagacatcaatgtcaagtggaagattgatggcagtgaacgacaa*<br>*aatggcgtcctgaacagttggactgatcaggacagcaaagacagcacctaca*<br>*gcatgagcagcaccctcacgttgaccaaggacgagtatgaacgacataacag*<br>*ctatacctgtgaggccactcacaagacatcaacttcacccattgtcaagagc*<br>*ttcaacaggaatgagtgt* | 189 |
| LOB12.3 VH chain | aa | DVQLVESGGGLVQPGRSLKLSCAASGFIFSYFDMAWVRQAPTKGLEWVASIS<br>PDGSIPYYRDSVKGRFTVSRENAKSSLYLQMDSLRSEDTATYYCARRSYGGY<br>SEIDYWGQGVMVTVSS | 190 |
| | DNA | gacgtgcaactggtagagagcggtgggggcctcgtacaacccggtcggagtt<br>tgaagttgtcctgcgccgcgtcaggattcatctttagttactttgacatggc<br>ttgggttcgacaagcacccacgaaaggacttgagtgggtcgcttcaatatct | 191 |

TABLE 10-continued

Exemplary immunomodulatory fusion proteins

| Name | Type | Amino acid sequence | SEQ ID NO |
|---|---|---|---|
| | | cccgacgggagcatcccctactatagggattccgttaaaggacgcttcactg<br>tttcacgagaaaatgcaaaatcttcactttacttgcaaatggatagtttgcg<br>atcagaagacaccgcaacttactactgcgcaaggcggtcttatggggggtat<br>agcgaaatagactattgggggcaaggagtgatggttacggtttcatcc | |
| LOB12.3 HC-ABP10 LOB12.3 HC **bold** mIgG1 *italics* ABP10 ***bold italics*** | aa | **DVQLVESGGGLVQPGRSLKLSCAASGFIFSYFDMAWVRQAPTKGLEWVASI**<br>**SPDGSIPYYRDSVKGRFTVSRENAKSSLYLQMDSLRSEDTATYYCARRSYG**<br>**GYSEIDYWGQGVMVTVSS***ATTKGPSVYPLAPGSAAQTNSMVTLGCLVKGYF*<br>*PEPVTVTWNSGSLSSGVHTFPAVLQSDLYTLSSSVTVPSSTWPSQTVTCNV*<br>*AHPASSTKVDKKIVPRDCGCKPCICTVPEVSSVFIFPPKPKDVLTITLTPK*<br>*VTCVVVDISKDDPEVQFSWFVDDVEVHTAQTKPREEQINSTFRSVSELPIM*<br>*HQDWLNGKEFKCRVNSAAFPAPIEKTISKTKGRPKAPQVYTIPPPKEQMAK*<br>*DKVSLTCMITNFFPEDITVEWQWNGQPAENYKNTQPIMDTDGSYFVYSKLN*<br>*VQKSNWEAGNTFTCSVLHEGLHNHHTEKSLSHSPGK*GGGSGGGSGGGSGGG<br>S***FQSEEQQGGGSGGSEEGGMESEESNGGGSGGSEEGG*** | 192 |
| LOB12.3 HC-ABP10 LOB12.3 HC **bold** mIgG1 *italics* ABP10 ***bold italics*** | DNA | **gacgtgcaactggtagagagcggtgggggcctcgtacaacccggtcggagtt**<br>**tgaagttgtcctgcgccgcgtcaggattcatctttagttactttgacatggc**<br>**ttgggttcgacaagcacccacgaaaggacttgagtgggtcgcttcaatatct**<br>**cccgacgggagcatcccctactatagggattccgttaaaggacgcttcactg**<br>**tttcacgagaaaatgcaaaatcttcactttacttgcaaatggatagtttgcg**<br>**atcagaagacaccgcaacttactactgcgcaaggcggtcttatggggggtat**<br>**agcgaaatagactattgggggcaaggagtgatggttacggtttcatcc***GCCA*<br>*CCACCAAGGGCCCATCTGTCTATCCACTGGCCCCTGGATCTGCTGCCCAAAC*<br>*TAACTCCATGGTGACCCTGGGATGCCTGGTCAAGGGCTATTTCCCTGAGCCA*<br>*GTGACAGTGACCTGGAACTCTGGATCCCTGTCCAGCGGTGTGCACACCTTCC*<br>*CAGCTGTCCTGCAGTCTGACCTCTACACTCTGAGCAGCTCAGTGACTGTCCC*<br>*CTCCAGCACCTGGCCCAGCCAGACCGTCACCTGCAACGTTGCCCACCCGGCC*<br>*AGCAGCACCAAGGTGGACAAGAAAATTGTGCCCAGGGATTGTGGTTGTAAGC*<br>*CTTGCATATGTACAGTCCCAGAAGTATCATCTGTCTTCATCTTCCCCCCAAA*<br>*GCCCAAGGATGTGCTCACCATTACTCTGACTCCTAAGGTCACGTGTGTTGTG*<br>*GTAGACATCAGCAAGGATGATCCCGAGGTCCAGTTCAGCTGGTTTGTAGATG*<br>*ATGTGGAGGTGCACACAGCTCAGACGAAACCCCGGGAGGAGCAGATCAACAG*<br>*CACTTTCCGTTCAGTCAGTGAACTTCCCATCATGCACCAGGACTGGCTCAAT*<br>*GGCAAGGAGTTCAAATGCAGGGTCAACAGTGCAGCTTTCCCTGCCCCCATCG*<br>*AGAAAACCATCTCCAAAACCAAAGGCAGACCGAAGGCTCCACAGGTGTACAC*<br>*CATTCCACCTCCCAAGGAGCAGATGGCCAAGGATAAAGTCAGTCTGACCTGC*<br>*ATGATAACAAACTTCTTCCCTGAAGACATTACTGTGGAGTGGCAGTGGAATG*<br>*GGCAGCCAGCGGAGAACTACAAGAACACTCAGCCCATCATGGACACAGATGG*<br>*CTCTTACTTCGTCTACAGCAAGCTCAATGTGCAGAAGAGCAACTGGGAGGCA*<br>*GGAAATACTTTCACCTGCTCTGTGTTACATGAGGGCCTGCACAACCACCATA*<br>*CTGAGAAGAGCCTCTCCCACTCTCCTGGTAAA*GGCGGAGGTTCTGGAGGTGG<br>CTCCGGTGGAGGTTCTGGAGGTGGCTCC***TTCCAATCAGAAGAGCAACAGGGT***<br>***GGGGGTTCCGGCGGTAGCGAGGAGGGTGGGATGGAGAGTGAAGAATCAAATG***<br>***GTGGGGGTTCCGGCGGTAGCGAGGAGGGTGGG*** GGAGGTGGATGA | 193 |
| OX86 VL chain | aa | *DIVMTQGALPNPVPSGESASITCRSSQSLVYKDGQTYLNWFLQRPGQSPQLL*<br>*TYWMSTRASGVSDRFSGSGSGTYFTLKISRVRAEDAGVYYCQQVREYPFTFG*<br>*SGTKLEIK* | 194 |
| | DNA | GATATCGTGATGACCCAGGGCGCTCTGCCCAATCCTGTTCCTTCTGGCGAGA<br>GCGCCAGCATCACCTGTAGAAGCTCTCAGAGCCTGGTGTACAAGGACGGCCA<br>GACCTACCTGAACTGGTTCCTGCAAAGACCCGGCCAGTCTCCTCAGCTGCTG<br>ACCTACTGGATGAGCACAAGAGCCAGCGGCGTGTCCGATAGATTTTCTGGCA<br>GCGGCTCCGGCACCTACTTCACCCTGAAGATCTCCAGAGTGCGCGCCGAAGA<br>TGCCGGCGTGTACTACTGTCAGCAAGTGCGCGAGTACCCCTTCACATTCGGC<br>AGCGGCACCAAGCTGGAAATCAAG | 195 |
| Murine kappa chain | aa | *RADAAPTVSIFPPSSEQLTSGGASVVCFLNNFYPKDINVKWKIDGSERQNGV*<br>*LNSWTDQDSKDSTYSMSSTLTLTKDEYERHNSYTCEATHKTSTSPIVKSFNR*<br>*NEC* | 196 |
| | DNA | cgggctgatgctgcaccaactgtatccatcttcccaccatccagtgagcagt<br>taacatctggaggtgcctcagtcgtgtgcttcttgaacaacttctaccccaa<br>agacatcaatgtcaagtggaagattgatggcagtgaacgacaaaatggcgtc<br>ctgaacagttggactgatcaggacagcaaagacagcacctacagcatgagca<br>gcaccctcacgttgaccaaggacgagtatgaacgacataacagctatacctg<br>tgaggccactcacaagacatcaacttcacccattgtcaagagcttcaacagg<br>aatgagtgt | 197 |

TABLE 10-continued

Exemplary immunomodulatory fusion proteins

| Name | Type | Amino acid sequence | SEQ ID NO |
|---|---|---|---|
| OX86 LC<br>OX86 LC<br>**bold**<br>Murine<br>kappa<br>chain<br>*italics* | aa | **DIVMTQGALPNPVPSGESASITCRSSQSLVYKDGQTYLNWFLQRPGQSPQLL**<br>**TYWMSTRASGVSDRFSGSGSGTYFTLKISRVRAEDAGVYYCQQVREYPFTFG**<br>**SGTKLETK***RADAAPTVSIFPPSSEQLTSGGASVVCFLNNFYPKDINVKWKID*<br>*GSERQNGVLNSWTDQDSKDSTYSMSSTLTLTKDEYERHNSYTCEATHKTSTS*<br>*PIVKSFNRNEC* | 198 |
| OX86 LC<br>OX86 LC<br>**bold**<br>Murine<br>kappa<br>chain<br>*italics* | DNA | **GATATCGTGATGACCCAGGGCGCTCTGCCCAATCCTGTTCCTTCTGGCGAGA**<br>**GCGCCAGCATCACCTGTAGAAGCTCTCAGAGCCTGGTGTACAAGGACGGCCA**<br>**GACCTACCTGAACTGGTTCCTGCAAAGACCCGGCCAGTCTCCTCAGCTGCTG**<br>**ACCTACTGGATGAGCACAAGAGCCAGCGGCGTGTCCGATAGATTTTCTGGCA**<br>**GCGGCTCCGGCACCTACTTCACCCTGAAGATCTCCAGAGTGCGCGCCGAAGA**<br>**TGCCGGCGTGTACTACTGTCAGCAAGTGCGCGAGTACCCCTTCACATTCGGC**<br>**AGCGGCACCAAGCTGGAAATCAAG***cgggctgatgctgcaccaactgtatcca*<br>*tcttcccaccatccagtgagcagttaacatctggaggtgcctcagtcgtgtg*<br>*cttcttgaacaacttctaccccaaagacatcaatgtcaagtggaagattgat*<br>*ggcagtgaacgacaaaatggcgtcctgaacagttggactgatcaggacagca*<br>*aagacagcacctacagcatgagcagcaccctcacgttgaccaaggacgagta*<br>*tgaacgacataacagctatacctgtgaggccactcacaagacatcaacttca*<br>*cccattgtcaagagcttcaacaggaatgagtgt* | 199 |
| OX86 VH<br>chain | aa | QVQLKESGPGLVQPSQTLSLTCTVSGFSLTGYNLHWVRQPPGKGLEWMGRMR<br>YDGDTYYNSVLKSRLSISRDTSKNQVFLKMNSLQTDDTAIYYCTRDGRGDSF<br>DYWGQGVMVTVSS | 200 |
| | DNA | CAGGTGCAGCTGAAAGAGTCTGGACCTGGACTGGTGCAGCCCAGCCAAACAC<br>TGAGCCTGACCTGTACCGTGTCCGGCTTTAGCCTGACCGGCTACAACCTGCA<br>CTGGGTCCGACAGCCACCTGGCAAAGGACTGGAATGGATGGGCAGAATGAGA<br>TACGACGGCGACACCTACTACAACAGCGTGCTGAAGTCCCGGCTGAGCATCA<br>GCAGAGACACCAGCAAGAACCAGGTGTTCCTGAAGATGAACAGCCTGCAGAC<br>CGACGACACCGCCATCTACTACTGCACCAGAGATGGCAGAGGCGACAGCTTC<br>GATTATTGGGGCCAGGGCGTGATGGTCACCGTGTCCTCT | 201 |
| OX86 HC-<br>ABP10<br>OX86 HC<br>**bold**<br>mIgG1<br>*italics*<br>ABP10 ***bold***<br>***italics*** | aa | **QVQLKESGPGLVQPSQTLSLTCTVSGFSLTGYNLHWVRQPPGKGLEWMGRMR**<br>**YDGDTYYNSVLKSRLSISRDTSKNQVFLKMNSLQTDDTAIYYCTRDGRGDSF**<br>**DYWGQGVMVTVSS***ATTKGPSVYPLAPGSAAQTNSMVTLGCLVKGYFPEPVTV*<br>*TWNSGSLSSGVHTFPAVLQSDLYTLSSSVTVPSSTWPSQTVTCNVAHPASST*<br>*KVDKKIVPRDCGCKPCICTVPEVSSVFIFPPKPKDVLTITLTPKVTCVVVDI*<br>*SKDDPEVQFSWFVDDVEVHTAQTKPREEQINSTFRSVSELPIMHQDWLNGKE*<br>*FKCRVNSAAFPAPIEKTISKTKGRPKAPQVYTIPPPKEQMAKDKVSLTCMIT*<br>*NFFPEDITVEWQWNGQPAENYKNTQPIMDTDGSYFVYSKLNVQKSNWEAGNT*<br>*FTCSVLHEGLHNHHTEKSLSHSPGK*GGGSGGGSGGGSGGGS***FQSEEQQGGGS***<br>***GGSEEGGMESEESNGGGSGGSEEGG*** | 202 |
| OX86 HC-<br>ABP10<br>OX86 HC<br>**bold**<br>mIgG1<br>*italics*<br>ABP10 ***bold***<br>***italics*** | DNA | **CAGGTGCAGCTGAAAGAGTCTGGACCTGGACTGGTGCAGCCCAGCCAAACAC**<br>**TGAGCCTGACCTGTACCGTGTCCGGCTTTAGCCTGACCGGCTACAACCTGCA**<br>**CTGGGTCCGACAGCCACCTGGCAAAGGACTGGAATGGATGGGCAGAATGAGA**<br>**TACGACGGCGACACCTACTACAACAGCGTGCTGAAGTCCCGGCTGAGCATCA**<br>**GCAGAGACACCAGCAAGAACCAGGTGTTCCTGAAGATGAACAGCCTGCAGAC**<br>**CGACGACACCGCCATCTACTACTGCACCAGAGATGGCAGAGGCGACAGCTTC**<br>**GATTATTGGGGCCAGGGCGTGATGGTCACCGTGTCCTCT***GCCACCACCAAGG*<br>*GCCCATCTGTCTATCCACTGGCCCCTGGATCTGCTGCCCAAACTAACTCCAT*<br>*GGTGACCCTGGGATGCCTGGTCAAGGGCTATTTCCCTGAGCCAGTGACAGTG*<br>*ACCTGGAACTCTGGATCCCTGTCCAGCGGTGTGCACACCTTCCCAGCTGTCC*<br>*TGCAGTCTGACCTCTACACTCTGAGCAGCTCAGTGACTGTCCCCTCCAGCAC*<br>*CTGGCCCAGCCAGACCGTCACCTGCAACGTTGCCCACCCGGCCAGCAGCACC*<br>*AAGGTGGACAAGAAAATTGTGCCCAGGGATTGTGGTTGTAAGCCTTGCATAT*<br>*GTACAGTCCCAGAAGTATCATCTGTCTTCATCTTCCCCCCAAAGCCCAAGGA*<br>*TGTGCTCACCATTACTCTGACTCCTAAGGTCACGTGTGTTGTGGTAGACATC*<br>*AGCAAGGATGATCCCGAGGTCCAGTTCAGCTGGTTTGTAGATGATGTGGAGG*<br>*TGCACACAGCTCAGACGAAACCCCGGGAGGAGCAGATCAACAGCACTTTCCG*<br>*TTCAGTCAGTGAACTTCCCATCATGCACCAGGACTGGCTCAATGGCAAGGAG*<br>*TTCAAATGCAGGGTCAACAGTGCAGCTTTCCCTGCCCCCATCGAGAAAACCA*<br>*TCTCCAAAACCAAAGGCAGACCGAAGGCTCCACAGGTGTACACCATTCCACC*<br>*TCCCAAGGAGCAGATGGCCAAGGATAAAGTCAGTCTGACCTGCATGATAACA*<br>*AACTTCTTCCCTGAAGACATTACTGTGGAGTGGCAGTGGAATGGGCAGCCAG*<br>*CGGAGAACTACAAGAACACTCAGCCCATCATGGACACAGATGGCTCTTACTT*<br>*CGTCTACAGCAAGCTCAATGTGCAGAAGAGCAACTGGGAGGCAGGAAATACT*<br>*TTCACCTGCTCTGTGTTACATGAGGGCCTGCACAACCACCATACTGAGAAGA*<br>*GCCTCTCCCACTCTCCTGGTAAA*GGCGGAGGTTCTGGAGGTGGCTCCGGTGG<br>AGGTTCTGGAGGTGGCTCC***TTCCAATCAGAAGAGCAACAGGGTGGGGGTTCC***<br>***GGCGGTAGCGAGGAGGGTGGGATGGAGAGTGAAGAATCAAATGGTGGGGGTT***<br>***CCGGCGGTAGCGAGGAGGGTGGG*** GGAGGTGGATGA | 203 |

TABLE 10-continued

| Exemplary immunomodulatory fusion proteins | | | |
|---|---|---|---|
| Name | Type | Amino acid sequence | SEQ ID NO |
| MSA-ABP10<br>MSA **bold**<br>ABP10 ***bold italics*** | aa | **EAHKSEIAHRYNDLGEQHFKGLVLIAFSQYLQKCSYDEHAKLVQEVTDFAKT**<br>**CVADESAANCDKSLHTLFGDKLCAIPNLRENYGELADCCTKQEPERNECFLQ**<br>**HKDDNPSLPPFERPEAEAMCTSFKENPTTFMGHYLHEVARRHPYFYAPELLY**<br>**YAEQYNEILTQCCAEADKESCLTPKLDGVKEKALVSSVRQRMKCSSMQKFGE**<br>**RAFKAWAVARLSQTFPNADFAEITKLATDLTKVNKECCHGDLLECADDRAEL**<br>**AKYMCENQATISSKLQTCCDKPLLKKAHCLSEVEHDTMPADLPAIAADFVED**<br>**QEVCKNYAEAKDVFLGTFLYEYSRRHPDYSVSLLLRLAKKYEATLEKCCAEA**<br>**NPPACYGTVLAEFQPLVEEPKNLVKTNCDLYEKLGEYGFQNAILVRYTQKAP**<br>**QVSTPTLVEAARNLGRVGTKCCTLPEDQRLPCVEDYLSAILNRVCLLHEKTP**<br>**VSEHVTKCCSGSLVERRPCFSALTVDETYVPKEFKAETFTFHSDICTLPEKE**<br>**KQIKKQTALAELVKHKPKATAEQLKTVMDDFAQFLDTCCKAADKDTCFSTEG**<br>**PNLVTRCKDALA**GGGS***FQSEEQQGGGSGGSEEGGMESEESNGGGSGGSEEGG***<br>GGGSHHHHHH | 204 |
| MSA-ABP10<br>MSA **bold**<br>ABP10 ***bold italics*** | DNA | **GAAGCACACAAGAGTGAGATCGCCCATCGGTATAATGATTTGGGAGAACAAC**<br>**ATTTCAAAGGCCTAGTCCTGATTGCCTTTTCCCAGTATCTCCAGAAATGCTC**<br>**ATACGATGAGCATGCCAAATTAGTGCAGGAAGTAACAGACTTTGCAAAGACG**<br>**TGTGTTGCCGATGAGTCTGCCGCCAACTGTGACAAATCCCTTCACACTCTTT**<br>**TTGGAGATAAGTTGTGTGCCATTCCAAACCTCCGTGAAAACTATGGTGAACT**<br>**GGCTGACTGCTGTACAAAACAAGAGCCCGAAAGAAACGAATGTTTCCTGCAA**<br>**CACAAAGATGACAACCCCAGCCTGCCACCATTTGAAAGGCCAGAGGCTGAGG**<br>**CCATGTGCACCTCCTTTAAGGAAAACCCAACCACCTTTATGGGACACTATTT**<br>**GCATGAAGTTGCCAGAAGACATCCTTATTTCTATGCCCCAGAACTTCTTTAC**<br>**TATGCTGAGCAGTACAATGAGATTCTGACCCAGTGTTGTGCAGAGGCTGACA**<br>**AGGAAAGCTGCCTGACCCCGAAGCTTGATGGTGTGAAGGAGAAAGCATTGGT**<br>**CTCATCTGTCCGTCAGAGAATGAAGTGCTCCAGTATGCAGAAGTTTGGAGAG**<br>**AGAGCTTTTAAAGCATGGGCAGTAGCTCGTCTGAGCCAGACATTCCCCAATG**<br>**CTGACTTTGCAGAAATCACCAAATTGGCAACAGACCTGACCAAAGTCAACAA**<br>**GGAGTGCTGCCATGGTGACCTGCTGGAATGCGCAGATGACAGGGCGGAACTT**<br>**GCCAAGTACATGTGTGAAAACCAGGCGACTATCTCCAGCAAACTGCAGACTT**<br>**GCTGCGATAAACCACTGTTGAAGAAAGCCCACTGTCTTAGTGAGGTGGAGCA**<br>**TGACACCATGCCTGCTGATCTGCCTGCCATTGCTGCTGATTTTGTTGAGGAC**<br>**CAGGAAGTGTGCAAGAACTATGCTGAGGCCAAGGATGTCTTCCTGGGCACGT**<br>**TCTTGTATGAATATTCAAGAAGACACCCTGATTACTCTGTATCCCTGTTGCT**<br>**GAGACTTGCTAAGAAATATGAAGCCACTCTGGAAAAGTGCTGCGCTGAAGCC**<br>**AATCCTCCCGCATGCTACGGCACAGTGCTTGCTGAATTTCAGCCTCTTGTAG**<br>**AAGAGCCTAAGAACTTGGTCAAAACCAACTGTGATCTTTACGAGAAGCTTGG**<br>**AGAATATGGATTCCAAAATGCCATTCTAGTTCGCTACACCCAGAAAGCACCT**<br>**CAGGTGTCAACCCCAACTCTCGTGGAGGCTGCAAGAAACCTAGGAAGAGTGG**<br>**GCACCAAGTGTTGTACACTTCCTGAAGATCAGAGACTGCCTTGTGTGGAAGA**<br>**CTATCTGTCTGCAATCCTGAACCGTGTGTGTCTGCTGCATGAGAAGACCCCA**<br>**GTGAGTGAGCATGTTACCAAGTGCTGTAGTGGATCCCTGGTGGAAAGGCGGC**<br>**CATGCTTCTCTGCTCTGACAGTTGATGAAACATATGTCCCCAAAGAGTTTAA**<br>**AGCTGAGACCTTCACCTTCCACTCTGATATCTGCACACTTCCAGAGAAGGAG**<br>**AAGCAGATTAAGAAACAAACGGCTCTTGCTGAGCTGGTGAAGCACAAGCCCA**<br>**AGGCTACAGCGGAGCAACTGAAGACTGTCATGGATGACTTTGCACAGTTCCT**<br>**GGATACATGTTGCAAGGCTGCTGACAAGGACACCTGCTTCTCGACTGAGGGT**<br>**CCAAACCTTGTCACTAGATGCAAAGACGCCTTAGCC**GGTGGAGGTAGT***TTCC***<br>***AATCAGAAGAGCAACAGGGTGGGGGTTCCGGCGGTAGCGAGGAGGGTGGGAT***<br>***GGAGAGTGAAGAATCAAATGGTGGGGGTTCCGGCGGTAGCGAGGAGGGTGGG***<br>GGAGGTGGATCACACCATCACCACCATCAC | 205 |

What is claimed is:

1. An immunomodulatory fusion protein comprising:
   (a) an immunomodulatory domain, wherein the immunomodulatory domain is or comprises interleukin-12 (IL-12); and
   (b) a metal hydroxide-binding peptide having an amino acid sequence motif comprising at least one phosphorylated amino acid, which sequence motif is or comprises: S-X-E, S-X-pS, or S-X-Q-X-X-D-E (SEQ ID NO: 206), wherein X is any amino acid.

2. The immunomodulatory fusion protein of claim 1, wherein the amino acid sequence motif is or comprises: S-X-E, wherein X is E, S, V, H, Q, or G.

3. The immunomodulatory fusion protein of claim 1, wherein the metal hydroxide-binding peptide comprises an amino acid sequence selected from FQSEEQQ (SEQ ID NO: 129), MESEESN (SEQ ID NO: 130), and GGSEEGG (SEQ ID NO: 131).

4. The immunomodulatory fusion protein of claim 1, wherein the metal hydroxide-binding peptide is or comprises the amino acid sequence GGSEEGG (SEQ ID NO: 131).

5. The immunomodulatory fusion protein of claim 1, wherein the IL-12 is or comprises IL-12(p35) (IL-12A) having the amino acid sequence of SEQ ID NO: 3, or having an amino acid sequence having 1, 2, or 3 substitutions relative to SEQ ID NO: 3.

6. The immunomodulatory fusion protein of claim 1, wherein the IL-12 is or comprises IL-12(p40) (IL-12B) having the amino acid sequence of SEQ ID NO: 2, or having an amino acid sequence having 1, 2, or 3 substitutions relative to SEQ ID NO: 2.

7. The immunomodulatory fusion protein of claim 1, wherein the IL-12 is a single chain fusion of IL-12(p35) (IL-12A) and IL-12(p40) (IL-12B).

8. The immunomodulatory fusion protein of claim 7, wherein the single chain fusion comprises IL-12(p40) (IL-12B) located N-terminal to IL-12(p35) (IL-12A).

9. The immunomodulatory fusion protein of claim 7, wherein the IL-12(p40) (IL-12B) is or comprises the amino acid sequence of SEQ ID NO: 2, and wherein the IL-12(p35) (IL-12A) is or comprises the amino acid sequence of SEQ ID NO: 3.

10. The immunomodulatory fusion protein of claim 7, wherein the IL-12(p40) (IL-12B) is fused directly to IL-12 (p35) (IL-12B).

11. The immunomodulatory fusion protein of claim 7, wherein the IL-12(p40) (IL-12B) is fused to IL-12(p35) (IL-12B) via an amino acid linker.

12. An immunomodulatory fusion protein-metal hydroxide complex comprising:
   (a) an immunomodulatory fusion protein comprising:
      (i) an immunomodulatory domain, wherein the immunomodulatory domain is or comprises interleukin-12 (IL-12), and
      (ii) a metal hydroxide-binding peptide having an amino acid sequence motif comprising at least one phosphorylated amino acid, which sequence motif is or comprises: S-X-E, S-X-pS, or S-X-Q-X-X-D-E (SEO ID NO: 206), wherein X is any amino acid, and
   (b) a metal hydroxide,
   wherein the immunomodulatory fusion protein is adsorbed via ligand exchange to the metal hydroxide via the at least one phosphorylated amino acid of the metal hydroxide-binding peptide, thereby forming the immunomodulatory fusion protein-metal hydroxide complex.

13. The immunomodulatory fusion protein-metal hydroxide complex of claim 12, wherein the amino acid sequence motif is or comprises: S-X-E, wherein X is E, S, V, H, Q, or G.

14. The immunomodulatory fusion protein-metal hydroxide complex of claim 12, wherein the metal hydroxide-binding peptide comprises an amino acid sequence selected from FQSEEQQ (SEQ ID NO: 129), MESEESN (SEQ ID NO: 130), and GGSEEGG (SEQ ID NO: 131).

15. The immunomodulatory fusion protein-metal hydroxide complex of claim 12, wherein the IL-12 is or comprises IL-12(p35) (IL-12A) having the amino acid sequence of SEQ ID NO: 3, or having an amino acid sequence having 1, 2, or 3 substitutions relative to SEQ ID NO: 3.

16. The immunomodulatory fusion protein-metal hydroxide complex of claim 12, wherein the IL-12 is or comprises IL-12(p40) (IL-12B) having the amino acid sequence of SEQ ID NO: 2, or having an amino acid sequence having 1, 2, or 3 substitutions relative to SEQ ID NO: 2.

17. The immunomodulatory fusion protein-metal hydroxide complex of claim 12, wherein the IL-12 is a single chain fusion of IL-12(p35) (IL-12A) and IL-12(p40) (IL-12B).

18. The immunomodulatory fusion protein-metal hydroxide complex of claim 17, wherein the single chain fusion comprises IL-12(p40) (IL-12B) located N-terminal to IL-12 (p35) (IL-12A).

19. The immunomodulatory fusion protein-metal hydroxide complex of claim 17, wherein the IL-12 (p40) (IL-12B) is or comprises the amino acid sequence of SEQ ID NO: 2, and wherein the IL-12 (p35) (IL-12A) is or comprises the amino acid sequence of SEQ ID NO: 3.

20. The immunomodulatory fusion protein-metal hydroxide complex of claim 17, wherein the IL-12 (p40) (IL-12B) is fused directly to IL-12(p35) (IL-12B).

21. The immunomodulatory fusion protein-metal hydroxide complex of claim 17, wherein the IL-12 (p40) (IL-12B) is fused to IL-12(p35) (IL-12B) via an amino acid linker.

22. The immunomodulatory fusion protein-metal hydroxide complex of claim 12, wherein the metal hydroxide-binding peptide is or comprises the amino acid sequence GGSEEGG (SEQ ID NO: 131).

23. The immunomodulatory fusion protein-metal hydroxide complex of claim 12, wherein the metal hydroxide is or comprises one or more of aluminum hydroxide, aluminum phosphate, calcium hydroxide, calcium phosphate, iron hydroxide, magnesium hydroxide, barium hydroxide, calcium hydroxide, zinc hydroxide, and zirconium hydroxide.

24. The immunomodulatory fusion protein-metal hydroxide complex of claim 23, wherein the metal hydroxide is or comprises aluminum hydroxide.

* * * * *

SEQUENCE LISTING

```
Sequence total quantity: 240
SEQ ID NO: 1            moltype = AA  length = 133
FEATURE                 Location/Qualifiers
REGION                  1..133
                        note = Synthetic: IL-2
source                  1..133
                        mol_type = protein
                        organism = synthetic construct
SEQUENCE: 1
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 2            moltype = AA  length = 306
FEATURE                 Location/Qualifiers
```

-continued

```
REGION                  1..306
                        note = Synthetic: Wild Type IL12B without signal (IL12B)
                         Amino Acids
source                  1..306
                        mol_type = protein
                        organism = synthetic construct
SEQUENCE: 2
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCS                                                             306

SEQ ID NO: 3            moltype = AA  length = 197
FEATURE                 Location/Qualifiers
REGION                  1..197
                        note = Synthetic: Wild Type IL12A without signal peptide
                         Amino acids
source                  1..197
                        mol_type = protein
                        organism = synthetic construct
SEQUENCE: 3
RNLPVATPDP GMFPCLHHSQ NLLRAVSNML QKARQTLEFY PCTSEEIDHE DITKDKTSTV  60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNAS                                                 197

SEQ ID NO: 4            moltype = AA  length = 175
FEATURE                 Location/Qualifiers
REGION                  1..175
                        note = Synthetic: IL-15Ra
source                  1..175
                        mol_type = protein
                        organism = synthetic construct
SEQUENCE: 4
ITCPPPMSVE HADIWVKSYS LYSRERYICN SGFKRKAGTS SLTECVLNKA TNVAHWTTPS  60
LKCIRDPALV HQRPAPPSTV TTAGVTPQPE SLSPSGKEPA ASSPSSNNTA ATTAAIVPGS  120
QLMPSKSPST GTTEISSHES SHGTPSQTTA KNWELTASAS HQPPGVYPQG HSDTT       175

SEQ ID NO: 5            moltype = AA  length = 114
FEATURE                 Location/Qualifiers
REGION                  1..114
                        note = Synthetic: IL-15
source                  1..114
                        mol_type = protein
                        organism = synthetic construct
SEQUENCE: 5
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 6            moltype = AA  length = 157
FEATURE                 Location/Qualifiers
REGION                  1..157
                        note = Synthetic: TNF-alpha
source                  1..157
                        mol_type = protein
                        organism = synthetic construct
SEQUENCE: 6
VRSSSRTPSD KPVAHVVANP QAEGQLQWLN RRANALLANG VELRDNQLVV PSEGLYLIYS  60
QVLFKGQGCP STHVLLTHTI SRIAVSYQTK VNLLSAIKSP CQRETPEGAE AKPWYEPIYL  120
GGVFQLEKGD RLSAEINRPD YLDFAESGQV YFGIIAL                           157

SEQ ID NO: 7            moltype = AA  length = 138
FEATURE                 Location/Qualifiers
REGION                  1..138
                        note = Synthetic: IFN-gamma
source                  1..138
                        mol_type = protein
                        organism = synthetic construct
SEQUENCE: 7
QDPYVKEAEN LKKYFNAGHS DVADNGTLFL GILKNWKEES DRKIMQSQIV SFYFKLFKNF  60
KDDQSIQKSV ETIKEDMNVK FFNSNKKKRD DFEKLTNYSV TDLNVQRKAI HELIQVMAEL  120
SPAAKTGKRK RSQMLFRG                                                138

SEQ ID NO: 8            moltype = AA  length = 165
FEATURE                 Location/Qualifiers
REGION                  1..165
                        note = Synthetic: IFN-alpha
```

```
source                  1..165
                        mol_type = protein
                        organism = synthetic construct
SEQUENCE: 8
CDLPQTHSLG SRRTLMLLAQ MRKISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 9            moltype = AA  length = 133
FEATURE                 Location/Qualifiers
REGION                  1..133
                        note = Synthetic: IL-21
source                  1..133
                        mol_type = protein
                        organism = synthetic construct
SEQUENCE: 9
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDS                                                     133

SEQ ID NO: 10           moltype = AA  length = 449
FEATURE                 Location/Qualifiers
REGION                  1..449
                        note = Synthetic: IL-6
source                  1..449
                        mol_type = protein
                        organism = synthetic construct
SEQUENCE: 10
LAPRRCPAQE VARGVLTSLP GDSVTLTCPG VEPEDNATVH WVLRKPAAGS HPSRWAGMGR  60
RLLLRSVQLH DSGNYSCYRA GRPAGTVHLL VDVPPEEPQL SCFRKSPLSN VVCEWGPRST  120
PSLTTKAVLL VRKFQNSPAE DFQEPCQYSQ ESQKFSCQLA VPEGDSSFYI VSMCVASSVG  180
SKFSKTQTFQ GCGILQPDPP ANITVTAVAR NPRWLSVTWQ DPHSWNSSFY RLRFELRYRA  240
ERSKTFTTWM VKDLQHHCVI HDAWSGLRHV VQLRAQEEFG QGEWSEWSPE AMGTPWTESR  300
SPPAENEVST PMQALTTNKD DDNILFRDSA NATSLPVQDS SSVPLPTFLV AGGSLAFGTL  360
LCIAIVLRFK KTWKLRALKE GKTSMHPPYS LGQLVPERPR PTPVLVPLIS PPVSPSSLGS  420
DNTSSHNRPD ARDPRSPYDI SNTDYFFPR                                    449

SEQ ID NO: 11           moltype = AA  length = 400
FEATURE                 Location/Qualifiers
REGION                  1..400
                        note = Synthetic: IL-5
source                  1..400
                        mol_type = protein
                        organism = synthetic construct
SEQUENCE: 11
DLLPDEKISL LPPVNFTIKV TGLAQVLLQW KPNPDQEQRN VNLEYQVKIN APKEDDYETR  60
ITESKCVTIL HKGFSASVRT ILQNDHSLLA SSWASAELHA PPGSPGTSIV NLTCTTNTTE  120
DNYSRLRSYQ VSLHCTWLVG TDAPEDTQYF LYYRYGSWTE ECQEYSKDTL GRNIACWFPR  180
TFILSKGRDW LAVLVNGSSK HSAIRPFDQL FALHAIDQIN PPLNVTAEIE GTRLSIQWEK  240
PVSAFPIHCF DYEVKIHNTR NGYLQIEKLM TNAFISIIDD LSKYDVQVRA AVSSMCREAG  300
LWSEWSQPIY VGNDEHKPLR EWFVIVIMAT ICFILLILSL ICKICHLWIK LFPPIPAPKS  360
NIKDLFVTTN YEKAGSSETE IEVICYIEKP GVETLEDSVF                         400

SEQ ID NO: 12           moltype = AA  length = 77
FEATURE                 Location/Qualifiers
REGION                  1..77
                        note = Synthetic: IL-8
source                  1..77
                        mol_type = protein
                        organism = synthetic construct
SEQUENCE: 12
AVLPRSAKEL RCQCIKTYSK PFHPKFIKEL RVIESGPHCA NTEIIVKLSD GRELCLDPKE  60
NWVQRVVEKF LKRAENS                                                 77

SEQ ID NO: 13           moltype = AA  length = 152
FEATURE                 Location/Qualifiers
REGION                  1..152
                        note = Synthetic: IL-7
source                  1..152
                        mol_type = protein
                        organism = synthetic construct
SEQUENCE: 13
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EH                                152

SEQ ID NO: 14           moltype = AA  length = 132
FEATURE                 Location/Qualifiers
REGION                  1..132
```

```
                         note = Synthetic: IL-17A
source                   1..132
                         mol_type = protein
                         organism = synthetic construct
SEQUENCE: 14
GITIPRNPGC PNSEDKNFPR TVMVNLNIHN RNTNTNPKRS SDYYNRSTSP WNLHRNEDPE  60
RYPSVIWEAK CRHLGCINAD GNVDYHMNSV PIQQEILVLR REPPHCPNSF RLEKILVSVG  120
CTCVTPIVHH VA                                                      132

SEQ ID NO: 15            moltype = AA  length = 170
FEATURE                  Location/Qualifiers
REGION                   1..170
                         note = Synthetic: IL-23alpha
source                   1..170
                         mol_type = protein
                         organism = synthetic construct
SEQUENCE: 15
RAVPGGSSPA WTQCQQLSQK LCTLAWSAHP LVGHMDLREE GDEETTNDVP HIQCGDGCDP  60
QGLRDNSQFC LQRIHQGLIF YEKLLGSDIF TGEPSLLPDS PVGQLHASLL GLSQLLQPEG  120
HHWETQQIPS LSPSQPWQRL LLRFKILRSL QAFVAVAARV FAHGAATLSP             170

SEQ ID NO: 16            moltype = AA  length = 157
FEATURE                  Location/Qualifiers
REGION                   1..157
                         note = Synthetic: IL-18
source                   1..157
                         mol_type = protein
                         organism = synthetic construct
SEQUENCE: 16
YFGKLESKLS VIRNLNDQVL FIDQGNRPLF EDMTDSDCRD NAPRTIFIIS MYKDSQPRGM  60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                           157

SEQ ID NO: 17            moltype = AA  length = 159
FEATURE                  Location/Qualifiers
REGION                   1..159
                         note = Synthetic: IL-1alpha
source                   1..159
                         mol_type = protein
                         organism = synthetic construct
SEQUENCE: 17
SAPFSFLSNV KYNFMRIIKY EFILNDALNQ SIIRANDQYL TAAALHNLDE AVKFDMGAYK  60
SSKDDAKITV ILRISKTQLY VTAQDEDQPV LLKEMPEIPK TITGSETNLL FFWETHGTKN  120
YFTSVAHPNL FIATKQDYWV CLAGGPPSIT DFQILENQA                         159

SEQ ID NO: 18            moltype = AA  length = 153
FEATURE                  Location/Qualifiers
REGION                   1..153
                         note = Synthetic: IL-1beta
source                   1..153
                         mol_type = protein
                         organism = synthetic construct
SEQUENCE: 18
APVRSLNCTL RDSQQKSLVM SGPYELKALH LQGQDMEQQV VFSMSFVQGE ESNDKIPVAL  60
GLKEKNLYLS CVLKDDKPTL QLESVDPKNY PKKKMEKRFV FNKIEINNKL EFESAQFPNW  120
YISTSQAENM PVFLGGTKGG QDITDFTMQF VSS                               153

SEQ ID NO: 19            moltype = AA  length = 129
FEATURE                  Location/Qualifiers
REGION                   1..129
                         note = Synthetic: IL-4
source                   1..129
                         mol_type = protein
                         organism = synthetic construct
SEQUENCE: 19
HKCDITLQEI IKTLNSLTEQ KTLCTELTVT DIFAASKNTT EKETFCRAAT VLRQFYSHHE  60
KDTRCLGATA QQFHRHKQLI RFLKRLDRNL WGLAGLNSCP VKEANQSTLE NFLERLKTIM  120
REKYSKCSS                                                          129

SEQ ID NO: 20            moltype = AA  length = 133
FEATURE                  Location/Qualifiers
REGION                   1..133
                         note = Synthetic: IL-3
source                   1..133
                         mol_type = protein
                         organism = synthetic construct
SEQUENCE: 20
APMTQTTPLK TSWVNCSNMI DEIITHLKQP PLPLLDFNNL NGEDQDILME NNLRRPNLEA  60
FNRAVKSLQN ASAIESILKN LLPCLPLATA APTRHPIHIK DGDWNEFRRK LTFYLKTLEN  120
```

```
AQAQQTTLSL AIF                                                    133

SEQ ID NO: 21          moltype = AA  length = 160
FEATURE                Location/Qualifiers
REGION                 1..160
                       note = Synthetic: IL-10
source                 1..160
                       mol_type = protein
                       organism = synthetic construct
SEQUENCE: 21
SPGQGTQSEN SCTHFPGNLP NMLRDLRDAF SRVKTFFQMK DQLDNLLLKE SLLEDFKGYL  60
GCQALSEMIQ FYLEEVMPQA ENQDPDIKAH VNSLGENLKT LRLRLRRCHR FLPCENKSKA  120
VEQVKNAFNK LQEKGIYKAM SEFDIFINYI EAYMTMKIRN                       160

SEQ ID NO: 22          moltype = AA  length = 111
FEATURE                Location/Qualifiers
REGION                 1..111
                       note = Synthetic: IL-13
source                 1..111
                       mol_type = protein
                       organism = synthetic construct
SEQUENCE: 22
PVPPSTALRE LIEELVNITQ NQKAPLCNGS MVWSINLTAG MYCAALESLI NVSGCSAIEK  60
TQRMLSGFCP HKVSAGQFSS LHVRDTKIEV AQFVKDLLLH LKKLFREGRF N           111

SEQ ID NO: 23          moltype = AA  length = 132
FEATURE                Location/Qualifiers
REGION                 1..132
                       note = Synthetic: IL-17a
source                 1..132
                       mol_type = protein
                       organism = synthetic construct
SEQUENCE: 23
GITIPRNPGC PNSEDKNFPR TVMVNLNIHN RNTNTNPKRS SDYYNRSTSP WNLHRNEDPE  60
RYPSVIWEAK CRHLGCINAD GNVDYHMNSV PIQQEILVLR REPPHCPNSF RLEKILVSVG  120
CTCVTPIVHH VA                                                     132

SEQ ID NO: 24          moltype = AA  length = 126
FEATURE                Location/Qualifiers
REGION                 1..126
                       note = Synthetic: IL-9
source                 1..126
                       mol_type = protein
                       organism = synthetic construct
SEQUENCE: 24
QGCPTLAGIL DINFLINKMQ EDPASKCHCS ANVTSCLCLG IPSDNCTRPC FSERLSQMTN  60
TTMQTRYPLI FSRVKKSVEV LKNNKCPYFS CEQPCNQTTA GNALTFLKSL LEIFQKEKMR  120
GMRGKI                                                            126

SEQ ID NO: 25          moltype = AA  length = 138
FEATURE                Location/Qualifiers
REGION                 1..138
                       note = Synthetic: IFN-gamma
source                 1..138
                       mol_type = protein
                       organism = synthetic construct
SEQUENCE: 25
QDPYVKEAEN LKKYFNAGHS DVADNGTLFL GILKNWKEES DRKIMQSQIV SFYFKLFKNF  60
KDDQSIQKSV ETIKEDMNVK FFNSNKKKRD DFEKLTNYSV TDLNVQRKAI HELIQVMAEL  120
SPAAKTGKRK RSQMLFRG                                               138

SEQ ID NO: 26          moltype = AA  length = 165
FEATURE                Location/Qualifiers
REGION                 1..165
                       note = Synthetic: IFN-alpha
source                 1..165
                       mol_type = protein
                       organism = synthetic construct
SEQUENCE: 26
CDLPQTHSLG SRRTLMLLAQ MRKISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 27          moltype = AA  length = 127
FEATURE                Location/Qualifiers
REGION                 1..127
                       note = Synthetic: GM-CSF
source                 1..127
                       mol_type = protein
```

```
                        organism = synthetic construct
SEQUENCE: 27
APARSPSPST QPWEHVNAIQ EARRLLNLSR DTAAEMNETV EVISEMFDLQ EPTCLQTRLE  60
LYKQGLRGSL TKLKGPLTMM ASHYKQHCPP TPETSCATQI ITFESFKENL KDFLLVIPFD  120
CWEPVQE                                                            127

SEQ ID NO: 28           moltype = AA  length = 209
FEATURE                 Location/Qualifiers
REGION                  1..209
                        note = Synthetic: FLT3L
source                  1..209
                        mol_type = protein
                        organism = synthetic construct
SEQUENCE: 28
TQDCSFQHSP ISSDFAVKIR ELSDYLLQDY PVTVASNLQD EELCGGLWRL VLAQRWMERL  60
KTVAGSKMQG LLERVNTEIH FVTKCAFQPP PSCLRFVQTN ISRLLQETSE QLVALKPWIT  120
RQNFSRCLEL QCQPDSSTLP PPWSPRPLEA TAPTAPQPPL LLLLLLPVGL LLLAAAWCLH  180
WQRTRRRTPR PGEQVPPVPS PQDLLLVEH                                    209

SEQ ID NO: 29           moltype = AA  length = 178
FEATURE                 Location/Qualifiers
REGION                  1..178
                        note = Synthetic: G-CSF
source                  1..178
                        mol_type = protein
                        organism = synthetic construct
SEQUENCE: 29
ATPLGPASSL PQSFLLKCLE QVRKIQGDGA ALQEKLVSEC ATYKLCHPEE LVLLGHSLGI  60
PWAPLSSCPS QALQLAGCLS QLHSGLFLYQ GLLQALEGIS PELGPTLDTL QLDVADFATT  120
IWQQMEELGM APALQPTQGA MPAFASAFQR RAGGVLVASH LQSFLEVSYR VLRHLAQP    178

SEQ ID NO: 30           moltype = AA  length = 180
FEATURE                 Location/Qualifiers
REGION                  1..180
                        note = Synthetic: LIF
source                  1..180
                        mol_type = protein
                        organism = synthetic construct
SEQUENCE: 30
SPLPITPVNA TCAIRHPCHN NLMNQIRSQL AQLNGSANAL FILYYTAQGE PFPNNLDKLC  60
GPNVTDFPPF HANGTEKAKL VELYRIVVYL GTSLGNITRD QKILNPSALS LHSKLNATAD  120
ILRGLLSNVL CRLCSKYHVG HVDVTYGPDT SGKDVFQKKK LGCQLLGKYK QIIAVLAQAF  180

SEQ ID NO: 31           moltype = AA  length = 522
FEATURE                 Location/Qualifiers
REGION                  1..522
                        note = Synthetic: M-CSF
source                  1..522
                        mol_type = protein
                        organism = synthetic construct
SEQUENCE: 31
EEVSEYCSHM IGSGHLQSLQ RLIDSQMETS CQITFEFVDQ EQLKDPVCYL KKAFLLVQDI  60
MEDTMRFRDN TPNAIAIVQL QELSLRLKSC FTKDYEEHDK ACVRTFYETP LQLLEKVKNV  120
FNETKNLLDK DWNIFSKNCN NSFAECSSQD VVTKPDCNCL YPKAIPSSDP ASVSPHQPLA  180
PSMAPVAGLT WEDSEGTEGS SLLPGEQPLH TVDPGSAKQR PPRSTCQSFE PPETPVVKDS  240
TIGGSPQPRP SVGAFNPGME DILDSAMGTN WVPEEASGEA SEIPVPQGTE LSPSRPGGGS  300
MQTEPARPSN FLSASSPLPA SAKGQQPADV TGTALPRVGP VRPTGQDWNH TPQKTDHPSA  360
LLRDPPEPGS PRISSLRPQG LSNPSTLSAQ PQLSRSHSSG SVLPLGELEG RRSTRDRRSP  420
AEPEGGPASE GAARPLPRFN SVPLTDTGHE RQSEGSFSPQ LQESVFHLLV PSVILVLLAV  480
GGLLFYRWRR RSHQEPQRAD SPLEQPEGSP LTQDDRQVEL PV                     522

SEQ ID NO: 32           moltype = AA  length = 73
FEATURE                 Location/Qualifiers
REGION                  1..73
                        note = Synthetic: MIP-2
source                  1..73
                        mol_type = protein
                        organism = synthetic construct
SEQUENCE: 32
APLATELRCQ CLQTLQGIHL KNIQSVKVKS PGPHCAQTEV IATLKNGQKA CLNPASPMVK  60
KIIEKMLKNG KSN                                                     73

SEQ ID NO: 33           moltype = AA  length = 69
FEATURE                 Location/Qualifiers
REGION                  1..69
                        note = Synthetic: MIP-1beta
source                  1..69
                        mol_type = protein
                        organism = synthetic construct
```

```
SEQUENCE: 33
APMGSDPPTA CCFSYTARKL PRNFVVDYYE TSSLCSQPAV VFQTKRSKQV CADPSESWVQ  60
EYVYDLELN                                                          69

SEQ ID NO: 34          moltype = AA  length = 73
FEATURE                Location/Qualifiers
REGION                 1..73
                       note = Synthetic: KP (aka CXCL1)
source                 1..73
                       mol_type = protein
                       organism = synthetic construct
SEQUENCE: 34
ASVATELRCQ CLQTLQGIHP KNIQSVNVKS PGPHCAQTEV IATLKNGRKA CLNPASPIVK  60
KIIEKMLNSD KSN                                                     73

SEQ ID NO: 35          moltype = AA  length = 103
FEATURE                Location/Qualifiers
REGION                 1..103
                       note = Synthetic: MIG (aka CXCL9)
source                 1..103
                       mol_type = protein
                       organism = synthetic construct
SEQUENCE: 35
TPVVRKGRCS CISTNQGTIH LQSLKDLKQF APSPSCEKIE IIATLKNGVQ TCLNPDSADV  60
KELIKKWEKQ VSQKKKQKNG KKHQKKKVLK VRKSQRSRQK KTT                    103

SEQ ID NO: 36          moltype = AA  length = 77
FEATURE                Location/Qualifiers
REGION                 1..77
                       note = Synthetic: IP-10 (CXCL10)
source                 1..77
                       mol_type = protein
                       organism = synthetic construct
SEQUENCE: 36
VPLSRTVRCT CISISNQPVN PRSLEKLEII PASQFCPRVE IIATMKKKGE KRCLNPESKA  60
IKNLLKAVSK ERSKRSP                                                 77

SEQ ID NO: 37          moltype = AA  length = 76
FEATURE                Location/Qualifiers
REGION                 1..76
                       note = Synthetic: MCP-1
source                 1..76
                       mol_type = protein
                       organism = synthetic construct
SEQUENCE: 37
QPDAINAPVT CCYNFTNRKI SVQRLASYRR ITSSKCPKEA VIFKTIVAKE ICADPKQKWV  60
QDSMDHLDKQ TQTPKT                                                  76

SEQ ID NO: 38          moltype = AA  length = 74
FEATURE                Location/Qualifiers
REGION                 1..74
                       note = Synthetic: Eotaxin
source                 1..74
                       mol_type = protein
                       organism = synthetic construct
SEQUENCE: 38
GPASVPTTCC FNLANRKIPL QRLESYRRIT SGKCPQKAVI FKTKLAKDIC ADPKKKWVQD  60
SMKYLDQKSP TPKP                                                    74

SEQ ID NO: 39          moltype = AA  length = 68
FEATURE                Location/Qualifiers
REGION                 1..68
                       note = Synthetic: RANTES
source                 1..68
                       mol_type = protein
                       organism = synthetic construct
SEQUENCE: 39
SPYSSDTTPC CFAYIARPLP RAHIKEYFYT SGKCSNPAVV FVTRKNRQVC ANPEKKWVRE  60
YINSLEMS                                                           68

SEQ ID NO: 40          moltype = AA  length = 78
FEATURE                Location/Qualifiers
REGION                 1..78
                       note = Synthetic: LIX
source                 1..78
                       mol_type = protein
                       organism = synthetic construct
SEQUENCE: 40
AGPAAAVLRE LRCVCLQTTQ GVHPKMISNL QVFAIGPQCS KVEVVASLKN GKEICLDPEA  60
```

```
PFLKKVIQKI LDGGNKEN                                          78

SEQ ID NO: 41          moltype = AA  length = 69
FEATURE                Location/Qualifiers
REGION                 1..69
                       note = Synthetic: MIP-1alpha
source                 1..69
                       mol_type = protein
                       organism = synthetic construct
SEQUENCE: 41
SLAADTPTAC CFSYTSRQIP QNFIADYFET SSQCSKPGVI FLTKRSRQVC ADPSEEWVQK  60
YVSDLELSA                                                    69

SEQ ID NO: 42          moltype = AA  length = 287
FEATURE                Location/Qualifiers
REGION                 1..287
                       note = Synthetic: PD-1
source                 1..287
                       mol_type = protein
                       organism = synthetic construct
SEQUENCE: 42
MQIPQAPWPV VWAVLQLGWR PGWFLDSPDP WNPPTFFPAL LVVTEGDNAT FTCSFSNTSE  60
SFVLNWYRMS PSNQTDKLAA FPEDRSQPGQ DCRFRVTQLP NGRDFHMSVV RARRNDSGTY  120
LCGAISLAPK AQIKESLRAE LRVTERRAEV PTAHPSPSPR PAGQFQTLVV GVVGGLLGSL  180
VLLVWVLAVI CSRAARGTIG ARRTGQPLKE DPSAVPVFSV DYGELDFQWR EKTPEPPVPC  240
VPEQTEYATI VFPSGMGTSS PARRGSADGP RSAQPLRPED GHCSWPL             287

SEQ ID NO: 43          moltype = AA  length = 290
FEATURE                Location/Qualifiers
REGION                 1..290
                       note = Synthetic: PD-L-1
source                 1..290
                       mol_type = protein
                       organism = synthetic construct
SEQUENCE: 43
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERTH  240
LVILGAILLC LGVALTFIFR LRKGRMMDVK KCGIQDTNSK KQSDTHLEET           290

SEQ ID NO: 44          moltype = AA  length = 223
FEATURE                Location/Qualifiers
REGION                 1..223
                       note = Synthetic: CTLA-4
source                 1..223
                       mol_type = protein
                       organism = synthetic construct
SEQUENCE: 44
MACLGFQRHK AQLNLATRTW PCTLLFFLLF IPVFCKAMHV AQPAVVLASS RGIASFVCEY  60
ASPGKATEVR VTVLRQADSQ VTEVCAATYM MGNELTFLDD SICTGTSSGN QVNLTIQGLR  120
AMDTGLYICK VELMYPPPYY LGIGNGTQIY VIDPEPCPDS DFLLWILAAV SSGLFFYSFL  180
LTAVSLSKML KKRSPLTTGV YVKMPPTEPE CEKQFQPYFI PIN                 223

SEQ ID NO: 45          moltype = AA  length = 525
FEATURE                Location/Qualifiers
REGION                 1..525
                       note = Synthetic: LAG3
source                 1..525
                       mol_type = protein
                       organism = synthetic construct
SEQUENCE: 45
MWEAQFLGLL FLQPLWVAPV KPLQPGAEVP VVWAQEGAPA QLPCSPTIPL QDLSLLRRAG  60
VTWQHQPDSG PPAAAPGHPL APGPHPAAPS SWGPRPRRYT VLSVGPGGLR SGRLPLQPRV  120
QLDERGRQRG DFSLWLRPAR RADAGEYRAA VHLRDRALSC RLRLRLGQAS MTASPPGSLR  180
ASDWVILNCS FSRPDRPASV HWFRNRGQGR VPVRESPHHH LAESFLFLPQ VSPMDSGPWG  240
CILTYRDGFN VSIMYNLTVL GLEPPTPLTV YAGAGSRVGL PCRLPAGVGT RSFLTAKWTP  300
PGGGPDLLVT GDNGDFTLRL EDVSQAQAGT YTCHIHLQEQ QLNATVTLAI ITVTPKSFGS  360
PGSLGKLLCE VTPVSGQERF VWSSLDTPSQ RSFSGPWLEA QEAQLLSQPW QCQLYQGERL  420
LGAAVYFTEL SSPGAQRSGR APGALPAGHL LLFLILGVLS LLLLVTGAFG FHLWRRQWRP  480
RRFSALEQGI HPPQAQSKIE ELEQEPEPEP EPEPEPEPEP EPEQL               525

SEQ ID NO: 46          moltype = AA  length = 300
FEATURE                Location/Qualifiers
REGION                 1..300
                       note = Synthetic: TIM3
source                 1..300
                       mol_type = protein
                       organism = synthetic construct
```

```
SEQUENCE: 46
MFSHLPFDCV LLLLLLLLTR SSEVEYRAEV GQNAYLPCFY TPAAPGNLVP VCWGKGACPV  60
FECGNVVLRT DERDVNYWTS RYWLNGDFRK GDVSLTIENV TLADSGIYCC RIQIPGIMND  120
EKFNLKLVIK PAKVTPAPTR QRDFTAAFPR MLTTRGHGPA ETQTLGSLPD INLTQISTLA  180
NELRDSRLAN DLRDSGATIR GIYIGAGICA GLALALIFGA LIFKWYSHSK EKIQNLSLIS  240
LANLPPSGLA NAVAEGIRSE ENIYTIEENV YEVEEPNEYY CYVSSRQQPS QPLGCRFAMP  300

SEQ ID NO: 47          moltype = AA  length = 532
FEATURE                Location/Qualifiers
REGION                 1..532
                       note = Synthetic: B7-H3
source                 1..532
                       mol_type = protein
                       organism = synthetic construct
SEQUENCE: 47
MLRRRGSPGM GVHVGAALGA LWFCLTGALE VQVPEDPVVA LVGTDATLCC SFSPEPGFSL  60
QLNLIWQLTD TKQLVHSFAE GQDQGSAYAN RTALFPDLLA QGNASLRLQR VRVADEGSFC  120
FVSIRDFGSA AVSLQVAAPY SKPSMTLEPN KDLRPGDTVT ITCSSYQGYP EAEVFWQDGQ  180
GVPLTGNVTT SQMANEQGLF DVHSILRVVL GANGTYSCLV RNPVLQQDAH SSVTITPQRS  240
PTGAVEVQVP EDPVVALVGT DATLRCSFSP EPGFSLAQLN LIWQLTDTKQ LVHSFTEGRD  300
QGSAYANRTA LFPDLLAQGN ASLRLQRVRV ADEGSFTCFV SIRDFGSAAV SLQVAAPYSK  360
PSMTLEPNKD LRPGDTVTIT CSSYRGYPEA EVFWQDGQGV PLTGNVTTSQ MANEQGLFDV  420
HSVLRVVLGA NGTYSCLVRN PVLQQDAHGS VTITGQPMTF PPEALWVTVG LSVCLIALLV  480
ALAFVCWRKI KQSCEEENAG AEDQDGEGEG SKTALQPLKH SDSKEDDGQE IA          532

SEQ ID NO: 48          moltype = AA  length = 166
FEATURE                Location/Qualifiers
REGION                 1..166
                       note = Synthetic: B7-H4
source                 1..166
                       mol_type = protein
                       organism = synthetic construct
SEQUENCE: 48
MASLGQILFW SIISIIIILA GAIALIIGFG ISAFSMPEVN VDYNASSETL RCEAPRWFPQ  60
PTVVWASQVD QGANFSEVSN TSFELNSENV TMKVVSVLYN VTINNTYSCM IENDIAKATG  120
DIKVTESEIK RRSHLQLLNS KASLCVSSFF AISWALLPLS PYLMLK                166

SEQ ID NO: 49          moltype = AA  length = 177
FEATURE                Location/Qualifiers
REGION                 1..177
                       note = Synthetic: TNF-alpha extracellular domain
source                 1..177
                       mol_type = protein
                       organism = synthetic construct
SEQUENCE: 49
GPQREEFPRD LSLISPLAQA VRSSSRTPSD KPVAHVVANP QAEGQLQWLN RRANALLANG  60
VELRDNQLVV PSEGLYLIYS QVLFKGQGCP STHVLLTHTI SRIAVSYQTK VNLLSAIKSP  120
CQRETPEGAE AKPWYEPIYL GGVFQLEKGD RLSAEINRPD YLDFAESGQV YFGIIAL     177

SEQ ID NO: 50          moltype = AA  length = 182
FEATURE                Location/Qualifiers
REGION                 1..182
                       note = Synthetic: LIGHT extracellular domain
source                 1..182
                       mol_type = protein
                       organism = synthetic construct
SEQUENCE: 50
LQLHWRLGEM VTRLPDGPAG SWEQLIQERR SHEVNPAAHL TGANSSLTGS GGPLLWETQL  60
GLAFLRGLSY HDGALVVTKA GYYYIYSKVQ LGGVGCPLGL ASTITHGLYK RTPRYPEELE  120
LLVSQQSPCG RATSSSRVWW DSSFLGGVVH LEAGEKVVVR VLDERLVRLR DGTRSYFGAF  180
MV                                                                182

SEQ ID NO: 51          moltype = AA  length = 171
FEATURE                Location/Qualifiers
REGION                 1..171
                       note = Synthetic: LT-alpha extracellular domain
source                 1..171
                       mol_type = protein
                       organism = synthetic construct
SEQUENCE: 51
LPGVGLTPSA AQTARQHPKM HLAHSTLKPA AHLIGDPSKQ NSLLWRANTD RAFLQDGFSL  60
SNNSLLVPTS GIYFVYSQVV FSGKAYSPKA TSSPLYLAHE VQLFSSQYPF HVPLLSSQKM  120
VYPGLQEPWL HSMYHGAAFQ LTQGDQLSTH TDGIPHLVLS PSTVFFGAFA L           171

SEQ ID NO: 52          moltype = AA  length = 196
FEATURE                Location/Qualifiers
REGION                 1..196
                       note = Synthetic: LT-beta extracellular domain
source                 1..196
```

```
                         mol_type = protein
                         organism = synthetic construct
SEQUENCE: 52
QDQGGLVTET ADPGAQAQQG LGFQKLPEEE PETDLSPGLP AAHLIGAPLK GQGLGWETTK  60
EQAFLTSGTQ FSDAEGLALP QDGLYYLYCL VGYRGRAPPG GGDPQGRSVT LRSSLYRAGG  120
AYGPGTPELL LEGAETVTPV LDPARRQGYG PLWYTSVGFG GLVQLRRGER VYVNISHPDM  180
VDFARGKTFF GAVMVG                                                 196

SEQ ID NO: 53            moltype = AA  length = 127
FEATURE                  Location/Qualifiers
REGION                   1..127
                         note = Synthetic: BTLA extracellular domain
source                   1..127
                         mol_type = protein
                         organism = synthetic construct
SEQUENCE: 53
KESCDVQLYI KRQSEHSILA GDPFELECPV KYCANRPHVT WCKLNGTTCV KLEDRQTSWK  60
EEKNISFFIL HFEPVLPNDN GSYRCSANFQ SNLIESHSTT LYVTDVKSAS ERPSKDEMAS  120
RPWLLYR                                                           127

SEQ ID NO: 54            moltype = AA  length = 133
FEATURE                  Location/Qualifiers
REGION                   1..133
                         note = Synthetic: CD160 extracellular domain
source                   1..133
                         mol_type = protein
                         organism = synthetic construct
SEQUENCE: 54
INITSSASQE GTRLNLICTV WHKKEEAEGF VVFLCKDRSG DCSPETSLKQ LRLKRDPGID  60
GVGEISSQLM FTISQVTPLH SGTYQCCARS QKSGIRLQGH FFSILFTETG NYTVTGLKQR  120
QHLEFSHNEG TLS                                                    133

SEQ ID NO: 55            moltype = AA  length = 149
FEATURE                  Location/Qualifiers
REGION                   1..149
                         note = Synthetic: CD40L extracellular domain
source                   1..149
                         mol_type = protein
                         organism = synthetic construct
SEQUENCE: 55
MQKGDQNPQI AAHVISEASS KTTSVLQWAE KGYYTMSNNL VTLENGKQLT VKRQGLYYIY  60
AQVTFCSNRE ASSQAPFIAS LCLKSPGRFE RILLRAANTH SSAKPCGQQS IHLGGVFELQ  120
PGASVFVNVT DPSQVSHGTG FTSFGLLKL                                   149

SEQ ID NO: 56            moltype = AA  length = 152
FEATURE                  Location/Qualifiers
REGION                   1..152
                         note = Synthetic: FasL extracellular domain
source                   1..152
                         mol_type = protein
                         organism = synthetic construct
SEQUENCE: 56
QIGHPSPPPE KKELRKVAHL TGKSNSRSMP LEWEDTYGIV LLSGVKYKKG GLVINETGLY  60
FVYSKVYFRG QSCNNLPLSH KVYMRNSKYP QDLVMMEGKM MSYCTTGQMW ARSSYLGAVF  120
NLTSADHLYV NVSELSLVNF EESQTFFGLY KL                               152

SEQ ID NO: 57            moltype = AA  length = 577
FEATURE                  Location/Qualifiers
REGION                   1..577
                         note = Synthetic: CD30L extracellular domain
source                   1..577
                         mol_type = protein
                         organism = synthetic construct
SEQUENCE: 57
FPQDRPFEDT CHGNPSHYYD KAVRRCCYRC PMGLFPTQQC PQRPTDCRKQ CEPDYYLDEA  60
DRCTACVTCS RDDLVEKTPC AWNSSRVCEC RPGMFCSTSA VNSCARCFFH SVCPAGMIVK  120
FPGTAQKNTV CEPASPGVSP ACASPENCKE PSSGTIPQAK PTPVSPATSS ASTMPVRGGT  180
RLAQEAASKL TRAPDSPSSV GRPSSDPGLS PTQPCPEGSG DCRKQCEPDY YLDEAGRCTA  240
CVSCSRDDLV EKTPCAWNSS RTCECRPGMI CATSATNSCA RCVPYPICAA ETVTKPQDMA  300
EKDTTFEAPP LGTQPDCNPT PENGEAPAST SPTQSLLVDS QASKTLPIPT SAPVALSSTG  360
KPVLDAGPVL FWVILVLVVV VGSSAFLLCH RRACRKRIRQ KLHLCYPVQT SQPKLELVDS  420
RPRRSSTQLR SGASVTEPVA EERGLMSQPL METCHSVGAA YLESLPLQDA SPAGGPSSPR  480
DLPEPRVSTE HTNNKIEKIY IMKADTVIVG TVKAELPEGR GLAGPAEPEL EEELEADHTP  540
HYPEQETEPP LGSCSDVMLS VEEEGKEDPL PTAASGK                          577

SEQ ID NO: 58            moltype = AA  length = 205
FEATURE                  Location/Qualifiers
REGION                   1..205
                         note = Synthetic: 4-1BBL extracellular domain
```

```
source                 1..205
                       mol_type = protein
                       organism = synthetic construct
SEQUENCE: 58
ACPWAVSGAR ASPGSAASPR LREGPELSPD DPAGLLDLRQ GMFAQLVAQN VLLIDGPLSW  60
YSDPGLAGVS LTGGLSYKED TKELVVAKAG VYYVFFQLEL RRVVAGEGSG SVSLALHLQP  120
LRSAAGAAAL ALTVDLPPAS SEARNSAFGF QGRLLHLSAG QRLGVHLHTE ARARHAWQLT  180
QGATVLGLFR VTPEIPAGLP SPRSE                                       205

SEQ ID NO: 59          moltype = AA  length = 172
FEATURE                Location/Qualifiers
REGION                 1..172
                       note = Synthetic: CD27L extracellular domain
source                 1..172
                       mol_type = protein
                       organism = synthetic construct
SEQUENCE: 59
ATPAPKSCPE RHYWAQGKLC CQMCEPGTFL VKDCDQHRKA AQCDPCIPGV SFSPDHHTRP  60
HCESCRHCNS GLLVRNCTIT ANAECACRNG WQCRDKECTE CDPLPNPSLT ARSSQALSPH  120
PQPTHLPYVS EMLEARTAGH MQTLADFRQL PARTLSTHWP PQRSLCSSDF IR          172

SEQ ID NO: 60          moltype = AA  length = 186
FEATURE                Location/Qualifiers
REGION                 1..186
                       note = Synthetic: OX40L extracellular domain
source                 1..186
                       mol_type = protein
                       organism = synthetic construct
SEQUENCE: 60
LHCVGDTYPS NDRCCHECRP GNGMVSRCSR SQNTVCRPCG PGFYNDVVSS KPCKPCTWCN  60
LRSGSERKQL CTATQDTVCR CRAGTQPLDS YKPGVDCAPC PPGHFSPGDN QACKPWTNCT  120
LAGKHTLQPA SNSSDAICED RDPPATQPQE TQGPPARPIT VQPTEAWPRT SQGPSTRPVE  180
VPGGRA                                                            186

SEQ ID NO: 61          moltype = AA  length = 156
FEATURE                Location/Qualifiers
REGION                 1..156
                       note = Synthetic: TWEAK extracellular domain
source                 1..156
                       mol_type = protein
                       organism = synthetic construct
SEQUENCE: 61
SAPKGRKTRA RRAIAAHYEV HPRPGQDGAQ AGVDGTVSGW EEARINSSSP LRYNRQIGEF  60
IVTRAGLYYL YCQVHFDEGK AVYLKLDLLV DGVLALRCLE EFSATAASSL GPQLRLCQVS  120
GLLALRPGSS LRIRTLPWAH LKAAPFLTYF GLFQVH                           156

SEQ ID NO: 62          moltype = AA  length = 146
FEATURE                Location/Qualifiers
REGION                 1..146
                       note = Synthetic: APRIL extracellular domain
source                 1..146
                       mol_type = protein
                       organism = synthetic construct
SEQUENCE: 62
AVLTQKQKKQ HSVLHLVPIN ATSKDDSDVT EVMWQPALRR GRGLQAQGYG VRIQDAGVYL  60
LYSQVLFQDV TFTMGQVVSR EGQGRQETLF RCIRSMPSHP DRAYNSCYSA GVFHLHQGDI  120
LSVIIPRARA KLNLSPHGTF LGFVKL                                      146

SEQ ID NO: 63          moltype = AA  length = 152
FEATURE                Location/Qualifiers
REGION                 1..152
                       note = Synthetic: BAFF extracellular domain
source                 1..152
                       mol_type = protein
                       organism = synthetic construct
SEQUENCE: 63
AVQGPEETVT QDCLQLIADS ETPTIQKGSY TFVPWLLSFK RGSALEEKEN KILVKETGYF  60
FIYGQVLYTD KTYAMGHLIQ RKKVHVFGDE LSLVTLFRCI QNMPETLPNN SCYSAGIAKL  120
EEGDELQLAI PRENAQISLD GDVTFFGALK LL                               152

SEQ ID NO: 64          moltype = AA  length = 249
FEATURE                Location/Qualifiers
REGION                 1..249
                       note = Synthetic: RANKL extracellular domain
source                 1..249
                       mol_type = protein
                       organism = synthetic construct
SEQUENCE: 64
YFRAQMDPNR ISEDGTHCIY RILRLHENAD FQDTTLESQD TKLIPDSCRR IKQAFQGAVQ  60
```

-continued

```
KELQHIVGSQ HIRAEKAMVD GSWLDLAKRS KLEAQPFAHL TINATDIPSG SHKVSLSSWY  120
HDRGWAKISN MTFSNGKLIV NQDGFYYLYA NICFRHHETS GDLATEYLQL MVYVTKTSIK  180
IPSSHTLMKG GSTKYWSGNS EFHFYSINVG GFFKLRSGEE ISIEVSNPSL LDPDQDATYF  240
GAFKVRDID                                                          249

SEQ ID NO: 65          moltype = AA  length = 243
FEATURE                Location/Qualifiers
REGION                 1..243
                       note = Synthetic: TRAIL extracellular domain
source                 1..243
                       mol_type = protein
                       organism = synthetic construct
SEQUENCE: 65
TNELKQMQDK YSKSGIACFL KEDDSYWDPN DEESMNSPCW QVKWQLRQLV RKMILRTSEE  60
TISTVQEKQQ NISPLVRERG PQRVAAHITG TRGRSNTLSS PNSKNEKALG RKINSWESSR  120
SGHSFLSNLH LRNGELVIHE KGFYYIYSQT YFRFQEEIKE NTKNDKQMVQ YIYKYTSYPD  180
PILLMKSARN SCWSKDAEYG LYSIYQGGIF ELKENDRIFV SVTNEHLIDM DHEASFFGAF  240
LVG                                                                243

SEQ ID NO: 66          moltype = AA  length = 329
FEATURE                Location/Qualifiers
REGION                 1..329
                       note = Synthetic: EDA1 extracellular domain
source                 1..329
                       mol_type = protein
                       organism = synthetic construct
SEQUENCE: 66
ELRSELRRER GAESRLGGSG TPGTSGTLSS LGGLDPDSPI TSHLGQPSPK QQPLEPGEAA  60
LHSDSQDGHQ MALLNFFFPD EKPYSEEESR RVRRNKRSKS NEGADGPVKN KKKGKKAGPP  120
GPNGPPGPPG PPGPQGPPGI PGIPGIPGTT VMGPPGPPGP PGPQGPPGLQ GPSGAADKAG  180
TRENQPAVVH LQGQGSAIQV KNDLSGGVLN DWSRITMNPK VFKLHPRSGE LEVLVDGTYF  240
IYSQVEVYYI NFTDFASYEV VVDEKPFLQC TRSIETGKTN YNTCYTAGVC LLKARQKIAV  300
KMVHADISIN MSKHTTFFGA IRLGEAPAS                                    329

SEQ ID NO: 67          moltype = AA  length = 73
FEATURE                Location/Qualifiers
REGION                 1..73
                       note = Synthetic: EDA2 extracellular domain
source                 1..73
                       mol_type = protein
                       organism = synthetic construct
SEQUENCE: 67
ELRSELRRER GAESRLGGSG TPGTSGTLSS LGGLDPDSPI TSHLGQPSPK QQPLEPGEAA  60
LHSDSQDGHQ GHQ                                                     73

SEQ ID NO: 68          moltype = AA  length = 128
FEATURE                Location/Qualifiers
REGION                 1..128
                       note = Synthetic: GITRL extracellular domain
source                 1..128
                       mol_type = protein
                       organism = synthetic construct
SEQUENCE: 68
QLETAKEPCM AKFGPLPSKW QMASSEPPCV NKVSDWKLEI LQNGLYLIYG QVAPNANYND  60
VAPFEVRLYK NKDMIQTLTN KSKIQNVGGT YELHVGDTID LIFNSEHQVL KNNTYWGIIL  120
LANPQFIS                                                           128

SEQ ID NO: 69          moltype = AA  length = 208
FEATURE                Location/Qualifiers
REGION                 1..208
                       note = Synthetic: CD80 (B7-1) extracellular domain
source                 1..208
                       mol_type = protein
                       organism = synthetic construct
SEQUENCE: 69
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 70          moltype = AA  length = 224
FEATURE                Location/Qualifiers
REGION                 1..224
                       note = Synthetic: CD86 (B7-2) extracellular domain
source                 1..224
                       mol_type = protein
                       organism = synthetic construct
SEQUENCE: 70
APLKIQAYFN ETADLPCQFA NSQNQSLSEL VVFWQDQENL VLNEVYLGKE KFDSVHSKYM  60
```

```
GRTSFDSDSW TLRLHNLQIK DKGLYQCIIH HKKPTGMIRI HQMNSELSVL ANFSQPEIVP  120
ISNITENVYI NLTCSSIHGY PEPKKMSVLL RTKNSTIEYD GVMQKSQDNV TELYDVSISL  180
SVSFPDVTSN MTIFCILETD KTRLLSSPFS IELEDPQPPP DHIP                   224

SEQ ID NO: 71           moltype = AA  length = 238
FEATURE                 Location/Qualifiers
REGION                  1..238
                        note = Synthetic: ICOSLG extracellular domain
source                  1..238
                        mol_type = protein
                        organism = synthetic construct
SEQUENCE: 71
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 72           moltype = AA  length = 284
FEATURE                 Location/Qualifiers
REGION                  1..284
                        note = Synthetic: MICA extracellular domain
source                  1..284
                        mol_type = protein
                        organism = synthetic construct
SEQUENCE: 72
EPHSLRYNLT VLSWDGSVQS GFLTEVHLDG QPFLRCDRQK CRAKPQGQWA EDVLGNKTWD  60
RETRDLTGNG KDLRMTLAHI KDQKEGLHSL QEIRVCEIHE DNSTRSSQHF YYDGELFLSQ  120
NLETKEWTMP QSSRAQTLAM NVRNFLKEDA MKTKTHYHAM HADCLQELRR YLKSGVVLRR  180
TVPPMVNVTR SEASEGNITV TCRASGFYPW NITLSWRQDG VSLSHDTQQW GDVLPDGNGT  240
YQTWVATRIC QGEEQRFTCY MEHSGNHSTH PVPSGKVLVL QSHW                   284

SEQ ID NO: 73           moltype = AA  length = 287
FEATURE                 Location/Qualifiers
REGION                  1..287
                        note = Synthetic: MICB extracellular domain
source                  1..287
                        mol_type = protein
                        organism = synthetic construct
SEQUENCE: 73
AEPHSLRYNL MVLSQDESVQ SGFLAEGHLD GQPFLRYDRQ KRRAKPQGQW AEDVLGAKTW  60
DTETEDLTEN GQDLRRTLTH IKDQKGGLHS LQEIRVCEIH EDSSTRGSRH FYYDGELFLS  120
QNLETQESTV PQSSRAQTLA MNVTNFWKED AMKTKTHYRA MQADCLQKLQ RYLKSGVAIR  180
RTVPPMVNVT CSEVSEGNIT VTCRASSFYP RNITLTWRQD GVSLSHNTQQ WGDVLPDGNG  240
TYQTWVATRI RQGEEQRFTC YMEHSGNHGT HPVPSGKVLV LQSQRTD                287

SEQ ID NO: 74           moltype = AA  length = 191
FEATURE                 Location/Qualifiers
REGION                  1..191
                        note = Synthetic: ULBP1 extracellular domain
source                  1..191
                        mol_type = protein
                        organism = synthetic construct
SEQUENCE: 74
GWVDTHCLCY DFIITPKSRP EPQWCEVQGL VDERPFLHYD CVNHKAKAFA SLGKKVNVTK  60
TWEEQTETLR DVVDFLKGQL LDIQVENLIP IEPLTLQARM SCEHEAHGHG RGSWQFLFNG  120
QKFLLFDSNN RKWTALHPGA KKMTEKWEKN RDVTMFFQKI SLGDCKMWLE EFLMYWEQML  180
DPTKPPSLAP G                                                       191

SEQ ID NO: 75           moltype = AA  length = 191
FEATURE                 Location/Qualifiers
REGION                  1..191
                        note = Synthetic: ULBP2 extracellular domain
source                  1..191
                        mol_type = protein
                        organism = synthetic construct
SEQUENCE: 75
GRADPHSLCY DITVIPKFRP GPRWCAVQGQ VDEKTFLHYD CGNKTVTPVS PLGKKLNVTT  60
AWKAQNPVLR EVVDILTEQL RDIQLENYTP KEPLTLQARM SCEQKAEGHS SGSWQFSFDG  120
QIFLLFDSEK RMWTTVHPGA RKMKEKWEND KVVAMSFHYF SMGDCIGWLE DFLMGMDSTL  180
EPSAGAPLAM S                                                       191

SEQ ID NO: 76           moltype = AA  length = 188
FEATURE                 Location/Qualifiers
REGION                  1..188
                        note = Synthetic: ULBP3 extracellular domain
source                  1..188
                        mol_type = protein
                        organism = synthetic construct
SEQUENCE: 76
```

-continued

```
DAHSLWYNFT IIHLPRHGQQ WCEVQSQVDQ KNFLSYDCGS DKVLSMGHLE EQLYATDAWG  60
KQLEMLREVG QRLRLELADT ELEDFTPSGP LTLQVRMSCE CEADGYIRGS WQFSFDGRKF  120
LLFDSNNRKW TVVHAGARRM KEKWEKDSGL TTFFKMVSMR DCKSWLRDFL MHRKKRLEPT  180
APPTMAPG                                                          188

SEQ ID NO: 77          moltype = AA  length = 195
FEATURE                Location/Qualifiers
REGION                 1..195
                       note = Synthetic: ULBP4 extracellular domain
source                 1..195
                       mol_type = protein
                       organism = synthetic construct
SEQUENCE: 77
HSLCFNFTIK SLSRPGQPWC EAQVFLNKNL FLQYNSDNNM VKPLGLLGKK VYATSTWGEL  60
TQTLGEVGRD LRMLLCDIKP QIKTSDPSTL QVEMFCQREA ERCTGASWQF ATNGEKSLLF  120
DAMNMTWTVI NHEASKIKET WKKDRGLEKY FRKLSKGDCD HWLREFLGHW EAMPEPTVSP  180
VNASDIHWSS SSLPD                                                  195

SEQ ID NO: 78          moltype = AA  length = 193
FEATURE                Location/Qualifiers
REGION                 1..193
                       note = Synthetic: ULBP5, isoform 1 extracellular domain
source                 1..193
                       mol_type = protein
                       organism = synthetic construct
SEQUENCE: 78
GLADPHSLCY DITVIPKFRP GPRWCAVQGQ VDEKTFLHYD CGSKTVTPVS PLGKKLNVTT  60
AWKAQNPVLR EVVDILTEQL LDIQLENYIP KEPLTLQARM SCEQKAEGHG SGSWQLSFDG  120
QIFLLFDSEN RMWTTVHPGA RKMKEKWEND KDMTMSFHYI SMGDCTGWLE DFLMGMDSTL  180
EPSAGAPPTM SSG                                                    193

SEQ ID NO: 79          moltype = AA  length = 188
FEATURE                Location/Qualifiers
REGION                 1..188
                       note = Synthetic: ULBP5, isoform 2 extracellular domain
source                 1..188
                       mol_type = protein
                       organism = synthetic construct
SEQUENCE: 79
GLADPHSLCY DITVIPKFRP GPRWCAVQGQ VDEKTFLHYD CGSKTVTPVS PLGKKLNVTT  60
AWKAQNPVLR EVVDILTEQL LDIQLENYIP KEPLTLQARM SCEQKAEGHG SGSWQLSFDG  120
QIFLLFDSEN RMWTTVHPGA RKMKEKWEND KDMTMSFHYI SMGDCTGWLE DFLMGMDSTL  180
EPSAGGTV                                                          188

SEQ ID NO: 80          moltype = AA  length = 193
FEATURE                Location/Qualifiers
REGION                 1..193
                       note = Synthetic: ULBP6 extracellular domain
source                 1..193
                       mol_type = protein
                       organism = synthetic construct
SEQUENCE: 80
RRDDPHSLCY DITVIPKFRP GPRWCAVQGQ VDEKTFLHYD CGNKTVTPVS PLGKKLNVTM  60
AWKAQNPVLR EVVDILTEQL LDIQLENYTP KEPLTLQARM SCEQKAEGHS SGSWQFSIDG  120
QTFLLFDSEK RMWTTVHPGA RKMKEKWEND KDVAMSFHYI SMGDCIGWLE DFLMGMDSTL  180
EPSAGAPLAM SSG                                                    193

SEQ ID NO: 81          moltype = AA  length = 217
FEATURE                Location/Qualifiers
REGION                 1..217
                       note = Synthetic: SLAMF1 extracellular domain
source                 1..217
                       mol_type = protein
                       organism = synthetic construct
SEQUENCE: 81
ASYGTGGRMM NCPKILRQLG SKVLLPLTYE RINKSMNKSI HIVVTMAKSL ENSVENKIVS  60
LDPSEAGPPR YLGDRYKFYL ENLTLGIRES RKEDEGWYLM TLEKNVSVQR FCLQLRLYEQ  120
VSTPEIKVLN KTQENGTCTL ILGCTVEKGD HVAYSWSEKA GTHPLNPANS SHLLSLTLGP  180
QHADNIYICT VSNPISNNSQ TFSPWPGCRT DPSETKP                          217

SEQ ID NO: 82          moltype = AA  length = 194
FEATURE                Location/Qualifiers
REGION                 1..194
                       note = Synthetic: SLAMF2 extracellular domain
source                 1..194
                       mol_type = protein
                       organism = synthetic construct
SEQUENCE: 82
QGHLVHMTVV SGSNVTLNIS ESLPENYKQL TWFYTFDQKI VEWDSRKSKY FESKFKGRVR  60
```

```
LDPQSGALYI SKVQKEDNST YIMRVLKKTG NEQEWKIKLQ VLDPVPKPVI KIEKIEDMDD  120
NCYLKLSCVI PGESVNYTWY GDKRPFPKEL QNSVLETTLM PHNYSRCYTC QVSNSVSSKN  180
GTVCLSPPCT LARS                                                    194

SEQ ID NO: 83          moltype = AA  length = 407
FEATURE                Location/Qualifiers
REGION                 1..407
                       note = Synthetic: SLAMF3 extracellular domain
source                 1..407
                       mol_type = protein
                       organism = synthetic construct
SEQUENCE: 83
KDSAPTVVSG ILGGSVTLPL NISVDTEIEN VIWIGPKNAL AFARPKENVT IMVKSYLGRL  60
DITKWSYSLC ISNLTLNDAG SYKAQINQRN FEVTTEEEFT LFVYEQLQEP QVTMKSVKVS  120
ENFSCNITLM CSVKGAEKSV LYSWTPREPH ASESNGGSIL TVSRTPCDPD LPYICTAQNP  180
VSQRSSLPVH VGQFCTDPGA SRGGTTGETV VGVLGEPVTL PLALPACRDT EKVVWLFNTS  240
IISKEREEAA TADPLIKSRD PYKNRVWVSS QDCSLKISQL KIEDAGPYHA YVCSEASSVT  300
SMTHVTLLIY RRLRKPKITW SLRHSEDGIC RISLTCSVED GGNTVMYTWT PLQKEAVVSQ  360
GESHLNVSWR SSENHPNLTC TASNPVSRSS HQFLSENICS GPERNTK                407

SEQ ID NO: 84          moltype = AA  length = 208
FEATURE                Location/Qualifiers
REGION                 1..208
                       note = Synthetic: SLAMF4 extracellular domain
source                 1..208
                       mol_type = protein
                       organism = synthetic construct
SEQUENCE: 84
CQGSADHVVS ISGVPLQLQP NSIQTKVDSI AWKKLLPSQN GFHHILKWEN GSLPSNTSND  60
RFSFIVKNLS LLIKAAQQQD SGLYCLEVTS ISGKVQTATF QVFVFESLLP DKVEKPRLQG  120
QGKILDRGRC QVALSCLVSR DGNVSYAWYR GSKLIQTAGN LTYLDEEVDI NGTHTYTCNV  180
SNPVSWESHT LNLTQDCQNA HQEFRFWP                                     208

SEQ ID NO: 85          moltype = AA  length = 204
FEATURE                Location/Qualifiers
REGION                 1..204
                       note = Synthetic: SLAMF5 extracellular domain
source                 1..204
                       mol_type = protein
                       organism = synthetic construct
SEQUENCE: 85
KDSEIFTVNG ILGESVTFPV NIQEPRQVKI IAWTSKTSVA YVTPGDSETA PVVTVTHRNY  60
YERIHALGPN YNLVISDLRM EDAGDYKADI NTQADPYTTT KRYNLQIYRR LGKPKITQSL  120
MASVNSTCNV TLTCSVEKEE KNVTYNWSPL GEEGNVLQIF QTPEDQELTY TCTAQNPVSN  180
NSDSISARQL CADIAMGFRT HHTG                                         204

SEQ ID NO: 86          moltype = AA  length = 205
FEATURE                Location/Qualifiers
REGION                 1..205
                       note = Synthetic: SLAMF6 extracellular domain
source                 1..205
                       mol_type = protein
                       organism = synthetic construct
SEQUENCE: 86
QSSLTPLMVN GILGESVTLP LEFPAGEKVN FITWLFNETS LAFIVPHETK SPEIHVTNPK  60
QGKRLNFTQS YSLQLSNLKM EDTGSYRAQI STKTSAKLSS YTLRILRQLR NIQVTNHSQL  120
FQNMTCELHL TCSVEDADDN VSFRWEALGN TLSSQPNLTV SWDPRISSEQ DYTCIAENAV  180
SNLSFSVSAQ KLCEDVKIQY TDTKM                                        205

SEQ ID NO: 87          moltype = AA  length = 204
FEATURE                Location/Qualifiers
REGION                 1..204
                       note = Synthetic: SLAMF7 extracellular domain
source                 1..204
                       mol_type = protein
                       organism = synthetic construct
SEQUENCE: 87
SGPVKELVGS VGGAVTFPLK SKVKQVDSIV WTFNTTPLVT IQPEGGTIIV TQNRNRERVD  60
FPDGGYSLKL SKLKKNDSGI YYVGIYSSSL QQPSTQEYVL HVYEHLSKPK VTMGLQSNKN  120
GTCVTNLTCC MEHGEEDVIY TWKALGQAAN ESHNGSILPI SWRWGESDMT FICVARNPVS  180
RNFSSPILAR KLCEGAADDP DSSM                                         204

SEQ ID NO: 88          moltype = AA  length = 585
FEATURE                Location/Qualifiers
REGION                 1..585
                       note = misc_feature - Human serum albumin (HSA)
source                 1..585
                       mol_type = protein
                       organism = Homo sapiens
```

```
SEQUENCE: 88
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQGLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV GSKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DCLSVFLNQL CVLHEKTPVS DRVTKCCTES  480
LVNGRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGL                 585

SEQ ID NO: 89          moltype = AA  length = 330
FEATURE                Location/Qualifiers
REGION                 1..330
                       note = misc_feature - Human IgG1 constant region (amino
                        acid sequence)
source                 1..330
                       mol_type = protein
                       organism = Homo sapiens
SEQUENCE: 89
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 90          moltype = AA  length = 232
FEATURE                Location/Qualifiers
REGION                 1..232
                       note = misc_feature - Human IgG1 Fc domain (amino acid
                        sequence)
source                 1..232
                       mol_type = protein
                       organism = Homo sapiens
SEQUENCE: 90
EPKSCDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 91          moltype = AA  length = 18
FEATURE                Location/Qualifiers
REGION                 1..18
                       note = Synthetic: ABP3
MOD_RES                3
                       note = phosphorylated serine
MOD_RES                14
                       note = phosphorylated serine
source                 1..18
                       mol_type = protein
                       organism = synthetic construct
SEQUENCE: 91
FQSEEQQGGG SGGSEEGG                                              18

SEQ ID NO: 92          moltype = DNA  length = 54
FEATURE                Location/Qualifiers
misc_feature           1..54
                       note = Synthetic: ABP3
source                 1..54
                       mol_type = other DNA
                       organism = synthetic construct
SEQUENCE: 92
ttccaatcag aagagcaaca gggtgggggt tccggcggta gcgaggaggg tggg        54

SEQ ID NO: 93          moltype = AA  length = 16
FEATURE                Location/Qualifiers
REGION                 1..16
                       note = Synthetic: ABP4
MOD_RES                3
                       note = phosphorylated serine
MOD_RES                14
                       note = phosphorylated serine
source                 1..16
                       mol_type = protein
                       organism = synthetic construct
SEQUENCE: 93
MESEESNGGG SGGSEE                                                16
```

```
SEQ ID NO: 94          moltype = DNA  length = 48
FEATURE                Location/Qualifiers
misc_feature           1..48
                       note = Synthetic: ABP4
source                 1..48
                       mol_type = other DNA
                       organism = synthetic construct
SEQUENCE: 94
atggagagtg aagaatcaaa tggtgggggt tccggcggta gcgaggag              48

SEQ ID NO: 95          moltype = AA  length = 14
FEATURE                Location/Qualifiers
REGION                 1..14
                       note = Synthetic: ABP5
MOD_RES                4
                       note = phosphorylated serine
MOD_RES                11
                       note = phosphorylated serine
source                 1..14
                       mol_type = protein
                       organism = synthetic construct
SEQUENCE: 95
FRISHELDSA SSEV                                                   14

SEQ ID NO: 96          moltype = DNA  length = 42
FEATURE                Location/Qualifiers
misc_feature           1..42
                       note = Synthetic: ABP5
source                 1..42
                       mol_type = other DNA
                       organism = synthetic construct
SEQUENCE: 96
tttagaattt cccacgagct tgacagtgca tcttctgagg tg                    42

SEQ ID NO: 97          moltype = AA  length = 15
FEATURE                Location/Qualifiers
REGION                 1..15
                       note = Synthetic: ABP6
MOD_RES                3
                       note = phosphorylated serine
MOD_RES                6
                       note = phosphorylated serine
MOD_RES                12
                       note = phosphorylated serine
source                 1..15
                       mol_type = protein
                       organism = synthetic construct
SEQUENCE: 97
ASSQESGEEA GSQEN                                                  15

SEQ ID NO: 98          moltype = DNA  length = 45
FEATURE                Location/Qualifiers
misc_feature           1..45
                       note = Synthetic: ABP6
source                 1..45
                       mol_type = other DNA
                       organism = synthetic construct
SEQUENCE: 98
gcttcttccc aggaaagcgg tgaagaggct ggcagtcagg agaac                 45

SEQ ID NO: 99          moltype = AA  length = 13
FEATURE                Location/Qualifiers
REGION                 1..13
                       note = Synthetic: ABP7
MOD_RES                8
                       note = phosphorylated serine
source                 1..13
                       mol_type = protein
                       organism = synthetic construct
SEQUENCE: 99
KKIEKFQSEE QQQ                                                    13

SEQ ID NO: 100         moltype = DNA  length = 39
FEATURE                Location/Qualifiers
misc_feature           1..39
                       note = Synthetic: ABP7
source                 1..39
                       mol_type = other DNA
```

```
                       organism = synthetic construct
SEQUENCE: 100
aagaaaatag aaaagtttca gtccgaagag cagcaacaa                  39

SEQ ID NO: 101         moltype = AA  length = 18
FEATURE                Location/Qualifiers
REGION                 1..18
                       note = Synthetic: ABP8
MOD_RES                3
                       note = phosphorylated serine
MOD_RES                10
                       note = phosphorylated serine
MOD_RES                14
                       note = phosphorylated serine
source                 1..18
                       mol_type = protein
                       organism = synthetic construct
SEQUENCE: 101
TVSSETDSIS SEESVEHI                                         18

SEQ ID NO: 102         moltype = DNA  length = 54
FEATURE                Location/Qualifiers
misc_feature           1..54
                       note = Synthetic: ABP8
source                 1..54
                       mol_type = other DNA
                       organism = synthetic construct
SEQUENCE: 102
actgtaagca gcgaaacaga ctcaatatct tcagaagaaa gtgtcgaaca catt 54

SEQ ID NO: 103         moltype = AA  length = 36
FEATURE                Location/Qualifiers
REGION                 1..36
                       note = Synthetic: ABP10
MOD_RES                3
                       note = phosphorylated serine
MOD_RES                14
                       note = phosphorylated serine
MOD_RES                21
                       note = phosphorylated serine
MOD_RES                32
                       note = phosphorylated serine
source                 1..36
                       mol_type = protein
                       organism = synthetic construct
SEQUENCE: 103
FQSEEQQGGG SGGSEEGGME SEESNGGGSG GSEEGG                     36

SEQ ID NO: 104         moltype = DNA  length = 108
FEATURE                Location/Qualifiers
misc_feature           1..108
                       note = Synthetic: ABP10
source                 1..108
                       mol_type = other DNA
                       organism = synthetic construct
SEQUENCE: 104
ttccaatcag aagagcaaca gggtgggggt tccggcggta gcgaggaggg tgggatggag  60
agtgaagaat caaatggtgg gggttccggc ggtagcgagg agggtggg        108

SEQ ID NO: 105         moltype = AA  length = 36
FEATURE                Location/Qualifiers
REGION                 1..36
                       note = Synthetic: ABP11
MOD_RES                3
                       note = phosphorylated serine
MOD_RES                14
                       note = phosphorylated serine
MOD_RES                21
                       note = phosphorylated serine
MOD_RES                32
                       note = phosphorylated serine
source                 1..36
                       mol_type = protein
                       organism = synthetic construct
SEQUENCE: 105
MESEESNGGG SGGSEEGGME SEESNGGGSG GSEEGG                     36

SEQ ID NO: 106         moltype = DNA  length = 102
FEATURE                Location/Qualifiers
```

```
misc_feature           1..102
                       note = Synthetic: ABP11
source                 1..102
                       mol_type = other DNA
                       organism = synthetic construct
SEQUENCE: 106
atggagagtg aagaatcaaa tggtgggggt tccggcggta gcgaggaggg tgggatggag  60
agtgaagaat caaatggtgg gggttccggc ggtagcgagg ag                     102

SEQ ID NO: 107         moltype = AA  length = 36
FEATURE                Location/Qualifiers
REGION                 1..36
                       note = Synthetic: ABP12
MOD_RES                3
                       note = phosphorylated serine
MOD_RES                10
                       note = phosphorylated serine
MOD_RES                14
                       note = phosphorylated serine
MOD_RES                21
                       note = phosphorylated serine
MOD_RES                28
                       note = phosphorylated serine
MOD_RES                32
                       note = phosphorylated serine
source                 1..36
                       mol_type = protein
                       organism = synthetic construct
SEQUENCE: 107
TVSSETDSIS SEESVEHITV SSETDSISSE ESVEHI                            36

SEQ ID NO: 108         moltype = DNA  length = 108
FEATURE                Location/Qualifiers
misc_feature           1..108
                       note = Synthetic: ABP12
source                 1..108
                       mol_type = other DNA
                       organism = synthetic construct
SEQUENCE: 108
actgtaagca gcgaaacaga ctcaatatct tcagaagaaa gtgtcgaaca cattactgtg  60
agcagtgaaa ctgactctat ctcctctgag gagtctgtag aacatata               108

SEQ ID NO: 109         moltype = AA  length = 36
FEATURE                Location/Qualifiers
REGION                 1..36
                       note = Synthetic: ABP13
source                 1..36
                       mol_type = protein
                       organism = synthetic construct
SEQUENCE: 109
FQAEEQQGGG SGGAEEGGME AEESNGGGSG GAEEGG                            36

SEQ ID NO: 110         moltype = DNA  length = 108
FEATURE                Location/Qualifiers
misc_feature           1..108
                       note = Synthetic: ABP13
source                 1..108
                       mol_type = other DNA
                       organism = synthetic construct
SEQUENCE: 110
ttccaagcag aagaacaaca gggtgggggt tccggcggtg cggaggaggg tgggatggag  60
gcagaagaat caaatggtgg gggttccggc ggtgcggagg agggtggg               108

SEQ ID NO: 111         moltype = AA  length = 36
FEATURE                Location/Qualifiers
REGION                 1..36
                       note = Synthetic: ABP14
source                 1..36
                       mol_type = protein
                       organism = synthetic construct
SEQUENCE: 111
MEAEESNGGG SGGAEEGGME AEESNGGGSG GAEEGG                            36

SEQ ID NO: 112         moltype = DNA  length = 102
FEATURE                Location/Qualifiers
misc_feature           1..102
                       note = Synthetic: ABP14
source                 1..102
                       mol_type = other DNA
```

```
                        organism = synthetic construct
SEQUENCE: 112
atggaggcag aagaatcaaa tggtgggggt tccggcggtg cggaggaggg tgggatggag  60
gcagaagaat caaatggtgg gggttccggc ggtgcggagg ag                     102

SEQ ID NO: 113          moltype = AA  length = 40
FEATURE                 Location/Qualifiers
REGION                  1..40
                        note = Synthetic: ABP15
source                  1..40
                        mol_type = protein
                        organism = synthetic construct
SEQUENCE: 113
RRFQSEEQQG GGSGGSEEGG RRMESEESNG GGSGGSEEGG                        40

SEQ ID NO: 114          moltype = DNA  length = 120
FEATURE                 Location/Qualifiers
misc_feature            1..120
                        note = Synthetic: ABP15
source                  1..120
                        mol_type = other DNA
                        organism = synthetic construct
SEQUENCE: 114
cgccggttcc aatcagaaga gcaacagggt gggggttccg gcggtagcga ggagggtggg  60
aggagaatgg agagtgaaga atcaaatggt gggggttccg gcggtagcga ggagggtggg  120

SEQ ID NO: 115          moltype = AA  length = 36
FEATURE                 Location/Qualifiers
REGION                  1..36
                        note = Synthetic: ABP16
MOD_RES                 3
                        note = phosphorylated serine
MOD_RES                 14
                        note = phosphorylated serine
MOD_RES                 21
                        note = phosphorylated serine
MOD_RES                 32
                        note = phosphorylated serine
source                  1..36
                        mol_type = protein
                        organism = synthetic construct
SEQUENCE: 115
FQSEEQQGGG SGGSEEGGFQ SEEQQGGGSG GSEEGG                            36

SEQ ID NO: 116          moltype = DNA  length = 108
FEATURE                 Location/Qualifiers
misc_feature            1..108
                        note = Synthetic: ABP16
source                  1..108
                        mol_type = other DNA
                        organism = synthetic construct
SEQUENCE: 116
ttccaatcag aagagcaaca gggtgggggt tccggcggta gcgaggaggg tgggtttcaa  60
agcgaagaac aacagggtgg gggttccggc ggtagcgagg agggtggg               108

SEQ ID NO: 117          moltype = AA  length = 12
FEATURE                 Location/Qualifiers
REGION                  1..12
                        note = Synthetic: ABP17
source                  1..12
                        mol_type = protein
                        organism = synthetic construct
SEQUENCE: 117
SEESEESEES EE                                                      12

SEQ ID NO: 118          moltype = DNA  length = 36
FEATURE                 Location/Qualifiers
misc_feature            1..36
                        note = Synthetic: ABP17
source                  1..36
                        mol_type = other DNA
                        organism = synthetic construct
SEQUENCE: 118
tctgaagaat ccgaggagag tgaagagtca gaggag                            36

SEQ ID NO: 119          moltype = AA  length = 13
FEATURE                 Location/Qualifiers
REGION                  1..13
                        note = Synthetic: ABP18
```

```
source                  1..13
                        mol_type = protein
                        organism = synthetic construct
SEQUENCE: 119
GGGSGGSEEG GGS                                                          13

SEQ ID NO: 120          moltype = DNA  length = 39
FEATURE                 Location/Qualifiers
misc_feature            1..39
                        note = Synthetic: ABP18
source                  1..39
                        mol_type = other DNA
                        organism = synthetic construct
SEQUENCE: 120
ggtgggggtt ccggcggtag cgaggagggt ggcggtagc                              39

SEQ ID NO: 121          moltype = AA  length = 16
FEATURE                 Location/Qualifiers
REGION                  1..16
                        note = Synthetic: ABP19
source                  1..16
                        mol_type = protein
                        organism = synthetic construct
SEQUENCE: 121
GGGSGGSEES EEGGGS                                                       16

SEQ ID NO: 122          moltype = DNA  length = 48
FEATURE                 Location/Qualifiers
misc_feature            1..48
                        note = Synthetic: ABP19
source                  1..48
                        mol_type = other DNA
                        organism = synthetic construct
SEQUENCE: 122
ggtgggggtt ccggcggttc agaagagagc gaggagggtg gcggtagc                    48

SEQ ID NO: 123          moltype = AA  length = 19
FEATURE                 Location/Qualifiers
REGION                  1..19
                        note = Synthetic: ABP20
source                  1..19
                        mol_type = protein
                        organism = synthetic construct
SEQUENCE: 123
GGGSGGSEES EESEEGGGS                                                    19

SEQ ID NO: 124          moltype = DNA  length = 57
FEATURE                 Location/Qualifiers
misc_feature            1..57
                        note = Synthetic: ABP20
source                  1..57
                        mol_type = other DNA
                        organism = synthetic construct
SEQUENCE: 124
ggtgggggtt ccggcggtag cgaagaatca gaagagagcg aggagggggg tggtagc          57

SEQ ID NO: 125          moltype = AA  length = 22
FEATURE                 Location/Qualifiers
REGION                  1..22
                        note = Synthetic: ABP21
source                  1..22
                        mol_type = protein
                        organism = synthetic construct
SEQUENCE: 125
GGGSGGSEES EESEESEEGG GS                                                22

SEQ ID NO: 126          moltype = DNA  length = 66
FEATURE                 Location/Qualifiers
misc_feature            1..66
                        note = Synthetic: ABP21
source                  1..66
                        mol_type = other DNA
                        organism = synthetic construct
SEQUENCE: 126
ggtgggggtt ccggcggttc cgaggagagc gaagaatcag aagagagcga ggagggggt  60
ggcagc                                                                  66

SEQ ID NO: 127          moltype =   length =
SEQUENCE: 127
```

```
000

SEQ ID NO: 128          moltype =   length =
SEQUENCE: 128
000

SEQ ID NO: 129          moltype = AA  length = 7
FEATURE                 Location/Qualifiers
REGION                  1..7
                        note = Synthetic: ABP24
MOD_RES                 3
                        note = phosphorylated serine
source                  1..7
                        mol_type = protein
                        organism = synthetic construct
SEQUENCE: 129
FQSEEQQ                                                                   7

SEQ ID NO: 130          moltype = AA  length = 7
FEATURE                 Location/Qualifiers
REGION                  1..7
                        note = Synthetic: ABP25
MOD_RES                 3
                        note = phosphorylated serine
source                  1..7
                        mol_type = protein
                        organism = synthetic construct
SEQUENCE: 130
MESEESN                                                                   7

SEQ ID NO: 131          moltype = AA  length = 7
FEATURE                 Location/Qualifiers
REGION                  1..7
                        note = Synthetic: ABP26
MOD_RES                 3
                        note = phosphorylated serine
source                  1..7
                        mol_type = protein
                        organism = synthetic construct
SEQUENCE: 131
GGSEEGG                                                                   7

SEQ ID NO: 132          moltype = AA  length = 4
FEATURE                 Location/Qualifiers
REGION                  1..4
                        note = Synthetic: L (linker)
source                  1..4
                        mol_type = protein
                        organism = synthetic construct
SEQUENCE: 132
GGGS                                                                      4

SEQ ID NO: 133          moltype = AA  length = 13
FEATURE                 Location/Qualifiers
REGION                  1..13
                        note = Synthetic: ABP27
REGION                  1..2
                        note = misc_feature - Xaa can be any naturally occurring
                         amino acid
SITE                    4
                        note = misc_feature - Xaa can be any naturally occurring
                         amino acid
REGION                  6..7
                        note = misc_feature - Xaa can be any naturally occurring
                         amino acid
SITE                    8
                        note = misc_feature - Xaa is a peptide linker
SITE                    10
                        note = misc_feature - Xaa can be any naturally occurring
                         amino acid
REGION                  12..13
                        note = misc_feature - Xaa can be any naturally occurring
                         amino acid
source                  1..13
                        mol_type = protein
                        organism = synthetic construct
SEQUENCE: 133
XXSXEXXXSX EXX                                                            13
```

```
SEQ ID NO: 134          moltype = AA  length = 18
FEATURE                 Location/Qualifiers
REGION                  1..18
                        note = Synthetic: ABP28
REGION                  1..2
                        note = misc_feature - Xaa can be any naturally occurring
                         amino acid
REGION                  6..7
                        note = misc_feature - Xaa can be any naturally occurring
                         amino acid
source                  1..18
                        mol_type = protein
                        organism = synthetic construct
SEQUENCE: 134
XXSEEXXGGG SGGSEEGG                                             18

SEQ ID NO: 135          moltype = AA  length = 570
FEATURE                 Location/Qualifiers
REGION                  1..570
                        note = Synthetic: Fam20C
source                  1..570
                        mol_type = protein
                        organism = synthetic construct
SEQUENCE: 135
MVFLVACALH IALDLLPRLE RRGARPSGEP GCSCAQPAAE VAAPGWAQVR GRPGEPPAAS  60
SAAGDAGWPN KHTLRILQDF SSDPSSNLSS HSLEKLPPAA EPAERALRGR DPGALRPHDP  120
AHRPLLRDPG PRRSESPPGP GGDASLLARL FEHPLYRVAV PPLTEEDVLF NVNSDTRLSP  180
KAAENPDWPH AGAEGAEFLS PGEAAVDSYP NWLKFHIGIN RYELYSRHNP AIEALLHDLS  240
SQRITSVAMK SGGTQLKLIM TFQNYGQALF KPMKQTREQE TPPDFFYFSD YERHNAEIAA  300
FHLDRILDFR RVPPVAGRMV NMTKEIRDVT RDKKLWRTFF ISPANNICFY GECSYYCSTE  360
HALCGKPDQI EGSLAAFLPD LSLAKRKTWR NPWRRSYHKR KKAEWEVDPD YCEEVKQTPP  420
YDSSHRILDV MDMTIFDFLM GNMDRHHYET FEKFGNETFI IHLDNGRGFG KYSHDELSIL  480
VPLQQCCRIR KSTYLRLQLL AKEEYKLSLL MAESLRGDQV APVLYQPHLE ALDRRLRVVL  540
KAVRDCVERN GLHSVVDDDL DTEHRAASAR                                570

SEQ ID NO: 136          moltype = AA  length = 578
FEATURE                 Location/Qualifiers
REGION                  1..578
                        note = Synthetic: Fam20C-KDEL
source                  1..578
                        mol_type = protein
                        organism = synthetic construct
SEQUENCE: 136
MVFLVACALH IALDLLPRLE RRGARPSGEP GCSCAQPAAE VAAPGWAQVR GRPGEPPAAS  60
SAAGDAGWPN KHTLRILQDF SSDPSSNLSS HSLEKLPPAA EPAERALRGR DPGALRPHDP  120
AHRPLLRDPG PRRSESPPGP GGDASLLARL FEHPLYRVAV PPLTEEDVLF NVNSDTRLSP  180
KAAENPDWPH AGAEGAEFLS PGEAAVDSYP NWLKFHIGIN RYELYSRHNP AIEALLHDLS  240
SQRITSVAMK SGGTQLKLIM TFQNYGQALF KPMKQTREQE TPPDFFYFSD YERHNAEIAA  300
FHLDRILDFR RVPPVAGRMV NMTKEIRDVT RDKKLWRTFF ISPANNICFY GECSYYCSTE  360
HALCGKPDQI EGSLAAFLPD LSLAKRKTWR NPWRRSYHKR KKAEWEVDPD YCEEVKQTPP  420
YDSSHRILDV MDMTIFDFLM GNMDRHHYET FEKFGNETFI IHLDNGRGFG KYSHDELSIL  480
VPLQQCCRIR KSTYLRLQLL AKEEYKLSLL MAESLRGDQV APVLYQPHLE ALDRRLRVVL  540
KAVRDCVERN GLHSVVDDDL DTEHRAASAR GGGSKDEL                       578

SEQ ID NO: 137          moltype = DNA  length = 1500
FEATURE                 Location/Qualifiers
misc_feature            1..1500
                        note = Synthetic: Fam20C-KDEL
source                  1..1500
                        mol_type = other DNA
                        organism = synthetic construct
SEQUENCE: 137
gacttcagct ccgacccctc ctccaacctc tcgtcccact cgctggagaa actgccgccc  60
gcggccgagc cggccgagcg cgccttgcgg gggcgggatc ccggcgccct aagaccccac  120
gaccccgcgc accggccgct gctgcgagac cccggcccgc gtcggtccga gtcgcccccc  180
ggccccggcg gagacgcctc cctcctggcc aggctgttcg agcacccgct ttaccgggtg  240
gcggttccgc cgctcacgga ggaggacgtc ctgttcaatg tgaacagcga caccaggctc  300
agccccaaag cggcggagaa cccggactgg ccgcatgcgg gtgctgaagg tgcagaattc  360
ctctcccccg gggaggcggc cgtggactcc tatcccaact ggctcaagtt ccacattggt  420
atcaaccggt acgagctgta ctccagacac aaccccggcca tcgaggccct gctgcacgac  480
ctcagctccc agaggatcac cagcgtggcc atgaagtcgg ggggcacgca gctgaagctc  540
atcatgacct tccagaatta cgggcaagcg ctgttcaaac ccatgaaaca aacgagggag  600
caggagacac cccctgactt tttttatttc tctgactacg agaggcacaa tgcggagatt  660
gctgccttcc acctggacag gatcctggac ttccgccggg tccctcccgt ggccggcagg  720
atggtcaaca tgaccaagga gatccgggac gtcacacggg acaagaagct ctggaggacc  780
ttcttcatct ctccagccaa caacatctgc ttctacggcg agtgttccta ctactgctcc  840
acggagcacg ccctgtgcgg gaagccagac cagatcgagg gctcgctggc ggccttcctg  900
cccgacctgt ccctggccaa gaggaagacc tggcggaacc cttggcggcg ttcctaccac  960
aagcgcaaga aggccgagtg ggaggtggac cctgactact gcgaggaggt gaagcagaca  1020
```

```
ccgccctacg acagcagcca ccgcatcctg gacgtcatgg acatgacgat cttcgacttc  1080
ctcatgggaa acatggaccg tcaccactac gagacttttg agaagtttgg gaatgaaacg  1140
ttcatcatcc acttagacaa tggaagaggg tttgggaagt attcgcacga cgagctctcc  1200
atcctggtgc cgctacagca gtgctgcagg atccggaagt ccacctacct gcgtctgcag  1260
ctcctggcca aggaggagta caagctgagc ctgctgatgg ccgagtctct gcgggggac   1320
caggtggcac ccgtgctgta ccagccgcac ctggaggccc tggaccggcg gctccgcgtc  1380
gtgctaaagg ccgtccggga ctgcgtggag aggaacgggc tccacagcgt ggtggatgac  1440
gacctggaca ctgagcacag agccgcctcg gcgaggggag gtggatcaaa agatgaactg  1500

SEQ ID NO: 138         moltype = AA  length = 570
FEATURE                Location/Qualifiers
REGION                 1..570
                       note = Synthetic: Fam20C-(D456A)
source                 1..570
                       mol_type = protein
                       organism = synthetic construct
SEQUENCE: 138
MVFLVACALH IALDLLPRLE RRGARPSGEP GCSCAQPAAE VAAPGWAQVR GRPGEPPAAS  60
SAAGDAGWPN KHTLRILQDF SSDPSSNLSS HSLEKLPPAA EPAERALRGR DPGALRPHDP  120
AHRPLLRDPG PRRSESPPGP GGDASLLARL FEHPLYRVAV PPLTEEDVLF NVNSDTRLSP  180
KAAENPDWPH AGAEGAEFLS PGEAAVDSYP NWLKFHIGIN RYELYSRHNP AIEALLHDLS  240
SQRITSVAMK SGGTQLKLIM TFQNYGQALF KPMKQTREQE TPPDFFYFSD YERHNAEIAA  300
FHLDRILDFR RVPPVAGRMV NMTKEIRDVT RDKKLWRTFF ISPANNICFY GECSYYCSTE  360
HALCGKPDQI EGSLAAFLPD LSLAKRKTWR NPWRRSYHKR KKAEWEVDPD YCEEVKQTPP  420
YDSSHRILDV MDMTIFDFLM GNMDRHHYET FEKFGNETFI IHLANGRGFG KYSHDELSIL  480
VPLQQCCRIR KSTYLRLQLL AKEEYKLSLL MAESLRGDQV APVLYQPHLE ALDRRLRVVL  540
KAVRDCVERN GLHSVVDDDL DTEHRAASAR                                   570

SEQ ID NO: 139         moltype = AA  length = 578
FEATURE                Location/Qualifiers
REGION                 1..578
                       note = Synthetic: Fam20C (D456A)-KDEL
source                 1..578
                       mol_type = protein
                       organism = synthetic construct
SEQUENCE: 139
MVFLVACALH IALDLLPRLE RRGARPSGEP GCSCAQPAAE VAAPGWAQVR GRPGEPPAAS  60
SAAGDAGWPN KHTLRILQDF SSDPSSNLSS HSLEKLPPAA EPAERALRGR DPGALRPHDP  120
AHRPLLRDPG PRRSESPPGP GGDASLLARL FEHPLYRVAV PPLTEEDVLF NVNSDTRLSP  180
KAAENPDWPH AGAEGAEFLS PGEAAVDSYP NWLKFHIGIN RYELYSRHNP AIEALLHDLS  240
SQRITSVAMK SGGTQLKLIM TFQNYGQALF KPMKQTREQE TPPDFFYFSD YERHNAEIAA  300
FHLDRILDFR RVPPVAGRMV NMTKEIRDVT RDKKLWRTFF ISPANNICFY GECSYYCSTE  360
HALCGKPDQI EGSLAAFLPD LSLAKRKTWR NPWRRSYHKR KKAEWEVDPD YCEEVKQTPP  420
YDSSHRILDV MDMTIFDFLM GNMDRHHYET FEKFGNETFI IHLANGRGFG KYSHDELSIL  480
VPLQQCCRIR KSTYLRLQLL AKEEYKLSLL MAESLRGDQV APVLYQPHLE ALDRRLRVVL  540
KAVRDCVERN GLHSVVDDDL DTEHRAASAR GGGSKDEL                          578

SEQ ID NO: 140         moltype = DNA  length = 1734
FEATURE                Location/Qualifiers
misc_feature           1..1734
                       note = Synthetic: Fam20C (D456A)-KDEL
source                 1..1734
                       mol_type = other DNA
                       organism = synthetic construct
SEQUENCE: 140
atggtgttcc tggtggcctg cgcgctgcac atcgccctgg acctgctgcc caggctggag  60
cgacgcggcg cgcggccctc gggggagccc ggctgttcgt gcgcgcagcc cgccgccgag  120
gtggccgcgc ccggctgggc ccaggttcgg ggccgccccg gggagccccc ggccgcctcc  180
tccgccgccg gcgacgcggg ctggcccaac aagcacacgc tccgcatcct gcaggacttc  240
agctccgacc cctcctccaa cctctcgtcc cactcgctgg agaaactgcc gcccgcggcc  300
gagccggccg agcgcgcctt gcgggggcgg gatcccggcg ccctaagacc ccacgacccc  360
gcgcaccggc cgctgctgcg agaccccggc ccgcgtcggt ccgagtcgcc ccccggcccc  420
ggcggagacg cctccctcct ggccaggctg ttcgagcacc cgctttaccg ggtggcggtt  480
ccgccgctca cggaggagga cgtcctgttc aatgtgaaca gcgacaccag gctcagcccc  540
aaagcggcgg agaacccgga ctggccgcat gcgggtgctg aaggtgcaga attcctctcc  600
cccggggagg cggccgtgga ctcctatccc aactggctca agttccacat tggtatcaac  660
cggtacgagc tgtactccag acacaacccg gccatcgagg ccctgctgca cgacctcagc  720
tcccagagga tcaccagcgt ggccatgaag tcgggggca cgcagctgaa gctcatcatg   780
accttccaga attacgggca agcgctgttc aaacccatga aacaaacgag ggagcaggag  840
acaccccctg acttttttta tttctctgac tacgagaggc acaatgcgga gattgctgcc  900
ttccacctgg acaggatcct ggacttccgc cgggtccctc ccgtggccgg caggatggtc  960
aacatgacca aggagatccg ggacgtcaca cgggacaaga agctctggag gaccttcttc  1020
atctctccag ccaacaacat ctgcttctac ggcgagtgtt cctactactg ctccacggag  1080
cacgccctgt gcgggaagcc agaccagatc gagggctcgc tggcggcctt cctgcccgac  1140
ctgtccctgg ccaagaggaa gacctggcgg aacccttggc ggcgttccta ccacaagcgc  1200
aagaaggccg agtgggaggt ggaccctgac tactgcgagg aggtgaagca gacaccgccc  1260
tacgacagca gccaccgcat cctggacgtc atggacatga cgatcttcga cttcctcatg  1320
ggaaacatgg accgtcacca ctacgagact tttgagaagt ttgggaatga aacgttcatc  1380
atccacttag ctaatggaag agggtttggg aagtattcgc acgacgagct ctccatcctg  1440
```

```
gtgccgctac agcagtgctg caggatccgg aagtccacct acctgcgtct gcagctcctg  1500
gccaaggagg agtacaagct gagcctgctg atggccgagt ctctgcgggg ggaccaggtg  1560
gcacccgtgc tgtaccagcc gcacctggag gccctggacc ggcggctccg cgtcgtgcta  1620
aaggccgtcc gggactgcgt ggagaggaac gggctccaca gcgtggtgga tgacgacctg  1680
gacactgagc acagagccgc ctcggcgagg ggaggtggat caaaagatga actg        1734

SEQ ID NO: 141          moltype = AA  length = 584
FEATURE                 Location/Qualifiers
REGION                  1..584
                        note = misc_feature - Mouse serum albumin (MSA)
source                  1..584
                        mol_type = protein
                        organism = Mus musculus
SEQUENCE: 141
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALA                   584

SEQ ID NO: 142          moltype = DNA  length = 1752
FEATURE                 Location/Qualifiers
misc_feature            1..1752
                        note = Mouse serum albumin (MSA)
source                  1..1752
                        mol_type = unassigned DNA
                        organism = Mus musculus
SEQUENCE: 142
gaagcacaca agagtgagat cgcccatcgg tataatgatt tgggagaaca acatttcaaa  60
ggcctagtcc tgattgcctt ttcccagtat ctccagaaat gctcatacga tgagcatgcc  120
aaattagtgc aggaagtaac agactttgca aagacgtgtg ttgccgatga gtctgccgcc  180
aactgtgaca aatcccttca cactcttttt ggagataagt tgtgtgccat tccaaacctc  240
cgtgaaaact atggtgaact ggctgactgc tgtacaaaac aagagcccga aagaaacgaa  300
tgtttcctgc aacacaaaga tgacaacccc agcctgccac catttgaaag gccagaggct  360
gaggccatgt gcacctcctt taaggaaaac ccaaccacct ttatgggaca ctatttgcat  420
gaagttgcca gaagacatcc ttatttctat gccccagaac ttctttacta tgctgagcag  480
tacaatgaga ttctgaccca gtgttgtgca gaggctgaca aggaaagctg cctgaccccg  540
aagcttgatg gtgtgaagga gaaagcattg gtctcatctg tccgtcagag aatgaagtgc  600
tccagtatgc agaagtttgg agagagagct tttaaagcat gggcagtagc tcgtctgagc  660
cagacattcc ccaatgctga ctttgcagaa atcaccaaat tggcaacaga cctgaccaaa  720
gtcaacaagg agtgctgcca tggtgacctg ctggaatgcg cagatgacag ggcggaactt  780
gccaagtaca tgtgtgaaaa ccaggcgact atctccagca aactgcagac ttgctgcgat  840
aaaccactgt tgaagaaagc ccactgtctt agtgaggtgg agcatgacac catgcctgct  900
gatctgcctg ccattgctgc tgattttgtt gaggaccagg aagtgtgcaa gaactatgct  960
gaggccaagg atgtcttcct gggcacgttc ttgtatgaat attcaagaag acaccctgat  1020
tactctgtat ccctgttgct gagacttgct aagaaatatg aagccactct ggaaaagtgc  1080
tgcgctgaag ccaatcctcc cgcatgctac ggcacagtgc ttgctgaatt tcagcctctt  1140
gtagaagagc ctaagaactt ggtcaaaacc aactgtgatc tttacgagaa gcttggagaa  1200
tatggattcc aaaatgccat tctagttcgc tacacccaga aagcacctca ggtgtcaacc  1260
ccaactctcg tggaggctgc aagaaaccta ggaagagtgg gcaccaagtg ttgtacactt  1320
cctgaagatc agagactgcc ttgtgtggaa gactatctgt ctgcaatcct gaaccgtgtg  1380
tgtctgctgc atgagaagac cccagtgagt gagcatgtta ccaagtgctg tagtggatcc  1440
ctggtggaaa ggcggccatg cttctctgct ctgacagttg atgaaacata tgtccccaaa  1500
gagtttaaag ctgagacctt caccttccac tctgatatct gcacacttcc agagaaggag  1560
aagcagatta agaaacaaac ggctcttgct gagctggtga agcacaagcc caaggctaca  1620
gcggagcaac tgaagactgt catggatgac tttgcacagt tcctggatac atgttgcaag  1680
gctgctgaca aggacacctg cttctcgact gagggtccaa accttgtcac tagatgcaaa  1740
gacgccttag cc                                                      1752

SEQ ID NO: 143          moltype = AA  length = 149
FEATURE                 Location/Qualifiers
REGION                  1..149
                        note = misc_feature - Murine IL2
source                  1..149
                        mol_type = protein
                        organism = Mus musculus
SEQUENCE: 143
APTSSSTSSS TAEAQQQQQQ QQQQQQHLEQ LLMDLQELLS RMENYRNLKL PRMLTFKFYL  60
PKQATELKDL QCLEDELGPL RHVLDLTQSK SFQLEDAENF ISNIRVTVVK LKGSDNTFEC  120
QFDDESATVV DFLRRWIAFC QSIISTSPQ                                    149

SEQ ID NO: 144          moltype = DNA  length = 447
FEATURE                 Location/Qualifiers
misc_feature            1..447
```

```
                        note = Murine IL3
source                  1..447
                        mol_type = unassigned DNA
                        organism = Mus musculus
SEQUENCE: 144
gcacccactt caagctccac ttcaagctct acagcggaag cacagcagca gcagcagcag  60
cagcagcagc agcagcagca cctggagcag ctgttgatgg acctacagga gctcctgagc  120
aggatggaga attacaggaa cctgaaactc cccaggatgc tcaccttcaa attttacttg  180
cccaagcagg ccacagaatt gaaagatctt cagtgcctag aagatgaact tggacctctg  240
cggcatgttc tggatttgac tcaaagcaaa agctttcaat tggaagatgc tgagaatttc  300
atcagcaata tcagagtaac tgttgtaaaa ctaaagggct ctgacaacac atttgagtgc  360
caattcgatg atgagtcagc aactgtggtg gactttctga ggagatggat agccttctgt  420
caaagcatca tctcaacaag ccctcaa                                      447

SEQ ID NO: 145          moltype = AA  length = 6
FEATURE                 Location/Qualifiers
REGION                  1..6
                        note = Synthetic: His-tag
source                  1..6
                        mol_type = protein
                        organism = synthetic construct
SEQUENCE: 145
HHHHHH                                                             6

SEQ ID NO: 146          moltype = AA  length = 787
FEATURE                 Location/Qualifiers
REGION                  1..787
                        note = misc_feature - Murine MSA-IL2-ABP10
source                  1..787
                        mol_type = protein
                        organism = Mus musculus
SEQUENCE: 146
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALAGGGSAP TSSSTSSSTA  600
EAQQQQQQQQ QQQQHLEQLL MDLQELLSRM ENYRNLKLPR MLTFKFYLPK QATELKDLQC  660
LEDELGPLRH VLDLTQSKSF QLEDAENFIS NIRVTVVKLK GSDNTFECQF DDESATVVDF  720
LRRWIAFCQS IISTSPQGGG SFQSEEQQGG GSGGSEEGGM ESEESNGGGS GGSEEGGGGG  780
SHHHHHH                                                            787

SEQ ID NO: 147          moltype = DNA  length = 2361
FEATURE                 Location/Qualifiers
misc_feature            1..2361
                        note = Murine MSA-IL2-ABP10
source                  1..2361
                        mol_type = unassigned DNA
                        organism = Mus musculus
SEQUENCE: 147
gaagcacaca agagtgagat cgcccatcgg tataatgatt tgggagaaca acatttcaaa  60
ggcctagtcc tgattgcctt ttcccagtat ctccagaaat gctcatacga tgagcatgcc  120
aaattagtgc aggaagtaac agactttgca aagacgtgtg ttgccgatga gtctgccgcc  180
aactgtgaca aatcccttca cactcttttt ggagataagt tgtgtgccat tccaaacctc  240
cgtgaaaact atggtgaact ggctgactgc tgtacaaaac aagagcccga aagaaacgaa  300
tgtttcctgc aacacaaaga tgacaacccc agcctgccac catttgaaag gccagaggct  360
gaggccatgt gcacctcctt taaggaaaac ccaaccacct ttatgggaca ctatttgcat  420
gaagttgcca gaagacatcc ttatttctat gccccagaac ttctttacta tgctgagcag  480
tacaatgaga ttctgaccca gtgttgtgca gaggctgaca aggaaagctg cctgaccccg  540
aagcttgatg gtgtgaagga gaaagcattg gtctcatctg tccgtcagag aatgaagtgc  600
tccagtatgc agaagtttgg agagagagct tttaaagcat gggcagtagc tcgtctgagc  660
cagacattcc ccaatgctga ctttgcagaa atcaccaaat tggcaacaga cctgaccaaa  720
gtcaacaagg agtgctgcca tggtgacctg ctggaatgcg cagatgacag ggcggaactt  780
gccaagtaca tgtgtgaaaa ccaggcgact atctccagca aactgcagac ttgctgcgat  840
aaaccactgt tgaagaaagc ccactgtctt agtgaggtgg agcatgacac catgcctgct  900
gatctgcctg ccattgctgc tgattttgtt gaggaccagg aagtgtgcaa gaactatgct  960
gaggccaagg atgtcttcct gggcacgttc ttgtatgaat attcaagaag acaccctgat  1020
tactctgtat ccctgttgct gagacttgct aagaaatatg aagccactct ggaaaagtgc  1080
tgcgctgaag ccaatcctcc cgcatgctac ggcacagtgc ttgctgaatt tcagcctctt  1140
gtagaagagc ctaagaactt ggtcaaaacc aactgtgatc tttacgagaa gcttggagaa  1200
tatggattcc aaaatgccat tctagttcgc tacacccaga aagcacctca ggtgtcaacc  1260
ccaactctcg tggaggctgc aagaaaccta ggaagagtgg gcaccaagtg ttgtacactt  1320
cctgaagatc agagactgcc ttgtgtggaa gactatctgt ctgcaatcct gaaccgtgtg  1380
tgtctgctgc atgagaagac cccagtgagt gagcatgtta ccaagtgctg tagtggatcc  1440
```

```
ctggtggaaa ggcggccatg cttctctgct ctgacagttg atgaaacata tgtccccaaa  1500
gagtttaaag ctgagacctt caccttccac tctgatatct gcacacttcc agagaaggag  1560
aagcagatta agaaacaaac ggctcttgct gagctggtga agcacaagcc caaggctaca  1620
gcggagcaac tgaagactgt catggatgac tttgcacagt tcctggatac atgttgcaag  1680
gctgctgaca aggacacctg cttctcgact gagggtccaa accttgtcac tagatgcaaa  1740
gacgccttag ccggaggggg ctccgcaccc acttcaagct ccacttcaag ctctacagcg  1800
gaagcacagc agcagcagca gcagcagcag cagcagcagc agcacctgga gcagctgttg  1860
atggacctac aggagctcct gagcaggatg gagaattaca ggaacctgaa actccccagg  1920
atgctcacct tcaaatttta cttgcccaag caggccacag aattgaaaga tcttcagtgc  1980
ctagaagatg aacttggacc tctgcggcat gttctggatt tgactcaaag caaaagcttt  2040
caattggaag atgctgagaa tttcatcagc aatatcagag taactgttgt aaaactaaag  2100
ggctctgaca acacatttga gtgccaattc gatgatgagt cagcaactgt ggtggacttt  2160
ctgaggagat ggatagcctt ctgtcaaagc atcatctcaa caagccctca aggtggaggt  2220
agtttccaat cagaagagca acagggtggg ggttccggcg gtagcgagga gggtgggatg  2280
gagagtgaag aatcaaatgg tgggggttcc ggcggtagcg aggagggtgg gggaggtgga  2340
tcacaccatc accaccatca c                                           2361
```

```
SEQ ID NO: 148         moltype = AA  length = 783
FEATURE                Location/Qualifiers
REGION                 1..783
                       note = misc_feature - Murine ABP10-MSA-IL2
source                 1..783
                       mol_type = protein
                       organism = Mus musculus
SEQUENCE: 148
FQSEEQQGGG SGGSEEGGME SEESNGGGSG GSEEGGGGGS EAHKSEIAHR YNDLGEQHFK  60
GLVLIAFSQY LQKCSYDEHA KLVQEVTDFA KTCVADESAA NCDKSLHTLF GDKLCAIPNL  120
RENYGELADC CTKQEPERNE CFLQHKDDNP SLPPFERPEA EAMCTSFKEN PTTFMGHYLH  180
EVARRHPYFY APELLYYAEQ YNEILTQCCA EADKESCLTP KLDGVKEKAL VSSVRQRMKC  240
SSMQKFGERA FKAWAVARLS QTFPNADFAE ITKLATDLTK VNKECCHGDL LECADDRAEL  300
AKYMCENQAT ISSKLQTCCD KPLLKKAHCL SEVEHDTMPA DLPAIAADFV EDQEVCKNYA  360
EAKDVFLGTF LYEYSRRHPD YSVSLLLRLA KKYEATLEKC CAEANPPACY GTVLAEFQPL  420
VEEPKNLVKT NCDLYEKLGE YGFQNAILVR YTQKAPQVST PTLVEAARNL GRVGTKCCTL  480
PEDQRLPCVE DYLSAILNRV CLLHEKTPVS EHVTKCCSGS LVERRPCFSA LTVDETYVPK  540
EFKAETFTFH SDICTLPEKE KQIKKQTALA ELVKHKPKAT AEQLKTVMDD FAQFLDTCCK  600
AADKDTCFST EGPNLVTRCK DALAGGGSAP TSSSTSSSTA EAQQQQQQQQ QQQQHLEQLL  660
MDLQELLSRM ENYRNLKLPR MLTFKFYLPK QATELKDLQC LEDELGPLRH VLDLTQSKSF  720
QLEDAENFIS NIRVTVVKLK GSDNTFECQF DDESATVVDF LRRWIAFCQS IISTSPQHHH  780
HHH                                                               783
```

```
SEQ ID NO: 149         moltype = DNA  length = 2349
FEATURE                Location/Qualifiers
misc_feature           1..2349
                       note = Murine ABP10-MSA-IL2
source                 1..2349
                       mol_type = unassigned DNA
                       organism = Mus musculus
SEQUENCE: 149
ttccaatcag aagagcaaca gggtgggggt tccggcggta gcgaggaggg tgggatggag  60
agtgaagaat caaatggtgg gggttccggc ggtagcgagg agggtggggg aggtggatca  120
gaagcacaca agagtgagat cgcccatcgg tataatgatt tgggagaaca acatttcaaa  180
ggcctagtcc tgattgcctt ttcccagtat ctccagaaat gctcatacga tgagcatgcc  240
aaattagtgc aggaagtaac agactttgca aagacgtgtg ttgccgatga gtctgccgcc  300
aactgtgaca aatcccttca cactcttttt ggagataagt tgtgtgccat tccaaacctc  360
cgtgaaaact atggtgaact ggctgactgc tgtacaaaac aagagcccga aagaaacgaa  420
tgtttcctgc aacacaaaga tgacaacccc agcctgccac catttgaaag gccagaggct  480
gaggccatgt gcacctcctt taaggaaaac ccaaccacct ttatgggaca ctatttgcat  540
gaagttgcca gaagacatcc ttatttctat gccccagaac ttctttacta tgctgagcag  600
tacaatgaga ttctgaccca gtgttgtgca gaggctgaca aggaaagctg cctgaccccg  660
aagcttgatg gtgtgaagga gaaagcattg gtctcatctg tccgtcagag aatgaagtgc  720
tccagtatgc agaagtttgg agagagagct tttaaagcat gggcagtagc tcgtctgagc  780
cagacattcc ccaatgctga ctttgcagaa atcaccaaat tggcaacaga cctgaccaaa  840
gtcaacaagg agtgctgcca tggtgacctg ctggaatgcg cagatgacag ggcggaactt  900
gccaagtaca tgtgtgaaaa ccaggcgact atctccagca aactgcagac ttgctgcgat  960
aaaccactgt tgaagaaagc ccactgtctt agtgaggtgg agcatgacac catgcctgct  1020
gatctgcctg ccattgctgc tgattttgtt gaggaccagg aagtgtgcaa gaactatgct  1080
gaggccaagg atgtcttcct gggcacgttc ttgtatgaat attcaagaag acaccctgat  1140
tactctgtat ccctgttgct gagacttgct aagaaatatg aagccactct ggaaaagtgc  1200
tgcgctgaag ccaatcctcc cgcatgctac ggcacagtgc ttgctgaatt tcagcctctt  1260
gtagaagagc ctaagaactt ggtcaaaacc aactgtgatc tttacgagaa gcttggagaa  1320
tatggattcc aaaatgccat tctagttcgc tacacccaga aagcacctca ggtgtcaacc  1380
ccaactctcg tggaggctgc aagaaaccta ggaagagtgg gcaccaagtg ttgtacactt  1440
cctgaagatc agagactgcc ttgtgtggaa gactatctgt ctgcaatcct gaaccgtgtg  1500
tgtctgctgc atgagaagac cccagtgagt gagcatgtta ccaagtgctg tagtggatcc  1560
ctggtggaaa ggcggccatg cttctctgct ctgacagttg atgaaacata tgtccccaaa  1620
gagtttaaag ctgagacctt caccttccac tctgatatct gcacacttcc agagaaggag  1680
aagcagatta agaaacaaac ggctcttgct gagctggtga agcacaagcc caaggctaca  1740
gcggagcaac tgaagactgt catggatgac tttgcacagt tcctggatac atgttgcaag  1800
gctgctgaca aggacacctg cttctcgact gagggtccaa accttgtcac tagatgcaaa  1860
```

```
gacgccttag ccggaggggg ctccgcaccc acttcaagct ccacttcaag ctctacagcg  1920
gaagcacagc agcagcagca gcagcagcag cagcagcagc agcacctgga gcagctgttg  1980
atggacctac aggagctcct gagcaggatg gagaattaca ggaacctgaa actccccagg  2040
atgctcacct tcaaatttta cttgcccaag caggccacag aattgaaaga tcttcagtgc  2100
ctagaagatg aacttggacc tctgcggcat gttctggatt tgactcaaag caaaagcttt  2160
caattggaag atgctgagaa tttcatcagc aatatcagag taactgttgt aaaactaaag  2220
ggctctgaca acacatttga gtgccaattc gatgatgagt cagcaactgt ggtggacttt  2280
ctgaggagat ggatagcctt ctgtcaaagc atcatctcaa caagccctca acaccatcac  2340
caccatcac                                                          2349

SEQ ID NO: 150         moltype = AA  length = 769
FEATURE                Location/Qualifiers
REGION                 1..769
                       note = misc_feature - Murine MSA-IL2-ABP8
source                 1..769
                       mol_type = protein
                       organism = Mus musculus
SEQUENCE: 150
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALAGGGSAP TSSSTSSSTA  600
EAQQQQQQQQ QQQQHLEQLL MDLQELLSRM ENYRNLKLPR MLTFKFYLPK QATELKDLQC  660
LEDELGPLRH VLDLTQSKSF QLEDAENFIS NIRVTVVKLK GSDNTFECQF DDESATVVDF  720
LRRWIAFCQS IISTSPQGGG STVSSETDSI SSEESVEHIG GGSHHHHHH              769

SEQ ID NO: 151         moltype = DNA  length = 2307
FEATURE                Location/Qualifiers
misc_feature           1..2307
                       note = Murine MSA-IL2-ABP8
source                 1..2307
                       mol_type = unassigned DNA
                       organism = Mus musculus
SEQUENCE: 151
gaagcacaca agagtgagat cgcccatcgg tataatgatt tgggagaaca acatttcaaa  60
ggcctagtcc tgattgcctt ttcccagtat ctccagaaat gctcatacga tgagcatgcc  120
aaattagtgc aggaagtaac agactttgca aagacgtgtg ttgccgatga gtctgccgcc  180
aactgtgaca aatcccttca cactcttttt ggagataagt tgtgtgccat tccaaacctc  240
cgtgaaaact atggtgaact ggctgactgc tgtacaaaac aagagcccga aagaaacgaa  300
tgtttcctgc aacacaaaga tgacaacccc agcctgccac catttgaaag gccagaggct  360
gaggccatgt gcacctcctt taaggaaaac ccaaccacct ttatgggaca ctatttgcat  420
gaagttgcca gaagacatcc ttatttctat gccccagaac ttctttacta tgctgagcag  480
tacaatgaga ttctgaccca gtgttgtgca gaggctgaca aggaaagctg cctgaccccg  540
aagcttgatg gtgtgaagga gaaagcattg gtctcatctg tccgtcagag aatgaagtgc  600
tccagtatgc agaagtttgg agagagagct tttaaagcat gggcagtagc tcgtctgagc  660
cagacattcc ccaatgctga ctttgcagaa atcaccaaat tggcaacaga cctgaccaaa  720
gtcaacaagg agtgctgcca tggtgacctg ctggaatgcg cagatgacag ggcggaactt  780
gccaagtaca tgtgtgaaaa ccaggcgact atctccagca aactgcagac ttgctgcgat  840
aaaccactgt tgaagaaagc ccactgtctt agtgaggtgg agcatgacac catgcctgct  900
gatctgcctg ccattgctgc tgattttgtt gaggaccagg aagtgtgcaa gaactatgct  960
gaggccaagg atgtcttcct gggcacgttc ttgtatgaat attcaagaag acaccctgat  1020
tactctgtat ccctgttgct gagacttgct aagaaatatg aagccactct ggaaaagtgc  1080
tgcgctgaag ccaatcctcc cgcatgctac ggcacagtgc ttgctgaatt tcagcctctt  1140
gtagaagagc ctaagaactt ggtcaaaacc aactgtgatc tttacgagaa gcttggagaa  1200
tatggattcc aaaatgccat tctagttcgc tacacccaga aagcacctca ggtgtcaacc  1260
ccaactctcg tggaggctgc aagaaaccta ggaagagtgg gcaccaagtg ttgtacactt  1320
cctgaagatc agagactgcc ttgtgtggaa gactatctgt ctgcaatcct gaaccgtgtg  1380
tgtctgctgc atgagaagac cccagtgagt gagcatgtta ccaagtgctg tagtggatcc  1440
ctggtggaaa ggcggccatg cttctctgct ctgacagttg atgaaacata tgtccccaaa  1500
gagtttaaag ctgagacctt caccttccac tctgatatct gcacacttcc agagaaggag  1560
aagcagatta agaaacaaac ggctcttgct gagctggtga agcacaagcc caaggctaca  1620
gcggagcaac tgaagactgt catggatgac tttgcacagt tcctggatac atgttgcaag  1680
gctgctgaca aggacacctg cttctcgact gagggtccaa accttgtcac tagatgcaaa  1740
gacgccttag ccggaggggg ctccgcaccc acttcaagct ccacttcaag ctctacagcg  1800
gaagcacagc agcagcagca gcagcagcag cagcagcagc agcacctgga gcagctgttg  1860
atggacctac aggagctcct gagcaggatg gagaattaca ggaacctgaa actccccagg  1920
atgctcacct tcaaatttta cttgcccaag caggccacag aattgaaaga tcttcagtgc  1980
ctagaagatg aacttggacc tctgcggcat gttctggatt tgactcaaag caaaagcttt  2040
caattggaag atgctgagaa tttcatcagc aatatcagag taactgttgt aaaactaaag  2100
ggctctgaca acacatttga gtgccaattc gatgatgagt cagcaactgt ggtggacttt  2160
ctgaggagat ggatagcctt ctgtcaaagc atcatctcaa caagccctca aggtggaggt  2220
agtactgtaa gcagcgaaac agactcaata tcttcagaag aaagtgtcga acacattgga  2280
ggtggatcac accatcacca ccatcac                                      2307
```

```
SEQ ID NO: 152          moltype = AA  length = 763
FEATURE                 Location/Qualifiers
REGION                  1..763
                        note = misc_feature - Murine MSA-IL2-ABP17
source                  1..763
                        mol_type = protein
                        organism = Mus musculus
SEQUENCE: 152
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALAGGGSAP TSSSTSSSTA  600
EAQQQQQQQQ QQQQHLEQLL MDLQELLSRM ENYRNLKLPR MLTFKFYLPK QATELKDLQC  660
LEDELGPLRH VLDLTQSKSF QLEDAENFIS NIRVTVVKLK GSDNTFECQF DDESATVVDF  720
LRRWIAFCQS IISTSPQGGG GSEESEESEE SEEGGGGHHH HHH                   763

SEQ ID NO: 153          moltype = DNA  length = 2289
FEATURE                 Location/Qualifiers
misc_feature            1..2289
                        note = Murine MSA-IL2-ABP17
source                  1..2289
                        mol_type = unassigned DNA
                        organism = Mus musculus
SEQUENCE: 153
gaagcacaca agagtgagat cgcccatcgg tataatgatt tgggagaaca acatttcaaa  60
ggcctagtcc tgattgcctt ttcccagtat ctccagaaat gctcatacga tgagcatgcc  120
aaattagtgc aggaagtaac agactttgca aagacgtgtg ttgccgatga gtctgccgcc  180
aactgtgaca aatcccttca cactcttttt ggagataagt tgtgtgccat tccaaacctc  240
cgtgaaaact atggtgaact ggctgactgc tgtacaaaac aagagcccga aagaaacgaa  300
tgtttcctgc aacacaaaga tgacaacccc agcctgccac catttgaaag gccagaggct  360
gaggccatgt gcacctcctt taaggaaaac ccaaccacct ttatgggaca ctatttgcat  420
gaagttgcca gaagacatcc ttatttctat gccccagaac ttctttacta tgctgagcag  480
tacaatgaga ttctgaccca gtgttgtgca gaggctgaca aggaaagctg cctgaccccg  540
aagcttgatg gtgtgaagga gaaagcattg gtctcatctg tccgtcagag aatgaagtgc  600
tccagtatgc agaagtttgg agagagagct tttaaagcat gggcagtagc tcgtctgagc  660
cagacattcc ccaatgctga ctttgcagaa atcaccaaat tggcaacaga cctgaccaaa  720
gtcaacaagg agtgctgcca tggtgacctg ctggaatgcg cagatgacag ggcggaactt  780
gccaagtaca tgtgtgaaaa ccaggcgact atctccagca aactgcagac ttgctgcgat  840
aaaccactgt tgaagaaagc ccactgtctt agtgaggtgg agcatgacac catgcctgct  900
gatctgcctg ccattgctgc tgattttgtt gaggaccagg aagtgtgcaa gaactatgct  960
gaggccaagg atgtcttcct gggcacgttc ttgtatgaat attcaagaag acaccctgat  1020
tactctgtat ccctgttgct gagacttgct aagaaatatg aagccactct ggaaaagtgc  1080
tgcgctgaag ccaatcctcc cgcatgctac ggcacagtgc ttgctgaatt tcagcctctt  1140
gtagaagagc ctaagaactt ggtcaaaacc aactgtgatc tttacgagaa gcttggagaa  1200
tatggattcc aaaatgccat tctagttcgc tacacccaga aagcacctca ggtgtcaacc  1260
ccaactctcg tggaggctgc aagaaaccta ggaagagtgg gcaccaagtg ttgtacactt  1320
cctgaagatc agagactgcc ttgtgtggaa gactatctgt ctgcaatcct gaaccgtgtg  1380
tgtctgctgc atgagaagac cccagtgagt gagcatgtta ccaagtgctg tagtggatcc  1440
ctggtggaaa ggcggccatg cttctctgct ctgacagttg atgaaacata tgtccccaaa  1500
gagtttaaag ctgagacctt caccttccac tctgatatct gcacacttcc agagaaggag  1560
aagcagatta agaaacaaac ggctcttgct gagctggtga agcacaagcc caaggctaca  1620
gcggagcaac tgaagactgt catggatgac tttgcacagt tcctggatac atgttgcaag  1680
gctgctgaca aggacacctg cttctcgact gagggtccaa accttgtcac tagatgcaaa  1740
gacgccttag ccggaggggg ctccgcaccc acttcaagct ccacttcaag ctctacagcg  1800
gaagcacagc agcagcagca gcagcagcag cagcagcagc agcacctgga gcagctgttg  1860
atggacctac aggagctcct gagcaggatg gagaattaca ggaacctgaa actccccagg  1920
atgctcacct tcaaatttta cttgcccaag caggccacag aattgaaaga tcttcagtgc  1980
ctagaagatg aacttggacc tctgcggcat gttctggatt tgactcaaag caaaagcttt  2040
caattggaag atgctgagaa tttcatcagc aatatcagag taactgttgt aaaactaaag  2100
ggctctgaca acacatttga gtgccaattc gatgatgagt cagcaactgt ggtggacttt  2160
ctgaggagat ggatagcctt ctgtcaaagc atcatctcaa caagccctca aggggggga  2220
ggctctgaag aatccgagga gagtgaagag tcagaggagg gtggcggggg gcaccatcac  2280
caccatcac                                                         2289

SEQ ID NO: 154          moltype = AA  length = 129
FEATURE                 Location/Qualifiers
REGION                  1..129
                        note = Synthetic: Lysozyme
source                  1..129
                        mol_type = protein
                        organism = synthetic construct
SEQUENCE: 154
```

```
KVFGRCELAA AMKRHGLDNY RGYSLGNWVC AAKFESNFNT QATNRNTDGS TDYGILQINS  60
RWWCNDGRTP GSRNLCNIPC SALLSSDITA SVNCAKKIVS DGNGMNAWVA WRNRCKGTDV  120
QAWIRGCRL                                                          129

SEQ ID NO: 155         moltype = DNA  length = 387
FEATURE                Location/Qualifiers
misc_feature           1..387
                       note = Synthetic: Lysozyme
source                 1..387
                       mol_type = other DNA
                       organism = synthetic construct
SEQUENCE: 155
aaagtctttg gacgatgtga gctggcagca gctatgaagc gtcacggact tgataactat  60
cggggataca gcctgggaaa ctgggtgtgt gccgcaaaat tcgagagtaa cttcaacacc  120
caggctacaa accgtaacac cgatgggagt accgactacg gaatcctaca gatcaacagc  180
cgctggtggt gcaacgatgg caggaccccca ggctccagga acctgtgcaa catcccgtgc  240
tcagccctgc tgagctcaga cataacagcg agcgtgaact gcgcgaagaa gatcgtcagc  300
gatggaaacg gcatgaacgc gtgggtcgcc tggcgcaacc gctgcaaggg caccgacgtc  360
caggcgtgga tcagaggctg ccggctg                                      387

SEQ ID NO: 156         moltype = AA  length = 179
FEATURE                Location/Qualifiers
REGION                 1..179
                       note = Synthetic: Lysozyme-ABP10
source                 1..179
                       mol_type = protein
                       organism = synthetic construct
SEQUENCE: 156
KVFGRCELAA AMKRHGLDNY RGYSLGNWVC AAKFESNFNT QATNRNTDGS TDYGILQINS  60
RWWCNDGRTP GSRNLCNIPC SALLSSDITA SVNCAKKIVS DGNGMNAWVA WRNRCKGTDV  120
QAWIRGCRLG GGSFQSEEQQ GGGSGGSEEG GMESEESNGG GSGGSEEGGG GGSHHHHHH   179

SEQ ID NO: 157         moltype = DNA  length = 537
FEATURE                Location/Qualifiers
misc_feature           1..537
                       note = Synthetic: Lyzsozyme-ABP10
source                 1..537
                       mol_type = other DNA
                       organism = synthetic construct
SEQUENCE: 157
aaagtctttg gacgatgtga gctggcagca gctatgaagc gtcacggact tgataactat  60
cggggataca gcctgggaaa ctgggtgtgt gccgcaaaat tcgagagtaa cttcaacacc  120
caggctacaa accgtaacac cgatgggagt accgactacg gaatcctaca gatcaacagc  180
cgctggtggt gcaacgatgg caggaccccca ggctccagga acctgtgcaa catcccgtgc  240
tcagccctgc tgagctcaga cataacagcg agcgtgaact gcgcgaagaa gatcgtcagc  300
gatggaaacg gcatgaacgc gtgggtcgcc tggcgcaacc gctgcaaggg caccgacgtc  360
caggcgtgga tcagaggctg ccggctgggt ggaggtagtt tccaatcaga agagcaacag  420
ggtgggggtt ccggcggtag cgaggagggt gggatggaga gtgaagaatc aaatggtggg  480
ggttccggcg gtagcgagga gggtggggga ggtggatcac accatcacca ccatcac     537

SEQ ID NO: 158         moltype = AA  length = 133
FEATURE                Location/Qualifiers
REGION                 1..133
                       note = misc_feature - Murine IFNg
source                 1..133
                       mol_type = protein
                       organism = Mus musculus
SEQUENCE: 158
HGTVIESLES LNNYFNSSGI DVEEKSLFLD IWRNWQKDGD MKILQSQIIS FYLRLFEVLK  60
DNQAISNNIS VIESHLITTF FSNSKAKKDA FMSIAKFEVN NPQVQRQAFN ELIRVVHQLL  120
PESSLRKRKR SRC                                                     133

SEQ ID NO: 159         moltype = DNA  length = 399
FEATURE                Location/Qualifiers
misc_feature           1..399
                       note = Murine IFNg
source                 1..399
                       mol_type = unassigned DNA
                       organism = Mus musculus
SEQUENCE: 159
cacggcacag tcattgaaag cctagaaagt ctgaataact attttaactc aagtggcata  60
gatgtggaag aaaagagtct cttcttggat atctggagga actggcaaaa ggatggtgac  120
atgaaaatcc tgcagagcca gattatctct ttctacctca gactctttga agtcttgaaa  180
gacaatcagg ccatcagcaa caacataagc gtcattgaat cacacctgat tactaccttc  240
ttcagcaaca gcaaggcgaa aaaggatgca ttcatgagta ttgccaagtt tgaggtcaac  300
aacccacagg tccagcgcca agcattcaat gagctcatcc gagtggtcca ccagctgttg  360
ccggaatcca gcctcaggaa gcggaaaagg agtcgctgc                         399

SEQ ID NO: 160         moltype = AA  length = 922
```

```
FEATURE                 Location/Qualifiers
REGION                  1..922
                        note = Synthetic: mIFNg-mIFNg-MSA-ABP10
source                  1..922
                        mol_type = protein
                        organism = synthetic construct
SEQUENCE: 160
HGTVIESLES LNNYFNSSGI DVEEKSLFLD IWRNWQKDGD MKILQSQIIS FYLRLFEVLK  60
DNQAISNNIS VIESHLITTF FSNSKAKKDA FMSIAKFEVN NPQVQRQAFN ELIRVVHQLL  120
PESSLRKRKR SRCGGGSGGG SGGGSGGGSH GTVIESLESL NNYFNSSGID VEEKSLFLDI  180
WRNWQKDGDM KILQSQIISF YLRLFEVLKD NQAISNNISV IESHLITTFF SNSKAKKDAF  240
MSIAKFEVNN PQVQRQAFNE LIRVVHQLLP ESSLRKRKRS RCGSGGGSEA HKSEIAHRYN  300
DLGEQHFKGL VLIAFSQYLQ KCSYDEHAKL VQEVTDFAKT CVADESAANC DKSLHTLFGD  360
KLCAIPNLRE NYGELADCCT KQEPERNECF LQHKDDNPSL PPFERPEAEA MCTSFKENPT  420
TFMGHYLHEV ARRHPYFYAP ELLYYAEQYN EILTQCCAEA DKESCLTPKL DGVKEKALVS  480
SVRQRMKCSS MQKFGERAFK AWAVARLSQT FPNADFAEIT KLATDLTKVN KECCHGDLLE  540
CADDRAELAK YMCENQATIS SKLQTCCDKP LLKKAHCLSE VEHDTMPADL PAIAADFVED  600
QEVCKNYAEA KDVFLGTFLY EYSRRHPDYS VSLLLRLAKK YEATLEKCCA EANPPACYGT  660
VLAEFQPLVE EPKNLVKTNC DLYEKLGEYG FQNAILVRYT QKAPQVSTPT LVEAARNLGR  720
VGTKCCTLPE DQRLPCVEDY LSAILNRVCL LHEKTPVSEH VTKCCSGSLV ERRPCFSALT  780
VDETYVPKEF KAETFTFHSD ICTLPEKEKQ IKKQTALAEL VKHKPKATAE QLKTVMDDFA  840
QFLDTCCKAA DKDTCFSTEG PNLVTRCKDA LAGGGSFQSE EQQGGGSGGS EEGGMESEES  900
NGGGSGGSEE GGGGGSHHHH HH                                          922

SEQ ID NO: 161          moltype = DNA  length = 2766
FEATURE                 Location/Qualifiers
misc_feature            1..2766
                        note = Synthetic: mIFNg-mIFNg-MSA-ABP10
source                  1..2766
                        mol_type = other DNA
                        organism = synthetic construct
SEQUENCE: 161
cacggcacag tcattgaaag cctagaaagt ctgaataact attttaactc aagtggcata  60
gatgtggaag aaaagagtct cttcttggat atctggagga actggcaaaa ggatggtgac  120
atgaaaatcc tgcagagcca gattatctct ttctacctca gactctttga agtcttgaaa  180
gacaatcagg ccatcagcaa caacataagc gtcattgaat cacacctgat tactaccttc  240
ttcagcaaca gcaaggcgaa aaaggatgca ttcatgagta ttgccaagtt tgaggtcaac  300
aacccacagg tccagcgcca agcattcaat gagctcatcc gagtggtcca ccagctgttg  360
ccggaatcca gcctcaggaa gcggaaaagg agtcgctgcg gcggaggttc tggaggtggc  420
tccggtggag gttctggagg tggctcccac ggcacagtca ttgaaagcct agaaagtctg  480
aataactatt ttaactcaag tggcatagat gtggaagaaa agagtctctt cttggatatc  540
tggaggaact ggcaaaagga tggtgacatg aaaatcctgc agagccagat tatctctttc  600
tacctcagac tctttgaagt cttgaaagac aatcaggcca tcagcaacaa cataagcgtc  660
attgaatcac acctgattac taccttcttc agcaacagca aggcgaaaaa ggatgcattc  720
atgagtattg ccaagtttga ggtcaacaac ccacaggtcc agcgccaagc attcaatgag  780
ctcatccgag tggtccacca gctgttgccg gaatccagcc tcaggaagcg gaaaaggagt  840
cgctgcggtt ccggtggcgg atccgaagca cacaagagtg agatcgccca tcggtataat  900
gatttgggag aacaacattt caaaggccta gtcctgattg ccttttccca gtatctccag  960
aaatgctcat acgatgagca tgccaaatta gtgcaggaag taacagactt tgcaaagacg  1020
tgtgttgccg atgagtctgc cgccaactgt gacaaatccc ttcacactct tttggagat  1080
aagttgtgtg ccattccaaa cctccgtgaa aactatggtg aactggctga ctgctgtaca  1140
aaacaagagc ccgaaagaaa cgaatgtttc ctgcaacaca aagatgacaa ccccagcctg  1200
ccaccatttg aaaggccaga ggctgaggcc atgtgcacct cctttaagga aaacccaacc  1260
acctttatgg gacactattt gcatgaagtt gccagaagac atccttattt ctatgcccca  1320
gaacttcttt actatgctga gcagtacaat gagattctga cccagtgttg tgcagaggct  1380
gacaaggaaa gctgcctgac cccgaagctt gatggtgtga aggagaaagc attggtctca  1440
tctgtccgtc agagaatgaa gtgctccagt atgcagaagt ttggagagag agcttttaaa  1500
gcatgggcag tagctcgtct gagccagaca ttccccaatg ctgactttgc agaaatcacc  1560
aaattggcaa cagacctgac caaagtcaac aaggagtgct gccatggtga cctgctggaa  1620
tgcgcagatg acagggcgga acttgccaag tacatgtgtg aaaaccaggc gactatctcc  1680
agcaaactgc agacttgctg cgataaacca ctgttgaaga aagcccactg tcttagtgag  1740
gtggagcatg acaccatgcc tgctgatctg cctgccattg ctgctgattt tgttgaggac  1800
caggaagtgt gcaagaacta tgctgaggcc aaggatgtct tcctgggcac gttcttgtat  1860
gaatattcaa gaagacaccc tgattactct gtatccctgt tgctgagact tgctaagaaa  1920
tatgaagcca ctctggaaaa gtgctgcgct gaagccaatc ctcccgcatg ctacggcaca  1980
gtgcttgctg aatttcagcc tcttgtagaa gagcctaaga acttggtcaa aaccaactgt  2040
gatctttacg agaagcttgg agaatatgga ttccaaaatg ccattctagt tcgctacacc  2100
cagaaagcac ctcaggtgtc aaccccaact ctcgtggagg ctgcaagaaa cctaggaaga  2160
gtgggcacca agtgttgtac acttcctgaa gatcagagac tgccttgtgt ggaagactat  2220
ctgtctgcaa tcctgaaccg tgtgtgtctg ctgcatgaga agaccccagt gagtgagcat  2280
gttaccaagt gctgtagtgg atccctggtg gaaaggcggc catgcttctc tgctctgaca  2340
gttgatgaaa catatgtccc caaagagttt aaagctgaga ccttcacctt ccactctgat  2400
atctgcacac ttccagagaa ggagaagcag attaagaaac aaacggctct tgctgagctg  2460
gtgaagcaca agcccaaggc tacagcggag caactgaaga ctgtcatgga tgactttgca  2520
cagttcctgg atacatgttg caaggctgct gacaaggaca cctgcttctc gactgagggt  2580
ccaaaccttg tcactagatg caaagacgcc ttagccggtg gaggtagttt ccaatcagaa  2640
gagcaacagg gtgggggttc cggcggtagc gaggagggtg ggatggagag tgaagaatca  2700
aatggtgggg gttccggcgg tagcgaggag ggtgggggag gtggatcaca ccatcaccac  2760
catcac                                                            2766
```

```
SEQ ID NO: 162          moltype = AA  length = 338
FEATURE                 Location/Qualifiers
REGION                  1..338
                        note = Synthetic: mIFNg-mIFNg-ABP10
source                  1..338
                        mol_type = protein
                        organism = synthetic construct
SEQUENCE: 162
HGTVIESLES LNNYFNSSGI DVEEKSLFLD IWRNWQKDGD MKILQSQIIS FYLRLFEVLK  60
DNQAISNNIS VIESHLITTF FSNSKAKKDA FMSIAKFEVN NPQVQRQAFN ELIRVVHQLL  120
PESSLRKRKR SRCGGGSGGG SGGGSGGGSH GTVIESLESL NNYFNSSGID VEEKSLFLDI  180
WRNWQKDGDM KILQSQIISF YLRLFEVLKD NQAISNNISV IESHLITTFF SNSKAKKDAF  240
MSIAKFEVNN PQVQRQAFNE LIRVVHQLLP ESSLRKRKRS RCGSGGGSGG GSFQSEEQQG  300
GGSGGSEEGG MESEESNGGG SGGSEEGGGG GSHHHHHH                          338

SEQ ID NO: 163          moltype = DNA  length = 1014
FEATURE                 Location/Qualifiers
misc_feature            1..1014
                        note = Synthetic: mIFNg-mIFNg-ABP10
source                  1..1014
                        mol_type = other DNA
                        organism = synthetic construct
SEQUENCE: 163
cacggcacag tcattgaaag cctagaaagt ctgaataact attttaactc aagtggcata  60
gatgtggaag aaaagagtct cttcttggat atctggagga actggcaaaa ggatggtgac  120
atgaaaatcc tgcagagcca gattatctct ttctacctca gactctttga agtcttgaaa  180
gacaatcagg ccatcagcaa caacataagc gtcattgaat cacacctgat tactaccttc  240
ttcagcaaca gcaaggcgaa aaaggatgca ttcatgagta ttgccaagtt tgaggtcaac  300
aacccacagg tccagcgcca agcattcaat gagctcatcc gagtggtcca ccagctgttg  360
ccggaatcca gcctcaggaa gcggaaaagg agtcgctgcg gcggaggttc tggaggtggc  420
tccggtggag gttctggagg tggctcccac ggcacagtca ttgaaagcct agaaagtctg  480
aataactatt ttaactcaag tggcatagat gtggaagaaa agagtctctt cttggatatc  540
tggaggaact ggcaaaagga tggtgacatg aaaatcctgc agagccagat tatctctttc  600
tacctcagac tctttgaagt cttgaaagac aatcaggcca tcagcaacaa cataagcgtc  660
attgaatcac acctgattac taccttcttc agcaacagca aggcgaaaaa ggatgcattc  720
atgagtattg ccaagtttga ggtcaacaac ccacaggtcc agcgccaagc attcaatgag  780
ctcatccgag tggtccacca gctgttgccg gaatccagcc tcaggaagcg gaaaaggagt  840
cgctgcggtt ccggtggcgg atccggtgga ggtagtttcc aatcagaaga gcaacagggt  900
gggggttccg gcggtagcga ggagggtggg atggagagtg aagaatcaaa tggtgggggt  960
tccggcggta gcgaggaggg tgggggaggt ggatcacacc atcaccacca tcac        1014

SEQ ID NO: 164          moltype = AA  length = 313
FEATURE                 Location/Qualifiers
REGION                  1..313
                        note = misc_feature - Murine IL12p40
source                  1..313
                        mol_type = protein
                        organism = Mus musculus
SEQUENCE: 164
MWELEKDVYV VEVDWTPDAP GETVNLTCDT PEEDDITWTS DQRHGVIGSG KTLTITVKEF  60
LDAGQYTCHK GGETLSHSHL LLHKKENGIW STEILKNFKN KTFLKCEAPN YSGRFTCSWL  120
VQRNMDLKFN IKSSSSSPDS RAVTCGMASL SAEKVTLDQR DYEKYSVSCQ EDVTCPTAEE  180
TLPIELALEA RQQNKYENYS TSFFIRDIIK PDPPKNLQMK PLKNSQVEVS WEYPDSWSTP  240
HSYFSLKFFV RIQRKKEKMK ETEEGCNQKG AFLVEKTSTE VQCKGGNVCV QAQDRYYNSS  300
CSKWACVPCR VRS                                                     313

SEQ ID NO: 165          moltype = DNA  length = 939
FEATURE                 Location/Qualifiers
misc_feature            1..939
                        note = Murine IL12p41
source                  1..939
                        mol_type = unassigned DNA
                        organism = Mus musculus
SEQUENCE: 165
atgtgggagc tggagaaaga cgtttatgtt gtagaggtgg actggactcc cgatgcccct  60
ggagaaacag tgaacctcac ctgtgacacg cctgaagaag atgacatcac ctggacctca  120
gaccagagac atggagtcat aggctctgga aagaccctga ccatcactgt caaagagttt  180
ctagatgctg gccagtacac ctgccacaaa ggaggcgaga ctctgagcca ctcacatctg  240
ctgctccaca agaaggaaaa tggaatttgg tccactgaaa ttttaaaaaa tttcaaaaac  300
aagactttcc tgaagtgtga agcaccaaat tactccggac ggttcacgtg ctcatggctg  360
gtgcaaagaa acatggactt gaagttcaac atcaagagca gtagcagttc ccctgactct  420
cgggcagtga catgtggaat ggcgtctctg tctgcagaga aggtcacact ggaccaaagg  480
gactatgaga agtattcagt gtcctgccag gaggatgtca cctgcccaac tgccgaggag  540
accctgccca ttgaactggc gttggaagca cggcagcaga ataaatatga gaactacagc  600
accagcttct tcatcaggga catcatcaaa ccagacccgc ccaagaactt gcagatgaag  660
cctttgaaga actcacaggt ggaggtcagc tgggagtacc ctgactcctg gagcactccc  720
cattcctact tctccctcaa gttctttgtt cgaatccagc gcaagaaaga aaagatgaag  780
gagacagagg aggggtgtaa ccagaaaggt gcgttcctcg tagagaagac atctaccgaa  840
```

```
gtccaatgca aaggcgggaa tgtctgcgtg caagctcagg atcgctatta caattcctca  900
tgcagcaagt gggcatgtgt tccctgcagg gtccgatcc                         939

SEQ ID NO: 166         moltype = AA  length = 193
FEATURE                Location/Qualifiers
REGION                 1..193
                       note = misc_feature - Murine IL12p35
source                 1..193
                       mol_type = protein
                       organism = Mus musculus
SEQUENCE: 166
RVIPVSGPAR CLSQSRNLLK TTDDMVKTAR EKLKHYSCTA EDIDHEDITR DQTSTLKTCL  60
PLELHKNESC LATRETSSTT RGSCLPPQKT SLMMTLCLGS IYEDLKMYQT EFQAINAALQ  120
NHNHQQIILD KGMLVAIDEL MQSLNHNGET LRQKPPVGEA DPYRVKMKLC ILLHAFSTRV  180
VTINRVMGYL SSA                                                     193

SEQ ID NO: 167         moltype = DNA  length = 579
FEATURE                Location/Qualifiers
misc_feature           1..579
                       note = Murine IL12p36
source                 1..579
                       mol_type = unassigned DNA
                       organism = Mus musculus
SEQUENCE: 167
agggtcattc cagtctctgg acctgccagg tgtcttagcc agtcccgaaa cctgctgaag  60
accacagatg acatggtgaa gacggccaga gaaaaactga aacattattc ctgcactgct  120
gaagacatcg atcatgaaga catcacacgg gaccaaacca gcacattgaa gacctgttta  180
ccactggaac tacacaagaa cgagagttgc ctggctacta gagagacttc ttccacaaca  240
agagggagct gcctgccccc acagaagacg tctttgatga tgaccctgtg ccttggtagc  300
atctatgagg acttgaagat gtaccagaca gagttccagg ccatcaacgc agcacttcag  360
aatcacaacc atcagcagat cattctagac aagggcatgc tggtggccat cgatgagctg  420
atgcagtctc tgaatcataa tggcgagact ctgcgccaga aacctcctgt gggagaagca  480
gacccttaca gagtgaaaat gaagctctgc atcctgcttc acgccttcag cacccgcgtc  540
gtgaccatca acagggtgat gggctatctg agctccgcc                         579

SEQ ID NO: 168         moltype = AA  length = 1161
FEATURE                Location/Qualifiers
REGION                 1..1161
                       note = misc_feature - Murine scIL12-MSA-ABP10
source                 1..1161
                       mol_type = protein
                       organism = Mus musculus
SEQUENCE: 168
MWELEKDVYV VEVDWTPDAP GETVNLTCDT PEEDDITWTS DQRHGVIGSG KTLTITVKEF  60
LDAGQYTCHK GGETLSHSHL LLHKKENGIW STEILKNFKN KTFLKCEAPN YSGRFTCSWL  120
VQRNMDLKFN IKSSSSSPDS RAVTCGMASL SAEKVTLDQR DYEKYSVSCQ EDVTCPTAEE  180
TLPIELALEA RQQNKYENYS TSFFIRDIIK PDPPKNLQMK PLKNSQVEVS WEYPDSWSTP  240
HSYFSLKFFV RIQRKKEKMK ETEEGCNQKG AFLVEKTSTE VQCKGGNVCV QAQDRYYNSS  300
CSKWACVPCR VRSGGSGGGS GGGSGGGSRV IPVSGPARCL SQSRNLLKTT DDMVKTAREK  360
LKHYSCTAED IDHEDITRDQ TSTLKTCLPL ELHKNESCLA TRETSSTTRG SCLPPQKTSL  420
MMTLCLGSIY EDLKMYQTEF QAINAALQNH NHQQIILDKG MLVAIDELMQ SLNHNGETLR  480
QKPPVGEADP YRVKMKLCIL LHAFSTRVVT INRVMGYLSS AGSGGGSEAH KSEIAHRYND  540
LGEQHFKGLV LIAFSQYLQK CSYDEHAKLV QEVTDFAKTC VADESAANCD KSLHTLFGDK  600
LCAIPNLREN YGELADCCTK QEPERNECFL QHKDDNPSLP PFERPEAEAM CTSFKENPTT  660
FMGHYLHEVA RRHPYFYAPE LLYYAEQYNE ILTQCCAEAD KESCLTPKLD GVKEKALVSS  720
VRQRMKCSSM QKFGERAFKA WAVARLSQTF PNADFAEITK LATDLTKVNK ECCHGDLLEC  780
ADDRAELAKY MCENQATISS KLQTCCDKPL LKKAHCLSEV EHDTMPADLP AIAADFVEDQ  840
EVCKNYAEAK DVFLGTFLYE YSRRHPDYSV SLLLRLAKKY EATLEKCCAE ANPPACYGTV  900
LAEFQPLVEE PKNLVKTNCD LYEKLGEYGF QNAILVRYTQ KAPQVSTPTL VEAARNLGRV  960
GTKCCTLPED QRLPCVEDYL SAILNRVCLL HEKTPVSEHV TKCCSGSLVE RRPCFSALTV  1020
DETYVPKEFK AETFTFHSDI CTLPEKEKQI KKQTALAELV KHKPKATAEQ LKTVMDDFAQ  1080
FLDTCCKAAD KDTCFSTEGP NLVTRCKDAL AGGGSFQSEE QQGGGSGGSE EGGMESEESN  1140
GGGSGGSEEG GGGGSHHHHH H                                            1161

SEQ ID NO: 169         moltype = DNA  length = 3483
FEATURE                Location/Qualifiers
misc_feature           1..3483
                       note = Murine scIL12-MSA-ABP10
source                 1..3483
                       mol_type = unassigned DNA
                       organism = Mus musculus
SEQUENCE: 169
atgtgggagc tggagaaaga cgtttatgtt gtagaggtgg actggactcc cgatgcccct  60
ggagaaacag tgaacctcac ctgtgacacg cctgaagaag atgacatcac ctggacctca  120
gaccagagac atggagtcat aggctctgga aagaccctga ccatcactgt caaagagttt  180
ctagatgctg gccagtacac ctgccacaaa ggaggcgaga ctctgagcca ctcacatctg  240
ctgctccaca agaaggaaaa tggaatttgg tccactgaaa ttttaaaaaa tttcaaaaac  300
aagactttcc tgaagtgtga agcaccaaat tactccggac ggttcacgtg ctcatggctg  360
gtgcaaagaa acatggactt gaagttcaac atcaagagca gtagcagttc ccctgactct  420
```

```
cgggcagtga catgtggaat ggcgtctctg tctgcagaga aggtcacact ggaccaaagg  480
gactatgaga agtattcagt gtcctgccag gaggatgtca cctgcccaac tgccgaggag  540
accctgccca ttgaactggc gttggaagca cggcagcaga ataaatatga gaactacagc  600
accagcttct tcatcaggga catcatcaaa ccagacccgc ccaagaactt gcagatgaag  660
cctttgaaga actcacaggt ggaggtcagc tgggagtacc ctgactcctg gagcactccc  720
cattcctact tctccctcaa gttctttgtt cgaatccagc gcaagaaaga aaagatgaag  780
gagacagagg aggggtgtaa ccagaaaggt gcgttcctcg tagagaagac atctaccgaa  840
gtccaatgca aaggcgggaa tgtctgcgtg caagctcagg atcgctatta caattcctca  900
tgcagcaagt gggcatgtgt tccctgcagg gtccgatccg gaggttccgg tggtggatcc  960
ggaggtggct ccggcggcgg atccagggtc attccagtct ctggacctgc caggtgtctt  1020
agccagtccc gaaacctgct gaagaccaca gatgacatgg tgaagacggc cagagaaaaa  1080
ctgaaacatt attcctgcac tgctgaagac atcgatcatg aagacatcac acgggaccaa  1140
accagcacat tgaagacctg tttaccactg gaactacaca agaacgagag ttgcctggct  1200
actagagaga cttcttccac aacaagaggg agctgcctgc ccccacagaa gacgtctttg  1260
atgatgaccc tgtgccttgg tagcatctat gaggacttga agatgtacca gacagagttc  1320
caggccatca acgcagcact tcagaatcac aaccatcagc agatcattct agacaagggc  1380
atgctggtgg ccatcgatga gctgatgcag tctctgaatc ataatggcga gactctgcgc  1440
cagaaacctc ctgtgggaga agcagaccct tacagagtga aaatgaagct ctgcatcctg  1500
cttcacgcct tcagcacccg cgtcgtgacc atcaacaggg tgatgggcta tctgagctcc  1560
gccggttccg gtggcggatc cgaagcacac aagagtgaga tcgcccatcg gtataatgat  1620
ttgggagaac aacatttcaa aggcctagtc ctgattgcct tttcccagta tctccagaaa  1680
tgctcatacg atgagcatgc caaattagtg caggaagtaa cagactttgc aaagacgtgt  1740
gttgccgatg agtctgccgc caactgtgac aaatcccttc acactctttt tggagataag  1800
ttgtgtgcca ttccaaacct ccgtgaaaac tatggtgaac tggctgactg ctgtacaaaa  1860
caagagcccg aaagaaacga atgtttcctg caacacaaag atgacaaccc cagcctgcca  1920
ccatttgaaa ggccagaggc tgaggccatg tgcacctcct ttaaggaaaa cccaaccacc  1980
tttatgggac actatttgca tgaagttgcc agaagacatc cttatttcta tgccccagaa  2040
cttctttact atgctgagca gtacaatgag attctgaccc agtgttgtgc agaggctgac  2100
aaggaaagct gcctgacccc gaagcttgat ggtgtgaagg agaaagcatt ggtctcatct  2160
gtccgtcaga gaatgaagtg ctccagtatg cagaagtttg gagagagagc ttttaaagca  2220
tgggcagtag ctcgtctgag ccagacattc cccaatgctg actttgcaga aatcaccaaa  2280
ttggcaacag acctgaccaa agtcaacaag gagtgctgcc atggtgacct gctggaatgc  2340
gcagatgaca gggcggaact tgccaagtac atgtgtgaaa accaggcgac tatctccagc  2400
aaactgcaga cttgctgcga taaaccactg ttgaagaaag cccactgtct tagtgaggtg  2460
gagcatgaca ccatgcctgc tgatctgcct gccattgctg ctgattttgt tgaggaccag  2520
gaagtgtgca agaactatgc tgaggccaag gatgtcttcc tgggcacgtt cttgtatgaa  2580
tattcaagaa gacaccctga ttactctgta tccctgttgc tgagacttgc taagaaatat  2640
gaagccactc tggaaaagtg ctgcgctgaa gccaatcctc ccgcatgcta cggcacagtg  2700
cttgctgaat ttcagcctct tgtagaagag cctaagaact tggtcaaaac caactgtgat  2760
ctttacgaga agcttggaga atatggattc caaaatgcca ttctagttcg ctacacccag  2820
aaagcacctc aggtgtcaac cccaactctc gtggaggctg caagaaacct aggaagagtg  2880
ggcaccaagt gttgtacact tcctgaagat cagagactgc cttgtgtgga agactatctg  2940
tctgcaatcc tgaaccgtgt gtgtctgctg catgagaaga ccccagtgag tgagcatgtt  3000
accaagtgct gtagtggatc cctggtggaa aggcggccat gcttctctgc tctgacagtt  3060
gatgaaacat atgtccccaa agagtttaaa gctgagacct tcaccttcca ctctgatatc  3120
tgcacacttc cagagaagga gaagcagatt aagaaacaaa cggctcttgc tgagctggtg  3180
aagcacaagc ccaaggctac agcggagcaa ctgaagactg tcatggatga ctttgcacag  3240
ttcctggata catgttgcaa ggctgctgac aaggacacct gcttctcgac tgagggtcca  3300
aaccttgtca ctagatgcaa agacgcctta gccggtggag gtagtttcca atcagaagag  3360
caacagggtg ggggttccgg cggtagcgag gagggtggga tggagagtga agaatcaaat  3420
ggtgggggtt ccggcggtag cgaggagggt gggggaggtg gatcacacca tcaccaccat  3480
cac                                                                3483

SEQ ID NO: 170         moltype = AA  length = 1137
FEATURE                Location/Qualifiers
REGION                 1..1137
                       note = misc_feature - Murine scIL12-MSA-ABP17
source                 1..1137
                       mol_type = protein
                       organism = Mus musculus
SEQUENCE: 170
MWELEKDVYV VEVDWTPDAP GETVNLTCDT PEEDDITWTS DQRHGVIGSG KTLTITVKEF  60
LDAGQYTCHK GGETLSHSHL LLHKKENGIW STEILKNFKN KTFLKCEAPN YSGRFTCSWL  120
VQRNMDLKFN IKSSSSSPDS RAVTCGMASL SAEKVTLDQR DYEKYSVSCQ EDVTCPTAEE  180
TLPIELALEA RQQNKYENYS TSFFIRDIIK PDPPKNLQMK PLKNSQVEVS WEYPDSWSTP  240
HSYFSLKFFV RIQRKKEKMK ETEEGCNQKG AFLVEKTSTE VQCKGGNVCV QAQDRYYNSS  300
CSKWACVPCR VRSGGSGGGS GGGSGGGSRV IPVSGPARCL SQSRNLLKTT DDMVKTAREK  360
LKHYSCTAED IDHEDITRDQ TSTLKTCLPL ELHKNESCLA TRETSSTTRG SCLPPQKTSL  420
MMTLCLGSIY EDLKMYQTEF QAINAALQNH NHQQIILDKG MLVAIDELMQ SLNHNGETLR  480
QKPPVGEADP YRVKMKLCIL LHAFSTRVVT INRVMGYLSS AGSGGGSEAH KSEIAHRYND  540
LGEQHFKGLV LIAFSQYLQK CSYDEHAKLV QEVTDFAKTC VADESAANCD KSLHTLFGDK  600
LCAIPNLREN YGELADCCTK QEPERNECFL QHKDDNPSLP PFERPEAEAM CTSFKENPTT  660
FMGHYLHEVA RRHPYFYAPE LLYYAEQYNE ILTQCCAEAD KESCLTPKLD GVKEKALVSS  720
VRQRMKCSSM QKFGERAFKA WAVARLSQTF PNADFAEITK LATDLTKVNK ECCHGDLLEC  780
ADDRAELAKY MCENQATISS KLQTCCDKPL LKKAHCLSEV EHDTMPADLP AIAADFVEDQ  840
EVCKNYAEAK DVFLGTFLYE YSRRHPDYSV SLLLRLAKKY EATLEKCCAE ANPPACYGTV  900
LAEFQPLVEE PKNLVKTNCD LYEKLGEYGF QNAILVRYTQ KAPQVSTPTL VEAARNLGRV  960
GTKCCTLPED QRLPCVEDYL SAILNRVCLL HEKTPVSEHV TKCCSGSLVE RRPCFSALTV  1020
DETYVPKEFK AETFTFHSDI CTLPEKEKQI KKQTALAELV KHKPKATAEQ LKTVMDDFAQ  1080
```

```
FLDTCCKAAD KDTCFSTEGP NLVTRCKDAL AGGGGSEESE ESEESEEGGG GHHHHHH     1137

SEQ ID NO: 171         moltype = DNA  length = 3411
FEATURE                Location/Qualifiers
misc_feature           1..3411
                       note = Murine scIL12-MSA-ABP17
source                 1..3411
                       mol_type = unassigned DNA
                       organism = Mus musculus
SEQUENCE: 171
atgtgggagc tggagaaaga cgtttatgtt gtagaggtgg actggactcc cgatgcccct  60
ggagaaacag tgaacctcac ctgtgacacg cctgaagaag atgacatcac ctggacctca  120
gaccagagac atggagtcat aggctctgga aagaccctga ccatcactgt caaagagttt  180
ctagatgctg gccagtacac ctgccacaaa ggaggcgaga ctctgagcca ctcacatctg  240
ctgctccaca agaaggaaaa tggaatttgg tccactgaaa ttttaaaaaa tttcaaaaac  300
aagactttcc tgaagtgtga agcaccaaat tactccggac ggttcacgtg ctcatggctg  360
gtgcaaagaa acatggactt gaagttcaac atcaagagca gtagcagttc ccctgactct  420
cgggcagtga catgtggaat ggcgtctctg tctgcagaga aggtcacact ggaccaaagg  480
gactatgaga agtattcagt gtcctgccag gaggatgtca cctgcccaac tgccgaggag  540
accctgccca ttgaactggc gttggaagca cggcagcaga ataaatatga gaactacagc  600
accagcttct tcatcaggga catcatcaaa ccagacccgc ccaagaactt gcagatgaag  660
cctttgaaga actcacaggt ggaggtcagc tgggagtacc ctgactcctg gagcactccc  720
cattcctact tctccctcaa gttctttgtt cgaatccagc gcaagaaaga aaagatgaag  780
gagacagagg aggggtgtaa ccagaaaggt gcgttcctcg tagagaagac atctaccgaa  840
gtccaatgca aaggcgggaa tgtctgcgtg caagctcagg atcgctatta caattcctca  900
tgcagcaagt gggcatgtgt tccctgcagg gtccgatccg gaggttccgg tggtggatcc  960
ggaggtggct ccggcggcgg atccagggtc attccagtct ctggacctgc caggtgtctt  1020
agccagtccc gaaacctgct gaagaccaca gatgacatgg tgaagacggc cagagaaaaa  1080
ctgaaacatt attcctgcac tgctgaagac atcgatcatg aagacatcac acgggaccaa  1140
accagcacat tgaagacctg tttaccactg gaactacaca agaacgagag ttgcctggct  1200
actagagaga cttcttccac aacaagaggg agctgcctgc ccccacagaa gacgtctttg  1260
atgatgaccc tgtgccttgg tagcatctat gaggacttga agatgtacca gacagagttc  1320
caggccatca acgcagcact tcagaatcac aaccatcagc agatcattct agacaagggc  1380
atgctggtgg ccatcgatga gctgatgcag tctctgaatc ataatggcga gactctgcgc  1440
cagaaacctc ctgtgggaga agcagaccct tacagagtga aaatgaagct ctgcatcctg  1500
cttcacgcct tcagcacccg cgtcgtgacc atcaacaggg tgatgggcta tctgagctcc  1560
gccggttccg gtggcggatc cgaagcacac aagagtgaga tcgcccatcg gtataatgat  1620
ttgggagaac aacatttcaa aggcctagtc ctgattgcct tttcccagta tctccagaaa  1680
tgctcatacg atgagcatgc caaattagtg caggaagtaa cagactttgc aaagacgtgt  1740
gttgccgatg agtctgccgc caactgtgac aaatcccttc acactctttt tggagataag  1800
ttgtgtgcca ttccaaacct ccgtgaaaac tatggtgaac tggctgactg ctgtacaaaa  1860
caagagcccg aaagaaacga atgtttcctg caacacaaag atgacaaccc cagcctgcca  1920
ccatttgaaa ggccagaggc tgaggccatg tgcacctcct ttaaggaaaa cccaaccacc  1980
tttatgggac actatttgca tgaagttgcc agaagacatc cttatttcta tgccccagaa  2040
cttctttact atgctgagca gtacaatgag attctgaccc agtgttgtgc agaggctgac  2100
aaggaaagct gcctgacccc gaagcttgat ggtgtgaagg agaaagcatt ggtctcatct  2160
gtccgtcaga gaatgaagtg ctccagtatg cagaagtttg gagagagagc ttttaaagca  2220
tgggcagtag ctcgtctgag ccagacattc cccaatgctg actttgcaga aatcaccaaa  2280
ttggcaacag acctgaccaa agtcaacaag gagtgctgcc atggtgacct gctggaatgc  2340
gcagatgaca gggcggaact tgccaagtac atgtgtgaaa accaggcgac tatctccagc  2400
aaactgcaga cttgctgcga taaaccactg ttgaagaaag cccactgtct tagtgaggtg  2460
gagcatgaca ccatgcctgc tgatctgcct gccattgctg ctgattttgt tgaggaccag  2520
gaagtgtgca agaactatgc tgaggccaag gatgtcttcc tgggcacgtt cttgtatgaa  2580
tattcaagaa gacaccctga ttactctgta tccctgttgc tgagacttgc taagaaatat  2640
gaagccactc tggaaaagtg ctgcgctgaa gccaatcctc ccgcatgcta cggcacagtg  2700
cttgctgaat ttcagcctct tgtagaagag cctaagaact tggtcaaaac caactgtgat  2760
ctttacgaga agcttggaga atatggattc caaaatgcca ttctagttcg ctacacccag  2820
aaagcacctc aggtgtcaac cccaactctc gtggaggctg caagaaacct aggaagagtg  2880
ggcaccaagt gttgtacact tcctgaagat cagagactgc cttgtgtgga agactatctg  2940
tctgcaatcc tgaaccgtgt gtgtctgctg catgagaaga ccccagtgag tgagcatgtt  3000
accaagtgct gtagtggatc cctggtggaa aggcggccat gcttctctgc tctgacagtt  3060
gatgaaacat atgtccccaa agagtttaaa gctgagacct tcaccttcca ctctgatatc  3120
tgcacacttc cagagaagga gaagcagatt aagaaacaaa cggctcttgc tgagctggtg  3180
aagcacaagc ccaaggctac agcggagcaa ctgaagactg tcatggatga ctttgcacag  3240
ttcctggata catgttgcaa ggctgctgac aaggacacct gcttctcgac tgagggtcca  3300
aaccttgtca ctagatgcaa agacgcctta gccgggggggg gaggctctga agaatccgag  3360
gagagtgaag agtcagagga gggtggcggg ggcaccatc accaccatca c         3411

SEQ ID NO: 172         moltype = AA  length = 573
FEATURE                Location/Qualifiers
REGION                 1..573
                       note = misc_feature - Murine scIL12-ABP10
source                 1..573
                       mol_type = protein
                       organism = Mus musculus
SEQUENCE: 172
MWELEKDVYV VEVDWTPDAP GETVNLTCDT PEEDDITWTS DQRHGVIGSG KTLTITVKEF  60
LDAGQYTCHK GGETLSHSHL LLHKKENGIW STEILKNFKN KTFLKCEAPN YSGRFTCSWL  120
VQRNMDLKFN IKSSSSSPDS RAVTCGMASL SAEKVTLDQR DYEKYSVSCQ EDVTCPTAEE  180
```

```
TLPIELALEA RQQNKYENYS TSFFIRDIIK PDPPKNLQMK PLKNSQVEVS WEYPDSWSTP  240
HSYFSLKFFV RIQRKKEKMK ETEEGCNQKG AFLVEKTSTE VQCKGGNVCV QAQDRYYNSS  300
CSKWACVPCR VRSGGSGGGS GGGSGGGSRV IPVSGPARCL SQSRNLLKTT DDMVKTAREK  360
LKHYSCTAED IDHEDITRDQ TSTLKTCLPL ELHKNESCLA TRETSSTTRG SCLPPQKTSL  420
MMTLCLGSIY EDLKMYQTEF QAINAALQNH NHQQIILDKG MLVAIDELMQ SLNHNGETLR  480
QKPPVGEADP YRVKMKLCIL LHAFSTRVVT INRVMGYLSS AGSGGGSFQS EEQQGGGSGG  540
SEEGGMESEE SNGGGSGGSE EGGGGGSHHH HHH                               573

SEQ ID NO: 173          moltype = DNA  length = 1719
FEATURE                 Location/Qualifiers
misc_feature            1..1719
                        note = Murine scIL12-ABP10
source                  1..1719
                        mol_type = unassigned DNA
                        organism = Mus musculus
SEQUENCE: 173
atgtgggagc tggagaaaga cgtttatgtt gtagaggtgg actggactcc cgatgcccct  60
ggagaaacag tgaacctcac ctgtgacacg cctgaagaag atgacatcac ctggacctca  120
gaccagagac atggagtcat aggctctgga aagaccctga ccatcactgt caaagagttt  180
ctagatgctg gccagtacac ctgccacaaa ggaggcgaga ctctgagcca ctcacatctg  240
ctgctccaca agaaggaaaa tggaatttgg tccactgaaa ttttaaaaaa tttcaaaaac  300
aagactttcc tgaagtgtga agcaccaaat tactccggac ggttcacgtg ctcatggctg  360
gtgcaaagaa acatggactt gaagttcaac atcaagagca gtagcagttc ccctgactct  420
cgggcagtga catgtggaat ggcgtctctg tctgcagaga aggtcacact ggaccaaagg  480
gactatgaga agtattcagt gtcctgccag gaggatgtca cctgcccaac tgccgaggag  540
accctgccca ttgaactggc gttggaagca cggcagcaga ataaatatga gaactacagc  600
accagcttct tcatcaggga catcatcaaa ccagacccgc ccaagaactt gcagatgaag  660
cctttgaaga actcacaggt ggaggtcagc tgggagtacc ctgactcctg gagcactccc  720
cattcctact tctccctcaa gttctttgtt cgaatccagc gcaagaaaga aaagatgaag  780
gagacagagg aggggtgtaa ccagaaaggt gcgttcctcg tagagaagac atctaccgaa  840
gtccaatgca aaggcgggaa tgtctgcgtg caagctcagg atcgctatta caattcctca  900
tgcagcaagt gggcatgtgt tccctgcagg gtccgatccg gaggttccgg tggtggatcc  960
ggaggtggct ccggcggcgg atccagggtc attccagtct ctggacctgc caggtgtctt  1020
agccagtccc gaaacctgct gaagaccaca gatgacatgg tgaagacggc cagagaaaaa  1080
ctgaaacatt attcctgcac tgctgaagac atcgatcatg aagacatcac acgggaccaa  1140
accagcacat tgaagacctg tttaccactg gaactacaca agaacgagag ttgcctggct  1200
actagagaga cttcttccac aacaagaggg agctgcctgc ccccacagaa gacgtctttg  1260
atgatgaccc tgtgccttgg tagcatctat gaggacttga agatgtacca gacagagttc  1320
caggccatca acgcagcact tcagaatcac aaccatcagc agatcattct agacaagggc  1380
atgctggtgg ccatcgatga gctgatgcag tctctgaatc ataatggcga gactctgcgc  1440
cagaaacctc ctgtgggaga agcagaccct tacagagtga aaatgaagct ctgcatcctg  1500
cttcacgcct tcagcacccg cgtcgtgacc atcaacaggg tgatgggcta tctgagctcc  1560
gccggttccg gtggaggtag tttccaatca gaagagcaac agggtggggg ttccggcggt  1620
agcgaggagg gtgggatgga gagtgaagaa tcaaatggtg gggttccgg cggtagcgag  1680
gagggtgggg gaggtggatc acaccatcac caccatcac                         1719

SEQ ID NO: 174          moltype = AA  length = 547
FEATURE                 Location/Qualifiers
REGION                  1..547
                        note = misc_feature - Murine scIL12-ABP17
source                  1..547
                        mol_type = protein
                        organism = Mus musculus
SEQUENCE: 174
MWELEKDVYV VEVDWTPDAP GETVNLTCDT PEEDDITWTS DQRHGVIGSG KTLTITVKEF  60
LDAGQYTCHK GGETLSHSHL LLHKKENGIW STEILKNFKN KTFLKCEAPN YSGRFTCSWL  120
VQRNMDLKFN IKSSSSSPDS RAVTCGMASL SAEKVTLDQR DYEKYSVSCQ EDVTCPTAEE  180
TLPIELALEA RQQNKYENYS TSFFIRDIIK PDPPKNLQMK PLKNSQVEVS WEYPDSWSTP  240
HSYFSLKFFV RIQRKKEKMK ETEEGCNQKG AFLVEKTSTE VQCKGGNVCV QAQDRYYNSS  300
CSKWACVPCR VRSGGSGGGS GGGSGGGSRV IPVSGPARCL SQSRNLLKTT DDMVKTAREK  360
LKHYSCTAED IDHEDITRDQ TSTLKTCLPL ELHKNESCLA TRETSSTTRG SCLPPQKTSL  420
MMTLCLGSIY EDLKMYQTEF QAINAALQNH NHQQIILDKG MLVAIDELMQ SLNHNGETLR  480
QKPPVGEADP YRVKMKLCIL LHAFSTRVVT INRVMGYLSS AGGGGSEESE ESEESEEGGG  540
GHHHHHH                                                            547

SEQ ID NO: 175          moltype = DNA  length = 1641
FEATURE                 Location/Qualifiers
misc_feature            1..1641
                        note = Murine scIL12-ABP17
source                  1..1641
                        mol_type = unassigned DNA
                        organism = Mus musculus
SEQUENCE: 175
atgtgggagc tggagaaaga cgtttatgtt gtagaggtgg actggactcc cgatgcccct  60
ggagaaacag tgaacctcac ctgtgacacg cctgaagaag atgacatcac ctggacctca  120
gaccagagac atggagtcat aggctctgga aagaccctga ccatcactgt caaagagttt  180
ctagatgctg gccagtacac ctgccacaaa ggaggcgaga ctctgagcca ctcacatctg  240
ctgctccaca agaaggaaaa tggaatttgg tccactgaaa ttttaaaaaa tttcaaaaac  300
aagactttcc tgaagtgtga agcaccaaat tactccggac ggttcacgtg ctcatggctg  360
```

```
gtgcaaagaa acatggactt gaagttcaac atcaagagca gtagcagttc ccctgactct  420
cgggcagtga catgtggaat ggcgtctctg tctgcagaga aggtcacact ggaccaaagg  480
gactatgaga agtattcagt gtcctgccag gaggatgtca cctgcccaac tgccgaggag  540
accctgccca ttgaactggc gttggaagca cggcagcaga ataaatatga gaactacagc  600
accagcttct tcatcaggga catcatcaaa ccagacccgc ccaagaactt gcagatgaag  660
cctttgaaga actcacaggt ggaggtcagc tgggagtacc ctgactcctg gagcactccc  720
cattcctact tctccctcaa gttctttgtt cgaatccagc gcaagaaaga aaagatgaag  780
gagacagagg aggggtgtaa ccagaaaggt gcgttcctcg tagagaagac atctaccgaa  840
gtccaatgca aaggcgggaa tgtctgcgtg caagctcagg atcgctatta caattcctca  900
tgcagcaagt gggcatgtgt tccctgcagg gtccgatccg gaggttccgg tggtggatcc  960
ggaggtggct ccggcggcgg atccagggtc attccagtct ctggacctgc caggtgtctt  1020
agccagtccc gaaacctgct gaagaccaca gatgacatgg tgaagacggc cagagaaaaa  1080
ctgaaacatt attcctgcac tgctgaagac atcgatcatg aagacatcac acgggaccaa  1140
accagcacat tgaagacctg tttaccactg gaactacaca agaacgagag ttgcctggct  1200
actagagaga cttcttccac aacaagaggg agctgcctgc ccccacagaa gacgtctttg  1260
atgatgaccc tgtgccttgg tagcatctat gaggacttga agatgtacca gacagagttc  1320
caggccatca acgcagcact tcagaatcac aaccatcagc agatcattct agacaagggc  1380
atgctggtgg ccatcgatga gctgatgcag tctctgaatc ataatggcga gactctgcgc  1440
cagaaacctc ctgtgggaga agcagaccct tacagagtga aaatgaagct ctgcatcctg  1500
cttcacgcct tcagcacccg cgtcgtgacc atcaacaggg tgatgggcta tctgagctcc  1560
gccgggggggg gaggctctga agaatccgag gagagtgaag agtcagagga gggtggcggg  1620
gggcaccatc accaccatca c                                           1641
```

```
SEQ ID NO: 176         moltype = AA  length = 105
FEATURE                Location/Qualifiers
REGION                 1..105
                       note = Synthetic: 3/23 VL chain
source                 1..105
                       mol_type = protein
                       organism = synthetic construct
SEQUENCE: 176
TVLTQSPALA VSPGERVTIS CRASESVSTR MHWYQQRPGQ PPKLLIYVAS RLESGVPARF  60
SGGGSGTDFT LTIDPVEAND TATYFCQQSW NDPWTFGGGT KLELK                  105
```

```
SEQ ID NO: 177         moltype = DNA  length = 315
FEATURE                Location/Qualifiers
misc_feature           1..315
                       note = Synthetic: 3/23 VL chain
source                 1..315
                       mol_type = other DNA
                       organism = synthetic construct
SEQUENCE: 177
actgtgctga cccagtctcc tgctttggct gtgtctccag gagagagggt taccatctcc  60
tgtagggcca gtgagagtgt cagtacacgt atgcactggt accaacagag accaggacag  120
ccacccaaac tcctcatcta cgttgcatcc cgcctagaat ctggagtccc tgccaggttc  180
agtggcggtg ggtctgggac agactttacc ctcaccatag atcctgtgga ggctaatgat  240
actgcaacct atttctgtca gcagagttgg aatgatccgt ggacgttcgg tggaggcacc  300
aagctggaat tgaaa                                                  315
```

```
SEQ ID NO: 178         moltype = AA  length = 212
FEATURE                Location/Qualifiers
REGION                 1..212
                       note = Synthetic: 3/23 LC
source                 1..212
                       mol_type = protein
                       organism = synthetic construct
SEQUENCE: 178
TVLTQSPALA VSPGERVTIS CRASESVSTR MHWYQQRPGQ PPKLLIYVAS RLESGVPARF  60
SGGGSGTDFT LTIDPVEAND TATYFCQQSW NDPWTFGGGT KLELKRADAA PTVSIFPPSS  120
EQLTSGGASV VCFLNNFYPK DINVKWKIDG SERQNGVLNS WTDQDSKDST YSMSSTLTLT  180
KDEYERHNSY TCEATHKTST SPIVKSFNRN EC                                212
```

```
SEQ ID NO: 179         moltype = DNA  length = 636
FEATURE                Location/Qualifiers
misc_feature           1..636
                       note = Synthetic: 3/23 LC
source                 1..636
                       mol_type = other DNA
                       organism = synthetic construct
SEQUENCE: 179
actgtgctga cccagtctcc tgctttggct gtgtctccag gagagagggt taccatctcc  60
tgtagggcca gtgagagtgt cagtacacgt atgcactggt accaacagag accaggacag  120
ccacccaaac tcctcatcta cgttgcatcc cgcctagaat ctggagtccc tgccaggttc  180
agtggcggtg ggtctgggac agactttacc ctcaccatag atcctgtgga ggctaatgat  240
actgcaacct atttctgtca gcagagttgg aatgatccgt ggacgttcgg tggaggcacc  300
aagctggaat tgaaacgggc tgatgctgca ccaactgtat ccatcttccc accatccagt  360
gagcagttaa catctggagg tgcctcagtc gtgtgcttct tgaacaactt ctaccccaaa  420
gacatcaatg tcaagtggaa gattgatggc agtgaacgac aaaatggcgt cctgaacagt  480
tggactgatc aggacagcaa agacagcacc tacagcatga gcagcaccct cacgttgacc  540
```

```
aaggacgagt atgaacgaca taacagctat acctgtgagg ccactcacaa gacatcaact  600
tcacccattg tcaagagctt caacaggaat gagtgt                            636

SEQ ID NO: 180         moltype = AA  length = 115
FEATURE                Location/Qualifiers
REGION                 1..115
                       note = Synthetic: 3/23 VH chain
source                 1..115
                       mol_type = protein
                       organism = synthetic construct
SEQUENCE: 180
VQLVESGGGL VQPGRSLKLS CAASGFTLSD YYMAWVRQAP KKGLEWVASI NYEGSSTYYG  60
ESVKGRFTIS RDNAKSTLYL QMNSLRSEDT ATYYCVRHDN YFDYWGQGVL VTVSS       115

SEQ ID NO: 181         moltype = DNA  length = 345
FEATURE                Location/Qualifiers
misc_feature           1..345
                       note = Synthetic: 3/23 VH chain
source                 1..345
                       mol_type = other DNA
                       organism = synthetic construct
SEQUENCE: 181
gtgcagttgg tggagtctgg gggaggctta gtgcagcctg gaaggtccct gaaactctcc  60
tgtgcagcct caggattcac tctcagtgac tattacatgg cctgggtccg ccaggctcca  120
aagaagggtc tggagtgggt cgcatccatt aattatgagg gtagtagcac ttactatgga  180
gagtccgtga agggccgatt cactatctcc agagataacg caaaaagcac cctatacctg  240
caaatgaaca gtctgaggtc tgaggacacg gccacttatt attgtgtaag acatgataac  300
tactttgatt attggggcca aggagtacta gtcacagtct cctca                 345

SEQ ID NO: 182         moltype = AA  length = 325
FEATURE                Location/Qualifiers
REGION                 1..325
                       note = Synthetic: mIgG1
source                 1..325
                       mol_type = protein
                       organism = synthetic construct
SEQUENCE: 182
ATTKGPSVYP LAPGSAAQTN SMVTLGCLVK GYFPEPVTVT WNSGSLSSGV HTFPAVLQSD  60
LYTLSSSVTV PSSTWPSQTV TCNVAHPASS TKVDKKIVPR DCGCKPCICT VPEVSSVFIF  120
PPKPKDVLTI TLTPKVTCVV VDISKDDPEV QFSWFVDDVE VHTAQTKPRE EQINSTFRSV  180
SELPIMHQDW LNGKEFKCRV NSAAFPAPIE KTISKTKGRP KAPQVYTIPP PKEQMAKDKV  240
SLTCMITNFF PEDITVEWQW NGQPAENYKN TQPIMDTDGS YFVYSKLNVQ KSNWEAGNTF  300
TCSVLHEGLH NHHTEKSLSH SPGKG                                        325

SEQ ID NO: 183         moltype = DNA  length = 972
FEATURE                Location/Qualifiers
misc_feature           1..972
                       note = Synthetic: mIgG2
source                 1..972
                       mol_type = other DNA
                       organism = synthetic construct
SEQUENCE: 183
gccaccacca agggcccatc tgtctatcca ctggcccctg gatctgctgc ccaaactaac  60
tccatggtga ccctgggatg cctggtcaag ggctatttcc ctgagccagt gacagtgacc  120
tggaactctg gatccctgtc cagcggtgtg cacaccttcc cagctgtcct gcagtctgac  180
ctctacactc tgagcagctc agtgactgtc ccctccagca cctggcccag ccagaccgtc  240
acctgcaacg ttgcccaccc ggccagcagc accaaggtgg acaagaaaat tgtgcccagg  300
gattgtggtt gtaagccttg catatgtaca gtcccagaag tatcatctgt cttcatcttc  360
cccccaaagc ccaaggatgt gctcaccatt actctgactc ctaaggtcac gtgtgttgtg  420
gtagacatca gcaaggatga tcccgaggtc cagttcagct ggtttgtaga tgatgtggag  480
gtgcacacag ctcagacgaa accccgggag gagcagatca acagcacttt ccgttcagtc  540
agtgaacttc ccatcatgca ccaggactgg ctcaatggca aggagttcaa atgcagggtc  600
aacagtgcag ctttccctgc ccccatcgag aaaaccatct ccaaaaccaa aggcagaccg  660
aaggctccac aggtgtacac cattccacct cccaaggagc agatggccaa ggataaagtc  720
agtctgacct gcatgataac aaacttcttc cctgaagaca ttactgtgga gtggcagtgg  780
aatgggcagc cagcggagaa ctacaagaac actcagccca tcatggacac agatggctct  840
tacttcgtct acagcaagct caatgtgcag aagagcaact gggaggcagg aaatactttc  900
acctgctctg tgttacatga gggcctgcac aaccaccata ctgagaagag cctctcccac  960
tctcctggta aa                                                      972

SEQ ID NO: 184         moltype = AA  length = 491
FEATURE                Location/Qualifiers
REGION                 1..491
                       note = Synthetic: 3/23 HC-ABP10
source                 1..491
                       mol_type = protein
                       organism = synthetic construct
SEQUENCE: 184
VQLVESGGGL VQPGRSLKLS CAASGFTLSD YYMAWVRQAP KKGLEWVASI NYEGSSTYYG  60
```

```
ESVKGRFTIS RDNAKSTLYL QMNSLRSEDT ATYYCVRHDN YFDYWGQGVL VTVSSATTKG  120
PSVYPLAPGS AAQTNSMVTL GCLVKGYFPE PVTVTWNSGS LSSGVHTFPA VLQSDLYTLS  180
SSVTVPSSTW PSQTVTCNVA HPASSTKVDK KIVPRDCGCK PCICTVPEVS SVFIFPPKPK  240
DVLTITLTPK VTCVVVDISK DDPEVQFSWF VDDVEVHTAQ TKPREEQINS TFRSVSELPI  300
MHQDWLNGKE FKCRVNSAAF PAPIEKTISK TKGRPKAPQV YTIPPPKEQM AKDKVSLTCM  360
ITNFFPEDIT VEWQWNGQPA ENYKNTQPIM DTDGSYFVYS KLNVQKSNWE AGNTFTCSVL  420
HEGLHNHHTE KSLSHSPGKG GGSGGGSGGG SGGGSFQSEE QQGGGSGGSE EGGMESEESN  480
GGGSGGSEEG G                                                       491

SEQ ID NO: 185         moltype = DNA  length = 1485
FEATURE                Location/Qualifiers
misc_feature           1..1485
                       note = Synthetic: 3/23 HC-ABP10
source                 1..1485
                       mol_type = other DNA
                       organism = synthetic construct
SEQUENCE: 185
gtgcagttgg tggagtctgg gggaggctta gtgcagcctg gaaggtccct gaaactctcc  60
tgtgcagcct caggattcac tctcagtgac tattacatgg cctgggtccg ccaggctcca  120
aagaagggtc tggagtgggt cgcatccatt aattatgagg gtagtagcac ttactatgga  180
gagtccgtga agggccgatt cactatctcc agagataacg caaaaagcac cctatacctg  240
caaatgaaca gtctgaggtc tgaggacacg gccacttatt attgtgtaag acatgataac  300
tactttgatt attggggcca aggagtacta gtcacagtct cctcagccac caccaagggc  360
ccatctgtct atccactggc ccctggatct gctgcccaaa ctaactccat ggtgaccctg  420
ggatgcctgg tcaagggcta tttccctgag ccagtgacag tgacctggaa ctctggatcc  480
ctgtccagcg gtgtgcacac cttcccagct gtcctgcagt ctgacctcta cactctgagc  540
agctcagtga ctgtcccctc cagcacctgg cccagccaga ccgtcacctg caacgttgcc  600
cacccggcca gcagcaccaa ggtggacaag aaaattgtgc ccagggattg tggttgtaag  660
ccttgcatat gtacagtccc agaagtatca tctgtcttca tcttcccccc aaagcccaag  720
gatgtgctca ccattactct gactcctaag gtcacgtgtg ttgtggtaga catcagcaag  780
gatgatcccg aggtccagtt cagctggttt gtagatgatg tggaggtgca cacagctcag  840
acgaaacccc gggaggagca gatcaacagc actttccgtt cagtcagtga acttcccatc  900
atgcaccagg actggctcaa tggcaaggag ttcaaatgca gggtcaacag tgcagctttc  960
cctgccccca tcgagaaaac catctccaaa accaaaggca gaccgaaggc tccacaggtg  1020
tacaccattc cacctcccaa ggagcagatg gccaaggata aagtcagtct gacctgcatg  1080
ataacaaact tcttccctga agacattact gtggagtggc agtggaatgg gcagccagcg  1140
gagaactaca agaacactca gcccatcatg gacacagatg gctcttactt cgtctacagc  1200
aagctcaatg tgcagaagag caactgggag gcaggaaata ctttcacctg ctctgtgtta  1260
catgagggcc tgcacaacca ccatactgag aagagcctct cccactctcc tggtaaaggc  1320
ggaggttctg gaggtggctc cggtggaggt tctggaggtg gctccttcca atcagaagag  1380
caacagggtg ggggttccgg cggtagcgag gagggtggga tggagagtga agaatcaaat  1440
ggtgggggtt ccggcggtag cgaggagggt gggggaggtg gatca                  1485

SEQ ID NO: 186         moltype = AA  length = 107
FEATURE                Location/Qualifiers
REGION                 1..107
                       note = Synthetic: LOB12.3 VL chain
source                 1..107
                       mol_type = protein
                       organism = synthetic construct
SEQUENCE: 186
DIQMTQSPAS LSASLEEIVT ITCQASQDIG NWLAWYHQKP GKSPQLLIYG STSLADGVPS  60
RFSGSSSGSQ YSLKISRLQV EDIGIYYCLQ AYGAPWTFGG GTKLELK                107

SEQ ID NO: 187         moltype = DNA  length = 321
FEATURE                Location/Qualifiers
misc_feature           1..321
                       note = Synthetic: LOB12.3 VL chain
source                 1..321
                       mol_type = other DNA
                       organism = synthetic construct
SEQUENCE: 187
gatattcaaa tgactcaatc tccggcaagt ctttccgcgt ccctcgaaga aatcgtcacg  60
ataacgtgcc aagcgagtca ggacatcggt aactggctgg cttggtatca tcagaaacct  120
ggtaaatcac cacaactgct tatatacggg tctacaagcc ttgcagatgg agtgccaagt  180
agattcagtg gtagttccag cggatctcaa tattctttga aaatatccag actccaggta  240
gaggatattg gaatttatta ctgccttcag gcttacggtg cgccctggac ttttggggga  300
ggtacaaagc tcgaacttaa a                                            321

SEQ ID NO: 188         moltype = AA  length = 214
FEATURE                Location/Qualifiers
REGION                 1..214
                       note = Synthetic: LOB12.3 LC
source                 1..214
                       mol_type = protein
                       organism = synthetic construct
SEQUENCE: 188
DIQMTQSPAS LSASLEEIVT ITCQASQDIG NWLAWYHQKP GKSPQLLIYG STSLADGVPS  60
RFSGSSSGSQ YSLKISRLQV EDIGIYYCLQ AYGAPWTFGG GTKLELKRAD AAPTVSIFPP  120
```

```
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 189          moltype = DNA  length = 642
FEATURE                 Location/Qualifiers
misc_feature            1..642
                        note = Synthetic: LOB12.3 LC
source                  1..642
                        mol_type = other DNA
                        organism = synthetic construct
SEQUENCE: 189
gatattcaaa tgactcaatc tccggcaagt ctttccgcgt ccctcgaaga aatcgtcacg  60
ataacgtgcc aagcgagtca ggacatcggt aactggctgg cttggtatca tcagaaacct  120
ggtaaatcac cacaactgct tatatacggg tctacaagcc ttgcagatgg agtgccaagt  180
agattcagtg gtagttccag cggatctcaa tattctttga aaatatccag actccaggta  240
gaggatattg gaatttatta ctgccttcag gcttacggtg cgccctggac ttttggggga  300
ggtacaaagc tcgaacttaa acgggctgat gctgcaccaa ctgtatccat cttcccacca  360
tccagtgagc agttaacatc tggaggtgcc tcagtcgtgt gcttcttgaa caacttctac  420
cccaaagaca tcaatgtcaa gtggaagatt gatggcagtg aacgacaaaa tggcgtcctg  480
aacagttgga ctgatcagga cagcaaagac agcacctaca gcatgagcag caccctcacg  540
ttgaccaagg acgagtatga acgacataac agctatacct gtgaggccac tcacaagaca  600
tcaacttcac ccattgtcaa gagcttcaac aggaatgagt gt                    642

SEQ ID NO: 190          moltype = AA  length = 120
FEATURE                 Location/Qualifiers
REGION                  1..120
                        note = Synthetic: LOB12.3 VH chain
source                  1..120
                        mol_type = protein
                        organism = synthetic construct
SEQUENCE: 190
DVQLVESGGG LVQPGRSLKL SCAASGFIFS YFDMAWVRQA PTKGLEWVAS ISPDGSIPYY  60
RDSVKGRFTV SRENAKSSLY LQMDSLRSED TATYYCARRS YGGYSEIDYW GQGVMVTVSS  120

SEQ ID NO: 191          moltype = DNA  length = 360
FEATURE                 Location/Qualifiers
misc_feature            1..360
                        note = Synthetic: LOB12.3 VH chain
source                  1..360
                        mol_type = other DNA
                        organism = synthetic construct
SEQUENCE: 191
gacgtgcaac tggtagagag cggtgggggc ctcgtacaac ccggtcggag tttgaagttg  60
tcctgcgccg cgtcaggatt catctttagt tactttgaca tggcttgggt tcgacaagca  120
cccacgaaag gacttgagtg ggtcgcttca atatctcccg acgggagcat cccctactat  180
agggattccg ttaaaggacg cttcactgtt tcacgagaaa atgcaaaatc ttcactttac  240
ttgcaaatgg atagtttgcg atcagaagac accgcaactt actactgcgc aaggcggtct  300
tatgggggt atagcgaaat agactattgg gggcaaggag tgatggttac ggtttcatcc  360

SEQ ID NO: 192          moltype = AA  length = 496
FEATURE                 Location/Qualifiers
REGION                  1..496
                        note = Synthetic: LOB12.3 HC-ABP10
source                  1..496
                        mol_type = protein
                        organism = synthetic construct
SEQUENCE: 192
DVQLVESGGG LVQPGRSLKL SCAASGFIFS YFDMAWVRQA PTKGLEWVAS ISPDGSIPYY  60
RDSVKGRFTV SRENAKSSLY LQMDSLRSED TATYYCARRS YGGYSEIDYW GQGVMVTVSS  120
ATTKGPSVYP LAPGSAAQTN SMVTLGCLVK GYFPEPVTVT WNSGSLSSGV HTFPAVLQSD  180
LYTLSSSVTV PSSTWPSQTV TCNVAHPASS TKVDKKIVPR DCGCKPCICT VPEVSSVFIF  240
PPKPKDVLTI TLTPKVTCVV VDISKDDPEV QFSWFVDDVE VHTAQTKPRE EQINSTFRSV  300
SELPIMHQDW LNGKEFKCRV NSAAFPAPIE KTISKTKGRP KAPQVYTIPP PKEQMAKDKV  360
SLTCMITNFF PEDITVEWQW NGQPAENYKN TQPIMDTDGS YFVYSKLNVQ KSNWEAGNTF  420
TCSVLHEGLH NHHTEKSLSH SPGKGGGSGG GSGGGSGGGS FQSEEQQGGG SGGSEEGGME  480
SEESNGGGSG GSEEGG                                                  496

SEQ ID NO: 193          moltype = DNA  length = 1500
FEATURE                 Location/Qualifiers
misc_feature            1..1500
                        note = Synthetic: LOB12.3 HC-ABP10
source                  1..1500
                        mol_type = other DNA
                        organism = synthetic construct
SEQUENCE: 193
gacgtgcaac tggtagagag cggtgggggc ctcgtacaac ccggtcggag tttgaagttg  60
tcctgcgccg cgtcaggatt catctttagt tactttgaca tggcttgggt tcgacaagca  120
cccacgaaag gacttgagtg ggtcgcttca atatctcccg acgggagcat cccctactat  180
agggattccg ttaaaggacg cttcactgtt tcacgagaaa atgcaaaatc ttcactttac  240
```

```
ttgcaaatgg atagtttgcg atcagaagac accgcaactt actactgcgc aaggcggtct  300
tatggggggt atagcgaaat agactattgg gggcaaggag tgatggttac ggtttcatcc  360
gccaccacca agggcccatc tgtctatcca ctggcccctg gatctgctgc ccaaactaac  420
tccatggtga ccctgggatg cctggtcaag ggctatttcc ctgagccagt gacagtgacc  480
tggaactctg gatccctgtc cagcggtgtg cacaccttcc cagctgtcct gcagtctgac  540
ctctacactc tgagcagctc agtgactgtc ccctccagca cctggcccag ccagaccgtc  600
acctgcaacg ttgcccaccc ggccagcagc accaaggtgg acaagaaaat tgtgcccagg  660
gattgtggtt gtaagccttg catatgtaca gtcccagaag tatcatctgt cttcatcttc  720
cccccaaagc ccaaggatgt gctcaccatt actctgactc ctaaggtcac gtgtgttgtg  780
gtagacatca gcaaggatga tcccgaggtc cagttcagct ggtttgtaga tgatgtggag  840
gtgcacacag ctcagacgaa accccgggag gagcagatca acagcacttt ccgttcagtc  900
agtgaacttc ccatcatgca ccaggactgg ctcaatggca aggagttcaa atgcagggtc  960
aacagtgcag ctttccctgc ccccatcgag aaaaccatct ccaaaaccaa aggcagaccg  1020
aaggctccac aggtgtacac cattccacct cccaaggagc agatggccaa ggataaagtc  1080
agtctgacct gcatgataac aaacttcttc cctgaagaca ttactgtgga gtggcagtgg  1140
aatgggcagc cagcggagaa ctacaagaac actcagccca tcatggacac agatggctct  1200
tacttcgtct acagcaagct caatgtgcag aagagcaact gggaggcagg aaatactttc  1260
acctgctctg tgttacatga gggcctgcac aaccaccata ctgagaagag cctctcccac  1320
tctcctggta aaggcggagg ttctggaggt ggctccggtg gaggttctgg aggtggctcc  1380
ttccaatcag aagagcaaca gggtgggggt tccggcggta gcgaggaggg tgggatggag  1440
agtgaagaat caaatggtgg gggttccggc ggtagcgagg agggtggggg aggtggatca  1500
```

```
SEQ ID NO: 194          moltype = AA  length = 112
FEATURE                 Location/Qualifiers
REGION                  1..112
                        note = Synthetic: OX86 VL chain
source                  1..112
                        mol_type = protein
                        organism = synthetic construct
SEQUENCE: 194
DIVMTQGALP NPVPSGESAS ITCRSSQSLV YKDGQTYLNW FLQRPGQSPQ LLTYWMSTRA  60
SGVSDRFSGS GSGTYFTLKI SRVRAEDAGV YYCQQVREYP FTFGSGTKLE IK          112
```

```
SEQ ID NO: 195          moltype = DNA  length = 336
FEATURE                 Location/Qualifiers
misc_feature            1..336
                        note = Synthetic: OX86 VL chain
source                  1..336
                        mol_type = other DNA
                        organism = synthetic construct
SEQUENCE: 195
gatatcgtga tgacccaggg cgctctgccc aatcctgttc cttctggcga gagcgccagc  60
atcacctgta gaagctctca gagcctggtg tacaaggacg gccagaccta cctgaactgg  120
ttcctgcaaa gacccggcca gtctcctcag ctgctgacct actggatgag cacaagagcc  180
agcggcgtgt ccgatagatt ttctggcagc ggctccggca cctacttcac cctgaagatc  240
tccagagtgc gcgccgaaga tgccggcgtg tactactgtc agcaagtgcg cgagtacccc  300
ttcacattcg gcagcggcac caagctggaa atcaag                            336
```

```
SEQ ID NO: 196          moltype = AA  length = 107
FEATURE                 Location/Qualifiers
REGION                  1..107
                        note = misc_feature - Murine kappa chain
source                  1..107
                        mol_type = protein
                        organism = Mus musculus
SEQUENCE: 196
RADAAPTVSI FPPSSEQLTS GGASVVCFLN NFYPKDINVK WKIDGSERQN GVLNSWTDQD  60
SKDSTYSMSS TLTLTKDEYE RHNSYTCEAT HKTSTSPIVK SFNRNEC                 107
```

```
SEQ ID NO: 197          moltype = DNA  length = 321
FEATURE                 Location/Qualifiers
misc_feature            1..321
                        note = Murine kappa chain
source                  1..321
                        mol_type = unassigned DNA
                        organism = Mus musculus
SEQUENCE: 197
cgggctgatg ctgcaccaac tgtatccatc ttcccaccat ccagtgagca gttaacatct  60
ggaggtgcct cagtcgtgtg cttcttgaac aacttctacc ccaaagacat caatgtcaag  120
tggaagattg atggcagtga acgacaaaat ggcgtcctga acagttggac tgatcaggac  180
agcaaagaca gcacctacag catgagcagc accctcacgt tgaccaagga cgagtatgaa  240
cgacataaca gctatacctg tgaggccact cacaagacat caacttcacc cattgtcaag  300
agcttcaaca ggaatgagtg t                                            321
```

```
SEQ ID NO: 198          moltype = AA  length = 219
FEATURE                 Location/Qualifiers
REGION                  1..219
                        note = Synthetic: OX86 LC
source                  1..219
```

```
                         mol_type = protein
                         organism = synthetic construct
SEQUENCE: 198
DIVMTQGALP NPVPSGESAS ITCRSSQSLV YKDGQTYLNW FLQRPGQSPQ LLTYWMSTRA  60
SGVSDRFSGS GSGTYFTLKI SRVRAEDAGV YYCQQVREYP FTFGSGTKLE IKRADAAPTV  120
SIFPPSSEQL TSGGASVVCF LNNFYPKDIN VKWKIDGSER QNGVLNSWTD QDSKDSTYSM  180
SSTLTLTKDE YERHNSYTCE ATHKTSTSPI VKSFNRNEC                         219

SEQ ID NO: 199           moltype = DNA  length = 657
FEATURE                  Location/Qualifiers
misc_feature             1..657
                         note = Synthetic: OX86 LC
source                   1..657
                         mol_type = other DNA
                         organism = synthetic construct
SEQUENCE: 199
gatatcgtga tgacccaggg cgctctgccc aatcctgttc cttctggcga gagcgccagc  60
atcacctgta gaagctctca gagcctggtg tacaaggacg gccagaccta cctgaactgg  120
ttcctgcaaa gacccggcca gtctcctcag ctgctgacct actggatgag cacaagagcc  180
agcggcgtgt ccgatagatt ttctggcagc ggctccggca cctacttcac cctgaagatc  240
tccagagtgc gcgccgaaga tgccggcgtg tactactgtc agcaagtgcg cgagtacccc  300
ttcacattcg gcagcggcac caagctggaa atcaagcggg ctgatgctgc accaactgta  360
tccatcttcc caccatccag tgagcagtta acatctggag gtgcctcagt cgtgtgcttc  420
ttgaacaact tctaccccaa agacatcaat gtcaagtgga agattgatgg cagtgaacga  480
caaaatggcg tcctgaacag ttggactgat caggacagca aagacagcac ctacagcatg  540
agcagcaccc tcacgttgac caaggacgag tatgaacgac ataacagcta tacctgtgag  600
gccactcaca agacatcaac ttcacccatt gtcaagagct tcaacaggaa tgagtgt     657

SEQ ID NO: 200           moltype = AA  length = 117
FEATURE                  Location/Qualifiers
REGION                   1..117
                         note = Synthetic: OX86 VH chain
source                   1..117
                         mol_type = protein
                         organism = synthetic construct
SEQUENCE: 200
QVQLKESGPG LVQPSQTLSL TCTVSGFSLT GYNLHWVRQP PGKGLEWMGR MRYDGDTYYN  60
SVLKSRLSIS RDTSKNQVFL KMNSLQTDDT AIYYCTRDGR GDSFDYWGQG VMVTVSS     117

SEQ ID NO: 201           moltype = DNA  length = 351
FEATURE                  Location/Qualifiers
misc_feature             1..351
                         note = Synthetic: OX86 VH chain
source                   1..351
                         mol_type = other DNA
                         organism = synthetic construct
SEQUENCE: 201
caggtgcagc tgaaagagtc tggacctgga ctggtgcagc ccagccaaac actgagcctg  60
acctgtaccg tgtccggctt tagcctgacc ggctacaacc tgcactgggt ccgacagcca  120
cctggcaaag gactggaatg gatgggcaga atgagatacg acggcgacac ctactacaac  180
agcgtgctga agtcccggct gagcatcagc agagacacca gcaagaacca ggtgttcctg  240
aagatgaaca gcctgcagac cgacgacacc gccatctact actgcaccag agatggcaga  300
ggcgacagct tcgattattg gggccagggc gtgatggtca ccgtgtcctc t           351

SEQ ID NO: 202           moltype = AA  length = 493
FEATURE                  Location/Qualifiers
REGION                   1..493
                         note = Synthetic: OX86 HC-ABP10
source                   1..493
                         mol_type = protein
                         organism = synthetic construct
SEQUENCE: 202
QVQLKESGPG LVQPSQTLSL TCTVSGFSLT GYNLHWVRQP PGKGLEWMGR MRYDGDTYYN  60
SVLKSRLSIS RDTSKNQVFL KMNSLQTDDT AIYYCTRDGR GDSFDYWGQG VMVTVSSATT  120
KGPSVYPLAP GSAAQTNSMV TLGCLVKGYF PEPVTVTWNS GSLSSGVHTF PAVLQSDLYT  180
LSSSVTVPSS TWPSQTVTCN VAHPASSTKV DKKIVPRDCG CKPCICTVPE VSSVFIFPPK  240
PKDVLTITLT PKVTCVVVDI SKDDPEVQFS WFVDDVEVHT AQTKPREEQI NSTFRSVSEL  300
PIMHQDWLNG KEFKCRVNSA AFPAPIEKTI SKTKGRPKAP QVYTIPPPKE QMAKDKVSLT  360
CMITNFFPED ITVEWQWNGQ PAENYKNTQP IMDTDGSYFV YSKLNVQKSN WEAGNTFTCS  420
VLHEGLHNHH TEKSLSHSPG KGGGSGGGSG GGSGGGSFQS EEQQGGGSGG SEEGGMESEE  480
SNGGGSGGSE EGG                                                     493

SEQ ID NO: 203           moltype = DNA  length = 1491
FEATURE                  Location/Qualifiers
misc_feature             1..1491
                         note = Synthetic: OX86 HC-ABP10
source                   1..1491
                         mol_type = other DNA
                         organism = synthetic construct
```

```
SEQUENCE: 203
caggtgcagc tgaaagagtc tggacctgga ctggtgcagc ccagccaaac actgagcctg  60
acctgtaccg tgtccggctt tagcctgacc ggctacaacc tgcactgggt ccgacagcca  120
cctggcaaag gactggaatg gatgggcaga atgagatacg acggcgacac ctactacaac  180
agcgtgctga agtcccggct gagcatcagc agagacacca gcaagaacca ggtgttcctg  240
aagatgaaca gcctgcagac cgacgacacc gccatctact actgcaccag agatggcaga  300
ggcgacagct tcgattattg gggccagggc gtgatggtca ccgtgtcctc tgccaccacc  360
aagggcccat ctgtctatcc actggcccct ggatctgctg cccaaactaa ctccatggtg  420
accctgggat gcctggtcaa gggctatttc cctgagccag tgacagtgac ctggaactct  480
ggatccctgt ccagcggtgt gcacaccttc ccagctgtcc tgcagtctga cctctacact  540
ctgagcagct cagtgactgt cccctccagc acctggccca gccagaccgt cacctgcaac  600
gttgcccacc cggccagcag caccaaggtg gacaagaaaa ttgtgcccag ggattgtggt  660
tgtaagcctt gcatatgtac agtcccagaa gtatcatctg tcttcatctt ccccccaaag  720
cccaaggatg tgctcaccat tactctgact cctaaggtca cgtgtgttgt ggtagacatc  780
agcaaggatg atcccgaggt ccagttcagc tggtttgtag atgatgtgga ggtgcacaca  840
gctcagacga aaccccggga ggagcagatc aacagcactt tccgttcagt cagtgaactt  900
cccatcatgc accaggactg gctcaatggc aaggagttca aatgcagggt caacagtgca  960
gctttccctg cccccatcga gaaaaccatc tccaaaacca aaggcagacc gaaggctcca  1020
caggtgtaca ccattccacc tcccaaggag cagatggcca aggataaagt cagtctgacc  1080
tgcatgataa caaacttctt ccctgaagac attactgtgg agtggcagtg gaatgggcag  1140
ccagcggaga actacaagaa cactcagccc atcatggaca cagatggctc ttacttcgtc  1200
tacagcaagc tcaatgtgca gaagagcaac tgggaggcag gaaatacttt cacctgctct  1260
gtgttacatg agggcctgca caaccaccat actgagaaga gcctctccca ctctcctggt  1320
aaaggcggag gttctggagg tggctccggt ggaggttctg gaggtggctc cttccaatca  1380
gaagagcaac agggtggggg ttccggcggt agcgaggagg gtgggatgga gagtgaagaa  1440
tcaaatggtg gggttccgg cggtagcgag gagggtgggg gaggtggatc a           1491

SEQ ID NO: 204          moltype = AA  length = 634
FEATURE                 Location/Qualifiers
REGION                  1..634
                        note = Synthetic: MSA-ABP10
source                  1..634
                        mol_type = protein
                        organism = synthetic construct
SEQUENCE: 204
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALAGGGSFQ SEEQQGGGSG  600
GSEEGGMESE ESNGGGSGGS EEGGGGGSHH HHHH                              634

SEQ ID NO: 205          moltype = DNA  length = 1902
FEATURE                 Location/Qualifiers
misc_feature            1..1902
                        note = Synthetic: MSA-ABP10
source                  1..1902
                        mol_type = other DNA
                        organism = synthetic construct
SEQUENCE: 205
gaagcacaca agagtgagat cgcccatcgg tataatgatt tgggagaaca acatttcaaa  60
ggcctagtcc tgattgcctt ttcccagtat ctccagaaat gctcatacga tgagcatgcc  120
aaattagtgc aggaagtaac agactttgca aagacgtgtg ttgccgatga gtctgccgcc  180
aactgtgaca aatcccttca cactcttttt ggagataagt tgtgtgccat tccaaacctc  240
cgtgaaaact atggtgaact ggctgactgc tgtacaaaac aagagcccga aagaaacgaa  300
tgtttcctgc aacacaaaga tgacaacccc agcctgccac catttgaaag gccagaggct  360
gaggccatgt gcacctcctt taaggaaaac ccaaccacct ttatgggaca ctatttgcat  420
gaagttgcca gaagacatcc ttatttctat gccccagaac ttctttacta tgctgagcag  480
tacaatgaga ttctgaccca gtgttgtgca gaggctgaca aggaaagctg cctgaccccg  540
aagcttgatg gtgtgaagga gaaagcattg gtctcatctg tccgtcagag aatgaagtgc  600
tccagtatgc agaagtttgg agagagagct tttaaagcat gggcagtagc tcgtctgagc  660
cagacattcc ccaatgctga ctttgcagaa atcaccaaat tggcaacaga cctgaccaaa  720
gtcaacaagg agtgctgcca tggtgacctg ctggaatgcg cagatgacag ggcggaactt  780
gccaagtaca tgtgtgaaaa ccaggcgact atctccagca aactgcagac ttgctgcgat  840
aaaccactgt tgaagaaagc ccactgtctt agtgaggtgg agcatgacac catgcctgct  900
gatctgcctg ccattgctgc tgattttgtt gaggaccagg aagtgtgcaa gaactatgct  960
gaggccaagg atgtcttcct gggcacgttc ttgtatgaat attcaagaag acaccctgat  1020
tactctgtat ccctgttgct gagacttgct aagaaatatg aagccactct ggaaaagtgc  1080
tgcgctgaag ccaatcctcc cgcatgctac ggcacagtgc ttgctgaatt tcagcctctt  1140
gtagaagagc ctaagaactt ggtcaaaacc aactgtgatc tttacgagaa gcttggagaa  1200
tatggattcc aaaatgccat tctagttcgc tacacccaga aagcacctca ggtgtcaacc  1260
ccaactctcg tggaggctgc aagaaaccta ggaagagtgg gcaccaagtg ttgtacactt  1320
cctgaagatc agagactgcc ttgtgtggaa gactatctgt ctgcaatcct gaaccgtgtg  1380
tgtctgctgc atgagaagac cccagtgagt gagcatgtta ccaagtgctg tagtggatcc  1440
```

```
ctggtggaaa ggcggccatg cttctctgct ctgacagttg atgaaacata tgtccccaaa  1500
gagtttaaag ctgagacctt caccttccac tctgatatct gcacacttcc agagaaggag  1560
aagcagatta agaaacaaac ggctcttgct gagctggtga agcacaagcc caaggctaca  1620
gcggagcaac tgaagactgt catggatgac tttgcacagt tcctggatac atgttgcaag  1680
gctgctgaca aggacacctg cttctcgact gagggtccaa accttgtcac tagatgcaaa  1740
gacgccttag ccggtggagg tagtttccaa tcagaagagc aacagggtgg gggttccggc  1800
ggtagcgagg agggtgggat ggagagtgaa gaatcaaatg gtgggggttc cggcggtagc  1860
gaggagggtg ggggaggtgg atcacaccat caccaccatc ac                    1902

SEQ ID NO: 206          moltype = AA  length = 7
FEATURE                 Location/Qualifiers
REGION                  1..7
                        note = Synthetic: peptide
SITE                    2
                        note = misc_feature - Xaa can be any naturally occurring
                         amino acid
REGION                  4..5
                        note = misc_feature - Xaa can be any naturally occurring
                         amino acid
source                  1..7
                        mol_type = protein
                        organism = synthetic construct
SEQUENCE: 206
SXQXXDE                                                            7

SEQ ID NO: 207          moltype = AA  length = 5
FEATURE                 Location/Qualifiers
REGION                  1..5
                        note = Synthetic: peptide
source                  1..5
                        mol_type = protein
                        organism = synthetic construct
SEQUENCE: 207
EEEYF                                                              5

SEQ ID NO: 208          moltype = AA  length = 7
FEATURE                 Location/Qualifiers
REGION                  1..7
                        note = Synthetic: peptide
SITE                    5
                        note = misc_feature - X is E or G
SITE                    6
                        note = misc_feature - Xaa can be any naturally occurring
                         amino acid
source                  1..7
                        mol_type = protein
                        organism = synthetic construct
SEQUENCE: 208
EEIYXXF                                                            7

SEQ ID NO: 209          moltype = AA  length = 4
FEATURE                 Location/Qualifiers
REGION                  1..4
                        note = Synthetic: peptide
source                  1..4
                        mol_type = protein
                        organism = synthetic construct
SEQUENCE: 209
YMMM                                                               4

SEQ ID NO: 210          moltype = AA  length = 8
FEATURE                 Location/Qualifiers
REGION                  1..8
                        note = Synthetic: peptide
SITE                    2
                        note = misc_feature - Xaa can be any naturally occurring
                         amino acid
REGION                  4..5
                        note = misc_feature - Xaa can be any naturally occurring
                         amino acid
source                  1..8
                        mol_type = protein
                        organism = synthetic construct
SEQUENCE: 210
SXQXXDEE                                                           8

SEQ ID NO: 211          moltype = AA  length = 5
FEATURE                 Location/Qualifiers
REGION                  1..5
```

```
                         note = Synthetic: peptide
SITE                     3
                         note = misc_feature - Xaa can be any naturally occurring
                          amino acid
source                   1..5
                         mol_type = protein
                         organism = synthetic construct
SEQUENCE: 211
LPXTG                                                                        5

SEQ ID NO: 212           moltype = AA  length = 5
FEATURE                  Location/Qualifiers
REGION                   1..5
                         note = Synthetic: peptide
SITE                     3
                         note = misc_feature - Xaa can be any naturally occurring
                          amino acid
source                   1..5
                         mol_type = protein
                         organism = synthetic construct
SEQUENCE: 212
LPXTA                                                                        5

SEQ ID NO: 213           moltype = AA  length = 25
FEATURE                  Location/Qualifiers
REGION                   1..25
                         note = Synthetic: Linker
REGION                   6..25
                         note = misc_feature - "Gly Gly Gly Gly Ser" may or may not
                          be present
source                   1..25
                         mol_type = protein
                         organism = synthetic construct
SEQUENCE: 213
GGGGSGGGGS GGGGSGGGGS GGGGS                                                  25

SEQ ID NO: 214           moltype = AA  length = 5
FEATURE                  Location/Qualifiers
REGION                   1..5
                         note = Synthetic: Linker
source                   1..5
                         mol_type = protein
                         organism = synthetic construct
SEQUENCE: 214
GGGGS                                                                        5

SEQ ID NO: 215           moltype = AA  length = 10
FEATURE                  Location/Qualifiers
REGION                   1..10
                         note = Synthetic: Linker
source                   1..10
                         mol_type = protein
                         organism = synthetic construct
SEQUENCE: 215
GGGGSGGGGS                                                                   10

SEQ ID NO: 216           moltype = AA  length = 15
FEATURE                  Location/Qualifiers
REGION                   1..15
                         note = Synthetic: Linker
source                   1..15
                         mol_type = protein
                         organism = synthetic construct
SEQUENCE: 216
GGGGSGGGGS GGGGS                                                             15

SEQ ID NO: 217           moltype = AA  length = 20
FEATURE                  Location/Qualifiers
REGION                   1..20
                         note = Synthetic: Linker
source                   1..20
                         mol_type = protein
                         organism = synthetic construct
SEQUENCE: 217
GGGGSGGGGS GGGGSGGGGS                                                        20

SEQ ID NO: 218           moltype = AA  length = 25
FEATURE                  Location/Qualifiers
REGION                   1..25
```

```
                        note = Synthetic: Linker
source                  1..25
                        mol_type = protein
                        organism = synthetic construct
SEQUENCE: 218
GGGGSGGGGS GGGGSGGGGS GGGGS                                         25

SEQ ID NO: 219          moltype = AA  length = 27
FEATURE                 Location/Qualifiers
REGION                  1..27
                        note = Synthetic: Linker
REGION                  12..26
                        note = misc_feature - "Glu Ala Ala Ala Lys" may or may not
                         be present
source                  1..27
                        mol_type = protein
                        organism = synthetic construct
SEQUENCE: 219
AEAAAKEAAA KEAAAKEAAA KEAAAKA                                       27

SEQ ID NO: 220          moltype = AA  length = 50
FEATURE                 Location/Qualifiers
REGION                  1..50
                        note = Synthetic: Linker
source                  1..50
                        mol_type = protein
                        organism = synthetic construct
SEQUENCE: 220
LEAEAAAKEA AAKEAAAKEA AAKALEAEAA AKEAAAKEAA AKEAAAKALE              50

SEQ ID NO: 221          moltype = AA  length = 10
FEATURE                 Location/Qualifiers
REGION                  1..10
                        note = Synthetic: Linker
REGION                  3..10
                        note = misc_feature - "Gly Ser" may or may not be present
source                  1..10
                        mol_type = protein
                        organism = synthetic construct
SEQUENCE: 221
GSGSGSGSGS                                                          10

SEQ ID NO: 222          moltype = AA  length = 4
FEATURE                 Location/Qualifiers
REGION                  1..4
                        note = Synthetic: Linker
source                  1..4
                        mol_type = protein
                        organism = synthetic construct
SEQUENCE: 222
GGSG                                                                4

SEQ ID NO: 223          moltype = AA  length = 20
FEATURE                 Location/Qualifiers
REGION                  1..20
                        note = Synthetic: Linker
REGION                  5..20
                        note = misc_feature - "Gly Gly Ser Gly" may or may not be
                         present
source                  1..20
                        mol_type = protein
                        organism = synthetic construct
SEQUENCE: 223
GGSGGGSGGG SGGGSGGGSG                                               20

SEQ ID NO: 224          moltype = AA  length = 4
FEATURE                 Location/Qualifiers
REGION                  1..4
                        note = Synthetic: Linker
source                  1..4
                        mol_type = protein
                        organism = synthetic construct
SEQUENCE: 224
GSAT                                                                4

SEQ ID NO: 225          moltype = AA  length = 30
FEATURE                 Location/Qualifiers
REGION                  1..30
                        note = Synthetic: Linker
```

```
REGION                  7..30
                        note = misc_feature - "Gly Gly Ser Gly Gly Ser" may or may
                         not be present
source                  1..30
                        mol_type = protein
                        organism = synthetic construct
SEQUENCE: 225
GGSGGSGGSG GSGGSGGSGG SGGSGGSGGS                                   30

SEQ ID NO: 226          moltype = DNA  length = 25
FEATURE                 Location/Qualifiers
misc_feature            1..25
                        note = Synthetic: lipophilic-CpG oligonucleotide
misc_feature            1..25
                        note = lipophilic compound on 5' end
misc_feature            2..5
                        note = g may or may not be present
source                  1..25
                        mol_type = other DNA
                        organism = synthetic construct
SEQUENCE: 226
gggggtccat gacgttcctg acgtt                                        25

SEQ ID NO: 227          moltype = DNA  length = 12
FEATURE                 Location/Qualifiers
misc_feature            1..12
                        note = Synthetic: Lipid-linker
misc_feature            1..12
                        note = lipophilic compound on 5' end
source                  1..12
                        mol_type = other DNA
                        organism = synthetic construct
SEQUENCE: 227
tttttttttt cg                                                      12

SEQ ID NO: 228          moltype = DNA  length = 12
FEATURE                 Location/Qualifiers
misc_feature            1..12
                        note = Synthetic: Lipid-linker
misc_feature            1..12
                        note = lipophilic compound on 5' end
source                  1..12
                        mol_type = other DNA
                        organism = synthetic construct
SEQUENCE: 228
ggtttttttt cg                                                      12

SEQ ID NO: 229          moltype = DNA  length = 12
FEATURE                 Location/Qualifiers
misc_feature            1..12
                        note = Synthetic: Lipid-linker
misc_feature            1..12
                        note = lipophilic compound on 5' end
source                  1..12
                        mol_type = other DNA
                        organism = synthetic construct
SEQUENCE: 229
ggggtttttt cg                                                      12

SEQ ID NO: 230          moltype = DNA  length = 12
FEATURE                 Location/Qualifiers
misc_feature            1..12
                        note = Synthetic: Lipid-linker
misc_feature            1..12
                        note = lipophilic compound on 5' end
source                  1..12
                        mol_type = other DNA
                        organism = synthetic construct
SEQUENCE: 230
ggggggtttt cg                                                      12

SEQ ID NO: 231          moltype = DNA  length = 12
FEATURE                 Location/Qualifiers
misc_feature            1..12
                        note = Synthetic: Lipid-linker
misc_feature            1..12
                        note = lipophilic compound on 5' end
source                  1..12
                        mol_type = other DNA
```

```
                         organism = synthetic construct
SEQUENCE: 231
gggggggtt cg                                                     12

SEQ ID NO: 232           moltype = DNA  length = 12
FEATURE                  Location/Qualifiers
misc_feature             1..12
                         note = Synthetic: Lipid-linker
misc_feature             1..12
                         note = lipophilic compound on 5' end
source                   1..12
                         mol_type = other DNA
                         organism = synthetic construct
SEQUENCE: 232
gggggggggg cg                                                    12

SEQ ID NO: 233           moltype = AA  length = 4
FEATURE                  Location/Qualifiers
REGION                   1..4
                         note = Synthetic: anchor peptide
source                   1..4
                         mol_type = protein
                         organism = synthetic construct
SEQUENCE: 233
KDEL                                                             4

SEQ ID NO: 234           moltype = AA  length = 4
FEATURE                  Location/Qualifiers
REGION                   1..4
                         note = Synthetic: anchor peptide
source                   1..4
                         mol_type = protein
                         organism = synthetic construct
SEQUENCE: 234
HDEL                                                             4

SEQ ID NO: 235           moltype = AA  length = 51
FEATURE                  Location/Qualifiers
REGION                   1..51
                         note = Synthetic: Linker
REGION                   7..51
                         note = misc_feature - "Gly Gly Gly Gly Ser" may or may not
                          be present
source                   1..51
                         mol_type = protein
                         organism = synthetic construct
SEQUENCE: 235
SGGGGSGGGG SGGGGSGGGG SGGGGSGGGG SGGGGSGGGG SGGGGSGGGG S         51

SEQ ID NO: 236           moltype = AA  length = 16
FEATURE                  Location/Qualifiers
REGION                   1..16
                         note = Synthetic: Linker
source                   1..16
                         mol_type = protein
                         organism = synthetic construct
SEQUENCE: 236
SGGGGSGGGG SGGGGS                                                16

SEQ ID NO: 237           moltype = AA  length = 21
FEATURE                  Location/Qualifiers
REGION                   1..21
                         note = Synthetic: Linker
source                   1..21
                         mol_type = protein
                         organism = synthetic construct
SEQUENCE: 237
SGGGGSGGGG SGGGGSGGGG S                                          21

SEQ ID NO: 238           moltype = AA  length = 30
FEATURE                  Location/Qualifiers
REGION                   1..30
                         note = Synthetic: Linker
REGION                   6..30
                         note = misc_feature - "Gly Gly Gly Gly Ser" may or may not
                          be present
source                   1..30
                         mol_type = protein
                         organism = synthetic construct
```

-continued

```
SEQUENCE: 238
GGGGSGGGGS GGGGSGGGGS GGGGSGGGGS                                  30

SEQ ID NO: 239          moltype = AA  length = 24
FEATURE                 Location/Qualifiers
REGION                  1..24
                        note = Synthetic: Linker
REGION                  5..24
                        note = misc_feature - "Gly Gly Gly Ser" may or may not be
                         present
source                  1..24
                        mol_type = protein
                        organism = synthetic construct
SEQUENCE: 239
GGGSGGGSGG GSGGGSGGGS GGGS                                        24

SEQ ID NO: 240          moltype = AA  length = 4
FEATURE                 Location/Qualifiers
REGION                  1..4
                        note = Synthetic: Linker
source                  1..4
                        mol_type = protein
                        organism = synthetic construct
SEQUENCE: 240
GGGG                                                              4
```